United States Patent
Meis et al.

(10) Patent No.: US 12,059,479 B2
(45) Date of Patent: *Aug. 13, 2024

(54) MAKING AND USING IN VITRO-SYNTHESIZED SSRNA FOR INTRODUCING INTO MAMMALIAN CELLS TO INDUCE A BIOLOGICAL OR BIOCHEMICAL EFFECT

(71) Applicant: CELLSCRIPT, LLC, Madison, WI (US)

(72) Inventors: Judith Meis, Fitchburg, WI (US); Anthony Person, Madison, WI (US); Cynthia Chin, Madison, WI (US); Jerome Jendrisak, Middleton, WI (US); Gary Dahl, Madison, WI (US)

(73) Assignee: CELLSCRIPT, LLC, Madison, WI (US)

( * ) Notice: Subject to any disclaimer, the term of this patent is extended or adjusted under 35 U.S.C. 154(b) by 191 days.

This patent is subject to a terminal disclaimer.

(21) Appl. No.: 17/463,007

(22) Filed: Aug. 31, 2021

(65) Prior Publication Data

US 2022/0257795 A1 Aug. 18, 2022

Related U.S. Application Data

(63) Continuation of application No. 16/225,489, filed on Dec. 19, 2018, now Pat. No. 11,135,314, which is a continuation of application No. 14/368,399, filed as application No. PCT/US2012/072301 on Dec. 31, 2012, now Pat. No. 10,201,620.

(60) Provisional application No. 61/651,738, filed on May 25, 2012, provisional application No. 61/582,050, filed on Dec. 30, 2011, provisional application No. 61/582,080, filed on Dec. 30, 2011.

(51) Int. Cl.

| A61K 48/00 | (2006.01) |
| A61K 31/7105 | (2006.01) |
| A61K 33/06 | (2006.01) |
| A61K 38/00 | (2006.01) |
| C12N 5/074 | (2010.01) |
| C12N 5/077 | (2010.01) |
| C12N 5/0793 | (2010.01) |
| C12N 15/10 | (2006.01) |
| C12N 15/87 | (2006.01) |
| C12P 19/34 | (2006.01) |
| C12P 19/38 | (2006.01) |
| C12P 21/02 | (2006.01) |

(52) U.S. Cl.
CPC ...... *A61K 48/0066* (2013.01); *A61K 31/7105* (2013.01); *A61K 33/06* (2013.01); *A61K 38/005* (2013.01); *A61K 48/0041* (2013.01); *C12N 5/0619* (2013.01); *C12N 5/0658* (2013.01); *C12N 5/0696* (2013.01); *C12N 15/1003* (2013.01); *C12N 15/1096* (2013.01); *C12N 15/87* (2013.01); *C12P 19/34* (2013.01); *C12P 19/38* (2013.01); *C12P 21/02* (2013.01); *C12N 2501/60* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/73* (2013.01); *C12N 2506/1307* (2013.01); *C12N 2510/00* (2013.01); *C12Y 301/26003* (2013.01)

(58) Field of Classification Search
None
See application file for complete search history.

(56) References Cited

U.S. PATENT DOCUMENTS

| 5,824,497 A | 10/1998 | Andrews et al. |
| 7,335,471 B2 | 2/2008 | Guillerez et al. |
| 8,039,214 B2 | 10/2011 | Dahl et al. |
| 8,278,036 B2 | 10/2012 | Kariko et al. |
| 8,329,887 B2 | 12/2012 | Dahl et al. |
| 8,808,982 B2 | 8/2014 | Dahl et al. |
| 2005/0054847 A1* | 3/2005 | Madden ............... C07H 21/02 536/25.4 |

(Continued)

FOREIGN PATENT DOCUMENTS

| EP | 2072618 | 6/2009 |
| WO | WO 2007/024708 | 3/2007 |

(Continued)

OTHER PUBLICATIONS

Mellits Nucleic acid research, 5401-5406 (Year: 1990).*
Nathania et al Biochemistry 49, 7164-7178 (Year: 2010).*
Sun et al Nucleic acid research, 33, 807-815, (Year: 2005).*
Yang Proc Natl Acad Sci U S A. Jul. 23;99(15):99 (Year: 2002).*
Kariko et al Mol. Ther. 16, 1833-1840 (Year: 2008).*
Strak et al Annu. Rev. Biochem . . . 67:227-64, (Year: 1998).*
Pe'ery Methods vol. 11: 371-381 (Year: 1997).*
Aasen et al. 2008. Efficient and rapid generation of induced pluripotent stem cells from human keratinocytes. Nature Biotech 26: 1276-84.

(Continued)

*Primary Examiner* — Anoop K Singh
(74) *Attorney, Agent, or Firm* — Jason R. Bond; Casimir Jones, S.C.

(57) ABSTRACT

The present invention relates to compositions, kits and methods for making and using RNA compositions comprising in vitro-synthesized ssRNA inducing a biological or biochemical effect in a mammalian cell or organism into which the RNA composition is repeatedly or continuously introduced. In certain embodiments, the invention provides compositions and methods for changing the state of differentiation or phenotype of a human or other vertebrate cell. For example, the present invention provides mRNA and methods for reprogramming cells that exhibit a first differentiated state or phenotype to cells that exhibit a second differentiated state or phenotype, such as to reprogram human somatic cells to pluripotent stem cells.

16 Claims, 85 Drawing Sheets
Specification includes a Sequence Listing.

(56) References Cited

U.S. PATENT DOCUMENTS

| | | | |
|---|---|---|---|
| 2005/0137155 | A1 | 6/2005 | McSwiggen et al. |
| 2007/0087437 | A1 | 4/2007 | Hu |
| 2007/0281336 | A1* | 12/2007 | Jendrisak ............ C12N 15/1075 |
| | | | 435/325 |
| 2008/0239143 | A1 | 10/2008 | Shin et al. |
| 2009/0286852 | A1 | 11/2009 | Kariko et al. |
| 2010/0167286 | A1 | 7/2010 | Reijo Pera et al. |
| 2010/0273220 | A1 | 10/2010 | Yanik et al. |
| 2011/0065103 | A1 | 3/2011 | Sahin et al. |
| 2011/0143397 | A1* | 6/2011 | Kariko ................. C07K 14/505 |
| | | | 435/377 |
| 2012/0046346 | A1 | 2/2012 | Rossi et al. |
| 2012/0065252 | A1 | 3/2012 | Schrum et al. |
| 2012/0237978 | A1 | 9/2012 | Kobilka et al. |
| 2012/0251618 | A1 | 10/2012 | Schrum et al. |
| 2012/0322864 | A1 | 12/2012 | Rossi et al. |
| 2012/0322865 | A1 | 12/2012 | Rossi et al. |
| 2013/0189741 | A1 | 7/2013 | Dahl et al. |
| 2014/0315988 | A1 | 10/2014 | Dahl et al. |
| 2014/0328825 | A1 | 11/2014 | Meis et al. |

FOREIGN PATENT DOCUMENTS

| | | | |
|---|---|---|---|
| WO | WO 2008/151058 | 12/2008 | |
| WO | WO 2009/077134 | 6/2009 | |
| WO | WO-2009077134 A2 * | 6/2009 | .............. A61P 43/00 |
| WO | WO 2009/093022 | 7/2009 | |
| WO | WO 2009/101407 | 8/2009 | |
| WO | WO 2009/127230 | 10/2009 | |
| WO | WO 2011/071931 | 6/2011 | |
| WO | WO 2011/071936 | 6/2011 | |
| WO | WO 2013/003475 | 1/2013 | |
| WO | WO 2013/102203 | 7/2013 | |

OTHER PUBLICATIONS

Abuchowski et al. 1981. Reduction of plasma urate levels in the cockerel with polyethylene glycol-uricase, J Pharmacol Exp Ther. 219:352-354.

Abuchowski et al. 1981. Immunosuppressive properties and circulating life of Achromobacter glutaminase-asparaginase covalently attached to polyethylene glycol in man, Cancer Treat Rep. 65:1077-81.

Andrews-Pfannkoch et al. 2010. Applied and Environmental Microbiology 76: 5039-5045.

Angel & Yanik. 2010. Innate Immune Suppression Enables Frequent Transfection with RNA Encoding Reprogramming Proteins. PLoS One 5(7):e11756, 7 pages.

Aoi et al. 2008. Generation of pluripotent stem cells from adult mouse liver and stomach cells. Science 321: 699-702.

Amarasinghe et al. 2001. *Escherichia coli* Ribonuclease III: Affinity Purification of Hexahistidine—Tagged Enzyme and Assays for Substrate Binding and Cleavage. Methods in Enzymology. Academic Press. 342:143-158.

Baker et al. 2005. RNA-Guided RNA modification: functional organization of the archeal H/ACA RNP. Genes & Dev. 19:1239-1248.

Banerjee. 1980. 5'-terminal cap structure in eucaryotic messenger ribonucleic acids. Microbiol Rev 44: 175-205.

Barber. 1966. The chromatographic separation of ribonucleic acids. Biochem. Biophys. Acta 114:422-424.

Barkay. 1982. Processing of Bacteriophage T4 Primary Trascripts with Ribonuclease III. J Mol Virol 162:299-315.

Bernstein et al, Role for a bidentate ribonuclease in the initiation step of RNA interference. Nature 2001; 409(6818): 363-6.

Biocca et al. "Intracellular Expression of Anti-p21ras Single Chain Fv Fragments Inhibits Meiotic Maturation of Xenopus Oocytes." Biochemical and Biophysical Research Communications., 1993, 197:422-427.

Bose, et al. 2004. Role of Nucleolin in Human Parainfluenza Virus Type 3 Infection of Human Lung Epithelial Cells. J. Virol. 78:8146-58.

Buccoliero et al, Elevation of lung surfactant phosphatidylcholine in mouse models of Sandhoff and of Niemann-Pick A disease. J Inherit Metab Dis 2004;27(5): 641-8.

Campbell et al. 2002. Pre-steady-state and Stopped-flow Fluorescence Analysis of *Escherichia coli* Ribonuclease III: Insights into Mechanism and Conformational Changes Associated with Binding and Catalysis. J Mol Biol 317:21-40.

Capoccia et al. "G-CSF and AMD3100 mobilize monocytes into the blood that stimulate angiogenesis in vivo through a paracrine mechanism," Blood. 2006. 108(7): 2438-2445.

Caudy et al. 2002. Fragile X-related protein and ViG associate with the RNA interference machinery. Genes & Devel 16: 2491-96.

Cazenave et al. 1994. RNA template-directed RNA synthesis by T7 RNA polymerase. Proc Natl Acad Sci USA 91: 6972-6976.

Chan et al. 2009. Live cell imaging distinguishes bona fide human iPS cells from partially reprogrammed cells. Nat Biotechnol 27: 1033-1037.

Clawson and Smuckler. 1982. Increased Amounts of Double-Stranded RNA in the Cytoplasm of the Rat Liver following Treatment with Carcinogens. Cancer Research 42: 3228-3231.

Conrad & Rauhut. 2002. Ribonuclease III: new sense from nuisance. The International Joural of Biochemistry & Cell Biology 34:116-129.

Copreni et al, Lentivirus-mediated gene transfer to the respiratory epithelium: a promising approach to gene therapy of cystic fibrosis. GeneTher 2004; 11 Suppl 1: S67-75.

Desrosiers et al. 1974. Identification of Mehtylated Nucleosides in Messenger RNA from Novikoff Hepatoma Cells. PNAS. 71:3971-3975.

Dong et al. 2005. Poly(d,I-lactide-co-glycolide)/montmorillonite nanoparticles for oral delivery of anticancer drugs. Biomaterials 26:6068-76.

Drews et al. 2012. The cytotoxic and immunological hurdles associated with non-viral mRNA-mediated reprogramming of human fibroblasts. Biomaterials 33: 4059-4068.

Dunn. 1976. Rnase III Cleavage of Single-stranded RNA. J Biol Chem 251:3807-3814.

Dunn. 1982. Ribonuclease III. The Enzymes. Paul D. Boyer ed. Academic Press. pp. 485-499.

Easton et al. 2010. Rapid, nondenaturing RNA purification and using weak anion-exchange fast performance liquid chromatography. RNA 16: 647-653.

Ebert et al. 2009. Induced pluripotent stem cells from a spinal muscular atrophy patient. Nature 457: 277-280.

Edmonds. 1990. Polyadenylate polymerases. Methods Enzymol 181: 161-170.

Epicentre Forum Publication, vol. 14-1 Published in Apr. 2007, 24 pages.

Faissner et al. 1982. Analysis of Poly peptides of the Tree Shrew (Tupaia) Herpesvirus by Gel Electrophoresis. J. Gen. Virol. 59:139-148.

Feng et al. 2008. PU.1 and C/EBPa/b convert fibroblasts into macrophage-like cells. Proc. Natl. Acad. Sci. USA 105: 6057-6062.

Filippov et al. 2000. A novel type of RNase III family proteins in eukaryotes. Gene. 245: 213-221.

Franklin. 1966. Purification and Properties of the Replicative Intermediate of the RNA Bacteriophage R17. Proc. Natl. Acad. Sci. USA 55:1504-1511.

Gantier et al. 2007. The response of mammalian cells to double-stranded RNA. Cytokine Growth Factor Rev 18: 363-371.

Gasche et al. 1999. Sequential Treatment of Anemia in Ulcerative Colitis with Intravenous Iron and Erythropletin. Digestion. 60:262-267.

Gershon. 2000. (A)-tail of two polymerase structures. Nat Struct Biol 7: 819-821.

Gjerde et al. 2009. RNA Purification and Analysis, Wiley-VCH Only TOC Provided. Will provide specific pages upon Examiner request.

(56) References Cited

OTHER PUBLICATIONS

Gonzalez et al. 2009. Generation of mouse-induced pluripotent stem cells by transient expression of a single nonviral polycistronic vector. Proc Natl Acad Sci U S A 106: 8918-8922.
Graf and Enver. 2009. Forcing cells to change lineages. Nature 462: 587-594.
Grentzmann et al, A dual-luciferase reporter system for studying recoding signals. RNA 1998;4(4): 479-86.
Grudzien et al. 2004. Novel cap analogs for in vitro synthesis of mRNAs with high translational efficiency. RNA 10: 1479-1487.
Grudzien-Nogalska et al. 2007. Phosphorothioate cap analogs stabilize mRNA and increase translational efficiency in mammalian cells. RNA 13: 1745-1755.
Gunnery & Matthews. 1995. Functional mRNA Can Be Generated by RNA Polymerase III.
Guo et al. 2000. Structure and function of a cap-independent translation element that functions in either the 3' or the 5' untranslated region. RNA. 6:1808-1820.
Hagen et al. 1978. Effect of RNase III on efficiency of translation of bacteriophage T7 lysozyme mRNA. J Virol 26: 793-804.
Hancock. 1995. Reticulocyte Lysate Assay for In Vitro Translation and Posttranslational Modification of Ras Proteins. Methods in Enzymology. 255:60-65.
Higman et al. 1992. The vaccinia virus mRNA (guanine-N7-)-methyltransferase requires both subunits of the mRNA capping enzyme for activity. J Biol Chem 267: 16430-16437.
Higman et al. 1994. The mRNA (guanine-7-)methyltransferase domain of the vaccinia virus mRNA capping enzyme. Expression in *Escherichia coli* and structural and kinetic comparison to the intact capping enzyme. J Biol Chem 269: 14974-14981.
Hornung et al. 2006. 5'-Triphosphate RNA is the ligand for RIG-I. Science 314: 994-997.
Huangfu et al. 2008. Induction of pluripotent stem cells from primary human fibroblasts with only Oct4 and Sox2. Nat Biotechnol 26: 1269-1275.
Ieda et al. 2010. Direct reprogramming of fibroblasts into functional cardiomyocytes by defined factors. Cell 142: 375-386.
Jemielity et al. 2003. Novel "anti-reverse" cap analogs with superior translational properties. RNA 9: 1108-1122.
Jiang, et al, 2005. Topical application of ketoconazole stimulates hair growth in C3H/HeN mice. J Dermatol, 32(4): 243-7.
Jiang et al. 2011. Structural basis of RNA recognition and activation by innate immune receptor RIG-I. Nature 479: 423-427.
Kalal et al. 2002. Tipping the balance between necrosis and apoptosis in human and murine cells treated with interferon and dsRNA. Cell Death and Differentiation 9: 981-994.
Kariko et al, 1998, Phosphate-enhanced transfection of cationic lipid-complexed mRNA and plasmid DNA. Biochim Biophys Acta 1369, 320-334.
Kariko et al. 2004. mRNA is an endogenous ligand for toll-like receptor 3. J Biol Chem 279: 12542-12550.
Kariko et al. 2005. Suppression of RNA recognition by Toll-like receptors: the impact of nucleoside modification and the evolutionary origin of RNA. Immunity 23: 165-175.
Kariko et al. 2008. Incorporation of pseudouridine into mRNA yields superior nonimmunogenic vector with increased translational capacity and biological stability. Mol Ther 16: 1833-1840.
Kariko et al. 2011. Generating the optimal mRNA for therapy: HPLC purification eliminates immune activation and improves translation of mucleoside-modified, protein-encoding mRNA. Nucleic Acid Res 39:e142, 10 pages.
Kariko et al. 2012. Increased Erythropoiesis in Mice Injected with Submicrogram Quantities of Pseudouridine-containing mRNA Encoding Erythropoietin. Mol Ther 20:948-953.
Kato et al. 2008. Length-dependent recognition of double-stranded ribonucleic acids by retinoic acid-inducible gene-I and melanoma differentiation-associated gene 5. J Exp. Med. 205: 1601-1610.
Katre et al., 1987. Chemical modification of recombinant interleukin 2 by polyethylene glycol increases its potency in the murine Meth A sarcoma model. PNAS 84:1487-91.
Kim et al., 2008. Generation of human induced pluripotent stem cells by dirct delivery of reprogramming proteins. Cell Stem Cell 4:472-476.
Kiyota et al. 2011. An Arabidopsis RNase III-like protein, AtRTL2, cleaves double-stranded RNA in vitro. J Plant Res. 124: 405-414.
Kormann et al. 2011. Expression of therapeutic proteins after delivery of chemically modified mRNA in mice. Nature Biotechnology 29:154-157.
Koski et al. 2004. Cutting Edge: Innate Immune System Discriminates between RNA Containing Bacterial versus Eukaryotic Structural Features that Prime for High-Level IL-12 Secretion by Dendritic Cells. J Immunol. 127:3989-3993.
Kowalska et al. 2008. Synthesis and characterization of mRNA cap analogs containing phosphorothioate substitutions that bind tightly to eIF4E and are resistant to the decapping pyrophosphatase DcpS. RNA 14: 1119-1131.
Kozak 1987. An analysis of 5'-noncoding sequences from 699 vertebrate messenger RNAs. Nucleic Acids Res. 15: 8125-8148.
Kreig and Melton. 1984. Functional messenger RNAs are produced by SP6 in vitro transcription of cloned cDNAs. Nucleic Acid Res 12:7057-7070.
Ladewig et al. 2012. Small molecules enable highly efficient neuronal conversion of human fibroblasts. Nat Methods 9:575-578.
Langer. 1990. New methods of drug delivery Science 249: 1527-1533.
Lee et al. 2003. The nuclear RNase III Drosha initiates microRNA processing. Nature 425: 415-419.
Lee et al. 2009. Modelling pathogenesis and treatment of familial dysautonomia using patient-specific iPSCs. Nature 461: 402-406.
Leonard et al. 2008. The TLR3 signaling complex forms by cooperative receptor dimerization. Proc Natl Acad Sci USA 105: 258-263.
Lewandowski et al. 1971. Separation of the infectious ribonucleic acid of potato spindle tuber virus from double-stranded ribonucleic acid of plant tissue extracts. J. Virol. 8: 809-812.
Li et al. 1993. Ribonuclease III cleavage of bacteriophage T7 processing signal. Divalent cation specificity, and specific anion effects. Nucleic Acids Res 21: 1919-1925.
Lobenberg et al. 1998. Improved body distribution of 14C-labelled AZT bound to nanoparticles in rats determined by radioluminography. J Drug Target 5:171.
Lopez-Berestien. 1989. Treatment of Systemic Fungal Infections with Liposomal-Amphotericin B, In Liposomes in the Therapy of Infectious Diseases and Cancer. Lopez-Erestein & Fidler eds. pp. 317-327.
Lukacs. 1994. Detection of virus infection in plants and differentiation between coexisting viruses by monoclonal antibodies to double-stranded RNA. J. Virol. Methods 47: 255-272.
Lukacs. 1997. Detection of sense: antisense duplexes by structure-specific anti-RNA antibodies. In: Antisense Technology. A Practical Approach, C. Lichtenstein and W. Nellen (eds), pp. 281-295. IRL Press, Oxford.
McAllister et al. 1993. The phage RNA polymerases are related to DNA polymerases and reverse transcriptases. Molecular Microbiology 10: 1-6.
McElwee et al, Transfer of CD8(+) cells induces localized hair loss whereas CD4(+)/CD25(−) cells promote systemic alopecia areata and CD4(+)/CD25(+) cells blockade disease onset in the C3H/HeJ mouse model. J Invest Dermatol 2005;124(5): 947-57.
McGlynn, et al, Differential subcellular localization of cholesterol, gangliosides, and glycosaminoglycans in murine models of mucopolysaccharide storage disorders. J Comp Neurol 2004 20;480(4): 415-26.
Mackie. 1988. Vectors for the synthesis of specific RNAs in vitro. Biotechnology 10: 253-267.
Maehr et al. 2009. Generation of pluripotent stem cells from patients with type 1 diabetes. Proc Natl Acad Sci U S A 106: 15768-15773.
Martin et al. 1975. Purification of mRNA guanylyltransferase and mRNA (guanine-7-) methyltransferase from vaccinia virions. J Biol Chem 250: 9322-9329.
Matsuda et al. 2000. Molecular cloning and characterization of a novel human gene HERNA which encodes a putative RNA-helicase. Biochim. Biophys. Acta. 1490: 163-169.

(56) References Cited

OTHER PUBLICATIONS

Mellits et al. 1990. Removal of double-stranded contaminants from RNA transcripts: synthesis of adenovirus VA RNA1 from a T7 vector. Nucleic Acids Research 18: 5401-5406.
Minskaia et al. 2006. Discovery of an RNA virus 3'->5' exoribonuclease that is critically involved in coronavirus RNA synthesis. Proc Natl Acad Sci USA. 103: 5108-5113.
Myette and Niles. 1996. Domain structure of the vaccinia virus mRNA capping enzyme. Expression in *Escherichia coli* of a subdomain possessing the RNA 5'-triphosphatase and guanylyltransferase activities and a kinetic comparison to the full-size enzyme. J Biol Chem 271: 11936-11944.
Nakagawa et al. 2008. Generation of induced pluripotent stem cells without Myc from mouse and human fibroblasts. Nat Biotechnol 26: 101-106.
Naz et al. 2002. Novel human prostate-specific cDNA: molecular cloning, expression, and immunobiology of the recombinant protein. Biochem Biophys Res Commun. 297:1075-84.
Nicholson. 1996. Structure, reactivity, and biology of double-stranded RNA. Progr Nucleic Acid Res Mol Biol 52: 1-65.
Nielsen PE. 1999. Peptide nucleic acids as therapeutic agents. Curr Opin Struct Biol 9:353-57.
Newmark et al. 1982. Preparation and Properties of Adducts of Streptokinase and Streptokinase-Plasmin Complex with Poly ethylene Glycol and Pluronic Polyol F38. J. Appl. Biochem. 4:185-189.
Okita et al. 2008. Generation of mouse induced pluripotent stem cells without viral vectors. Science 322: 949-953.
Ozawa et al. 2006. Amplification and analysis of cDNA generated from a single cell by 5'-RACE: application to isolation of antibody heavy and light chain variable gene sequences from single B cells. Biotechniques 40: 469-470, 472, 474 passim.
Pang et al. 2011. Induction of human neuronal cells by defined transcription factors. Nature 476: 220-223.
Passini et al, AAV vector-mediated correction of brain pathology in a mouse model of Niemann-Pick A disease. Mol Ther 2005;11(5): 754-62.
Pays. 1977. Characterization of Double-Stranded Ribonucleic Acid Sequences Present in the Intial Transcription Products of Rat Liver Chromatin. Biochem. J. 165:237-245.
Pe'ery et al. 1997. Synthesis and Purification of Single-=Stranded RNA for Use in Experiments with PKR and in Cell-Free Translation Systems. Methods: A companion to Methods in Enzymology, Academic Press Inc., New York, 11(4):371-381.
Peng et al. 2002. Synthesis and application of a chain-terminating dinucleotide mRNA cap analog. Org Lett 4: 161-164.
Petit et al. "G-CSF Induces Stem Cell Mobilization by Decreasing Bone Marrow SDF-1 and Up-Regulating CXCR4," Nature Immunol., 2002, 3: 687-694.
Pichlmair et al. 2006. RIG-I-mediated antiviral responses to single-stranded RNA bearing 5'-triphosphates. Science 314: 997-1001.
Plews et al. 2010. Activation of pluripotency genes in human fibroblast cells by a novel mRNA based approach, PLoS One 5(12):e14397, 12 pages.
Pradilla et al. 2004. Prevention of vasospasm following subarachnoid hemorrage in rabbits by anti-CD11/CD18 monoclonal antibody therapy. J Neurosurg. 101:88-92.
Probst et al. 2006. Characterization of the ribonuclease activity on the skin surface. Genet Vaccines Ther. 4: 4, 9 pages.
Purchio et al. Methods in Enzymology: Methods for molecular cloning in eukaryotic cells (2003).
Qi et al. 2010. Cap binding and immune evasion revealed by Lassa nucleoprotein structure. Nature 468: 779-783.
Racila et al. 2010. Transient expression of OCT 4 IS sufficient to allow human keratinocytes to change their differentiation pathway. Gene Therapy 18:294-303.
Robertson et al. 1968. Purification and Properties of Ribonuclease III from *Escherichia coli*. J Biol Chem 243:82-91.
Robertson et al. 1975. Sensitive methods for detection and characterization of double helical ribonucleic acid. J Biol Chem 250: 418-425.
Robertson. 1982. *Escherichia coli* Ribonuclease III Cleavage Sites. Cell 30:669-672.
Robertson et al. 1996. Paradoxical interactions between human delta hepatitis agent RNA and the cellular protein kinase PKR. Journal of Virology 70(8):5611-5617.
Rosa & Brivanlou. 2010. Synthetic mRNAs: Powerful Tools for Reprogramming and Differentiation of Human Cells. Cell Stem Cell 7:549-550.
Saito et al. 2008. Innate immunity induced by composition-dependent RIG-I recognition of hepatitis C virus RNA. Nature 454: 523-527.
Sakuma et al. 1999. Mucoadhesion of polystyrene nanoparticles having surface hydrophilic polymeric chains in the gastrointestinal tract. Int J Pharm 177:161-72.
Sambrook and Russell, eds., Molecular Cloning, (2001) Only TOC Provided. Will provide specific pages upon Examiner Request.
Santini et al., 2000. Type I interferon as a powerful adjuvant for monocyte-derived dendritic cell development and activity in vitro and in Hu-PBL-SCID mice. J Exp Med 191: 1777-178.
Satoh et al, X-linked immunodeficient mice spontaneously produce lupus-related anti¬20 RNA helicase A autoantibodies, but are resistant to pristane-induced lupus. Int Immunol 2003, 15(9):1117-24.
Schlee et al. 2009. Approaching the RNA ligand for RIG-I. Immunol Rev 227: 66-74.
Scholte, et al.(Animal models of cystic fibrosis. J Cyst Fibros 2004; 3 Suppl2: 183-90.
Schonborn et al. 1991. Monoclonal antibodies to double-stranded RNA as probes of RNA structure in crude nucleic acid extracts. Nucleic Acids Res. 19: 2993-3000.
Shuman et al. 1980. Purification and characterization of a GTP-pyrophosphate exchange activity from vaccinia virions. Association of the GTP-pyrophosphate exchange activity with vaccinia mRNA guanylyltransferase. RNA (guanine-7-)methyltransferase complex (capping enzyme). J Biol Chem 255: 11588-11598.
Shuman. 1995. Capping enzyme in eukaryotic mRNA synthesis. Prog Nucleic Acid Res Mol Biol 50: 101-129.
Shuman. 2001. Structure, mechanism, and evolution of the mRNA capping apparatus. Prog Nucleic Acid Res Mol Biol 66: 1-40.
Simonaro et al, Joint and bone disease in mucopolysaccharidoses VI and VII: identification of new therapeutic targets and biomarkers using animal models. Pediatr Res 2005;57(5 Pt 1): 701-7.
Sousa et al. 2000. Use of T7 RNA Polymerase and Its Mutants for Incorporation of Nucleoside Analogs into RNA. Methods in Enzymology. 317:65-74.
Stadtfeld et al. 2008. Induced pluripotent stem cells generated without viral integration. Science 322: 945-949.
Stark et al. 1998. How cells respond to interferons. Annu Rev Biochem. 67:227-64.
Stepinski et al. 2001. Synthesis and properties of mRNAs containing the novel "anti-reverse" cap analogs 7-methyl(3'-O-methyl)GpppG and 7-methyl (3'-deoxy)GpppG. RNA 7: 1486-1495.
Stewart et al. 1972. Increased susceptibility of cells treated with interferon to the toxicity of polyriboinosinic: polyribocytidylic acid. Proc Nat Acad Sci USA 69: 1851-1854.
Studier et al. 1986. Use of bacteriophage T7 RNA polymerase to direct selective high-level expression of cloned genes. J Mol Biol 189: 113-130.
Sul et al. 2012. Perspectives on cell reprogramming with RNA. Cell 30: 243-249.
Sun et al. 2005. Catalytic mechanism of *Escherichia coli* ribonuclease III: kinetic and inhibitor evidence for the involvement of two magnesium ions in RNA phosphodiester hydrolysis. Nucleic Acid Res. 33(3):807-15.
Szabo et al. 2010. Direct conversion of human fibroblasts to multilineage blood progenitors. Nature. 468: 521-526.
Takahashi and Yamanaka. 2006. Induction of pluripotent stem cells from mouse embryonic and adult fibroblast cultures by defined factors. Cell 126: 663-676.
Takahashi et al. 2007. Induction of pluripotent stem cells from adult human fibroblasts by defined factors. Cell 131: 861-872.

(56) References Cited

OTHER PUBLICATIONS

Tanaka et al. 2005. Inhibition of heart transplant injury and graft coronary artery disease after prolonged organ ischemia by selective protein kinase C regulators. J Thorac Cardiovasc Surg 129(5): 1160-7.
Tavernier et al. 2012. Activation of pluripotency-associated genes in mouse embryonic fibroblasts by non-viral transfection with in vitro-derived mRNAs encoding Oct4, Sox2, Klf4 and cMyc. Biomaterials 33:412-417.
Treat et al., in Liposomes in the Therapy of Infectious Disease and Cancer, Lopez-Berestein and Fidler (eds.), Liss, New York, pp. 353-365 (1989).
Triana-Alonso et al. 1995. Self-coded 3'-extension of run-off transcripts produces aberrant products during in vitro transcription with T7 RNA polymerase. J Biol Chem 270: 6298-6307.
Uzri et al. 2009. Nucleotide sequences and modifications that determine RIG-I/RNA binding and signaling activities. J. Virol. 83: 4174-4184.
Vierbuchen T et al. 2010. Direct conversion of fibroblasts to functional neurons by defined factors. Nature 463: 1035-1041.
Virovic et al. 2005. Novel delivery methods for treatment of viral hepatitis: an update. Expert Opin Drug Deliv 2:707-17.
Wan et al. 2010. Hotair: Flight of noncoding RNA in genome regulation: Prospects and mechanisms. Cell Cycle 9: 3391-3392.
Wang et al. 1997. Phylogeny of mRNA capping enzymes. Proc Natl Acad Sci U S A 94: 9573-9578.
Wang et al. 2011. Phosphorylation regulates c-Myc's oncogenic activity in the mammary gland. Cancer Res. 71: 925-936.
Warren et al. 2010. Highly Efficient Reprogramming to Pluripotency and Directed Differentiation of Human Cells with Synthetic Modified mRNA. Cell Stem Cell 7:618-630.
Wasylishen et al. 2011. New model systems provide insights into Myc-induced transformation. Oncogene. 30: 3727-3734.
Weissman et al, 2000. HIV Gag mRNA Transfection of Dendritic Cells (DC) Delivers Encoded Antigen to MHC Class I and II Molecules, Causes DC Maturation, and Induces a Potent Human In Vitro Primary Immune Response. J Immunol 165:4710-4717.
Wernig et al. 2002. Tau EGFP embryonic stem cells: an efficient tool for neuronal lineage selection and transplantation. J. Neurosci. Res. 69: 918-924.
Wianny et al. 2000. Specific interference with gene function by double-stranded RNA in early mouse development. Nat. Cell Biol. 2: 70-75.
Wilusz. 1988. A 64 kd nuclear protein binds to RNA segments that include the AAUAAA polyadenylation motif. Cell 52: 221-228.
Woltjen et al. 2009. piggyBac transposition reprograms fibroblasts to induced pluripotent stem cells. Nature 458: 766-770.
Woo et al. 2007. Hotair lifts noncoding RNAs to new levels. Cell 129: 1257-1259.
Wu et al. 2000. Human RNase III is a 160-kDa protein involved in preribosomal RNA processing [In Process Citation]. J. Biol. Chem. 275: 36957-65.
Xu et al. 2001. Feeder-free growth of undifferentiated human embryonic stem cells. Nat Biotechnol 19: 971-974.
Yakubov et al. 2010. Reprogramming of human fibroblasts to pluripotent stem cells using mRNA of four transcription factors. Biochemical and Biophysical Research Communications 394:189-193.
Yang et al. 2001. Specific double-stranded RNA interference in undifferentiated mouse embryonic stem cells. Mol Cell Biol 21: 7807-7816.
Yang et al. 2002. Short RNA duplexes produced by hydrolysis with *Escherichia coli* Rnase III mediate effective RNA interference in mammalian cells. PNAS. 99:9942-9947.
Yang et al. 2011. Induced neuronal cells: how to make and define a neuron. Cell Stem Cell 9: 517-525.
Yu et al, Sustained correction of B-cell development and function in a murine model of X-linked agammaglobulinemia (XLA) using retroviral-mediated gene transfer. Blood. 2004 104(5): 1281-90.
Yu et al. 2007. Induced pluripotent stem cell lines derived from human somatic cells. Science 318: 1917-1920.
Yu et al. 2009. Human induced pluripotent stem cells free of vector and transgene sequences. Science 324: 797-801.
Zelcer et al. 1981. The detection and characterization of viral-related double-stranded RNAs in tobacco mosaic virus-infected plants, Virology, 113(2):417-27.
Zelcer et al. 1982. Potato Spindle Tuber Viroid-infected Tissues Contain RNA Complementary to the Entire Viroid. J. Gen. Virol. 59: 139-148.
Zhou et al. 2009. Generation of induced pluripotent stem cells using recombinant proteins. Cell Stem Cell 4: 381-384.
Zimmerman et al. 2001. Electrolyte-and pH-stabilities of aqueous solid lipid nanoparticle (SLN) dispersions in artificial gastrointestinal media. Eur J Pharm Biopharm 52:203.
Zonta et al., Uretero-neocystostomy in a swine model of kidney transplantation: a new technique. J Surg Res. Apr. 2005; 124(2):250-5.
Zust et al. 2011. Ribose 2'-O-methylation provides a molecular signature for the distinction of self and non-self mRNA dependent on the RNA sensor Mda5. Nature Immunol. 12: 137-143.
Extended European Search Report for EP 10836557.8, mailed May 13, 2014, 12 pages.
International Search Report and Written Opinion for PCT/US2010/059317, mailed Aug. 22, 2011, 13 pages.
International Search Report and Written Opinion for PCT/US2010/059305, mailed Aug. 23, 2011, 12 pages.
International Search Report and Written Opinion for PCT/US2012/072301, mailed May 14, 2013, 33 pages.

\* cited by examiner

FIG. 12
A.
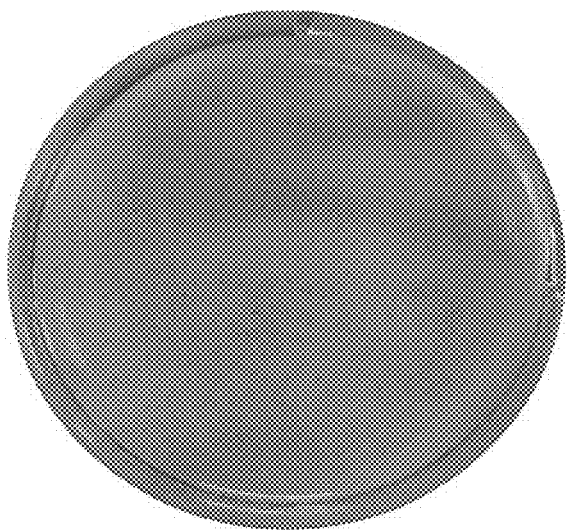
B.
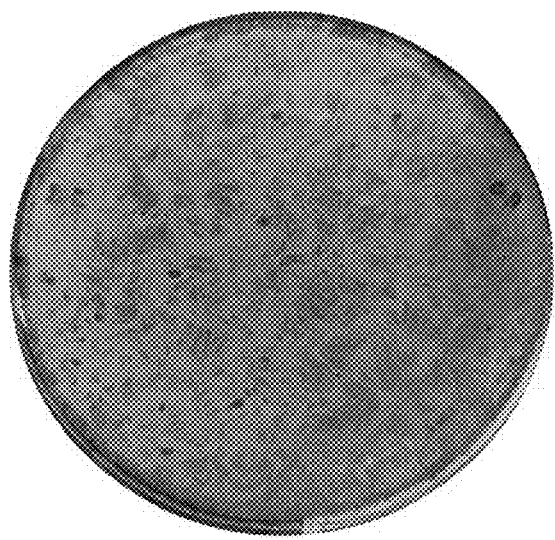
C.
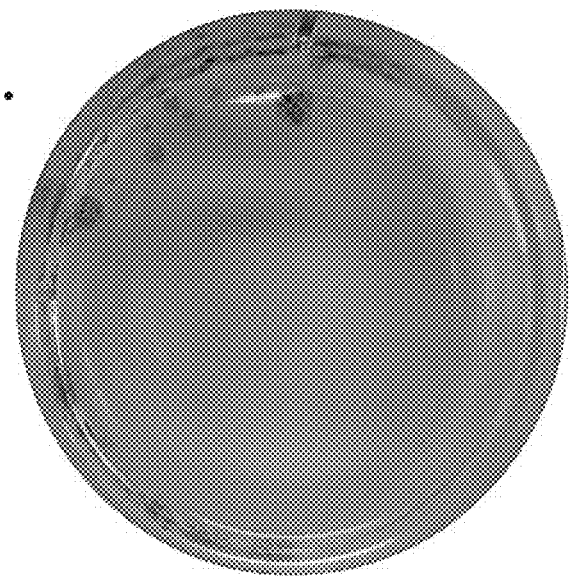

FIG. 15
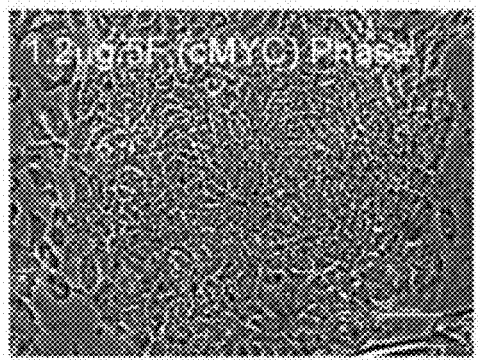
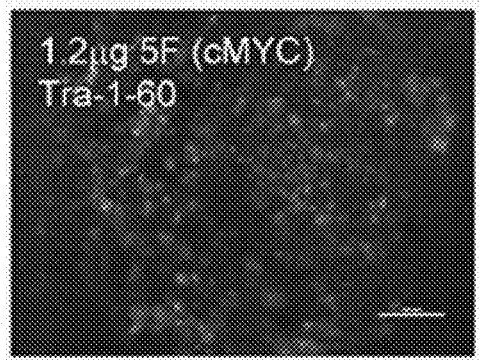
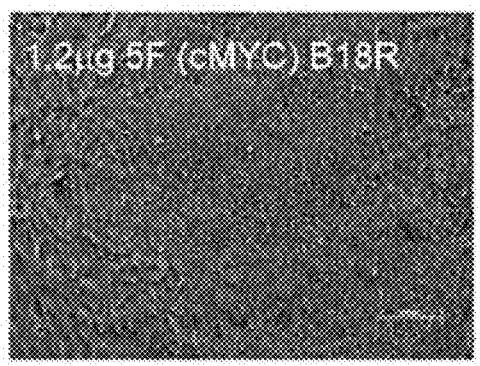
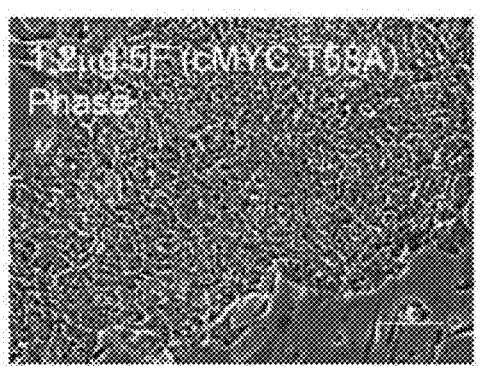
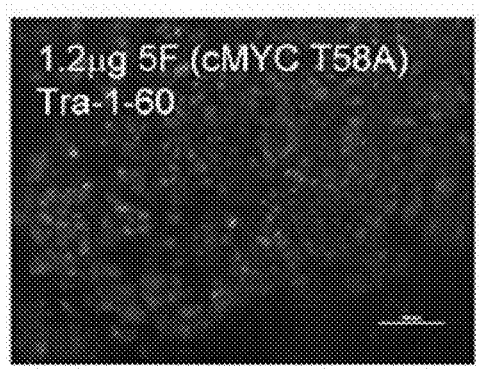
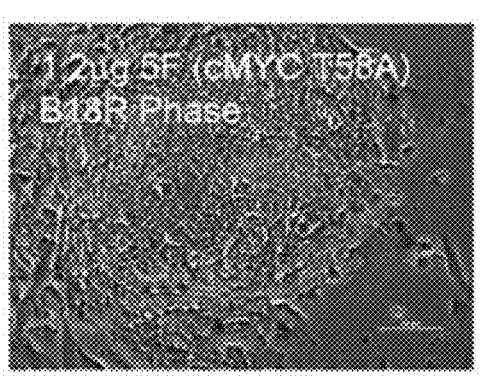

FIG. 21A
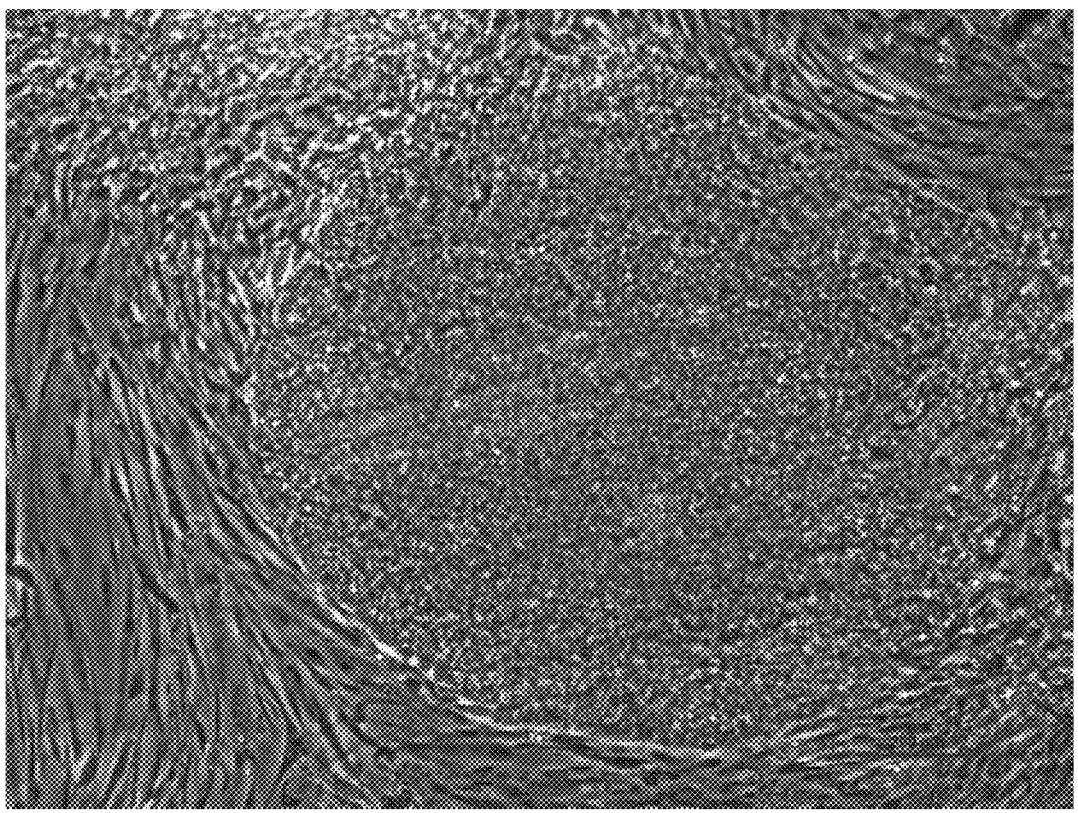
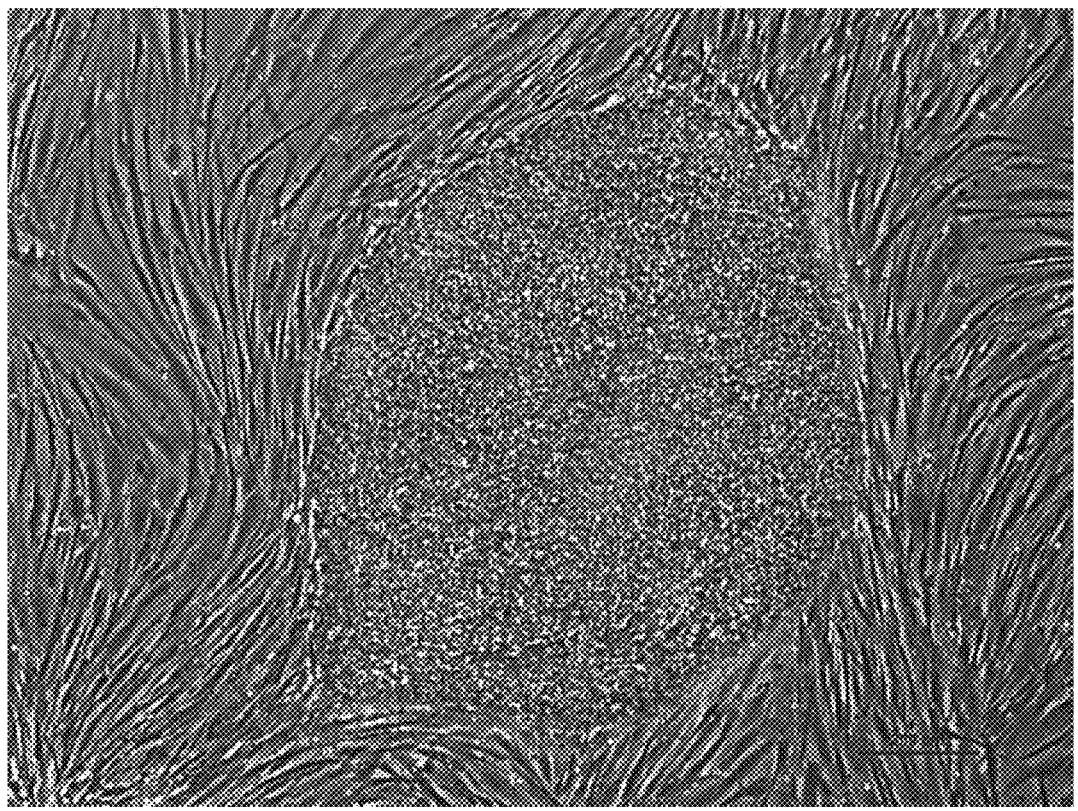

FIG. 24
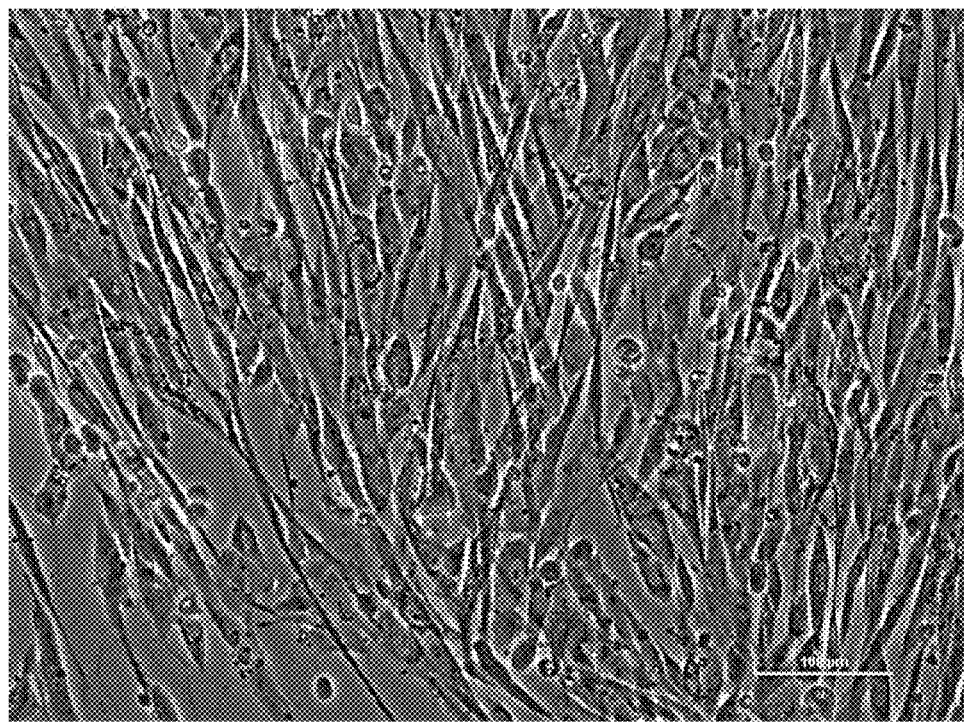
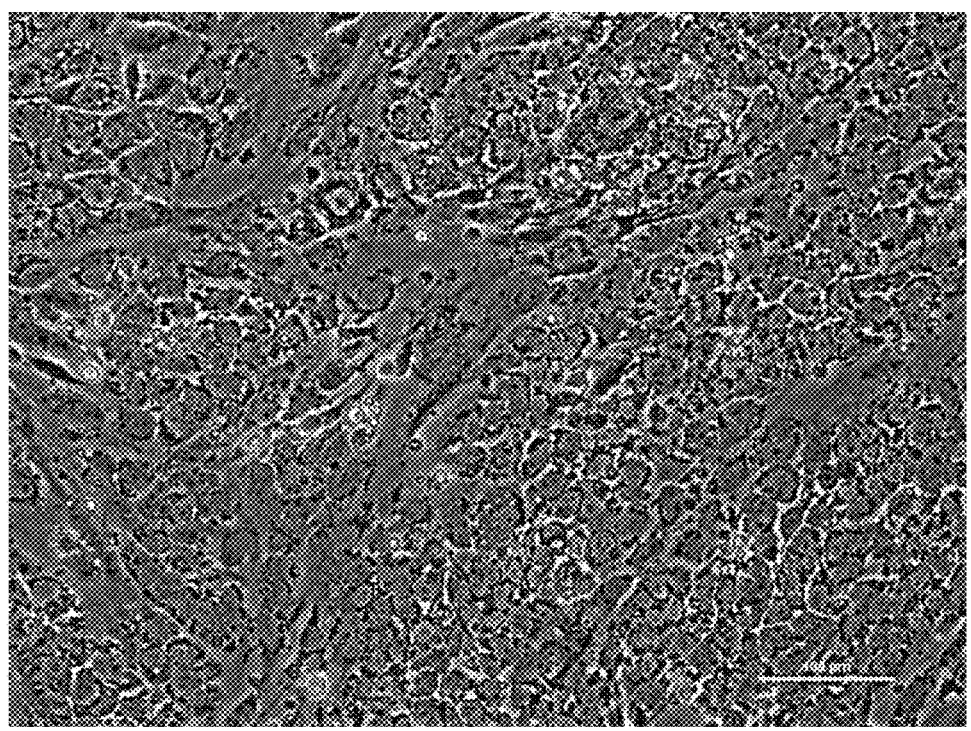

FIG. 25
A. 10X magnification    4X magnification
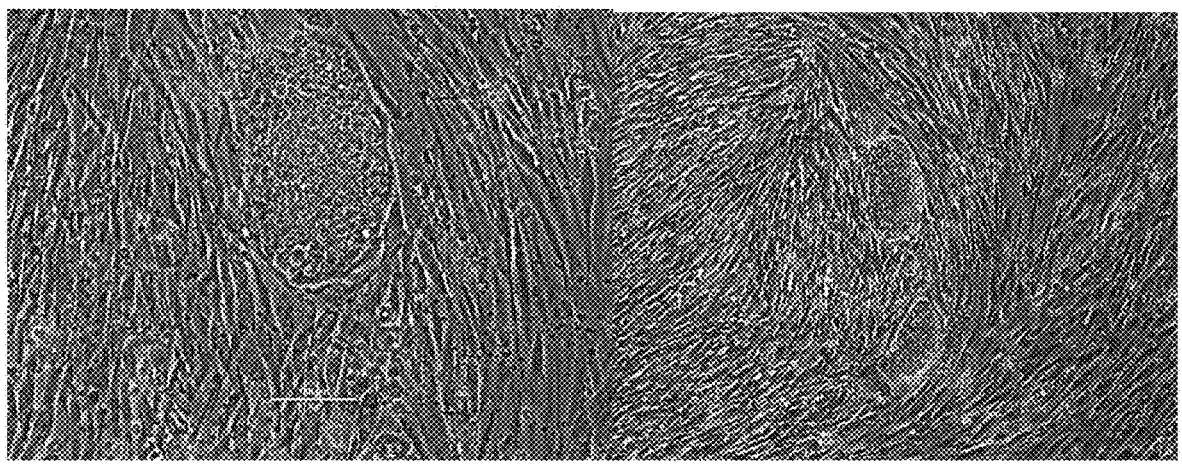
B. 10X magnification    4X magnification
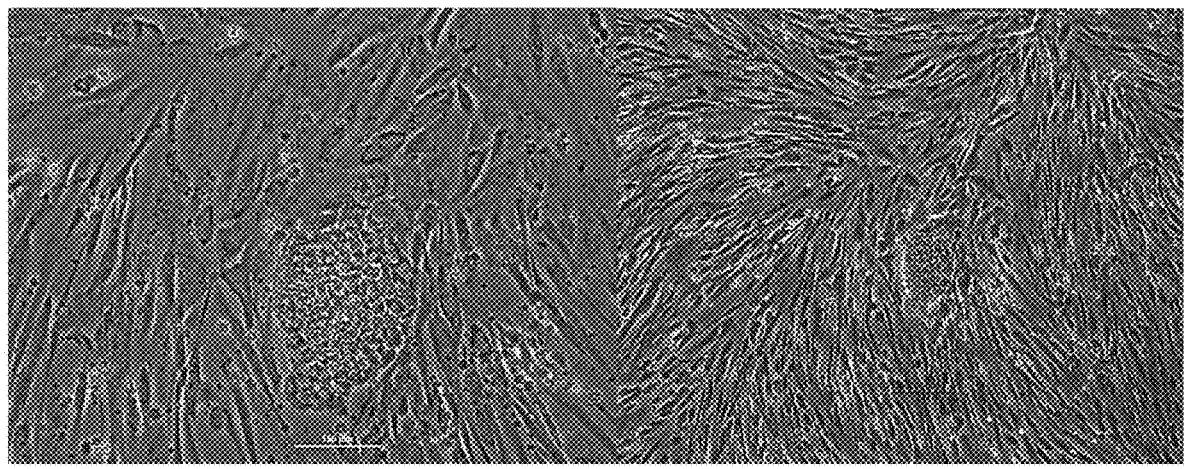

FIG. 26A
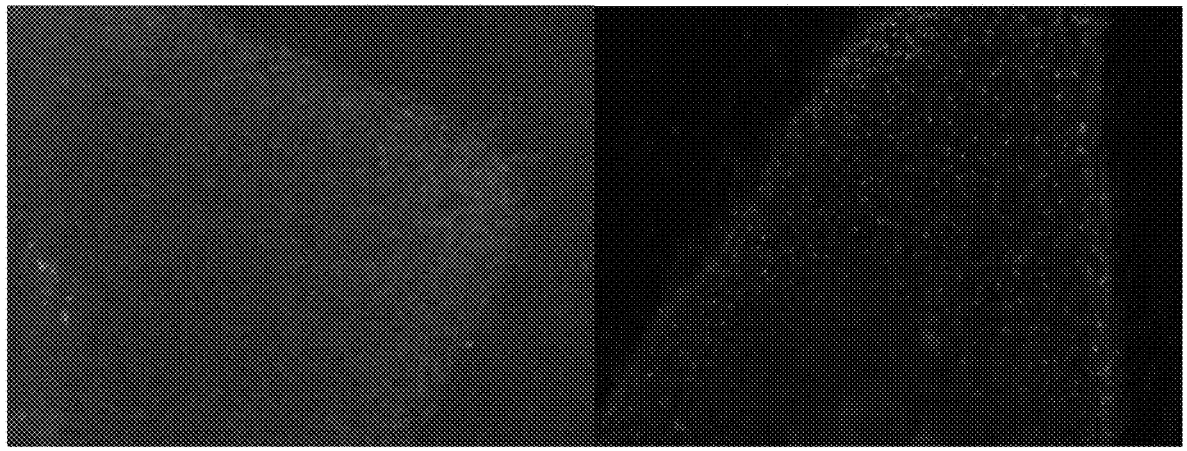
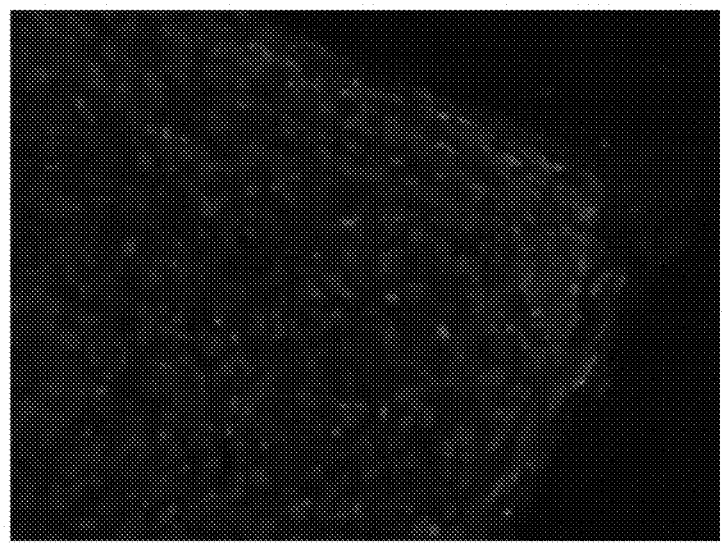

FIG. 26B
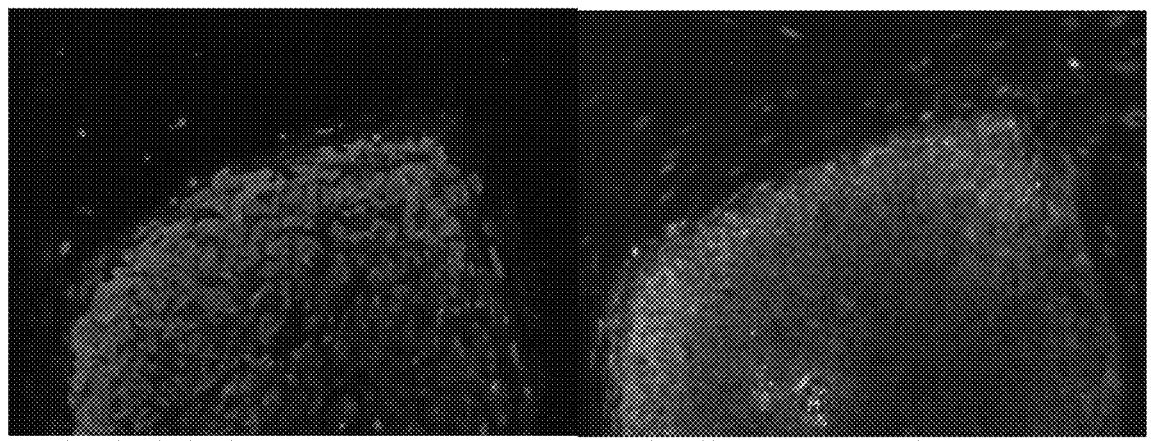
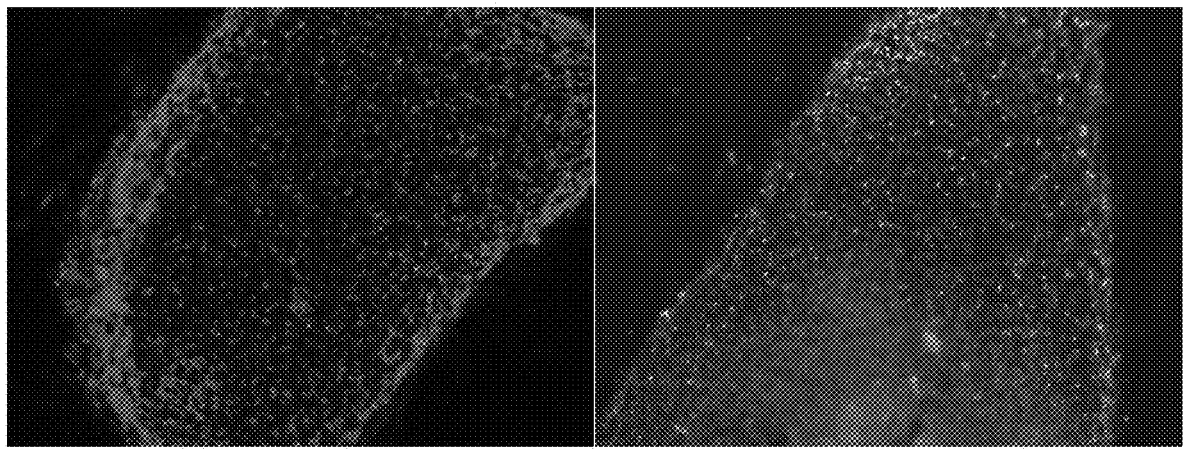

FIG. 29A
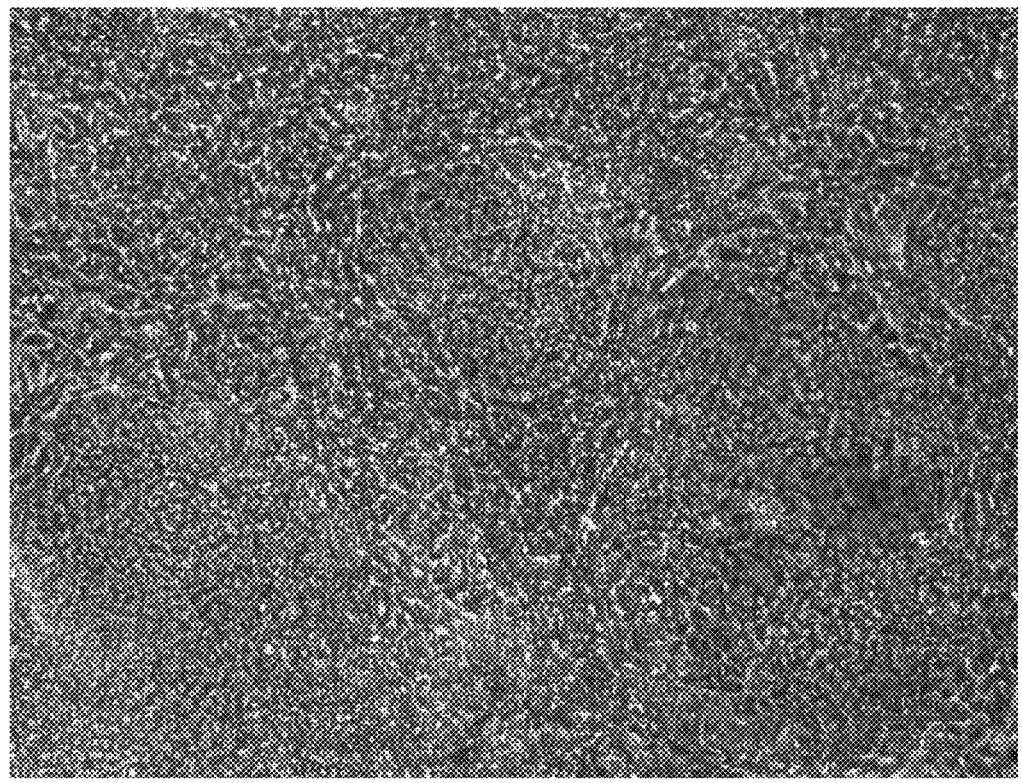
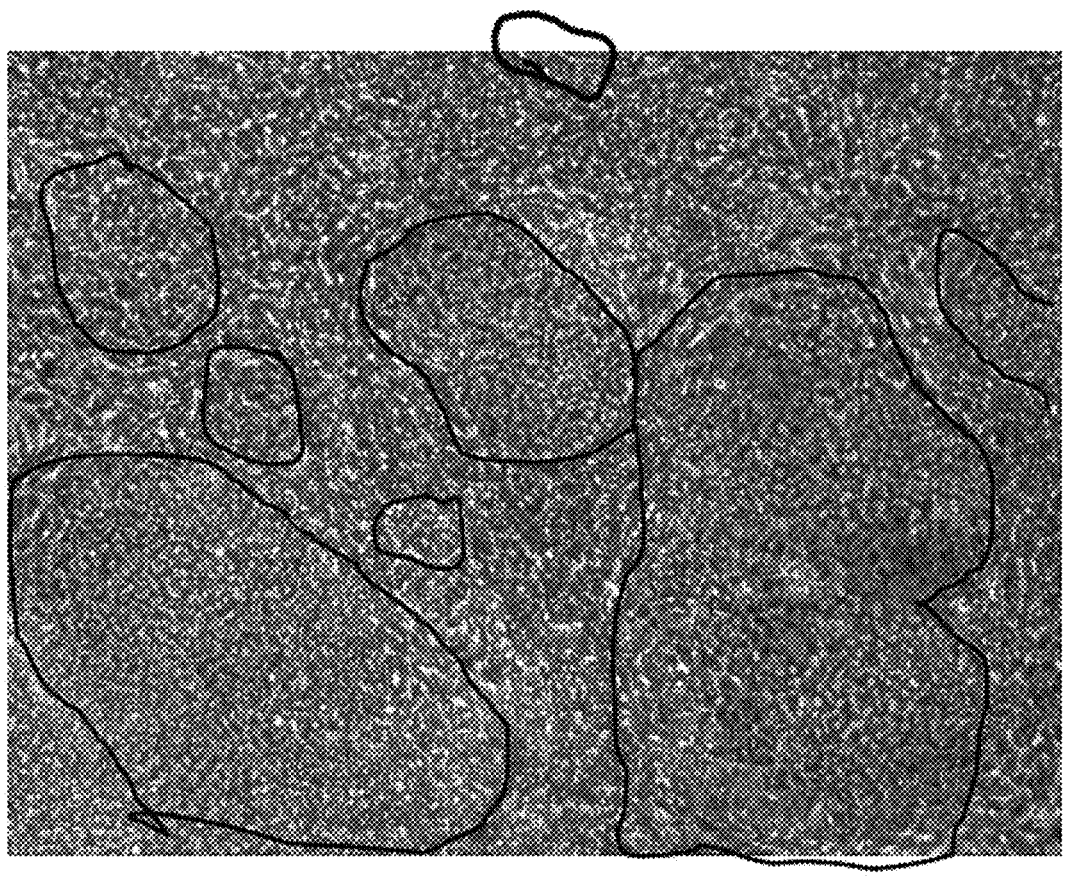

FIG. 29B
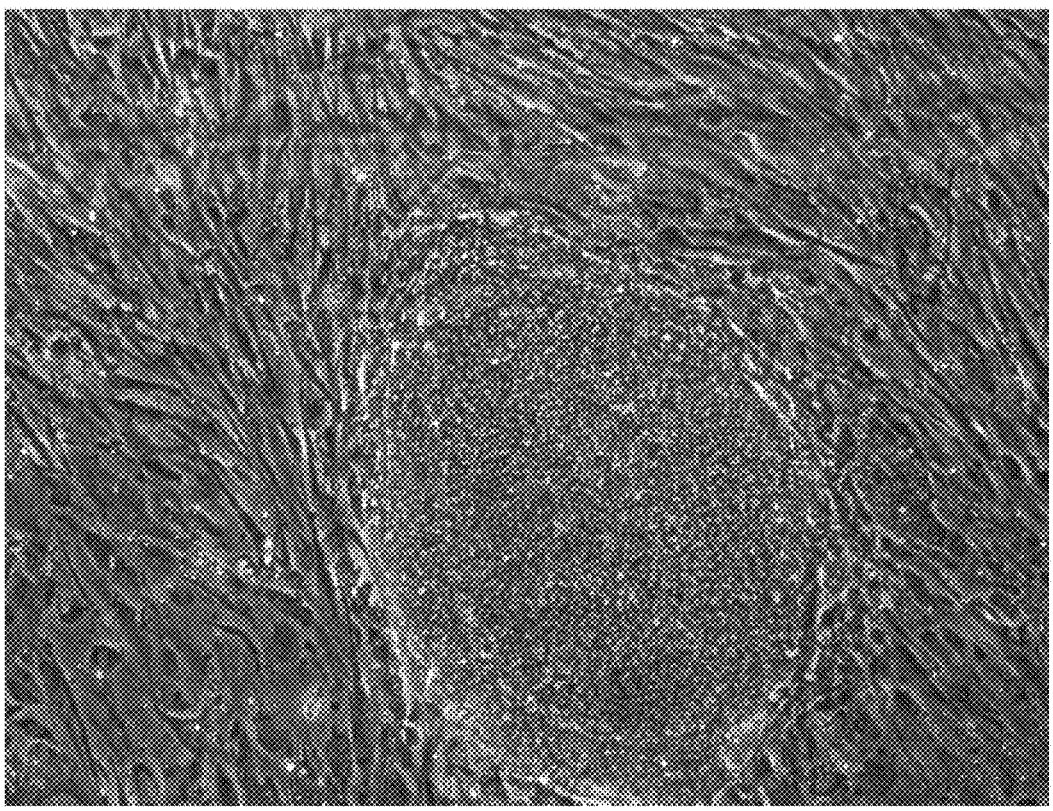

FIG. 31
A.
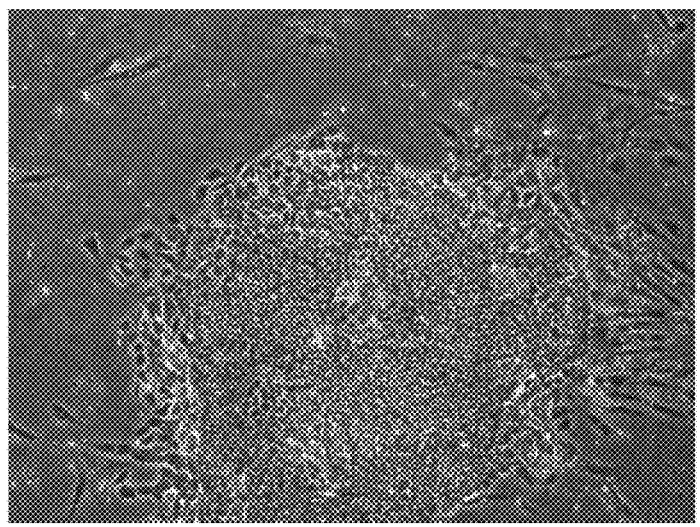
B.
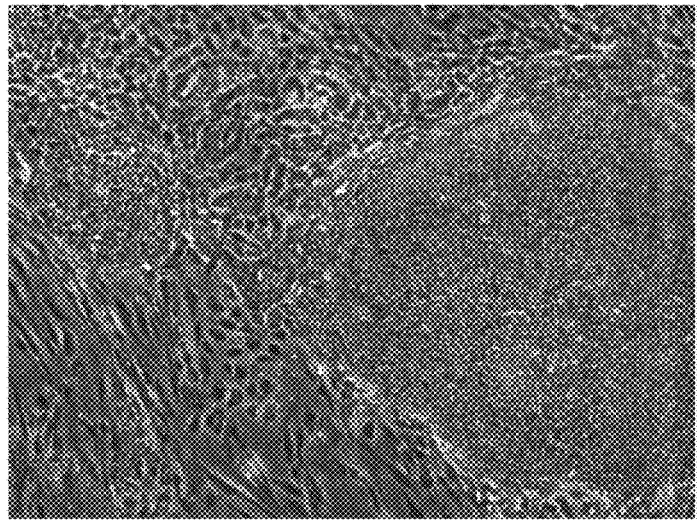
C.
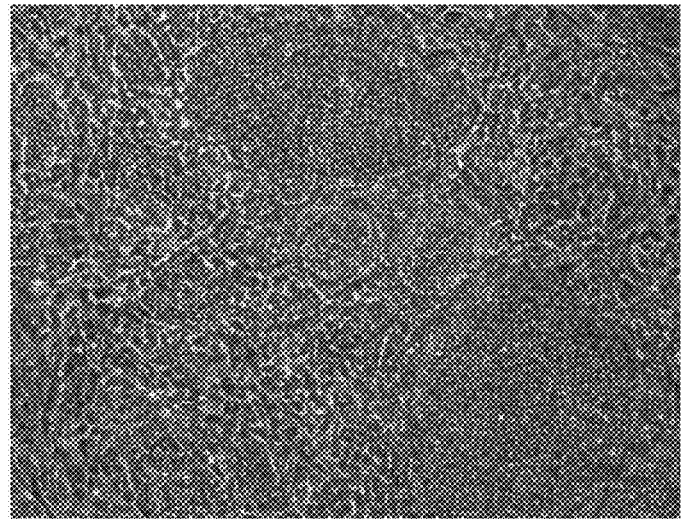

FIG. 32A
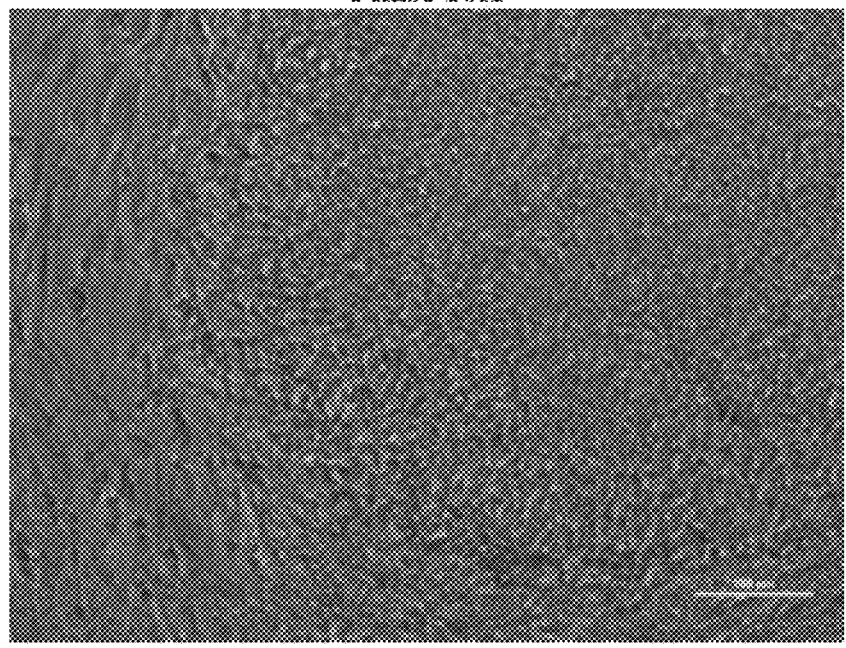
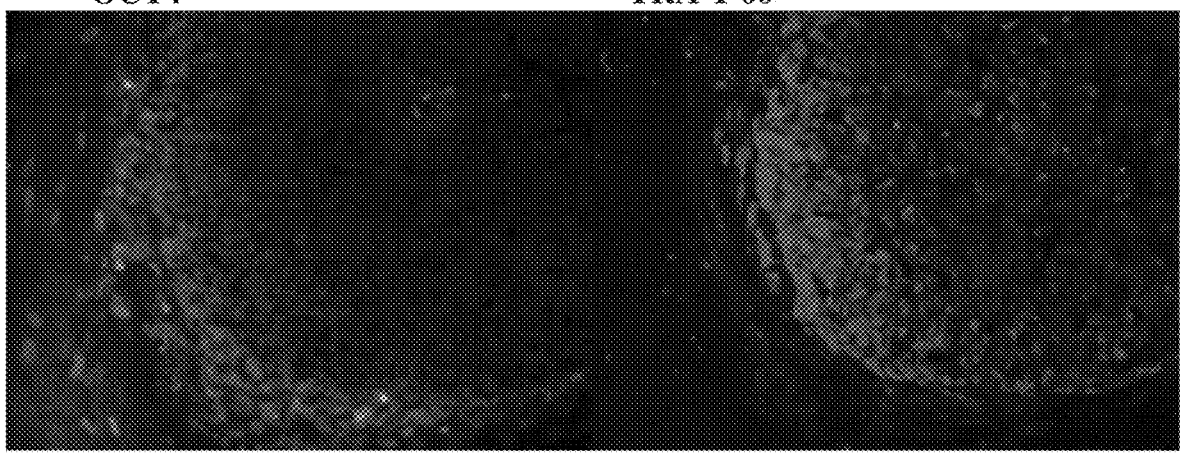

FIG. 32B
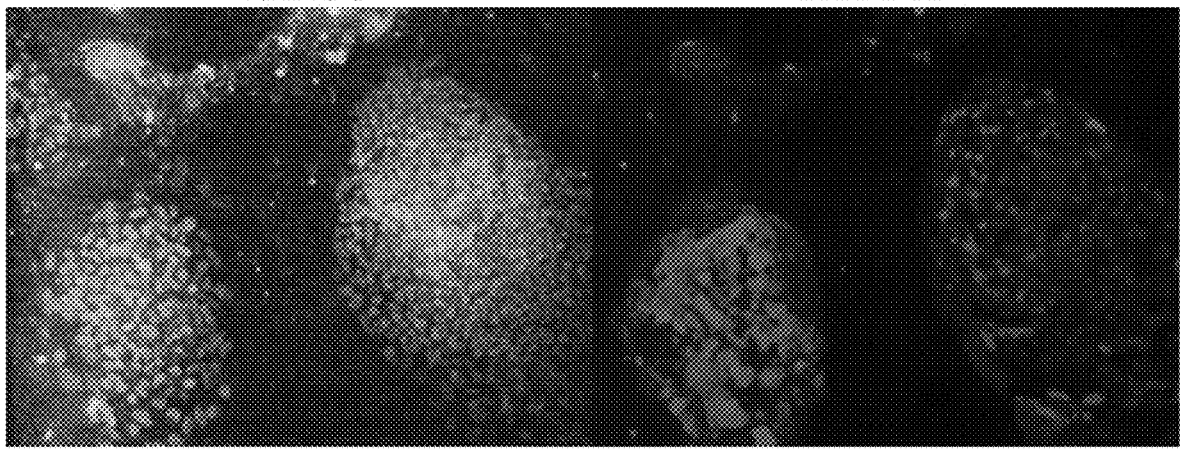
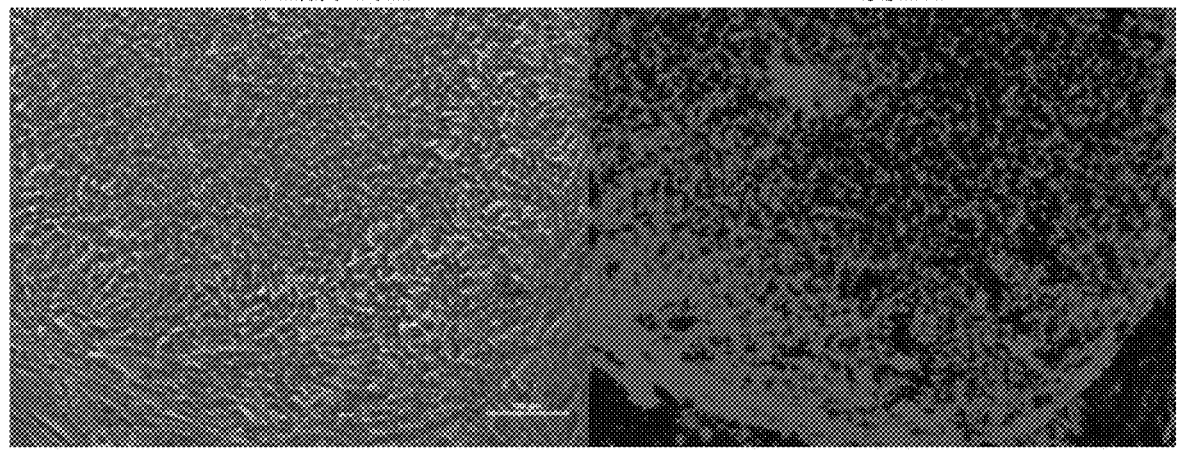

4X magnification 4X magnification

FIG. 40
A.      5 Factor Pseudouridine RIII KLMO3S Colonies
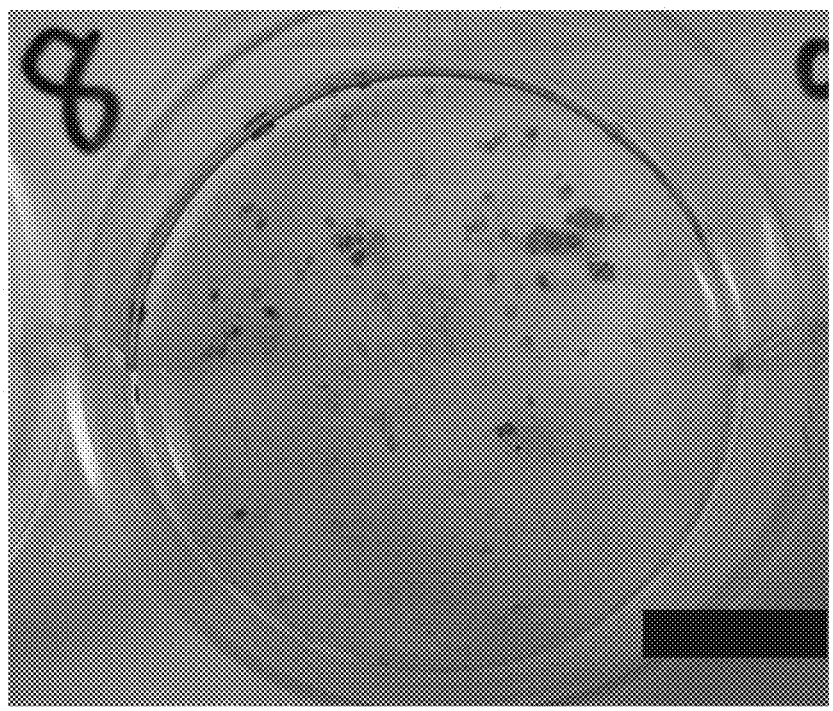
B.      5 Factor Pseudouridine RIII K3LMO3S Colonies
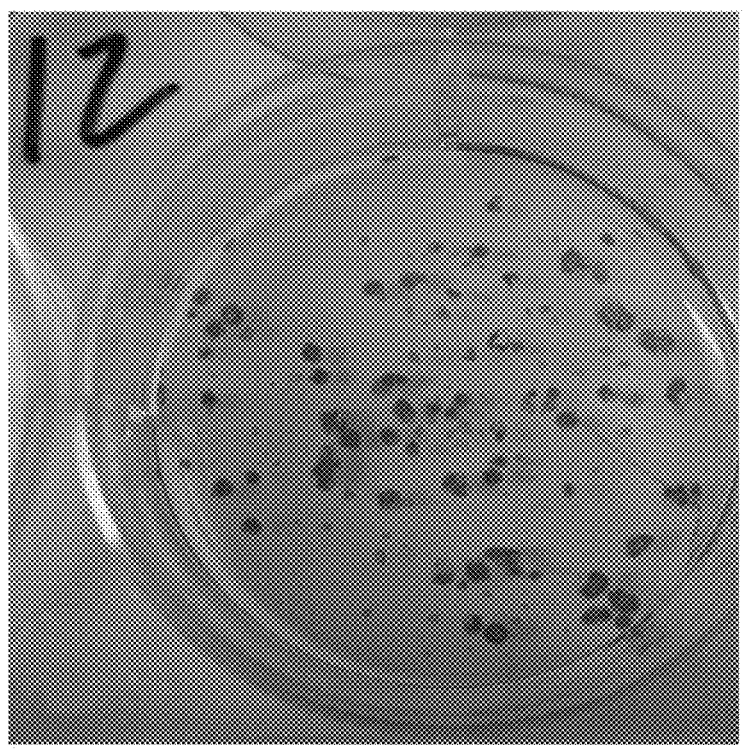

FIG. 43
A.
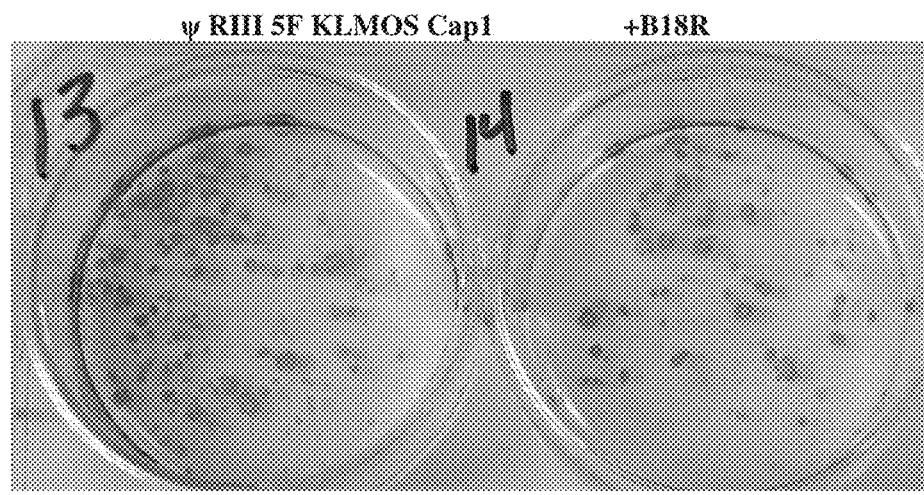
B.
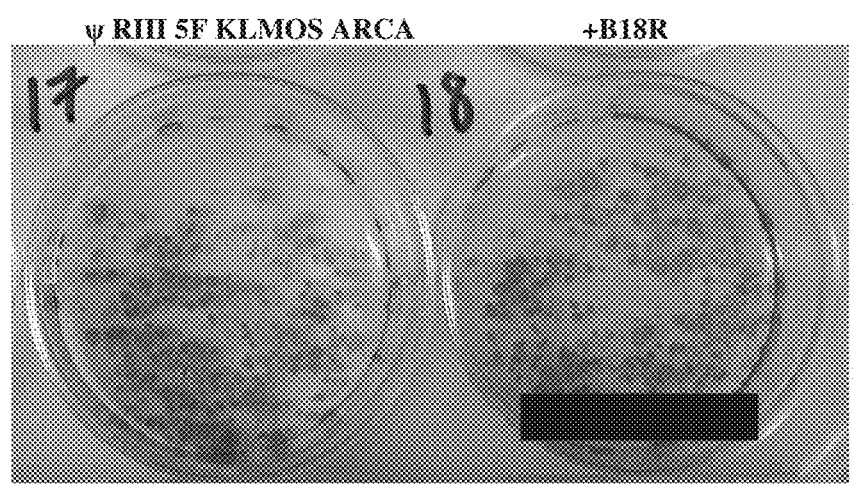
C.
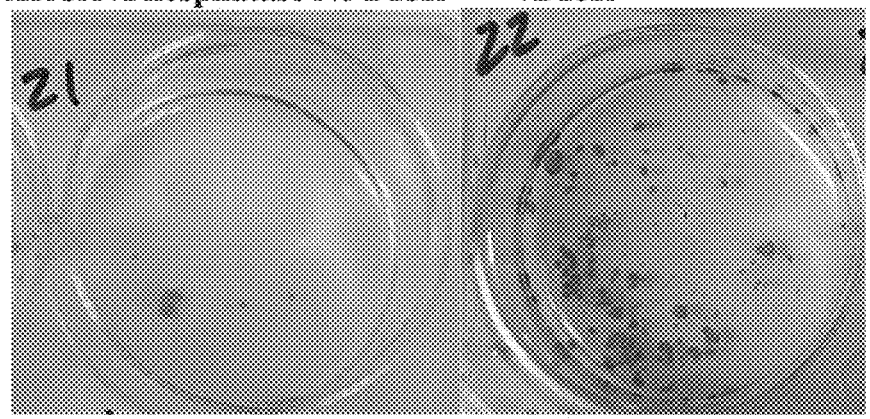

FIG. 44A
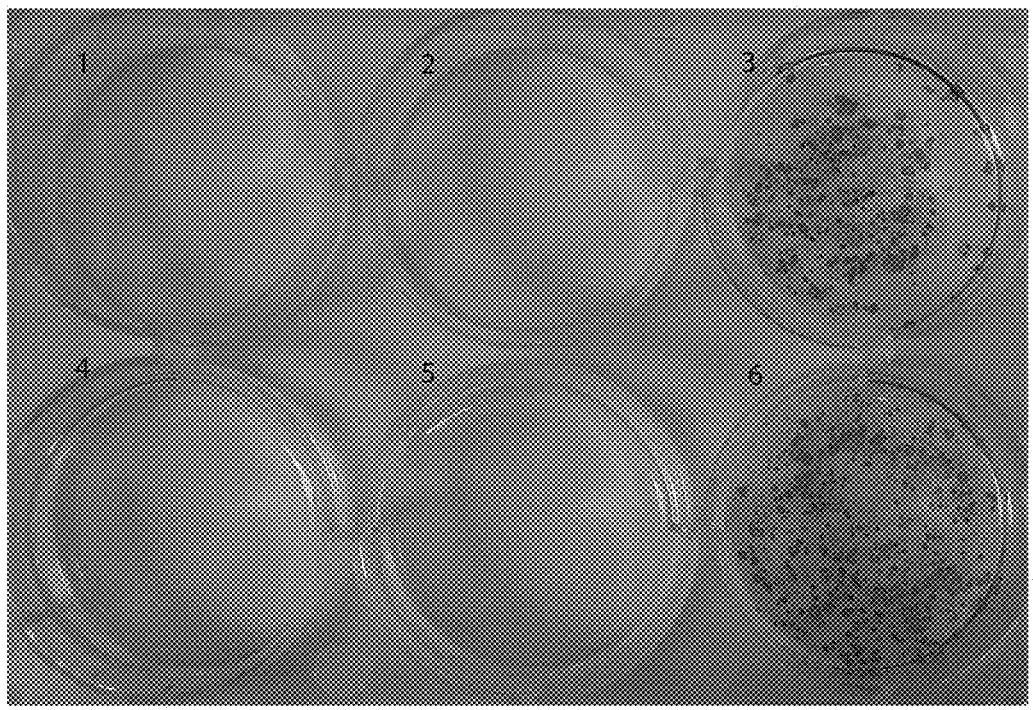
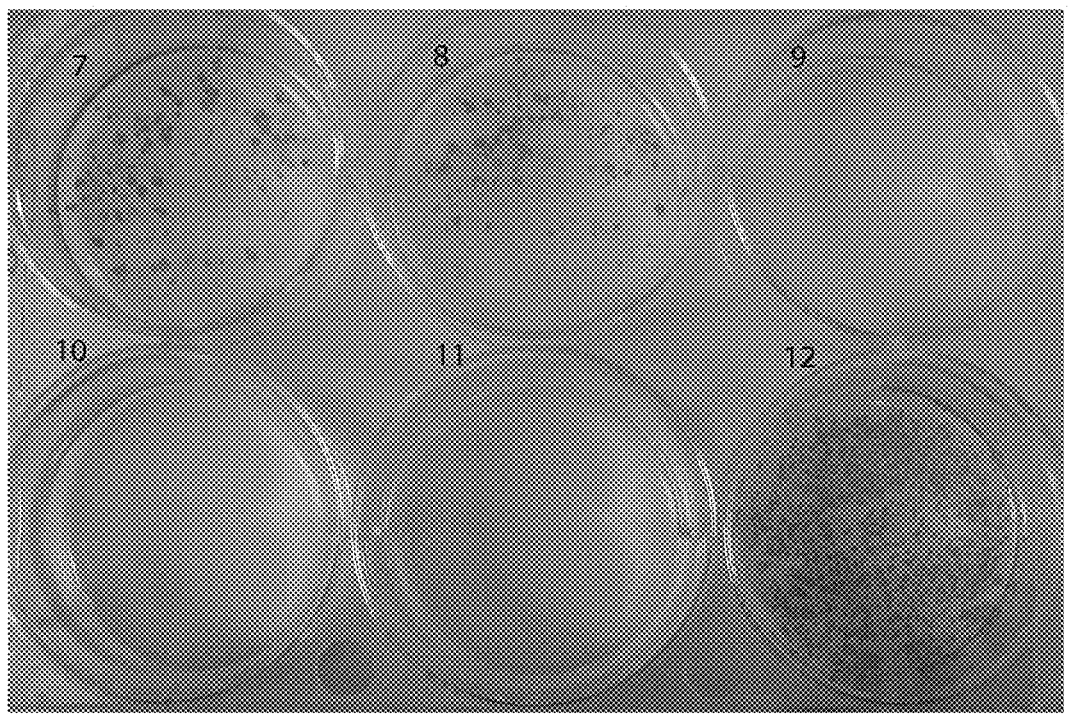
FIG. 44B

FIG. 44C
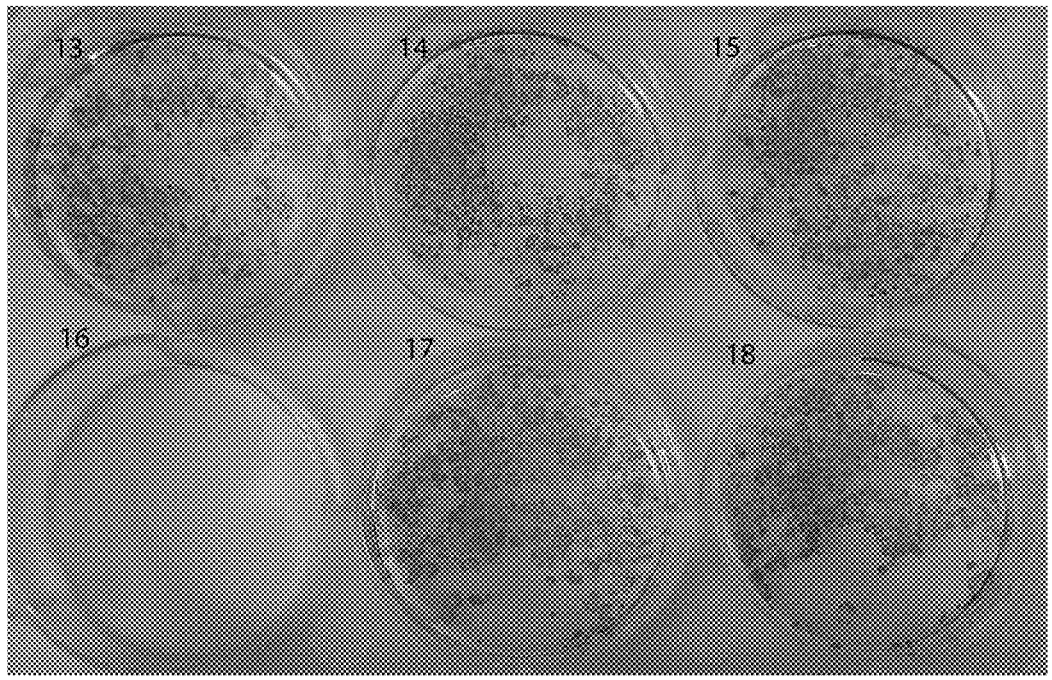
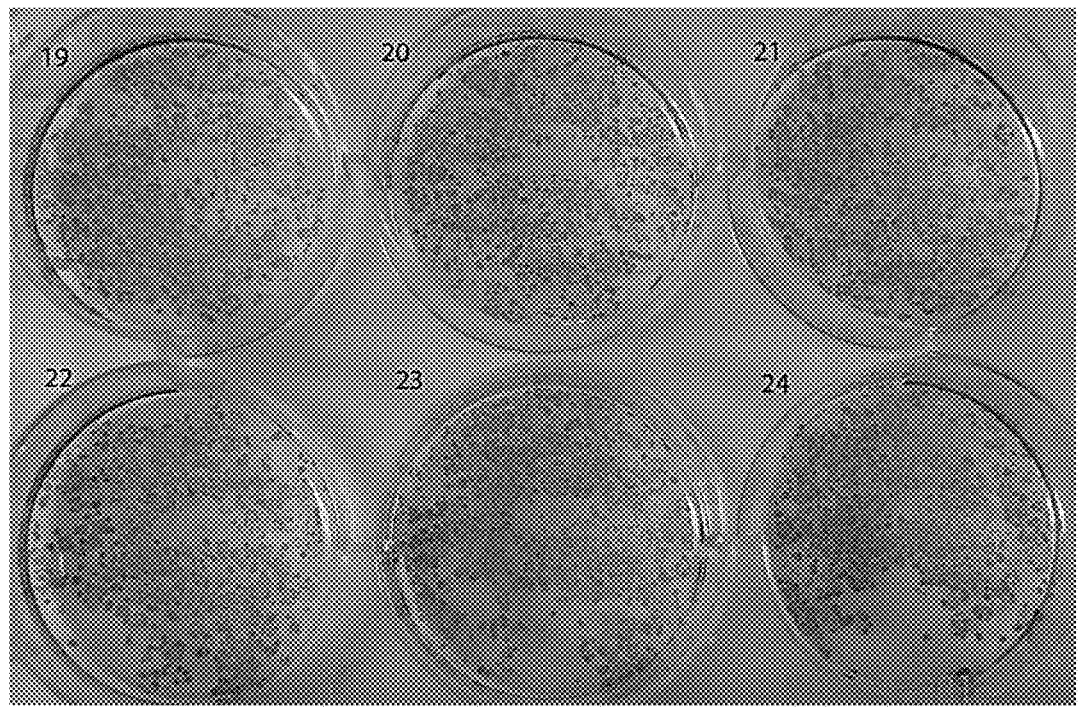
FIG. 44D

FIG. 45A
Class III Beta Tubulin (Neurons) 10X
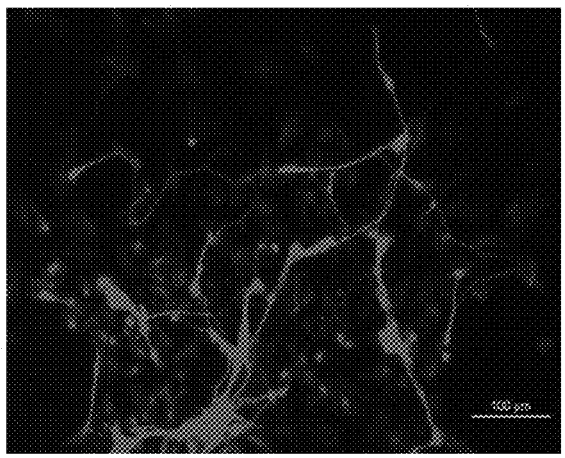
Phase 10X
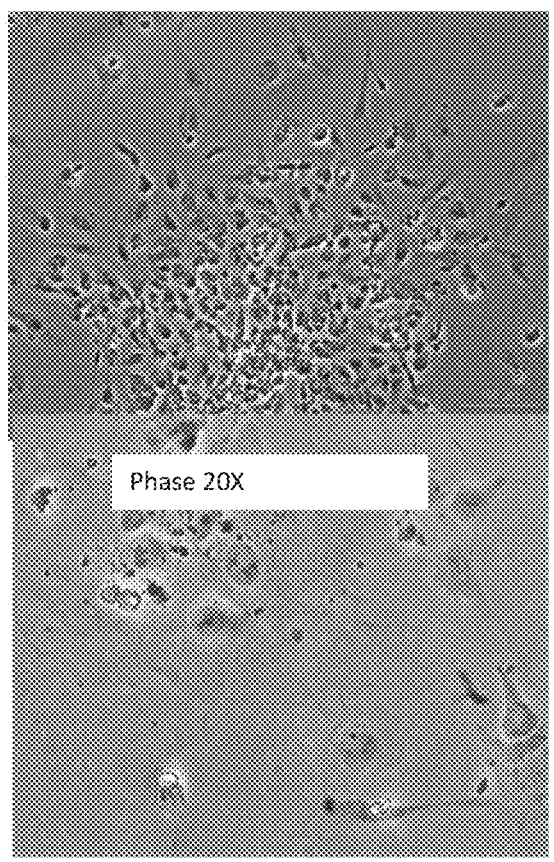
Sox17 20X
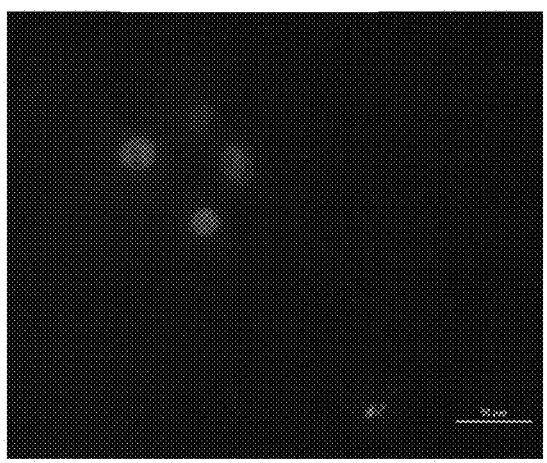
Phase 20X
Cardiac TroponinT (Cardiomyocytes) 20X
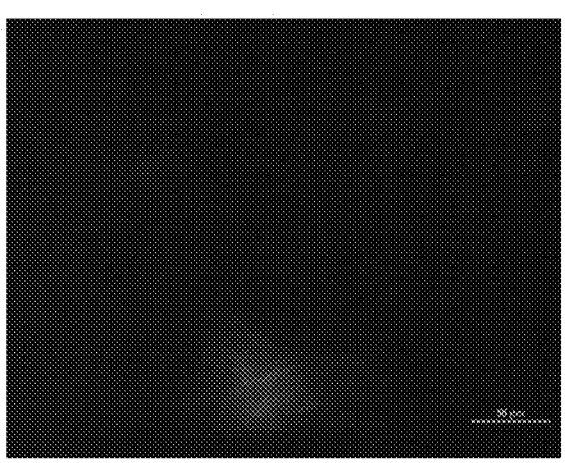
Phase 20X
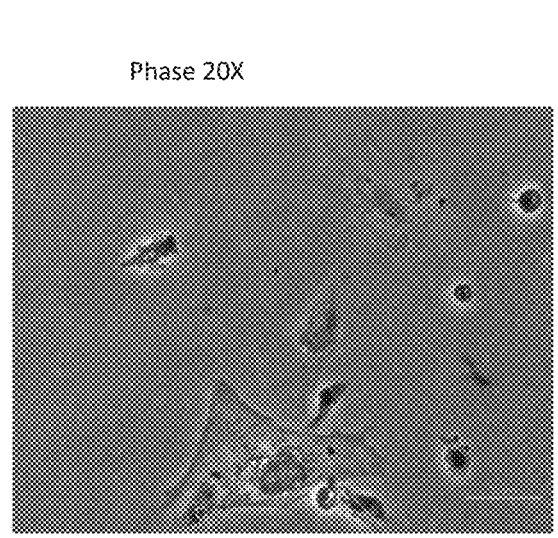

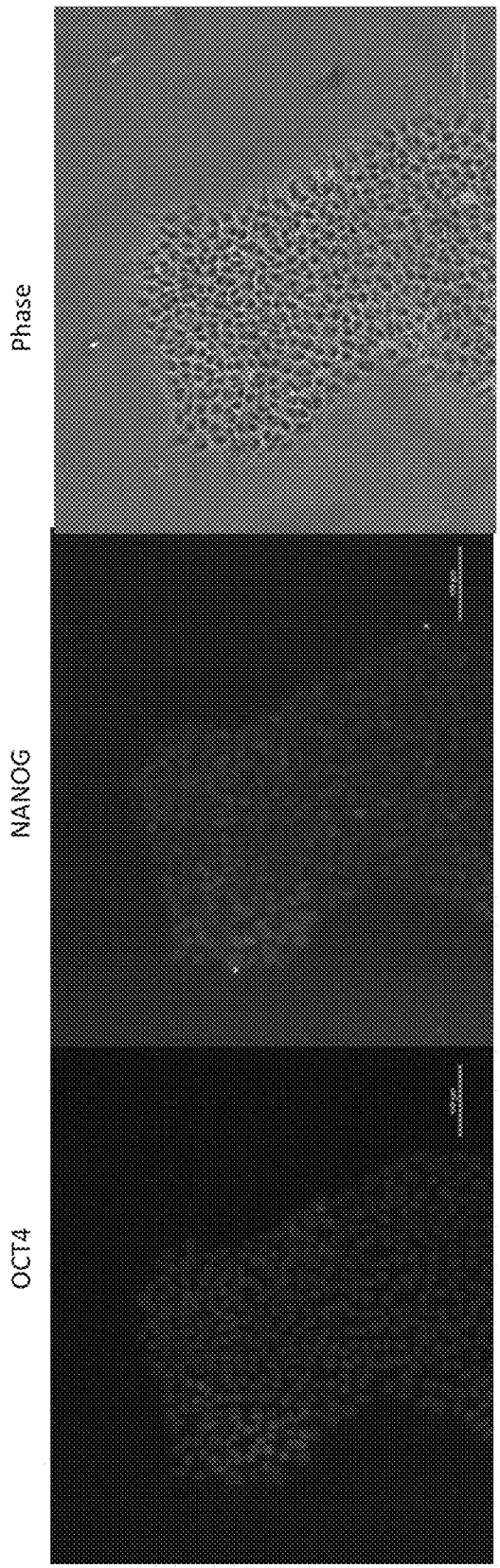

FIG. 46A
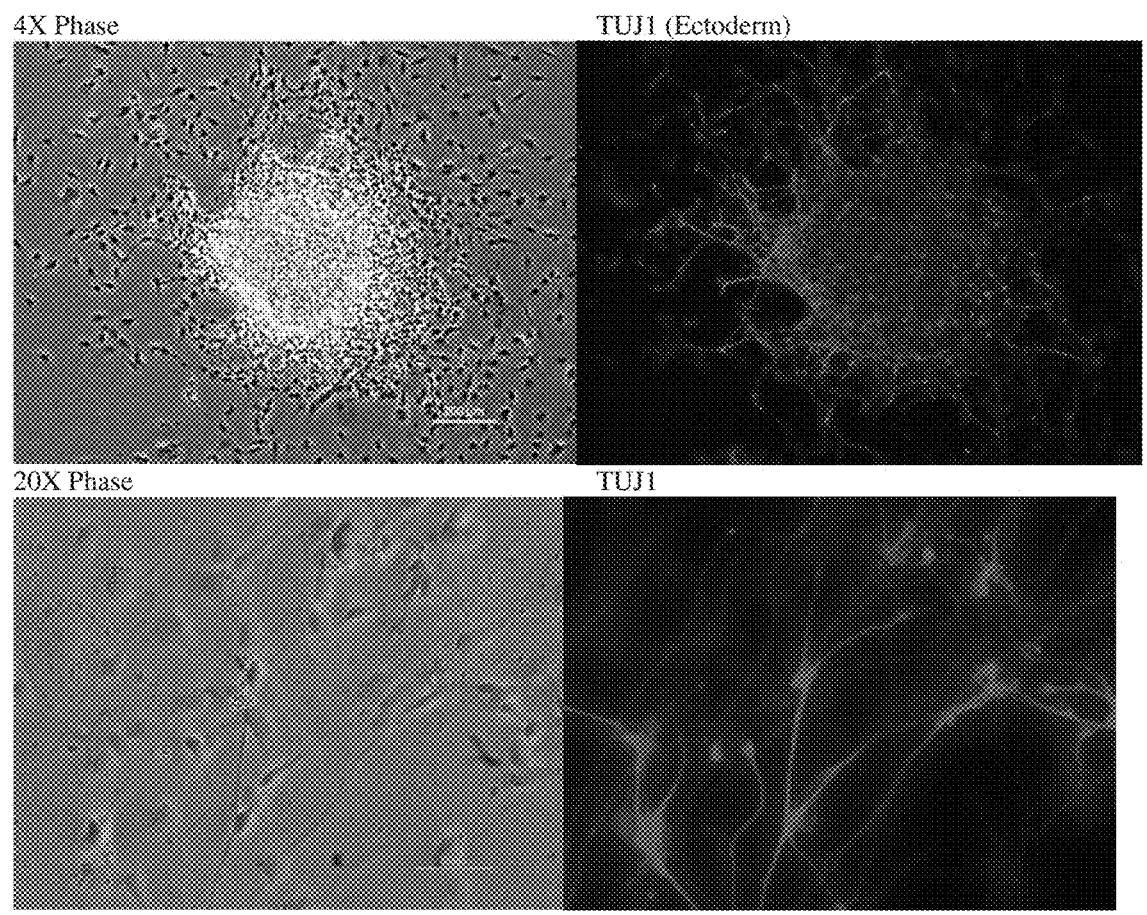
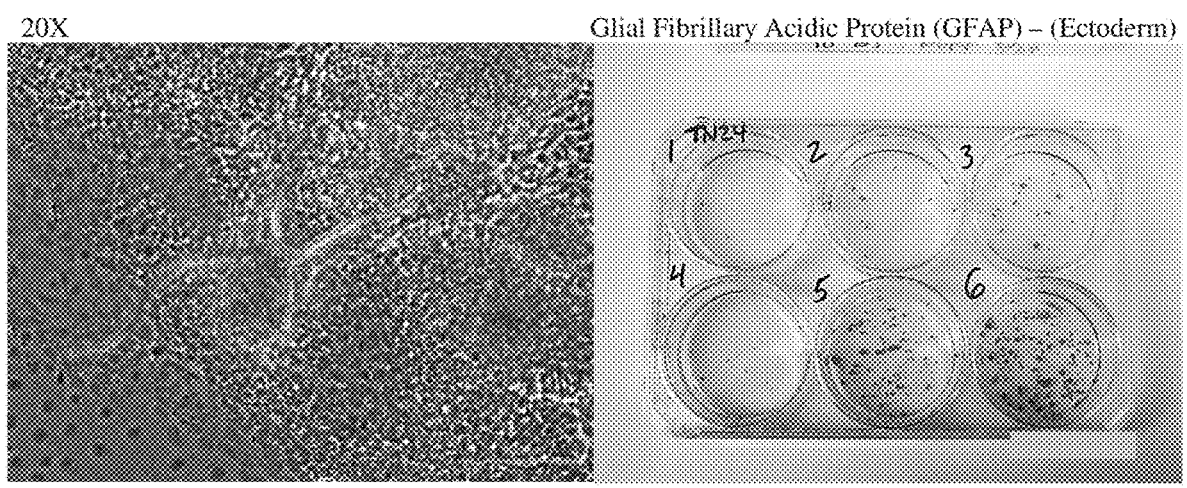

FIG. 46B
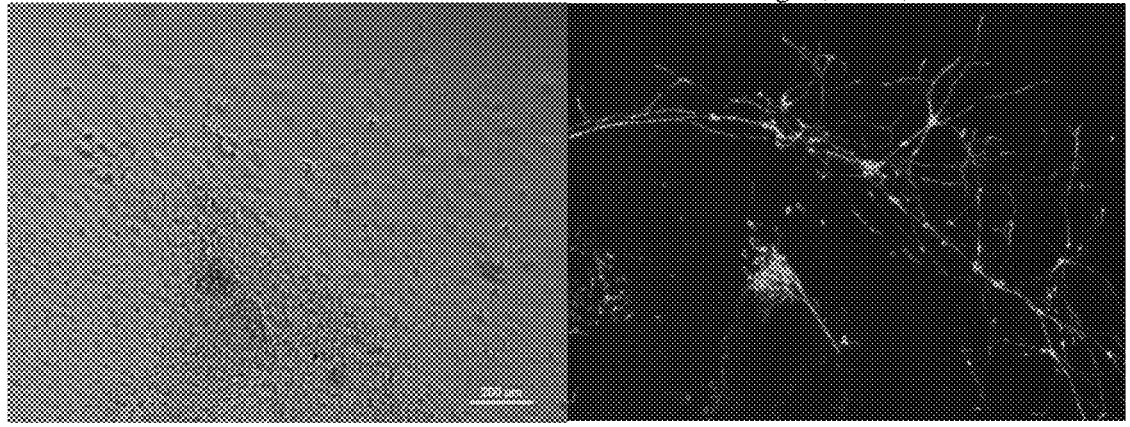
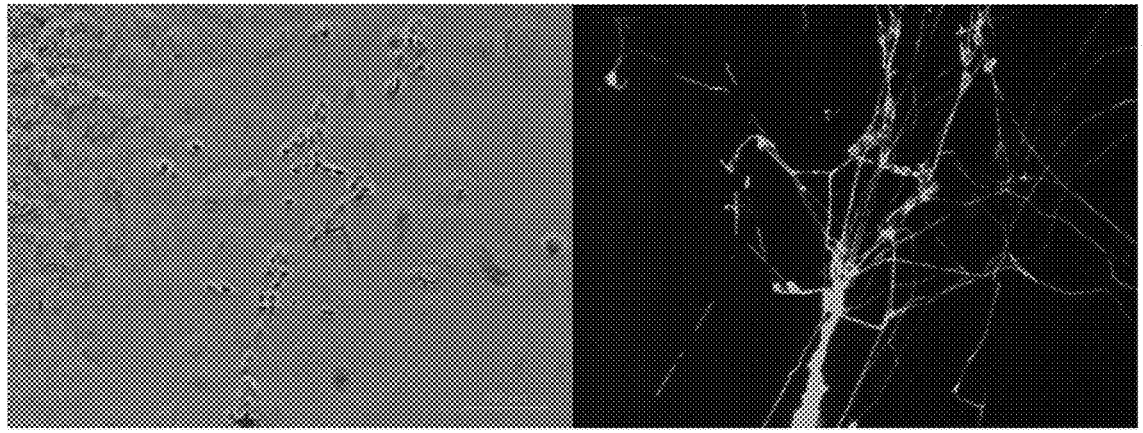
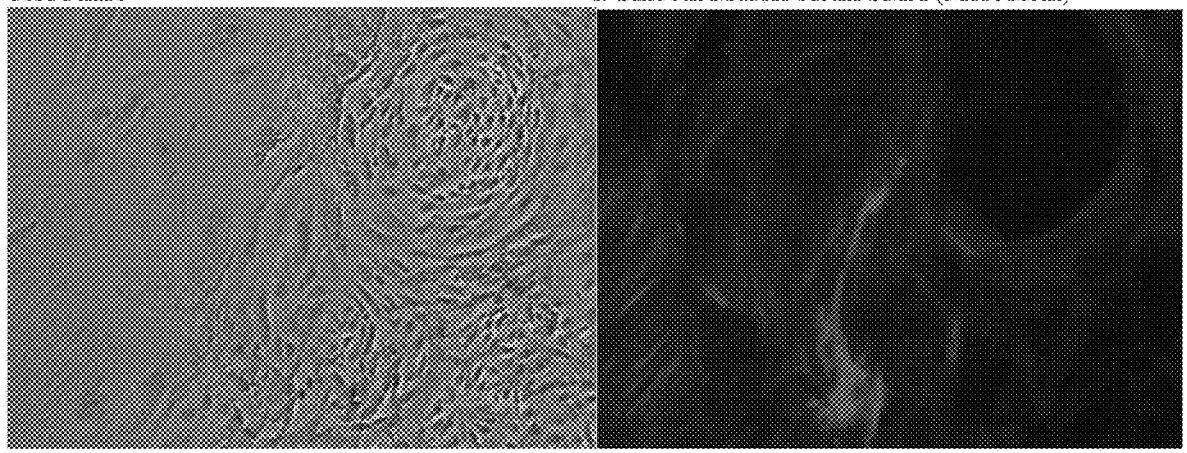

FIG. 46C
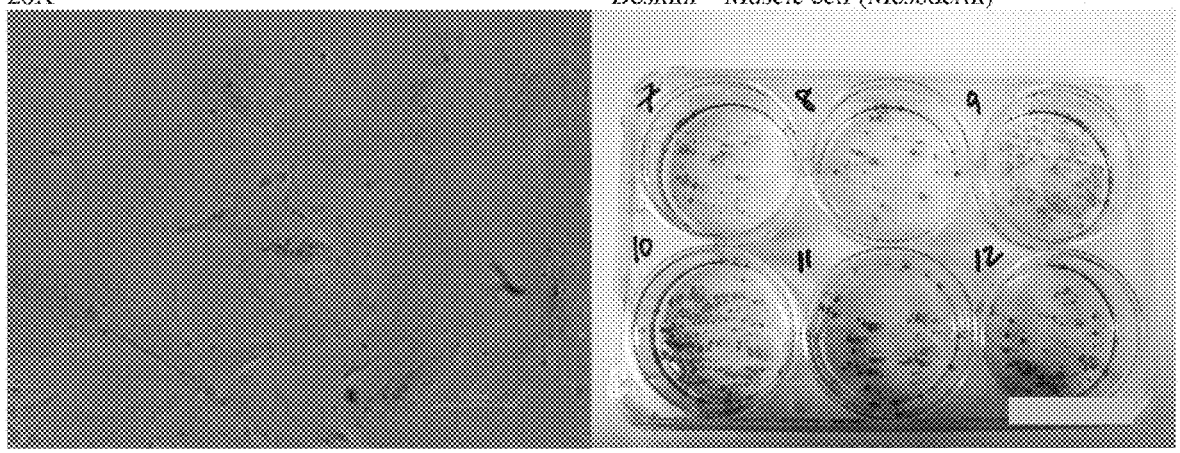
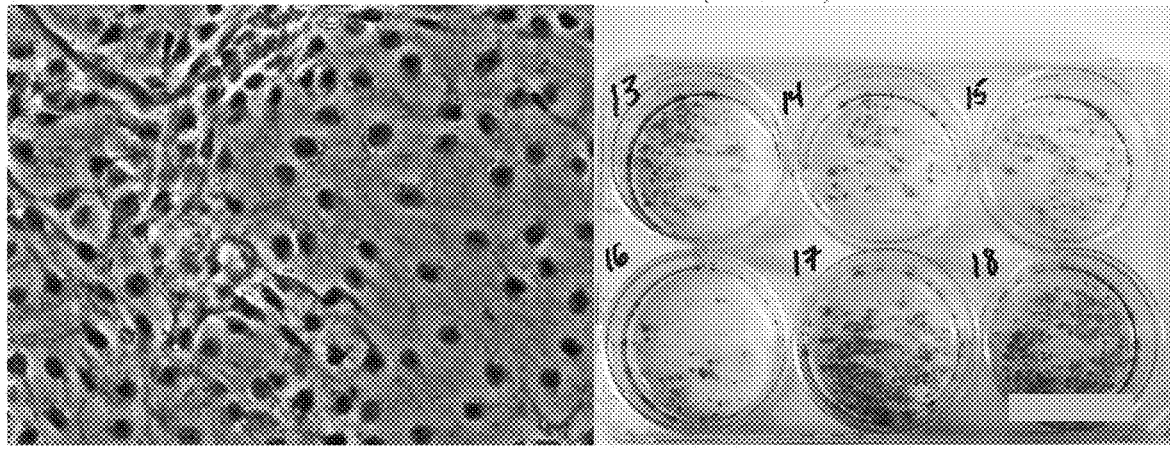

FIG. 46D
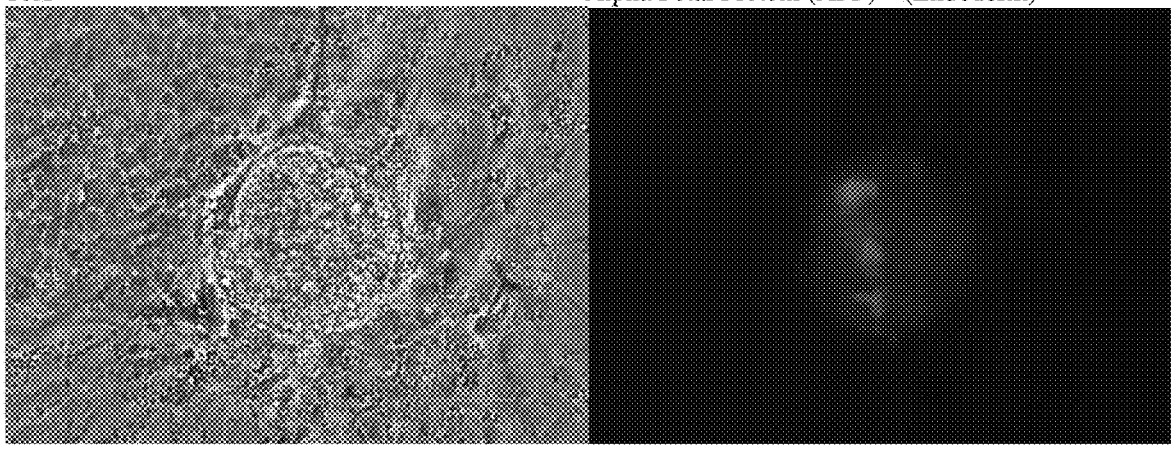
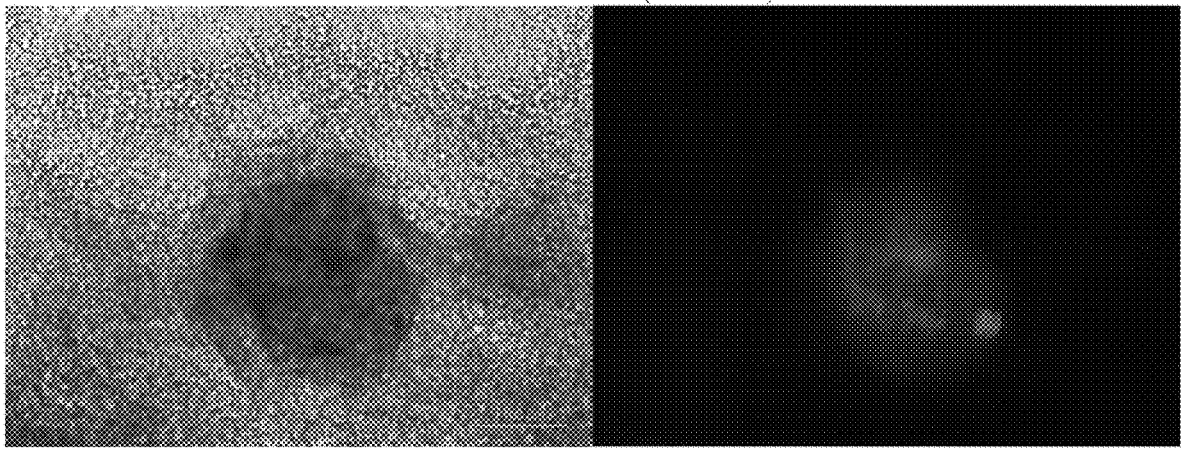

FIG. 47A
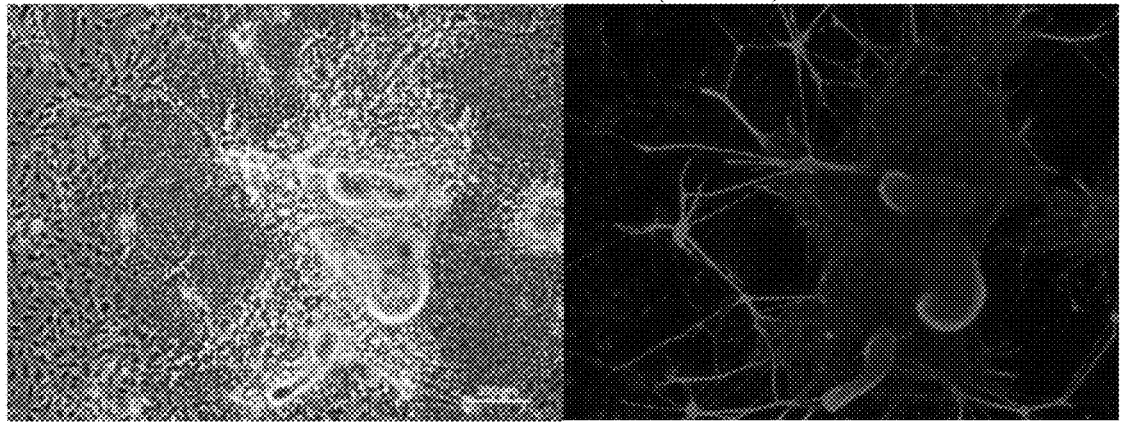
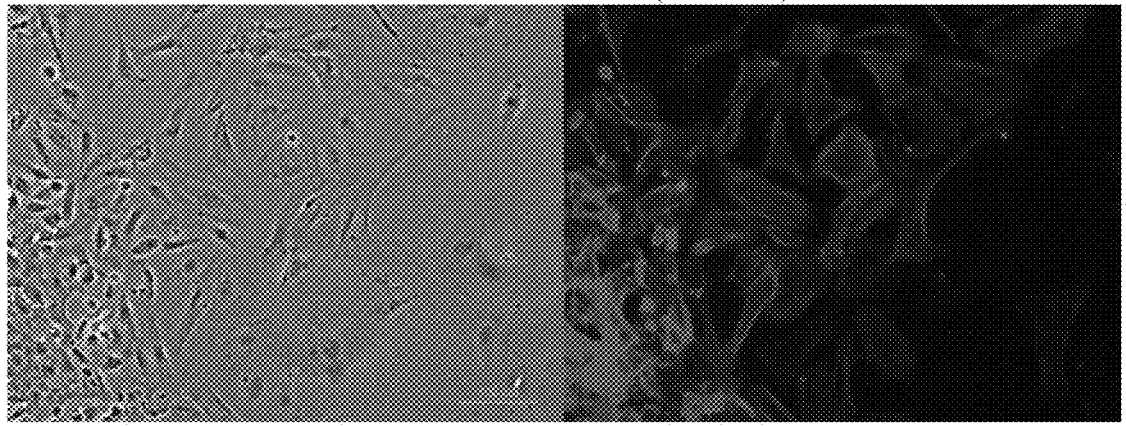
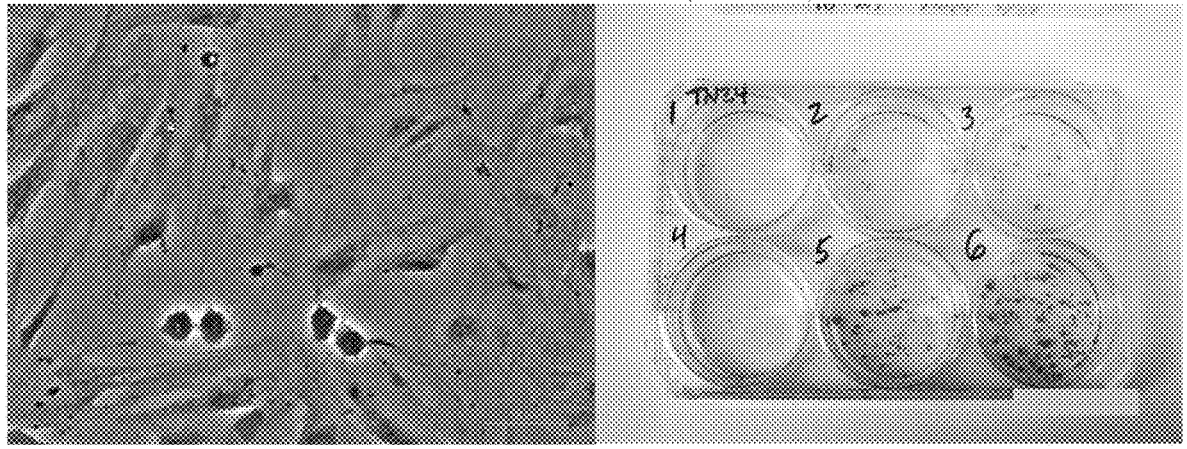

FIG. 48C
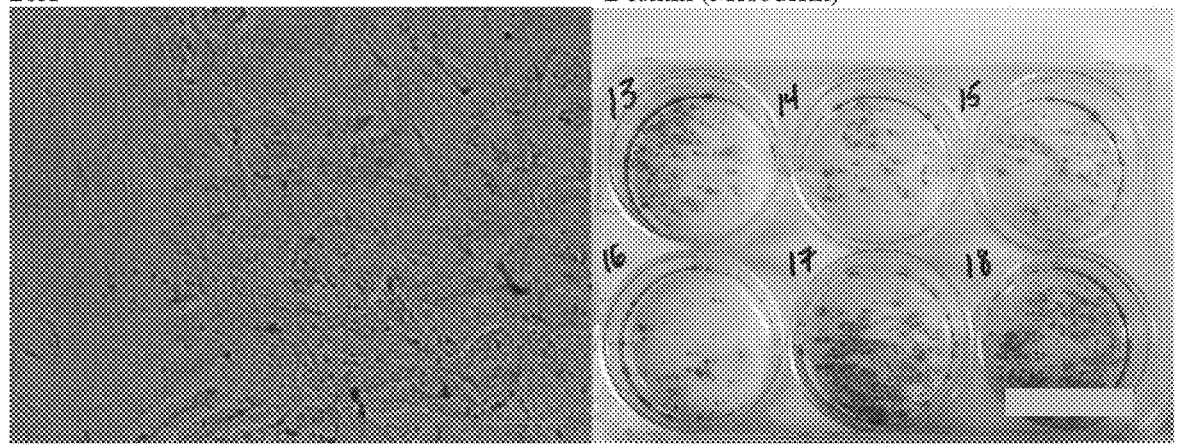
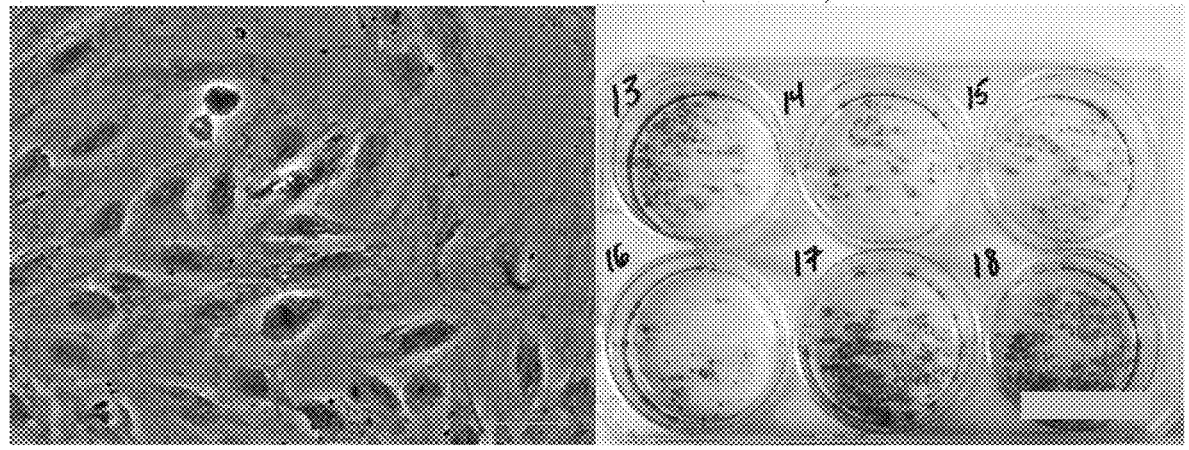

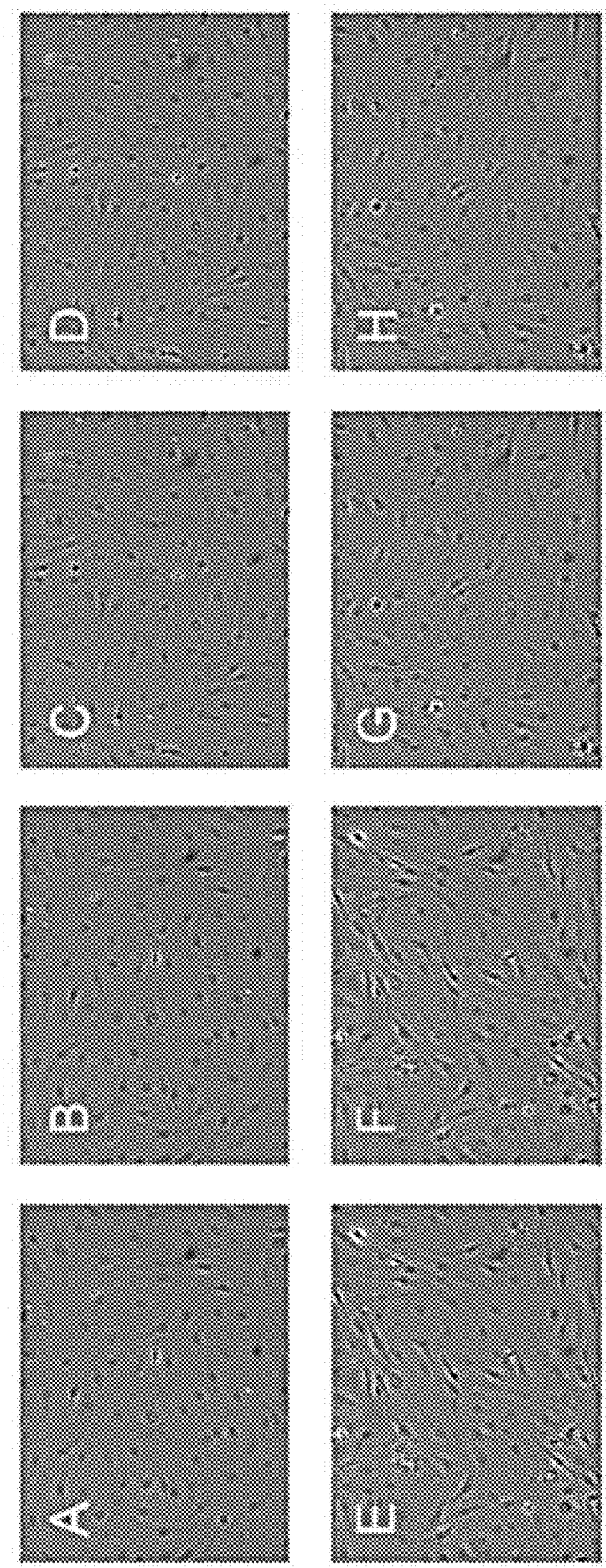
FIG. 49A-H

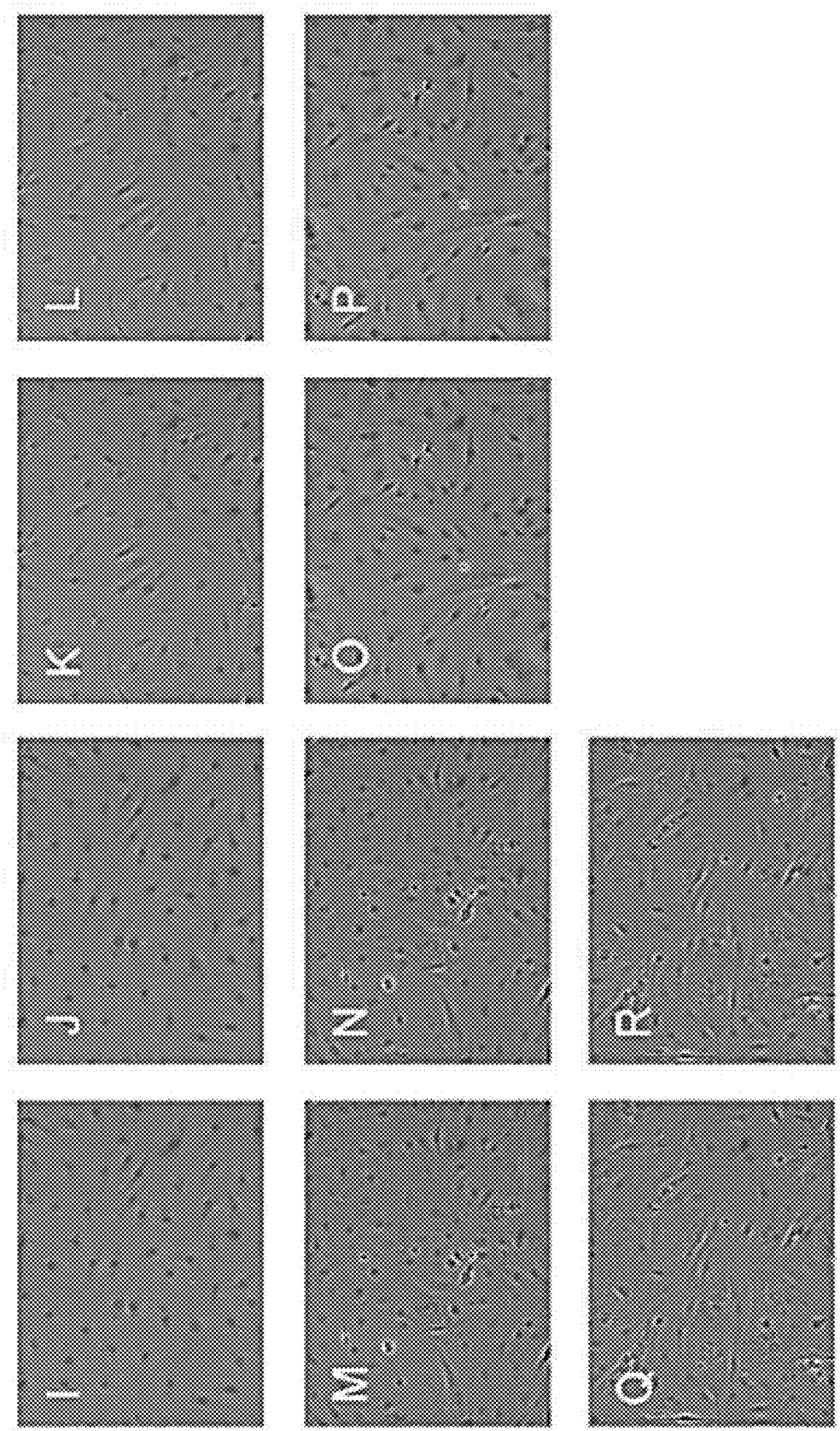
FIG. 49I-R

FIG. 50A
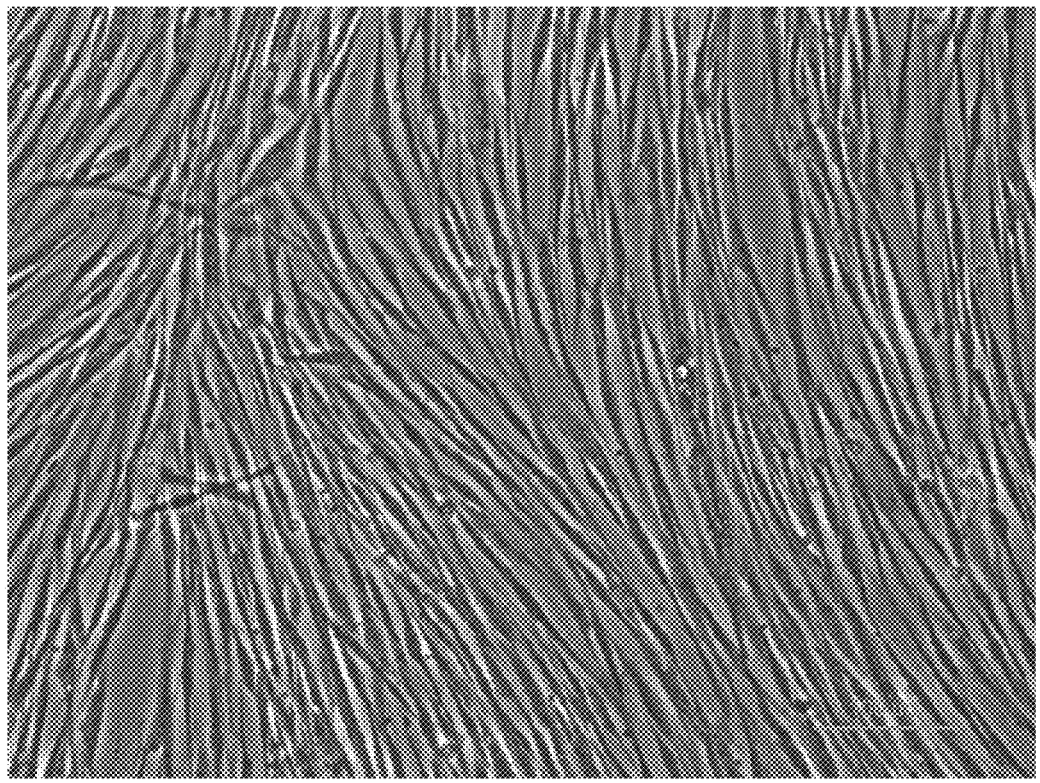
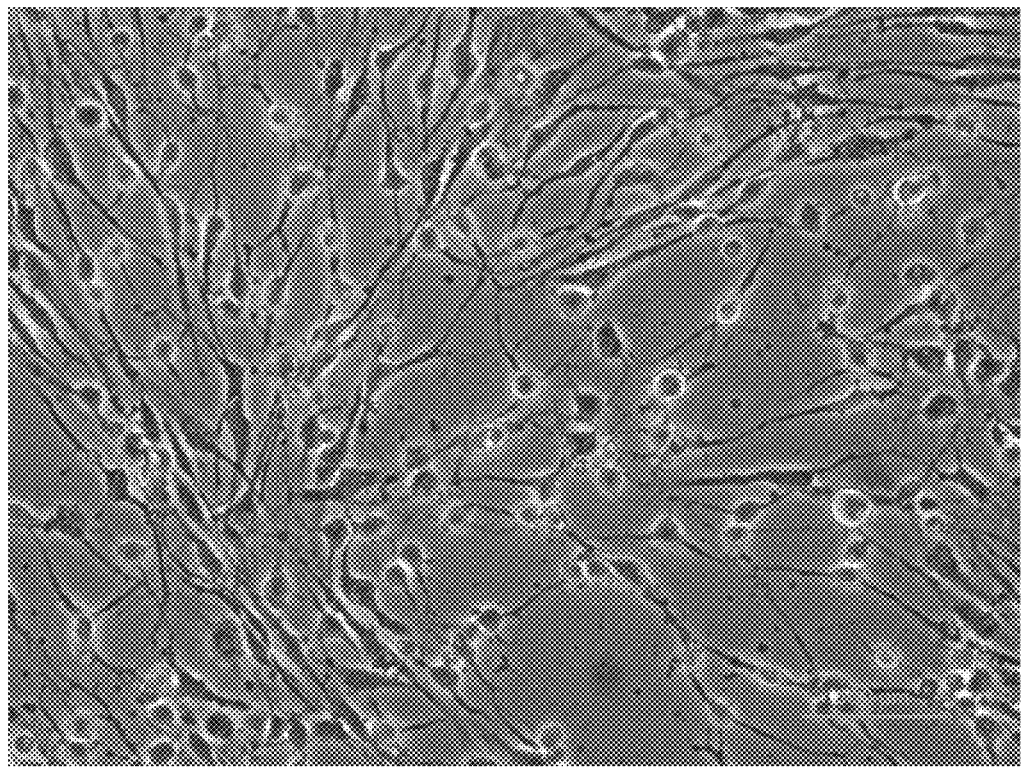
FIG. 50B

FIG. 51A
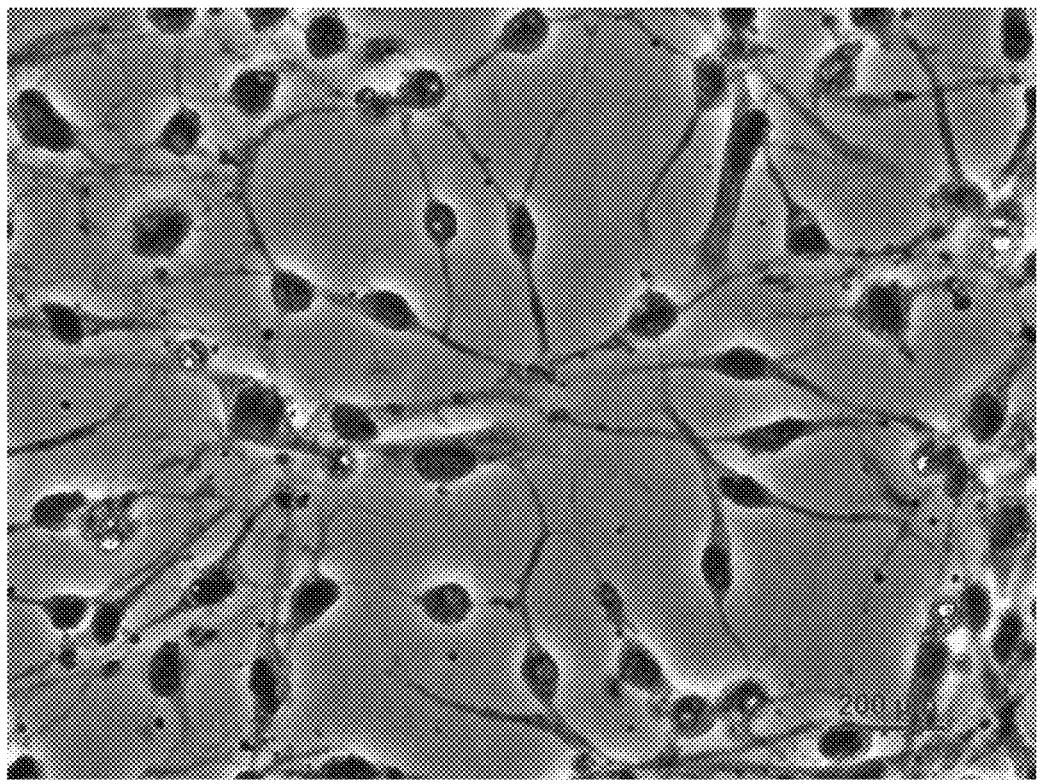
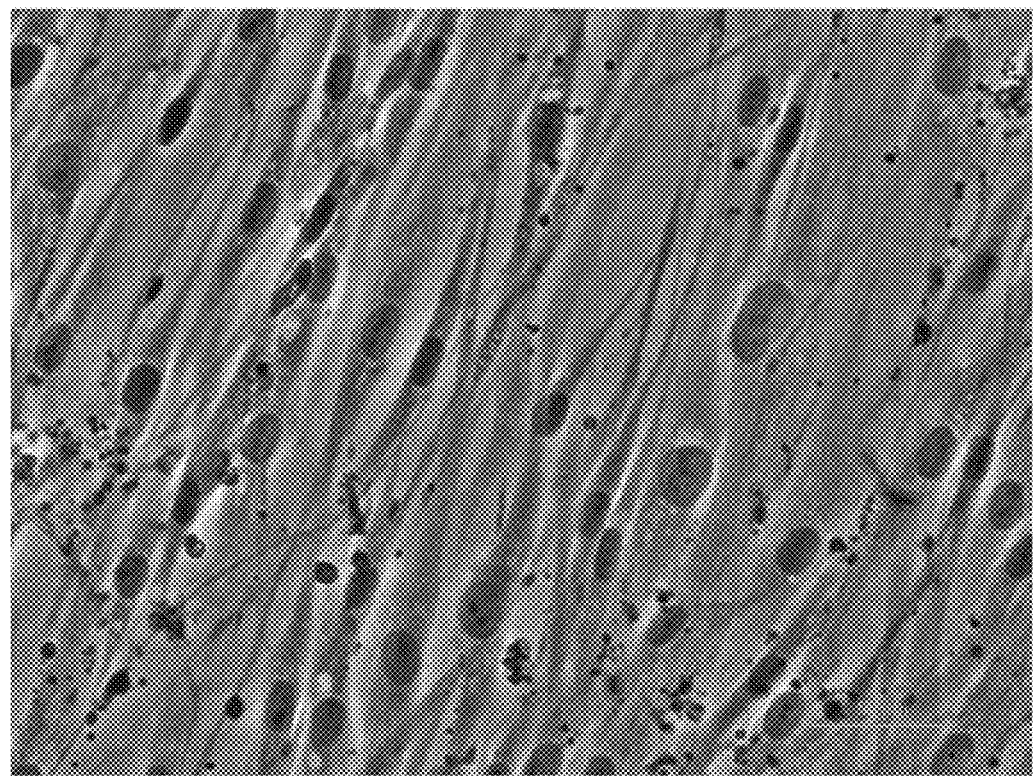
FIG. 51B

SEQUENCE LISTING

```
<160> NUMBER OF SEQ ID NOS: 16

<210> SEQ ID NO 1
<211> LENGTH: 269
<212> TYPE: DNA
<213> ORGANISM: Artificial sequence
<220> FEATURE:
<223> OTHER INFORMATION: Synthetic

<400> SEQUENCE: 1
taatacgact cactataggg taatacaagc ttgcttgttc tttttgcaga agctcagaat      60
aaacgctcaa ctttggcaga tctgatatca ctagtgactg actaggatct ggttaccact    120
```

```
aaaccagcct caagaacacc cgaatggagt ctctaagcta cataatacca acttacactt    180
acaaaatgtt gtcccccaaa atgtagccat tcgtatctgc tcctaataaa agaaagttt    240 cttcacattc tggatcctct agagtcgac                                      269
```

<210> SEQ ID NO 2
<211> LENGTH: 4017
<212> TYPE: DNA
<213> ORGANISM: Artificial sequence
<220> FEATURE:
<223> OTHER INFORMATION: Synthetic

<400> SEQUENCE: 2

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ctaatacgac tcactatagg    420
gtaatacaag cttgcttgtt ctttttgcag aagctcagaa taaacgctca actttggcag    480
atctcggtcg ccaccatggc gggacacctg gcttcagatt ttgccttctc gcccctcca    540 ggtggtggag gtgatgggcc aggggggccg gagccgggct ggttgatcc tcggacctgg    600 ctaagcttcc aaggccctcc tggagggcca ggaatcgggc cggggttgg gccaggctct    660 gaggtgtggg ggattccccc atgccccccg ccgtatgagt tctgtggggg gatggcgtac    720
tgtgggcccc aggttggagt ggggctagtg ccccaaggcg gcttggagac ctctcagcct    780
gagggcgaag caggagtcgg ggtggagagc aactccgatg gggcctcccc ggagccctgc    840
accgtcaccc ctggtgccgt gaagctggag aaggagaagc tggagcaaaa cccggaggag    900
tcccaggaca tcaaagctct gcagaaagaa ctcgagcaat tgccaagct cctgaagcag    960 aagaggatca ccctgggata tacacaggcc gatgtgggc tcaccctggg ggttctattt   1020
gggaaggtat tcagccaaac gaccatctgc cgctttgagg ctctgcagct tagcttcaag   1080
aacatgtgta gctgcggcc cttgctgcag aagtgggtgg aggaagctga caacaatgaa   1140
aatcttcagg agatatgcaa agcagaaacc ctcgtgcagg cccgaaagag aaagcgaacc   1200
agtatcgaga accgagtgag aggcaacctg gagaatttgt tcctgcagtg cccgaaaccc   1260
acactgcagc agatcagcca atcgcccag cagcttgggc tcgagaagga tgtggtccga   1320
gtgtggttct gtaaccggcg ccagaagggc aagcgatcaa gcagcgacta tgcacaacga   1380
gaggattttg aggctgctgg gtctcctttc tcaggggac cagtgtcctt tcctctggcc   1440
ccagggcccc attttggtac cccaggctat gggagccctc acttcactgc actgtactcc   1500
tcggtccctt tccctgaggg ggaagccttt cccccctgtct ctgtcaccac tctgggctct   1560
cccatgcatt caaactgaga tatcactagt gactgactag gatctggtta ccactaaacc   1620
agcctcaaga acaccgaat ggagtctcta agctacataa taccaactta cactttacaa   1680
aatgttgtcc cccaaaatgt agccattcgt atctgctcct aataaaaga agtttcttc   1740 acattctgga tcctctagag tcgacctgca ggcatgcaag cttggcgtaa tcatggtcat   1800
agctgtttcc tgtgtgaaat tgttatccgc tcacaattcc acacaacata cgagccggaa   1860
gcataaagtg taaagcctgg ggtgcctaat gagtgagcta actcacatta attgcgttgc   1920
```

-continued

```
gctcactgcc cgctttccag tcgggaaacc tgtcgtgcca gctgcattaa tgaatcggcc      1980
aacgcgcggg gagaggcggt ttgcgtattg ggcgctcttc cgcttcctcg ctcactgact      2040
cgctgcgctc ggtcgttcgg ctgcggcgag cggtatcagc tcactcaaag gcggtaatac      2100
ggttatccac agaatcaggg gataacgcag gaaagaacat gtgagcaaaa ggccagcaaa      2160
aggccaggaa ccgtaaaaag gccgcgttgc tggcgttttt ccataggctc cgcccccctg      2220
acgagcatca caaaaatcga cgctcaagtc agaggtggcg aaacccgaca ggactataaa      2280
gataccaggc gtttccccct ggaagctccc tcgtgcgctc tcctgttccg accctgccgc      2340
ttaccggata cctgtccgcc tttctccctt cgggaagcgt ggcgctttct catagctcac      2400
gctgtaggta tctcagttcg gtgtaggtcg ttcgctccaa gctgggctgt gtgcacgaac      2460
cccccgttca gcccgaccgc tgcgccttat ccggtaacta tcgtcttgag tccaacccgg      2520
taagacacga cttatcgcca ctggcagcag ccactggtaa caggattagc agagcgaggt      2580
atgtaggcgg tgctacagag ttcttgaagt ggtggcctaa ctacggctac actagaagaa      2640
cagtatttgg tatctgcgct ctgctgaagc cagttacctt cggaaaaaga gttggtagct      2700
cttgatccgg caaacaaacc accgctggta gcggtggttt ttttgtttgc aagcagcaga      2760
ttacgcgcag aaaaaaagga tctcaagaag atcctttgat cttttctacg gggtctgacg      2820
ctcagtggaa cgaaaactca cgttaaggga ttttggtcat gagattatca aaaaggatct      2880
tcacctagat cctttttaaat taaaaatgaa gttttaaatc aatctaaagt atatatgagt      2940
aaacttggtc tgacagttac caatgcttaa tcagtgaggc acctatctca gcgatctgtc      3000
tatttcgttc atccatagtt gcctgactcc ccgtcgtgta gataactacg atacgggagg      3060
gcttaccatc tggccccagt gctgcaatga taccgcgaga cccacgctca ccggctccag      3120
atttatcagc aataaaccag ccagccggaa gggccgagcg cagaagtggt cctgcaactt      3180
tatccgcctc catccagtct attaattgtt gccgggaagc tagagtaagt agttcgccag      3240
ttaatagttt gcgcaacgtt gttgccattg ctacaggcat cgtggtgtca cgctcgtcgt      3300
ttggtatggc ttcattcagc tccggttccc aacgatcaag gcgagttaca tgatcccca     3360 tgttgtgcaa aaaagcggtt agctccttcg gtcctccgat cgttgtcaga agtaagttgg      3420
ccgcagtgtt atcactcatg gttatggcag cactgcataa ttctcttact gtcatgccat      3480
ccgtaagatg cttttctgtg actggtgagt actcaaccaa gtcattctga ataagtgta      3540 tgcggcgacc gagttgctct tgcccggcgt caatacggga taataccgcg ccacatagca      3600
gaactttaaa agtgctcatc attggaaaac gttcttcggg gcgaaaactc tcaaggatct      3660
taccgctgtt gagatccagt tcgatgtaac ccactcgtgc acccaactga tcttcagcat      3720
cttttacttt caccagcgtt tctgggtgag caaaaacagg aaggcaaaat gccgcaaaaa      3780
agggaataag ggcgacacgg aaatgttgaa tactcatact cttccttttt caatattatt      3840
gaagcattta tcagggttat tgtctcatga gcggatacat atttgaatgt atttagaaaa      3900
ataaacaaat aggggttccg cgcacatttc cccgaaaagt gccacctgac gtctaagaaa      3960
ccattattat catgacatta acctataaaa ataggcgtat cacgaggccc tttcgtc       4017
```

<210> SEQ ID NO 3
<211> LENGTH: 3888
<212> TYPE: DNA
<213> ORGANISM: Artificial sequence
<220> FEATURE:
<223> OTHER INFORMATION: Synthetic

```
<400> SEQUENCE: 3
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ctaatacgac tcactatagg     420
gtaatacaag cttgcttgtt cttttttgcag aagctcagaa taaacgctca actttggcag     480
atctcggtcg ccaccatgta caacatgatg gagacggagc tgaagccgcc gggcccgcag     540
caaacttcgg ggggcggcgg cggcaactcc accgcggcgg cggccggcgg caaccagaaa     600
aacagcccgg accgcgtcaa gcggcccatg aatgccttca tggtgtggtc ccgcgggcag     660
cggcgcaaga tggcccagga gaaccccaag atgcacaact cggagatcag caagcgcctg     720
ggcgccgagt ggaaactttt gtcggagacg gagaagcggc cgttcatcga cgaggctaag     780
cggctgcgag cgctgcacat gaaggagcac ccggattata ataccggcc ccggcggaaa     840 accaagacgc tcatgaagaa ggataagtac acgctgcccg gcgggctgct ggccccggc     900 ggcaatagca tggcgagcgg ggtcggggtg ggcgccggcc tgggcgcggg cgtgaaccag     960
cgcatggaca gttacgcgca catgaacggc tggagcaacg gcagctacag catgatgcag    1020
gaccagctgg gctaccgca gcacccgggc ctcaatgcgc acggcgcagc gcagatgcag    1080
cccatgcacc gctacgacgt gagcgccctg cagtacaact ccatgaccag ctcgcagacc    1140
tacatgaacg gctcgcccac ctacagcatg tcctactcgc agcagggcac ccctggcatg    1200
gctcttggct ccatgggttc ggtggtcaag tccgaggcca gctccagccc cctgtggtt    1260 acctcttcct cccactccag ggcgcctgc caggccgggg acctccggga catgatcagc    1320
atgtatctcc ccggcgccga ggtgccggaa cccgccgccc ccagcagact tcacatgtcc    1380
cagcactacc agagcggccc ggtgcccggc acggccatta acggcacact gcccctctca    1440
cacatgtgag atatcactag tgactgacta ggatctggtt accactaaac cagcctcaag    1500
aacacccgaa tggagtctct aagctacata ataccaactt acactttaca aaatgttgtc    1560
ccccaaaatg tagccattcg tatctgctcc taataaaaag aaagtttctt cacattctgg    1620
atcctctaga gtcgacctgc aggcatgcaa gcttggcgta atcatggtca tagctgtttc    1680
ctgtgtgaaa ttgttatccg ctcacaattc cacacaacat acgagccgga agcataaagt    1740
gtaaagcctg gggtgcctaa tgagtgagct aactcacatt aattgcgttg cgctcactgc    1800
ccgctttcca gtcgggaaac ctgtcgtgcc agctgcatta atgaatcggc caacgcgcgg    1860
ggagaggcgg tttgcgtatt gggcgctctt ccgcttcctc gctcactgac tcgctgcgct    1920
cggtcgttcg gctgcggcga gcggtatcag ctcactcaaa ggcggtaata cggttatcca    1980
cagaatcagg ggataacgca ggaaagaaca tgtgagcaaa aggccagcaa aaggccagga    2040
accgtaaaaa ggccgcgttg ctggcgtttt tccataggct ccgcccccct gacgagcatc    2100
acaaaaatcg acgctcaagt cagaggtggc gaaacccgac aggactataa agataccagg    2160
cgtttccccc tggaagctcc ctcgtgcgct ctcctgttcc gaccctgccg cttaccggat    2220
acctgtccgc ctttctccct tcgggaagcg tggcgctttc tcatagctca cgctgtaggt    2280
atctcagttc ggtgtaggtc gttcgctcca agctgggctg tgtgcacgaa ccccccgttc    2340
```

```
agcccgaccg ctgcgcctta tccggtaact atcgtcttga gtccaacccg gtaagacacg    2400
acttatcgcc actggcagca gccactggta acaggattag cagagcgagg tatgtaggcg    2460
gtgctacaga gttcttgaag tggtggccta actacggcta cactagaaga acagtatttg    2520
gtatctgcgc tctgctgaag ccagttacct tcggaaaaag agttggtagc tcttgatccg    2580
gcaaacaaac caccgctggt agcggtggtt ttttgtttg caagcagcag attacgcgca    2640
gaaaaaaagg atctcaagaa gatcctttga tcttttctac ggggtctgac gctcagtgga    2700
acgaaaactc acgttaaggg attttggtca tgagattatc aaaaaggatc ttcacctaga    2760
tccttttaaa ttaaaaatga agttttaaat caatctaaag tatatatgag taaacttggt    2820
ctgacagtta ccaatgctta atcagtgagg cacctatctc agcgatctgt ctatttcgtt    2880
catccatagt tgcctgactc cccgtcgtgt agataactac gatacgggag ggcttaccat    2940
ctggccccag tgctgcaatg ataccgcgag acccacgctc accggctcca gatttatcag    3000
caataaacca gccagccgga agggccgagc gcagaagtgg tcctgcaact ttatccgcct    3060
ccatccagtc tattaattgt tgccgggaag ctagagtaag tagttcgcca gttaatagtt    3120
tgcgcaacgt tgttgccatt gctacaggca tcgtggtgtc acgctcgtcg tttggtatgg    3180
cttcattcag ctccggttcc caacgatcaa ggcgagttac atgatccccc atgttgtgca    3240
aaaaagcggt tagctccttc ggtcctccga tcgttgtcag aagtaagttg gccgcagtgt    3300
tatcactcat ggttatggca gcactgcata attctcttac tgtcatgcca tccgtaagat    3360
gcttttctgt gactggtgag tactcaacca agtcattctg agaatagtgt atgcggcgac    3420
cgagttgctc ttgcccggcg tcaatacggg ataataccgc gccacatagc agaactttaa    3480
aagtgctcat cattggaaaa cgttcttcgg ggcgaaaact ctcaaggatc ttaccgctgt    3540
tgagatccag ttcgatgtaa cccactcgtg cacccaactg atcttcagca tcttttactt    3600
tcaccagcgt ttctgggtga gcaaaaacag gaaggcaaaa tgccgcaaaa aagggaataa    3660
gggcgacacg gaaatgttga atactcatac tcttcctttt tcaatattat tgaagcattt    3720
atcagggtta ttgtctcatg agcggataca tatttgaatg tatttagaaa aataaacaaa    3780
taggggttcc gcgcacattt ccccgaaaag tgccacctga cgtctaagaa accattatta    3840
tcatgacatt aacctataaa aataggcgta tcacgaggcc ctttcgtc    3888

<210> SEQ ID NO 4
<211> LENGTH: 4369
<212> TYPE: DNA
<213> ORGANISM: Artificial sequence
<220> FEATURE:
<223> OTHER INFORMATION: Synthetic

<400> SEQUENCE: 4
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ctaatacgac tcactatagg     420
gtaatacaag cttgcttgtt cttttgtgcag aagctcagaa taaacgctca actttggcag     480
```

| | |
|---|---|
| atctgccacc atgaggcagc cacctggcga gtctgacatg gctgtcagcg acgcgctgct | 540 |
| cccatctttc tccacgttcg cgtctggccc ggcgggaagg gagaagacac tgcgtcaagc | 600 |
| aggtgccccg aataaccgct ggcgggagga gctctcccac atgaagcgac ttcccccagt | 660 |
| gcttcccggc cgcccctatg acctggcggc ggcgaccgtg gccacagacc tggagagcgg | 720 |
| cggagccggt gcggcttgcg gcggtagcaa cctggcgccc ctacctcgga gagagaccga | 780 |
| ggagttcaac gatctcctgg acctggactt tattctctcc aattcgctga cccatcctcc | 840 |
| ggagtcagtg gccgccaccg tgtcctcgtc agcgtcagcc tcctcttcgt cgtcgccgtc | 900 |
| gagcagcggc cctgccagcg cgccctccac ctgcagcttc acctatccga tccgggccgg | 960 |
| gaacgacccg ggcgtggcgc cgggcggcac gggcggaggc ctcctctatg gcagggagtc | 1020 |
| cgctcccccct ccgacggctc ccttcaacct ggcggacatc aacgacgtga gccctcggg | 1080 |
| cggcttcgtg gccgagctcc tgcggccaga attggacccg gtgtacattc cgccgcagca | 1140 |
| gccgcagccg ccaggtggcg ggctgatggg caagttcgtg ctgaaggcgt cgctgagcgc | 1200 |
| ccctggcagc gagtacggca gcccgtcggt catcagcgtc agcaaaggca gccctgacgg | 1260 |
| cagccacccg gtggtggtgg cgccctacaa cggcgggccg ccgcgcacgt gccccaagat | 1320 |
| caagcaggag gcggtctctt cgtgcaccca cttgggcgct ggaccccctc tcagcaatgg | 1380 |
| ccaccggccg gctgcacacg acttcccccct ggggcggcag ctccccagca ggactacccc | 1440 |
| gaccctgggt cttgaggaag tgctgagcag cagggactgt caccctgccc tgccgcttcc | 1500 |
| tcccggcttc catccccacc cggggcccaa ttacccatcc ttcctgcccg atcagatgca | 1560 |
| gccgcaagtc ccgccgctcc attaccaaga gctcatgcca cccggttcct gcatgccaga | 1620 |
| ggagcccaag ccaaagaggg gaagacgatc gtggccccgg aaaaggaccg ccacccacac | 1680 |
| ttgtgattac gcgggctgcg gcaaaaccta cacaaagagt tcccatctca aggcacacct | 1740 |
| gcgaacccac acaggtgaga aaccttacca ctgtgactgg gacggctgtg gatggaaatt | 1800 |
| cgcccgctca gatgaactga ccaggcacta ccgtaaacac acggggcacc gcccgttcca | 1860 |
| gtgccaaaaa tgcgaccgag cattttccag gtcggaccac ctcgccttac acatgaagag | 1920 |
| gcatttttaa gatatcacta gtgactgact aggatctggt taccactaaa ccagcctcaa | 1980 |
| gaacacccga atggagtctc taagctacat aataccaact tacactttac aaaatgttgt | 2040 |
| cccccaaaat gtagccattc gtatctgctc ctaataaaaa gaaagtttct tcacattctg | 2100 |
| gatcctctag agtcgacctg caggcatgca agcttggcgt aatcatggtc atagctgttt | 2160 |
| cctgtgtgaa attgttatcc gctcacaatt ccacacaaca tacgagccgg aagcataaag | 2220 |
| tgtaaagcct ggggtgccta atgagtgagc taactcacat taattgcgtt gcgctcactg | 2280 |
| cccgctttcc agtcgggaaa cctgtcgtgc cagctgcatt aatgaatcgg ccaacgcgcg | 2340 |
| gggagaggcg gtttgcgtat tgggcgctct tccgcttcct cgctcactga ctcgctgcgc | 2400 |
| tcggtcgttc ggctgcggcg agcggtatca gctcactcaa aggcggtaat acggttatcc | 2460 |
| acagaatcag gggataacgc aggaaagaac atgtgagcaa aaggccagca aaaggccagg | 2520 |
| aaccgtaaaa aggccgcgtt gctggcgttt ttccataggc tccgcccccc tgacgagcat | 2580 |
| cacaaaaatc gacgctcaag tcagaggtgg cgaaacccga caggactata agataccagg | 2640 |
| gcgtttcccc ctggaagctc cctcgtgcgc tctcctgttc cgaccctgcc gcttaccgga | 2700 |
| tacctgtccg cctttctccc ttcgggaagc gtggcgcttt ctcatagctc acgctgtagg | 2760 |
| tatctcagtt cggtgtaggt cgttcgctcc aagctgggct gtgtgcacga accccccgtt | 2820 |
| cagcccgacc gctgcgcctt atccggtaac tatcgtcttg agtccaaccc ggtaagacac | 2880 |

-continued

```
gacttatcgc cactggcagc agccactggt aacaggatta gcagagcgag gtatgtaggc      2940
ggtgctacag agttcttgaa gtggtggcct aactacggct acactagaag aacagtattt      3000
ggtatctgcg ctctgctgaa gccagttacc ttcggaaaaa gagttggtag ctcttgatcc      3060
ggcaaacaaa ccaccgctgg tagcggtggt ttttttgttt gcaagcagca gattacgcgc      3120
agaaaaaaag gatctcaaga agatcctttg atcttttcta cggggtctga cgctcagtgg      3180
aacgaaaact cacgttaagg gattttggtc atgagattat caaaaaggat cttcacctag      3240
atccttttaa attaaaaatg aagttttaaa tcaatctaaa gtatatatga gtaaacttgg      3300
tctgacagtt accaatgctt aatcagtgag gcacctatct cagcgatctg tctatttcgt      3360
tcatccatag ttgcctgact ccccgtcgtg tagataacta cgatacggga gggcttacca      3420
tctggcccca gtgctgcaat gataccgcga gacccacgct caccggctcc agatttatca      3480
gcaataaacc agccagccgg aagggccgag cgcagaagtg gtcctgcaac tttatccgcc      3540
tccatccagt ctattaattg ttgccgggaa gctagagtaa gtagttcgcc agttaatagt      3600
ttgcgcaacg ttgttgccat tgctacaggc atcgtggtgt cacgctcgtc gtttggtatg      3660
gcttcattca gctccggttc caacgatcaa ggcgagtta catgatcccc catgttgtgc      3720
aaaaaagcgg ttagctcctt cggtcctccg atcgttgtca gaagtaagtt ggccgcagtg      3780
ttatcactca tggttatggc agcactgcat aattctctta ctgtcatgcc atccgtaaga      3840
tgcttttctg tgactggtga gtactcaacc aagtcattct gagaatagtg tatgcggcga      3900
ccgagttgct cttgcccggc gtcaatacgg gataataccg cgccacatag cagaacttta      3960
aaagtgctca tcattggaaa acgttcttcg ggcgaaaac tctcaaggat cttaccgctg      4020
ttgagatcca gttcgatgta acccactcgt gcacccaact gatcttcagc atcttttact      4080
ttcaccagcg tttctgggtg agcaaaaaca ggaaggcaaa atgccgcaaa aaagggaata      4140
agggcgacac ggaaatgttg aatactcata ctcttccttt ttcaatatta ttgaagcatt      4200
tatcagggtt attgtctcat gagcggatac atatttgaat gtatttagaa aaataaacaa      4260
ataggggttc cgcgcacatt tccccgaaaa gtgccacctg acgtctaaga aaccattatt      4320
atcatgacat taacctataa aaataggcgt atcacgaggc cctttcgtc                 4369
```

<210> SEQ ID NO 5
<211> LENGTH: 3559
<212> TYPE: DNA
<213> ORGANISM: Artificial sequence
<220> FEATURE:
<223> OTHER INFORMATION: Synthetic

<400> SEQUENCE: 5

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt ctaatacgac tcactatagg      420
gtaatacaag cttgcttgtt cttttttgcag aagctcagaa taaacgctca actttggcag      480
atctgccacc atgggctccg tgtccaacca gcagtttgca ggtggctgcg ccaaggcggc      540
```

```
agaagaggcg cccgaggagg cgccggagga cgcggcccgg gcggcggacg agcctcagct    600
gctgcacggt gcgggcatct gtaagtggtt caacgtgcgc atggggttcg gcttcctgtc    660
catgaccgcc cgcgccgggg tcgcgctcga ccccccagtg gatgtctttg tgcaccagag    720
taagctgcac atggaagggt tccggagctt aaggagggt gaggcagtgg agttcacctt     780
taagaagtca gccaagggtc tggaatccat ccgtgtcacc ggacctggtg gagtattctg    840
tattgggagt gagaggcggc caaaggaaa gagcatgcag aagcgcagat caaaaggaga     900
caggtgctac aactgtggag gtctagatca tcatgccaag gaatgcaagc tgccacccca    960
gcccaagaag tgccacttct gccagagcat cagcccatatg gtagcctcat gtccgctgaa  1020
ggcccagcag ggccctagtg cacagggaaa gccaacctac tttcgagagg aagaagaaga   1080
aatccacagc cctaccctgc tcccggaggc acagaattga gatatcacta gtgactgact   1140
aggatctggt taccactaaa ccagcctcaa gaacacccga atggagtctc taagctacat    1200
aataccaact tacactttac aaaatgttgt cccccaaaat gtagccattc gtatctgctc    1260
ctaataaaaa gaaagtttct tcacattctg gatcctctag agtcgacctg caggcatgca    1320
agcttggcgt aatcatggtc atagctgttt cctgtgtgaa attgttatcc gctcacaatt    1380
ccacacaaca tacgagccgg aagcataaag tgtaaagcct ggggtgccta atgagtgagc    1440
taactcacat taattgcgtt gcgctcactg cccgctttcc agtcgggaaa cctgtcgtgc    1500
cagctgcatt aatgaatcgg ccaacgcgcg gggagaggcg gtttgcgtat tgggcgctct    1560
tccgcttcct cgctcactga ctcgctgcgc tcggtcgttc ggctgcggcg agcggtatca    1620
gctcactcaa aggcggtaat acggttatcc acagaatcag gggataacgc aggaaagaac    1680
atgtgagcaa aaggccagca aaaggccagg aaccgtaaaa aggccgcgtt gctggcgttt    1740
ttccataggc tccgcccccc tgacgagcat cacaaaaatc gacgctcaag tcagaggtgg    1800
cgaaacccga caggactata agataccag gcgtttcccc ctggaagctc cctcgtgcgc     1860
tctcctgttc cgaccctgcc gcttaccgga tacctgtccg cctttctccc ttcgggaagc    1920
gtggcgcttt ctcatagctc acgctgtagg tatctcagtt cggtgtaggt cgttcgctcc    1980
aagctgggct gtgtgcacga accccccgtt cagcccgacc gctgcgcctt atccggtaac    2040
tatcgtcttg agtccaaccc ggtaagacac gacttatcgc cactggcagc agccactggt    2100
aacaggatta gcagagcgag gtatgtaggc ggtgctacag agttcttgaa gtggtggcct    2160
aactacggct acactagaag aacagtattt ggtatctgcg ctctgctgaa gccagttacc    2220
ttcggaaaaa gagttggtag ctcttgatcc ggcaaacaaa ccaccgctgg tagcggtggt    2280
ttttttgttt gcaagcagca gattacgcgc agaaaaaaag gatctcaaga agatcctttg    2340
atcttttcta cggggtctga cgctcagtgg aacgaaaact cacgttaagg gattttggtc    2400
atgagattat caaaaaggat cttcacctag atccttttaa attaaaaatg aagttttaaa    2460
tcaatctaaa gtatatatga gtaaacttgg tctgacagtt accaatgctt aatcagtgag    2520
gcacctatct cagcgatctg tctatttcgt tcatccatag ttgcctgact ccccgtcgtg    2580
tagataacta cgatacggga gggcttacca tctggcccca gtgctgcaat gataccgcga    2640
gacccacgct caccggctcc agatttatca gcaataaacc agccagccgg aagggccgag    2700
cgcagaagtg gtcctgcaac tttatccgcc tccatccagt ctattaattg ttgccgggaa    2760
gctagagtaa gtagttcgcc agttaatagt ttgcgcaacg ttgttgccat tgctacaggc    2820
atcgtggtgt cacgctcgtc gtttggtatg gcttcattca gctccggttc caacgatca     2880 aggcgagtta catgatcccc catgttgtgc aaaaaagcgg ttagctcctt cggtcctccg    2940
```

| | |
|---|---|
| atcgttgtca gaagtaagtt ggccgcagtg ttatcactca tggttatggc agcactgcat | 3000 |
| aattctctta ctgtcatgcc atccgtaaga tgcttttctg tgactggtga gtactcaacc | 3060 |
| aagtcattct gagaatagtg tatgcggcga ccgagttgct cttgcccggc gtcaatacgg | 3120 |
| gataataccg cgccacatag cagaacttta aaagtgctca tcattggaaa acgttcttcg | 3180 |
| gggcgaaaac tctcaaggat cttaccgctg ttgagatcca gttcgatgta acccactcgt | 3240 |
| gcacccaact gatcttcagc atcttttact ttcaccagcg tttctgggtg agcaaaaaca | 3300 |
| ggaaggcaaa atgccgcaaa aagggaata agggcgacac ggaaatgttg aatactcata | 3360 |
| ctcttccttt ttcaatatta ttgaagcatt tatcagggtt attgtctcat gagcggatac | 3420 |
| atatttgaat gtatttagaa aaataaacaa ataggggttc cgcgcacatt tccccgaaaa | 3480 |
| gtgccacctg acgtctaaga aaccattatt atcatgacat taacctataa aataggcgt | 3540 |
| atcacgaggc cctttcgtc | 3559 |

<210> SEQ ID NO 6
<211> LENGTH: 3847
<212> TYPE: DNA
<213> ORGANISM: Artificial sequence
<220> FEATURE:
<223> OTHER INFORMATION: Synthetic

<400> SEQUENCE: 6

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt ctaatacgac tcactatagg | 420 |
| gtaatacaag cttgcttgtt cttttttgcag aagctcagaa taaacgctca actttggcag | 480 |
| atctgccacc atgagtgtgg atccagcttg tccccaaagc ttgccttgct ttgaagcatc | 540 |
| cgactgtaaa gaatcttcac ctatgcctgt gatttgtggg cctgaagaaa actatccatc | 600 |
| cttgcaaatg tcttctgctg agatgcctca cacagagact gtctctcctc ttccttcctc | 660 |
| catggatctg cttattcagg acagccctga ttcttccacc agtcccaaag caaacaacc | 720 |
| cacttctgca gagaatagtg tcgcaaaaaa ggaagacaag gtcccggtca agaaacagaa | 780 |
| gaccagaact gtgttctctt ccacccagct gtgtgtactc aatgatagat tcagagaca | 840 |
| gaaatacctc agcctccagc agatgcaaga actctccaac atcctgaacc tcagctacaa | 900 |
| acaggtgaag acctggttcc agaaccagag aatgaaatct aagaggtggc agaaaaacaa | 960 |
| ctggccgaag aatagcaatg gtgtgacgca gaaggcctca gcacctacct accccagcct | 1020 |
| ctactcttcc taccaccagg gatgcctggt gaacccgact gggaaccttc caatgtggag | 1080 |
| caaccagacc tggaacaatt caacctggag caaccagacc cagaacatcc agtcctggag | 1140 |
| caaccactcc tggaacactc agacctggtg cacccaatcc tggaacaatc aggcctggaa | 1200 |
| cagtcccttc tataactgtg gagaggaatc tctgcagtcc tgcatgcact tccagccaaa | 1260 |
| ttctcctgcc agtgacttgg aggctgcctt ggaagctgct ggggaaggcc ttaatgtaat | 1320 |
| acagcagacc actaggtatt ttagtactcc acaaaccatg gatttattcc taaactactc | 1380 |

```
catgaacatg caacctgaag acgtgtgaga tatcactagt gactgactag gatctggtta    1440
ccactaaacc agcctcaaga acacccgaat ggagtctcta agctacataa taccaactta    1500
cactttacaa aatgttgtcc cccaaaatgt agccattcgt atctgctcct aataaaaaga    1560
aagtttcttc acattctgga tcctctagag tcgacctgca ggcatgcaag cttggcgtaa    1620
tcatggtcat agctgtttcc tgtgtgaaat tgttatccgc tcacaattcc acacaacata    1680
cgagccggaa gcataaagtg taaagcctgg ggtgcctaat gagtgagcta actcacatta    1740
attgcgttgc gctcactgcc cgctttccag tcgggaaacc tgtcgtgcca gctgcattaa    1800
tgaatcggcc aacgcgcggg gagaggcggt ttgcgtattg ggcgctcttc cgcttcctcg    1860
ctcactgact cgctgcgctc ggtcgttcgg ctgcggcgag cggtatcagc tcactcaaag    1920
gcggtaatac ggttatccac agaatcaggg gataacgcag gaaagaacat gtgagcaaaa    1980
ggccagcaaa aggccaggaa ccgtaaaaag gccgcgttgc tggcgttttt ccataggctc    2040
cgcccccctg acgagcatca caaaaatcga cgctcaagtc agaggtggcg aaacccgaca    2100
ggactataaa gataccaggc gtttccccct ggaagctccc tcgtgcgctc tcctgttccg    2160
accctgccgc ttaccggata cctgtccgcc tttctccctt cgggaagcgt ggcgctttct    2220
catagctcac gctgtaggta tctcagttcg gtgtaggtcg ttcgctccaa gctgggctgt    2280
gtgcacgaac cccccgttca gcccgaccgc tgcgccttat ccggtaacta tcgtcttgag    2340
tccaacccgg taagacacga cttatcgcca ctggcagcag ccactggtaa caggattagc    2400
agagcgaggt atgtaggcgg tgctacagag ttcttgaagt ggtggcctaa ctacggctac    2460
actagaagaa cagtatttgg tatctgcgct ctgctgaagc cagttacctt cggaaaaaga    2520
gttggtagct cttgatccgg caaacaaacc accgctggta gcggtggttt ttttgtttgc    2580
aagcagcaga ttacgcgcag aaaaaaagga tctcaagaag atcctttgat cttttctacg    2640
gggtctgacg ctcagtggaa cgaaaactca cgttaaggga ttttggtcat gagattatca    2700
aaaaggatct tcacctagat ccttttaaat taaaaatgaa gttttaaatc aatctaaagt    2760
atatatgagt aaacttggtc tgacagttac caatgcttaa tcagtgaggc acctatctca    2820
gcgatctgtc tatttcgttc atccatagtt gcctgactcc ccgtcgtgta gataactacg    2880
atacgggagg gcttaccatc tggccccagt gctgcaatga taccgcgaga cccacgctca    2940
ccggctccag atttatcagc aataaaccag ccagccggaa gggccgagcg cagaagtggt    3000
cctgcaactt tatccgcctc catccagtct attaattgtt gccgggaagc tagagtaagt    3060
agttcgccag ttaatagttt gcgcaacgtt gttgccattg ctacaggcat cgtggtgtca    3120
cgctcgtcgt ttggtatggc ttcattcagc tccggttccc aacgatcaag gcgagttaca    3180
tgatccccca tgttgtgcaa aaaagcggtt agctccttcg gtcctccgat cgttgtcaga    3240
agtaagttgg ccgcagtgtt atcactcatg gttatggcag cactgcataa ttctcttact    3300
gtcatgccat ccgtaagatg cttttctgtg actggtgagt actcaaccaa gtcattctga    3360
gaatagtgta tgcggcgacc gagttgctct tgcccggcgt caatacggga taataccgcg    3420
ccacatagca gaactttaaa agtgctcatc attggaaaac gttcttcggg gcgaaaactc    3480
tcaaggatct taccgctgtt gagatccagt tcgatgtaac ccactcgtgc acccaactga    3540
tcttcagcat cttttacttt caccagcgtt tctgggtgag caaaaacagg aaggcaaaat    3600
gccgcaaaaa agggaataag ggcgacacgg aaatgttgaa tactcatact cttccttttt    3660
caatattatt gaagcattta tcagggttat tgtctcatga gcggatacat atttgaatgt    3720
atttagaaaa ataaacaaat aggggttccg cgcacatttc cccgaaaagt gccacctgac    3780
```

| | |
|---|---|
| gtctaagaaa ccattattat catgacatta acctataaaa ataggcgtat cacgaggccc | 3840 |
| tttcgtc | 3847 |

<210> SEQ ID NO 7
<211> LENGTH: 4304
<212> TYPE: DNA
<213> ORGANISM: Artificial sequence
<220> FEATURE:
<223> OTHER INFORMATION: Synthetic

<400> SEQUENCE: 7

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt ctaatacgac tcactatagg | 420 |
| gtaatacaag cttgcttgtt cttttttgcag aagctcagaa taaacgctca actttggcag | 480 |
| atctgataat cgccaccat ggattttttt cgggtagtgg aaaaccagca gcctcccgcg | 540 |
| acgatgcccc tcaacgttag cttcaccaac aggaactatg acctcgacta cgactcggtg | 600 |
| cagccgtatt tctactgcga cgaggaggag aacttctacc agcagcagca gcagagcgag | 660 |
| ctgcagcccc cggcgcccag cgaggatatc tggaagaaat cgagctgct gcccacccccg | 720 |
| cccctgtccc ctagccgccg ctccgggctc tgctcgccct cctacgttgc ggtcacaccc | 780 |
| ttctcccttc ggggagacaa cgacggcggt ggcgggagct tctccacggc cgaccagctg | 840 |
| gagatggtga ccgagctgct gggaggagac atggtgaacc agagtttcat ctgcgacccg | 900 |
| gacgacgaga ccttcatcaa aaacatcatc atccaggact gtatgtggag cggcttctcg | 960 |
| gccgccgcca gctcgtctc agagaagctg gcctcctacc aggctgcgcg caaagacagc | 1020 |
| ggcagcccga accccgcccg cggccacagc gtctgctcca cctccagctt gtacctgcag | 1080 |
| gatctgagcg ccgccgcctc agagtgcatc gaccccctcgg tggtcttccc ctaccctctc | 1140 |
| aacgacagca gctcgcccaa gtcctgcgcc tcgcaagact ccagcgcctt ctctccgtcc | 1200 |
| tcggattctc tgctctcctc gacggagtcc tccccgcagg gcagccccga gcccctggtg | 1260 |
| ctccatgagg agacaccgcc caccaccagc agcgactctg aggaggaaca agaagatgag | 1320 |
| gaagaaatcg atgttgtttc tgtggaaaag aggcaggctc ctggcaaaag gtcagagtct | 1380 |
| ggatcacctt ctgctggagg ccacagcaaa cctcctcaca gcccactggt cctcaagagg | 1440 |
| tgccacgtct ccacacatca gcacaactac gcagcgcctc cctccactcg gaaggactat | 1500 |
| cctgctgcca gagggtcaa gttggacagt gtcagagtcc tgagacagat cagcaacaac | 1560 |
| cgaaaatgca ccagccccag gtcctcggac accgaggaga atgtcaagag gcgaacacac | 1620 |
| aacgtcttgg agcgccagag gaggaacgag ctaaaacgga gcttttttgc cctgcgtgac | 1680 |
| cagatcccgg agttggaaaa caatgaaaag gccccccaagg tagttatcct taaaaaagcc | 1740 |
| acagcataca tcctgtccgt ccaagcagag gagcaaaagc tcatttctga agaggacttg | 1800 |
| ttgcggaaac gacgagaaca gttgaaacac aaacttgaac agctacgaa ctcttgtgcg | 1860 |
| taaggatcat cactagtgac tgactaggat ctggttacca ctaaaccagc ctcaagaaca | 1920 |

```
cccgaatgga gtctctaagc tacataatac caacttacac tttacaaaat gttgtccccc    1980
aaaatgtagc cattcgtatc tgctcctaat aaaaagaaag tttcttcaca ttctggatcc    2040
tctagagtcg acctgcaggc atgcaagctt ggcgtaatca tggtcatagc tgtttcctgt    2100
gtgaaattgt tatccgctca caattccaca acatacga gccggaagca taaagtgtaa     2160
agcctggggt gcctaatgag tgagctaact cacattaatt gcgttgcgct cactgcccgc    2220
tttccagtcg ggaaacctgt cgtgccagct gcattaatga atcggccaac gcgcggggag    2280
aggcggtttg cgtattgggc gctcttccgc ttcctcgctc actgactcgc tgcgctcggt    2340
cgttcggctg cggcgagcgg tatcagctca ctcaaaggcg gtaatacggt tatccacaga    2400
atcaggggat aacgcaggaa agaacatgtg agcaaaaggc cagcaaaagg ccaggaaccg    2460
taaaaaggcc gcgttgctgg cgttttttcca taggctccgc cccctgacg agcatcacaa    2520 aaatcgacgc tcaagtcaga ggtggcgaaa cccgacagga ctataaagat accaggcgtt    2580 tcccctgga agctcctcg tgcgctctc tgttccgacc ctgccgctta ccggatacct      2640
gtccgccttt ctcccttcgg gaagcgtggc gctttctcat agctcacgct gtaggtatct    2700
cagttcggtg taggtcgttc gctccaagct gggctgtgtg cacgaacccc ccgttcagcc    2760
cgaccgctgc gccttatccg gtaactatcg tcttgagtcc aacccggtaa gacacgactt    2820
atcgccactg gcagcagcca ctggtaacag gattagcaga gcgaggtatg taggcggtgc    2880
tacagagttc ttgaagtggt ggcctaacta cggctacact agaagaacag tatttggtat    2940
ctgcgctctg ctgaagccag ttaccttcgg aaaagagtt ggtagctctt gatccggcaa     3000
acaaaccacc gctggtagcg tggtttttt tgtttgcaag cagcagatta cgcgcagaaa    3060
aaaaggatct caagaagatc ctttgatctt ttctacgggg tctgacgctc agtggaacga    3120
aaactcacgt taagggattt tggtcatgag attatcaaaa aggatcttca cctagatcct    3180
tttaaattaa aaatgaagtt ttaaatcaat ctaaagtata tatgagtaaa cttggtctga    3240
cagttaccaa tgcttaatca gtgaggcacc tatctcagcg atctgtctat ttcgttcatc    3300
catagttgcc tgactccccg tcgtgtagat aactacgata cgggagggct taccatctgg    3360
ccccagtgct gcaatgatac cgcgagaccc acgctcaccg gctccagatt tatcagcaat    3420
aaaccagcca gccggaaggg ccgagcgcag aagtggtcct gcaactttat ccgcctccat    3480
ccagtctatt aattgttgcc gggaagctag agtaagtagt tcgccagtta atagtttgcg    3540
caacgttgtt gccattgcta caggcatcgt ggtgtcacgc tcgtcgtttg gtatggcttc    3600
attcagctcc ggttcccaac gatcaaggcg agttacatga tcccccatgt tgtgcaaaaa    3660
agcggttagc tccttcggtc ctccgatcgt tgtcagaagt aagttggccg cagtgttatc    3720
actcatggtt atggcagcac tgcataattc tcttactgtc atgccatccg taagatgctt    3780
ttctgtgact ggtgagtact caaccaagtc attctgagaa tagtgtatgc ggcgaccgag    3840
ttgctcttgc ccggcgtcaa tacgggataa taccgcgcca catagcagaa ctttaaaagt    3900
gctcatcatt ggaaaacgtt cttcggggcg aaaactctca aggatcttac cgctgttgag    3960
atccagttcg atgtaaccca ctcgtgcacc caactgatct tcagcatctt ttactttcac    4020
cagcgtttct gggtgagcaa aaacaggaag gcaaaatgcc gcaaaaaagg gaataagggc    4080
gacacggaaa tgttgaatac tcatactctt ccttttcaa tattattgaa gcatttatca    4140
gggttattgt ctcatgagcg gatacatatt tgaatgtatt tagaaaaata aacaaatagg    4200
ggttccgcgc acatttcccc gaaaagtgcc acctgacgtc taagaaacca ttattatcat    4260
gacattaacc tataaaaata ggcgtatcac gaggcccttt cgtc                     4304
```

<210> SEQ ID NO 8
<211> LENGTH: 4251
<212> TYPE: DNA
<213> ORGANISM: Artificial sequence
<220> FEATURE:
<223> OTHER INFORMATION: Synthetic

<400> SEQUENCE: 8

| | | | | | | |
|---|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | ctaatacgac | tcactatagg | 420 |
| gtaatacaag | cttgcttgtt | cttttttgcag | aagctcagaa | taaacgctca | actttggcag | 480 |
| atctgccacc | atgcccctca | acgttagctt | caccaacagg | aactatgacc | tcgactacga | 540 |
| ctcggtgcag | ccgtatttct | actgcgacga | ggaggagaac | ttctaccagc | agcagcagca | 600 |
| gagcgagctg | cagcccccgg | cgcccagcga | ggatatctgg | aagaaattcg | agctgctgcc | 660 |
| cgcgccgccc | ctgtccccta | gccgccgctc | cgggctctgc | tcgcctcct | acgttgcggt | 720 |
| cacacccttc | tcccttcggg | gagacaacga | cggcggtggc | gggagcttct | ccacggccga | 780 |
| ccagctggag | atggtgaccg | agctgctggg | aggagacatg | gtgaaccaga | gtttcatctg | 840 |
| cgacccggac | gacgagacct | tcatcaaaaa | catcatcatc | caggactgta | tgtggagcgg | 900 |
| cttctcggcc | gccgccaagc | tcgtctcaga | gaagctggcc | tcctaccagg | ctgcgcgcaa | 960 |
| agacagcggc | agcccgaacc | ccgccgcgcg | ccacagcgtc | tgctccacct | ccagcttgta | 1020 |
| cctgcaggat | ctgagcgccg | ccgcctcaga | gtgcatcgac | ccctcggtgg | tcttcccta | 1080 |
| ccctctcaac | gacagcagct | cgcccaagtc | ctgcgcctcg | caagactcca | gcgccttctc | 1140 |
| tccgtcctcg | gattctctgc | tctcctcgac | ggagtcctcc | ccgcagggca | gccccgagcc | 1200 |
| cctggtgctc | catgaggaga | caccgccac | caccagcagc | gactctgagg | aggaacaaga | 1260 |
| agatgaggaa | gaaatcgatg | ttgtttctgt | ggaaaagagg | caggctcctg | gcaaaaggtc | 1320 |
| agagtctgga | tcaccttctg | ctggaggcca | cagcaaacct | cctcacagcc | cactggtcct | 1380 |
| caagaggtgc | cacgtctcca | cacatcagca | caactacgca | gcgcctccct | ccactcggaa | 1440 |
| ggactatcct | gctgccaaga | gggtcaagtt | ggacagtgtc | agagtcctga | gacagatcag | 1500 |
| caacaaccga | aaatgcacca | gccccaggtc | ctcggacacc | gaggagaatg | tcaagaggcg | 1560 |
| aacacacaac | gtcttggagc | gccagaggag | gaacgagcta | aaacggagct | ttttgccct | 1620 |
| gcgtgaccag | atcccggagt | tggaaaacaa | tgaaaaggcc | cccaaggtag | ttatccttaa | 1680 |
| aaaagccaca | gcatacatcc | tgtccgtcca | agcagaggag | caaaagctca | tttctgaaga | 1740 |
| ggacttgttg | cggaaacgac | gagaacagtt | gaaacacaaa | cttgaacagc | tacggaactc | 1800 |
| ttgtgcgtaa | ggatcatcac | tagtgactga | ctaggatctg | gttaccacta | aaccagcctc | 1860 |
| aagaacaccc | gaatggagtc | tctaagctac | ataataccaa | cttacacttt | acaaaatgtt | 1920 |
| gtcccccaaa | atgtagccat | tcgtatctgc | tcctaataaa | aagaaagttt | cttcacattc | 1980 |
| tggatcctct | agagtcgacc | tgcaggcatg | caagcttggc | gtaatcatgg | tcatagctgt | 2040 |

```
ttcctgtgtg aaattgttat ccgctcacaa ttccacacaa catacgagcc ggaagcataa    2100
agtgtaaagc ctggggtgcc taatgagtga gctaactcac attaattgcg ttgcgctcac    2160
tgcccgcttt ccagtcggga aacctgtcgt gccagctgca ttaatgaatc ggccaacgcg    2220
cggggagagg cggtttgcgt attgggcgct cttccgcttc ctcgctcact gactcgctgc    2280
gctcggtcgt tcggctgcgg cgagcggtat cagctcactc aaaggcggta atacggttat    2340
ccacagaatc aggggataac gcaggaaaga acatgtgagc aaaaggccag caaaaggcca    2400
ggaaccgtaa aaaggccgcg ttgctggcgt ttttccatag gctccgcccc cctgacgagc    2460
atcacaaaaa tcgacgctca agtcagaggt ggcgaaaccc gacaggacta taaagatacc    2520
aggcgtttcc ccctggaagc tccctcgtgc gctctcctgt tccgaccctg ccgcttaccg    2580
gatacctgtc cgcctttctc ccttcgggaa gcgtggcgct ttctcatagc tcacgctgta    2640
ggtatctcag ttcggtgtag tcgttcgctc caagctggg ctgtgtgcac gaaccccccg    2700
ttcagcccga ccgctgcgcc ttatccggta actatcgtct tgagtccaac ccggtaagac    2760
acgacttatc gccactggca gcagccactg gtaacaggat tagcagagcg aggtatgtag    2820
gcggtgctac agagttcttg aagtggtggc ctaactacgg ctacactaga agaacagtat    2880
ttggtatctg cgctctgctg aagccagtta ccttcggaaa aagagttggt agctcttgat    2940
ccggcaaaca aaccaccgct ggtagcggtg ttttttttgt ttgcaagcag cagattacgc    3000
gcagaaaaaa aggatctcaa gaagatcctt tgatctttc tacggggtct gacgctcagt    3060
ggaacgaaaa ctcacgttaa gggattttgg tcatgagatt atcaaaaagg atcttcacct    3120
agatcctttt aaattaaaaa tgaagtttta atcaatcta agtatatat gagtaaactt    3180 ggtctgacag ttaccaatgc ttaatcagtg aggcacctat ctcagcgatc tgtctatttc    3240
gttcatccat agttgcctga ctccccgtcg tgtagataac tacgatacgg gagggcttac    3300
catctggccc cagtgctgca atgataccgc gagacccacg ctcaccggct ccagatttat    3360
cagcaataaa ccagccagcc ggaagggccg agcgcagaag tggtcctgca actttatccg    3420
cctccatcca gtctattaat tgttgccggg aagctagagt aagtagttcg ccagttaata    3480
gtttgcgcaa cgttgttgcc attgctacag gcatcgtggt gtcacgctcg tcgtttggta    3540
tggcttcatt cagctccggt tcccaacgat caaggcgagt tacatgatcc cccatgttgt    3600
gcaaaaaagc ggttagctcc ttcggtcctc cgatcgttgt cagaagtaag ttggccgcag    3660
tgttatcact catggttatg gcagcactgc ataattctct tactgtcatg ccatccgtaa    3720 gatgctttc tgtgactggt gagtactcaa ccaagtcatt ctgagaatag tgtatgcggc    3780
gaccgagttg ctcttgcccg gcgtcaatac gggataatac cgcgccacat agcagaactt    3840
taaaagtgct catcattgga aaacgttctt cggggcgaaa actctcaagg atcttaccgc    3900
tgttgagatc cagttcgatg taacccactc gtgcacccaa ctgatcttca gcatctttta    3960
ctttcaccag cgtttctggg tgagcaaaaa caggaaggca aaatgccgca aaaaagggaa    4020
taagggcgac acggaaatgt tgaatactca tactcttcct ttttcaatat tattgaagca    4080
tttatcaggg ttattgtctc atgagcggat acatatttga atgtatttag aaaaataaac    4140 aaatagggt tccgcgcaca tttccccgaa aagtgccacc tgacgtctaa gaaaccatta    4200
ttatcatgac attaacctat aaaaataggc gtatcacgag gcccttcgt c                4251
```

<210> SEQ ID NO 9
<211> LENGTH: 4251
<212> TYPE: DNA
<213> ORGANISM: Artificial sequence
<220> FEATURE:
<223> OTHER INFORMATION: Synthetic

<400> SEQUENCE: 9

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ctaatacgac tcactatagg     420
gtaatacaag cttgcttgtt cttttttgcag aagctcagaa taaacgctca actttggcag     480
atctgccacc atgcccctca cgttagcttc caccaacagg aactatgacc tcgactacga     540
ctcggtgcag ccgtatttct actgcgacga ggaggagaac ttctaccagc agcagcagca     600
gagcgagctg cagcccccgg cgcccagcga ggatatctgg aagaaattcg agctgctgcc     660
cacccccgcc ctgtccccta gccgccgctc cgggctctgc tcgccctcct acgttgcggt     720
cacacccttc tcccttcggg gagacaacga cggcggtggc gggagcttct ccacggccga     780
ccagctggag atggtgaccg agctgctggg aggagacatg gtgaaccaga gtttcatctg     840
cgacccggac gacgagacct tcatcaaaaa catcatcatc caggactgta tgtggagcgg     900
cttctcggcc gccgccaagc tcgtctcaga aagctggcc tcctaccagg ctgcgcgcaa     960
agacagcggc agcccgaacc ccgcccgcgg ccacagcgtc tgctccacct ccagcttgta    1020
cctgcaggat ctgagcgccg ccgcctcaga gtgcatcgac ccctcggtgg tcttcccta    1080
ccctctcaac gacagcagct cgcccaagtc ctgcgcctcg caagactcca gcgccttctc    1140
tccgtcctcg gattctctgc tctcctcgac ggagtcctcc ccgcagggca gccccgagcc    1200
cctggtgctc catgaggaga caccgcccac caccagcagc gactctgagg aggaacaaga    1260
agatgaggaa gaaatcgatg ttgtttctgt ggaaaagagg caggctcctg gcaaaaggtc    1320
agagtctgga tcaccttctg ctggaggcca cagcaaacct cctcacagcc cactggtcct    1380
caagaggtgc cacgtctcca cacatcagca caactacgca gcgcctcct ccactcggaa    1440
ggactatcct gctgccaaga gggtcaagtt ggacagtgtc agagtcctga cagatcag    1500
caacaaccga aaatgcacca gccccaggtc ctcggacacc gaggagaatg tcaagaggcg    1560
aacacacaac gtcttggagc gccagaggag gaacgagcta aaacggagct tttttgccct    1620
gcgtgaccag atcccggagt tggaaaacaa tgaaaaggcc cccaaggtag ttatccttaa    1680
aaaagccaca gcatacatcc tgtccgtcca agcagaggag caaaagctca tttctgaaga    1740
ggacttgttg cggaaacgac gagaacagtt gaaacacaaa cttgaacagc tacggaactc    1800
ttgtgcgtaa ggatcatcac tagtgactga ctaggatctg gttaccacta aaccagcctc    1860
aagaacaccc gaatggagtc tctaagctac ataataccaa cttacacttt acaaaatgtt    1920
gtcccccaaa atgtagccat tcgtatctgc tcctaataaa aagaaagttt cttcacattc    1980
tggatcctct agagtcgacc tgcaggcatg caagcttggc gtaatcatgg tcatagctgt    2040
ttcctgtgtg aaattgttat ccgctcacaa ttccacacaa catacgagcc ggaagcataa    2100
agtgtaaagc ctggggtgcc taatgagtga gctaactcac attaattgcg ttgcgctcac    2160
tgcccgcttt ccagtcggga aacctgtcgt gccagctgca ttaatgaatc ggccaacgcg    2220
```

```
cggggagagg cggtttgcgt attgggcgct cttccgcttc ctcgctcact gactcgctgc    2280
gctcggtcgt tcggctgcgg cgagcggtat cagctcactc aaaggcggta atacggttat    2340
ccacagaatc agggagataac gcaggaaaga acatgtgagc aaaaggccag caaaaggcca    2400
ggaaccgtaa aaaggccgcg ttgctggcgt ttttccatag gctccgcccc cctgacgagc    2460
atcacaaaaa tcgacgctca agtcagaggt ggcgaaaccc gacaggacta taaagatacc    2520
aggcgtttcc ccctggaagc tccctcgtgc gctctcctgt tccgaccctg ccgcttaccg    2580
gatacctgtc cgcctttctc ccttcgggaa gcgtggcgct ttctcatagc tcacgctgta    2640
ggtatctcag ttcggtgtag gtcgttcgct ccaagctggg ctgtgtgcac gaaccccccg    2700
ttcagcccga ccgctgcgcc ttatccggta actatcgtct tgagtccaac ccggtaagac    2760
acgacttatc gccactggca gcagccactg gtaacaggat tagcagagcg aggtatgtag    2820
gcggtgctac agagttcttg aagtggtggc ctaactacgg ctacactaga agaacagtat    2880
ttggtatctg cgctctgctg aagccagtta ccttcggaaa aagagttggt agctcttgat    2940
ccggcaaaca aaccaccgct ggtagcggtg gttttttgt ttgcaagcag cagattacgc    3000
gcagaaaaaa aggatctcaa gaagatcctt tgatcttttc tacggggtct gacgctcagt    3060
ggaacgaaaa ctcacgttaa gggattttgg tcatgagatt atcaaaaagg atcttcacct    3120
agatcctttt aaattaaaaa tgaagtttta aatcaatcta agtatatat gagtaaactt    3180 ggtctgacag ttaccaatgc ttaatcagtg aggcacctat ctcagcgatc tgtctatttc    3240
gttcatccat agttgcctga ctccccgtcg tgtagataac tacgatacgg gagggcttac    3300
catctggccc cagtgctgca atgataccgc gagacccacg ctcaccggct ccagatttat    3360
cagcaataaa ccagccagcc ggaagggccg agcgcagaag tggtcctgca actttatccg    3420
cctccatcca gtctattaat tgttgccggg aagctagagt aagtagttcg ccagttaata    3480
gtttgcgcaa cgttgttgcc attgctacag gcatcgtggt gtcacgctcg tcgtttggta    3540
tggcttcatt cagctccggt tcccaacgat caaggcgagt tacatgatcc cccatgttgt    3600
gcaaaaaagc ggttagctcc ttcggtcctc cgatcgttgt cagaagtaag ttggccgcag    3660
tgttatcact catggttatg gcagcactgc ataattctct tactgtcatg ccatccgtaa    3720
gatgcttttc tgtgactggt gagtactcaa ccaagtcatt ctgagaatag tgtatgcggc    3780
gaccgagttg ctcttgcccg gcgtcaatac gggataatac cgcgccacat agcagaactt    3840
taaaagtgct catcattgga aaacgttctt cggggcgaaa actctcaagg atcttaccgc    3900
tgttgagatc cagttcgatg taacccactc gtgcacccaa ctgatcttca gcatctttta    3960
ctttcaccag cgtttctggg tgagcaaaaa caggaaggca aaatgccgca aaaagggaa    4020 taagggcgac acggaaatgt tgaatactca tactcttcct ttttcaatat tattgaagca    4080
tttatcaggg ttattgtctc atgagcggat acatatttga atgtatttag aaaaataaac    4140
aaataggggt tccgcgcaca tttccccgaa aagtgccacc tgacgtctaa gaaaccatta    4200
ttatcatgac attaacctat aaaaataggc gtatcacgag gccctttcgt c             4251

<210> SEQ ID NO 10
<211> LENGTH: 4018
<212> TYPE: DNA
<213> ORGANISM: Artificial sequence
<220> FEATURE:
<223> OTHER INFORMATION: Synthetic
```

<400> SEQUENCE: 10

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta cgccagggt    360
tttcccagtc acgacgttgt aaaacgacgg ccagtgaatt ctaatacgac tcactatagg   420
gtaatacaag cttgcttgtt cttttttgcag aagctcagaa taaacgctca actttggcag  480
atctgccacc atggactacg actcgtacca gcactatttc tacgactatg actgcgggga   540
ggatttctac cgctccacgg cgcccagcga ggacatctgg aagaaattcg agctggtgcc   600
atcgcccccc acgtcgccgc cctgggcctt ggtcccggc gcaggggacc cggccccgg    660
gattggtccc ccggagccgt ggcccggagg gtgcaccgga gacgaagcgg aatcccgggg   720
ccactcgaaa ggctggggca ggaactacgc ctccatcata cgccgtgact gcatgtggag   780
cggcttctcg gcccgggaac ggctggagag agctgtgagc gaccggctcg ctcctggcgc   840
gccccggggg aacccgccca aggcgtccgc cgccccggac tgcactccca gcctcgaagc   900
cggcaacccg gcgcccgccg cccctgtcc gctgggcgaa cccaagaccc aggcctgctc    960
cgggtccgag agcccaagcg actcggaaa tgaagaaatt gatgttgtga cagtagagaa  1020
gaggcagtct ctgggtattc ggaagccggt caccatcacg gtgcgagcag accccctgga  1080
tccctgcatg aagcatttcc acatctccat ccatcagcaa cagcacaact atgctgcccg  1140
ttttcctcca gaaagctgct cccaagaaga ggcttcagag aggggtcccc aagaagaggt  1200
tctggagaga gatgctgcag ggaaaagga agatgaggag gatgaagaga ttgtgagtcc   1260
cccacctgta gaaagtgagg ctgcccagtc ctgccacccc aaacctgtca gttctgatac  1320
tgaggatgtg accaagagga agaatcacaa cttcctggag cgcaagaggc ggaatgacct  1380
gcgttcgcga ttcttggcgc tgagggacca ggtgcccacc ctggccagct gctcaaggc   1440
ccccaaagta gtgatcctaa gcaaggcctt ggaatacttg caagccctgg tggggctga   1500
gaagaggatg gctacagaga aaagacagct ccgatgccgg cagcagcagt tgcagaaaag  1560
aattgcatac ctcactggct actaaactag tgactgacta ggatctggtt accactaaac  1620
cagcctcaag aacacccgaa tggagtctct aagctacata ataccaactt acactttaca  1680
aaatgttgtc ccccaaaatg tagccattcg tatctgctcc taataaaag aaagtttctt   1740
cacattctgg atcctctaga gtcgacctgc aggcatgcaa gcttggcgta atcatggtca  1800
tagctgtttc ctgtgtgaaa ttgttatccg ctcacaattc cacacaacat acgagccgga  1860
agcataaagt gtaaagcctg gggtgcctaa tgagtgagct aactcacatt aattgcgttg  1920
cgctcactgc ccgctttcca gtcgggaaac ctgtcgtgcc agctgcatta tgaatcggc   1980
caacgcgcgg ggagaggcgg tttgcgtatt gggcgctctt ccgcttcctc gctcactgac  2040
tcgctgcgct cggtcgttcg gctgcggcga gcggtatcag ctcactcaaa ggcggtaata  2100
cggttatcca cagaatcagg ggataacgca ggaaagaaca tgtgagcaaa aggccagcaa  2160
aaggccagga accgtaaaaa ggccgcgttg ctggcgtttt tccataggct ccgcccccct  2220
gacgagcatc acaaaaatcg acgctcaagt cagaggtggc gaaacccgac aggactataa  2280
```

-continued

```
agataccagg cgtttccccc tggaagctcc ctcgtgcgct ctcctgttcc gaccctgccg    2340
cttaccggat acctgtccgc cttttctccct tcgggaagcg tggcgctttc tcatagctca    2400
cgctgtaggt atctcagttc ggtgtaggtc gttcgctcca agctgggctg tgtgcacgaa    2460
ccccccgttc agcccgaccg ctgcgcctta tccgtaacct atcgtcttga gtccaacccg    2520
gtaagacacg acttatcgcc actggcagca gccactggta acaggattag cagagcgagg    2580
tatgtaggcg gtgctacaga gttcttgaag tggtggccta actacggcta cactagaaga    2640
acagtatttg gtatctgcgc tctgctgaag ccagttacct tcggaaaaag agttggtagc    2700
tcttgatccg gcaaacaaac caccgctggt agcggtggtt ttttgtttg caagcagcag    2760 attacgcgca gaaaaaaagg atctcaagaa gatcctttga tcttttctac ggggtctgac    2820
gctcagtgga acgaaaactc acgttaaggg attttggtca tgagattatc aaaaaggatc    2880
ttcacctaga tccttttaaa ttaaaaatga agttttaaat caatctaaag tatatatgag    2940
taaacttggt ctgacagtta ccaatgctta atcagtgagg cacctatctc agcgatctgt    3000
ctatttcgtt catccatagt tgcctgactc cccgtcgtgt agataactac gatacgggag    3060
ggcttaccat ctggccccag tgctgcaatg ataccgcgag acccacgctc accggctcca    3120
gatttatcag caataaacca gccagccgga agggccgagc gcagaagtgg tcctgcaact    3180
ttatccgcct ccatccagtc tattaattgt tgccgggaag ctagagtaag tagttcgcca    3240
gttaatagtt tgcgcaacgt tgttgccatt gctacaggca tcgtggtgtc acgctcgtcg    3300
tttggtatgg cttcattcag ctccggttcc caacgatcaa ggcgagttac atgatccccc    3360
atgttgtgca aaaaagcggt tagctccttc ggtcctccga tcgttgtcag aagtaagttg    3420
gccgcagtgt tatcactcat ggttatggca gcactgcata attctcttac tgtcatgcca    3480
tccgtaagat gcttttctgt gactggtgag tactcaacca agtcattctg agaatagtgt    3540
atgcggcgac cgagttgctc ttgcccggcg tcaatacggg ataataccgc gccacatagc    3600
agaactttaa aagtgctcat cattggaaaa cgttcttcgg ggcgaaaact ctcaaggatc    3660
ttaccgctgt tgagatccag ttcgatgtaa cccactcgtg cacccaactg atcttcagca    3720
tcttttactt tcaccagcgt ttctgggtga gcaaaaacag gaaggcaaaa tgccgcaaaa    3780
aagggaataa gggcgacacg gaaatgttga atactcatac tcttcctttt tcaatattat    3840
tgaagcattt atcagggtta ttgtctcatg agcggataca tatttgaatg tatttagaaa    3900
aataaacaaa tagggggttcc gcgcacattt ccccgaaaag tgccacctga cgtctaagaa    3960
accattatta tcatgacatt aacctataaa aataggcgta tcacgaggcc ctttcgtc     4018
```

<210> SEQ ID NO 11
<211> LENGTH: 738
<212> TYPE: RNA
<213> ORGANISM: Homo sapiens

<400> SEQUENCE: 11

```
auggaaagcu cugccaagau ggagagcggc ggcgccggcc agcagcccca gccgcagccc      60
cagcagcccu uccugccgcc cgcagccugu uucuuugcca cggccgcagc cgcggcggcc     120
gcagccgccg cagcggcagc gcagagcgcg cagcagcagc agcagcagca gcagcagcag     180
cagcagcagc aggcgccgca gcugagaccg cggccgacg ccagcccuc aggggcggu       240 cacaagucag cgcccaagca agucaagcga cagcgcucgu cuucgcccga acugaugcgc     300
ugcaaacgcc ggcucaacuu cagcggcuuu ggcuacagcc ugccgcagca gcagccggcc     360
gccguggcgc gccgcaacga gcgcgagcgc aaccgcguca aguuggucaa ccugggcuuu     420
```

| | |
|---|---:|
| gccacccuuc gggagcacgu ccccaacggc gcggccaaca agaagaugag uaagguggag | 480 |
| acacugcgcu cggcggucga guacauccgc gcgcugcagc agcugcugga cgagcaugac | 540 |
| gcggugagcg ccgccuucca ggcaggcguc cugucgccca ccaucccccc caacuacucc | 600 |
| aacgacuuga acuccauggc cggcucgccg gucucauccu acucgucgga cgagggcucu | 660 |
| uacgacccgc ucagccccga ggagcaggag cuucucgacu ucaccaacug guucagaucu | 720 |
| gauaucacua gugacuga | 738 |

<210> SEQ ID NO 12
<211> LENGTH: 3576
<212> TYPE: RNA
<213> ORGANISM: Homo sapiens

<400> SEQUENCE: 12

| | |
|---|---:|
| auggaggugg acaccgagga gaagcggcau cgcacgcggu ccaaaggggu ucgaguuccc | 60 |
| guggaaccag ccauacaaga gcuguucagc ugucccaccc cuggcuguga cggcagugguu | 120 |
| caugucagug gcaaauaugc aagacacaga aguguauaug uugucccuu ggcgaaaaaa | 180 |
| agaaaaacac aagauaaaca gccccaggaa ccugcuccua aacgaaagcc auuugccgug | 240 |
| aaagcagaca gcuccucagu ggaugagugu gacgacagug auggacugga ggacauggau | 300 |
| gagaaggagg aggaugaggg ggaggaguac uccgaggaca augacgagcc aggggaugag | 360 |
| gacgaggagg acgaggaggg ggaccgggag gaggaggagg agaucgagga ggaggaugag | 420 |
| gacgaugacg aggauggaga agauguggag gaugaagaag aggaagagga ggaggaggag | 480 |
| gaggaggaag aggaagaaga aaacgaagac caucaaauga auugucacaa uacucgaaua | 540 |
| augcaagaca cagaaaagga ugauaacaau aaugacgaau augacaauua cgaugaacug | 600 |
| guggccaagu cauuguuaaa ccucggcaaa aucgcugagg augcagccua ccgggccagg | 660 |
| acugagucag aaaugaacag caauaccucc aauagucugg aagacgauag ugacaaaaac | 720 |
| gaaaaccugg gucggaaaag ugaguugagu uuagacuuag acagugaugu uguuagagaa | 780 |
| acaguggacu cccuuaaaacu auuagcccaa ggacacggug uugugcucuc agaaaacaug | 840 |
| aaugacagaa auuaugcaga cagcaugucg cagcaagaca uagaaauau gaauuacguc | 900 |
| auguuggga agcccaugaa caauggacuc auggaaaaga uggugagga gagcgaugag | 960 |
| gagguguguc ugagcagucu ggagguguuug aggaaucagu gcuucgaccu ggccaggaag | 1020 |
| cucagugaga ccaacccgca ggagaggaau ccgcagcaga acaugaacau ccgucagcau | 1080 |
| guccggccag aagaggacuu cccaggaagg acgccggaca gaaacuacuc ggacaugcug | 1140 |
| aaccucaugc ggcuggagga gcaguugagc ccccggucga gaguguugc cagcugugcg | 1200 |
| aaggaggaug ggugucauga gcgggacgac gauaccaccu cugugaacuc ggacaggucu | 1260 |
| gaagaggugu ucgacaugac caaggggaac cugacccugc uggagaaagc caucgcuuug | 1320 |
| gaaacggaaa gagcaaaggc caugaggag aagauggcca uggaagcugg gagagggac | 1380 |
| aauaugaggu cauaugagga ccagucuccg agacaacuuc ccggggagga cagaaagccu | 1440 |
| aaauccagug acagccaugu caaaaagcca acuauagauc ccucaagaac agaaaagaaa | 1500 |
| gagagcaagu guccaccccc cggguguaau ggaaccggcc acuaacugg gcuguacca | 1560 |
| caucaccgca gccugaccgg augcccgcac aaagauaggg uccuccagaa auccuugcc | 1620 |
| augcaugaaa uguccucaa guugcccacu ccgggcugca cggggcgcgg gcaugucaac | 1680 |
| agcaacagga acucccaccg aagccucucc ggaugcccga ucgcugcagc agagaaacug | 1740 |

| | |
|---|---|
| gccaaggcac aggaaaagca ccagagcugc gacgugucca aguccagcca ggccucggac | 1800 |
| cgcgugcuca ggccaaugug cuuugugaag cagcuggaga uuccucagua uggcuacaga | 1860 |
| aacaaugucc ccacaacuac gccgcguucc aaccuggcca aggagcucga gaaauauucc | 1920 |
| aagaccucgu uugaauacaa caguuacgac aaccauacuu auggcaagcg agccauagcu | 1980 |
| cccaaggugc aaaccaggga uauauccccc aaaggauaug augaugcgaa gcgguacugc | 2040 |
| aaggacccca gccccagcag cagcagcacc agcagcuacg cgcccagcag cagcagcaac | 2100 |
| cugagcugcg gcggggcag cagcgccagc agcacgugca gcaagagcag cuucgacuac | 2160 |
| acgcacgaca uggaggcggc ccacauggcg gccaccgcca uccucaaccu guccacgcgc | 2220 |
| ugccgcgaga ugccgcagaa ccugagcacc aagccgcagg accugugcgc cacgcggaac | 2280 |
| ccugacaugg aggugga uga gaacgggacc cuggaccuca gcaugaacaa gcagaggccg | 2340 |
| cgggacagcu gcugccccau ccugaccccu cuggagccca ugucccccca gcagcaggca | 2400 |
| gugaugaaca accgguguuu ccagcugggc gagggcgacu gcuggacuu gcccguagac | 2460 |
| uacaccaaaa ugaaaccccg gaggauagac gaggacgagu ccaaagacau uacuccagaa | 2520 |
| gacuuggacc cauuccagga ggcucuagaa gaaagacggu auccggggga ggugaccauc | 2580 |
| ccaaguccca aacccaagua cccucagugc aaggagagca aaaaggacuu aauaacucug | 2640 |
| ucuggcugcc cccuggcgga caaaagcauu cgaaguaugc uggccaccag cucccaagaa | 2700 |
| cucaagugcc ccacgccugg cugugauggu ucuggacaua ucaccggcaa uuaugcuucu | 2760 |
| caucggagcc uuucaggyug cccaagagca aagaaaagug guaucaggau agcacagagc | 2820 |
| aaagaagaua aagaagauca agaacccauc aggugccggu uccccgggug cgacggccag | 2880 |
| ggccacauca cuggaagua cgcgucccau cgcagcgccu ccgggugccc cuuggcggcc | 2940 |
| aagaggcaga aagacgggua ccugaauggc ucccaguucu ccuggaaguc ggucaagacg | 3000 |
| gaaggcaugu ccugccccac gccaggaugc gacggcucag gccacgucag cggcagcuuc | 3060 |
| cucacacacc gcagcuuguc aggaugcccc agagccacgu cagcgaugaa gaaggcaaag | 3120 |
| cuuucuggag agcagaugcu gaccaucaaa cagcgggcca gcaacgguau agaaaaugau | 3180 |
| gaagaaauca aacaguuaga ugaagaaauc aaggagcuaa augaauccaa uucccagaug | 3240 |
| gaagccgaua ugauuaaacu cagaacucag auuaccacga uggagagcaa ccugaagacc | 3300 |
| aucgaagagg agaacaaagu gauugagcag cagaacgagu cucuccucca cgagcuggcg | 3360 |
| aaccugagcc agucucugau ccacagccug gcuaacaucc agcugccgca cauggaucca | 3420 |
| aucaaugaac aaaauuuuga ugcuuacgug acuacuuuga cggaaaugua uacaaaucaa | 3480 |
| gaucguuauc agaguccaga aaauaaagcc cuacuggaaa auauaaagca ggcugugaga | 3540 |
| ggaauucagg ucagaucuga uaucacuagu gacuga | 3576 |

<210> SEQ ID NO 13
<211> LENGTH: 1281
<212> TYPE: RNA
<213> ORGANISM: Homo sapiens

<400> SEQUENCE: 13

| | |
|---|---|
| augggcgagc ucagcccca agguccucca agcuggacag acgagugucu caguucucag | 60 |
| gacgaggagc acgaggcaga caagaaggag gacgaccucg aagccaugaa cgcagaggag | 120 |
| gacucacuga gaacgggggg agaggaggag gacgaagaug aggaccugga agaggaggaa | 180 |
| gaagaggaag aggaggauga cgaucaaaag cccaagagac gcggcccaa aaagaagaag | 240 |
| augacuaagg cucgccugga gcguuuuaaa uugagacgca ugaaggcuaa cgcccgggag | 300 |

```
cggaaccgca ugcacggacu gaacgcggcg cuagacaacc ugcgcaaggu ggugccuugc    360
uauucuaaga cgcagaagcu guccaaaauc gagacucugc gcuuggccaa gaacuacauc    420
ugggcucugu cggagauccu gcgcucaggc aaaagcccag accuggucuc cuucguucag    480
acgcuuugca agggcuuauc ccaacccacc accaaccugg uugcgggcug ccugcaacuc    540
aauccucgga cuuucugcc ugagcagaac caggacaugc cccccaccu gccgacggcc      600
```

(Note: line 600 in image reads "aauccucgga cuuuucugcc ugagcagaac caggacaugc cccccaccu gccgacggcc")

```
agcgcuuccu ucccuguaca ccccuacucc uaccagucgc cugggcugcc cagaccgccu    660
uacgguacca uggacagcuc ccaugucuuc cacguuaagc uccgccgca cgccuacagc     720 gcagcgcugg agcccuucuu ugaaagcccu cugacugauu gcaccagccc uuccuuugau    780
ggaccccuca gccgccgcu cagcaucaau ggcaacuucu cuucaaaca cgaaccgucc      840 gccgaguuug agaaaaauua ugccuuuacc augcacauc cugcagcgac acuggcaggg    900
gcccaaagcc acggaucaau cuucucaggc accgcugccc cucgcugcga auccccaua     960 gacaauauua uguccuucga uagccauuca caucugagc gagucaugag ugcccagcuc   1020 aauugccauau uucaugauua gaggcacgcc aguuucacca uuccgggaa acgaacccac   1080 ugugcuuaca gugacugucg guuuacaaa aggcagcccu uugggacua cugcugcaaa    1140 gugcaaauac uccaagcuuc aagugauaua uguauuuauu gucauuacug ccuuuggaag   1200 aaacaggggga ucaaaguucc uguucaccuu auguauuauu uucuauagcu cuucuauuua   1260
aaaaauaaaa aaauacagua a                                               1281
```

<210> SEQ ID NO 14
<211> LENGTH: 1311
<212> TYPE: RNA
<213> ORGANISM: Artificial sequence
<220> FEATURE:
<223> OTHER INFORMATION: Synthetic

<400> SEQUENCE: 14

```
auggcgaccg cagcgucuaa ccacuacagc cugcucaccu ccagcgccuc caucgugcac     60
gccgagccgc ccggcggcau gcagcagggc gcggggggcu accgcgaagc gcagagccug   120
gugcagggcg acuacggcgc ucugcagagc aacggacacc cgcucagcca cgcucaccag   180
uggaucacag cgcuguccca cggcggcggc ggggcggcg cgacggcuc cccgugguce    240 accagccccc ugggccagcc ggacaucaag ccccgcgugg uggugcagca gggcggccgc    300
ggagacgagc ugcacgggcc aggcgcccug cagcagcagc aucagcagca gcaacagcaa    360
cagcagcagc aacagcagca acagcagcag cagcagcagc aacagcggcc gccgcaucug    420
gugcaccacg ccgcuaacca ccacccggga cccggggcau ggcggagcgc ggcggcugca    480
gcgcaccucc cacccuccau gggagcgucc aacggcggcu ugcucuacuc gcagcccagc    540 uucacggguga acggcaugcu gggcgccggc gggcagucgg ccgggcugca ccaccacggc    600
cugcgggacg cgcacgacga gccacaccau gccgaccacc acccgcaccc gcacucgcac    660
ccacaccagc agccgccgcc ccgccgcccc cgcagggucc cgccuggcca cccaggcgcg   720
caccacgacc cgcacucgga cgaggacacg ccgaccucgg acgaccugga gcaguucgcc    780
aagcaguuca gcagcggcg gaucaaacug ggauuuuac aagcggacgu ggggcuggcu     840
cugggcaccc uguauggcaa cguguucucg cagaccacca ucugcagguu ugaggcccug    900
cagcugagcu ucaagaacau gugcaagcug aagccuuugu ugaacaagug guugaggag     960 gcggacucgu ccucgggcag ccccacgagc auagacaaga ucgcagcgca agggcgcaag   1020
```

| | |
|---|---|
| cggaaaaagc ggaccuccau cgaggugagc gucaaggggg cucuggagag ccauuuccuc | 1080 |
| aaaugcccca agcccucggc ccaggagauc accucccucg cggacagcuu acagcuggag | 1140 |
| aaggaggugg ugagaguuug guuuuguaac aggagacaga aagagaaaag gaugacoccu | 1200 |
| cccggaggga cucugccggg cgccgaggau guguacgggg ggaguaggga cacuccacca | 1260 |
| caccacgggg ugcagacgcc cguccagaga ucaucacuag ugacugacua g | 1311 |

<210> SEQ ID NO 15
<211> LENGTH: 1332
<212> TYPE: RNA
<213> ORGANISM: Homo sapiens

<400> SEQUENCE: 15

| | |
|---|---|
| auggcgaccg cagcgucuaa ccacuacagc cugcucaccu ccagcgccuc caucgugcac | 60 |
| gccgagccgc ccggcggcau gcagcagggc gcggggggcu accgcgaagc gcagagccug | 120 |
| gugcagggcg acuacggcgc ucugcagagc aacggacacc cgcucagcca cgcucaccag | 180 |
| uggaucaccg cgcuguccca cggcggcggc ggcggggggcg guggcggcgg cgggggggc | 240 |
| ggggggcggcg gcggggggcgg cggcgacggc ucccoguggu ccaccagccc ccugggccag | 300 |
| ccggacauca agcccucggu ggugugcag cagggcggcc gcggagacga gcugcacggg | 360 |
| ccaggcgccc ugcagcagca gcaucagcag cagcaacagc aacagcagca gcaacagcag | 420 |
| caacagcagc agcagcagca gcaacagcgg ccgccgcauc uggugcacca cgccgcuaac | 480 |
| caccacccgg acccggggc augggcgagc gcggcggcug cagcgcaccu cccacccucc | 540 |
| augggagcgu ccaacggcgg cuugcucuac ucgcagccca gcuucacggu gaacggcaug | 600 |
| cugggcgccg gcgggcagcc ggccggucug caccaccacg gccugcggga cgcgcacgac | 660 |
| gagccacacc augccgacca ccaccccgcac ccgcacucgc acccacacca gcagccgccg | 720 |
| ccccccgccgc ccccgcaggg uccgccuggc cacccaggcg cgcaccacga cccgcacucg | 780 |
| gacgaggaca cgccgaccuc ggacgaccug gagcaguucg ccaagcaguu caagcagcgg | 840 |
| cggaucaaac ugggauuuac ccaagcggac gugggcugg cucugggcac ccuguauggc | 900 |
| aacguguucu cgcagaccac caucugcagg uuugaggccc ugcagcugag cuucaagaac | 960 |
| augugcaagc ugaagccuuu guugaacaag ugguuggagg aggcggacuc guccucgggc | 1020 |
| agccccacga gcauagacaa gaucagcgcg caagggcgca agcggaaaaa gcggaccucc | 1080 |
| aucgagguga gcgucaaggg ggcucuggag agccauuucc ucaaaugccc caagcccucg | 1140 |
| gcccaggaga ucaccucccu cgcggacagc uuacagcugg agaaggaggu ggugagaguu | 1200 |
| ugguuuguaa acaggagaca gaaagagaaa aggaugaccc cucccggagg gacucugccg | 1260 |
| ggcgccgagg auguguacgg ggggaguagg gacacuccac cacaccacgg ggugcagacg | 1320 |
| cccguccagu ga | 1332 |

<210> SEQ ID NO 16
<211> LENGTH: 1215
<212> TYPE: RNA
<213> ORGANISM: Homo sapiens

<400> SEQUENCE: 16

| | |
|---|---|
| ggguaauaca agcuugcuug uucuuuuugc agaagcucag aauaaacgcu caacuuuggc | 60 |
| agaucugcca ccauggagcu acugucgcca ccgcuccgcg acguagaccu gacggcccc | 120 |
| gacggcucuc ucugcccuu ugccacaacg gacgacuucu augacgaccc cguuucgac | 180 |
| uccccggacc ugcgcuucuu cgaagaccug gacccgcgcc ugaugcacgu gggcgcgcuc | 240 |

```
cugaaacccg aagagcacuc gcacuucccc gcggcggugc acccggcccc gggcgcacgu      300
gaggacgagc augugcgcgc gcccagcggg caccaccagg cgggccgcug ccuacugugg      360
gccugcaagg cgugcaagcg caagaccacc aacgccgacc gccgcaaggc cgccaccaug     420
cgcgagcggc gccgccugag caaaguaaau gaggccuuug agacacucaa gcgcugcacg     480
ucgagcaauc caaaccagcg guugcccaag guggagaucc ugcgcaacgc cauccgcuau     540
aucgagggcc ugcaggcucu gcugcgcgac caggacgccg cgccccugg cgccgcagcc     600 gccuucuaug cgccgggccc gcugcccccg ggccgcggcg gcgagcacua cagcggcgac     660
uccgacgcgu ccagcccgcg cuccaacugc uccgacggca ugauggacua cagcggcccc     720
ccgagcggcg cccggcggcg gaacugcuac gaaggcgccu acuacaacga ggcgcccagc     780
gaacccaggc ccgggaagag ugcggcggug ucgagccuag acugccuguc cagcaucgug     840
gagcgcaucu ccaccgagag cccugcggcg cccgcccucc ugcuggcgga cgugccuucu     900
gagucgccuc cgcgcaggca agaggcugcc gcccccagcg agggagagag cagcggcgac     960
cccacccagu caccggacgc cgcccccgcag ugcccugcgg gugcgaaccc caacccgaua   1020
uaccaggugc ucugaacuag ugacugacua ggaucugguu accacuaaac cagccucaag   1080
aacacccgaa uggagucucu aagcuacaua auaccaacuu acacuuuaca aaauguuguc    1140
ccccaaaaug uagccauucg uaucugcucc uaauaaaaag aaaguuucuu cacauucugg    1200
auccucuaga gucga                                                     1215
```

MAKING AND USING IN VITRO-SYNTHESIZED SSRNA FOR INTRODUCING INTO MAMMALIAN CELLS TO INDUCE A BIOLOGICAL OR BIOCHEMICAL EFFECT

The present application is a continuation of U.S. patent application Ser. No. 16/225,489, filed Dec. 19, 2018, now allowed, which is a continuation of U.S. patent application Ser. No. 14/368,399, filed Jun. 24, 2014, now U.S. Pat. No. 10,201,620, issued Feb. 12, 2019, which is a § 371 US National Entry Application of PCT/US2012/072301, filed Dec. 31, 2012, which claims priority to the following applications: U.S. Provisional Application Ser. No. 61/582,050 filed Dec. 30, 2011; and U.S. Provisional Application Ser. No. 61/582,080 filed Dec. 30, 2011; U.S. Provisional Application Ser. No. 61/651,738 filed May 25, 2012; each of which are herein incorporated by reference as it fully set forth therein.

SEQUENCE LISTING

The text of the computer readable sequence listing filed herewith, titled "32359-306_SEQUENCE_LISTING_ST25", created Mar. 15, 2022, having a file size of 62,708 bytes, is hereby incorporated by reference in its entirety.

FIELD OF THE INVENTION

The present invention relates to RNA compositions, systems, kits, and methods for making and using RNA compositions comprising in vitro-synthesized ssRNA or mRNA to induce a biological or biochemical effect in human or other mammalian cells into which the RNA composition is repeatedly or continuously introduced. In certain embodiments, the present invention pertains to RNA compositions and methods for making and using the same for inducing biological or biochemical effects in cells that are ex vivo in culture or cells that are in vivo in a tissue, organ or organism, wherein the biological effect may be induced in the cells, or in a tissue, organ or organism that contains the cells. In certain embodiments, the RNA compositions are "substantially free," "virtually free," "essentially free," "practically free," "extremely free," or "absolutely free" of dsRNA. In some embodiments, the biological or biochemical effect comprises reprogramming cells that exhibit a first differentiated state or phenotype to cells that exhibit a second differentiated state or phenotype, such as to reprogram human somatic cells to pluripotent stem cells, or to induce human fibroblast cells to neuron cells.

BACKGROUND

In 2006, it was reported (Takahashi and Yamanaka 2006) that the introduction of genes encoding four protein factors (OCT4 (Octamer-4; POU class 5 homeobox 1), SOX2 (SRY (sex determining region Y)-box 2), KLF4 (Krueppel-like factor 4), and c-MYC) into differentiated mouse somatic cells induced those cells to become pluripotent stem cells, (referred to herein as "induced pluripotent stem cells," "iPS cells," or "iPSCs"). Following this original report, pluripotent stem cells were also induced by transforming human somatic cells with genes encoding the similar human protein factors (OCT4, SOX2, KLF4, and c-MYC) (Takahashi et al. 2007), or by transforming human somatic cells with genes encoding human OCT4 and SOX2 factors plus genes encoding two other human factors, NANOG and LIN28 (Lin-28 homolog A) (Yu et al. 2007). All of these methods used retroviruses or lentiviruses to integrate genes encoding the reprogramming factors into the genomes of the transformed cells and the somatic cells were reprogrammed into iPS cells only over a long period of time (e.g., in excess of a week).

The generation iPS cells from differentiated somatic cells offers great promise as a possible means for treating diseases through cell transplantation. The possibility to generate iPS cells from somatic cells from individual patients also may enable development of patient-specific therapies with less risk due to immune rejection. Still further, generation of iPS cells from disease-specific somatic cells offers promise as a means to study and develop drugs to treat specific disease states (Ebert et al. 2009, Lee et al. 2009, Maehr et al. 2009).

Viral delivery of genes encoding protein reprogramming factors (or "iPSC factors") provides a highly efficient way to make iPS cells from somatic cells, but the integration of exogenous DNA into the genome, whether random or non-random, creates unpredictable outcomes and can ultimately lead to cancer (Nakagawa et al. 2008). New reports show that iPS cells can be created (at lower efficiency) by using other methods that do not require genome integration. For example, repeated transfections of expression plasmids containing genes for OCT4, SOX2, KLF4 and c-MYC into mouse embryonic fibroblasts to generate iPS cells was demonstrated (Okita et al. 2008). Induced pluripotent stem cells were also generated from human somatic cells by introduction of a plasmid that expressed genes encoding human OCT4, SOX2, c-MYC, KLF4, NANOG and LIN28 (Yu et al. 2009). Other successful approaches for generating iPS cells include treating somatic cells with: recombinant protein reprogramming factors (Zhou et al. 2009); non-integrating adenoviruses (Stadtfeld et al. 2008); or piggyBac transposons (Woltjen et al. 2009) to deliver reprogramming factors. Presently, the generation of iPS cells using these non-viral delivery techniques to deliver reprogramming factors is extremely inefficient. Future methods for generating iPS cells for potential clinical applications will need to increase the speed and efficiency of iPS cell formation while maintaining genome integrity.

SUMMARY OF THE INVENTION

The present invention relates to RNA compositions, systems, kits, and methods for making and using RNA compositions comprising in vitro-synthesized ssRNA or mRNA to induce a biological or biochemical effect in human or other mammalian cells into which the RNA composition is repeatedly or continuously introduced. In certain embodiments, the present invention pertains to RNA compositions and methods for making and using the same for inducing biological or biochemical effects in cells that are ex vivo in culture or cells that are in vivo in a tissue, organ or organism, wherein the biological effect may be induced in the cells, or in a tissue, organ or organism that contains the cells.

In 2006, it was reported (Takahashi and Yamanaka 2006) that the introduction of genes encoding four protein factors (OCT4 (Octamer-4; POU class 5 homeobox 1), SOX2 (SRY (sex determining region Y)-box 2), KLF4 (Krueppel-like factor 4), and c-MYC) into differentiated mouse somatic cells induced those cells to become pluripotent stem cells, (referred to herein as "induced pluripotent stem cells," "iPS cells," or "iPSCs"). Following this original report, pluripotent stem cells were also induced by transforming human somatic cells with genes encoding the similar human protein factors (OCT4, SOX2, KLF4, and c-MYC) (Takahashi et al.

2007), or by transforming human somatic cells with genes encoding human OCT4 and SOX2 factors plus genes encoding two other human factors, NANOG and LIN28 (Lin-28 homolog A) (Yu et al. 2007). All of these methods used retroviruses or lentiviruses to integrate genes encoding the reprogramming factors into the genomes of the transformed cells and the somatic cells were reprogrammed into iPS cells only over a long period of time (e.g., in excess of a week).

The generation iPS cells from differentiated somatic cells offers great promise as a possible means for treating diseases through cell transplantation. The possibility to generate iPS cells from somatic cells from individual patients also may enable development of patient-specific therapies with less risk due to immune rejection. Still further, generation of iPS cells from disease-specific somatic cells offers promise as a means to study and develop drugs to treat specific disease states (Ebert et al. 2009, Lee et al. 2009, Maehr et al. 2009).

Viral delivery of genes encoding protein reprogramming factors (or "iPSC factors") provides a highly efficient way to make iPS cells from somatic cells, but the integration of exogenous DNA into the genome, whether random or non-random, creates unpredictable outcomes and can ultimately lead to cancer (Nakagawa et al. 2008). New reports show that iPS cells can be created (at lower efficiency) by using other methods that do not require genome integration. For example, repeated transfections of expression plasmids containing genes for OCT4, SOX2, KLF4 and c-MYC into mouse embryonic fibroblasts to generate iPS cells was demonstrated (Okita et al. 2008). Induced pluripotent stem cells were also generated from human somatic cells by introduction of a plasmid that expressed genes encoding human OCT4, SOX2, c-MYC, KLF4, NANOG and LIN28 (Yu et al. 2009). Other successful approaches for generating iPS cells include treating somatic cells with: recombinant protein reprogramming factors (Zhou et al. 2009); non-integrating adenoviruses (Stadtfeld et al. 2008); or piggyBac transposons (Woltjen et al. 2009) to deliver reprogramming factors. Presently, the generation of iPS cells using these non-viral delivery techniques to deliver reprogramming factors is extremely inefficient. Future methods for generating iPS cells for potential clinical applications will need to increase the speed and efficiency of iPS cell formation while maintaining genome integrity.

Immediately after disclosures by the laboratories of K. Yamanaka (Takahashi K et al., 2007) and J A Thomson (Yu J et al. 2007) reporting induction of iPS cells from human somatic cells by viral or plasmid vectors which expressed genes encoding certain iPSC induction factors, one of the Applicants conceived that it might be possible to induce iPSCs by repeatedly transfecting human or animal somatic cells with in vitro-synthesized mRNAs encoding such iPSC induction factors.

Introduction of in vitro-synthesized mRNA into eukaryotic cells and organisms by means such as microinjection, electroporation and lipid-mediated transfection has been used to express encoded proteins since the introduction of SP6, T7 and T3 in vitro transcription systems about 30 years ago (e.g., Krieg, P A and Melton, D A, 1984). Such work, usually involving one-time introductions into eukaryotic cells of an mRNA encoding a particular gene-encoded protein of interest, followed by assays and/or analyses of the proteins expressed, have yielded important information about mRNA processing, the expression and activities of genes, and in vitro and in vivo translation of the encoded proteins. However, mRNA also was perceived to have certain disadvantages. For example, scientists perceive RNA to be more labile than DNA and believe that great care is needed to avoid degradation of RNA by a wide variety of ubiquitous ribonucleases, as exemplified by RNases on human skin (Probst J et al., 2006).

Still further, many scientists have found that repeated transfection of cells with in vitro-synthesized mRNA was cytotoxic to the cells and resulted cell death. For example, although Plews et al. (Plews J R et al., 2010) observed that pluripotency genes were activated upon transfection of human fibroblast cells with mRNAs encoding KLF4, c-MYC, OCT4 and SOX2 and LT proteins, they were unable to generate long-lived iPSC lines, because, as they stated, "in all instances, very few cells survived and typically senesced within a week after treatment." When they also did brief treatments of the cells with certain small molecules such as valproic acid following mRNA transfection, they observed increased activation of pluripotency genes compared to mRNA transfection alone, but stated "during our attempt of multiple rounds of microporation transfection, such treatment caused massive cell death." Plews et al. also seemed to be skeptical of the results of Yakubov et al. (Yakubov et al., 2010), when they stated "Yakubov and colleagues obtained similar AP positive colonies as us, however no differentiation analyses were done, thus it is hard to evaluate the pluripotency of the iPS cells."

Ugur Sahin et al. (Sahin U et al., 2011) also encountered great problems with cytotoxicity and cell viability during attempts to reprogram somatic cells to iPSCs with mRNA. After electroporating somatic cells with ARCA-capped in vitro-transcribed mRNAs encoding the four transcription factors OCT4, SOX2, KLF4, and cMYC daily for multiple days, they observed that the mRNAs were translated and some markers for iPSCs were induced. However, they noted that "repetitive electroporation is associated with a loss of cell viability which became apparent only after the second electroporation. The viability further decreased with every following electroporation." They attempted to "rescue" the cells that were being electroporated by continually adding more cells of the same type as they were electroporating, but they did not state how they could distinguish the previously electroporated cells from the new cells among the viable cells at the end of their electroporations. Apparently, they obtained no iPSC colonies that could be propagated or differentiated into other cells types, which are characteristics of iPSCs, because they concluded their description of the experiment by stating that "The outgrowth of pluripotent colonies from these cells is still under investigation."

Similarly, in a recent paper on the repeated delivery of mRNAs encoding reprogramming factors KLF4, c-MYC, OCT4 and SOX2 into human fibroblasts, K Drews et al. (Drews K et al., 2012) reported that "upon repeated transfections, the mRNAs induced severe loss of cell viability as demonstrated by MTT cytotoxicity assays. Microarray-derived transcriptome data revealed that the poor cell survival was mainly due to the innate immune response triggered by the exogenous mRNAs. We validated the influence of mRNA transfection on key immune response-associated transcript levels, including IFNB1, RIG-I, PKR, IL12A, IRF7 AND CCL5, by quantitative PCR and directly compared these with levels induced by other methods previously published to mediate reprogramming in somatic cells."

Such cytotoxicity and cell death as a result of repeated or continuous introductions of in vitro-synthesized mRNA into cells may be due to induction of RNA sensors and innate immune response mechanisms. Human and animal cells possess wide array of RNA sensors and innate immune response mechanisms that recognize and respond to exogenous RNA molecules that may enter the cells, such as during viral or bacterial infection. These cellular RNA sensors and innate immune response mechanisms, if activated, can result in inhibition of protein synthesis, cytotoxicity, and programmed cell death via apoptotic signaling.

In support of this idea, Angel and Yanik (2010) showed that transfection of cells with in vitro-synthesized mRNA activated innate immunity that caused significant cell death and that inhibition of innate immune response genes using siRNA against IFN-beta, STAT2 and EIFAK2 (PKR) enabled frequent transfection of human fibroblasts with in vitro-synthesized protein-encoding mRNA.

Kariko and Weissman (Kariko, et al., 2005; Kariko, et al., 2008; Kariko, et al., 2012) found that in vitro-synthesized modified mRNAs, in which canonical nucleosides were replaced by certain modified nucleosides (e.g. pseudouridine=ψ and e.g., 5-methylcytidine nucleosides=$m^5C$), were much less immunogenic and were expressed into proteins at higher levels compared to the corresponding in vitro-synthesized unmodified mRNAs. This work also supports the idea that the innate immune response needs to be reduced in order to express proteins encoded by repeatedly transfected mRNA.

L. Warren et al. (Warren et al., 2010) reported reprogramming of human somatic cells to iPSC colonies that could be continuously grown in culture and differentiated into cells comprising all 3 germ layers. They did this reprogramming by repeatedly transfecting somatic cells with ARCA-capped phosphatase-treated (ψ and $m^5C$)-modified mRNAs encoding KMOS or KMOSL transcription factors, where K=KLF4), M=MYC, O=OCT4, S=SOX2, L=LIN28, in medium containing B18R protein as an interferon inhibitor. Thus, Warren et al. used multiple methods to try to evade or counteract the cellular RNA sensors and innate immune response mechanisms, including making the mRNA with two modified nucleotides which Kariko et al. had shown to result in a lower innate immune response, phosphatasing the mRNA to remove the 5'triphosphate from the 20% of the mRNA molecules which were not capped during the in vitro transcription reaction, and also added B18R protein as an innate immune response inhibitor. Similar in vitro-synthesized mRNAs and methods, with some improvements, were used in a subsequent publication (Warren et al., 2012).

Kariko et al. (Kariko et al., 2011A) disclosed expression of KMOSLN transcription factors (N=NANOG) and reprogramming of human somatic cells (e.g., fibroblasts or keratinocytes) to iPSCs using mixtures of purified or treated in vitro-synthesized ψ-modified mRNAs (or mRNAs comprising other modified nucleosides) encoding certain of these transcription factors, without use of any added innate immune response inhibitor. The use of pseudouridine in place of uridine decreased the innate immune response increased expression of the transcription factor proteins encoded by the mRNA and, even then, purification or treatment of the mRNA was necessary for successful reprogramming. This work further indicated that it was important and beneficial to evade or reduce the innate immune response in order to decrease or eliminate cytotoxicity and cell death and induce reprogramming to iPSCs by repeatedly introducing protein-encoding mRNAs into somatic cells. The applicants believe that it is critical for successful reprogramming or induction of other biological or biochemical effects that in vitro-synthesized mRNAs which are to be repeatedly or continuously introduced into human and animal cells among other uses, must avoid inducing and activating the numerous RNA sensors and innate immune response mechanisms that protect them against pathogens comprising RNA.

However, in a recent paper, Lee et al. (Lee J, 2012), reviewed by L. A. J O'Neill (2012), argues just the opposite—that activation of innate immunity by modified mRNA encoding KMOS proteins is required for efficient reprogramming of somatic cells to iPSCs. These authors believe their data show that activation of toll-like receptor 3 (TLR3)-mediated pathways (e.g., induction of type I IFN) is necessary for efficient induction of pluripotency genes and induction of human iPSCs.

Resolution of this problem is important. Despite intense research, it is not yet fully known in the art how or why cells recognize and tolerate endogenous mRNA molecules but do not tolerate repeated cellular introduction of mRNA molecules synthesized by in vitro transcription, capping and polyadenylation. J. Eberwine and co-workers (Sul J-Y et al., 2012), who have focused on trying to use mRNA transcriptomes isolated from cells to direct cell to cell phenotypic conversion, were perplexed by why scientists working on reprogramming using mRNA were encountering problems with cytotoxicity and cell death and using modified mRNA to reduce those effects, in view of the fact that they did not observe similar effects using mRNA isolated from cells.

Thus, it is not understood what specific chemical and structural features of in vitro-synthesized mRNA are recognized by human or mammalian cellular RNA sensors to prevent such repeated cellular introductions. Identifying these features and finding ways to be able to repeatedly or continuously introduce such in vitro-synthesized mRNAs into human and animal cells would enable mRNA to be used to induce biological or biochemical effects in cells, not only for reprogramming, but also for a wide variety of other important applications (e.g., for clinical research or for regenerative medicine or immunotherapy) in cell biology, agriculture and medicine.

The reprogramming of human or animal somatic cells to iPSCs by repeated or continuous transfection of in vitro-synthesized mRNAs encoding iPSC factors provides an excellent model system for identifying which features of the in vitro-synthesized mRNAs are detected and which cellular RNA sensors and innate immune response mechanisms induce cytotoxicity and cell death. Reprogramming is an excellent model because it requires daily transfections of multiple mRNAs over a period of about 8 to about 18 days. Knowledge gained from reprogramming experiments will result in easier, faster, more efficient and more effective cellular reprogramming, and also will likely lead to improved methods for inducing many other biological or biochemical effects ex vivo in cells in culture or in vivo in cells in tissues, organs or organisms that contain them by repeated or continuous introduction of in vitro-synthesized mRNA encoding one or more proteins.

Thus, the Applicants believe that methods and compositions developed for this reprogramming model system may lead to: methods for making RNA compositions comprising ssRNA for introduction into mammalian cells to induce a biological or biochemical effect; new RNA compositions that are more effective in inducing a biological or biochemical effect upon their introduction into mammalian cells; new methods for reprogramming cells from a first state of differentiation or phenotype to a second state of differentiation or phenotype (including dedifferentiation, transdifferentiation, and differentiation or re-differentiation); and new methods for inducing other biological or biochemical effects in human or animal cells ex vivo in culture or in vivo in cells in tissues, organs or organisms by repeated or continuous introduction of in vitro-synthesized mRNAs encoding one or more other proteins of interest into the cells.

What is needed in the art is a better understanding of what specific chemical and structural features of in vitro-synthesized mRNAs are recognized by cellular RNA sensors and innate immune response mechanisms to prevent repeated cellular introductions of the mRNAs. What is needed in the art are new methods, compositions and kits for making, purifying and treating in vitro-synthesized mRNAs so that they can be repeatedly or continuously introduced into human or animal (e.g., mammalian) cells ex vivo in culture or in human or animal (e.g., mammalian) cells in vivo in tissues, organs or organisms that contain the cells without activating RNA sensors or inducing an innate immune response that results in significant cytotoxicity, cell death or inhibition of the desired biochemical or biological effect for which the in vitro-synthesized mRNAs are introduced into said cells. What is needed are new RNA compositions, new methods for making such RNA compositions comprising in vitro-synthesized ssRNA or mRNA encoding one or more proteins, methods for using such RNA compositions to repeatedly or continuously transfect human or animal (e.g., mammalian) cells in order to cause a biological or biochemical effect (e.g., to reprogram a cell that exhibits a first state of differentiation comprising a somatic cell to a cell that exhibits a second state of differentiation comprising an iPS cell) with higher efficiency and without inducing significant cytotoxicity or cell death.

Little or nothing is known about the results that could be obtained when such treated or purified RNA compositions are introduced into living cells in culture or in human or animal subjects. What is needed in the art are better methods to generate RNA compositions comprising ssRNA or mRNA for repeated or continuous introduction into cells ex vivo in culture or in vivo in human or animal subjects (e.g., for biological and clinical research, agriculture or clinical applications).

Repeated or continuous introduction of mRNA into cells to induce a biological or biochemical effect (e.g., for reprogramming) may provide benefits over introduction of DNA or protein molecules. For example, introduction of mRNA into a cell is less likely than DNA to result in genome insertions or genetic modifications, with related permanent effects for the cells. Also, it may be easier to introduce mRNA into a cell, wherein it is properly post-translationally modified for optimal expression, than to make and deliver proteins with a particular glycosylation or other post-translational modification appropriate for the particular cell. Thus, what is needed are effective methods for making, for repeatedly or continuously introducing, and for expressing mRNA in living cells to induce biological or biochemical effects (e.g., in the biologic, agricultural and clinical fields of use, e.g., for use in regenerative medicine, cell reprogramming, cell-based therapies, enzyme replacement therapies, cell, tissue and organ transplantation or repair, tissue or organ engineering, and immunotherapies).

In certain embodiments, the present invention pertains to embodiments of compositions, reaction mixtures, kits and methods that comprise or use one or more in vitro-synthesized single-stranded RNAs (ssRNAs) or messenger RNAs (mRNAs) (sometimes also referred to as ssRNA or mRNA molecules). With respect to the present invention, an "in vitro-synthesized ssRNA or mRNA" herein means and refers to ssRNA or mRNA that is synthesized or prepared using a method comprising in vitro transcription of one or more DNA templates by an RNA polymerase. Still further, unless specifically stated otherwise, the terms "ssRNA" or "mRNA" when used herein with reference to an embodiment of the present invention shall mean an "in vitro-synthesized ssRNA or mRNA" as defined above. In preferred embodiments, the in vitro-synthesized ssRNA or mRNA encodes (or exhibits a coding sequence of) at least one protein or polypeptide. In some preferred embodiments, the ssRNA or mRNA encodes at least one protein that is capable of effecting a biological or biochemical effect when repeatedly or continuously introduced into a human or animal cell (e.g., a mammalian cell). In some preferred embodiments, the invention comprises a composition comprising ssRNA or mRNA, and, unless specifically stated otherwise, the term "RNA composition" shall mean an RNA composition comprising or consisting of in vitro-synthesized ssRNA or mRNA. In some preferred embodiments, the invention comprises an RNA composition comprising or consisting of in vitro-synthesized ssRNA or mRNA that encodes one protein or polypeptide. In some preferred embodiments, the invention comprises an RNA composition comprising or consisting of a mixture of multiple different in vitro-synthesized ssRNAs or mRNAs, each of which encodes a different protein. Other embodiments of the invention comprise an RNA composition comprising or consisting of in vitro-synthesized ssRNA that does not encode a protein or polypeptide, but instead exhibits the sequence of at least one long non-coding RNA (ncRNA). Still other embodiments comprise various reaction mixtures, kits and methods that comprise or use an RNA composition.

One embodiment of the present invention is a method for treating in vitro-synthesized ssRNA or mRNA to generate an RNA composition that is "substantially free of dsRNA," "virtually free of dsRNA," "essentially free of dsRNA," "practically free of dsRNA," "extremely free of dsRNA," or "absolutely free of dsRNA," meaning, respectively, that less than about: 0.5%, 0.1%, 0.05%, 0.01%, 0.001% or 0.0002% of the mass of the RNA in the treated ssRNA composition is dsRNA of a size greater than about 40 basepairs, (or greater than about 30 basepairs) the method comprising: contacting the in vitro-synthesized ssRNA or mRNA with RNase III protein in a buffered aqueous solution comprising magnesium cations at a concentration of about 1-4 mM; and a salt providing an ionic strength at least equivalent to about 50 mM potassium acetate or potassium glutamate, and incubating under conditions wherein the RNA composition is generated.

Thus, one embodiment of the present invention is a method for treating in vitro-synthesized ssRNA or mRNA to generate a treated RNA composition wherein less than about: 0.5%, 0.1%, 0.05%, 0.01%, 0.001% or 0.0002%, respectively, of the mass of the RNA in the treated RNA composition is dsRNA of a size greater than about 40 basepairs (or greater than about 30 basepairs), the method comprising: contacting the in vitro-synthesized ssRNA or mRNA with RNase III protein in a buffered aqueous solution comprising magnesium cations at a concentration of about 1-4 mM; and a salt providing an ionic strength at least equivalent to about 50 mM potassium acetate or potassium glutamate, and incubating under conditions wherein the treated RNA composition is generated. However, unless otherwise obvious from the description or otherwise specifically stated, whenever we say that an "RNA composition" is used in a method described herein wherein the RNA composition is repeatedly or continuously contacted with or introduced into a human or animal cell (e.g., a mammalian cell) to induce a biological or biochemical effect (e.g., to reprogram a cell that exhibits a first differentiated state or phenotype to a second differentiated state or phenotype), we mean (and it will be understood) that said RNA composition is either a treated RNA composition that was generated using the presently described method, or is a purified RNA composition wherein less than: 0.01%, 0.001% or 0.0002% (or a specifically stated percentage) of the mass of the RNA in the purified RNA composition is dsRNA of a size greater than about 40 basepairs (or greater than about 30 basepairs), even when said RNA composition is not referred to as a "treated RNA composition" or a "purified RNA composition."

One embodiment of the invention is an RNA treatment reaction mixture comprising: a) an in vitro-synthesized ssRNA or mRNA (e.g., that encodes one or more proteins or one or more long non-coding RNAs (ncRNAs); b) a double-stranded RNA (dsRNA)-specific endoribonuclease III (endoRNase III or RNase III) protein; c) magnesium cations at a concentration of about 1-4 mM; and d) a salt providing an ionic strength at least equivalent to 50 mM potassium acetate or potassium glutamate; wherein said RNA treatment reaction mixture is practically free, extremely free or absolutely free of dsRNA, meaning that less than 0.01%, less than 0.001% or less than 0.0002%, respectively, of the RNA in the RNA treatment reaction mixture is dsRNA of a size greater than about 40 basepairs (or greater than about 30 base pairs).

Prior to the present invention, said RNA treatment reaction mixture and said method for making a treated RNA composition wherein less than 0.01%, less than 0.001% or less than 0.0002% of the RNA in the RNA treatment reaction mixture or RNA composition was dsRNA of a size greater than about 40 basepairs were not known in the art, as evidenced by the EXAMPLES disclosed herein. For example, treatment of an RNA composition comprising in vitro-transcribed unmodified GAUC ssRNA (e.g., mRNAs encoding iPSC induction factors) using RNase III as described in the art (e.g., Robertson, 1968) did not generate a treated RNA composition that resulted in reprogramming human fibroblasts to iPSCs when the treated RNA composition was repeatedly introduced into the fibroblast cells (e.g., see reprogramming results using RNase III treatments with 10 mM magnesium acetate in the Table in EXAMPLE 10), whereas the RNase III treatment method of the present invention did result in successful reprogramming (e.g., see reprogramming results using RNase III treatments with about 1-4 mM magnesium acetate in the Table in EXAMPLE 10). This surprising and unexpected result was further explained by the results of other experiments (e.g., see EXAMPLE 22). For example, the Table in EXAMPLE 22 shows that the addition of dsRNA at a level of only about 0.001% or more of the total RNA in an RNA composition comprising a mixture of highly purified unmodified ssRNAs (e.g., mRNAs encoding iPSC induction factors) is sufficient to effectively inhibit reprogramming of human fibroblasts in culture to iPSCs.

Thus, some embodiments of the method for treating in vitro-synthesized ssRNA or mRNA, generate an RNA composition that is substantially free, virtually free, essentially free, practically free, extremely free or absolutely free of dsRNA, Preferred embodiments of the present invention comprise RNA compositions comprising ssRNA or mRNA that are at least practically free of double-stranded RNA (e.g., practically, extremely or absolutely dsRNA-free compositions), methods and kits for making at least practically dsRNA-free compositions, and kits and methods comprising and/or for using at least practically dsRNA-free compositions.

One particular embodiment of the invention is an RNA composition that is at least practically free of dsRNA, wherein said RNA composition comprises in vitro-synthesized ssRNA (e.g., ncRNA or mRNA (e.g., encoding one or more proteins), and wherein said RNA composition is: "practically free of dsRNA," "extremely free of dsRNA," or "absolutely free of dsRNA," meaning, respectively, that less than: 0.01%, 0.001%, or 0.0002% of the RNA in the RNA composition comprises dsRNA of a size greater than about 40 basepairs. For example, one particular embodiment of the invention is an RNA composition comprising one or more in vitro-synthesized ssRNAs or mRNAs encoding one or more protein transcription factors, wherein the RNA composition is practically free, extremely free or absolutely free of dsRNA. Another RNA composition of the invention is a reaction mixture comprising an RNA treatment reaction mixture comprising: a) an in vitro-synthesized ssRNA or mRNA that encodes one or more proteins transcription factors; b) a double-stranded RNA (dsRNA)-specific endoribonuclease III (endoRNase III or RNase III) protein; c) magnesium cations at a concentration of about 1-4 mM; and d) a salt providing an ionic strength at least equivalent to 50 mM potassium acetate or potassium glutamate; wherein said RNA treatment reaction mixture is practically free, extremely free or absolutely free of dsRNA, meaning that less than 0.01%, less than 0.001% or less than 0.0002%, respectively, of the RNA in the RNA treatment reaction mixture is dsRNA of a size greater than about 40 basepairs.

In some embodiments, the amounts and relative amounts of dsRNA to non-contaminant ssRNA or mRNA is determined using a dsRNA-specific antibody as described herein. In some embodiments, the amounts and relative amounts of non-contaminant mRNA molecules and RNA contaminant molecules (or a particular RNA contaminant) may be determined by HPLC or other methods used in the art to separate and quantify RNA molecules.

Thus, the present invention provides methods for synthesizing an in vitro transcribed (IVT) RNA composition, and then contacting the IVT RNA composition with a dsRNA-specific RNase, such as RNase III, under conditions wherein contaminant dsRNA can be reproducibly digested and ssRNA molecules that do not induce or activate a dsRNA innate immune response pathway or RNA sensor can reliably be generated.

When the Applicants attempted to use RNase III as described in the art (e.g., by Robertson et al., 1968, and by Mellits et al., 1990) as a potential solution to treat ssRNA comprising mRNA molecules for translation in living cells, the Applicants were surprised to find that the RNase III-treated ssRNAs were toxic. Thus, human cells that were transfected with various doses of the RNase III-treated ssRNAs, either daily or every-other-day for up to 3 weeks, appeared increasingly less healthy during the course of said introducing and finally died. Further, the Applicants found that RNase III-treated ssRNAs obtained using the protocol originally described by Robertson et al. remained contaminated with significant amounts of dsRNA based on dot-blot immunoassays using two different dsRNA-specific antibodies (J2 and K1 antibodies; English and Scientific Consulting, Szirák, Hungary).

Accordingly, the Applicants found that RNase III-treated ssRNA prepared as described in the art could not be introduced into human cells for in vivo translation. Still further, extending the reaction incubation time of the RNase III reaction also did not noticeably reduce the toxicity of the ssRNA to the cells or reduce the amount of contaminant dsRNA to below the detection levels of the dsRNA-specific antibodies. Increasing the reaction time also appeared to result in greater degradation of the ssRNA, based on staining of electrophoresis gels, and less expression of the ssRNA.

Mellits et al. (1990) provided guidance related to the RNase III protocol that it may be necessary to "optimize the digestion conditions with respect to enzyme/substrate ratio, salt concentration, and temperature for a particular RNA."

Accordingly, the present Applicants modified the RNase III protocol by varying the amount of RNase III relative to a constant amount of RNA treated. However, increasing or decreasing the amount of enzyme relative to the amount of RNA did not affect the amount of dsRNA that remained after the protocol.

Next, the present Applicants carefully evaluated whether changing the concentration or type of monovalent salt (including other salts than the $NH_4Cl$ salt taught with respect to the standard Robertson RNase III assay protocol would positively affect the results. Provided that the monovalent salt concentration was sufficient to maintain the duplex state of the dsRNA (e.g., at least 50 mM or greater, the different concentrations did not result in increased digestion of the contaminant dsRNA molecules. At high monovalent salt concentrations, there appeared to be a slight inhibition of RNase III activity. Longer RNase III reaction times or higher reaction temperatures appeared to increase degradation of the ssRNA of interest without increasing digestion of the contaminating dsRNA.

The present Applicants next designed an RNA substrate comprising both single-stranded portions and a double-stranded portion in order to more accurately and precisely evaluate both the dsRNA-specific activity and the specificity of digestion for dsRNA rather than ssRNA since the various RNase III reaction conditions could be assayed using this single substrate (FIG. 1). As shown in FIG. 1, correct digestion of this RNA substrate would be expected to result in complete digestion of the central 1671-basepair dsRNA portion, while leaving ssRNA tails of 136 bases and 255 bases intact. This substrate turned out to be a valuable tool in the present studies.

Using this substrate, very surprisingly and unexpectedly, the present Applicants discovered a dramatic improvement in both the RNase III activity and specificity when the concentration of divalent magnesium cations was decreased by about 10-fold compared to the concentration taught in the art (e.g., Robertson et al., 1968). Thus, at a concentration of 1 mM divalent magnesium cations, the single-stranded tails of the substrate remained intact and the dsRNA central portion was completely digested. The substrate was then used to precisely titrate the optimal range of divalent magnesium concentration. Surprisingly, whereas the literature (e.g., Robertson et al., 1968) had reported that "[m]agnesium stimulates activity over a broad range between 0.005 M and 0.1 M), the present Applicants found that it was necessary to use a concentration of divalent magnesium of about 4 mM or less, and preferably about 1-3 mM, or 1-2 mM) in order to sufficiently digest the dsRNA so that the RNA composition comprising ssRNA molecules did not induce or activate a dsRNA-specific innate immune response or RNA sensor pathways that resulted in a substantial decrease in protein synthesis, increase in cell toxicity, or cell death. Still further, at this lower magnesium cation concentration range, the yield of intact ssRNA molecules increased. Both of these effects—decreased levels of dsRNA and increased levels of intact ssRNA—resulted in higher levels of translation of mRNAs encoding a variety of different proteins comprising reprogramming factors and much less toxicity to the cells, as reflected by much lower levels of cellular expression of a various innate immune response-related genes (based on quantitative RT-PCR analysis).

Specifically, the RNase III protocol taught in the art since about 1968 has taught to use magnesium acetate at 10 mM. However, the present Applicants found that a 10 mM concentration of magnesium acetate resulted in toxicity to the cells due to induction and/or activation of a strong innate immune response. However, surprisingly and unexpectedly, the present Applicants found that treating the ssRNA with RNase III in a reaction mixture comprising only about 1-4 mM, and more preferably about 1-3 mM magnesium acetate, resulted in ssRNA that was intact (without noticeable smearing of the ssRNA band on electrophoresis) and with much less dsRNA (which we much later determined to be at least practically free, extremely free or absolutely free of the dsRNA), which ssRNA also resulted in much less toxicity and cell death when repeatedly introduced into human or animal cells.

Evidence for the more complete digestion of dsRNA, while better maintaining the integrity of the ssRNA during the RNase III digestion is shown in EXAMPLE 1 and FIG. 2. As shown in FIG. 2, at magnesium acetate concentrations between 1 and 4 mM, the 1671-basepair dsRNA region of the RNA substrate was completely digested and the two ssRNA fragments of 255 and 136 nucleotides remained intact. At a concentration of 5 mM magnesium acetate, the ssRNAs were noticeably more degraded, as seen by the smear under the ssRNA bands, and this degradation increased as the magnesium acetate concentration increased to from 6 to 10 mM magnesium acetate, with very significant smearing at 10 mM.

Dot blot assays of digestion of varying amounts of dsRNA by RNase III in the presence of different concentrations of divalent magnesium acetate using a dsRNA-specific antibody, as shown in EXAMPLE 2 and EXAMPLE 3 (FIG. 3 and FIG. 4, respectively) confirmed that the dsRNA was most effectively digested by the RNase III treatment in a reaction mixture comprising a final concentration of between about 1 mM and about 4 mM magnesium acetate, and more preferably, between about 2 mM and about 4 mM magnesium acetate. When the RNase III treatment of in vitro-synthesized ssRNA was performed at this concentration range, the present Applicants found in other experiments that the toxicity of the treated ssRNA upon repeated daily transfection into cells was significantly reduced compared to ssRNA treated at magnesium cation concentrations higher than 4 mM (e.g., at 10 mM as taught by Mellits et al., 1990), and this reduction in toxicity of the ssRNA during repeated transfections was critical to be able to successfully reprogram human somatic cells to induced pluripotent stem (iPS) cells.

Accordingly, the method developed by the present Applicants was found to be essential, effective, and reproducible for achieving successful reprogramming of human somatic cells using ssRNAs encoding reprogramming factors. The method is capable of treating both small and large quantities of RNA by removing dsRNA contaminants generated during in vitro transcription while maintaining the integrity of the ssRNA.

The method has been shown to be unexpectedly successful in reducing induction and/or activation of innate immune response signaling pathways and RNA sensors (e.g., TLR3-mediated interferon induction) in human cells in response introducing in vitro-synthesized ssRNA into the cells, even after multiple (e.g., daily) transfections for up to about 21 days. For example, if no purification or RNase III treatment is performed to remove dsRNA, it is not possible to successfully reprogram BJ fibroblasts to iPS cells. This is because even minute quantities of contaminating dsRNA, when transfected every day for multiple days (e.g., daily for >2 days, >3 days, >5 days, >8 days, >10 days, >12 days, >14 days, >16 days, >18 days, or >20 days) results in high toxicity to the cells. For example, the present Applicants have observed that most or all of the fibroblast cells die if transfected for more than about 6 to about 10 days with in vitro-transcribed mRNAs encoding iPSC induction factors which have not been purified or treated to remove the dsRNA (with survival time depending upon the dose of ssRNAs transfected, the particular cells, the transfection reagent or method used, and other factors). However, by using the presently-described RNase III treatment method comprising use of about 1 mM to about 4 mM of divalent magnesium cations to digest dsRNA contaminant molecules in in vitro-synthesized ssRNA (e.g., mRNA), thereby reducing the TLR3-mediated innate immune response, it was possible to efficiently reprogram human BJ fibroblasts to induced pluripotent stem cells (iPSCs) by transfecting the cells with RNase III-treated unmodified ssRNAs comprising cap1 5'-capped mRNAs having approximately 150-base poly(A) tails, which mRNAs encoded iPSC induction factors, daily for up to 18 days (e.g., see EXAMPLE 10); in contrast, no reprogramming of BJ fibroblasts to iPSCs was observed in EXAMPLE 10 when the same unmodified ssRNAs were treated with RNase III in the presence of 10 mM divalent magnesium cations. Still further, unmodified ssRNAs treated with RNase III in the presence of 1-4 mM divalent magnesium cations resulted in much less toxicity and death of the BJ fibroblasts compared to the same unmodified ssRNAs treated with RNase III in the presence of 10 mM divalent magnesium cations. For example, in this particular experiment, this is a main factor for why greater than 100 iPSCs were induced in BJ fibroblasts transfected every day for 13 days with the 1.2 micrograms of a 3:1:1:1:1:1 molar mix of the unmodified ssRNAs encoding OCT4, SOX2, KLF4, LIN28, NANOG, and cMYC(T58A), respectively, that was treated with RNase III in the presence of 1 mM divalent magnesium cations and 200 mM potassium acetate as the monovalent salt, whereas no reprogramming of BJ fibroblasts to iPSCs was observed if the same unmodified ssRNAs were treated with RNase III in the presence of 10 mM divalent magnesium cations. Those with knowledge in the art will especially recognize the power of the present RNase III treatment method to prepare in vitro-transcribed ssRNA that is capable of inducing a biological or biochemical effect upon repeated or continuous introduction into cells in view of the fact that, it is believed that, prior to the work described herein, no one had reported or described in the art the use of unmodified GAUC mRNAs encoding iPSC factors to reprogram somatic cells to iPS cells which could be grown into iPS cell lines and differentiated into other types of cells representing all three germ layers (as described herein). Thus, the RNase III treatment method described herein provides, for the first time, a simple and straightforward method to remove even minute quantities of contaminating dsRNA from in vitro-synthesized mRNA, thereby successfully solving the problem of cell toxicity and cell death that results from using unpurified or untreated in vitro-synthesized mRNA.

As disclosed in Kariko et al. (Kariko et al., 2011), Drs. Weissman and Kariko, showed that HPLC could be used to purify in vitro-synthesized mRNA comprising modified nucleotides, such as pseudouridine or both pseudouridine and 5-methylcytidine, and, working with the present Applicants, showed that HPLC-purified modified mRNAs encoding iPSC induction factors could be used to reprogram somatic cells to iPS cells. The present Applicants show herein that the RNase III treatment method disclosed herein is approximately equivalent to HPLC purification for removing dsRNA from in vitro-synthesized mRNA based on a quantitative comparison of the number of iPS cells induced from fibroblasts using iPSC induction factor-encoding modified mRNAs purified by HPLC or treated with the RNase III treatment described herein (e.g., see tables in the Results for EXAMPLE 15 and EXAMPLE 27). While the present invention is not limited to any particular mechanism or theory, and an understanding of the mechanism or theory is not necessary to successfully practice the present invention, since mRNAs were purified as single peaks by HPLC, our finding that HPLC-purified and RNase III-treated mRNAs appear to be quantitatively equivalent in inducing iPS cells from somatic cells strongly suggests that dsRNA generated during the in vitro transcription reaction is the sole contaminant in the CAP1 poly(A)-tailed pseudouridine-modified mRNAs that induced the innate immune responses that we observed if the mRNAs were not purified by HPLC or treated using the presently-described RNase III treatment. Still further, in view of the equivalence of the RNase III treatment to HPLC in terms of removing the dsRNA contaminant, those with skill in the art will recognize the advantages and benefits of the RNase III treatment method over HPLC purification. For example, the RNase III treatment method described herein does not require scientists to learn how to operate and purchase expensive equipment, columns, and reagents, and does not require washing of columns, or generate organic solvent waste, as does HPLC. The RNase III treatment is also much faster and easier than HPLC, requiring minimum hands-on time and only about 30 minutes for the treatment itself, plus a small amount of additional time for organic extraction, ammonium acetate precipitation, ethanol washes of the precipitate, followed by storage as a dry pellet or, if desired, suspension in an aqueous solution. When performed as described for the standard RNase III treatment, the Applicants have found the method to be extremely reliable and reproducible with at least a couple of dozen different mRNAs. For example, the Applicants have used the RNase III treatment method routinely for preparation of mRNAs encoding different transcription factors that were repeatedly or continuously transfected into human or animal cells for use in reprogramming the cells from one state of differentiation to another, without encountering unexpected problems. The Applicants were surprised that, as described in EXAMPLE 23, the RNase III treatment was necessary for reprogramming of mouse mesenchymal stem cells to myoblast cells using modified mRNA encoding MYOD. Thus, even though only two daily transfections were needed for the reprogramming using mRNA prepared using the RNase III treatment, no myoblasts were induced by mRNA encoding MYOD which had not been prepared using the presently-described RNase III treatment. This indicates that RNA sensors or innate immune responses can inhibit a desired biological or biochemical effect even when only a short amount of time and a small number of transfections are needed.

The Applicants have also used the RNase III treatment method to prepare other mRNAs for repeated or continuous transfection into human or animal cells in order to induce biological or biochemical effects other than reprogramming of cells from one state of differentiation to another, and have found that the resulting RNase III-treated mRNAs were less toxic and were translated into protein at higher levels than the same mRNAs that were not RNase III-treated.

In general, due to the simplicity of the protocol, the RNase III treatment method can also be used to treat many in vitro-synthesized RNAs simultaneously in parallel and, since it involves simple steps, such as pipetting, the method is also capable of being automated by use of a robot, or scaled up for treatment of any desired amount of RNA.

If capping and polyadenylation of in vitro-transcribed ssRNAs is done post-transcriptionally using a capping enzyme comprising RNA guanyltransferase and a poly(A) polymerase, preferably the RNase III treatment is performed after the in vitro transcription and before capping and polyadenylation. However, we have also achieved good results (e.g., for reprogramming somatic cells to iPSCs) when the RNase III treatment was applied to ssRNAs after capping or polyadenylation. As shown herein, the RNase III treatment was also successful for removing dsRNA from in vitro-transcribed ssRNA that was capped co-transcriptionally using a dinucleotide cap analog (e.g., an ARCA) and/or polyadenylated during in vitro transcription of a DNA template that also encoded the poly(A) tail.

As discussed above and elsewhere herein, reprogramming of fibroblasts to iPS cells using unmodified or pseudouridine modified in vitro-transcribed ssRNA was not observed unless the ssRNA was purified (e.g., by a method such as chromatography (e.g., HPLC), electrophoresis, or treated using the presently described RNase III treatment). Without being bound by theory, we believe that this is because even minute quantities of contaminating dsRNA, when transfected every day for 18 days, would result in high toxicity to the cells. For example, even minute quantities of contaminating dsRNA induce high levels of type I interferons, which in turn inhibit translation in the cells in a PKR-dependent mechanism. Further, the type I interferons induce thousands of genes to defend the cells against invasion by the dsRNA, which is the same mechanism that the cell uses to protect itself against pathogenic dsRNA viruses. Still further, it has been reported that type I and type II interferons can sensitize cells to dsRNA-induced cytotoxicity, which might tip the balance from necrosis to apoptosis (Stewart II, W E et al., 1972; Kalai, M et al., 2002). Thus, the fact that the ssRNAs are introduced into the cells every day for multiple days (e.g., up to 18 or more days to induce iPS cells) may be an important factor in cytotoxicity and apoptosis. The innate immune response is induced, leading to interferon production, which in turn causes protein translation to be decreased or shut down for a longer time, and eventually, the apoptotic signaling pathways are activated, leading to cell death.

Thus, we believe the presently described methods are important because they reduce the levels of contaminating dsRNA so that the purified or treated ssRNAs can be introduced into the cells without inducing cytotoxicity and cell death, including wherein the purified or treated ssRNAs are repeatedly introduced into the living human or animal cells (e.g., daily for multiple days or multiple weeks for cells in culture or, potentially, daily or weekly for multiple weeks, months or even years when introduced into cells in a human or animal organism).

In some embodiments, the RNase III treatment methods are useful for preparing any ssRNA for translation or expression in human or animal cells, and can be performed on multiple samples simultaneously in less than one hour, with only minutes of hands-on time. Due to the simplicity of the methods, they are also amenable to automation and scale-up (e.g., for high-throughput applications).

Surprisingly and unexpectedly, when this method was used to generated treated ssRNAs from in vitro-synthesized ssRNAs comprising or consisting of either only unmodified ribonucleosides (G,A,C,U), or Ψ- and/or m⁵C-modified ribonucleosides that encoded iPSC induction factors (e.g., OCT4, SOX2, KLF4, LIN28, NANOG and either c-MYC, c-MYC(T58A), or L-MYC), the treated ssRNAs were highly efficient in reprogramming human somatic cells (e.g., fibroblasts or keratinocytes) to pluripotent stem cells (iPSCs) when introduced into the cells once daily for ~10 to ~21 days, without using any agent that reduces the expression of proteins in an innate immune response pathway (e.g., without B18R protein). After making stable iPSC lines (meaning cell lines which maintained iPSC cell markers and the ability to differentiate into cells of all 3 germ layers over an extended period of time) from iPSC colonies, they were confirmed to be iPSCs based on immunostaining for iPSC markers and were differentiated into cells representing all three germ layers using an embryoid body differentiation assay. Induction of iPSCs using ssRNAs without an inhibitor or agent (e.g., B18R protein) that reduces the expression of an innate immune response pathway or using ssRNA consisting of only unmodified canonical ribonucleosides has not been reported by others, it is believed, and clearly shows the power of the method for making treated protein-encoding ssRNA for translation in human or animal cells.

In certain embodiments, the ssRNAs treated using RNase III comprise one or more different ssRNA molecules that are treated with RNase III enzyme in a reaction buffer comprising divalent magnesium cations at a final concentration of about 1 mM to about 4 mM. In certain preferred embodiments, one or more different ssRNAs are treated using an RNase III treatment method comprise with RNase III enzyme in a reaction buffer comprising divalent magnesium cations at a final concentration of about 1 to about 3 mM, more preferably about 1 mM, about 2 mM or about 3 mM. In some embodiments, the method generates ssRNA that is substantially free of dsRNA, meaning that, after the RNase III treatment and cleanup, greater than about 99.5% of the RNA is ssRNA and less than about 0.5% of the RNA is dsRNA greater than about 40 bp (or greater than about 30 bp). In some embodiments, the method generates ssRNA that is virtually free of dsRNA, meaning that, after the RNase III treatment and cleanup, greater than about 99.9% of the RNA is ssRNA and less than about 0.1% of the RNA is dsRNA greater than about 40 bp (or greater than about 30 bp). In some embodiments, the method generates ssRNA that is essentially free of dsRNA, meaning that, after the RNase III treatment and cleanup, greater than about 99.95% of the RNA is ssRNA and less than about 0.05% of the RNA is dsRNA greater than about 40 bp (or greater than 30 bp). In some embodiments, the method generates ssRNA that is practically free of dsRNA, meaning that, after the RNase III treatment and cleanup, greater than about 99.99% of the RNA is ssRNA and less than about 0.01% of the RNA is dsRNA greater than about 40 bp (or greater than 30 bp). In some embodiments, the method generates ssRNA that is extremely free of dsRNA, meaning that, after the RNase III treatment and cleanup, greater than about 99.999% of the RNA is ssRNA and less than about 0.001% of the RNA is dsRNA greater than about 40 bp (or greater than about 30 bp). In some embodiments, the method generates ssRNA that is absolutely free of dsRNA, meaning that, after the RNase III treatment and cleanup, greater than about 99.9998% of the RNA is ssRNA and less than about 0.0002% of the RNA is dsRNA greater than about 40 bp (or greater than about 30 bp).

In one embodiment, the dsRNA-specific RNase is RNase III and the method comprises treating in vitro-synthesized ssRNAs with the RNase III in a reaction mixture comprising divalent magnesium cations at a concentration of about 1 mM to about 4 mM, and then removing the RNase III digestion products and reaction mixture components to generate the treated ssRNAs that are substantially, virtually, essentially, practically, extremely or absolutely free of dsRNA.

In certain preferred embodiments, the RNase III-treated ssRNAs generated using the methods do not result in an innate immune response that results in substantial inhibition of cellular protein synthesis or dsRNA-induced apoptosis after introducing the treated ssRNAs into the cells at least two times or at least three times. In one preferred embodiment, the one or more in vitro-synthesized ssRNAs encode induced pluripotent stem cell (iPSC) induction factors, the cells that exhibit a first differentiated state are human or animal somatic cells, and the treated ssRNAs or purified ssRNAs are introduced into said cells on each of about 15 to about 21 days (e.g., 15, 16, 17, 18, 19, 20, or 21 days) to generate cells that exhibit a second differentiated state or phenotype of an iPS cell.

One embodiment of the invention is a method for making treated ssRNAs for use in reprogramming eukaryotic cells that exhibit a first differentiated state or phenotype to cells that exhibit a second differentiated state or phenotype by introducing said ssRNAs into said cells at least three times over a period of at least three days, said method comprising: (i) treating one or more in vitro-synthesized ssRNAs, each of which encodes a reprogramming factor, with RNase III in a reaction mixture comprising divalent magnesium cations at a concentration of about 1 mM to about 4 mM for sufficient time and under conditions wherein dsRNA is digested to generate treated ssRNAs; and (ii) cleaning up the treated ssRNAs to remove the components of the RNase III reaction mixture and the dsRNA digestion products to generate ssRNAs that are at least essentially, practically, extremely or absolutely free of dsRNA.

In some embodiments, the divalent magnesium cations are at a concentration of about 1 mM to about 4 mM, or preferably, about 1 mM to about 3 mM, or more preferably, about 2 mM to about 3 mM, or most preferably, about 2 mM.

In some embodiments, the reaction mixture further comprises a monovalent salt at sufficient concentration wherein the complementary strands of contaminant dsRNA remain annealed (e.g., at least about 50 mM, preferably about 50 mM to about 100 mM, more preferably about 100 mM to about 200 mM, or most preferably about 200 mM). In some embodiments, a divalent salt may be used in place of a monovalent salt, although a divalent salt is not preferred. For example, in some embodiments of the methods, the monovalent salt is selected from the group consisting of ammonium chloride, ammonium acetate, potassium glutamate, potassium chloride, potassium acetate, sodium acetate, sodium chlorate, lithium chloride, rubidium chloride and sodium chloride. However, the invention is not limited to a particular monovalent salt or other salt, although some monovalent salts, such as potassium glutamate and potassium acetate, are preferred. Any salt that maintains ionic strength so as to maintain the double-stranded nature of contaminant dsRNA during the RNase III treatment, and in which the RNase III is active and the ssRNA is not degraded, can be used for the method.

In some embodiments, the reaction buffer has a pH in which the in vitro-synthesized ssRNA is stable and the RNase III is active (e.g., a pH between ~7 and ~9).

In accordance with one embodiment, the present invention provides a method comprising: incubating a dsRNA-specific RNase (e.g., RNase III) with an RNA composition comprising one or more different ssRNA molecules and contaminant dsRNA molecules, and then cleaning up the ssRNA molecules in the treated preparation by salt precipitation, PAGE or agarose gel electrophoresis, column chromatography (including using a spin column or HPLC column), or any other methods known in the art, whereby the digested contaminant dsRNA molecules are removed and a purified or treated RNA composition comprising ssRNA molecules is obtained.

In some embodiments, the compositions described above are packaged in a kit.

In some of the embodiments of the invention, the method further comprises: introducing the purified or treated ssRNAs, wherein said purified or treated ssRNAs encode condition-specific (e.g., cancer-specific) proteins, into human or animal immune cells ex vivo in culture (e.g., T-cells or antigen presenting cells such as dendritic cells) that exhibit a first differentiated state or phenotype (either in culture or in a human or animal subject) and culturing the cells under conditions wherein the cells exhibit a second differentiated state or phenotype wherein they express the condition-specific proteins or peptides derived therefrom.

In still other embodiments, the purified or treated RNA composition, ssRNAs or mRNAs made using an RNase III treatment method of the invention, or which comprise a reaction mixture or RNA composition of the invention, or which are used in a method for inducing a biological or biochemical effect (e.g., for reprogramming) encode one or more transcription factors, growth factors, cytokines, cluster of differentiation (CD) molecules, interferons, interleukins, cell signaling proteins, protein receptors, protein hormones, antibody molecules, or long non-coding RNAs involved in cellular differentiation or maintenance thereof.

In some embodiments, the biological composition comprising RNA composition, or ssRNA or mRNA that is substantially, virtually, essentially, practically, extremely or absolutely free of dsRNA molecules generated using the method comprises or consists of ssRNA or mRNA that encodes a protein on the surface of human cells which is classified as a cluster of differentiation or cluster of designation (CD) molecule, selected from the group consisting of: CD1a; CD1b; CD1c; CD1d; CD1e; CD2; CD3d; CD3e; CD3g; CD4; CD5; CD6; CD7; CD8a; CD8b; CD9; CD10; CD11a; CD11b; CD11c; CD11d; CDw12; CD14; CD16a; CD16b; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD44; CD45; CD46; CD47; CD48; CD49a; CD49b; CD49c; CD49d; CD49e; CD49f; CD50; CD51; CD52; CD53; CD54; CD55; CD56; CD57; CD58; CD59; CD61; CD62E; CD62L; CD62P; CD63; CD64; CD66a; CD66b; CD66c; CD66d; CD66e; CD66f; CD68; CD69; CD70; CD71; CD72; CD74; CD79a; CD79b; CD80; CD81; CD82; CD83; CD84; CD85a; CD85c; CD85d; CD85e; CD85f; CD85g; CD85h; CD85i; CD85j; CD85k; CD86; CD87; CD88; CD89; CD90; CD91; CD92; CD93; CD94; CD95; CD96; CD97; CD98; CD99; CD100; CD101; CD102; CD103; CD104; CD105; CD106; CD107a; CD107b; CD108; CD109; CD110; CD111; CD112; CD113; CD114; CD115; CD116; CD117; CD118; CD119; CD120a; CD120b; CD121a; CD121b; CD122; CD123; CD124; CD125; CD126; CD127; CD129; CD130; CD131; CD132; CD133; CD134; CD135; CD136; CD137; CD138; CD139; CD140a; CD140b; CD141; CD142; CD143; CD144; CD146; CD147; CD148; CD150; CD151; CD152; CD153; CD154; CD155; CD156a; CD156b; CD157; CD158a; CD158b1; CD158b2; CD158c; CD158d; CD158e; CD158f1; CD158g; CD158h; CD158i;

CD158j; CD158k; CD158z; CD159a; CD159c; CD160; CD161; CD162; CD163; CD163b; CD164; CD165; CD166; CD167a; CD167b; CD168; CD169; CD170; CD171; CD172a; CD172b; CD172g; CD173; CD177; CD178; CD179a; CD179b; CD180; CD181; CD182; CD183; CD184; CD185; CD186; CD191; CD192; CD193; CD194; CD195; CD196; CD197; CDw198; CDw199; CD200; CD201; CD202b; CD203a; CD203c; CD204; CD205; CD206; CD207; CD208; CD209; CD210; CDw210b; CD212; CD213a1; CD213a2; CD214; CD215; CD217; CD218a; CD218b; CD220; CD221; CD222; CD223; CD224; CD225; CD227; CD228; CD229; CD230; CD231; CD232; CD233; CD234; CD235a; CD235b; CD236; CD238; CD239; CD240CE; CD240D; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD270; CD271; CD272; CD273; CD274; CD275; CD276; CD277; CD278; CD279; CD280; CD281; CD282; CD283; CD284; CD286; CD288; CD289; CD290; CD292; CDw293; CD294; CD295; CD296; CD297; CD298; CD299; CD300a; CD300b; CD300c; CD300d; CD300e; CD300f; CD300g; CD301; CD302; CD303; CD304; CD305; CD306; CD307a; CD307b; CD307c; CD307d; CD307e; CD309; CD312; CD314; CD315; CD316; CD317; CD318; CD319; CD320; CD321; CD322; CD324; CD325; CD326; CD327; CD328; CD329; CD331; CD332; CD333; CD334; CD335; CD336; CD337; CD338; CD339; CD340; CD344; CD349; CD350; CD351; CD352; CD353; CD354; CD355; CD357; CD358; CD360; CD361; CD362; and CD363. In preferred embodiments, the cluster of differentiation molecule is at least practically free, extremely free or absolutely free of dsRNA molecules.

In some embodiments of the compositions, reaction mixtures, system, kits and methods of the invention for using any of the foregoing, the in vitro-synthesized ssRNA or mRNA encodes a protein selected from the group consisting of: erythropoietin (EPO); a detectable enzyme selected from firefly luciferase, *Renilla* luciferase, bacterial beta-galactosidase (lacZ), and green fluorescent protein (GFP); a transcription factor selected from MYC and SRY or MCOP; a growth factor or cytokine selected from the group consisting of platelet-derived growth factor (PDGF), vascular endothelial growth factor (VEGF), transforming growth factor-beta1 (TGF-beta1), insulin-like growth factor (IGF), alpha-melanocyte-stimulating hormone (alpha-MSH); insulin-like growth factor-I (IGF-I); IL-4; IL-13; and IL-10; inducible nitric oxide synthase (iNOS); a heat shock protein; Cystic Fibrosis Transmembrane Conductance Regulator (CFTR); an enzyme with antioxidant activity selected from among catalase, phospholipid hydroperoxide glutathione peroxidase, superoxide dismutase-1, and superoxide dismutase-2; Bruton's tyrosine kinase; adenosine deaminase; ectonucleoside triphosphate diphosphydrolase; ABCA4; ABCD3; ACADM; AGL; AGT; ALDH4A1; ALPL; AMPD1; APOA2; AVSD1; BRCD2; C1QA; C1QB; C1QG; C8A; C8B; CACNA1S; CCV; CD3Z; CDC2L1; CHML; CHS1; CIAS1; CLCNKB; CMD1A; CMH2; CMM; COL11A1; COL8A2; COL9A2; CPT2; CRB1; CSE; CSF3R; CTPA; CTSK; DBT; DIO1; DISC1; DPYD; EKV; ENO1; ENO1P; EPB41; EPHX1; F13B; F5; FCGR2A; FCGR2B; FCGR3A; FCHL; FH; FMO3; FMO4; FUCA1; FY; GALE; GBA; GFND; GJA8; GJB3; GLC3B; HF1; HMGCL; HPC1; HRD; HRPT2; HSD3B2; HSPG2; KCNQ4; KCS; KIF1B; LAMB3; LAMC2; LGMD1B; LMNA; LOR; MCKD1; MCL1; MPZ; MTHFR; MTR; MUTYH; MYOC; NB; NCF2; NEM1; NPHS2; NPPA; NRAS; NTRK1; OPTA2; PBX1; PCHC; PGD; PHA2A; PHGDH; PKLR; PKP1; PLA2G2A; PLOD; PPOX; PPTO; PRCC; PRG4; PSEN2; PTOS1; REN; RFX5; RHD; RMD1; RPE65; SCCD; SERPINC1; SJS1; SLC19A2; SLC2A1; SPG23; SPTA1; TAL1; TNFSF6; TNNT2; TPM3; TSHB; UMPK; UOX; UROD; USH2A; VMGLOM; VWS; WS2B; ABCB11; ABCG5; ABCG8; ACADL; ACP1; AGXT; AHHR; ALMS1; ALPP; ALS2; APOB; BDE; BDMR; BJS; BMPR2; CHRNA1; CMCWTD; CNGA3; COL3A1; COLAA3; COL4A4; COL6A3; CPS1; CRYGA; CRYGEP1; CYP1B1; CYP27A1; DBI; DES; DYSF; EDAR; EFEMP1; EIF2AK3; ERCC3; FSHR; GINGF; GLC1B; GPD2; GYPC; HADHA; HADHB; HOXD13; HPE2; IGKC; IHH; IRS1; ITGA6; KHK; KYNU; LCT; LHCGR; LSFC; MSH2; MSH6; NEB; NMTC; NPHP1; PAFAH1P1; PAX3; PAX8; PMS1; PNKD; PPH1; PROC; REG1A; SAG; SFTPB; SLC11A1; SLC3A1; SOS1; SPG4; SRD5A2; TCL4; TGFA; TMD; TPO; UGT1A@; UV24; WSS; XDH; ZAP70; ZFHX1B; ACAA1; AGS1; AGTR1; AHSG; AMT; ARMET; BBS3; BCHE; BCPM; BTD; CASR; CCR2; CCR5; CDL1; CMT2B; COL7A1; CP; CPO; CRV; CTNNB1; DEM; ETM1; FANCD2; FIH; FOXL2; GBE1; GLB1; GLCLC; GNAI2; GNAT1; GP9; GPX1; HGD; HRG; ITIH1; KNG; LPP; LRS1; MCCC1; MDS1; MHS4; MITF; MLH1; MYL3; MYMY; OPA1; P2RY12; PBXP1; PCCB; POU1F1; PPARG; PROS1; PTHR1; RCA1; RHO; SCA7; SCLC1; SCN5A; SI; SLC25A20; SLC2A2; TF; TGFBR2; THPO; THRB; TKT; TM4SF1; TRH; UMPS; UQCRC1; USH3A; VHL; WS2A; XPC; ZNF35; ADH1B; ADH1C; AFP; AGA; AIH2; ALB; ASMD; BFHD; CNGA1; CRBM; DCK; DSPP; DTDP2; ELONG; ENAM; ETFDH; EVC; F11; FABP2; FGA; FGB; FGFR3; FGG; FSHMD1A; GC; GNPTA; GNRHR; GYPA; HCA; HCL2; HD; HTN3; HVBS6; IDUA; IF; JPD; KIT; KLKB1; LQT4; MANBA; MLLT2; MSX1; MTP; NR3C2; PBT; PDE6B; PEE1; PITX2; PKD2; QDPR; SGCB; SLC25A4; SNCA; SOD3; STATH; TAPVR1; TYS; WBS2; WFS1; WHCR; ADAMTS2; ADRB2; AMCN; AP3B1; APC; ARSB; B4GALT7; BHR1; C6; C7; CCAL2; CKN1; CMDJ; CRHBP; CSF1R; DHFR; DIAPH1; DTR; EOS; EPD; ERVR; F12; FBN2; GDNF; GHR; GLRA1; GM2A; HEXB; HSD17B4; ITGA2; KFS; LGMDLA; LOX; LTC4S; MAN2A1; MCC; MCCC2; MSH3; MSX2; NR3C1; PCSK1; PDE6A; PFBI; RASA1; SCZD1; SDHA; SGCD; SLC22A5; SLC26A2; SLC6A3; SM1; SMA@; SMN1; SMN2; SPINK5; TCOF1; TELAB1; TGFBI; ALDH5A1; ARG1; AS; ASSP2; BCKDHB; BF; C2; C4A; CDKN1A; COL10A1; COL11A2; CYP21A2; DYX2; EJM1; ELOVL4; EPM2A; ESR1; EYA4; F13A1; FANCE; GCLC; GJA1; GLYS1; GMPR; GSE; HCR; HFE; HLA-A; HLA-DPB1; HLA-DRA; HPFH; ICS1; IDDM1; IFNGR1; IGAD1; IGF2R; ISCW; LAMA2; LAP; LCA5; LPA; MCDR1; MOCS1; MUT; MYB; NEU1; NKS1; NYS2; OA3; ODDD; OFCO; PARK2; PBCA; PBCRA1; PDB1; PEX3; PEX6; PEX7; PKHD1; PLA2G7; PLG; POLH; PPAC; PSORS1; PUJO; RCD1; RDS; RHAG; RP14; RUNX2; RWS; SCA1; SCZD3; SIASD; SOD2; ST8; TAP1; TAP2; TFAP2B; TNDM; TNF; TPBG; TPMT; TULP1; WISP3; AASS; ABCB1; ABCB4; ACHE; AQP1; ASL; ASNS; AUTS1; BPGM; BRAF; C7orf2; CACNA2D1; CCM1; CD36; CFTR; CHORDOMA; CLCN1; CMH6; CMT2D; COL1A2; CRS; CYMD; DFNA5; DLD; DYT11; EEC1; ELN; ETV1; FKBP6; GCK; GHRHR; GHS; GLI3; GPDS1; GUSB; HLXB9; HOXA13; HPFH2; HRX; IAB; IMMP2L; KCNH2; LAMB1; LEP; MET; NCF1; NM; OGDH; OPN1SW; PEX1; PGAM2; PMS2; PON1; PPP1R3A; PRSS1; PTC; PTPN12; RP10; RP9; SERPINE1;

SGCE; SHFM1; SHH; SLC26A3; SLC26A4; SLOS; SMAD1; TBXAS1; TWIST; ZWS1; ACHM3; ADRB3; ANK1; CA1; CA2; CCAL1; CLN8; CMT4A; CNGB3; COH1; CPP; CRH; CYPIIB1; CYPIIB2; DECR1; DPYS; DURS1; EBS1; ECA1; EGI; EXT1; EYA1; FGFR1; GNRH1; GSR; GULOP; HR; KCNQ3; KFM; KWE; LGCR; LPL; MCPH1; MOS; MYC; NAT1; NAT2; NBS1; PLAT; PLEC1; PRKDC; PXMP3; RP1; SCZD6; SFTPC; SGM1; SPG5A; STAR; TG; TRPS1; TTPA; VMD1; WRN; ABCA1; ABL1; ABO; ADAMTS13; AK1; ALAD; ALDH1A1; ALDOB; AMBP; AMCD1; ASS; BDMF; BSCL; C5; CDKN2A; CHAC; CLA1; CMD1B; COL5A1; CRAT; DBH; DNAI1; DYS; DYT1; ENG; FANCC; FBP1; FCMD; FRDA; GALT; GLDC; GNE; GSM1; GSN; HSD17B3; HSN1; IBM2; INVS; JBTS1; LALL; LCCS1; LCCS; LGMD2H; LMX1B; MLLT3; MROS; MSSE; NOTCH1; ORM1; PAPPA; PIP5KIB; PTCH; PTGS1; RLN1; RLN2; RMRP; ROR2; RPD1; SARDH; SPTLC1; STOM; TDFA; TEK; TMC1; TRIM32; TSC1; TYRP1; XPA; CACNB2; COL17A1; CUBN; CXCL12; CYP17; CYP2C19; CYP2C9; EGR2; EMX2; ERCC6; FGFR2; HK1; HPS1; IL2RA; LGI1; LIPA; MAT1A; MBL2; MKI67; MXI1; NODAL; OAT; OATL3; PAX2; PCBD; PEO1; PHYH; PNLIP; PSAP; PTEN; RBP4; RDPA; RET; SFTPA1; SFTPD; SHFM3; SIAL; THC2; TLX1; TNFRSF6; UFS; UROS; AA; ABCC8; ACAT1; ALX4; AMPD3; ANC; APOAL; APOA4; APOC3; ATM; BSCL2; BWS; CALCA; CAT; CCND1; CD3E; CD3G; CD59; CDKNLC; CLN2; CNTF; CPT1A; CTSC; DDB1; DDB2; DHCR7; DLAT; DRD4; ECB2; ED4; EVR1; EXT2; F2; FSHB; FTH1; G6PT1; G6PT2; GIF; HBB; HBBP1; HBD; HBE1; HBG1; HBG2; HMBS; HND; HOMG2; HRAS; HVBS1; IDDM2; IGER; INS; JBS; KCNJ11; KCNJ1; KCNQ1; LDHA; LRP5; MEN1; MLL; MYBPC3; MYO7A; NNO1; OPPG; OPTB1; PAX6; PC; PDX1; PGL2; PGR; PORC; PTH; PTS; PVRL1; PYGM; RAG1; RAG2; ROM1; RRAS2; SAA1; SCA5; SCZD2; SDHD; SERPING1; SMPD1; TCIRG1; TCL2; TECTA; TH; TREH; TSG101; TYR; USH1C; VMD2; VRNI; WT1; WT2; ZNF145; A2M; AAAS; ACADS; ACLS; ACVRL1; ALDH2; AMHR2; AOM; AQP2; ATD; ATP2A2; BDC; CIR; CD4; CDK4; CNA1; COL2A1; CYP27B1; DRPLA; ENUR2; FEOM1; FGF23; FPF; GNB3; GNS; HAL; HBP1; HMGA2; HMN2; HPD; IGF1; KCNA1; KERA; KRAS2; KRT1; KRT2A; KRT3; KRT4; KRT5; KRT6A; KRT6B; KRTHB6; LDHB; LYZ; MGCT; MPE; MVK; MYL2; OAP; PAH; PPKB; PRB3; PTPN11; PXR1; RLS; RSN; SAS; SAX1; SCA2; SCNN1A; SMAL; SPPM; SPSMA; TBX3; TBX5; TCF1; TPI1; TSC3; ULR; VDR; VWF; ATP7B; BRCA2; BRCD1; CLN5; CPB2; ED2; EDNRB; ENUR1; ERCC5; F10; F7; GJB2; GJB6; IPF1; MBS1; MCOR; NYS4; PCCA; RB1; RHOK; SCZD7; SGCG; SLC10A2; SLC25A15; STARP1; ZNF198; ACHM1; ARVD1; BCH; CTAA1; DAD1; DFNB5; EML1; GALC; GCH1; IBGC1; IGH@; IGHC group; IGHG1; IGHM; IGHR; IV; LTBP2; MJD; MNG1; MPD1; MPS3C; MYH6; MYH7; NP; NPC2; PABPN1; PSEN1; PYGL; RPGRIP1; SERPINA1; SERPINA3; SERPINA6; SLC7A7; SPG3A; SPTB; TCL1A; TGM1; TITF1; TMIP; TRA@; TSHR; USHLA; VP; ACCPN; AHO2; ANCR; B2M; BBS4; BLM; CAPN3; CDAN1; CDAN3; CLN6; CMH3; CYP19; CYP1A1; CYP1A2; DYX1; EPB42; ETFA; EYCL3; FAH; FBN1; FES; HCVS; HEXA; IVD; LCS1; LIPC; MYO5A; OCA2; OTSC1; PWCR; RLBP1; SLC12A1; SPG6; TPM1; UBE3A; WMS; ABCC6; ALDOA; APRT; ATP2A1; BBS2; CARD15; CATM; CDH1; CETP; CHST6; CLN3; CREBBP; CTH; CTM; CYBA; CYLD; DHS; DNASE1; DPEP1; ERCC4; FANCA; GALNS; GAN; HAGH; HBA1; HBA2; HBHR; HBQ1; HBZ; HBZP; HP; HSD11B2; IL4R; LIPB; MC1R; MEFV; MHC2TA; MLYCD; MMVP1; PHKB; PHKG2; PKD1; PKDTS; PMM2; PXE; SALL1; SCA4; SCNN1B; SCNN1G; SLC12A3; TAT; TSC2; VDI; WT3; ABR; ACACA; ACADVL; ACE; ALDH3A2; APOH; ASPA; AXIN2; BCL5; BHD; BLMH; BRCA1; CACD; CCA1; CCZS; CHRNB1; CHRNE; CMT1A; COL1A1; CORD5; CTNS; EPX; ERBB2; G6PC; GAA; GALK1; GCGR; GFAP; GH1; GH2; GPIBA; GPSC; GUCY2D; ITGA2B; ITGB3; ITGB4; KRT10; KRT12; KRT13; KRT14; KRT14L1; KRT14L2; KRT14L3; KRT16; KRT16L1; KRT16L2; KRT17; KRT9; MAPT; MDB; MDCR; MGI; MHS2; MKS1; MPO; MYO15A; NAGLU; NAPB; NF1; NME1; P4HB; PAFAH1B1; PECAM1; PEX12; PHB; PMP22; PRKAR1A; PRKCA; PRKWNK4; PRP8; PRPF8; PTLAH; RARA; RCV1; RMSA1; RP17; RSS; SCN4A; SERPINF2; SGCA; SGSH; SHBG; SLC2A4; SLC4A1; SLC6A4; SMCR; SOST; SOX9; SSTR2; SYM1; SYNS1; TCF2; THRA; TIMP2; TOC; TOP2A; TP53; TRIM37; VBCH; ATP8B1; BCL2; CNSN; CORD1; CYB5; DCC; F5F8D; FECH; FEO; LAMA3; LCFS2; MADH4; MAFD1; MC2R; MCL; MYP2; NPC1; SPPK; TGFBRE; TGIF; TTR; AD2; AMH; APOC2; APOE; ATHS; BAX; BCKDHA; BCL3; BFIC; C3; CACNA1A; CCO; CEACAM5; COMP; CRX; DBA; DDU; DFNA4; DLL3; DM1; DMWD; E11S; ELA2; EPOR; ERCC2; ETFB; EXT3; EYCL1; FTL; FUT1; FUT2; FUT6; GAMT; GCDH; GPI; GUSM; HB1; HCL1; HHC2; HHC3; ICAM3; INSR; JAK3; KLK3; LDLR; LHB; LIG1; LOH19CR1; LYL1; MAN2B1; MCOLN1; MDRV; MLLT1; NOTCH3; NPHS1; OFC3; OPA3; PEPD; PRPF31; PRTN3; PRX; PSG1; PVR; RYR1; SLC5A5; SLC7A9; STK11; TBXA2R; TGFB1; TNNI3; TYROBP; ADA; AHCY; AVP; CDAN2; CDPD1; CHED1; CHED2; CHRNA4; CST3; EDN3; EEGV1; FTLL1; GDF5; GNAS; GSS; HNF4A; JAG1; KCNQ2; MKKS; NBIA1; PCK1; PI3; PPCD; PPGB; PRNP; THBD; TOP1; AIRE; APP; CBS; COL6A1; COL6A2; CSTB; DCR; DSCR1; FPDMM; HLCS; HPE1; ITGB2; KCNE1; KNO; PRSS7; RUNX1; SOD1; TAM; ADSL; ARSA; BCR; CECR; CHEK2; COMT; CRYBB2; CSF2RB; CTHM; CYP2D6; CYP2D7P1; DGCR; DIA1; EWSR1; GGT1; MGCR; MN1; NAGA; NE2; OGS2; PDGFB; PPARA; PRODH; SCO2; SCZD4; SERPIND1; SLC5A1; SOX10; TCN2; TIMP3; TST; VCF; ABCD1; ACTL1; ADFN; AGMX2; AHDS; AIC; AIED; AIH3; ALAS2; AMCD; AMELX; ANOP1; AR; ARAF1; ARSC2; ARSE; ARTS; ARX; ASAT; ASSP5; ATP7A; ATRX; AVPR2; BFLS; BGN; BTK; BZX; C1HR; CACNA1F; CALB3; CBBM; CCT; CDR1; CFNS; CGF1; CHM; CHR39c; CIDX; CLA2; CLCN5; CLS; CMTX2; CMTX3; CND; COD1; COD2; COL4A5; COL4A6; CPX; CVD1; CYBB; DCX; DFN2; DFN4; DFN6; DHOF; DIAPH2; DKC1; DMD; DSS; DYT3; EBM; EBP; ED1; ELK1; EMD; EVR2; F8; F9; FCP1; FDPSL5; FGD1; FGS1; FMR1; FMR2; G6PD; GABRA3; GATA1; GDI1; GDXY; GJB1; GK; GLA; GPC3; GRPR; GTD; GUST; HMS1; HPRT1; HPT; HTC2; HTR2c; HYR; IDS; IHG1; IL2RG; INDX; IP1; IP2; JMS; KAL1; KFSD; LiCAM; LAMP2; MAA; MAFD2; MAOA; MAOB; MCF2; MCS; MEAX; MECP2; MF4; MGC1; MIC5; MID1; MLLT7; MLS; MRSD; MRX14; MRX1; MRX20; MRX2; MRX3; MRX40; MRXA; MSD; MTM1; MYCL2; MYP1; NDP; NHS; NPHL1; NROB1; NSX; NYS1; NYX; OA1; OASD; OCRL; ODT1; OFD1; OPA2; OPD1; OPEM; OPNILW; OPNIMW; OTC; P3; PDHA1; PDR; PFC; PFKFB1; PGK1; PGK1P1; PGS; PHEX; PHKA1; PHKA2; PHP; PIGA PLP1; POF1; POLA; POU3F4; PPMX; PRD; PRPS1;

PRPS2; PRS; RCCP2; RENBP; RENS1; RP2; RP6; RPGR; RPS4X; RPS6KA3; RS1; S11; SDYS; SEDL; SERPINA7; SH2D1A; SHFM2; SLC25A5; SMAX2; SRPX; SRS; STS; SYN1; SYP; TAF1; TAZ; TBX22; TDD; TFE3; THAS; THC; TIMM8A; TIM1; TKCR; TNFSF5; UBE1; UBE2A; WAS; WSN; WTS; WWS; XIC; XIST; XK; XM; XS; ZFX; ZIC3; ZNF261; ZNF41; ZNF6; AMELY; ASSP6; AZF1; AZF2; DAZ; GCY; RPS4Y; SMCY; ZFY; ABAT; AEZ; AFA; AFD1; ASAH1; ASD1; ASMT; CCAT; CECR9; CEPA; CLA3; CLN4; CSF2RA; CTS1; DF; DIH1; DWS; DYT2; DYT4; EBR3; ECT; EEF1A1L14; EYCL2; FANCB; GCSH; GCSL; GIP; GTS; HHG; HMI; HOAC; HOKPP2; HRPT1; HSD3B3; HTC1; HV1S; ICHQ; ICR1; ICR5; IL3RA; KAL2; KMS; KRT18; KSS; LCAT; LHON; LIMM; MANBB; MCPH2; MEB; MELAS; MIC2; MPFD; MS; MSS; MTATP6; MTCO1; MTC03; MTCYB; MTND1; MTND2; MTND4; MTND5; MTND6; MTRNR1; MTRNR2; MTTE; MTTG; MTTI; MTTK MTTL1; MTTL2; MTTN; MTTP; MTTS1; NAMSD; OCD1; OPD2; PCK2; PCLD; PCOS1; PFKM; PKD3; PRCA1; PRO1; PROP1; RBS; RFXAP; RP; SHOX; SLC25A6; SPG5B; STO; SUOX; THM; and TD.

In some embodiments of any of the compositions, methods, and systems for inducing a biological or biochemical effect by repeatedly or continuously introducing a ssRNA or mRNA into a mammalian cell (e.g., that exhibits a first state of differentiation or phenotype, e.g., for reprogramming to a second state of differentiation or phenotype), the mammalian cell is selected from the group consisting of: an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius' cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, and a zymogenic cell.

In some embodiments of all of the methods, the purified or treated RNA composition does not generate an innate immune response that is sufficient to cause significant inhibition of cellular protein synthesis or dsRNA-induced apoptosis. In certain embodiments, the purified or treated RNA composition does not generate an innate immune response that is sufficient to cause significant inhibition of cellular protein synthesis or dsRNA-induced apoptosis when said introducing of the purified RNA composition into a living human or animal cell or subject is repeated at least 3 times (e.g., when introduced daily for multiple weeks or daily or weekly for multiple weeks, months or years). In preferred embodiments of the method for reprogramming a human or animal somatic cell to an iPS cell, the purified or treated RNA composition does not generate an innate immune response that is sufficient to cause substantial inhibition of cellular protein synthesis or dsRNA-induced apoptosis when said introducing of the purified or treated RNA composition into a living human or animal cell is repeated daily for about 10-18 or more days.

In some embodiments, the purified or treated ssRNAs are introduced daily or twice per day, with said introducing occurring about 1 time per week, 2 times per week, 3 times per week, 4 times per week, 5 times per week, 6 times per week, or daily for a period consisting of: (i) up to about 4 weeks for cells in culture; or (ii) for a period of weeks, months or years for the living human or animal subject.

In certain embodiments, the invention provides a method for treating, reducing or eliminating a symptom or disease of a human or animal subject that exhibits a disease condition, comprising: administering to the human or animal subject an effective dose of purified or treated ssRNAs, whereby the symptom or disease is reduced or eliminated.

In some embodiments the treated ssRNA or the purified or treated ssRNA is used to: reprogram cells that exhibit a first differentiated state or phenotype to cells that exhibit a second differentiated state or phenotype; compensate for a missing or defective protein; express a desired protein such as a transcription factor, cell signaling protein, growth factor, interferon, interleukin, cluster of differentiation (CD) molecule (e.g., see http://www. followed by "uniprot.org/docs/cdlist.txt"), protein hormone, protein receptor, or an antibody; express a long non-coding RNA molecule involved with differentiation (e.g., "HOTAIR" OR HOX antisense intergenic RNA; Wan Y and Chang H Y, 2010); or modulate or trigger a disease-specific immune response.

In certain embodiments, the invention provides a method for reprogramming a eukaryotic cell that exhibits a first differentiated state or phenotype to a cell that exhibits a second differentiated state or phenotype. Thus, in certain embodiments, the method further comprises: introducing the treated ssRNAs or the purified ssRNAs into a human or animal cell that exhibits a first differentiated state or phenotype and culturing the cell under conditions wherein the cell exhibits a second differentiated state or phenotype. In one preferred embodiment of this method, the treated ssRNAs or the purified ssRNAs are purified ssRNAs that encode a protein. In one preferred embodiment of this method, the purified ssRNAs encode induced pluripotent stem cell (iPSC) induction factors, the cells that exhibit a first differentiated state are human or animal somatic cells, and the purified ssRNAs are introduced into said cells daily for about 7 to about 21 days to generate cells that exhibit a second differentiated state or phenotype comprising iPSCs.

In certain embodiments, the invention provides a method for reducing or eliminating a symptom or disease of a human or animal subject that exhibits a disease condition, comprising: administering introducing into the subject the cell that exhibits the second differentiated state or phenotype, whereby the symptom or disease is reduced or eliminated.

In some preferred embodiments of the methods, the one or more in vitro-synthesized ssRNAs and/or the purified ssRNAs exhibit at least one heterologous 5' UTR sequence, Kozak sequence, IRES sequence, or 3' UTR sequence that results in greater translation into the encoded protein when said respective ssRNAs are introduced into eukaryotic cells compared to the same ssRNAs that do not exhibit said respective 5' UTR sequence, Kozak sequence, IRES sequence, or 3' UTR sequence. In some particular preferred embodiments, the 5' UTR or 3' UTR is a sequence exhibited by a Xenopus or human alpha- (α-) globin or beta- (β-) globin mRNA, or wherein the 5' UTR is a sequence exhibited by tobacco etch virus (TEV) RNA.

In some embodiments of the methods, the treated ssRNAs or the purified ssRNAs exhibit a 5' cap comprising 7-methylguanine or an anti-reverse cap analog (ARCA). In some embodiments, the treated ssRNAs or the purified ssRNAs further comprise a 5' cap that has a cap1 structure, wherein the 2' hydroxyl of the ribose in the 5' penultimate nucleotide is methylated (e.g., using RNA 2'-O-methyltransferase, e.g., using the SCRIPTCAP™ 2'-O-methyltransferase kit, CELLSCRIPT, Inc.).

In some embodiments, wherein the treated ssRNAs or the purified ssRNAs exhibit a 5' cap, the one or more in vitro-synthesized ssRNAs used for said treating in said method exhibit the 5' cap (i.e., prior to said treating). Thus, in some embodiments, the one or more in vitro-synthesized ssRNAs used for said treating comprise capped ssRNAs. In some of these embodiments, the one or more in vitro-synthesized ssRNA molecules that exhibit the 5' cap were synthesized prior to their use for said treating: (i) co-transcriptionally by incorporation of a cap analog (e.g., an anti-reverse cap analog or ARCA) during in vitro transcription of (e.g., using the MESSAGEMAX™ T7 ARCA-capped message transcription kit or the INCOGNITO™ T7 ARCA 5ᵐC- and Ψ-RNA transcription kit, CELLSCRIPT, Inc., Madison, WI, USA); or (ii) post-transcriptionally by incubating in vitro-transcribed ssRNA molecules with a capping enzyme system comprising RNA guanyltransferase under conditions wherein the in vitro-transcribed ssRNA molecules are 5'-capped, including wherein the capping enzyme system results in methylation of the 2' hydroxyl of the ribose in the 5' penultimate nucleotide (e.g., using T7 mSCRIPT™ standard mRNA production system, or using a separate in vitro transcription system, such as the T7-SCRIBE™ standard RNA IVT kit, the INCOGNITO™ T7 Ψ-RNA transcription kit, or the INCOGNITO™ T7 5mC- and Ψ-RNA transcription kit to obtain ssRNA, and the SCRIPTCAP™ m⁷G capping system to obtain cap0 RNA (all from CELLSCRIPT, Inc.); in some embodiments, the capping enzyme system further results in methylation of the 2' hydroxyl of the ribose in the 5' penultimate nucleotide to generate cap1 RNA, and the method further comprises: incubating with RNA 2'-O-methyltransferase (e.g., using the SCRIPTCAP™ 2'-O-methyltransferase kit, CELLSCRIPT, Inc.).

In some preferred embodiments wherein the treated ssRNAs or the purified ssRNAs exhibit a 5' cap, the one or more in vitro-synthesized ssRNAs used in said method for said treating are uncapped and the method further comprises: post-transcriptionally capping the treated ssRNAs or the purified ssRNAs to generate 5' capped treated ssRNAs or 5' capped purified ssRNAs. In some embodiments, said post-transcriptional capping of the treated ssRNAs or the purified ssRNAs is performed as described above and/or in the product literature provided with the SCRIPTCAP™ m⁷G Capping System, the SCRIPTCAP™ 2'-O-methyltransferase kit, or the 17 mSCRIPT™ standard mRNA production system with respect to the capping enzyme system components (all from CELLSCRIPT, Inc., Madison, WI, USA).

In some preferred embodiments, the one or more in vitro-synthesized ssRNAs used for said treating are substantially free of uncapped RNAs that exhibit a 5'-triphosphate group (which are considered to be one type of "contaminant RNA molecules" herein). In some preferred embodiments, the treated ssRNAs and/or the purified ssRNAs generated from a method are substantially free of uncapped RNAs that exhibit a 5'-triphosphate group. In certain embodiments, the one or more in vitro-synthesized ssRNAs used for said treating, the treated ssRNAs, and/or the purified ssRNAs consist of a population of ssRNA molecules having: (i) greater than 90% capped ssRNA molecules; (ii) greater than 95% capped ssRNA molecules; (iii) greater than 99% capped ssRNA molecules; or (iv) greater than 99.9% capped ssRNA molecules. In some embodiments wherein the population of ssRNA molecules also comprises contaminant uncapped RNA molecules that exhibit a 5'-triphosphate group, the method further comprises: incubating the one or more in vitro-synthesized ssRNAs used for said treating, or the treated ssRNAs or the purified ssRNAs generated from the method with an alkaline phosphatase (e.g., NTPhosphatase™, epicentre technologies, Madison, WI, USA) or with RNA 5' polyphosphatase (epicentre technologies) to remove the triphosphate groups from contaminating uncapped ssRNAs; in some embodiments, the one or more in vitro-synthesized ssRNAs used for said treating, or the treated ssRNAs or the purified ssRNAs that are incubated with RNA 5'polyphosphatase are further incubated with TERMINATOR™ 5'-phosphate-dependent nuclease or Xm1 exoribonuclease (e.g., from *Saccharomyces cerevisae*) to digest said contaminating uncapped ssRNAs. These methods for incubating with alkaline phosphatase or with RNA 5' polyphosphatase and TERMINATOR™ 5'-phosphate-dependent nuclease or Xm1 exoribonuclease are particularly useful to remove uncapped ssRNAs from capped ssRNAs that were made by co-transcriptional capping by incorporating a cap analog during an in vitro transcription reaction.

In some preferred embodiments of the methods, the one or more in vitro-synthesized ssRNAs, the treated ssRNAS, or the purified ssRNAs are polyadenylated. In some embodiments, the one or more in vitro-synthesized ssRNAs, the treated ssRNAS, or the purified ssRNAs exhibit a poly-A tail of about 50 to about 200 nucleotides. However the poly-A tail is not limited with respect to the number of nucleotides and the poly-A tail can exhibit more than 200 or less than 50 nucleotides.

In some embodiments, the one or more in vitro-synthesized ssRNAs, the treated ssRNAS, and/or the purified ssRNAs exhibit a poly-A tail of 50-100 nucleotides, 100-200 nucleotides, 150-200 nucleotides, or greater than 200 nucleotides. In some preferred embodiments, the one or more in vitro-synthesized ssRNAs, the treated ssRNAS, and/or the purified ssRNAs exhibit a poly-A tail of 150-200 nucleotides in length. In some embodiments, the one or more in vitro-synthesized ssRNAs are polyadenylated by in vitro transcription of a DNA template that comprises a terminal oligo(dT) sequence that is complementary to the poly-A tail. In some preferred embodiments, the one or more in vitro-synthesized ssRNAs, the treated ssRNAS, or the purified ssRNAs are polyadenylated by post-transcriptional polyadenylation using a poly(A) polymerase or poly-A polymerase (e.g., poly-A polymerase derived from E. coli or Saccharomyces cerevisiae; or a poly-A polymerase from a commercial source, e.g., A-PLUS™ poly(A) polymerase, CELLSCRIPT, Inc., Madison, WI 53713, USA). However, unless specifically stated with respect to a particular method, the invention is not limited to use of a particular poly(A) polymerase, and any suitable poly(A) polymerase can be used. A "poly(A) polymerase" or "poly-A polymerase" or "PAP", when used herein, means a template-independent RNA polymerase found in most eukaryotes, prokaryotes, and eukaryotic viruses that selectively uses ATP to incorporate AMP residues to 3'-hydroxylated ends of RNA. Since PAP enzymes that have been studied from plants, animals, bacteria and viruses all catalyze the same overall reaction (e.g., see Edmonds, M, 1990), are highly conserved structurally (e.g., see Gershon, P, 2000), and lack intrinsic specificity for particular sequences or sizes of RNA molecules if the PAP is separated from proteins that recognize AAUAAA polyadenylation signals (Wilusz, J and Shenk, T, 1988), purified wild-type and recombinant PAP enzymes from any of a variety of sources can be used in the kits and methods of the present invention. The invention is also not limited to the methods for polyadenylating the one or more in vitro-synthesized ssRNAs, the treated ssRNAS, or the purified ssRNAs described herein and any other suitable method in the art may be used for said polyadenylating.

In some embodiments of the methods, the one or more in vitro-synthesized ssRNAs comprise at least one modified ribonucleoside selected from the group consisting of pseudouridine ($\Psi$), 1-methyl-pseudouridine ($m^1\Psi$), 5-methylcytidine ($m^5C$), 5-methyluridine ($m^5U$), 2'-O-methyluridine (Um or $m^{2'-O}U$), 2-thiouridine ($s^2U$), and $N^6$-methyladenosine ($m^6A$) in place of at least a portion of the corresponding unmodified canonical ribonucleoside. In some embodiments wherein the one or more in vitro-synthesized ssRNAs comprise at least one modified ribonucleoside, the at least one modified ribonucleoside is selected from the group consisting of: (i) pseudouridine ($\Psi$), 1-methyl-pseudouridine ($m^1\Psi$), 5-methyluridine ($m^5U$), 2'-O-methyluridine (Um or $m^{2'-O}U$), and 2-thiouridine ($s^2U$) in place of all or substantially all of the canonical uridine residues; (ii) 5-methylcytidine ($m^5C$) in place of all or substantially all of the canonical cytidine residues; and/or (iii) $N^6$-methyladenosine ($m^6A$) in place of all or substantially all of the canonical adenosine residues. In some preferred embodiments wherein the one or more in vitro-synthesized ssRNAs comprise at least one modified ribonucleoside, the at least one modified ribonucleoside consists of pseudouridine ($\Psi$) or 1-methyl-pseudouridine ($m^1\Psi$) in place of all or substantially all of the canonical uridine residues, and/or 5-methylcytidine ($m^5C$) in place of all or substantially all of the canonical cytidine residues. In some preferred embodiments, wherein the in vitro-synthesized ssRNAs comprise pseudouridine ($\Psi$) or 1-methyl-pseudouridine ($m^1\Psi$) in place of all or substantially all of the canonical uridine residues, the in vitro-synthesized ssRNAs also comprise 5-methylcytidine ($m^5C$) in place of all or substantially all of the canonical cytidine residues.

In some embodiments of the methods wherein the one or more in vitro-synthesized ssRNAs comprise at least one modified ribonucleoside, the one or more in vitro-synthesized ssRNAs are synthesized by in vitro transcription (IVT) of a DNA template that encodes each said at least one protein or polypeptide reprogramming factor using an RNA polymerase that initiates said transcription from a cognate RNA polymerase promoter that is joined to said DNA template and ribonucleoside 5' triphosphates (NTPs) comprising at least one modified ribonucleoside 5' triphosphate selected from the group consisting of pseudouridine 5' triphosphate ($\Psi$TP), 1-methyl-pseudouridine 5' triphosphate ($m^1\Psi$P), 5-methylcytidine 5' triphosphate ($m^5$CTP), 5-methyluridine 5' triphosphate ($m^5$UTP), 2'-O-methyluridine 5' triphosphate (UmTP or $m^{2'-O}$UTP), 2-thiouridine 5' triphosphate ($s^2$UTP), and $N^6$-methyladenosine 5' triphosphate ($m^6$ATP); in some preferred embodiments, the modified NTP is used in place of all or substantially all of the corresponding unmodified NTP in the IVT reaction (e.g., $\omega$TP, $m^1\Psi$P, $m^5$UTP, $m^{2'-O}$UTP or $s^2$UTP in place of UTP: $m^5$CTP in place of CTP; or $m^6$ATP in place of ATP).

In some embodiments of the methods, the one or more in vitro-synthesized ssRNAs are substantially free of modified ribonucleosides (other than those ribonucleosides comprising the 5' cap structure, if a 5' cap is present, including the 5' penultimate nucleoside when the one or more in vitro-synthesized ssRNAs exhibit a cap1 cap structure). In some embodiments of the methods, except for the ribonucleosides comprising the 5' cap, if present, the one or more in vitro-synthesized ssRNAs comprise only the canonical ribonucleosides G, A, C and U. In some embodiments of the methods, the one or more in vitro-synthesized ssRNAs that encode each said at least one protein or polypeptide reprogramming factor was synthesized by in vitro transcription of a DNA template by an RNA polymerase using the canonical NTPs: GTP, ATP, CTP and UTP.

In some of the embodiments of the method for making purified ssRNAs wherein the one or more in vitro-synthesized ssRNAs comprise either one or more modified ribonucleosides (e.g. $\Psi$ and/or $m^5C$) or only unmodified ribonucleosides (G, A, C and U) and encode one or more protein or polypeptide reprogramming factors, the method further comprises: introducing the purified or treated ssRNAs into a eukaryotic cell that exhibits a first differentiated state or phenotype at least three times over a period of at least three days and culturing the cells under conditions wherein the cells exhibit a second differentiated state or phenotype. In some of these embodiments, the eukaryotic cell that exhibits a first differentiated state or phenotype is a human or animal somatic cell, the purified or treated ssRNAs encode reprogramming factors comprising induced pluripotent stem cell (iPS cell) induction factors, and the cells that exhibit a second differentiated state or phenotype are iPS cells; in these embodiments the introducing of the purified or treated ssRNAs at least three times over a period of at least three days means about at least seven times over at least seven days to about at least 21 times over at least 21 days.

Surprisingly and unexpectedly, the present Applicants found that this method for reprogramming eukaryotic cells by introducing into the cells purified or treated ssRNAs encoding iPS cell induction factors resulted in reprogramming of human or animal somatic cells (e.g., fibroblasts, kerotinocytes) to iPS cells, both when purified or treated ssRNAs comprising modified ribonucleosides such as $\Psi$ and/or $m^5C$ were used, and when purified or treated ssRNAs consisting of only unmodified canonical ribonucleosides, G, A, C and U, were used. Prior to the results of the present Applicants, it is believed that only modified ssRNAs had been used for reprogramming cells. Prior to the results of the present Applicants, it is believed that nobody had ever shown reprogramming of human or animal somatic cells to iPS cells with ssRNAs consisting of only unmodified canonical ribonucleosides.

Still further, prior to the work disclosed in the present application, it is believed that nobody had ever demonstrated reprogramming of a human or animal somatic cell to an iPS cell using modified ssRNAs without contacting the cells with an inhibitor of the interferon signaling pathway, such as the B18R protein as an inhibitor of type I interferon, prior to introducing said ssRNAs encoding the iPS cell induction factors. Thus, the ability of the methods of the present invention to generate purified or treated ssRNAs that result in efficient induction of iPS cells from human or animal somatic cells further demonstrates the significance and breadth of this method for making purified or treated ssRNAs for translation in living cells.

The ability of the methods of the present invention to generate treated ssRNAs that do not activate RNA sensors or RNA signaling pathways, such as TLR3 pathways, and do not induce apoptosis pathways, even after introducing the treated ssRNAs into the cells 18 or more times over at least 18 days, further demonstrates the power of the methods of the present invention, and the comparative advantage of these methods over other methods known in the art.

In certain embodiments, methods for treating in vitro-synthesized ssRNAs with RNase III can be performed in less than an hour, with only a few minutes of hands-on time, and many different ssRNAs can be treated simultaneously, making the method easily adaptable to high-throughput production of purified ssRNAs. Since, in certain embodiments, certain methods described herein primarily comprise an enzymatic step, which may, for example, be performed by simple pipetting steps, in some embodiments, the present method is performed unattended using a laboratory robot. Thus, the invention provides, in certain embodiments, an automated method for making purified ssRNAs for reprogramming human or animal somatic cells to iPS cells or for reprogramming one type of somatic cell to another type of somatic cell.

In addition to the above, the present Applicants have also found that purified ssRNAs comprising modified nucleosides that are purified by an HPLC purification method can also be used for reprogramming human somatic cells to iPS cells, as disclosed herein. However, the present methods using RNase III treatment are much easier, faster and more economical in terms of time, materials and reagents than HPLC purification methods for generating purified ssRNAs for reprogramming eukaryotic somatic cells to iPS cells or for other applications.

In some preferred embodiments of the methods, compositions or kits of the invention, the treated RNA composition comprising ssRNA or mRNA is repeatedly or continuously contacted with or repeatedly or continuously introduced into a human or animal (e.g., mammalian) cell that is ex vivo in culture or in vivo in an organism, wherein the RNA composition is capable of inducing a biological or biochemical effect (e.g., reprogramming of the cell from a first differentiated state or phenotype to a second differentiated state or phenotype). Thus, one embodiment of the invention is a method for inducing a biological or biochemical effect in a human or animal cell (e.g., mammalian cell), comprising: repeatedly or continuously introducing an RNA composition comprising one or more ssRNAs or mRNAs encoding one or more proteins (e.g., one or more protein reprogramming factors, e.g., one or more transcription factors) into a human or animal cell in culture, and culturing under conditions wherein the biological or biochemical effect is induced.

In some embodiments, the biological effect comprises reprogramming a cell that exhibits a first differentiated state or phenotype to a cell that exhibits a second differentiated state of phenotype. In some embodiments, the human or mammalian cell that exhibits a first differentiated state or phenotype is a somatic cell (e.g., a fibroblast, keratinocyte, or blood cell), the ssRNAs or mRNAs encode one or more reprogramming factors or iPSC induction factors selected from the group consisting of OCT4, SOX2, KLF4, LIN28, NANOG, and a MYC family protein chosen from among wild-type c-MYC, mutant c-MYC(T58A), and L-MYC, and the cell that exhibits the second differentiated state or phenotype is an iPS cell. In some embodiments, wherein the human or mammalian cell that exhibits a first differentiated state or phenotype is a somatic cell (e.g., a fibroblast cell), said culturing comprises culturing the cells in the absence of feeder cells in the presence of at least one small molecule inhibitor of transforming growth factor-beta (TGF-beta or TGFβ), at least one small molecule inhibitor of mitogen-activated protein kinase (MAPK/ERK kinase or MEK), or at least one small molecule inhibitor for both TGF-beta and MEK; in some of these embodiments, the cells are cultured: (i) on feeder cells; (ii) on a biological substrate that does not comprise live feeder cells (e.g., an extracellular matrix extract, e.g., a gelatinous protein mixture secreted by Engelbreth-Holm-Swarm (EHS) mouse sarcoma cells, e.g., as marketed under tradenames such as MATRIGEL™ or CULTREX BME (BD Biosciences); or one or more biomolecules, e.g., purified human vitronectin protein); (iii) directly on a culture dish surface to which the first type of cells adhere and grow to form a monolayer in the absence of feeder cells or a biological substrate.

One other embodiment of the present invention is a Feeder-free Reprogramming Medium consisting of Dulbecco's modified Eagle medium with nutrient mixture F-12 (DMEM/F12; Invitrogen) supplemented with 20% KNOCKOUT™ serum replacement (Invitrogen), 2 mM GLUTAMAX™-I (Invitrogen), 0.1 mM non-essential amino acids solution (Invitrogen), and 0.5-15 micromolar MEK signaling pathway inhibitor (e.g., STEMOLECULE™ PD0325901, Stemgent, Cambridge, MA, USA). In some embodiments, the Feeder-free Reprogramming Medium further comprises transforming growth factor β (TGFβ) inhibitor (e.g., STEMOLECULE™ SB431542, Stemgent™). In some embodiments, the Feeder-free Reprogramming Medium further comprises about 100 ng/ml basic human recombinant fibroblast growth factor. In some embodiments, the Feeder-free Reprogramming Medium further comprises penicillin and streptomycin antibiotics.

As shown in EXAMPLE 23, when unmodified GAUC Luc2 dsRNA or modified GAψC-dsRNA was added daily for two days with the respective GAUC mRNA or GAψC mRNA encoding MYOD mRNA, reprogramming of mouse mesenchymal stem cells to myoblast cells was induced only if the amount of added Luc2 dsRNA was less than about 0.01% of the total mass of RNA used for reprogramming, However, when modified GAψm$^5$C Luc2 dsRNA was added daily for two days with GAψm$^5$C mRNA encoding MYOD mRNA, myoblast cells were induced when the Luc2 dsRNA was less than about 0.1% of the total mass of RNA in the RNA composition.

Thus, one embodiment of the invention is a method for reprogramming a human or mammalian non-myoblast cell (e.g., a mouse mesenchymal stem cell) to a myoblast cell comprising: daily, for at least two days, introducing into non-myoblast cells an RNA composition comprising in vitro-synthesized GAUC mRNA or GAψC mRNA encoding MYOD protein or a functional fragment or variant thereof, wherein said RNA composition is at least practically free of dsRNA, and culturing under conditions wherein at least a portion of said non-myoblast cells are reprogrammed or differentiated into myoblast cells.

Thus, one other embodiment of the invention is a method for reprogramming a human or mammalian non-myoblast cell (e.g., a mouse mesenchymal stem cell) to a myoblast cell comprising: daily, for at least two days, introducing into non-myoblast cells an RNA composition comprising in vitro-synthesized GAψm$^5$C mRNA encoding MYOD protein or a functional fragment or variant thereof, wherein said RNA composition is at least virtually free, essentially free, or more preferably practically free of dsRNA, and culturing under conditions wherein at least a portion of said non-myoblast cells are reprogrammed or differentiated into myoblast cells.

When unmodified GAUC Luc2 dsRNA was added daily with the GAψC-mRNAs encoding ASCL1, MYT1L, NEUROD1, and POU3F2 (AMNP) reprogramming factors, neurons were induced only if the amount of added unmodified GAUC Luc2 dsRNA was less than about 0.01% of the total mass of RNA used for reprogramming, and significant numbers of neurons were generated only if the amount of added unmodified GAUC Luc2 dsRNA was less than about 0.001% of the total mass of RNA used for reprogramming. When modified GAψC Luc2 dsRNA was added daily with the GAψC-mRNAs encoding AMNP reprogramming factors, neurons were induced only if pseudouridine-modified GAψC Luc2 dsRNA was less than about 0.02% of the total mass of RNA used for reprogramming, and significant numbers of neurons were generated only if the amount of added unmodified GAUC Luc2 dsRNA was less than about 0.004% of the total mass of RNA used for reprogramming. These results show, for certain embodiments, that the dsRNA should generally be reduced to below those levels (e.g., using the RNase III treatment methods described herein) in order to reprogram human fibroblasts to neuron cells as shown in EXAMPLE 24.

Thus, one other embodiment of the invention is a method for reprogramming non-neuron somatic cells (e.g., human fibroblast cells) to neuron cells, the method comprising: daily, for multiple days (e.g., for about six or more days), introducing into non-neuron somatic cells ex vivo in culture, an RNA composition comprising in vitro-synthesized ssRNA or mRNA encoding at least one protein selected from the group consisting of: ASCL1, MYT1L, NEUROD1 and POU3F2 or functional fragment or variant of any thereof, wherein said RNA composition is at least practically free, or more preferably, extremely free or absolutely free of dsRNA, and culturing under conditions wherein at least a portion of said non-neuron somatic cells are reprogrammed or transdifferentiated into neuron cells.

Another embodiment of the invention is a method for reprogramming a human or mammalian non-cardiac fibroblast cells to a cardiac fibroblast cells, the method comprising: daily, for multiple days, introducing into human or mammalian fibroblasts ex vivo in culture an RNA composition comprising in vitro-synthesized ssRNA or mRNA encoding at least one protein transcription factor or reprogramming factor selected from the group consisting of: ETS2, MESP1, GATA4, HAND2, TBX5 and MEF2C, or a functional fragment or variant of any thereof, wherein the RNA composition is practically free, extremely free or absolutely free of dsRNA, and culturing under conditions wherein the non-cardiac fibroblast cells are reprogrammed into cardiac fibroblast cells.

One embodiment of the invention is a method for reprogramming a human or mammalian fibroblast cells to dopaminergic neuron cells, the method comprising: daily, for multiple days, introducing into human or mammalian fibroblasts ex vivo in culture an RNA composition comprising in vitro-synthesized ssRNA or mRNA encoding at least one protein transcription factor or reprogramming factor selected from the group consisting of: ASCL1, EN1, FOXA2, LMX1A, NURR1 and PITX3, or a functional fragment or variant of any thereof; wherein the RNA composition is extremely free or absolutely free of dsRNA, and culturing under conditions wherein the fibroblast cells are reprogrammed into dopaminergic neuron cells.

One embodiment of the invention is a method for reprogramming a human or mammalian fibroblast cells to hepatocytes, the method comprising: daily, for multiple days, introducing into human or mammalian fibroblasts ex vivo in culture an RNA composition comprising in vitro-synthesized ssRNA or mRNA encoding at least one protein transcription factor or reprogramming factor selected from the group consisting of: HNF1α or functional fragment or variant thereof, HNF4α, FOXA1, FOXA2, FOXA3 and GATA4, or functional fragment or variant of any thereof; wherein the RNA composition is absolutely free of dsRNA, and culturing under conditions wherein the fibroblast cells are reprogrammed into hepatocytes.

In some preferred embodiments, the RNA composition or the in vitro-synthesized ssRNA or mRNA composing the RNA composition that is practically free of dsRNA, extremely free of dsRNA, or absolutely free of dsRNA is less immunogenic (or induces a detectably lower immune response or a detectably lower innate immune response) in said cell or in a human or animal (e.g., mammalian) tissue, organ or organism containing said cell than an RNA composition or the in vitro-synthesized ssRNA or mRNA composing the RNA composition that is not practically free of dsRNA, extremely free of dsRNA, or absolutely free of dsRNA. In some embodiments, the RNA composition or the in vitro-synthesized ssRNA or mRNA composing the RNA composition is analyzed to induce a detectably lower innate immune response as detected by a method selected from the group consisting of: (i) detecting that repeatedly contacting the mammalian cell with an amount of the modified RNA that results in detectable expression of the encoded protein after a single contacting does not detectably reduce expression of the protein, whereas repeatedly contacting the mammalian cell with the same quantity of the unmodified RNA does detectably reduce expression of the encoded protein; (ii) detecting that the modified RNA results in a lower level of self-phosphorylation of RNA-activated protein kinase (PKR) and/or phosphorylation of the eukaryotic translation initiation factor (eIF2α) compared to the same quantity of the unmodified RNA counterpart based on in vitro phosphorylation assays; (iii) detecting that the quantity of one or more cytokines induced by the mammalian cell in response to unmodified RNA is higher than the quantity of said one or more cytokines induced by the mammalian cell in response to said modified RNA counterpart; (iv) detecting a difference in the level of expression of one or more dendritic cell (DC) activation markers in response to the unmodified RNA compared to the level of expression of said one or more DC activation markers in response to the same quantity of said modified RNA; (v) detecting a higher relative ability of said modified RNA to act as an adjuvant for an adaptive immune response compared to the same quantity of unmodified RNA counterpart; (vi) detecting a higher level of activation of toll-like receptor (TLR) signaling molecules in response to unmodified RNA compared to the same quantity of said modified RNA; and/or (vii) determining the quantity of the modified RNA to elicit an immune response measured in any of cells (i)-(vi) compared to the quantity of unmodified RNA to elicit the same immune response; particularly wherein: said one or more cytokines in (iii) are selected from the group consisting of: IL-12, IFN-alpha, TNF-alpha, RANTES, MIP-1alpha, MIP-1beta, IL-6, IFN-beta, and IL-8; said DC activation markers in (iv) are selected from the group consisting of: CD83, HLA-DR, CD80, and CD86; and/or said TLR signaling molecules in (vi) are selected from the group consisting of: TLR3, TLR7, and TLR8 signaling molecules. In some preferred embodiments the detectably lower innate immune response induced by said RNA composition or the in vitro-synthesized ssRNA or mRNA composing the RNA composition that is practically free of dsRNA, extremely free of dsRNA, or absolutely free of dsRNA compared to said RNA composition or the in vitro-synthesized ssRNA or mRNA composing the RNA composition that is not practically free of dsRNA, extremely free of dsRNA, or absolutely free of dsRNA is at least 2-fold lower using at least one of said cells for determining or measuring said detectable decrease in immunogenicity. For example, in some embodiments the RNA composition or the in vitro-synthesized ssRNA or mRNA composing the RNA composition that is practically, extremely or absolutely free of dsRNA is analyzed to induce a detectably lower innate immune response as described in U.S. Patent Application No. 20110143397, incorporated herein by reference, particularly as described in paragraph [0262] and in "Materials and Methods for Examples 35-38" and/or as described and shown for FIGS. 22-24 therein.

One embodiment of the invention is a method for making a biological composition (e.g., an RNA composition) that is at least practically free of dsRNA, the method comprising: treating the biological composition (e.g., an RNA composition or ssRNA or mRNA composing an RNA composition) with a dsRNA-specific protein in a buffered solution under conditions wherein the dsRNA-specific protein binds and/or reacts with dsRNA contaminants, and then removing the dsRNA-specific protein and the bound or reacted dsRNA contaminants to generate a treated RNA preparation (or treated ssRNA or mRNA composing the RNA composition) that is at least practically free of dsRNA. With respect to the methods, compositions or kits of the present invention, a "dsRNA-specific protein" herein means a protein that is not an antibody, which protein binds and/or reacts with dsRNA with much higher affinity and specificity than it binds and/or reacts with other non-dsRNA biomolecules. In some specific embodiments, the dsRNA-specific protein is a dsRNA-specific ribonuclease (RNase). In some preferred embodiments, the dsRNA-specific RNase is an endoribonuclease (endoRNase). Most preferably, the endoRNase of the methods, compositions or kits of the invention is RNase III.

One preferred embodiment of the invention, wherein the dsRNA-specific protein is RNase III, is a method for making a biological composition (e.g., an RNA composition) that is substantially free, virtually free, essentially free, practically free, extremely free, or absolutely free of dsRNA, the method comprising: contacting a biological composition (e.g., an RNA composition or ssRNA or mRNA composing an RNA composition) with RNase III in a buffered solution containing a magnesium salt comprising magnesium cations at a concentration of about 1 mM to about 4 mM under conditions wherein the RNase III binds and/or reacts with dsRNA that is present in the solution to generate a treated biological composition that is substantially free, virtually free, essentially free, practically free, extremely free, or absolutely free of dsRNA. When used to make an RNA composition that is substantially free, virtually free, essentially free, practically free, extremely free, or absolutely free of dsRNA, this method is sometimes referred to as an "RNase III treatment" or "RNase III treatment method" herein. In some preferred embodiments of the RNase III treatment method or embodiments of compositions or kits comprising or for practicing the RNase III treatment method, the buffered solution comprises a Tris buffer (e.g., 33 mM Tris-acetate, pH 8) as the buffer, In some other embodiments, a different buffer that maintain the pH at about pH 7.5-8 is used. In some embodiments, a different buffer or a different pH somewhat outside of the range of pH 7.5-8 is used. In preferred embodiments the solution further comprises a monovalent salt at a concentration of at least about 50 mM, and more preferably, the solution further comprises a monovalent salt at a concentration of about 50 mM to about 150 mM, and most preferably, the solution further comprises a monovalent salt at a concentration of about 150 mM or greater than 150 mM. In some embodiments of the method, the method further comprises cleaning up the biological composition from the RNase III and other components in the solution. Some embodiments of the invention comprise a biological composition (e.g., an RNA composition) or a kit comprising a biological composition (e.g., an RNA composition) that is generated using the RNase III treatment methods described herein, wherein the biological composition (e.g, an RNA composition or ssRNA or mRNA composing an RNA composition) is substantially free, virtually free, essentially free, practically free, extremely free, or absolutely free of dsRNA.

Some preferred embodiments of the invention wherein the biological composition is an RNA composition comprising ssRNA or mRNA are: (i) the method for making a biological composition that is substantially free, virtually free, essentially free, practically free, extremely free, or absolutely free of dsRNA, (ii) a biological composition that is substantially free, virtually free, essentially free, practically free, extremely free, or absolutely free of dsRNA made using the method, (iii) a kit comprising a biological composition that is substantially free, virtually free, essentially free, practically free, extremely free, or absolutely free of dsRNA, or (iv) a kit for making a biological composition that is substantially free, virtually free, essentially free, practically free, extremely free, or absolutely free of dsRNA, wherein said RNA composition is substantially free of dsRNA, virtually free of dsRNA, essentially free of dsRNA, practically free of dsRNA, extremely free of dsRNA, or absolutely free of dsRNA, meaning, respectively, that less than about: 0.5%, 0.1%, 0.05%, 0.01%, 0.001%, or 0.0002% of the RNA in the RNA composition comprises dsRNA of a size greater than about 40 basepairs (or greater than about 30 basepairs). In some preferred embodiments, the biological composition comprises or consists of an RNA composition comprising one or more in vitro-synthesized ssRNAs or mRNAs (or the one or more in vitro-synthesized ssRNAs or mRNAs) and the method comprises: contacting the RNA composition or the one or more ssRNAs or mRNAs with RNase III in a buffered solution comprising divalent magnesium cations at a concentration of about 1 mM to about 4 mM and a monovalent salt at a concentration of at least 50 mM and incubating under conditions wherein the RNase III binds to the dsRNA and is enzymatically active, and then cleaning up the RNA composition or the ssRNA or mRNAs from the RNase III and the other components, including the RNase III digestion products, to generate a treated RNA composition or treated ssRNAs or_mRNAs that is (are) substantially free, virtually free, essentially free, practically free, extremely free or absolutely free of dsRNA. In preferred embodiments of this method, treated RNA composition or treated ssRNAs or mRNAs is (are) practically free, extremely free or absolutely free of dsRNA. In some preferred embodiments of this method, the monovalent salt has a concentration of about 50 mM to about 100 mM, about 100 mM to about 200 mM, or about 200 mM to about 300 mM. In some preferred embodiments of the method, said cleaning up the ssRNAs or mRNAs comprises at least one step selected from: extracting with organic solvent (e.g., phenol and/or chloroform), precipitating the ssRNAs or mRNAs with ammonium acetate, and washing the precipitate with alcohol (e.g., 70% ethanol). In preferred embodiments the cleanup does not comprise a chromatographic column or electrophoretic gel device. In some embodiments, said cleanup comprises a gel (e.g., crosslinked dextran) filtration spin column. In certain preferred embodiments of this method, the buffered solution comprises divalent magnesium cations at a concentration of about 1.0 mM to about 3.0 mM, or more preferably, about 1.0 mM to about 2.0 mM.

In some embodiments of the method for making an RNA composition comprising ssRNA or mRNA that is substantially free, virtually free, essentially free, practically free, extremely free, or absolutely free of dsRNA, method further comprises at least one step selected from among ammonium acetate precipitation, alcohol precipitation, and organic extraction (e.g., phenol and/or chloroform extraction), (e.g., each as described in one or more of the Examples presented herein). In some preferred embodiments, the RNA composition comprises ssRNA or mRNA encoding one or more proteins, In some preferred embodiments of the method for making an RNA composition comprising ssRNA or mRNA that is substantially free, virtually free, essentially free, practically free, extremely free, or absolutely free of dsRNA, the method does not comprise any column chromatography (whether gravity flow or under pressure, e.g., HPLC or FPLC), electrophoresis, or other separation step comprising use of a resin, gel or membrane. Thus, some advantages of the present method for making an RNA composition comprising ssRNA or mRNA that is substantially free, virtually free, essentially free, practically free, extremely free, or absolutely free of dsRNA are that no such separation, chromatography, electrophoresis or special instrumentation is required, all of which may require special training, materials (e.g., columns, membranes), additional work and time (e.g., packing of columns, washing of columns, special analytic methods), and costs therefor, and which may be time consuming and require special analytic methods. Thus, the present method for making RNA compositions is much easier, faster, and economical than other methods, while generating RNA compositions that are equal or better for use in methods comprising contacting the RNA compositions with a human or animal cell (e.g., to induce a biological or biochemical effect, e.g., to reprogram a cell from a first differentiated state or phenotype to a second differentiated state or phenotype). In view of these advantages and benefits over methods for purification comprising a separation device (e.g., HPLC or preparative electrophoresis, we believe the presently described method for making a treated RNA composition will significantly accelerate work on methods for using RNA compositions comprising ssRNA or mRNA encoding one or more protein, which RNA compositions are practically free, extremely free or absolutely free of dsRNA, to induce a biological or biochemical effect by repeatedly or continuously introducing said RNA composition in to a human or animal (e.g., mammalian) cell (e.g., a cell that is ex vivo in culture or in vivo in a tissue, organ or organism)

In other embodiments of the compositions, reaction mixtures, kits and methods of the invention, the in vitro-synthesized ssRNA does not encode a protein or polypeptide, but instead comprises at least one long non-coding RNA (ncRNA). Thus, in some embodiments, the ssRNA exhibits a sequence of at least one long ncRNA. In some embodiments of the compositions, reaction mixtures, kits and methods of the invention, the in vitro-synthesized ssRNA exhibits a sequence of at least one long ncRNA that is capable of effecting a biological or biochemical effect upon its repeated or continuous introduction into a human or animal cell (e.g., a mammalian cell). In some embodiment of compositions, kits and methods of the invention, the ssRNA is at least one long ncRNA referred to "HOX antisense intergenic RNA" (Woo C J and Kingston R E, 2007), also known as "HOTAIR," "HOXAS," "HOXC-AS4," "HOXC11-AS1" or "NCRNA00072."

Some embodiments of the invention comprise (i) a method for making a biological composition (e.g., an RNA composition) that is substantially free, virtually free, essentially free, practically free, extremely free, or absolutely free of dsRNA, or (ii) a reaction mixture or biological composition (e.g., a reaction mixture) that is generated using the method for making a biological composition that is substantially free, virtually free, essentially free, practically free, extremely free, or absolutely free of dsRNA, or (iii) a kit comprising a biological composition that is substantially free, virtually free, essentially free, practically free, extremely free, or absolutely free of dsRNA, or (iv) a kit for making a biological composition that is substantially free, virtually free, essentially free, practically free, extremely free, or absolutely free of dsRNA, wherein the biological composition does not comprise an RNA composition or ssRNA or mRNA composing an RNA composition. With respect to these embodiments of the invention, by "substantially free, virtually free, essentially free, practically free, extremely free, or absolutely free of dsRNA," we mean that the biological composition in the final solution in which it is contacted with human or animal cells contains: less than about 5 nanograms of dsRNA per ml of solution, less than about 1 nanogram of dsRNA per ml of solution, less than about 500 picograms of dsRNA per ml of solution, less than about 100 picograms of dsRNA per ml of solution, less than about 10 picograms of dsRNA per ml of solution, or less than about 2 picograms of dsRNA per ml of solution, respectively. In particular embodiments of the method, biological composition or kit comprising a biological composition that is substantially free, virtually free, essentially free, practically free, extremely free, or absolutely free of dsRNA, the biological composition comprises one or more biologicals selected from the group consisting of: double-stranded DNA (dsDNA), single-stranded DNA (ssDNA), proteins, carbohydrates, lipids, glycoproteins, lipoproteins, growth factors, cytokines, cellular extracts, extracellular matrixes, serum, biological fluids, biological membranes, and media.

In some embodiments of the method for making a biological composition (e.g., an RNA composition) that is substantially free, virtually free, essentially free, practically free, extremely free, or absolutely free of dsRNA, the method further comprises contacting the solution with one or more deoxyribonucleases (DNases) to generate a biological composition that is virtually free, practically free, or extremely free of DNA, meaning that the biological composition in the final solution in which it is contacted with human or animal cells contains less than about one nanogram of DNA per ml of solution, less than about 100 picograms of DNA per ml of solution, or less than about 10 picograms of DNA per ml of solution. In some embodiments, the DNAse is a "type I DNase," meaning an endodeoxyribonuclease that digests single-stranded and double-stranded DNA to short oligonucleotides having a 5'-phosphate and a 3'-hydroxyl group (e.g., human, bovine or porcine pancreatic DNase I). In some embodiments, the DNAse is a single-strand-specific 3'-to-5' exodeoxyribonuclease that lacks ribonuclease activity, but that digests oligodeoxyribonucleotides having a free 3'-hydroxyl group to 5'-monodeoxyribonucleotides (e.g., *Escherichia coli* exonuclease I). In some embodiments, multiple DNases are used. Thus, in some embodiments of the biological compositions or kits comprising the a biological composition that is substantially free of dsRNA, virtually free, essentially free, practically free of dsRNA, extremely free of dsRNA, or absolutely free of dsRNA, the biological composition or kit is also virtually free, practically free, or extremely free of DNA.

In certain embodiments of the methods, compositions or kits of the invention, the RNA composition is treated or purified to be at least virtually dsRNA-free (e.g., virtually free of dsRNA, practically free of dsRNA, extremely free of dsRNA, or absolutely free of dsRNA) by separation of the ssRNA or mRNA from RNA contaminants comprising said RNA composition using one or more chromatographic or electrophoretic separation media (e.g., using a chromatographic or electrophoretic separation method discussed elsewhere herein). In some preferred embodiments of the methods, compositions or kits, the RNA composition is purified to be at least virtually dsRNA-free (e.g., virtually free of dsRNA, practically free of dsRNA, extremely free of dsRNA, or absolutely free of dsRNA) by separation of the ssRNA or mRNA from RNA contaminants by HPLC. In some preferred embodiments of the methods, compositions or kits, the in vitro-synthesized ssRNA or mRNA composing the RNA composition was purified (e.g., to be virtually free of dsRNA, practically free of dsRNA, extremely free of dsRNA, or absolutely free of dsRNA) by HPLC and analyzed for purity and immunogenicity as described in U.S. Patent Application No. 20110143397, incorporated herein by reference, particularly as described in paragraph [0262] and in "Materials and Methods for Examples 35-38" and/or as described and shown for FIGS. 22-24 therein.

Still another embodiment of the invention is a method for inducing a biological or biochemical effect in a human or other mammalian cell, either ex vivo in culture or in vivo in a human or mammalian organism, comprising: repeatedly or continuously contacting the cell with the at least practically dsRNA-free RNA composition over multiple days under conditions wherein the RNA composition is introduced into the cell and a biological or biochemical effect is induced. In some embodiments, the at least practically dsRNA-free RNA composition comprises ssRNA or mRNA that encodes one or more reprogramming factors and the biological or biochemical effect comprises reprogramming the cells from a first differentiated state or phenotype to a second differentiated state or phenotype. Thus, in some embodiments, the invention provides a rapid, efficient method for changing the state of differentiation or phenotype of a human or mammalian cell. For example, in some embodiments, the present invention provides at least practically dsRNA-free RNA compositions comprising ssRNA or mRNA and methods for their use to reprogram human or mammalian somatic cells to pluripotent stem cells. In some preferred embodiments, the at least practically dsRNA-free compositions used for said method is practically free of dsRNA, extremely free of dsRNA, or absolutely free of dsRNA.

Certain embodiments of the present invention provide ex vivo methods, and compositions and kits for rapidly and efficiently reprogramming human or animal cells in culture from a first differentiated state or phenotype to a second differentiated state or phenotype by repeatedly or continuously introducing purified or treated in vitro-synthesized mRNAs encoding multiple proteins (e.g., reprogramming factors) into the cells for multiple days, whereby the second differentiated state or phenotype is induced. For example, in some embodiments, human somatic cells, such as fibroblasts or keratinocytes, were reprogrammed (dedifferentiated) to induced pluripotent stem cells by repeatedly introducing in vitro-synthesized mRNAs encoding multiple iPSC reprogramming factor proteins into the cells daily for multiple days. In other embodiments, human non-neural somatic cells, such as fibroblasts, were reprogrammed (transdifferentiated) to neural cells by repeatedly introducing mRNAs encoding multiple neural cell reprogramming factor proteins daily for multiple days. In still other embodiments, mouse mesenchymal stem cells were reprogrammed (differentiated) to myoblast cells by introducing mRNA encoding MYOD protein daily for two days. Thus, in some embodiments, the invention provides general methods for reprogramming cells from a first differentiated state to a second differentiated state by repeatedly or continuously introducing mRNA encoding one or more proteins into the cells daily for 2 or more days.

In certain embodiments, the present invention provides methods for inducing a biological or biochemical effect in a human or animal cell (e.g., a mammalian cell; e.g., a cell in culture or in vivo or in a tissue, organ or organism that contains them) comprising: repeatedly or continuously introducing said treated and/or purified in vitro-synthesized mRNAs encoding one or more proteins that is/are capable of inducing the desired biological or biochemical effect into said cells. In some embodiments of the methods, the biological or biochemical effect comprises reprogramming of a cell from a first state of differentiation or phenotype to a second state of differentiation or phenotype. In some embodiments of the methods, the cell is a human or animal (e.g., mammalian) immune system cell, the in vitro-synthesized ssRNA or mRNA encodes one or more proteins comprising the immunoglobulin superfamily, and the biological or biochemical effect comprises binding of the one or more immunoglobulin superfamily proteins expressed on the surface of the immune system cells to one or more exogenous proteins or polypeptides, which exogenous proteins or polypeptide are either free or in or on the surface of a non-immune system cell, thereby initiating an immune response mechanism in response to said exogenous protein or polypeptide. In some embodiments of the methods, the cell is an antigen presenting cell (APC), such as a human or mammalian dendritic cell, and the biological or biochemical effect comprises presentation of a peptide derived from said one or more proteins encoded by the in vitro-synthesized ssRNA or mRNA on the surface of the APC; in certain preferred embodiments, the composition comprising in vitro-synthesized ssRNA or mRNA does not result in production of interferon. In other embodiments of the methods, the cell is a human or mammalian cell that contains a mutant gene encoding a defective protein and the biological or biochemical effect comprises expressing one or more proteins encoded by the in vitro-synthesized ssRNA or mRNA in said cells, thereby substituting or compensating for the defective protein.

In some embodiments of the methods, compositions and/or kits of the present invention, the ssRNA or mRNA encodes a protein. In some embodiments of the methods, compositions and/or kits of the present invention, the ssRNA or mRNA encodes a functional protein, wherein the term "functional" means that the protein is capable of causing a biochemical change or a biological effect (e.g., therapeutic treatment, such as a reduction of symptoms in a subject), whether direct or indirect (e.g., via a signaling pathway), in a cell in which the protein is present or in another cell that is affected by the protein or by the cell in which the protein is expressed. In some embodiments of the methods, compositions and/or kits of the present invention, the ssRNA or mRNA encodes a transcription factor. In some embodiments of the methods, compositions and/or kits of the present invention, the ssRNA or mRNA encodes an enzyme. In some embodiments of the methods, compositions and/or kits of the present invention, the ssRNA or mRNA encodes a cluster of differentiation or CD molecule. In some embodiments of the methods, compositions and/or kits of the present invention, the ssRNA or mRNA encodes an antibody. In some embodiments of the methods, compositions and/or kits of the present invention, the ssRNA or mRNA encodes a protein that is present on or in a cell membrane. In some embodiments of the methods, compositions and/or kits of the present invention, the ssRNA or mRNA encodes a protein that comprises a receptor for a signaling pathway. In some embodiments of the methods, compositions and/or kits of the present invention, the ssRNA or mRNA encodes an immune effector protein. In some embodiments of the methods, compositions and/or kits of the present invention, the ssRNA or mRNA encodes a complement protein of a vertebrate immune system. In some embodiments of the methods, compositions and/or kits of the present invention, the ssRNA or mRNA comprises a multiplicity of different mRNA molecules which encode a multiplicity of different proteins.

In some embodiments, the present invention relates to compositions, kits and rapid, efficient methods for changing the state of differentiation of a human or animal eukaryotic cell. For example, the present invention provides ssRNA or mRNA molecules and methods for their use to reprogram cells, such as to reprogram human or animal somatic cells to pluripotent stem cells.

In some embodiments, the present invention provides methods for changing or reprogramming the state of differentiation or differentiated state or phenotype of a human or animal cell comprising: introducing mRNA encoding at least one reprogramming factor into a cell that exhibits a first differentiated state or phenotype to generate a reprogrammed cell that exhibits a second differentiated state or phenotype (and compositions and kits therefor). In some embodiments, the present invention provides methods for changing or reprogramming the state of differentiation or differentiated state or phenotype of a human or animal cell (e.g., a mammalian cell) comprising: repeatedly on continuously, over a period of at least two days, introducing mRNA encoding at least one protein reprogramming factor into a cell that exhibits a first differentiated state or phenotype to generate a reprogrammed cell that exhibits a second differentiated state or phenotype (and compositions and kits therefor). In particular embodiments, the introducing comprises introducing mRNA encoding a plurality of reprogramming factors into the cell. In some embodiments, the present invention provides methods for changing the differentiated state or state of differentiation of a cell comprising: introducing an mRNA encoding an iPS cell induction factor into a somatic cell to generate a reprogrammed cell (and compositions and kits therefor). In some embodiments, the present invention provides methods for changing the differentiated state or state of differentiation of a cell comprising: repeatedly on continuously, over a period of at least two days, introducing an mRNA encoding at least one protein comprising an iPS cell induction factor into a somatic cell to generate a reprogrammed cell (and compositions and kits therefor). In certain embodiments, the introducing comprises delivering the mRNA to the somatic cell with a transfection reagent. In certain embodiments, the introducing comprises delivering the mRNA to the somatic cell by electrophoresis. In some embodiments, the introducing is repeated daily for at least 3 days. In some embodiments, the introducing is repeated daily for at least 4-8 days. In some embodiments, the introducing is repeated daily for at least 8-10 days. In some preferred embodiments, the introducing is repeated daily for at least 10 to 18 days. In some embodiments, the introducing is repeated daily for greater than 18 days. In some embodiments, the reprogrammed cell is a dedifferentiated cell and the process that occurs in this method is referred to as "dedifferentiation." One embodiment of a dedifferentiated cell is an induced pluripotent stem cell or iPS cell (or iPSC). In some preferred embodiments of the methods, the reprogrammed cell is an iPS cell. In further embodiments of the methods, the reprogrammed cell is a transdifferentiated cell and the process that occurs in this method is referred to as "transdifferentiation." In other embodiments, the cell that exhibits the second state of differentiation or phenotype is a differentiated or redifferentiated somatic cell and the process that occurs in this method is referred to as "differentiation" or "redifferentiation." In some embodiments wherein the introducing is repeated daily for at least 2 days, the mRNA encodes the protein MYOD, the cell that exhibits the first state of differentiation or first differentiated state is a somatic cell (e.g., a fibroblast or keratinocyte) or a mesenchymal stem cell, and the cell that exhibits the second differentiated state is a myoblast cell. In these embodiments, if the cell that exhibits the first differentiated state is a somatic cell (e.g., a fibroblast or keratinocyte), the process is transdifferentiation, whereas if the cell that exhibits the first differentiated state is a mesenchymal stem cell, and the process is differentiation. In some embodiments, wherein the introducing is repeated daily for at least 4-9 days, the mRNA encodes the proteins ASCL1, MYT1L, NEUROD1 and POU3F2, the cell that exhibits the first state of differentiation or first differentiated state is a somatic cell (e.g., a fibroblast or keratinocyte), and the cell that exhibits the second differentiated state is a neural cell; in this embodiment, the process is transdifferentiation. In some embodiments, wherein the introducing is repeated daily for at least 4-8 days, at least 8-10 days. at least 10 to 18 days, or for greater than 18 days, the mRNA encodes the proteins OCT4, SOX2, KLF4, and at least one MYC protein selected from the group consisting of wild-type c-MYC long, mutant c-MYC(T58A), wild-type c-MYC short and L-MYC, the cell that exhibits the first state of differentiation or first differentiated state is a somatic cell (e.g., a fibroblast or keratinocyte), and the cell that exhibits the second differentiated state is an iPS cell, and the process is dedifferentiation or iPS cell induction; in some of these embodiments, the mRNA further encodes one or both of the proteins LIN28 and NANOG. In some embodiments wherein mRNAs encoding multiple different proteins are used, the introducing comprises introducing a mixture of mRNAs encoding all of the proteins, wherein each mRNA encoding a particular protein is present in the same molar amount as each of the other mRNAs encoding other proteins. In some other embodiments, one or more mRNAs is present in a different molar ratio than the other mRNAs encoding other proteins. For example, in certain embodiments wherein the mRNAs encode OCT4, SOX2, KLF4, one or both of LIN28 and NANOG, and at least one MYC protein selected from the group consisting of wild-type c-MYC long, mutant c-MYC(T58A), wild-type c-MYC short and L-MYC, the mRNA encoding OCT4 is present in the mRNA mixture at approximately a 3-fold molar excess compared to the particular mRNAs introduced that encoded SOX2, KLF4, LIN28, NANOG, and the at least one MYC family protein; in some other embodiments, in addition to the higher molar excess of mRNA encoding OCT4, the mRNA encoding KLF4 is also present in the mRNA mixture at approximately a 1.5-fold to 3.5-fold molar excess compared to the particular mRNAs introduced that encode SOX2, LIN28, NANOG, and the at least one MYC family protein, In certain preferred embodiments of the methods for changing or reprogramming the state of differentiation or phenotype of a cell, the method is performed without the use any exogenous protein, siRNA, or small molecule agent that inhibits or reduces the activation, induction or the expression of one or more proteins in an innate immune response pathway. For example, in some embodiments of the methods for changing or reprogramming the differentiated state or phenotype of a human or animal cell, no siRNA or protein (e.g., B18R protein), antibody or small molecule inhibitor of an innate immune response pathway is used for said reprogramming. In other embodiments, the methods further comprise: treating the cells that exhibit the first differentiated state or phenotype with a protein, siRNA, or small molecule agent that inhibits or reduces the activation, induction or expression of one or more RNA sensors or proteins in an innate immune response pathway, wherein said treating is prior to and/or during said introducing of an mRNA encoding a reprogramming factor. In some embodiments, the agent that inhibits or reduces the activation, induction or expression of one or more RNA sensors or proteins in an innate immune response pathway is B18R protein. In some other embodiments, the agent is an mRNA that encodes a protein that inhibits or reduces the activation, induction or expression of one or more proteins comprising an RNA sensor or innate immune response pathway. In some preferred embodiments, the inhibitor is an mRNA that encodes B18R protein. In some other preferred embodiments, the inhibitor is an mRNA that encodes the Vaccinia virus E3L gene protein; in preferred embodiments, the mRNA that encodes the Vaccinia virus E3L gene protein is introduced into the cell at the same time as the mRNA encoding one or more reprogramming factors or iPS cell induction factors are introduced.

In certain preferred embodiments of the methods for changing or reprogramming the state of differentiation or phenotype of a cell, the method for reprogramming is performed by adding an RNase inhibitor (e.g., SCRIPT-GUARD™ RNase inhibitor, CELLSCRIPT, INC., Madison, WI, USA) to the media or compositions comprising ssRNA or mRNA used for said reprogramming. Also, some preferred embodiments of compositions or kits for said reprogramming further comprise an RNase inhibitor.

In some preferred embodiments of the compositions, kits or methods of the invention, the in vitro-synthesized ssRNA or mRNA comprises a 5' cap or cap (e.g., a cap comprising 7-methylguanine) on its 5' terminus and a poly(A) tail on its 3' terminus. In some embodiments, the 5' cap is incorporated into the in vitro-synthesized ssRNA or mRNA co-transcriptionally by use of a dinucleotide cap analog during in vitro transcription. In some embodiments the 5' cap is incorporated into the in vitro-synthesized ssRNA or mRNA post-transcriptionally by incubating uncapped ssRNA obtained from an in vitro transcription reaction with a capping enzyme comprising RNA guanyltransferase activity. In some embodiments, the 5' cap further comprises a 5'-terminal penultimate nucleotide that exhibits a 2'-O-methyl group on its ribose moiety; in some of these embodiments, the 2'-O-methyl group is incorporated into the in vitro-synthesized ssRNA or mRNA using RNA 2'-O-methyltransferase. In some preferred embodiments, the in vitro-synthesized ssRNA or mRNA further exhibits one or more sequences selected from among an untranslated region or UTR (e.g., a UTR which further enhances translation of protein in a cell into which the ssRNA or mRNA is introduced, e.g., a 5' UTR and/or 3' UTR of a Xenopus, human or other mammalian alpha- (α-) globin or beta- (β-) globin mRNA, or a UTR sequence exhibited by tobacco etch virus (TEV) RNA), a KOZAK sequence, a translation start codon, and a translation stop codon.

In particular embodiments of the methods, compositions or kits of the invention, the ssRNA or mRNA is polyadenylated. In some embodiments, the ssRNA or mRNA comprises a poly-A tail of about 50-200 nucleotides in length. In other embodiments, the ssRNA or mRNA comprises a poly-A tail 100-200 nucleotides in length. In other embodiments, the ssRNA or mRNA comprises a poly-A tail greater than 200 nucleotides in length. In some preferred embodiments, the ssRNA or mRNA comprises a poly-A tail of about 150-200 nucleotides in length. In some embodiments, the ssRNA or mRNA is made by synthesizing the poly-A tail by in vitro transcription of a DNA template that comprises a terminal oligo(dT) sequence that is complementary to the poly-A tail. In some preferred embodiments, the ssRNA or mRNA is made by post-transcriptional polyadenylation of the 3'-terminus of the mRNA ORF from an IVT reaction using a poly(A) polymerase (e.g., poly(A) polymerase derived from *E. coli* or *Saccharomyces cerevisiae*; or a poly(A) polymerase from a commercial source, e.g., A-PLUS™ poly(A) polymerase, CELLSCRIPT, INC., Madison, WI 53713, USA). Unless otherwise specifically stated with respect to a particular method, the invention is not limited to use of a particular poly(A) polymerase, and any suitable poly(A) polymerase can be used. The invention is not limited to particular methods described herein for polyadenylating a ssRNA for use in a method, or for making a composition or kit of the invention. Any suitable method in the art may be used for said polyadenylating.

In further embodiments of the methods, compositions or kits of the invention, the ssRNA or mRNA comprises capped mRNA. In certain preferred embodiments of the methods, compositions and kits, the ssRNA or mRNA is a population of ssRNA or mRNA molecules, the population having greater than 99% capped ssRNA or mRNA. In preferred embodiments of the methods, the capped mRNA exhibits a cap with a cap1 structure, wherein the 2'position of the ribose of the penultimate nucleotide to the 5' cap nucleotide is methylated.

In some embodiments of the methods, compositions or kits of the invention (e.g., for reprogramming a human or animal cell), the ssRNA or mRNA exhibits a 5' cap comprising 7-methylguanosine or 7-methylguanine. In some embodiments of the methods, compositions or kits, the ssRNA or mRNA exhibits an anti-reverse cap analog (ARCA). In some embodiments, the mRNA exhibits a phosphorothioate cap analog, also referred to as a "thio-ARCA" herein (Grudzien-Nogalska E et al., 2007; Kowalska J et al. 2008). In some embodiments, the ssRNA or mRNA further comprises a 5' cap that has a cap1 structure, wherein the 2' hydroxyl of the ribose of the 5' penultimate nucleotide is methylated (e.g., obtained by methylation using a SCRIPTCAP™ 2'-O-methyltransferase kit or using a the 2'-O-methylation components of the T7 mSCRIPT™ standard mRNA production system (CELLSCRIPT, INC., Madison, WI, USA). In some embodiments, the ssRNA or mRNA exhibits said 5'cap are synthesized: (i) co-transcriptionally, by incorporation of an anti-reverse cap analog (ARCA) during in vitro transcription of the ssRNA molecules (e.g., using a MESSAGEMAX™ T7 ARCA-capped message transcription kit, CELLSCRIPT, INC.); or (ii) post-transcriptionally (e.g., using T7 mSCRIPT™ standard mRNA production system, CELLSCRIPT, INC.) with a capping enzyme system, by incubating in vitro-transcribed ssRNA molecules under conditions wherein the in vitro-transcribed ssRNA molecules are 5'-capped, including wherein the capping enzyme system results in methylation of the 2' hydroxyl of the ribose in the 5' penultimate nucleotide. In some preferred embodiments, the ssRNA molecules are capped using a capping enzyme comprising RNA guanyltransferase and RNA 2'-O-methyltransferase. In some preferred embodiments, the ssRNA or mRNA is significantly free of uncapped RNA molecules that exhibit a 5'-triphosphate group (which are considered to be one type of "contaminant RNA molecules" herein). In certain embodiments, the ssRNA or mRNA consists of a population of ssRNA or mRNA molecules, the population having: (i) greater than 80% capped ssRNA or mRNA molecules; (ii) greater than 90% capped ssRNA or mRNA molecules; (iii) greater than 95% capped ssRNA or mRNA molecules; (iv) greater than 98% capped ssRNA or mRNA molecules; (v) greater than 99% capped ssRNA or mRNA molecules; or (vi) greater than 99.9% capped ssRNA or mRNA molecules. In some embodiments of the compositions, kits or methods wherein the ssRNA or mRNA also comprises contaminant uncapped RNA molecules that exhibit a 5'-triphosphate group (e.g., in embodiments wherein the ssRNA or mRNA used for said introducing of ssRNA or mRNA encoding at least one reprogramming factor into a cell that exhibits a first differentiated state or phenotype is capped co-transcriptionally using a cap analog), the ssRNA or mRNA used in the method for said introducing is first incubated with an alkaline phosphatase (e.g., NTPhosphatase™, Epicentre Technologies, Madison, WI, USA) or with RNA 5'polyphosphatase (CELLSCRIPT, INC., Madison, WI or Epicentre Technologies) to remove the 5'-triphosphate group from the contaminant uncapped RNA molecules; in some of these embodiments, the ssRNA or mRNA that is treated with RNA 5'polyphosphatase is further treated with TERMINATOR™ 5'-phosphate-dependent exonuclease (Epicentre Technologies) or Xm1 exoribonuclease to digest contaminant uncapped RNA molecules that exhibit a 5'-monophosphate group.

In some preferred embodiments of the methods, compositions and kits of the invention for reprogramming a human or animal cell, the ssRNA or mRNA exhibits at least one heterologous 5' UTR sequence, Kozak sequence, IRES sequence, or 3' UTR sequence that results in greater translation of the mRNA into at least one protein reprogramming factor in the human or animal cells compared to the same mRNA that does not exhibit said respective sequence. In some particular embodiments of the methods, compositions and kits, the 5' UTR or 3' UTR is a sequence exhibited by a Xenopus or human alpha- (α-) globin or beta- (β-) globin mRNA, or wherein the 5' UTR is a sequence exhibited by tobacco etch virus (TEV) RNA.

In certain embodiments of the methods, compositions or kits of the invention, except for the nucleotides comprising the cap, the ssRNA or mRNA comprises only the canonical ribonucleosides G, A, C and U. In additional embodiments, the ssRNA or mRNA comprises pseudouridine in place of uridine. In some embodiments of the methods, compositions or kits for reprogramming a human or animal cell, the ssRNA or mRNA comprises at least one modified ribonucleoside selected from the group consisting of pseudouridine (Ψ), 1-methyl-pseudouridine (m$^1$Ψ), 5-methylcytidine (m$^5$C), 5-methyluridine (m$^5$U), 2'-O-methyluridine (Um or m$^{2'-O}$U), 2-thiouridine (s$^2$U), and N$^6$-methyladenosine (m$^6$A) in place of at least a portion of the corresponding unmodified canonical ribonucleoside. In some embodiments of the methods, compositions or kits of the invention wherein the ssRNA or mRNA comprises at least one modified ribonucleoside, the at least one modified ribonucleoside is selected from the group consisting of: (i) pseudouridine (Ψ), 1-methyl-pseudouridine (m$^1$Ψ), 5-methyluridine (m$^5$U), 2'-O-methyluridine (Um or m$^{2'-O}$ U), and 2-thiouridine (s$^2$U) in place of all or almost all of the canonical uridine residues; (ii) 5-methylcytidine (m$^5$C) in place of all or almost all of the canonical cytidine residues; and/or (iii) N$^6$-methyladenosine (m$^6$A) in place of all or almost all of the canonical adenosine residues. In other embodiments, only a portion of a canonical ribonucleoside is replaced by the corresponding modified ribonucleoside, wherein a portion means 1-25%, 25-50%, or 50-99% of the canonical ribonucleoside is replaced. In some preferred embodiments of the methods, compositions or kits of the invention wherein the ssRNA or mRNA molecules comprise at least one modified ribonucleoside, the at least one modified ribonucleoside consists of pseudouridine (Ψ) in place of all or almost all of the canonical uridine residues, and/or 5-methylcytidine (m$^5$C) in place of all or almost all of the canonical cytidine residues. In some other embodiments, only a portion of the canonical uridine residues are replaced by pseudouridine residues and/or only a portion of the canonical cytidine residues are replaced by 5-methylcytidine residues, wherein a portion means 1-25%, 25-50%, or 50-99% of one or both canonical ribonucleosides are replaced.

In some embodiments of the methods, compositions or kits wherein the ssRNA or mRNA comprises at least one modified ribonucleoside, the ssRNA or mRNA is synthesized by in vitro transcription (IVT) of a DNA template that encodes each said at least one protein or polypeptide reprogramming factor using an RNA polymerase that initiates said transcription from a cognate RNA polymerase promoter that is joined to said DNA template and ribonucleoside 5' triphosphates (NTPs) comprising at least one modified ribonucleoside 5' triphosphate selected from the group consisting of pseudouridine 5' triphosphate (ΨTP), 1-methyl-pseudouridine 5' triphosphate (m$^1$ΨTP), 5-methylcytidine 5' triphosphate (m$^5$CTP), 5-methyluridine 5' triphosphate (m$^5$UTP), 2'-O-methyluridine 5' triphosphate (UmTP or m$^{2'-O}$UTP), 2-thiouridine 5' triphosphate (s$^2$UTP), and N[6]-methyladenosine 5' triphosphate (m[6]ATP). In some preferred embodiments, the modified NTP is used in place of all or almost all of the corresponding unmodified NTP in the IVT reaction (e.g., ΨTP, m[1]ΨTP, m[5]UTP, m[2'-O]UTP or s[2]UTP in place of UTP: m[5]CTP in place of CTP; or m[6]ATP in place of ATP) (e.g., using a T7 mSCRIPT™ standard mRNA production system (CELLSCRIPT, INC., Madison, WI, USA), wherein the canonical NTP is replaced by the corresponding modified NTP).

In other preferred embodiments of the methods, compositions or kits for reprogramming a human or animal cell, the ssRNA or mRNA does not contain a ribonucleoside comprising a modified nucleic acid base, other than the modified nucleic acid base (e.g., the 7-methylguanine base) comprising the 5' cap nucleotide (or, e.g., if the ssRNA or mRNA was synthesized using a dinucleotide cap analog, possibly also including a modified base in the 5' penultimate nucleoside). Thus, in some embodiments of the methods, compositions or kits for reprogramming a human or animal cell, except for the ribonucleoside(s) comprising the 5' cap, the ssRNA or mRNA comprises only the canonical ribonucleosides G, A, C and U. In some embodiments of the methods, compositions or kits for reprogramming a human or animal cell, the ssRNA or mRNA is synthesized by in vitro transcription (IVT) of a DNA template that encodes each said at least one protein or polypeptide reprogramming factor using the canonical NTPs: GTP, ATP, CTP and UTP (e.g., using a T7 mSCRIPT™ standard mRNA production system (CELLSCRIPT, INC., Madison, WI, USA).

Thus, one preferred embodiment of the invention is a method for reprogramming a eukaryotic cell (e.g., a human or animal cell, e.g., a mammalian cell) that exhibits a first differentiated state or phenotype to a cell that exhibits a second differentiated state or phenotype, comprising: repeatedly or continuously introducing a composition comprising in vitro-synthesized ssRNA or mRNA encoding a reprogramming factor into a cell that exhibits a first differentiated state or phenotype to generate a reprogrammed cell that exhibits a second differentiated state or phenotype, which ssRNA or mRNApredominantly consists of only unmodified nucleic acid bases (i.e., the canonical nucleic acid bases: guanine, adenine, cytosine, and uracil), except for the base comprising the 5' cap nucleotide or, potentially, the base of the 5' penultimate nucleoside which is linked to the cap nucleotide. Said another way, in these embodiments of the method, the ssRNA or mRNA predominantly consists of only the canonical nucleosides guanosine, adenosine, cytidine and uridine, except for the 5' cap nucleotide, and the 5' penultimate nucleoside when the ssRNA or mRNA molecules exhibit a cap1 cap structure (e.g., wherein the ssRNA, mRNA or precursor thereof was synthesized using only or predominantly GTP, ATP, CTP and UTP during in vitro transcription). In some embodiments, the ssRNA or mRNA is synthesized in vitro. In some embodiments of this method, the cell that exhibits the second differentiated state or phenotype is an iPS cell. In preferred embodiments of the methods, compositions or kits using unmodified ssRNA or mRNA, the ssRNA or mRNA is absolutely free of dsRNA. In additional embodiments, although the mRNA comprises almost entirely unmodified ribonucleosides except for the 5' cap, the ssRNA or mRNA can comprise certain modifications for a particular purpose, including a modified internucleoside linkage, such as a phosphorothioate, phosphorodithioate, phosphoroselenate, or phosphorodiselenate linkage (e.g., to provide resistance of the mRNA molecules to nucleases or other enzymes that are capable of degrading canonical phosphate linkages).

By "substantially free of dsRNA" we mean that less than about 0.5% of the total mass or weight of the ssRNA (or the mRNA, e.g., encoding one or more reprogramming factors or an iPS cell induction factors) is composed of dsRNA of a size greater than about 40 basepairs in length. By "virtually free of dsRNA" we mean that less than about 0.1% of the total mass or weight of the RNA comprising the ssRNA or mRNA (e.g., encoding one or more reprogramming factors or an iPS cell induction factors) is composed of dsRNA of a size greater than about 40 basepairs in length. By "essentially free of dsRNA" we mean less than 0.05% of the total mass or weight of the ssRNA (or the mRNA, e.g., encoding one or more reprogramming factors or an iPS cell induction factors) is composed of dsRNA of a size greater than about 40 basepairs in length. By "practically free of dsRNA" we mean that less than about 0.01% of the total mass or weight of the RNA comprising the ssRNA or mRNA (e.g, encoding one or more reprogramming factors or an iPS cell induction factors) is composed of dsRNA of a size greater than about 40 basepairs in length. By "extremely free of dsRNA" we mean that less than about 0.001% of the total mass or weight of the RNA comprising the ssRNA or mRNA (e.g., encoding one or more reprogramming factors or an iPS cell induction factors) is composed of dsRNA of a size greater than about 40 basepairs in length. By "absolutely free of dsRNA" we mean that less than about 0.0002% of the total mass or weight of the RNA comprising the ssRNA or mRNA (e.g., encoding one or more reprogramming factors or an iPS cell induction factors) is composed of dsRNA of a size greater than about 40 basepairs in length. In some embodiments, the amount of dsRNA (e.g., the amount of detectable dsRNA) of a size greater than about 40 basepairs in length is assayed by dot blot immunoassay using a dsRNA-specific antibody (e.g., the J2 dsRNA-specific antibody or the K1 dsRNA-specific antibody from English & Scientific Consulting, Szirák, Hungary) using standards of known quantity of dsRNA, as described herein, or using another assay that gives equivalent results to the assay described herein. It shall be understood herein that the results of the dot blot immunoassays using the J2 dsRNA-specific antibody will be based on comparing the assay results of the ssRNA or mRNA that is intended for introducing into a human or animal cell, organism or subject with the assay results of J2 dsRNA-specific antibody dot blot immunoassays performed at the same time with dsRNA standards comprising known quantities of dsRNA of the same or equivalent size and J2 antibody binding.

In some other embodiments, the amounts and relative amounts of non-contaminant mRNA molecules and RNA contaminant molecules (or a particular RNA contaminant, e.g., a dsRNA contaminant) may be determined by HPLC or other methods used in the art to separate and quantify RNA molecules. In some other embodiments, the amounts and relative amounts of non-contaminant mRNA molecules and RNA contaminant molecules (or a particular RNA contaminant, e.g., a dsRNA contaminant) is determined using a specific quantitative assay for a particular contaminant (e.g., dsRNA) in a known about of total RNA. In some other embodiments, the amount of dsRNA contaminants of a size greater than about 40 basepairs in length is determined based on measuring the $A_{260}$ absorbance of all column chromatography fractions or all agarose or polyacrylamide gel electrophoresis fractions from chromatography or electrophoresis, respectively, of a sufficient quantity of in vitro-synthesized or in vitro-transcribed ssRNA so that the absorbance of dsRNA contaminants in all fractions comprising RNA of a size other than the fraction or fractions confirmed to contain only RNA of the correct size and sequence as the ssRNA or mRNA of interest so that the appropriate purity level (e.g., substantially free, virtually free, essentially free, practically free, extremely free, or absolutely free will be capable of being measured. In preferred embodiments of the methods, compositions or kits, the ssRNA or mRNA encoding a reprogramming factor or an iPS cell induction factor is extremely free or absolutely free of dsRNA.

In preferred embodiments of the methods, compositions or kits, including wherein the ssRNA or mRNA comprises a modified ribonucleoside or, except for the cap, only unmodified ribonucleosides, the ssRNA or mRNA (e.g., encoding a reprogramming factor or an iPS cell induction factor) is virtually free, essentially free, practically free, extremely free, or absolutely free of detectable dsRNA.

In general, the level of dsRNA contaminant in the RNA composition comprising mRNA encoding at least one protein that results in an innate immune response, cellular toxicity or cell death depends upon several factors, such as the duration of the period of repeatedly or continuously contacting the cell with the RNA composition comprising the mRNA required to cause the biological or biochemical effect, the amount of mRNA in said composition, and the nucleotides composing said mRNA (e.g., whether the mRNA comprises modified nucleotides, e.g., the mRNA comprises GAψC or GAψm$^5$C nucleotides, or only GAUC unmodified nucleotides).

Thus, one preferred embodiment of the invention is a method for changing or reprogramming the state of differentiation or differentiated state or phenotype of a human or animal cell comprising: introducing ssRNA or mRNA encoding a reprogramming factor, which ssRNA or mRNA is at least practically free of dsRNA, into a cell that exhibits a first differentiated state or phenotype to generate a reprogrammed cell that exhibits a second differentiated state or phenotype. Another preferred embodiment is a method for changing or reprogramming the state of differentiation or differentiated state or phenotype of a human or animal cell comprising: introducing ssRNA or mRNA encoding a reprogramming factor, which ssRNA or mRNA is practically free of dsRNA, into a cell that exhibits a first differentiated state or phenotype to generate a reprogrammed cell that exhibits a second differentiated state or phenotype. Still another preferred embodiment is a method for changing or reprogramming the state of differentiation or differentiated state or phenotype of a human or animal cell comprising: introducing ssRNA or mRNA encoding a reprogramming factor, which ssRNA or mRNA is extremely free of dsRNA, into a cell that exhibits a first differentiated state or phenotype to generate a reprogrammed cell that exhibits a second differentiated state or phenotype. Still another preferred embodiment is a method for changing or reprogramming the state of differentiation or differentiated state or phenotype of a human or animal cell comprising: introducing ssRNA or mRNA encoding a reprogramming factor, which ssRNA or mRNA is absolutely free of dsRNA, into a cell that exhibits a first differentiated state or phenotype to generate a reprogrammed cell that exhibits a second differentiated state or phenotype. In particular embodiments of the methods, the introducing comprises introducing ssRNA or mRNA encoding a plurality of reprogramming factors into the cell. In some embodiments, the present invention provides methods for changing the differentiated state or state of differentiation of a cell comprising: introducing ssRNA or mRNA encoding at least one iPS cell induction factor, which ssRNA or mRNA is virtually free, essentially free, practically free, extremely free or absolutely free of dsRNA, into a somatic cell to generate a reprogrammed cell. In certain embodiments of the methods, the introducing comprises delivering the ssRNA or mRNA to the somatic cell with a transfection reagent. In some embodiments, the introducing is repeated daily for at least 3 days. In some preferred embodiments of the methods, the introducing is repeated daily for at least 4 to 8 days, 8 to 10 days, or for 10 to 18 days. In some embodiments, the introducing is repeated daily for greater than 18 days. In some embodiments, the reprogrammed cell is a dedifferentiated cell and the process that occurs in this method is referred to as "dedifferentiation." One embodiment of a dedifferentiated cell is an induced pluripotent stem cell or iPS cell (or iPSC). In some preferred embodiments of the methods, the reprogrammed cell is an iPS cell. In further embodiments of the methods, the reprogrammed cell is a transdifferentiated cell and the process that occurs in this method is referred to as "transdifferentiation." In other embodiments, the cell that exhibits the second state of differentiation or phenotype is a differentiated or redifferentiated somatic cell and the process that occurs in this method is referred to as "differentiation" or "redifferentiation." In certain preferred embodiments of the methods for changing or reprogramming the state of differentiation or phenotype of a cell, the method is performed without the use of any exogenous protein, siRNA, or small molecule agent that inhibits or reduces the activation, induction or the expression of one or more proteins in an innate immune response pathway. Thus, in some embodiments of the methods for changing or reprogramming the differentiated state or phenotype of a human or animal cell, no siRNA or protein (e.g., B18R protein), antibody or small molecule inhibitor of an innate immune response pathway is used for said reprogramming. In other embodiments, the methods further comprise: treating the cells that exhibit the first differentiated state or phenotype with a protein, siRNA, or small molecule agent that inhibits or reduces the activation, induction or expression of one or more RNA sensors or proteins in an innate immune response pathway, wherein said treating is prior to and/or during said introducing of an mRNA encoding a reprogramming factor. In some embodiments, the agent that inhibits or reduces the activation, induction or expression of one or more RNA sensors or proteins in an innate immune response pathway is B18R protein.

In some other embodiments, the agent is an Agent mRNA that encodes a protein that inhibits or reduces the activation, induction or expression of one or more proteins comprising an RNA sensor or innate immune response pathway. In some preferred embodiments, the inhibitor is an Agent mRNA that encodes B18R protein. In some other preferred embodiments, the inhibitor is an Agent mRNA that encodes the Vaccinia virus E3L gene protein; in preferred embodiments, the Agent mRNA that encodes the Vaccinia virus E3L gene protein is introduced into the cell at the same time as the mRNA encoding one or more reprogramming factors or iPS cell induction factors are introduced. In preferred embodiments of these methods, the Agent mRNA is capped. In some embodiments, greater than 90% of the RNA molecules comprising the Agent mRNA are capped. In preferred embodiments, greater than 99% of the RNA molecules comprising the Agent mRNA are capped. In some preferred embodiments of these embodiments, the Agent mRNA exhibits a cap with a cap1 structure, meaning that the 2' hydroxyls of the ribose of the 5' penultimate nucleotide of the RNA molecules comprising the Agent mRNA are methylated. In some embodiments of these methods, the Agent mRNA is polyadenylated. In preferred embodiments of these methods, the Agent mRNA exhibits a poly-A tail consisting of at least 50 A residues. In some preferred embodiments of these methods, the poly-A tail consists of at least 100-200 A residues. In some preferred embodiments of these methods, the Agent mRNA exhibits at least one heterologous 5' UTR sequence, Kozak sequence, IRES sequence, or 3' UTR sequence that results in greater translation of the mRNA into at least one protein reprogramming factor in the human or animal cells compared to the same Agent mRNA that does not exhibit said respective sequence. In some particular embodiments of these methods, the 5' UTR or 3' UTR is a sequence exhibited by a Xenopus or human alpha- (α-) globin or beta- (β-) globin mRNA, or wherein the 5' UTR is a sequence exhibited by tobacco etch virus (TEV) RNA. In some preferred embodiments of these methods, the Agent mRNA comprises or consists of at least one modified nucleoside selected from the group consisting of pseudouridine (Ψ), 1-methyl-pseudouridine (m$^1$Ψ), 5-methylcytidine (m$^5$C), 5-methyluridine (m$^5$U), 2'-O-methyluridine (Um or m$^{2'-O}$U), 2-thiouridine (s$^2$U), and N$^6$-methyladenosine (m$^6$A) in place of at least a portion of the corresponding unmodified canonical ribonucleoside. In some preferred embodiments, the at least one modified ribonucleoside is selected from the group consisting of: (i) pseudouridine (Ψ), 1-methyl-pseudouridine (m$^1$Ψ), 5-methyluridine (m$^5$U), 2'-O-methyluridine (Um or m$^{2'-}$$_o$U), and 2-thiouridine (s$^2$U) in place of all or almost all of the canonical uridine residues; (ii) 5-methylcytidine (m$^5$C) in place of all or almost all of the canonical cytidine residues; and/or (iii) N$^6$-methyladenosine (m$^6$A) in place of all or almost all of the canonical adenosine residues. In other embodiments of these methods, only a portion of a canonical ribonucleoside is replaced by the corresponding modified ribonucleoside, wherein a portion means 1-25%, 25-50%, or 50-99% of the canonical ribonucleoside is replaced. In other preferred embodiments, the at least one modified ribonucleoside consists of pseudouridine (Ψ) in place of all or almost all of the canonical uridine residues, and/or 5-methylcytidine (m$^5$C) in place of all or almost all of the canonical cytidine residues. In some other embodiments, only a portion of the canonical uridine residues are replaced by pseudouridine residues and/or only a portion of the canonical cytidine residues are replaced by 5-methylcytidine residues, wherein a portion means 1-25%, 25-50%, or 50-99% of one or both canonical ribonucleosides are replaced. In other preferred embodiments of these methods, except with respect to the nucleosides comprising the 5' cap, the mRNA consists of only unmodified canonical G, A, C and U nucleosides.

In preferred embodiments of the methods, compositions, or kits of the invention, the mRNA is extremely or absolutely free of dsRNA. Thus, since the mRNA used in the methods herein (or a precursor to the mRNA, such as in vitro-transcribed RNA (or IVT-RNA) prior to capping and/or polyadenylation) is preferably ssRNA, we sometimes refer to the mRNA herein as an "RNA composition comprising ssRNA molecules", an "RNA composition", or "ssRNA molecules"; therefore, whenever the terms "RNA composition comprising ssRNA molecules", "RNA composition" or "ssRNA molecules" are used herein with respect to a method, composition or kit comprising or for reprogramming a somatic cell to an iPS cell, those terms shall be understood to mean the "mRNA encoding a reprogramming factor or an iPS cell induction factor," including wherein the mRNA encodes a plurality of reprogramming factors or an iPS cell induction factors. Thus, in some preferred embodiments, the RNA composition or ssRNA or mRNA is absolutely free of dsRNA, meaning, for example, that for each one microgram or 1,000,000 picograms of RNA in the RNA composition, greater than 999,998 picograms comprises ssRNA and less than 2 picograms is dsRNA of a size greater than about 40 basepairs in length (e.g., when assayed by immunoassay using the J2 dsRNA-specific antibody (English & Scientific Consulting, Szirák, Hungary) as described herein or using another assay that gives equivalent results to the assay described herein).

In some specific embodiments, the dsRNA-specific RNase is an exoribonuclease (exoRNase). In some specific embodiments, the dsRNA-specific RNase is an exoribonuclease (e.g., a 3'-to-5' exoribonuclease, e.g., a Lassa virus exoRNase, Qi X et al., 2010; or coronavirus exoRNase, Hastie K M et al., 2011).

Without being bound by theory, the applicants found that, under conditions used, certain commercially antibodies (e.g., Schönborn J et al. 1991, Lukacs N 1994, Lukacs N. 1997; e.g., the J2 antibody from English & Scientific Consulting, Szirák, Hungary) that binds dsRNA, while very useful for certain dsRNA specific assays, did not appear to consistently remove sufficient amounts of dsRNA from ssRNA or mRNA or a precursor thereof for use in a method for making an purified or treated RNA composition for a composition, kit or method of the present invention, and, therefore, such dsRNA-specific antibodies are not included within definition of a dsRNA-specific protein herein. However, without being bound by theory, the applicants believe that it may be possible to generate one or more other dsRNA-specific antibodies, which could potentially be used, separately or in combination to make a purified or treated RNA composition.

In some embodiments, a combination of any of the above described methods is used. Thus, any one or more particular methods for generating mRNA that is substantially free, virtually free, essentially free, practically free, extremely free or absolutely free of dsRNA can be used in addition to or in conjunction with any other method for generating mRNA that is substantially free, virtually free, essentially free, practically free, extremely free or absolutely free of dsRNA. Thus, for example, although a method comprising contacting an in vitro-synthesized ssRNA with a dsRNA-specific antibody does not appear to generate a ssRNA that is substantially free, virtually free, essentially free, practically free, extremely free or absolutely free of dsRNA under the conditions used herein, in some embodiments, said method is used in addition to a method comprising HPLC or the RNase III treatment method described herein to generate ssRNA (e.g., mRNA) that is substantially free, virtually free, essentially free, practically free, extremely free or absolutely free.

In some preferred embodiments wherein the dsRNA-specific protein is RNase III, the method comprises: contacting the mRNA (or precursor thereof) with the RNase III in a buffered solution comprising divalent magnesium cations at a concentration of about 1 mM to about 4 mM and a monovalent salt at a concentration of at least 50 mM and incubating under conditions wherein the RNase III binds to the dsRNA and is enzymatically active, and then cleaning up the mRNA (or precursor thereof) from the RNase III and the other components, including the RNase III digestion products, to generate a treated mRNA (or precursor thereof) that is substantially free, virtually free, essentially free, practically free, extremely free or absolutely free of dsRNA. In certain preferred embodiments of this method, the buffered solution comprises divalent magnesium cations at a concentration of about 1 mM to about 3 mM, about 2.0 mM to about 4.0 mM, about 2 mM to about 3 mM, or about 2 mM. In some preferred embodiments of this method, the monovalent salt has a concentration of about 50 mM to about 100 mM, about 100 mM to about 200 mM, or about 200 mM to about 300 mM. Still further, the mRNA (or precursor thereof) can be extracted with phenol-chloroform, precipitated using ammonium acetate or purified by chromatography or other means as described elsewhere herein.

In some preferred embodiments (e.g., wherein the dsRNA-specific protein is RNase III), the method comprises: contacting the ssRNA or mRNA (or precursor thereof) with the dsRNA-specific protein (e.g., RNase III) in a buffered solution that contains a monovalent salt at a concentration of at least 50 mM (and more preferably, about 50 to about 150 mM, or about 150 mM to about 300 mM) but which lacks divalent magnesium cations, and incubating under conditions wherein the dsRNA-specific protein (e.g., RNase III) binds to the dsRNA but is not enzymatically active, and then cleaning up the ssRNA or mRNA (or precursor thereof) from the dsRNA-specific protein (e.g., RNase III), at least some of which is bound to the dsRNA, and from the other components, to generate ssRNA or mRNA that is substantially free, virtually free, essentially free, practically free, extremely free or absolutely free of dsRNA. In this embodiment, the present researchers utilize the very tight and specific binding of the dsRNA-specific protein (e.g., RNase III) for dsRNA, while performing the incubation in the absence of divalent magnesium cations so that the dsRNA-specific protein (e.g., RNase III) is not enzymatically active. Thus, in some embodiments, the dsRNA-specific protein (e.g., RNase III) is used as a binding agent for the dsRNA, which is then removed from the mRNA (or precursor thereof) by one of several means (e.g., by using an antibody that binds to the dsRNA-specific protein (e.g., RNase III) and/or an antibody that binds to the dsRNA (e.g., a dsRNA-specific antibody such as the J2 antibody; English and Scientific Consulting, Szirák, Hungary), which in turn can be precipitated using commercially available particles (e.g., magnetic particles or beads) to which protein A or protein G is attached to precipitate the antibody that is bound to the dsRNA-specific protein (e.g., RNase III), thereby purifying the mRNA (or precursor thereof). In some embodiments wherein a dsRNA-specific protein (e.g., RNase III) is used as a binding agent for the dsRNA, the dsRNA-specific protein (e.g., RNase III) is covalently derivatized with an affinity-binding molecule (e.g., biotin, or e.g., any other affinity-binding small molecule (e.g., preferably a small molecule) known in the art), which covalent derivatization does not abolish dsRNA binding by the protein or change the specificity of the dsRNA-specific protein for binding dsRNA. In some embodiments of the methods, compositions or kits, the derivatized dsRNA-specific protein (e.g., biotin-derivatized or biotinylated dsRNA-specific protein, e.g., biotinylated RNase III) is removed by contacting a solution containing the derivatized dsRNA-specific protein with a surface (e.g., magnetic particles or beads) that comprises another molecule that tightly and specifically binds the derivatized dsRNA-specific protein, including the derivatized dsRNA-specific protein that is bound to dsRNA contaminants; for example, in one specific embodiment, a solution containing biotinylated RNase III which was contacted with an RNA composition comprising ssRNA or mRNA and contaminant dsRNA (biotin-derivatized (or biotinylated) is further contacted with a surface to which streptavidin or avidin is covalently attached, thereby binding the biotinylated RNase III, including biotinylated RNase III bound to the contaminant dsRNA; upon removal from the solution of the surface to which the streptavidin or avidin is covalently attached, the solution is substantially free, virtually free, essentially free, practically free, extremely free or absolutely free of dsRNA. Thus, in these embodiments, said purifying the ssRNA or mRNA (or precursor thereof), comprises contacting the solution comprising the RNA composition and the derivatized dsRNA-specific protein (e.g., the biotinylated RNase III) with a surface to which binds the derivatized dsRNA-specific protein, and removing the surface from said solution.

In some preferred embodiments wherein the dsRNA-specific protein is a 3'-to-5' exoribonuclease, the method comprises: contacting the ssRNA or mRNA (or precursor thereof) with the 3'-to-5' exoribonuclease in a Tris-buffered (e.g., 20 mM; pH 7.5) solution comprising divalent magnesium cations (e.g., 5 mM) and a monovalent salt at a concentration of at least 50 mM (e.g., 150 mM NaCl) and incubating under conditions wherein the exoribonuclease binds to the dsRNA and is enzymatically active, and then cleaning up the mRNA (or precursor thereof) from the exoribonuclease and the other components, including the exoribonuclease digestion products, to generate treated mRNA (or precursor thereof) that is substantially free, virtually free, essentially free, practically free, extremely free or absolutely free of dsRNA.

In some embodiments wherein a purification method comprising a separation device is used to generate at least partially purified ssRNA or mRNA (e.g., a purification method comprising gravity flow or low pressure chromatography, HPLC or preparative electrophoresis), in addition to said purification method, the method further comprises (either prior to or after said purification method): contacting the ssRNA or mRNA (or precursor thereof) with a dsRNA-specific protein. In some embodiments, the dsRNA-specific protein is RNase III in a buffered solution that contains magnesium cations at a concentration of about 1 mM to about 4 mM and a monovalent salt at a concentration of at least about 100 mM (preferably, at least about 100-300 mM) to generate treated mRNA (or precursor thereof) that is substantially free, virtually free, essentially free, practically free, extremely free or absolutely free of dsRNA. In preferred embodiments, the treated mRNA (or precursor thereof) is at least practically free of dsRNA.

In some other embodiments, the dsRNA-specific protein is a dsRNA-specific antibody (e.g., the J2 or K1 antibody from English and Scientific Consulting, Szirák, Hungary) in a buffered solution that contains a monovalent salt at a concentration of at least about 100 mM (preferably, at least about 100-300 mM), and incubating under conditions wherein the dsRNA-specific antibody binds to the dsRNA, and then cleaning up the mRNA (or precursor thereof) from the dsRNA-specific antibody, at least some of which is bound to the dsRNA, and the other components to generate purified mRNA (or precursor thereof) that is substantially free, virtually free, essentially free, practically free, extremely free or absolutely free; in some embodiments, the dsRNA-specific antibody is used to assay for the amount of dsRNA present in the ssRNA (e.g., mRNA or precursor thereof). In some of these embodiments, the dsRNA-specific antibody can be removed from the mRNA (or precursor thereof) by one of several means (e.g., by using commercially available particles such as magnetic particles or beads to which protein A or protein G is attached to precipitate the dsRNA-specific antibody).

Still further, in some embodiments of any of the above methods, the treated or purified ssRNA or mRNA (or precursor thereof) is further cleaned up using the RNA Quick Cleanup Method comprising organic (e.g., phenol-chloroform) extraction, ammonium acetate precipitation, alcohol precipitation and/or alcohol washing of the precipitate (e.g., 70% ethanol washing). In some other embodiments, the ssRNA or mRNA (or precursor thereof) is further cleaned up or purified using a rapid gel filtration method with a cross-linked dextran (e.g., Sephadex, e.g., a Sephadex spin column) in order to separate low molecular weight molecules, such as salts, buffers, nucleotides and small oligonucleotides, solvents (e.g., phenol, chloroform) or detergents from the ssRNA or mRNA. In some other embodiments, the ssRNA or mRNA is purified or further purified by chromatography or other means as described elsewhere herein.

For example, in one embodiment, the present invention provides methods for synthesizing an in vitro transcribed (IVT) RNA composition, and then contacting the IVT RNA composition with a dsRNA-specific RNase, such as RNase III, under conditions wherein contaminant dsRNA can be reproducibly digested and ssRNA molecules that do not induce or activate a dsRNA innate immune response pathway or RNA sensor can reliably be generated.

In some embodiments of the methods, compositions or kits for reprogramming a eukaryotic cell, such as a human or animal cell, the ssRNA mRNA (or a precursor to the mRNA, such as IVT-RNA prior to capping and/or polyadenylation) is purified or treated using at least one method selected from the group consisting of: (i) a process comprising treating the mRNA (or a precursor thereof) with one or more enzymes that specifically digest one or more RNA contaminant molecules or contaminant DNA molecules; (ii) chromatography on a gravity flow or HPLC column and an eluant solution that results in removal of contaminant RNA molecules (particularly contaminant dsRNA molecules); and (iii) a process comprising treating the mRNA (or a precursor thereof) with a dsRNA-specific RNase in a reaction mixture under conditions wherein the dsRNA is digested; in some embodiments, the method further comprises: purifying the mRNA from the components of the dsRNA-specific RNase reaction mixture and the dsRNA digestion products. In some preferred embodiments of the method comprising treating the ssRNA or mRNA with a dsRNA-specific RNase, the dsRNA-specific RNase is an endoribonuclease (endoRNase). In some preferred embodiments, the endoRNase is RNase III (e.g., *E. coli* RNase III). In some other embodiments, the dsRNA-specific RNase is an exoribonuclease (exoRNase). In some embodiments, the exoRNase is a protein that exhibits dsRNA-specific 3'-to-5' exoRNase activity.

In some embodiments, the invention also provides a method for making the purified RNA compositions comprising ssRNA molecules that are substantially free, virtually free, essentially free, practically free, extremely free or absolutely free of contaminant dsRNA molecules, the method comprising: treating in vitro-synthesized RNA comprising one or more different ssRNA molecules and contaminant dsRNA molecules with a double-strand-specific RNase in a reaction mixture under conditions wherein the dsRNA is digested, and then purifying the ssRNA molecules from the components of the double-strand-specific RNase reaction mixture and the dsRNA digestion products. In some embodiments, the dsRNA-specific RNase is RNase III and the reaction mixture comprises divalent magnesium cations at a concentration of less than about 5 mM, preferably about 1 mM to about 4 mM, and most preferably about 2 mM to about 3 mM, or 2 mM. In some embodiments of this method, the ssRNA molecules are substantially free, virtually free, essentially free, practically free, extremely free or absolutely free of dsRNA contaminant molecules that activate an RNA sensor or an RNA interference (RNAi) response; in particular embodiments, the RNA sensor is selected from the group consisting of RNA-dependent protein kinase (PKR), retinoic acid-inducible gene-I (RIG-I), Toll-like receptor (TLR)3, TLR7, TLR8, melanoma differentiation associated gene-5 protein (MDA5), and 2'-5'oligoadenylate synthetase (2'-5' OAS or OAS). In certain embodiments, the purified RNA compositions or preparations generate no significant Toll-Like Receptor (TLR3)-mediated immune response when introduced into the cell.

In other embodiments, the iPS cell induction factor is selected from the group consisting of KLF4, LIN28, c-MYC, NANOG, OCT4, and SOX2. In particular embodiments, the introducing comprises introducing mRNA encoding a plurality of iPS cell induction factors into the somatic cell. In further embodiments, the plurality of iPS cell induction factors comprises each of KLF4, LIN28, c-MYC, NANOG, OCT4, and SOX2. In further embodiments, the plurality of iPS cell induction factors comprises OCT4, SOX2, KLF4, LIN28, NANOG, and at least one MYC protein selected from the group consisting of wild-type c-MYC long, mutant c-MYC(T58A), wild-type c-MYC short and L-MYC. In further embodiments, the plurality of iPS cell induction factors does not comprise LIN28 or NANOG. In preferred embodiments, the MYC protein in the plurality of iPS cell induction factors is c-MYC(T58A). In some embodiments, mRNA encodes one or more reprogramming factors or iPS cell induction factors selected from the group consisting of OCT4, SOX2, KLF4, LIN28, NANOG, wild-type c-MYC long, c-MYC(T58A) (Wang X et al., 2011; Wasylishen A R, et al. 2011), wild-type c-MYC short and L-MYC. In some embodiments, the mRNA encodes OCT4, SOX2, KLF4, and at least one MYC protein selected from the group consisting of wild-type c-MYC long, c-MYC(T58A), wild-type c-MYC short and L-MYC. In some preferred embodiments, the MYC protein encoded by the mRNA is the c-MYC(T58A). In some other preferred embodiments, the MYC protein encoded by the mRNA is wild-type c-MYC short. In some other preferred embodiments, the MYC protein encoded by the mRNA is L-MYC. In some embodiments, the mRNA further encodes the NANOG protein. In some embodiments, the mRNA used for reprogramming human or animal somatic cell to a dedifferentiated cell or an iPS cell encodes OCT4, SOX2, KLF4, LIN28, NANOG and at least one MYC protein selected from the group consisting of wild-type c-MYC long, c-MYC (T58A), wild-type c-MYC short and L-MYC.

In additional embodiments, the cell is a fibroblast. In other embodiments, the reprogrammed cell is a pluripotent stem cell. In other embodiments, the dedifferentiated cell expresses NANOG and TRA-1-60. In further embodiments, the cell is in vitro. In additional embodiments, the cell resides in culture. In particular embodiments, the cells reside in MEF-conditioned medium. In some preferred embodiments, an RNase inhibitor (e.g., SCRIPTGUARD™ RNase inhibitor, CELLSCRIPT, INC., Madison, WI, USA) is added to the culture medium if the medium contains serum, conditioned medium, or a cell extract. In some preferred embodiments, the cell is cultured in medium on an extracellular matrix (e.g., a MATRIGEL™-type matrix) in the absence of a feeder layer. In other embodiments, the cells reside in a human or animal subject.

In certain embodiments, the present invention provides compositions comprising an mRNA encoding a reprogramming factor or an iPS cell induction factor, the mRNA having pseudouridine or 1-methyl-pseudouridine in place of uridine. In certain embodiments wherein the mRNA encoding a reprogramming factor or an iPSC induction factor comprises pseudouridine or 1-methyl-pseudouridine in place of uridine, the mRNA also further comprises 5-methylcytidine in place of cytidine. In other embodiments, the composition comprises mRNA encoding a plurality of iPS cell induction factors, selected from the group consisting of KLF4, LIN28, c-MYC, NANOG, OCT4, and SOX2. In further embodiments, the plurality comprises three or more, or four or more, or five or more, or six iPS cell induction factors.

In certain embodiments, the compositions described above are packaged in a kit. In some embodiments, the compositions comprise a transfection reagent and an mRNA encoding a reprogramming factor or an iPS cell induction factor.

In some embodiments, the present invention provides compositions or systems or kits comprising: a) single-stranded RNA (ssRNA) that encodes a protein, wherein the ssRNA is a product of in vitro transcription of a DNA template by an RNA polymerase; b) a double-stranded RNA (dsRNA) specific endoribonuclease III (endoRNase III) protein (or other dsRNA-specific protein); and c) magnesium cations present at a concentration of about 1-4 mM. In particular embodiments, the magnesium cations are present at a concentration of about 1-3 mM. In certain embodiments, the magnesium ions are present at a concentration between about 1-3 mM (e.g., about 1.0 . . . 1.3 . . . 1.6 . . . 1.9 . . . 2.2 . . . 2.5 . . . 2.8 . . . and 3.0 mM). In particular embodiments, the compositions and systems further comprise a salt providing an ionic strength of at least equivalent to 50 mM potassium acetate or potassium glutamate (e.g., at least 50 mM . . . at least 75 mM . . . at least 100 mM . . . at least 150 mM or more). In some embodiments, the ssRNA: exhibits a therapeutic RNA sequence, is an mRNA encoding a therapeutic protein, is an mRNA encoding a reporter protein, or is an mRNA encoding a cell reprogramming factor.

In particular embodiments, the present invention provides compositions or systems comprising: a) a ssRNA or mRNA encoding a reprogramming factor, and b) magnesium ions present at a concentration of about 1-4 mM (e.g., about 1.0 . . . 1.3 . . . 1.6 . . . 1.9 . . . 2.2 . . . 2.5 . . . 2.8 . . . 3.0 . . . 3.4 . . . 3.8 . . . 4.2 . . . 4.8 mM).

In certain embodiments, the dsRNA-specific protein is a dsRNA-specific RNase, an endoribonuclease, or RNase III, or a 3'-to-5' exoribonuclease.

In some embodiments, the present invention provides methods of generating an RNA preparation (or RNA composition) comprising: contacting in vitro transcribed RNA with a composition comprising a) a double-stranded RNA-specific (dsRNA-specific) endoribonuclease III (endoRNase III) protein, and b) magnesium cations present at a concentration of about 1-4 mM; such that an RNA preparation is generated.

In certain embodiments, the RNA preparation is practically free, extremely free, absolutely free of dsRNA. In further embodiments, the methods further comprise cleaning up the RNA preparation by removing at least one of the endoRNase III, or nucleotides, from the RNA preparation. In certain embodiments, the methods further comprise: (i) extracting the RNA preparation with organic solvents (e.g., such as phenol and/or chloroform); (ii) precipitating the in vitro transcribed ssRNA with ammonium acetate; and/or (iii) washing the ammonium acetate precipitate with an alcohol such as 70% ethanol. In particular embodiments, the cleaning up employs a dsRNA-specific antibody. In other embodiments, the cleaning up further comprises: using an antibody that binds to the endoRNase III and/or the dsRNA-specific antibody and then precipitating the antibody with magnetic particles or beads to which protein A or protein G is attached.

In some embodiments, the present invention provides methods for obtaining translation of at least one protein of interest in a human or animal cell comprising: repeatedly or continuously introducing into the cell an RNA composition comprising mRNA that encodes the at least one protein of interest, wherein the RNA composition has been treated with RNase III, whereby the RNA composition is practically free, extremely free or absolutely free of dsRNA (e.g., meaning that less than 0.01%, less than 0.001%, or less than 0.0002%, respectively, of the RNA in the composition is dsRNA of a size greater than about 40 basepairs in length), and culturing the cell under conditions wherein the cell survives and grows, and wherein the mRNA is translated. In certain embodiments, cell is ex vivo in culture or in vivo. In further embodiments, composition generates substantially no Toll-Like Receptor 3 (TLR3) mediated immune response when introduced into or contacted with or injected into a human or animal cell or subject.

In other embodiments, the composition does not generate an innate immune response that is sufficient to cause substantial inhibition of cellular protein synthesis or dsRNA-induced apoptosis when the treated RNA composition is repeatedly introduced into a living human or animal cell or subject. In some embodiments, the cell is a somatic cell, a mesenchymal stem cell, a reprogrammed cell, a non-reprogrammed cell, or other type of cell. In particular embodiments, the method is performed without the use any exogenous protein (e.g., B18R), siRNA, or small molecule agent that inhibits or reduces the activation, induction or the expression of one or more proteins in an innate immune response pathway.

In certain embodiments, the method further comprises: treating the cell with a protein, siRNA, mRNA (e.g. encoding B18R or Vaccinia virus E3L, or K3L), or small molecule agent that inhibits or reduces the activation, induction or expression of one or more RNA sensors or proteins in an innate immune response pathway, wherein the treating is prior to and/or during the introducing.

In some embodiments, the cell exhibits a first differentiated state or phenotype prior to the introducing, and exhibits a second differentiated state or phenotype after the introducing.

In some embodiments, the cell, prior to the introducing is a non-reprogrammed cell and after the introducing is a reprogrammed cell, wherein the reprogrammed cell is a dedifferentiated cell, an induced pluripotent stem cell, a transdifferentiated cell, a differentiated or redifferentiated somatic cell. In further embodiments, the introducing is repeated daily for at least 2 days. In particular embodiments, the introducing is repeated daily for at least 3 days, 4 days, 5 days, 6 days, 7 days, 8 days, 9 days, 10 days, 11 days, 12 days, 13 days, 14 days, 15 days, 16 days, 17, days, 18 days, 19 days, 20 days, 21 days . . . 30 days . . . 50 days or more.

In some embodiments, the present invention provides compositions or system comprising: a) a buffer or other aqueous solution, and b) ssRNA molecules encoding at least one protein, wherein: i) the at least one protein is a reprogramming factor, and/or ii) wherein the ssRNA molecules contain at least one modified base that reduces the activation of an innate immune response pathway in a cell compared to ssRNA molecules exhibiting the same sequence but lacking the at least one modified base, and wherein the composition is practically free of double-stranded RNA molecules.

In certain embodiments, the ssRNA is characterized by at least one (or at least two, or at least three, or at least four, or at least five, or all) of the following: i) encodes a reprogramming factor; ii) encodes a CD protein, meaning a protein identified in the cluster of differentiation system; iii) encodes an enzyme; iv) encodes a protein in the immunoglobulin super family; v) encodes a cytokine or chemokine; vi) encodes a cell surface receptor protein; vi) encodes a protein in a cell signaling pathway; vii) encodes an antibody; viii) encodes a T cell receptor; vix) encodes a protein that reduces or suppresses an innate immune response comprising interferon (IFN) production or response; x) encodes a reporter protein; xi) contains one or more modified bases; xii) exhibits a cap structure; xiii) exhibits a Cap I structure where the 5' penultimate nucleotide comprises a 2'-O-methyl-ribosyl group; xiv) exhibits a poly A tail; xv) does not contain any modified bases other than a 5' cap nucleotide, if present; xvi) exhibits at least one heterologous sequence selected from among: a 5' UTR sequence, Kozak sequence, an IRES sequence, and 3' UTR sequence; and xvii) encodes an iPS cell induction factor.

In certain embodiments, the reporter is selected from among *Aequorea victoria* jellyfish aequorin; a luciferase (e.g., encoding one luciferase selected from the group consisting of: *Photinus pyralis* or North American firefly luciferase); *Luciola cruciata* or Japanese firefly or Genji-botaruluciferase; *Luciola italic* or Italian firefly luciferase); *Luciola lateralis* or Japanese firefly or Heike luciferase; *Luciola mingrelica* or East European firefly luciferase; *Photuris pennsylvanica* or Pennsylvania firefly luciferase; *Pyrophorus plagiophthalamus* or Click beetle luciferase; *Phrixothrix hirtus* or Railroad worm luciferase; *Renilla reniformis* or wild-type *Renilla* luciferase; *Renilla reniformis* Rluc8 mutant *Renilla* luciferase; *Renilla reniformis* Green *Renilla* luciferase; *Gaussia princeps* wild-type *Gaussia* luciferase; *Gaussia princeps Gaussia*-Dura luciferase; *Cypridina noctiluca* or *Cypridina* luciferase; *Cypridina hilgendorfii* or *Cypridina* or Vargula luciferase; *Metridia longa* or *Metridia* luciferase; and *Oplophorus gracilorostris* or OLuc luciferase; or encoding 2 different luciferases selected from the group consisting of native Firefly luciferase and *Renilla* luciferase; Red Firefly luciferase and wild-type *Renilla* luciferase; Red Firefly luciferase and Green *Renilla* luciferase; *Gaussia* luciferase and *Renilla* luciferase; *Gaussia* luciferase and Green *Renilla* luciferase; *Gaussia* luciferase and Firefly luciferase; *Gaussia* luciferase and Red Firefly luciferase; *Gaussia* luciferase and *Cypridina* luciferase; *Cypridina* luciferase and *Renilla* luciferase; *Cypridina* luciferase and Green *Renilla* luciferase; *Cypridina* luciferase and Red Firefly luciferase; or encoding 3 different luciferases selected from the group consisting of: *Cypridina* luciferase, *Gaussia* luciferase, and any Firefly luciferase; and *Cypridina* luciferase, any *Renilla* luciferase and Firefly luciferase); and a fluorescent protein (e.g., encoding a fluorescent protein selected from the group consisting of: a Phycobiliprotein (e.g. R-Phycoerythrin (R-PE), B-Phycoerythrin (B-PE), C-Phycocyanin (CPC), and Allophycocyanin (APC)); an *Aequorea* green fluorescent protein; an *Aequorea* blue fluorescent protein (BFP); an *Aequorea* cyan fluorescent protein (CFP); an *Aequorea* yellow fluorescent protein (YFP); an *Aequorea* violet-excitable green fluorescent protein (Sapphire); an *Aequorea* cyan-excitable enhanced green protein fluorescent protein (EGFP); *Discosoma* red fluorescent protein; a variant of monomeric *Discosoma* red fluorescent protein referred to as a *Discosoma* "mFruits" (m for monomeric) fluorescent protein [e.g. *Discosoma* yellow fluorescent protein (mHoneydew); *Discosoma* blue fluorescent protein (mBlueberry); *Discosoma* orange fluorescent protein (mOrange)]; *Zoanthus* yellow fluorescent protein; *Obelia* green fluorescent proteins; *Renilla reniformis* sea pansy green fluorescent proteins; Anthozoa fluorescent proteins; lancelet fluorescent protein; copepod crustacean fluorescent protein; *Entacmaea quadricolor* far-red fluorescent protein; *Anemonia sulcata* red fluorescent protein; *Trachyphyllia geoffroyi* "Kaede" red fluorescent protein; *Lobophyllia hemprichii* fluorescent protein; *Dendronephthya* fluorescent protein; a Cnidaria fluorescent protein; Arthropoda fluorescent protein; and Chordata fluorescent protein; a monomeric *Galaxea* fluorescent protein; a monomeric *Fungia concinna* fluorescent protein; a monomeric *Lobophyllia hemprichii* fluorescent protein; a monomeric *Pectiniidae* fluorescent protein; a monomeric *Dendronephthya* fluorescent protein; a monomeric *Montipora* fluorescent protein; and a monomeric *Clavularia* s fluorescent protein).

In particular embodiments, the ssRNA exhibits a cap structure comprising: i) a cap1 structure, wherein the 2' hydroxyl of the ribose in the 5' penultimate nucleotide is methylated, ii) a 5' cap comprising 7-methylguanine, and/or iii) an anti-reverse cap analog (ARCA), or a thio-ARCA. In further embodiments, the ssRNA molecule exhibits a poly-A tail composed of at least 50 A residues or at least 100-200 A residues (e.g., at least 50 . . . 75 . . . 100 . . . 150 . . . 200 . . . or more). In particular embodiments, the 5' UTR or 3' UTR exhibited by the ssRNA is a sequence exhibited by a Xenopus or human alpha- (α-) globin or beta- (β-) globin mRNA, or wherein the 5' UTR is a sequence exhibited by tobacco etch virus (TEV) RNA.

In other embodiments, the ssRNA comprises or consists of at least one modified ribonucleoside selected from the group consisting of pseudouridine (Ψ), 1-methyl-pseudouridine (m$^1$Ψ), 5-methylcytidine (m$^5$C), 5-methyluridine (m$^5$U), 2'-O-methyluridine (Um or m$^{2'\text{-}O}$U), 2-thiouridine (s$^2$U), and N$^6$-methyladenosine (m$^6$A) in place of at least a portion of the corresponding unmodified canonical ribonucleoside. In particular embodiments, with the exception of the 5' cap nucleotide if present, the ssRNA contains only the canonical G, A, C and U nucleic acid bases.

In some embodiments, the ssRNA comprises at least one modified ribonucleoside, the at least one modified ribonucleoside being selected from the group consisting of: (i) pseudouridine (Ψ), 1-methyl-pseudouridine (m$^1$Ψ), 5-methyluridine (m$^5$U), 2'-O-methyluridine (Um or m$^{2'\text{-}O}$U), and 2-thiouridine (s$^2$U) in place of all or almost all of the canonical uridine residues; (ii) 5-methylcytidine (m$^5$C) in place of all or almost all of the canonical cytidine residues; and/or (iii) N$^6$-methyladenosine (m$^6$A) in place of all or almost all of the canonical adenosine residues.

In further embodiments, only a portion of a canonical ribonucleoside is replaced by the corresponding modified ribonucleoside (e.g., wherein a portion means 1-25%, 25-50%, or 50-99% of the canonical ribonucleoside is replaced).

In certain embodiments, the at least one modified ribonucleoside comprises or consists of pseudouridine (Ψ) or 1-methyl-pseudouridine (m$^1$Ψ) in place of all or almost all of the canonical uridine residues, and/or 5-methylcytidine (m$^5$C) in place of all or almost all of the canonical cytidine residues.

In other embodiments, only a portion of the canonical uridine residues are replaced by pseudouridine or 1-methyl-pseudouridine residues and/or only a portion of the canonical cytidine residues are replaced by 5-methylcytidine residues (e.g., wherein a portion means 1-25%, 25-50%, or 50-99% of one or both canonical ribonucleosides are replaced).

In certain embodiments, except with respect to the nucleic acid bases comprising the 5' cap, the mRNA is composed of (or consists of) only unmodified canonical G, A, C and U nucleic acid bases. In other embodiments, the protein encoded by the ssRNA that reduces or suppresses an innate immune response comprising interferon (IFN) production or response is selected from among E3L protein, K3L protein, and B18R protein, or a functional fragment or variant of any thereof. In certain embodiments, the composition is practically free, extremely free or absolutely free of dsRNA.

In some embodiments, the ssRNA encodes at least one protein selected from the group consisting of: MYOD, ASCL1, MYT1L, NEUROD1, POU3F2, OCT4, SOX2, KLF4, LIN28, NANOG, MYC, c-MYC, c-MYC(T58A), L-MYC, ETS2, MESP1 GATA4, HAND2, TBX5, MEF2C, ASCL1, EN1, FOXA2, LMX1A, NURR1, PITX3, HNF1a, HNF4a, FOXA1, FOXA2, FOXA3, GATA4, erythropoietin, and a CD protein; or a functional fragment or variant of any of the preceding.

In further embodiments, the CD protein is selected from: a cell surface receptor, a ligand for a cell surface receptor, a cell signaling molecule, a cell adhesion molecule, a co-stimulating molecule, a complement system protein, a protein comprising a class I or class II major histocompatibility antigen, an inhibitor of a cell signaling molecule, a transporter of a cell signaling molecule, and an effector molecule of an innate or adaptive immune response. In other embodiments, the CD protein is selected from: CD1a; CD1b; CD1c; CD1d; CD1e; CD2; CD3d; CD3e; CD3g; CD4; CD5; CD6; CD7; CD8a; CD8b; CD9; CD10; CD11a; CD11b; CD11c; CD11d; CDw12; CD14; CD16a; CD16b; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD44; CD45; CD46; CD47; CD48; CD49a; CD49b; CD49c; CD49d; CD49e; CD49f; CD50; CD51; CD52; CD53; CD54; CD55; CD56; CD57; CD58; CD59; CD61; CD62E; CD62L; CD62P; CD63; CD64; CD66a; CD66b; CD66c; CD66d; CD66e; CD66f; CD68; CD69; CD70; CD71; CD72; CD74; CD79a; CD79b; CD80; CD81; CD82; CD83; CD84; CD85a; CD85c; CD85d; CD85e; CD85f; CD85g; CD85h; CD85i; CD85j; CD85k; CD86; CD87; CD88; CD89; CD90; CD91; CD92; CD93; CD94; CD95; CD96; CD97; CD98; CD99; CD100; CD101; CD102; CD103; CD104; CD105; CD106; CD107a; CD107b; CD108; CD109; CD110; CD111; CD112; CD113; CD114; CD115; CD116; CD117; CD118; CD119; CD120a; CD120b; CD121a; CD121b; CD122; CD123; CD124; CD125; CD126; CD127; CD129; CD130; CD131; CD132; CD133; CD134; CD135; CD136; CD137; CD138; CD139; CD140a; CD140b; CD141; CD142; CD143; CD144; CD146; CD147; CD148; CD150; CD151; CD152; CD153; CD154; CD155; CD156a; CD156b; CD157; CD158a; CD158b1; CD158b2; CD158c; CD158d; CD158e; CD158f1; CD158g; CD158h; CD158i; CD158j; CD158k; CD158z; CD159a; CD159c; CD160; CD161; CD162; CD163; CD163b; CD164; CD165; CD166; CD167a; CD167b; CD168; CD169; CD170; CD171; CD172a; CD172b; CD172g; CD173; CD177; CD178; CD179a; CD179b; CD180; CD181; CD182; CD183; CD184; CD185; CD186; CD191; CD192; CD193; CD194; CD195; CD196; CD197; CDw198; CDw199; CD200; CD201; CD202b; CD203a; CD203c; CD204; CD205; CD206; CD207; CD208; CD209; CD210; CDw210b; CD212; CD213a1; CD213a2; CD214; CD215; CD217; CD218a; CD218b; CD220; CD221; CD222; CD223; CD224; CD225; CD227; CD228; CD229; CD230; CD231; CD232; CD233; CD234; CD235a; CD235b; CD236; CD238; CD239; CD240CE; CD240D; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD270; CD271; CD272; CD273; CD274; CD275; CD276; CD277; CD278; CD279; CD280; CD281; CD282; CD283; CD284; CD286; CD288; CD289; CD290; CD292; CDw293; CD294; CD295; CD296; CD297; CD298; CD299; CD300a; CD300b; CD300c; CD300d; CD300e; CD300f; CD300g; CD301; CD302; CD303; CD304; CD305; CD306; CD307a; CD307b; CD307c; CD307d; CD307e; CD309; CD312; CD314; CD315; CD316; CD317; CD318; CD319; CD320; CD321; CD322; CD324; CD325; CD326; CD327; CD328; CD329; CD331; CD332; CD333; CD334; CD335; CD336; CD337; CD338; CD339; CD340; CD344; CD349; CD350; CD351; CD352; CD353; CD354; CD355; CD357; CD358; CD360; CD361; CD362; and CD363; or a functional fragment or variant of any of the preceding.

In further embodiments, the in vitro-transcribed ssRNA encodes a plurality of reprogramming factors. In further embodiments, the RNA preparation generates substantially no Toll-Like Receptor 3 (TLR3) mediated immune response when introduced into or contacted with or injected into a human or animal cell or subject. In additional embodiments, the RNA preparation does not generate an innate immune response that is sufficient to cause substantial inhibition of cellular protein synthesis or dsRNA-induced apoptosis when the treated RNA composition is repeatedly introduced into a living human or animal cell or subject.

In some embodiments, the present invention provides methods of making an RNA preparation comprising: a) processing in vitro transcribed RNA by: i) exposure to a dsRNA-specific endoribonuclease III protein in a reaction mixture comprising a salt that results in an ionic strength at least as high as potassium acetate at a concentration of about 50-300 mM and a final magnesium concentration of about 1-4 mM, and/or ii) passage through a chromatographic or electrophoretic separation device; wherein the processing the in vitro transcribed RNA generates an RNA preparation that is practically free, extremely free or absolutely free of double-stranded RNA, and wherein the in vitro transcribed RNA encodes at least one protein, wherein: i) the at least one protein is a reprogramming factor, and/or ii) wherein the in vitro transcribed RNA contains at least one modified base that reduces the induction or activation of an RNA sensor or innate immune response pathway in a cell.

In particular embodiments, the chromatographic separation device is a gravity flow or HPLC column. In certain embodiments, the present invention provides methods of making an RNA preparation comprising: a) contacting a composition containing single-stranded RNA (ssRNA) and double-stranded RNA (dsRNA) with a solution that contains RNase III and a monovalent salt at a concentration of at least 50 mM, but which lacks divalent magnesium cations, such that a mixture is generated, b) incubating the mixture under conditions such that the RNase III binds to the dsRNA but is not generally enzymatically active, and c) cleaning up the ssRNA from the RNase III, at least some of which is bound to the dsRNA, to generate an RNA preparation that contains ssRNA and is substantially free, virtually free, essentially free, or practically free of dsRNA (e.g., meaning, respectively, that less than: 0.5%, 0.1%, 0.05%, 0.01%, 0.001% or 0.0002% of the mass of the RNA in the treated ssRNA composition is dsRNA of a size greater than about 40 basepairs).

In some embodiments, the present invention provides methods of obtaining expression of at least one protein of interest in a cell comprising: contacting a cell with an RNA composition comprising in vitro-synthesized ssRNA that encode at least one protein of interest such that the at least one protein of interest is expressed in the cell, wherein the contacting: a) is conducted at least once daily for a plurality of days, or b) is conducted a plurality of time over at least 24 hours; and wherein the contacting does not induce an innate immune response that: i) kills the cell; ii) is sufficient to inhibit protein synthesis by two-fold or greater; and/or iii) induces or activates proteins involved in an apoptosis pathway.

In certain embodiments, the at least one protein of interest is a reprogramming factor, and wherein the plurality days is sufficient number of days to reprogram the cell. In certain embodiments, the plurality of days is at least 2 days, at least 3 days, 4 days, 5 days, 6 days, 7 days, 8 days, 9 days, 10 days, 11 days, 12 days, 13 days, 14 days, 15 days, 16 days, 17, days, 18 days, 19 days, 20 days, 21 days . . . 30 days . . . 50 days or more. In particular embodiments, the ssRNA comprises at least one of the following: a 5' cap, a 5' untranslated region, a 5' Kozak sequence, a 3' untranslated region, and a poly(A) tail. In further embodiments, the composition is at least practically free of double stranded RNA. In further embodiments, the cell is located in a subject or is located ex vivo in culture. In some embodiments, the composition is free of a protein, siRNA, or small molecule agent that inhibits or reduces the activation, induction or expression of one or more RNA sensors or proteins in an innate immune response pathway.

In certain embodiments, the cell is present in a culture medium, wherein the culture medium: i) is free of feeder cells, and/or ii) comprises at least one reagent selected from the group consisting of: a TGF-beta inhibitor and a MEK inhibitor. In other embodiments, the cell is present in a culture medium that lacks a biological substrate.

In some embodiments, the RNA molecule is a therapeutic RNA sequence, an mRNA encoding a therapeutic protein, an mRNA encoding a reporter protein, or an mRNA encoding a cell reprogramming factor.

In certain embodiments, the composition comprises at least one additional component selected from: i) a monovalent salt at a concentration of at least 50 mM; ii) a cell; iii) a protein, siRNA, or small molecule agent that inhibits or reduces the activation, induction or expression of one or more RNA sensors or proteins in an innate immune response pathway; and iv) a dsRNA binding protein. In some embodiments, the cell is a somatic cell, a mesenchymal stem cell, a reprogrammed cell, a non-reprogrammed cell, In particular embodiments, prior to the contacting, the composition is treated with a dsRNA-specific RNase such that substantially or practically all contaminant dsRNA is digested.

In particular embodiments, the cell before the contacting for a plurality of days exhibits a first differentiated state or phenotype, and after the contacting for a plurality of days, exhibit a second differentiated state or phenotype.

In particular embodiments, the present invention provides methods for making ssRNAs for use in reprogramming eukaryotic cells that exhibit a first differentiated state or phenotype to cells that exhibit a second differentiated state or phenotype by introducing the ssRNAs into the cells at least three times over a period of at least two days, the method comprising: (i) synthesizing one or more ssRNAs by in vitro transcription, each of which encodes a reprogramming factor; and (ii) treating the ssRNAs from step (i) with RNase III in a buffered solution having a pH of about 7 to about 9, a monovalent salt having at a concentration of about 100 mM or higher, divalent magnesium cations at a concentration of about 1 mM to less than 10 mM for sufficient time and under conditions wherein dsRNA is digested and ssRNAs that are substantially free of dsRNA are generated; in other embodiments, said introducing is for at least about: three days, . . . 6 days, . . . 8 days, . . . 10 days, . . . 15 days, . . . 18 days, . . . 21 days, . . . 28 days, . . . 35 days, . . . 42 days, . . . 50 days, . . . or greater than 50 days.

In some embodiments, the present invention provides compositions, kits, or systems comprising: a) a cell and/or RNA encoding at least one protein, wherein: i) the at least one protein is a reprogramming factor, and/or ii) wherein the RNA contains at least one modified base that reduces the activation of an innate immune response pathway in the cell; and b) a culture medium, wherein the culture medium: i) comprises at least one reagent selected from the group consisting of: a TGF-beta inhibitor and a MEK inhibitor; and/or ii) comprises a biological substrate for the cell, and is free of feeder cells; and/or iii) does not comprise either an extracellular matrix or other biological substrate or feeder cells. In some embodiments, wherein the culture medium does not comprise either an extracellular matrix or other biological substrate or feeder cells, the culture plate or vessel exhibits a treated surface on which the cells adhere and grow as a confluent layer.

In certain embodiments, the composition or system comprises both the cell and the RNA, wherein the RNA are present inside the cell. In particular embodiments, the cell is a reprogrammed cell. In certain embodiments, the reprogrammed cell is a dedifferentiated cell, an induced pluripotent stem, or a transdifferentiated cell. In some embodiments, the biological substrate comprises vitronectin protein and/or the gelatinous protein mixture secreted by Engelbreth-Holm-Swarm (EHS) mouse sarcoma cells.

In additional embodiments, the present invention provides methods of culturing a cell comprising: culturing cells on the culture medium described above or herein, wherein the cells comprise the RNA described herein. In some embodiments, the cells exhibit a first differentiated state or phenotype prior to the culturing, and exhibit a second differentiated state or phenotype after the culturing. In further embodiments, the cells, prior to the culturing, are non-reprogrammed cells and after the culturing are reprogrammed cells, wherein the reprogrammed cells are dedifferentiated cells, induced pluripotent stem cells, transdifferentiated cells, differentiated or redifferentiated somatic cells. In particular embodiments, the culturing is continued for at least 2 days, 3 days, . . . 10 days . . . 20 days, or more, or for 10-18 days or for about 2-25 days.

In certain embodiments, the present invention provides compositions, kits, and systems comprising: a mixture of mRNAs encoding iPSC reprogramming factors comprising KLF4 (K), MYC (M), OCT4 (0), and SOX2 (S), wherein the molar concentration of mRNA encoding O is about 3-times higher than the molar concentration of mRNA encoding M and S and wherein mRNA encoding K is between about 1 time and about 3 times the molar concentration of M and S, wherein the RNA composition is practically free, extremely free or absolutely free of dsRNA. In particular embodiments, the mRNAs further encode either LIN28 (L) or NANOG (N) or both, wherein the molar concentration of mRNA encoding L or N, if present, is the same or about the same as the molar concentration of M and S.

In some embodiments, the present invention provides compositions and systems comprising: a) a first mixture of different RNA molecules encoding ten different combinations of the following proteins: KLF4 or functional fragment or variant thereof (K), MYC or functional fragment or variant thereof(M), OCT4 or functional fragment or variant thereof(0), SOX2 or functional fragment or variant thereof (S), LIN28 or functional fragment or variant thereof (L), and NANOG or functional fragment or variant thereof (N), wherein the different RNA molecules are present in the composition or system in an approximate molar ratio selected from the group consisting of: $KMO_{2.5-3.5}SLN$; $KMO_{2.5-3.5}S$; $KMO_{2.5-3.5}SL$; $K_{1.5-2.5}MO_{2.5-3.5}SLN$; $K_{2.5-3.5}MO_{2.5-3.5}SLN$; $K_{1.5-2.5}MO_{2.5-3.5}SL$; $K_{2.5-3.5}MO_{2.5-3.5}SL$; $K_{1.5-2.5}MO_{2.5-3.5}S$; $K_{2.5-3.5}MO_{2.5-3.5}S$; or $K_{1.5-10.0}LMS$; and/or b) a second mixture of different RNA molecules encoding KLF4, c-MYC, OCT4, and SOX2, wherein no other reprogramming genes are present in the composition or system.

In particular embodiments, no other reprogramming RNA sequences are present in the composition or system than recited in the ten different combinations. In particular embodiments, the compositions further comprise a cell. In certain embodiments, the cell is a reprogrammed cell. In further embodiments, MYC is c-MYC, L-MYC, or c-MYC (T58A). In additional embodiments, the approximate molar ratios are selected from: $KMO_3SLN$; $KMO_3S$; $KMO_3SL$; $K_2MO_3SLN$; $K_3MO_3SLN$; $K_2MO_3SL$; $K_3MO_3SL$; $K_2MO_3S$; $K_3MO_3S$; or $K_{1.5-2.5}LMS$.

In certain embodiments, the present invention provides methods for changing or reprogramming the state of differentiation or differentiated state or phenotype of a cell comprising: introducing a plurality of different RNA molecules into a cell, wherein the cells exhibits a first differentiated state or phenotype prior to the introducing and exhibits a second differentiated state or phenotype after the introducing, and wherein the introducing results in an approximate molar ratio of the different RNA molecules in the cell selected from the group consisting of: $KMO_{2.5-3.5}SLN$; $KMO_{2.5-3.5}S$; $KMO_{2.5-3.5}SL$; $K_{1.5-2.5}MO_{2.5-3.5}SLN$; $K_{2.5-3.5}MO_{2.5-3.5}SLN$; $K_{1.5-2.5}MO_{2.5-3.5}SL$; $K_{2.5-3.5}MO_{2.5-3.5}SL$; $K_{1.5-2.5}MO_{2.5-3.5}S$; $K_{2.5-3.5}MO_{2.5-3.5}S$; or $K_{1.5-10.0}LMS$; wherein K is KLF4 or functional fragment thereof, M is MYC or a functional fragment thereof, 0 is OCT4 or functional fragment thereof, S is SOX2 or functional fragment thereof, L is LIN28 or functional fragment thereof, and N is NANOG or a functional fragment thereof. In particular embodiments, the MYC is c-MYC, L-MYC, or c-MYC(T58A).

In other embodiments, the present invention provides methods for changing or reprogramming the state of differentiation or differentiated state or phenotype of a cell comprising: introducing into a cell that exhibits a first differentiated state or phenotype: i) a first mRNA encoding KLF4, or functional fragment thereof, ii) a second mRNA encoding c-MYC, or functional fragment thereof, iii) a third mRNA encoding OCT-4, or functional fragment thereof, and iv) a fourth mRNA encoding SOX2, or functional fragment thereof, wherein the introducing generates a reprogrammed cell that exhibits a second differentiated state or phenotype, and wherein no other reprogramming factors, besides the first, second, third, and fourth mRNAs are used to reprogram the cell.

In certain embodiments, the present invention provides methods for changing or reprogramming the state of differentiation or differentiated state or phenotype of a cell comprising: introducing into a cell that exhibits a first differentiated state or phenotype an RNA molecule encoding c-MYC (T58A) such that a reprogrammed cell that exhibits a second differentiated state or phenotype is generated.

In some embodiments, the present invention provides methods for reducing or eliminating a symptom or disease of a eukaryotic subject that exhibits a disease condition, comprising: administering to the subject an effective dose of an RNA composition comprising ssRNA that encode at least one therapeutic protein, wherein the RNA composition is at least substantially free, virtually free, essentially free, or practically free of contaminant dsRNA, whereby the symptom or disease is reduced or eliminated. In some embodiments, the RNA composition is practically free, extremely free or absolutely free of dsRNA. In further embodiments, the RNA composition does not generate an innate immune response in the subject that is sufficient to cause substantial inhibition of cellular protein synthesis or dsRNA-induced apoptosis when the RNA composition is repeatedly or continuously administered to the subject. In some embodiments, the therapeutic protein is erythropoietin or truncated or mutated version thereof. In certain embodiments, the administering is conducted at least once per days for at least two days. In some embodiments, the administering is conducted at least daily at least 1-7 times per week for at least 1 week (e.g., at least 1 week, 2 weeks, 3 weeks, 4 weeks, . . . 10 weeks . . . 52 weeks or more).

In other embodiments, the administering is conducted daily or twice per day, with the administering occurring about 1 time per week, 2 times per week, 3 times per week, 4 times per week, 5 times per week, 6 times per week, or daily for a period of weeks, months or years.

In some embodiments, the present invention provides compositions or systems comprising: a) a reprogrammed or differentiated myoblast cell, wherein the myoblast cell comprises an exogenous RNA molecule encoding MYOD protein or functional fragment thereof, and/or b) a reprogrammed or transdifferentiated neuron cells, wherein the neuron cell comprises exogenous RNA molecules encoding at least one protein selected from the group consisting of: ASCL1 or functional fragment thereof, MYT1L or functional fragment thereof, NEUROD1 or functional fragment thereof, and POU3F2 or functional fragment thereof.

In certain embodiments, the present invention provides methods for reprogramming a non-myoblast cell to a myoblast cell comprising: a) daily, for at least two days, introducing into a non-myoblast cell a composition comprising in vitro-synthesized ssRNA or mRNA encoding MYOD protein or functional fragment or variant thereof, wherein the composition is at least practically free of dsRNA, and b) culturing under conditions wherein at least a portion of the non-myoblast cells are reprogrammed or differentiated into myoblast cells.

In particular embodiments, the present invention provides methods for reprogramming non-neuron somatic cells to neuron cells comprising: a) daily, for multiple days, introducing into non-neuron somatic cells a composition comprising in vitro-synthesized ssRNA or mRNA encoding at least one protein selected from the group consisting of: ASCL1 or functional fragment thereof, MYT1L or functional fragment thereof, NEUROD1 or functional fragment thereof, and POU3F2 or functional fragment thereof, wherein the composition is practically free, extremely free, or absolutely free of dsRNA, and b) culturing under conditions wherein at least a portion of the non-neuron somatic cells are reprogrammed or transdifferentiated into neuron cells. In certain embodiments, the introducing is conducted at least once daily for at least two days, three days . . . 10 days . . . 365 days, or more.

In some embodiments the present invention provides methods comprising contacting a plurality of cultured cells with a total daily dose (and no more than the total daily dose) of a composition comprising ssRNAs encoding at least one reprogramming factor, wherein said contacting is repeated for a sufficient number of days such that at least a portion of said plurality of cultured cells are reprogrammed from a first differentiated state or phenotype to a second differentiated state or phenotype, wherein said total daily dose is between about 0.1 microgram and about 1.2 micrograms of said ssRNAs per 10,000 to 100,000 initially plated cells (e.g., per 2 mls of culture medium). In some embodiments, the total daily dose is administered once per day. In some embodiments, the total daily dose is administered as two doses per 24 hours . . . 4 doses per 24 hours, 8 doses per 24 hours. In some embodiments, the mixture of ssRNAs encoding reprogramming factors are introduced continuously (e.g., into the culture medium) using a robotic or microfluidic device for said introducing. In some embodiments, mixture of ssRNAs encoding reprogramming factors are introduced continuously (e.g., into the culture medium) and the composition of the protein reprogramming factors encoded by the mRNA mixture is varied over time. In particular embodiments, the total daily dose is about 0.1, 0.2, 0.3, 0.4, 0.5, 0.6, 0.7, 0.8, 0.9, 1.0, 1.1, or about 1.2 micrograms of said ssRNA.

In some embodiments, the present invention provides compositions or systems comprising: a) a buffer or other aqueous solution, and b) RNA molecules encoding at least one protein, wherein: i) said at least one protein is a reprogramming factor, and/or ii) wherein said RNA molecules contain at least one modified base that reduces the activation of an innate immune response pathway in a cell, and wherein said composition is free of double-stranded RNA molecules to a level provided by HPLC purification, and wherein said composition would generate no detectable Toll-Like Receptor 3 (TLR3) mediated immune response when introduced into or contacted with or injected into a human or animal cell or subject.

DESCRIPTION OF THE FIGURES

The following FIGURES form part of the present specification and are included to further demonstrate certain aspects of the present invention. The invention may be better understood by reference to one or more of these FIGURES in combination with the detailed description of specific embodiments presented herein.

As shown in FIG. 1, correct digestion of this RNA substrate by a dsRNA-specific endoRNase, such as RNase III, would be expected to result in complete digestion of the central 1671-bp dsRNA portion, while leaving ssRNA tails of 136 bases and 255 bases intact.

FIG. 12 shows an example of alkaline phosphatase-stained candidate iPS cells generated from human BJ fibroblasts using a method of the invention wherein the BJ fibroblasts were transfected and cultured in feeder-free wells coated with a MATRIGEL™ GFR matrix in medium comprising: A) the Feeder-free Reprogramming Medium in EXAMPLE 11 of the present invention without LIF protein or, TGFβ or MEK small molecule inhibitors; B) the Feeder-free Reprogramming Medium in EXAMPLE 11 of the present invention with LIF protein and the small molecule inhibitors, SB431542 TGFβ inhibitor and PD0325901 MEK Inhibitor; and C) a PLURITON™ commercial reprogramming medium without further addition of LIF or any small molecule inhibitors. Examples of positive staining colonies are indicated by the arrows. (Note: in later experiments, we found that the method for reprogramming of cells that exhibited a first differentiated state or phenotype comprising human fibroblasts to cells that exhibited a second differentiated state or phenotype comprising iPSCs could be performed in the absence of feeder cells (i.e., feeder-free reprogramming) if the method further comprises the step of adding a TGFβ small molecule inhibitor and/or a MEK small molecule inhibitor (e.g., TGFβ inhibitor SB431542 and MEK Inhibitor PD0325901) to the medium during the steps of said repeatedly or continuously introducing of the RNA composition comprising ssRNA or mRNA encoding the reprogramming factors (e.g., iPSC reprogramming factors); in these embodiments, it was not necessary to add LIF protein.

FIG. 15 shows that BJ fibroblasts transfected for 18 straight days with mRNA reprogramming factors expressed the stem cell marker Tra-1-60. BJ fibroblasts were transfected with the five factors (5F) 3:1:1:1:1 molar ratio of (OCT4, SOX2, KLF4, LIN28 and c-MYC or c-MYC (T58A) RNaseIII treated, 5mC/ΨTP at a total dose 1.2 µg of mRNA per transfection for 18 days. B18R was used at 200 ng/ml in some of the treatments.

FIG. 17A shows the results for clone 2, FIG. 17B shows the results from clone 3, and FIG. 17C shows the results from clone 4.

FIG. 21A shows images of iPSCs generated from BJ fibroblasts on feeder cells.

FIG. 22A shows 4× magnification, FIG. 22B shows 10× magnification.

FIG. 23A shows OCT4 staining and FIG. 23B shows TRA-1-60 staining. FIG. 23C shows 20× magnification of an edge of a colone and shows high level LIN28 expression.

FIG. 23D shows LIN28 expression. It is noted that LIN28 mRNA was transfected, but 10 days had elapsed, so this would appear to show endogenous expression. FIG. 23E shows SSEA4 expression, an important iPSC marker. FIG. 23F shows NANOG expression and FIG. 23G shows SSEA4 expression. FIG. 23H shows a second example using a small colony at 20× magnification. FIG. 23I shows NANOG expression and FIG. 23J shows SSEA4 expression.

FIG. 24 shows morphological changes observed in BJ fibroblasts transitioning to iPSCs. On about Day 9, a change in morphology of BJ fibroblasts was observed as the slow-growing BJ fibroblasts changed into rapidly dividing epithelial cells.

FIG. 25 shows iPSC colonies appearing on Day 16. FIG. 25A shows first iPSC colonies appearing on Day 16 in well with no B18R protein. FIG. 25B shows first colonies appearing on Day 16 in well with B18R protein.

FIG. 26A-FIG. 26B shows immunostaining of iPSCs one month after first appearance of iPSC colonies. FIG. 26A shows staining for NANOG, SSEA4, and TRA-1-81, and FIG. 26B shows staining for TRA-1-60, OCT4, SSEA4, and DNMT3B.

FIG. 27A shows TUJ1 (ectoderm cells) at 4× magnification, FIG. 27B shows TUJ1 at 20× magnification, FIG. 27C shows 20× magnification of GFAP (ectoderm), FIG. 27D shows 4× magnification of NFL (ectoderm), FIG. 27E shows 10× magnification of NFL, FIG. 27F shows 10× magnification of alpha-smooth muscle actin SMA (mesoderm), FIG. 27G shows 20× magnification of Desmin muscle cells (mesoderm), FIG. 27H shows 20× magnification of SOX17 (endoderm), FIG. 27I shows 10× magnification of AFP (endoderm), and FIG. 27J shows 10× magnification of AFP.

FIG. 29A-FIG. 29B shows an example of a well with "too many colonies to count." The emerging colonies are the densely packed, rapidly dividing cells with an epithelial morphology. They no longer have the long thin BJ fibroblast morphology and the feeder cells can't be seen under the confluent colony forming layer of cells. Basically this entire well of cells is being reprogrammed to some extent, but not every cell will complete the process and form an iPSC colony. FIG. 29A shows two images, with the top image showing 4× magnification, and the bottom image blown up showing the same image with more obvious colonies outlined. FIG. 29B shows two images, with the top image showing a single colony on a background of fibroblast cells, and the bottom image from the edge of a particular well which shows white rounded colonies with dark background cells.

FIG. 31 shows an example of a well with efficient induction of iPSC colonies from BJ fibroblasts transfected daily for 18 days with up to 1.4 micrograms of a 3:1:1:1:1 molar ratio of unmodified mRNAs encoding OCT4, SOX2, KLF4, LIN28 and cMYC(T58A), both with and without pre-treatments of the cells with B18R protein prior to the transfections. (A) 1.4 micrograms of the mRNA reprogramming mix per well per day resulted in death of many cells, including feeder cells around this iPSC colony, but some iPSC colonies survived and were propagated. (B) One microgram of unmodified mRNA reprogramming mix per well per day resulted in less toxicity and generation of more iPS cells on Day 18. (C) Addition of B18R protein to the medium during reprogramming resulted in a confluent well of iPSC colonies—more than could be counted—and iPSC colonies from this well maintained the morphology and growth rates expected for iPSCs while being propagated continuously for more than two months.

FIG. 32A-FIG. 32B shows images of phase contrast and both live and fixed immunostained iPSCs generated from BJ fibroblasts using RNase III-treated, unmodified mRNAs encoding OCT4, SOX2, KLF4, LIN28 and cMYC(T58A) iPSC induction factors. FIG. 32A shows a phase 10× magnification, and expression of OCT4 and TRA-1-60. FIG. 32B shows expression of NANOG, TRA-1-81, a phase 10× magnification, and expression of SSEA4.

FIG. 33A shows, 4× phase, 10 phase, 10× OCT4, and 10× TRA1-60. FIG. 33B shows 4× phase, 10× phase, 10× SOX2, 10× TRA1-80, 10× phase, and 10× NANOG.

FIG. 40 shows alkaline phosphatase-positive colonies generated from BJ fibroblasts transfected with RNase III-treated mRNAs encoding $KLMO_3S$ (1:1:1:3:1) (FIG. 40A) and mRNAs encoding $K_3LMO_3S$ (3:1:1:3:1) (FIG. 40B).

FIG. 43 shows alkaline phosphatase-positive colonies generated from BJ fibroblasts transfected with RNase III-treated pseudouridine-modified, Cap1 mRNAs encoding KLMOS and KLMOS+B18R in FIG. 43A; RNase III-treated pseudouridine-modified, ARCA-capped mRNAs encoding KLMOS and KLMOS+B18R in FIG. 43B; and APex phosphatase treated, pseudouridine-modified, 5-methylcytidine ARCA capped KLMOS and KLMOS+B18R in FIG. 43C.

FIGS. 44A-D show alkaline phosphatase-positive colonies generated from BJ fibroblasts transfected with mRNAs $KLM_{T58A}OS$ (with standard 1:1:1:3:1 stoichiometry) having multiple degrees of variance. FIG. 44A shows Wells 1-6 exhibiting the following: Well 1—mRNAs are ARCA capped; Well 2—mRNAs are ARCA capped and APex phosphatase treated; Well 3—mRNAs are ARCA capped and APex phosphatase treated+B18R protein; Well 4—mRNAs are ARCA capped and RNase III treated (2 mM $Mg^{+2}$ buffer concentration); Well 5—mRNAs are ARCA capped and RNase III treated (2 mM $Mg^{+2}$ buffer concentration) and APex phosphatase treated; and Well 6—mRNAs are ARCA capped and RNase III treated (2 mM $Mg^{+2}$ buffer concentration) and APex phosphatase treated+B18R protein. FIG. 44B shows Wells 7-12 exhibiting the following: Well 7—mRNAs are ARCA capped and RNase III treated (2 mM $Mg^{+2}$ buffer concentration)+B18R protein; Well 8—mRNAs are ARCA capped and RNase III treated (2 mM $Mg^{+2}$ buffer concentration)+B18R protein (2×); Well 9—mRNAs have a Cap0 structure; Well 10—mRNAs have a Cap0 structure and RNase III treated (1 mM $Mg^{+2}$ buffer concentration); Well 11—mRNAs have a Cap0 structure and RNase III treated (2 mM $Mg^{+2}$ buffer concentration); and Well 12—mRNAs have a Cap0 structure and RNase III treated (1 mM $Mg^{+2}$ buffer concentration)+B18R protein. FIG. 44C shows Wells 13-18 exhibiting the following: Well 13—mRNAs have a Cap0 structure and RNase III treated (2 mM $Mg^{+2}$ buffer concentration)+B18R protein; Well 14—mRNAs have a Cap0 structure and RNase III treated (1 mM $Mg^{+2}$ buffer concentration)+B18R protein (2×); Well 15—mRNAs have a Cap0 structure and RNase III treated (1 mM $Mg^{+2}$ buffer concentration)+B18R protein (2λ); Well 16—mRNAs have a Cap1 structure; Well 17—mRNAs have a Cap1 structure and RNase III treated (1 mM $Mg^{+2}$ buffer concentration); and Well 18—mRNAs have a Cap1 structure and RNase III treated (2 mM $Mg^{+2}$ buffer concentration). FIG. 44D shows Wells 19-24 exhibiting the following: Well 19—mRNAs have a Cap1 structure and RNase III treated (1 mM $Mg^{+2}$ buffer concentration)+B18R protein; Well 20—mRNAs have a Cap1 structure and RNase III treated (2 mM $Mg^{+2}$ buffer concentration)+B18R protein; Well 21—mRNAs have a Cap1 structure and RNase III treated (1 mM $Mg^{+2}$ buffer concentration)+B18R protein (2×); Well 22—mRNAs have a Cap1 structure and RNase III treated (1 mM $Mg^{+2}$ buffer concentration)+B18R protein (2×); Well 23—mRNAs have a Cap1 structure and RNase III treated (1 mM $Mg^{+2}$ buffer concentration); and Well 24—mRNAs have a Cap1 structure and RNase III treated (2 mM $Mg^{+2}$ buffer concentration).

FIGS. 46A-D show images of immunostained feeder-free reprogrammed iPS cells generated from BJ fibroblasts using RNase III-treated or HPLC-purified unmodified or ψ-modified mRNAs encoding iPSC induction factors. The differentiated cells expressed markers representing all 3 germ layers of cells, including ectoderm markers, neuronal class III beta-tubulin (TUJ1) (FIG. 46A), Glial Fibrillary Acidic Protein (GFAP) and neurofilament-light (NF-L) (both FIG. 46B), the mesoderm markers, alpha-smooth muscle actin (α-smooth muscle actin, α-SMA or SMA) and desmin, and the endoderm markers, transcription factor SOX17 (FIG. 46C) and alpha fetoprotein (AFP) (shown in FIGS. 46C and D).

FIGS. 48A-C show images of immunostained feeder-free reprogrammed iPS cells (4 passages) generated from BJ fibroblasts that were HPLC-purified or RNase III-treated mRNA mixtures that contained the shorter cMyc T58A mRNA. The iPSCs stain positively for markers representing all 3 germ layers of cells. Cells were found that expressed the ectoderm marker neuronal class III beta-tubulin (TUJ1) (FIG. 48A), the mesoderm markers alpha-smooth muscle actin (SMA) (FIG. 48B) and desmin (FIG. 48C), and the endoderm marker SOX17 (FIG. 48C).

FIGS. 49A-R show that addition of certain amounts of dsRNA inhibits reprogramming of mouse mesenchymal stem cells to myoblasts, even though, in the absence of dsRNA, myoblasts were induced from the mesenchymal stem cells after only two daily transfections with mRNA encoding MYOD protein. This demonstrates the importance of induction of RNA sensors and innate immune response pathways by dsRNA and the importance of purifying the mRNA by chromatographic, electrophoretic or other column or gel separation methods, or treating the RNA composition or the ssRNA or mRNA composing using the RNase III treatment method disclosed herein. A) Untreated C3H10T1/2 mesenchymal stem cells (phase contrast). B) Untreated C3H10T1/2 cells (Myosin Heavy Chain, MHC in red). C) Mock Transfected (phase contrast). D) Mock Transfected (MHC). E) MYOD mRNA 0.5 µg/ml (phase contrast). F) MYOD mRNA 0.5 µg/ml (MHC). G) MYOD mRNA 0.5 µg/ml+luc2 dsRNA 0.1 µg/ml (phase contrast). H) MYOD mRNA 0.5 µg/ml+luc2 dsRNA 0.1 µg/ml (MHC). I) MYOD mRNA 0.5 µg/ml+luc2 dsRNA 0.01 µg/ml (phase contrast). J) MYOD mRNA 0.5 µg/ml+luc2 dsRNA 0.01 µg/ml (MHC). K) MYOD mRNA 0.5 µg/ml+luc2 dsRNA 0.001 µg/ml (phase contrast). L) MYOD mRNA 0.5 µg/ml+luc2 dsRNA 0.00001 µg/ml (MHC). M) MYOD mRNA 0.5 µg/ml+luc2 dsRNA 0.0001 µg/ml (phase contrast). N) MYOD mRNA 0.5 µg/ml+luc2 dsRNA 0.0001 µg/ml (MHC). O) MYOD mRNA 0.5 µg/ml+luc2 dsRNA 0.00001 µg/ml (phase contrast). P) MYOD mRNA 0.5 µg/ml+luc2 dsRNA 0.00001 µg/ml (MHC). Q) MYOD mRNA 0.5 µg/ml+luc2 dsRNA 0.000001 µg/ml (phase contrast). R) MYOD mRNA 0.5 µg/ml+luc2 dsRNA 0.000001 µg/ml (MHC).

FIGS. 50A-B show 10× phase contrast images of fibroblast cells that were transfected with either ψ-mRNAs encoding only A and N proteins (top) or ψ-mRNAs encoding AMNP proteins (bottom). FIG. 50A shows 10× phase IMR90 Mock transfected fibroblasts with original cell morphology. FIG. 50B shows 10× phase of cells transfected with RNase II-treated ψ-modified mRNAs encoding AMNP with neuron morphology.

FIGS. 51A-B show a 20× phase contrast image of the morphology exhibited by the reprogrammed fibroblast cells on day 7 (top; 51A). In this case, the top image shows the fibroblast cells that were transfected with ψ-mRNAs encoding AMNP proteins and the bottom image (51B) shows the fibroblast cells that were transfected with ψ-mRNAs encoding only A and N proteins. After fixation, the cells in the top image stained positively for microtubule-associated protein-2 (MAP2), a pan-neuronal marker.

DEFINITIONS

Figure 1:
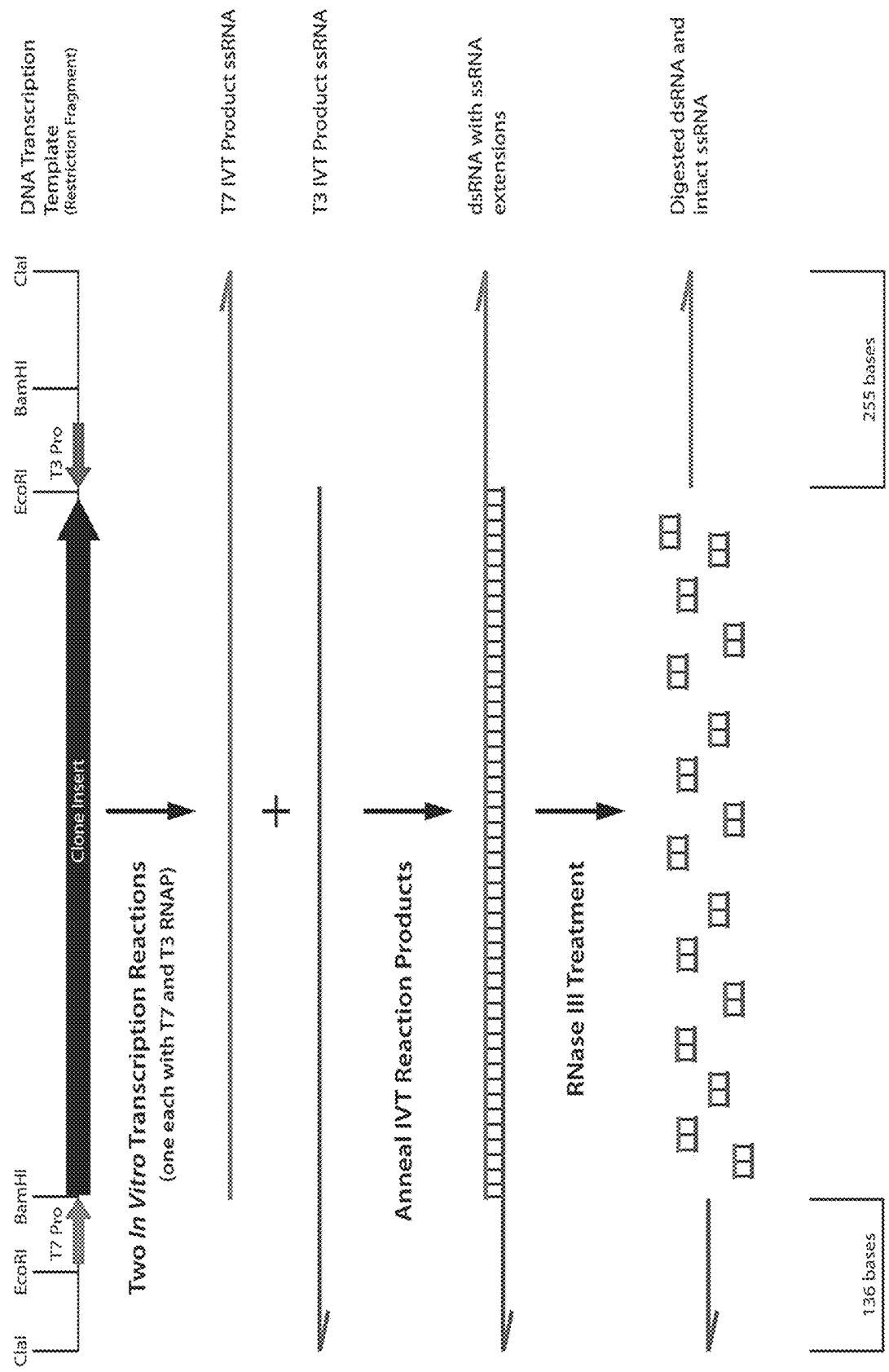
FIG. 1 is a schematic diagram depicting construction, annealing and RNase digestion III of an RNA substrate comprising a 1671-bp dsRNA region flanked by a 255-base and 136-base 3'-terminal ssRNA tails.

The present invention will be understood and interpreted based on terms as defined below.

The terms "comprising", "containing", "having", "include", and "including" are to be construed as "including, but not limited to" unless otherwise noted. The terms "a," "an," and "the" and similar referents in the context of describing the invention and, specifically, in the context of the appended claims, are to be construed to cover both the singular and the plural unless otherwise noted. The use of any and all examples or exemplary language ("for example", "e.g.", "such as") is intended merely to illustrate aspects or embodiments of the invention, and is not to be construed as limiting the scope thereof, unless otherwise claimed.

When the terms "about" or "approximately" are used herein to describe a number or quantity, the term shall be interpreted to mean the specified number or quantity plus or minus 20% of that number or quantity. For example, the statements "about 1 mM to 4 mM" or "about 1 to 4 mM" shall be interpreted to mean from 0.8 mM to 4.8 mM."

With respect to the use of the word "derived", such as for an RNA (including ssRNA or mRNA) or a polypeptide that is "derived" from a sample, biological sample, cell, tumor, or the like, it is meant that the RNA or polypeptide either was present in the sample, biological sample, cell, tumor, or the like, or was made using the RNA in the sample, biological sample, cell, tumor, or the like by a process such as an in vitro transcription reaction, or an RNA amplification reaction, wherein the RNA or polypeptide is either encoded by or a copy of all or a portion of the RNA or polypeptide molecules in the original sample, biological sample, cell, tumor, or the like. By way of example, such RNA can be from an in vitro transcription or an RNA amplification reaction, with or without cloning of cDNA, rather than being obtained directly from the sample, biological sample, cell, tumor, or the like, so long as the original RNA used for the in vitro transcription or an RNA amplification reaction was from the sample, biological sample, cell, tumor, or the like. In most embodiments of the present invention, a ssRNA or mRNA that is derived from a biological sample, cell, tumor, or the like is amplified from mRNA in the biological sample, cell, tumor, or the like using an RNA amplification reaction comprising in vitro transcription, as described elsewhere herein.

With respect embodiments of the present invention pertaining to the methods, compositions, systems and kits for introducing an RNA composition comprising in vitro-synthesized ssRNA or mRNA encoding one or more proteins into a human or animal (e.g., mammalian) cell (e.g., a cell that is ex vivo in culture or in vivo in a tissue, organ or organism) to induce a biological or biochemical effect, the terms "biological or biochemical effect" or "biological effect" or "biochemical effect" herein mean and refer to any effect in the cell into which the RNA composition is introduced or any effect in a tissue, organ or organism containing the cell into which the RNA composition is introduced, which effect would be expected or anticipated or understood by a person with knowledge in the art based on information and knowledge in the art about the protein encoded by said ssRNA or mRNA. For example, in some embodiments wherein the RNA comprises ssRNA or mRNA that encodes a wild-type non-mutated protein that has a known function (e.g., as an enzyme, growth factor, a cell surface receptor e.g., in a cell signaling pathway, a cytokine, a chemokine, or as an effector molecule in an active or innate immune response mechanism), the biological or biochemical effect of said introducing of said RNA composition into a cell that has a defective or non-functional mutant gene, wherein the cell's own protein is defective or non-functional in said cell, would be that the introduced RNA composition may substitute for or replace or complement the cell's defective or non-functional protein, thereby restoring the normal biological or biochemical effect of the wild-type protein encoded by the RNA composition comprising ssRNA or mRNA. By way of further example, in some embodiments wherein an mRNA encoding erythropoietin is introduced into a mammal cell in vivo in a mammal, one biological or biochemical effect is an increase in the hematocrit or erythrocyte volume fraction (EVF), reflecting an increase in the volume percentage (%) of red blood cells in blood of said mammal. Thus, although the present invention provides a method for inducing a broad range of biological or biochemical effects, those biological or biochemical effects are predictable and will be understood by those with knowledge in the art based on reading the description of the present inventions, and therefore are within the scope and coverage of the present invention.

The terms "sample" and "biological sample" are used in their broadest sense and encompass samples or specimens obtained from any source that contains or may contain eukaryotic cells, including biological and environmental sources. As used herein, the term "sample" when used to refer to biological samples obtained from organisms, includes bodily fluids (e.g., blood or saliva), feces, biopsies, swabs (e.g., buccal swabs), isolated cells, exudates, and the like. The organisms include animals and humans. However, these examples are not to be construed as limiting the types of samples or organisms that find use with the present invention. In addition, in order to perform research or study the results related to use of a method or composition of the invention, in some embodiments, a "sample" or "biological sample" comprises fixed cells, treated cells, cell lysates, and the like. In some embodiments, such as embodiments of the method wherein the mRNA is delivered into a cell from an organism that has a known disease or into a cell that exhibits a disease state or a known pathology, the "sample" or "biological sample" also comprises bacteria or viruses.

As used herein, the term "incubating" and variants thereof mean contacting one or more components of a reaction with another component or components, under conditions and for sufficient time such that a desired reaction product is formed.

"In vitro" herein refers to an artificial environment and to processes or reactions that occur within an artificial environment. In vitro environments can be composed of, but are not limited to, processes or reactions that occur in a test tube. The term "in vivo" refers to the natural environment and to processes or reactions that occur within a natural environment (e.g., in a living cell or a human or animal). "Ex vivo" herein refers to processes or reactions that occur within a cell in culture.

As used herein, a "nucleoside" refers to a molecule composed of a nucleic acid base (e.g., the canonical nucleic acid bases: guanine (G), adenine (A), thymine (T), uracil (U), or cytidine (C), or a modified nucleic acid base (e.g., 5-methylcytosine ($m^5C$)), that is covalently linked to a pentose sugar (e.g., ribose or 2'-deoxyribose). A nucleoside can also be modified. For example, pseudouridine (abbreviated by the Greek letter psi or Ψ) is a modified nucleoside composed of ribose which is linked to a carbon of uracil, whereas the canonical nucleoside uridine is linked to a nitrogen designated as the 1 position of uracil. A "nucleotide" or "mononucleotide" refers to a nucleoside that is phosphorylated at one or more of the hydroxyl groups of the pentose sugar. The number of phosphate groups can also be indicated (e.g., a "mononucleotide" is composed of a nucleoside that is phosphorylated at one of the hydroxyl groups of the pentose sugar).

Linear nucleic acid molecules are said to have a "5' terminus" (5' end) and a "3' terminus" (3' end) because, during synthesis (e.g., by a DNA or RNA polymerase (the latter process being referred to as "transcription"), mononucleotides are joined in one direction via a phosphodiester linkage to make oligonucleotides or polynucleotides, in a manner such that a phosphate on the 5' carbon of one mononucleotide sugar moiety is joined to an oxygen on the 3' carbon of the sugar moiety of its neighboring mononucleotide. Therefore, an end of a linear single-stranded oligonucleotide or polynucleotide or an end of one strand of a linear double-stranded nucleic acid (RNA or DNA) is referred to as the "5' end" if its 5' phosphate is not joined or linked to the oxygen of the 3' carbon of a mononucleotide sugar moiety, and as the "3' end" if its 3' oxygen is not joined to a 5' phosphate that is joined to a sugar moiety of a subsequent mononucleotide. A terminal nucleotide, as used herein, is the nucleotide at the end position of the 3' or 5' terminus.

In order to accomplish specific goals, a nucleic acid base, sugar moiety, or internucleoside (or internucleotide) linkage in one or more of the nucleotides of the mRNA that is introduced into a eukaryotic cell in the methods of the invention may comprise a modified base, sugar moiety, or internucleoside linkage. For example, in addition to the other modified nucleotides discussed elsewhere herein for performing the methods of the present invention, one or more of the nucleotides of the mRNA can also have a modified nucleic acid base comprising or consisting of: xanthine; allyamino-uracil; allyamino-thymidine; hypoxanthine; 2-aminoadenine; 5-propynyl uracil; 5-propynyl cytosine; 4-thiouracil; 6-thioguanine; an aza or deaza uracil; an aza or deaza thymidine; an aza or deaza cytosines; an aza or deaza adenine; or an aza or deaza guanines; or a nucleic acid base that is derivatized with a biotin moiety, a digoxigenin moiety, a fluorescent or chemiluminescent moiety, a quenching moiety or some other moiety in order to accomplish one or more specific other purposes; and/or one or more of the nucleotides of the mRNA can have a sugar moiety, such as, but not limited to: 2'-fluoro-2'-deoxyribose or 2'-O-methyl-ribose, which provide resistance to some nucleases; or 2'-amino-2'-deoxyribose or 2'-azido-2'-deoxyribose, which can be labeled by reacting them with visible, fluorescent, infrared fluorescent or other detectable dyes or chemicals having an electrophilic, photoreactive, alkynyl, or other reactive chemical moiety.

In some embodiments of the methods, compositions or kits of the invention, one or more of the nucleotides of the mRNA comprises a modified internucleoside linkage, such as a phosphorothioate, phosphorodithioate, phosphoroselenate, or phosphorodiselenate linkage, which are resistant to some nucleases, including in a thio-ARCA dinucleotide cap analog (Grudzien-Nogalska et al. 2007) that is used in an IVT reaction for co-transcriptional capping of the RNA, or in the poly(A) tail (e.g., by incorporation of a nucleotide that has the modified phosphorothioate, phosphorodithioate, phosphoroselenate, or phosphorodiselenate linkage during IVT of the RNA or, e.g., by incorporation of ATP that contains the modified phosphorothioate, phosphorodithioate, phosphoroselenate, or phosphorodiselenate linkage into a poly(A) tail on the RNA by polyadenylation using a poly(A) polymerase). The invention is not limited to the modified nucleic acid bases, sugar moieties, or internucleoside linkages listed, which are presented to show examples which may be used for a particular purpose in a method.

As used herein, a "nucleic acid" or a "polynucleotide" or an "oligonucleotide" is a polymer molecule comprising a covalently linked sequence or series of "mononucleosides," also referred to as "nucleosides," in which the 3'-position of the pentose sugar of one nucleoside is linked by an internucleoside linkage, such as, but not limited to, a phosphodiester bond, to the 5'-position of the pentose sugar of the next nucleoside (i.e., a 3' to 5' phosphodiester bond), and in which the nucleotides are linked in specific sequence; i.e., a linear order of nucleotides. In some embodiments, the oligonucleotide consists of or comprises ribonucleotides ("RNA"). A nucleoside linked to a phosphate group is referred to as a "nucleotide." The nucleotide that is linked to the 5'-position of the next nucleotide in the series is referred to as "5' of" or the "5' nucleotide" and the nucleotide that is linked to the 3'-position of the 5' nucleotide is referred to as "3' of" or the "3' nucleotide." The terms "3'-of" and "5'-of" are used herein with respect to the present invention to refer to the position or orientation of a particular nucleic acid sequence or genetic element within a strand of the particular nucleic acid, polynucleotide, or oligonucleotide being discussed (such as an RNA polymerase promoter, start codon, open reading frame, or stop codon relative to other sequences or genetic elements within a DNA strand; or a cap nucleotide, 5' or 3' untranslated region (5' UTR or 3' UTR), Kozak sequence, start codon, coding sequence, stop codon, or poly-A tail relative to other sequences within an mRNA strand). Thus, although the synthesis of RNA in a 5'-to-3' direction during transcription is thought of as proceeding in a "downstream" direction, the sense promoter sequence exhibited by an RNA polymerase promoter is referred to herein as being 3-of the transcribed template sequence on the template strand. Those with knowledge in the art will understand these terms in the context of nucleic acid chemistry and structure, particularly related to the 3'- and 5'-positions of sugar moieties of canonical nucleic acid nucleotides. By way of further example, a first sequence that is "5'-of" a second sequence means that the first sequence is exhibited at or closer to the 5'-terminus relative to the second sequence. If a first nucleic acid sequence is 3'-of a second sequence on one strand, the complement of the first sequence will be 5'-of the complement of the second sequence on the complementary strand.

Also, for a variety of reasons, a nucleic acid or polynucleotide of the invention may comprise one or more modified nucleic acid bases, sugar moieties, or internucleoside linkages. By way of example, some reasons for using nucleic acids or polynucleotides that contain modified bases, sugar moieties, or internucleoside linkages include, but are not limited to: (1) modification of the $T_m$; (2) changing the susceptibility of the polynucleotide to one or more nucleases; (3) providing a moiety for attachment of a label; (4) providing a label or a quencher for a label; or (5) providing a moiety, such as biotin, for attaching to another molecule which is in solution or bound to a surface. For example, in some embodiments, an oligonucleotide, such as the terminal tagging oligoribonucleotide, may be synthesized so that the random 3'-portion contains one or more conformationally restricted ribonucleic acid analogs, such as, but not limited to one or more ribonucleic acid analogs in which the ribose ring is "locked" with a methylene bridge connecting the 2'-O atom with the 4'-C atom (e.g., as available from Exiqon, Inc. under the trademark of "LNA™"); these modified nucleotides result in an increase in the $T_m$ or melting temperature by about 2 degrees to about 8 degrees centigrade per nucleotide monomer. If the $T_m$ is increased, it might be possible to reduce the number of random nucleotides in the random 3'-portion of the terminal tagging oligoribonucleotide. However, a modified nucleotide, such as an LNA must be validated to function in the method for its intended purpose, as well as satisfying other criteria of the method; for example, in some embodiments, one criterium for using the modified nucleotide in the method is that the oligonucleotide that contains it can be digested by a single-strand-specific RNase.

In order to accomplish the goals of the invention, by way of example, but not of limitation, the nucleic acid bases in the mononucleotides may comprise guanine, adenine, uracil, thymine, or cytidine, or alternatively, one or more of the nucleic acid bases may comprise a modified base, such as, but not limited to xanthine, allyamino-uracil, allyamino-thymidine, hypoxanthine, 2-aminoadenine, 5-propynyl uracil, 5-propynyl cytosine, 4-thiouracil, 6-thioguanine, aza and deaza uracils, thymidines, cytosines, adenines, or guanines. Still further, they may comprise a nucleic acid base that is derivatized with a biotin moiety, a digoxigenin moiety, a fluorescent or chemiluminescent moiety, a quenching moiety or some other moiety. The invention is not limited to the nucleic acid bases listed; this list is given to show an example of the broad range of bases which may be used for a particular purpose in a method.

With respect to nucleic acids or polynucleotides of the invention, one or more of the sugar moieties can comprise ribose or 2'-deoxyribose, or alternatively, one or more of the sugar moieties can be some other sugar moiety, such as, but not limited to, 2'-fluoro-2'-deoxyribose or 2'-O-methyl-ribose, which provide resistance to some nucleases, or 2'-amino-2'-deoxyribose or 2'-azido-2'-deoxyribose, which can be labeled by reacting them with visible, fluorescent, infrared fluorescent or other detectable dyes or chemicals having an electrophilic, photoreactive, alkynyl, or other reactive chemical moiety.

The internucleoside linkages of nucleic acids or polynucleotides of the invention can be phosphodiester linkages, or alternatively, one or more of the internucleoside linkages can comprise modified linkages, such as, but not limited to, phosphorothioate, phosphorodithioate, phosphoroselenate, or phosphorodiselenate linkages, which are resistant to some nucleases Oligonucleotides and polynucleotides, including chimeric (i.e., composite) molecules and oligonucleotides with modified bases, sugars, or internucleoside linkages are commercially available (e.g., TriLink Biotechnologies, San Diego, CA, USA or Integrated DNA Technologies, Coralville, IA).

Whenever we refer to an "RNase III-treated" sample or composition (e.g., an "RNase III-treated" RNA composition, ssRNA, capped and/or polyadenylated ssRNA, mRNA, ssRNA or mRNA, in vitro-transcribed ssRNA, IVT RNA, or the like), we mean that the sample or other composition that contains or may contain dsRNA has been treated with RNase III using an RNase III treatment or an "RNase III treatment method."

Whenever we refer to an "RNase III treatment" or "RNase III treatment method" or "treating a sample or composition with RNase III" herein, we mean incubating a sample or composition comprising ssRNA and which contains or may contain dsRNA (e.g., an RNA composition, ssRNA, capped and/or polyadenylated ssRNA, mRNA, ssRNA or mRNA, in vitro-transcribed ssRNA, IVT RNA, or the like) with RNase III enzyme in a buffered aqueous solution or reaction mixture under conditions wherein the RNase III is active [e.g., wherein the buffered aqueous solution has a pH of about pH 7 to pH 9 and comprises a salt or other compound at sufficient concentration to maintain an ionic strength equivalent to at least 50 mM potassium acetate or potassium glutamate (e.g., about 50-300 mM potassium acetate or potassium glutamate), and a magnesium compound that provides about 1 mM to about 4 mM of initially non-chelated divalent magnesium cations] and then optionally, in some embodiments, cleaning up the ssRNA in the sample or composition to remove the RNase III enzyme and/or nucleotides and/or small oligonucleotides and/or salt, and/or other RNase III treatment reaction components. In some embodiments of the RNase III treatment or RNase III treatment method or treating of a sample or composition with RNase III, the RNA quick cleanup method described herein is used for said cleaning up of the ssRNA in the sample or composition. However, in other embodiments another cleanup method is used for said cleaning up of the ssRNA.

The terms "purified" or "to purify" or "cleaned up" or "to clean up" herein refers to the removal of components (e.g., contaminants) from a sample (e.g., from in vitro-transcribed or in vitro-synthesized ssRNA, mRNA or a precursor thereof). For example, nucleic acids, such as in vitro-transcribed or in vitro-synthesized ssRNA, mRNA or a precursor thereof) are purified or cleaned up by removal of contaminating proteins in the in vitro transcription reaction mixture, or undesired nucleic acid species (e.g., the DNA template, or RNA contaminants other than the desired ssRNA or mRNA, such as dsRNA, or in vitro transcription products which are shorter or longer than the desired full-length ssRNA or mRNA encoded by the template. The removal of contaminants results in an increase in the percentage of desired nucleic acid (e.g., the desired ssRNA or mRNA) comprising the nucleic acid. The terms "purified" or "to purify," when used herein, refer to use of methods to remove contaminants by use of a chromatographic or electrophoretic separation device comprising a resin, matrix or gel or the like (e.g., by HPLC, FPLC or gravity flow column chromatography, or agarose or polyacrylamide electrophoresis"). In contrast, the terms "cleaned up" and "to clean up," when used herein, refer to use of methods to remove contaminants by extraction (e.g., organic solvent extraction, e.g., phenol and/or chloroform extraction), precipitation (e.g., precipitation of RNA with ammonium acetate), and washing of precipitates (e.g., washing of RNA precipitates with 70% ethanol), without use of a chromatographic or electrophoretic separation device comprising a resin, matrix or gel or the like. Thus, when a sample (e.g., in vitro-transcribed or in vitro-synthesized ssRNA or mRNA) is cleaned up, said method, in certain embodiments, is much easier, faster, much less expensive, required much less knowledge and training, and requires fewer and less expensive materials and less labor than would be required to purify the sample. In some other embodiments, a sample (e.g., in vitro-transcribed or in vitro-synthesized ssRNA or mRNA or a precursor thereof) is further cleaned up or purified using a rapid gel filtration method with a cross-linked dextran (e.g., Sephadex, e.g., a Sephadex spin column) in order to separate low molecular weight molecules, such as salts, buffers, nucleotides and small oligonucleotides, solvents (e.g., phenol, chloroform) or detergents from the ssRNA or mRNA.

The invention is not limited with respect to an RNA polymerase used for in vitro transcription or synthesis of a ssRNA or mRNA used in a method or comprising a composition, system or kit of the present invention. However, in some preferred embodiments, the ssRNA or mRNA is synthesized using a T7-type RNA polymerase. A "17-type RNA polymerase" (or "T7 RNAP") herein means 17 RNA polymerase (e.g., see Studier, F W et al., pp. 60-89 in Methods in Enzymology, Vol. 185, ed. by Goeddel, DV, Academic Press, 1990) or an RNAP derived from a "T7-type" bacteriophage, meaning a bacteriophage that has a similar genetic organization to that of bacteriophage T7. The genetic organization of all T7-type phages that have been examined has been found to be essentially the same as that of T7. Examples of T7-type bacteriophages according to the invention include *Escherichia coli* phages such as T3 and *Salmonella typhimurium* phages such as SP6, and *Klebsiella* phages such as K11 (McAllister W T and Raskin C A, 1993), as well as mutant forms of such RNAPs (e.g., Sousa et al., U.S. Pat. No. 5,849,546; Padilla, R and Sousa, R, *Nucleic Acids Res.,* 15: e138, 2002; Sousa, R and Mukherjee, S, *Prog Nucleic Acid Res Mol Biol.,* 73: 1-41, 2003; Guillerez, J, et al., U.S. Pat. No. 7,335,471 or U.S. Patent Application No. 20040091854). Thus, in some preferred embodiments of the methods wherein an RNA polymerase is used for in vitro transcription or synthesis of any ssRNA used in a method or composition herein, the RNA polymerase is selected from the group consisting of T7 RNAP, T3 RNAP, SP6 RNAP wild-type 17-type RNAPs, the Y639F mutant of T7 RNAP, the Y640F mutant of T3 RNAP, the Y631F mutant of SP6 RNAP, the Y662F mutant of *Klebsiella* phage K11 RNAP, the Y639F/H784A double-mutant of T7 RNAP, the P266L mutant of T7 RNAP, the P267L mutant of T3 RNAP, and the P239L mutant of SP6 RNAP, and the P289L mutant of *Klebsiella* phage K11 RNAP. However, in other embodiments, the ssRNA or mRNA is synthesized using another RNA polymerase that binds and initiates transcription at an RNA polymerase promoter that is joined to a coding sequence in the DNA template which that results in synthesis of the ssRNA or mRNA by said RNA polymerase.

A "template" is a nucleic acid molecule that serves to specify the sequence of nucleotides exhibited by a nucleic that is synthesized by a DNA-dependent or RNA-dependent nucleic acid polymerase. If the nucleic acid comprises two strands (i.e., is "double-stranded"), and sometimes even if the nucleic acid comprises only one strand (i.e., is "single-stranded"), the strand that serves to specify the sequence of nucleotides exhibited by a nucleic that is synthesized is the "template" or "the template strand." The nucleic acid synthesized by the nucleic acid polymerase is complementary to the template. Both RNA and DNA are always synthesized in the 5'-to-3' direction, beginning at the 3'-end of the template strand, and the two strands of a nucleic acid duplex always are aligned so that the 5' ends of the two strands are at opposite ends of the duplex (and, by necessity, so then are the 3' ends). A primer is required for both RNA and DNA templates to initiate synthesis by a DNA polymerase, but a primer is not required to initiate synthesis by a DNA-dependent RNA polymerase, which is usually called simply an "RNA polymerase."

"Transcription" or "in vitro transcription" or "IVT" means the formation or synthesis of an RNA molecule by an RNA polymerase using a DNA molecule as a template using an in vitro reaction or process.

An "RNA polymerase promoter" or a "promoter," as used herein, means a segment of DNA that exhibits a nucleotide sequence to which an RNA polymerase that recognizes said sequence is capable of binding and initiating synthesis of RNA. The RNA polymerase that recognizes the promoter may also be designated (e.g., a "T7 promoter" or a "T7 RNA polymerase promoter" or a "T7 RNAP promoter" is a promoter recognized by T7 RNA polymerase). Most, but not all, RNA polymerase promoters are double-stranded. If an RNA polymerase promoter is double-stranded, the RNA polymerase promoter exhibits (or has) a "sense promoter sequence" and an "anti-sense promoter sequence." As used herein, the "sense promoter sequence" is defined as the sequence of an RNA polymerase promoter that is joined to the template strand, in which case the sense promoter sequence is 3'-of the DNA sequence in the template strand that serves to specify the sequence of nucleotides exhibited by the RNA that is synthesized by the RNA polymerase that recognizes and binds to the RNA polymerase promoter. As used herein, the "anti-sense promoter sequence" is defined as the sequence of an RNA polymerase promoter that is complementary to the sense promoter sequence. If an RNA polymerase (e.g., phage N4 RNA polymerase) can synthesize RNA using a single-stranded RNA polymerase promoter, then the RNA polymerase promoter exhibits only the sense promoter sequence. It should be noted that the definitions of a "sense promoter sequence" and "anti-sense promoter sequence" may be the opposite of what would be expected by some people with knowledge in the art, but the terminology used herein was developed in the relatively new context of single-stranded RNA polymerase promoters. It is more easily understood and remembered by noting that a sense promoter sequence in the template strand (i.e., joined to the 3'-termini of the first-strand cDNA molecules) results in synthesis of sense RNA using the methods of the invention.

A "cap" or a "cap nucleotide" means a nucleoside-5'-triphosphate that, under suitable reaction conditions, is used as a substrate by a capping enzyme system and that is thereby joined to the 5'-end of an uncapped RNA comprising primary RNA transcripts (which have a 5'-triphosphate) or RNA having a 5'-diphosphate. The nucleotide that is so joined to the RNA is also referred to as a "cap nucleotide" herein. A "cap nucleotide" is a guanine nucleotide that is joined through its 5' end to the 5' end of a primary RNA transcript. The RNA that has the cap nucleotide joined to its 5' end is referred to as "capped RNA" or "capped RNA transcript" or "capped transcript." A common cap nucleoside is 7-methylguanosine or $N^7$-methylguanosine (sometimes referred to as "standard cap"), which has a structure designated as "$m^7G$," in which case the capped RNA or "$m^7G$-capped RNA" has a structure designated as $m^7G(5')ppp(5')N_1(pN)_x$-OH(3'), or more simply, as $m^7GpppN_1(pN)_x$ or $m^7G[5']ppp[5']N$, wherein $m^7G$ represents the 7-methylguanosine cap nucleoside, ppp represents the triphosphate bridge between the 5' carbons of the cap nucleoside and the first nucleotide of the primary RNA transcript, $N_1(pN)_x$-OH (3') represents the primary RNA transcript, of which $N_1$ is the most 5'-nucleotide, "p" represents a phosphate group, "G" represents a guanosine nucleoside, "m" represents the methyl group on the 7-position of guanine, and "[5']" indicates the position at which the "p" is joined to the ribose of the cap nucleotide and the first nucleoside of the mRNA transcript ("N"). In addition to this "standard cap," a variety of other naturally-occurring and synthetic cap analogs are known in the art. RNA that has any cap nucleotide is referred to as "capped RNA."

A capped RNA comprising a composition or system or kit or used in a method of the present invention is synthesized in vitro. In some embodiments, the capped RNA is synthesized post-transcriptionally from in vitro-transcribed RNA, by capping ssRNA that has a 5' triphosphate group or ssRNA that has a 5' diphosphate group using a capping enzyme system (e.g., using a capping enzyme system comprising an RNA guanyltransferase; e.g., vaccinia capping enzyme system or *Saccharomyces cerevisiae* capping enzyme system).

Alternatively, in some other embodiments, the capped RNA is synthesized co-transcriptionally by in vitro transcription (IVT) of a DNA template that contains an RNA polymerase promoter, wherein, in addition to the GTP, the IVT reaction also contains a dinucleotide cap analog (e.g., a $m^7GpppG$ cap analog or an $N^7$-methyl, 2'-O-methyl-GpppG ARCA cap analog or an $N^7$-methyl, 3'-O-methyl-GpppG ARCA cap analog) or a phosphorothioate dinucleotide cap analog or thio-ARCA (Grudzien-Nogalska E, et al., 2007) using methods known in the art (e.g., using an AMPLICAP™ T7 capping kit for making an $m^7GpppG$-capped RNA, or, e.g., using an INCOGNITO™ T7 ARCA 5mC- & Ψ-RNA transcription kit or a MESSAGEMAX™ T7 ARCA-capped message transcription kit for making an ARCA-capped RNA, CELLSCRIPT, INC, Madison, WI, USA). However, some embodiments of methods, compositions or systems or kits (e.g, in methods wherein the mRNA used for said introducing of mRNA encoding at least one reprogramming factor into a cell that exhibits a first differentiated state or phenotype, wherein the ssRNA or mRNA was capped co-transcriptionally using a cap analog), the ssRNA or mRNA is further treated with a phosphatase (e.g., as described elsewhere herein) to remove RNA molecules that exhibit a 5'-triphosphate group.

Post-transcriptional capping of a 5'-triphosphorylated primary mRNA transcript in vivo (or using a capping enzyme system in vitro) occurs via several enzymatic steps (Higman et al., 1992, Martin et al., 1975, *Myette and Niles*, 1996).

The following enzymatic reactions are generally involved in capping of eukaryotic mRNA:
(1) RNA triphosphatase cleaves the 5'-triphosphate of mRNA to a diphosphate,
$pppN_1(p)N_x$-OH(3')→$ppN_1(pN)_x$-OH(3')+Pi; and then
(2) RNA guanyltransferase catalyzes joining of GTP to the 5'-diphosphate of the most 5' nucleotide ($N_1$) of the mRNA,
$ppN_1(pN)_x$-OH(3')+GTP→$G(5')ppp(5')N_1(pN)_x$-OH(3')+PPi; and finally, (3) guanine-7-methyltransferase, using S-adenosyl-methionine (AdoMet) as a co-factor, catalyzes methylation of the 7-nitrogen of guanine in the cap nucleotide, G(5')ppp(5')N$_1$(pN)$_x$-OH(3')+AdoMet→m$^7$G(5')ppp(5') N$_1$(pN)$_x$-OH(3')+AdoHyc.

RNA that results from the action of the RNA triphosphatase and the RNA guanyltransferase enzymatic activities, as well as RNA that is additionally methylated by the guanine-7-methyltransferase enzymatic activity, is referred to herein as "5' capped RNA" or "capped RNA", and a "capping enzyme system comprising RNA guanyltransferase" or, more simply, a "capping enzyme system" or a "capping enzyme" herein means any combination of one or more polypeptides having the enzymatic activities that result in "capped RNA." Capping enzyme systems, including cloned forms of such enzymes, have been identified and purified from many sources and are well known in the art (Banerjee 1980, Higman et al., 1992 and 1994; Myette and Niles 1996, Shuman 1995 and 2001; Shuman et al. 1980; Wang et al. 1997). Any capping enzyme system that can convert uncapped RNA that has a 5' polyphosphate to capped RNA can be used to provide a capped RNA for any of the embodiments of the present invention. In some embodiments, the capping enzyme system is a poxvirus capping enzyme system. In some preferred embodiments, the capping enzyme system is vaccinia virus capping enzyme. In some embodiments, the capping enzyme system is *Saccharomyces cerevisiae* capping enzyme. Also, in view of the fact that genes encoding RNA triphosphatase, RNA guanyltransferase and guanine-7-methyltransferase from one source can complement deletions in one or all of these genes from another source, the capping enzyme system can originate from one source, or one or more of the RNA triphosphatase, RNA guanyltransferase, and/or guanine-7-methyltransferase activities can comprise a polypeptide from a different source.

The RNA compositions comprising ssRNA or mRNA used in the methods of the present invention can exhibit a modified cap nucleotide; in some embodiments, the ssRNA molecules are capped using a capping enzyme system as described by Jendrisak; J et al. in U.S. patent application Ser. No. 11/787,352 (Publication No. 20070281336, herein incorporated by reference). A "modified cap nucleotide" of the present invention means a cap nucleotide wherein the sugar, the nucleic acid base, or the internucleoside linkage is chemically modified compared to the corresponding canonical 7-methylguanosine cap nucleotide. Examples of a modified cap nucleotide include a cap nucleotide comprising: (i) a modified 2'- or 3'-deoxyguanosine-5'-triphosphate (or guanine 2'- or 3'-deoxyribonucleic acid-5'-triphosphate) wherein the 2'- or 3'-deoxy position of the deoxyribose sugar moiety is substituted with a group comprising an amino group, an azido group, a fluorine group, a methoxy group, a thiol (or mercapto) group or a methylthio (or methylmercapto) group; or (ii) a modified guanosine-5'-triphosphate, wherein the 06 oxygen of the guanine base is substituted with a methyl group; or (iii) 3'-deoxyguanosine. For the sake of clarity, it will be understood herein that an "alkoxy-substituted deoxyguanosine-5'-triphosphate" can also be referred to as an "O-alkyl-substituted guanosine-5'-triphosphate"; by way of example, but without limitation, 2'-methoxy-2'-deoxyguanosine-5'-triphosphate (2'-methoxy-2'-dGTP) and 3'-methoxy-3'-deoxyguanosine-5'-triphosphate (3'-methoxy-3'-dGTP) can also be referred to herein as 2'-O-methylguanosine-5'-triphosphate (2'-OMe-GTP) and 3'-O-methylguanosine-5'-triphosphate (3'-OMe-GTP), respectively. Following joining of the modified cap nucleotide to the 5'-end of the uncapped RNA comprising primary RNA transcripts (or RNA having a 5'-diphosphate), the portion of said modified cap nucleotide that is joined to the uncapped RNA comprising primary RNA transcripts (or RNA having a 5'-diphosphate) may be referred to herein as a "modified cap nucleoside" (i.e., without referring to the phosphate groups to which it is joined), but sometimes it is referred to as a "modified cap nucleotide".

A "modified-nucleotide-capped RNA" is a capped RNA molecule that is synthesized using a capping enzyme system and a modified cap nucleotide, wherein the cap nucleotide on its 5' terminus comprises the modified cap nucleotide, or a capped RNA that is synthesize co-transcriptionally in an in vitro transcription reaction that contains a modified dinucleotide cap analog wherein the dinucleotide cap analog contains the chemical modification in the cap nucleotide. In some embodiments, the modified dinucleotide cap analog is an anti-reverse cap analog or ARCA or a thio-ARCA (Grudzien et al. 2004, Grudzien-Nogalska et al., 2007, Jemiality et al. 2003, Peng et al. 2002, Stepinski et al. 2001).

A "primary RNA" or "primary RNA transcript" means an RNA molecule that is synthesized by an RNA polymerase in vivo or in vitro and which RNA molecule has a triphosphate on the 5'-carbon of its most 5' nucleotide.

Human and animal cells possess wide array of defense mechanisms comprising RNA sensors and signaling pathways to protect them against exogenous introduction of RNA. It is important to understand these cellular defense mechanisms and take them into account when designing RNA molecules to be introduced into a human or animal cell to reprogram the cell to another state of differentiation or phenotype (e.g., for clinical research or for regenerative medicine or immunotherapy) so that those RNA molecules avoid or minimize induction and/or activation of the numerous RNA sensors and signaling pathways. Among these are "dsRNA RNA sensors" and "dsRNA signaling pathways," which means and includes any of the mechanisms by which a human or animal cell recognizes and responds to dsRNA that is introduced into the cell, such as dsRNA that is introduced into the cell as a result of infection by virus. In particular, induction of the interferon (IFN) system by dsRNA is the prime activator of a mammalian cell's response to detection of dsRNA by cellular RNA sensors (e.g., see Gantier, M P and Williams, B R G, 2007, and Jiang, F et al. 2011, both incorporated herein by reference in their entirety). Following its activation by dsRNA, type-I IFN induces and activates a Ser/Thr protein kinase now commonly known as PKR (formerly also known as Eiflak2, Prkr, Tik, DAI, P1-eIF-2, and p68 kinase). PKR inhibits mRNA translation by catalyzing phosphorylation of the alpha subunit of the eukaryotic translation initiation factor 2 (eIF-2a). Cellular protein synthesis is inhibited when as little as 20% of the eIF-2a molecules are phosphorylated. Significant inhibition of protein synthesis reduces expression of ssRNA that is introduced, thereby counteracting the desired outcome for which the ssRNA was introduced in the first place, and if protein synthesis is prolonged, the cell is weakened and, ultimately, the cell progresses toward death. IFN also induces and/or activates other RNA sensors. For example, IFN induces a 2'-5'-oligoadenylate synthase (2'-5'OAS)/RNase L system. The 2'-5'OAS enzymes are composed of two domains that assemble in the cell to form a dsRNA activation site. Upon binding to dsRNA, the 2'-5'OAS is activated to a form that converts ATP to PPi and 2'-5'-linked oligoadenylates. In turn, the 2'-5'-linked oligoadenylates bind to enzymatically inactive RNase L monomers, which dimerize to form enzymatically active RNase L dimers. The active RNase L dimers then degrade RNA in the cell, further decreasing protein synthesis. Still further with respect to innate immune recognition of RNA that is introduced into a cell (e.g., by infection with an RNA virus), the cytoplamic or cytosolic receptors RIG-I (encoded by retinoic acid inducible gene I) and MDA5 (encoded by melanoma differentiation associated gene-5) have important roles. RIG-I appears to recognize and bind at least three elements of RNA structure: (i) it recognizes and preferentially binds blunt-ended short dsRNA with or without a 5-triphosphate group; (ii) it specifically recognizes and binds 5'-triphosphate groups on ssRNA or double-stranded RNA, but does not recognize or binds those RNAs if they are 5'-capped; and (iii) it recognizes and binds RNAs with polyuridine sequences (Kato H et al., 2008; Homung V et al. 2006; Jiang et al. 2011; Pichlmair A et al., 2006; Saito T et al., 2008; Schlee M et al., 2009; Uzri D and Gehrke L, 2009). On the other hand, MDA-5 specifically recognizes and binds to long dsRNA, rather than short dsRNA like RIG-I). Further, Zust et al. (2011) showed that MDA-5 also mediates sensing of ssRNA that lacks a 5' cap with a cap1 structure; thus, a mutant corona virus that lacked 2'-O-methyltransferase activity and made ssRNA had a cap0 structure resulted in MDA-5-dependent induction of type I interferons in mice, whereas wild-type corona virus that had 2'-O-methyltransferase activity and made ssRNA that had a cap1 structure did not result induction of type I interferons, and the induction of type I interferon by 2'-O-methyltransferase-deficient viruses was dependent on cytoplasmic MDA5. Upon detection of RNA exhibiting one or more of the elements they recognize, the cytoplasmic RNA sensors RIG I or MDA-5 then initiate signaling cascades that induce the expression of cytokines, including type I interferons (IFN-α and IFN-β), which are secreted by the activated cells to transmit danger signals to neighboring cells. These danger signals are transmitted by binding of the secreted interferons to type I interferon receptors on the surfaces of the neighboring cells and the activated type I interferon receptor (IFNAR) triggers a signaling pathway consisting of Jak and STAT transcription factors, thereby activating expression of numerous interferon-stimulated genes. Furthermore, it is known that dsRNA also binds to other cellular RNA sensors that result in induction and/or activation of many genes. For example, dsRNA directly or indirectly induces transcription factors of the IRF family, particularly IRF 1, IRF 3, IRF 5 and IRF 7, which, in turn, induce production of more type I IFN and type I IFN induces about one thousand IFN-stimulated genes. Induction of these and other RNA sensors and innate immune response pathways (e.g., toll-like receptors (TLRs) TLR3, TLR7, and TLR8; retinoic acid inducible gene I (RIG-I); melanoma differentiation associated gene-5 (MDA5); and possibly the helicase LGP2), result in inhibition of protein synthesis in the affected cell and, ultimately, dsRNA-induced apoptosis via death receptor signaling, including caspase-8 activation. PKR, RNase L, IRF3 and c-Jun N-terminal kinase have been reported to be components of the dsRNA-activated pro-apoptotic pathways. Thus, it is important that RNA molecules introduced into living human and animal cells must avoid inducing and activating the numerous RNA sensors and mechanisms that protect them against pathogens comprising RNA. Conceivably, RNA preparations containing even minute amounts of dsRNA can trigger an undesirable innate immune response in vivo, such as an interferon (IFN)-induced and/or IFN-activated response, which leads to translation suppression and cell death in vivo (Yang S et al., 2001; Wianny F and Zernicka-Goetz M, 2000).

In some EXAMPLES herein describing embodiments of the methods comprising reprogramming of cells that exhibited a first differentiated state or phenotype to cells that exhibited a second differentiated state or phenotype, qRT-PCR was performed on total cellular RNA purified from cells transfected with mRNA reprogramming mixes in order to quantify the levels mRNAs in those cells which would be indicative of induction of RNA sensors or innate immune system response genes. For example, in certain experiments, qRT-PCR was performed using primer pairs to amplify levels of expression for mRNAs encoding IFNB, RIG1, OAS3, and IFIT1 in cells that were being reprogrammed using mRNA mixes encoding the iPSC reprogramming factors, wherein said mRNAs were either treated using the RNase III treatment method described herein or purified by HPLC. For example, in these qRT-PCR assays, the expression levels of the mRNAs encoding IFNB, RIG1, OAS3, and IFIT1, normalized for expression levels of certain housekeeping genes, were low and the mRNA levels for these genes in the cells being transfected with RNase III-treated mRNA reprogramming mix were similar to the mRNA levels for these genes in the cells being transfected with the same mRNA reprogramming mix that was HPLC purified. Thus, in some embodiments, activation or induction of expression of one or more RNA sensor or innate immune response genes is detected, assayed, measured and/or quantified by detecting, assaying, measuring and/or quantifying the levels or relative levels of mRNA expressed in the cells by PCR or qRT-PCR (e.g., after introducing of mRNA reprogramming mixes into said cells).

In some embodiments, a composition, system, kit or method of the present invention comprises or uses a composition comprising in vitro-synthesized ssRNA or mRNA synthesized using an RNA amplification reaction, An "RNA amplification reaction" or an "RNA amplification method" means a method for increasing the amount of RNA corresponding to one or multiple desired RNA sequences in a sample. For example, in some embodiments, the RNA amplification method comprises: (a) synthesizing first-strand cDNA complementary to the one or more desired RNA molecules by RNA-dependent DNA polymerase or reverse transcriptase extension of one or more primers that anneal to the desired RNA molecules; (b) synthesizing double-stranded cDNA from the first-strand cDNA using a process wherein a functional RNA polymerase promoter is joined thereto; and (c) contacting the double-stranded cDNA with an RNA polymerase that binds to said promoter under transcription conditions whereby RNA corresponding to the one or more desired RNA molecules is obtained. Unless otherwise stated related to a specific embodiment of the invention, an RNA amplification reaction according to the present invention means a sense RNA amplification reaction, meaning an RNA amplification reaction that synthesizes sense RNA (e.g., RNA having the same sequence as an mRNA or other primary RNA transcript, rather than the complement of that sequence). Sense RNA amplification reactions known in the art, which are encompassed within this definition include, but are not limited to, the methods which synthesize sense RNA described in Ozawa et al. (2006) and in U.S. Patent Application Nos. 20090053775; 20050153333; 20030186237; 20040197802; and 20040171041. The RNA amplification method described in U.S. Patent Application No. 20090053775 (now U.S. Pat. Nos. 8,039,214 and 8,329,887) by Dahl and Sooknanan is a preferred method for obtaining amplified RNA derived from one or more cells, which amplified RNA is then used to make mRNA for use in the methods of the present invention.

As used herein, "RNase III" when used herein with respect to a method, composition, kit or system of the invention means an RNase III family endoRNase. In preferred embodiments of the methods, compositions or kits comprising RNase III or use or methods of use thereof, the RNase III binds and digests dsRNA containing a minimum of two turns of the A-form double helix, (approximately 20 bp), but not ssRNA, to small dsRNA oligoribonucleotides having a size of about 12 to 15 bp in length. In some preferred embodiments, the RNase III is a class I RNase III. In some preferred embodiments, the RNase III is derived from a microbial source (e.g., a prokaryotic source). In one preferred embodiment, the RNase III is an enzyme derived from *E. coli*, or a functional fragment or variant enzyme thereof. In some other embodiments, the RNase III generates dsRNA oligoribonucleotides less than about 30 nucleotides in length. In preferred embodiments, the RNase III exhibits at least 70%, at least 75%, at least 80%, at least 85%, at least 90%, at least 95%, approximately 96%, approximately 97%, approximately 98%, approximately 99%, or approximately 100% amino acid sequence identity with *E. coli* RNase III. However, RNase III, which is sometimes abbreviated as "RIII" herein, can be any double-strand-specific endoribonuclease (endoRNase) that digests dsRNA, but not ssRNA, to a similar extent as *Escherichia coli* RNase III, either under approximately similar reaction conditions as described herein, or under other reaction conditions which are optimal for another particular highly purified RNase III that lacks endoribonuclease and exoribonuclease activity on ssRNA. Optimal reaction conditions for other RNase III family enzymes can be identified by using the novel RNA substrate comprising both single-stranded and double-stranded portions developed herein (FIG. 1); this substrate enables rapid, accurate and precise assay and optimization of dsRNA-specific RNase activity and specificity of digestion of dsRNA versus ssRNA. As discussed herein, this substrate was used by the applicants to develop the RNase III treatment method of the present invention, which much more completely digests dsRNA contaminants in RNA samples comprising primarily ssRNA, while better preserving the ssRNA integrity than the RNase III assay method conditions by Robertson and co-workers in their 1968 paper (Robertson, H D et al, 1968) and used continuously and universally since that time (e.g., Robertson H D and Hunter T, 1975; Robertson H D, 1982; Mellits K H et al., 1990, Nicholson A W, 1996, Pe'ery T and Mathews M B. 1997).

An "RNA-dependent DNA polymerase" or "reverse transcriptase" is an enzyme that is capable of extending the 3'-end of a nucleic acid that is annealed to an RNA template to synthesize DNA that is complementary to the template ("complementary DNA" or "cDNA"). The 3'-end of the nucleic acid that is extended can be the 3'-end of the same RNA template, in which case cDNA synthesis is primed intramolecularly, or the 3'-end of the nucleic acid that is extended can be the 3'-end of another nucleic acid that is different from the RNA template and that is annealed to the RNA template, in which case cDNA synthesis is primed intermolecularly. All known reverse transcriptases also have the ability to make a complementary DNA copy from a DNA template; thus, they are both RNA- and DNA-dependent DNA polymerases.

As used herein, a "single-strand-specific DNase" means a DNase that specifically digests single-stranded DNA, but that does not digest single-stranded RNA or RNA or DNA that is annealed to or complexed with complementary RNA or DNA, whether said complementary RNA or DNA is part of another nucleic acid molecule (e.g., by intermolecular base-pairing) or a portion of the same nucleic acid molecule (e.g., by intramolecular base-pairing). The single-strand-specific DNase can be an endonuclease or an exonuclease, so long as it is active in specifically digesting single-stranded DNA to monomers or short oligodeoxyribonucleotides. In preferred embodiments, the products of digestion using the single-strand-specific DNase do not serve as primers in the presence of a single-stranded nucleic acid molecule that is capable of serving as a template under the reaction conditions used in the method. Exonuclease I, exonuclease VII, and Rec J exonuclease are exemplary single-strand-specific DNases.

As used herein, a "single-strand-specific RNase" means an RNase that specifically digests single-stranded RNA, but that does not digest single-stranded DNA or RNA or DNA that is annealed to or complexed with complementary RNA or DNA, whether said complementary RNA or DNA is part of another nucleic acid molecule (e.g., by intermolecular base-pairing) or a portion of the same nucleic acid molecule (e.g., by intramolecular basepairing). The single-strand-specific RNase can be an endonuclease or an exonuclease, so long as it is active in specifically digesting single-stranded RNA to monomers or short oligoribonucleotides that do not serve as primers in the presence of a single-stranded nucleic acid molecule that is capable of serving as a template under the reaction conditions used in the method. *E. coli* RNase I is an exemplary single-strand-specific RNase.

A "poly-A polymerase" or "poly(A) polymerase" ("PAP") means a template-independent RNA polymerase found in most eukaryotes, prokaryotes, and eukaryotic viruses that selectively uses ATP to incorporate AMP residues to 3'-hydroxylated ends of RNA. Since PAP enzymes that have been studied from plants, animals, bacteria and viruses all catalyze the same overall reaction (Edmonds 1990) are highly conserved structurally (Gershon 2000) and lack intrinsic specificity for particular sequences or sizes of RNA molecules if the PAP is separated from proteins that recognize AAUAAA polyadenylation signals (Wilusz and Shenk 1988), purified wild-type and recombinant PAP enzymes from any of a variety of sources can be used for the present invention. For example, in some embodiments of compositions, kits, or methods of the invention, a "polyadenylated" or "poly(A)-tailed" ssRNA or mRNA is made using a wild-type or recombinant *Saccharomyces* (e.g., from *S. cerevisiae*) PAP enzyme or *Escherichia* (e.g., *E. coli*) PAP enzyme. In some embodiments, the polyadenylated or poly(A)-tailed ssRNA or mRNA comprises or consists of one or more ssRNAs or mRNAs containing nucleosides comprising one or more modified nucleic acid bases that results in reduced induction or activation of an RNA sensor or innate immune response mechanism compared to nucleosides comprising canonical GAUC nucleic acid bases (e.g., each of which encodes a reprogramming factor, e.g., an iPS cell induction factor). In other embodiments, the polyadenylated or poly(A)-tailed ssRNA or mRNA comprises nucleosides comprising only canonical nucleic acid bases and does not comprise nucleosides comprising one or more modified nucleic acid bases that results in reduced induction or activation of an RNA sensor or innate immune response mechanism compared to GAUC bases.

In some preferred embodiments of compositions, kits, or methods of the invention, the ssRNA or mRNA comprises or consists of in vitro-synthesized (or in vitro-transcribed) ssRNA or mRNA (or ssRNA or mRNA molecules), each of which "encodes" (or "exhibits a coding region" or (coding sequence" ("cds") or "exhibits an open reading frame" ("ORF") of a particular protein or polypeptide (e.g., a particular protein or polypeptide reprogramming factor), meaning that each ssRNA or mRNA exhibits a linear array of codon triplets defined by the sequence of nucleotides that extends from the translation initiation codon to the translation termination codon for one particular protein or polypeptide. In addition to exhibiting the ORF of a particular protein, each ssRNA molecule may also exhibit other sequences 5'-of or 3'-of the ORF which are referred to as "5' or 3' untranslated regions" or "5' or 3' UTRs," which may serve different functions. For example, in some preferred embodiments, the 5' UTR comprises a Kozak consensus or Kozak sequence. A Kozak sequence is a sequence which occurs on eukaryotic mRNA and has the consensus (gcc) gccRccAUGG, where R is a purine (adenine or guanine) three bases upstream of the start codon (AUG), which is followed by another 'G' (Kozak M, 1987). The Kozak consensus sequence plays an important role in the initiation of the translation process.

In some preferred embodiments of compositions, kits, or methods of the invention, the one or more in vitro-synthesized ssRNAs or mRNAs and/or purified ssRNAs or mRNAs exhibit at least one heterologous 5' UTR sequence, Kozak sequence, IRES sequence, or 3' UTR sequence that results in greater translation into the encoded protein when said respective ssRNAs are introduced into eukaryotic cells compared to the same ssRNAs that do not exhibit said respective 5' UTR sequence, Kozak sequence, IRES sequence, or 3' UTR sequence. In some particular preferred embodiments, the 5' UTR or 3' UTR is a sequence exhibited by a Xenopus or human alpha- (α-) globin or beta- (β-) globin mRNA, or wherein the 5' UTR is a sequence exhibited by tobacco etch virus (TEV) RNA.

In some preferred embodiments of a composition, kit or method of the invention, the RNA composition comprising ssRNA or mRNA is treated or purified (e.g. by treating with a dsRNA-specific RNase (e.g., a dsRNA-specific endoribonuclease (endoRNase), e.g., wild-type or recombinant RNase III or an active fragment or variant thereof), treating with a dsRNA-specific antibody, and/or purifying by phenol-chloroform extraction, ammonium acetate precipitation, or chromatography, including by HPLC) (e.g., prior to use of said composition comprising ssRNA or mRNA in the method of the invention for reprogramming). In some embodiments of the compositions, kits or methods of the invention, the treated or purified ssRNA or mRNA exhibits a 5' cap comprising 7-methylguanine or an anti-reverse cap analog (ARCA, including an ARCA with a thio group in the triphosphate bridge). In some embodiments, the treated ssRNAs or purified ssRNA or mRNA further comprises a 5' cap that has a cap1 structure, wherein the 2' hydroxyl of the ribose in the 5' penultimate nucleotide is methylated. In some embodiments, wherein the treated or purified ssRNA or mRNA exhibits a 5' cap, the one or more in vitro-synthesized ssRNAs or mRNAs used for said treating and/or purifying exhibits the 5' cap (i.e., prior to said treating or purifying). Thus, in some embodiments, the one or more in vitro-synthesized ssRNAs or mRNAs used for said treating and/or purifying comprise capped ssRNAs or mRNAs. In some of these embodiments, the one or more in vitro-synthesized ssRNA molecules that exhibit the 5' cap were synthesized prior to said treating and/or purifying: (i) co-transcriptionally by incorporation of a cap analog (e.g., an anti-reverse cap analog or ARCA, or e.g., a thio-ARCA)) during in vitro transcription (e.g., using the MESSAGE-MAX™ T7 ARCA-capped message transcription kit or the INCOGNITO™ T7 ARCA 5$^m$C- and Ψ-RNA transcription kit, CELLSCRIPT, INC., Madison, WI, USA); or (ii) post-transcriptionally by incubating in vitro-transcribed ssRNA molecules with a capping enzyme system comprising RNA guanyltransferase under conditions wherein the in vitro-transcribed ssRNA molecules are 5'-capped, including wherein the capping enzyme system results in methylation of the 2' hydroxyl of the ribose in the 5' penultimate nucleotide (e.g., using T7 mSCRIPT™ standard mRNA production system, or using a separate in vitro transcription system, such as the T7-SCRIBE™ standard RNA IVT kit, the INCOGNITO™ T7 Ψ-RNA transcription kit, or the INCOGNITO™ T7 5mC- and Ψ-RNA transcription kit to obtain ssRNA, and the SCRIPTCAP™ m$^7$G capping system to obtain cap0 RNA (all from CELLSCRIPT, INC.); in some preferred embodiments, the capping enzyme system further results in methylation of the 2' hydroxyl of the ribose in the 5' penultimate nucleotide to generate cap1 RNA, and another step for synthesizing said in vitro-synthesized ssRNA or mRNA comprises: incubating the in vitro-transcribed ssRNA or mRNA with RNA 2'-O-methyltransferase (e.g., using the SCRIPTCAP™ 2'-O-methyltransferase kit, CELLSCRIPT, INC.).

In some preferred embodiments of a composition, kit or method of the invention, wherein the treated and/or purified ssRNA or mRNA exhibits a 5' cap, the one or more in vitro-synthesized ssRNAs are uncapped; in some embodiments, prior to use of the ssRNAs or mRNAs in a method for reprogramming, another step for synthesizing said in vitro-synthesized ssRNAs or mRNAs comprises: post-transcriptionally capping the treated and/or purified ssRNAs to generate 5' capped treated and/or 5' capped purified ssRNAs. In some preferred embodiments, said capping comprises capping with both a capping enzyme system comprising RNA guanyltransferase and 2'-O-methyltransferase. In some embodiments, said post-transcriptional capping of the treated and/or purified ssRNAs is performed as described above and/or in the product literature provided with the SCRIPTCAP™ m$^7$G Capping System, the SCRIPTCAP™ 2'-O-methyltransferase kit, or the T7 mSCRIPT™ standard mRNA production system with respect to the capping enzyme system components (all from CELLSCRIPT, INC., Madison, WI, USA).

In some preferred embodiments of a composition, kit, or method of the invention, the one or more in vitro-synthesized ssRNAs or mRNAs used for said treating are significantly free of uncapped RNAs that exhibit a 5'-triphosphate group (which are considered to be one type of "contaminant RNA molecules" herein). In some preferred embodiments, the RNA composition comprising treated and/or purified ssRNA or mRNA is significantly free of uncapped RNAs that exhibit a 5'-triphosphate group. In certain embodiments, the one or more in vitro-synthesized ssRNAs used for said treating, the treated ssRNAs, and/or the purified ssRNAs consist of a population of ssRNA molecules having: (i) greater than 90% capped ssRNA molecules; (ii) greater than 95% capped ssRNA molecules; (iii) greater than 98% capped ssRNA molecules (iv) greater than 99% capped ssRNA molecules; or (v) greater than 99.9% capped ssRNA molecules. In some embodiments wherein the population of ssRNA molecules also comprises contaminant uncapped RNA molecules that exhibit a 5'-triphosphate group, prior to using said RNA composition comprising said ssRNA molecules for reprogramming, the method further comprises: incubating the one or more in vitro-synthesized ssRNAs used for said treating, or the treated ssRNAs or the purified ssRNAs generated from the method with at least one enzyme to remove the triphosphate groups from contaminating uncapped ssRNAs. In some embodiments, the at least one enzyme is an alkaline phosphatase (e.g., NTPhosphatase™, epicentre technologies, Madison, WI, USA) or with RNA 5' polyphosphatase (epicentre technologies); in some embodiments wherein the at least one enzyme is RNA 5' polyphosphatase, said ssRNA molecules for reprogramming are further incubated with TERMINATOR™ 5'-phosphate-dependent nuclease (epicentre technologies) or Xm1 exoribonuclease (e.g., from *Saccharomyces cerevisae*) to digest said uncapped RNA from which the 5'-triphosphate group has been removed. These methods for incubating with alkaline phosphatase or with RNA 5' polyphosphatase and, optionally, also with TERMINATOR™ 5'-phosphate-dependent nuclease or Xm1 exoribonuclease, are particularly useful to remove uncapped ssRNAs from capped ssRNAs that were made by co-transcriptional capping by incorporating a cap analog during an in vitro transcription reaction.

"Stem cells" herein mean cells that have three general properties which make them different from other kinds of cells in the body: (1) they are capable of long-term self-renewal, meaning that, unlike specialized or differentiated cells which do not normally replicate themselves, they can proliferate by division of single cells into two daughter cells which are identical to the mother cell for long periods; (2) they are unspecialized, meaning they do not have any cell-specific structures for performing specialized functions; and (3) they can give rise to specialized cell types by a process called "differentiation." Information about stem cells is available on a National Institutes of Health website dedicated to that purpose (http://followed by "stemcells.nih.gov/info").

"Pluripotent stem cells" herein mean cells that can give rise to any type of cell in the body except those needed to support and develop a fetus in the womb.

Different methods are used to assay or evaluate a cell with respect to its pluripotent status. For example, the embryoid body spontaneous differentiation assay (e.g., see EXAMPLES) is sometimes used to evaluate the capability of cells or a cell line to differentiate into cell representing all three germ layers. Another method that is used is to perform fluorescent immunostaining assays using fluorescent antibodies that bind to proteins that are known to be expressed in pluripotent cells (e.g., see EXAMPLES). Still another type of assay that can be performed to evaluate pluripotency is quantitative reverse transcription polymerase chain reaction or qRT-PCR, sometimes simply called "qPCR" In these assays, qPCR is performed to quantify the relative level of expression of certain mRNAs encoding proteins that are known to be expressed or expressed at certain relative levels in pluripotent cells compared to the expression levels of certain housekeeping genes which are approximately constitutively expressed. Examples of pluripotency mRNAs which can be assayed by qRT-PCR include mRNAs encoding CRIPTO, GDF3, NANOG, OCT4 and REX1 (e.g., see EXAMPLES). For example, in some qRT-PCR assays performed using total cellular RNA isolated from 6 different IPSC lines generated in reprogramming experiments described herein, significantly higher levels of mRNAs encoding CRIPTO, GDF3, NANOG, OCT4 and REX1 were measured in the iPSC lines generated from mRNA reprogramming with RNase III-treated or HPLC-purified mRNA than was measured in the original human primary foreskin BJ fibroblast cells and the feeder cells (NUFFs) used in those experiments.

"Induced pluripotent stem cells" ("iPSCs") herein mean adult cells that have been genetically induced or reprogrammed to an embryonic stem cell-like state by being forced to express genes and factors important for maintaining certain defining properties of embryonic stem cells, such as expression of embryonic stem cell markers and being capable of differentiation into cells from all three germ layers.

An "iPSC line" herein means stem cells derived from a single iPSC colony that maintain these certain defining properties of embryonic stem cells upon repeated propagation in culture.

A "reprogramming factor" means a protein, polypeptide, or other biomolecule that, when used alone or in combination with other factors or conditions, causes a change in the state of differentiation of a cell in which the reprogramming factor is introduced or expressed. In some preferred embodiments of the methods of the present invention, the reprogramming factor is a protein or polypeptide that is encoded by an mRNA that is introduced into a cell, thereby generating a cell that exhibits a changed state of differentiation compared to the cell in which the mRNA was introduced. In some preferred embodiments of the methods of the present invention, the reprogramming factor is a transcription factor. One embodiment of a reprogramming factor used in a method of the present invention is an "iPS induction factor," meaning a protein, peptide, or other biomolecule that, when used alone or in combination with other factors or conditions, causes a change in the state of differentiation of a cell into which the iPS cell induction factor is introduced and/or expressed to an induced pluripotent stem cell (or iPSC).

An "mRNA reprogramming factor" means an mRNA that encodes a reprogramming factor consisting of a protein or polypeptide. An "mRNA iPSC induction factor" is one embodiment of an mRNA reprogramming factor and means an mRNA that encodes and iPSC induction factor.

The terms "mRNA reprogramming mix" or "mRNA reprogramming factor mix" or "ssRNA reprogramming mix" or "ssRNA reprogramming factor mix" are used interchangeably herein and mean a mixture of mRNAs encoding different reprogramming factors, each consisting of a protein or polypeptide.

Similarly, the terms "mRNA iPSC reprogramming mix" or "mRNA iPSC induction factor mix" or "ssRNA iPSC reprogramming mix" or "ssRNA iPSC induction mix" or "ssRNA iPSC induction factor mix" are used interchangeably herein and mean a mixture of mRNAs encoding different iPSC induction factors, each consisting of a protein or polypeptide. An "iPS cell induction factor" or "iPSC induction factor" is a protein, polypeptide, or other biomolecule that, when used alone or in combination with other reprogramming factors, causes the generation of a dedifferentiated cell or iPS cells from somatic cells. Examples of iPS cell induction factors include OCT4, SOX2, c-MYC, KLF4, NANOG and LIN28. iPS cell induction factors include full length polypeptide sequences or biologically active fragments thereof. Likewise an mRNA encoding an iPS cell induction factor may encode a full length polypeptide or biologically active fragments thereof. The DNA template sequences for mRNAs encoding exemplary iPS induction factors are shown in SEQ ID NOS: 2-10. In certain embodiments, the present invention employs the DNA template sequences or similar sequences shown in these SEQ ID NOS, including DNA template sequences encoding ssRNAs or mRNAs molecules that additionally comprise, joined to these ssRNA or mRNA sequences, oligoribonucleotides which exhibit any of the 5' and 3' UTR sequences, Kozak sequences, IRES sequences, cap nucleotides, and/or poly(A) sequences used in the experiments described herein (e.g., as shown in SEQ ID NO. 1), or other UTR or other sequences which are generally known in the art or discovered in the future which can be used in place of those used herein by joining them to these protein-coding mRNA sequences for the purpose of optimizing translation of the respective mRNA molecules in the cells and improving their stability in the cell in order to accomplish the methods described herein.

"Differentiation" or "cellular differentiation" means the naturally occurring biological process by which a cell that exhibits a less specialized state of differentiation or cell type (e.g., a fertilized egg cell, a cell in an embryo, or a cell in a eukaryotic organism) becomes a cell that exhibits a more specialized state of differentiation or cell type. Scientists, including biologists, cell biologists, immunologists, and embryologists, use a variety of methods and criteria to define, describe, or categorize different cells according to their "cell type," "differentiated state," or "state of differentiation." In general, a cell is defined, described, or categorized with respect to its "cell type," "differentiated state," or "state of differentiation" based on one or more phenotypes exhibited by that cell, which phenotypes can include shape, a biochemical or metabolic activity or function, the presence of certain biomolecules in the cell (e.g., based on stains that react with specific biomolecules), or on the cell (e.g., based on binding of one or more antibodies that react with specific biomolecules on the cell surface). For example, in some embodiments, different cell types are identified and sorted using a cell sorter or fluorescent-activated cell sorter (FACS) instrument. "Differentiation" or "cellular differentiation" can also occur to cells in culture. As used herein, it will be understood that the difference between a cell that exhibits a first state of differentiation, differentiated state, cell type or phenotype and a cell that exhibits a second state of differentiation, differentiated state, cell type or phenotype state can range from a difference in the relative expression of a single protein to differences in the expression of multiple proteins; thus, in some embodiments, the cell that exhibits a second state of differentiation, differentiated state, cell type or phenotype differs from the cell that exhibits a first state of differentiation, differentiated state, cell type or phenotype because the cell that exhibits a second state of differentiation, differentiated state, cell type or phenotype expresses a protein or multiple proteins that is or are encoded by mRNA molecule that are introduced into the cell that exhibits the first state of differentiation, differentiated state, cell type or phenotype, whereas in other embodiments, the cell that exhibits a second state of differentiation, differentiated state, cell type or phenotype differs from the cell that exhibits a first state of differentiation, differentiated state, cell type or phenotype because the cell that exhibits a second state of differentiation, differentiated state, cell type or phenotype expresses one or more proteins that are induced by mRNA molecules that are introduced into the cell that exhibits a first state of differentiation, differentiated state, cell type or phenotype, even though one or more of those proteins may not be encoded by said mRNA molecules that are introduced into the cell that exhibits a first state of differentiation, differentiated state, cell type or phenotype.

The term "reprogramming" as used herein means an induced or a non-naturally-occurring process of changing the state of differentiation or phenotype of a cell in response to delivery of one or more reprogramming factors into the cell, directly (e.g., by delivery of protein or polypeptide reprogramming factors into the cell) or indirectly (e.g., by delivery of the purified RNA preparation of the present invention which comprises one or more mRNA molecules, each of which encodes a reprogramming factor) and maintaining the cells under conditions (e.g., medium, temperature, oxygen and $CO_2$ levels, matrix, growth factors, cytokines, cytokine inhibitors, and other environmental conditions) that are conducive for differentiation. The term "reprogramming" when used herein is not intended to mean or refer to a specific direction or path of differentiation (e.g., from a less specialized cell type to a more specialized cell type) and does not exclude processes that proceed in a direction or path of differentiation than what is normally observed in nature. Thus, in different embodiments of the present invention, "reprogramming" means and includes any and all of the following:

(1) "Dedifferentiation", meaning a process by which a cell that exhibits a more specialized state of differentiation or cell type (e.g., a mammalian fibroblast, a keratinocyte, a muscle cell, or a neural cell) becomes a cell that exhibits a less specialized state of differentiation or cell type (e.g., a dedifferentiated cell or an iPS cell);

(2) "Transdifferentiation", meaning a process by which a cell that exhibits a more specialized state of differentiation or cell type (e.g., a mammalian fibroblast, a keratinocyte, or a neural cell) becomes a cell that exhibits another more specialized state of differentiation or cell type (e.g., from a fibroblast or keratinocyte to a muscle cell); and (3) "Redifferentiation" or "expected differentiation" or natural differentiation", meaning a process by which a cell that exhibits any particular state of differentiation or cell type becomes a cell that exhibits another state of differentiation or cell type as would be expected in nature if the cell was present in its natural place and environment (e.g., in an embryo or an organism), whether said process occurs in vivo in an organism or in culture (e.g., in response to one or more reprogramming factors).

A "double-strand-specific RNase" herein means an exoribonuclease or endoribonuclease that digests dsRNA, but not ssRNA, to monoribonucleotides or small oligoribonucleotides (e.g., to oligoribonucleotides having a size less than about 30 nucleotides), but that does not digest ssRNA.

A "dsRNA-specific 3'-to-5' exoribonuclease" means and includes any exoribonuclease that digests dsRNA, but not ssRNA, in a 3'-to-5' direction, starting from 3'-ends that are annealed to a complementary RNA.

By a "purified or treated RNA composition" (which, when used in a method of the present invention, is sometimes referred to only as "ssRNA", "mRNA" or an "RNA composition"), we mean a composition that comprises or consists of one or more treated or purified ssRNAs or mRNAs that is or are substantially free, virtually free, essentially free, practically free, extremely free or absolutely free of dsRNA molecules as defined herein.

For example, an RNA composition or ssRNA or mRNA that is substantially free of dsRNA molecules would contain less than five nanograms of dsRNA of a size greater than about 40 basepairs in length per microgram of RNA.

For example, an RNA composition or ssRNA or mRNA that is virtually free of dsRNA molecules would contain less than one nanogram of dsRNA of a size greater than about 40 basepairs in length per microgram of RNA.

For example, an RNA composition or ssRNA or mRNA that is essentially free of dsRNA molecules would contain less than 0.5 nanogram of dsRNA of a size greater than about 40 basepairs in length per microgram of RNA.

For example, an RNA composition or ssRNA or mRNA that is practically free of dsRNA molecules would contain less than 100 picograms of dsRNA of a size greater than about 40 basepairs in length per microgram of RNA.

For example, an RNA composition or ssRNA or mRNA that is extremely free of dsRNA molecules would contain less than 10 picograms of dsRNA of a size greater than about 40 basepairs in length per microgram of RNA.

For example, an RNA composition or ssRNA or mRNA that is absolutely free of dsRNA molecules would contain less than 2 picograms of dsRNA of a size greater than about 40 basepairs in length per microgram of RNA.

Similarly, it will also be understood herein that an "RNA composition" or a "ssRNA composition" or "ssRNA molecules" or "mRNA" or a "reprogramming mix" or a "ssRNA reprogramming mix" or an "mRNA reprogramming mix" or a "ssRNA iPSC reprogramming mix" or an "mRNA iPSC reprogramming mix" or a "ssRNA iPSC induction mix" or an "mRNA reprogramming factor mix" or "a mixture of reprogramming factors" or "a mixture of iPSC induction factors" (or the like) that is or are "practically free," "extremely free," or "absolutely free" of dsRNA herein means that less than 100 picograms, less than 10 picograms, or less than 2 picograms, respectively of dsRNA of a size greater than about 40 basepairs is present per microgram of RNA in said RNA composition, ssRNA composition, ssRNA molecules, ssRNA, mRNA, ssRNA iPSC reprogramming mix, mRNA iPSC reprogramming mix, mRNA reprogramming factor mix, mixture of reprogramming factors, mixture of iPSC induction factors, or the like. In some embodiments, the amount of dsRNA is determined using a dot blot assay wherein the amount of dsRNA is quantified by immunoassay using the J2 dsRNA-specific antibody (English & Scientific Consulting, Szirák, Hungary) (e.g., compared to known amounts of dsRNA standards spotted on nylon membranes in parallel assays using methods identical to or equivalent to those described herein). In other embodiments, the amount of dsRNA is determined by another method, such as by comparative HPLC using known standards.

DESCRIPTION OF THE INVENTION

In some embodiments, the present invention relates to compositions and methods for reprogramming somatic cells to pluripotent stem cells. For example, the present invention provides RNA compositions comprising ssRNA (e.g., mRNA molecules) and their use to reprogram human or animal (e.g., mammalian) somatic cells into pluripotent stem cells. For example, in some embodiments the invention provides pseudouridine-modified (Ψ-modified) and/or 5-methylcytidine-modified (m$^5$C-modified) ssRNA molecules that are at least practically free of dsRNA molecules, more preferably, at least extremely free of dsRNA molecules, and most preferably, absolutely free of dsRNA molecules and that encode reprogramming factors.

Experiments conducted during the development of embodiments of the present invention demonstrated that mRNA molecules can be administered to cells and induce a dedifferentiation process to generate dedifferentiated cells—including pluripotent stem cells. Thus, the present invention provides compositions and methods for generating dedifferentiated or iPS cells. Surprisingly, the administration of single-stranded mRNA that is at least practically free, and preferably at least extremely free or at least absolutely free of dsRNA can provide highly efficient generation of dedifferentiated or iPS cells. Unexpectedly and surprisingly, not only modified mRNA, such as pseudouridine- (Ψ-) and/or 5-methylcytidine-(m$^5$C-) modified mRNA encoding iPS cell induction factors, but also unmodified mRNA encoding said iPS cell induction factors, results in highly efficient generation of dedifferentiated cells or iPS cells.

In some embodiments, the present invention provides methods for dedifferentiating a somatic cell comprising: introducing mRNA encoding one or more iPSC induction factors into a somatic cell to generate a dedifferentiated cell.

In some embodiments, the present invention provides methods for dedifferentiating a somatic cell comprising: introducing a ssRNA composition comprising mRNA molecules encoding one or more iPSC induction factors into a somatic cell and maintaining the cell under conditions wherein the cell is viable and the mRNA that is introduced into the cell is expressed in sufficient amount and for sufficient time to generate a dedifferentiated cell. In some preferred embodiments, the dedifferentiated cell is an induced pluripotent stem cell (iPSC). In some embodiments of the methods of the present invention for reprogramming a cell from a first state of differentiation or phenotype to a second state of differentiation or phenotype comprising an iPS cell, or of compositions, systems or kits performing said method, or of compositions that result from use of said methods, the iPS cell expresses the inner cell mass-specific marker NANOG (which is one marker used to assay whether a dedifferentiated cell is an iPS cell, e.g., see Ganzalez et al. 2009, and Huangfu et al. 2008). In some other embodiments of the methods of the present invention for reprogramming a cell from a first state of differentiation or phenotype to a second state of differentiation or phenotype comprising an iPS cell, or of compositions, systems or kits performing said method, or of compositions that result from use of said methods, the iPS cell expresses TRA-1-60 (which is considered to be a more stringent marker of fully reprogrammed iPS cells used to assay whether a dedifferentiated cell is an iPS cell, e.g., see Chan et al. 2009). In preferred embodiments of this method or of compositions, systems or kits performing said method, or of compositions that result from use of said methods, the RNA composition comprising ssRNA or mRNA used for said introducing is substantially free, virtually free, essentially free, practically free, extremely free or absolutely free of dsRNA.

In some embodiments, the present invention provides methods for changing the state of differentiation (or differentiated state) of a eukaryotic cell (e.g., a human or animal cell) comprising: introducing a ssRNA composition comprising mRNA molecules encoding one or more reprogramming factors into a cell and maintaining the cell under conditions wherein the cell is viable and the mRNA that is introduced into the cell is expressed or translated into proteins in sufficient amounts and for sufficient time to generate a cell, wherein the cell exhibits a changed state of differentiation compared to the cell into which the mRNA was introduced. In preferred embodiments of this method, the ssRNA composition is substantially free, virtually free, essentially free, practically free, extremely free or absolutely free of dsRNA.

In some embodiments, the present invention provides methods for changing the state of differentiation of a eukaryotic cell (e.g., a human or animal cell) comprising: introducing a ssRNA composition comprising mRNA encoding one or more reprogramming factors into a cell and maintaining the cell under conditions wherein the cell is viable and the mRNA that is introduced into the cell is expressed or translated into proteins in sufficient amounts and for sufficient time to generate a cell that exhibits a changed state of differentiation compared to the cell into which the mRNA was introduced. In preferred embodiments of this method, the ssRNA composition is substantially free, virtually free, essentially free, practically free, extremely free or absolutely free of dsRNA. In some embodiments, the changed state of differentiation is a dedifferentiated state of differentiation compared to the cell into which the mRNA was introduced. For example, in some embodiments, the cell that exhibits the changed state of differentiation is a pluripotent stem cell that is dedifferentiated compared to a somatic cell into which the mRNA was introduced (e.g., a somatic cell that is differentiated into a fibroblast, a cardiomyocyte, or another differentiated cell type). In some embodiments, the cell into which the mRNA is introduced is a somatic cell of one lineage, phenotype, or function, and the cell that exhibits the changed state of differentiation is a somatic cell that exhibits a lineage, phenotype, or function that is different than that of the cell into which the mRNA was introduced; thus, in these embodiments, the method results in transdifferentiation (Graf and Enver 2009).

The methods of the invention are not limited with respect to a particular cell into which the mRNA is introduced. In some embodiments of any of the methods for reprogramming a eukaryotic cell, the cell into which the mRNA is introduced is derived from any multi-cellular eukaryote. In some preferred embodiments, the cell into which the mRNA is introduced is selected from among a human cell and an animal cell. In other embodiments, the cell into which the mRNA is introduced is selected from among a plant and a fungal cell. In some embodiments of any of the methods for reprogramming a eukaryotic cell, the cell into which the mRNA is introduced is a normal cell that is from an organism that is free of a known disease. In some embodiments of any of the methods for reprogramming a eukaryotic cell, the cell into which the mRNA is introduced is a cell from an organism that has a known disease. In some embodiments of any of the methods for reprogramming a eukaryotic cell, the cell into which the mRNA is introduced is a cell that is free of a known pathology. In some embodiments of any of the methods for reprogramming a eukaryotic cell, the cell into which the mRNA is introduced is a cell that exhibits a disease state or a known pathology (e.g., a cancer cell, or a pancreatic beta cell that exhibits metabolic properties characteristic of a diabetic cell).

The invention is not limited to the use of a specific cell type (e.g., to a specific somatic cell type) in embodiments of the methods comprising introducing mRNA encoding one or more iPSC cell induction factors in order to generate a dedifferentiated cell (e.g., a dedifferentiated cell or an iPS cell). Any cell that is subject to dedifferentiation using iPS cell induction factors is contemplated. Such cells include, but are not limited to, fibroblasts, keratinocytes, adipocytes, lymphocytes, T-cells, B-Cells, cells in mononuclear cord blood, buccal mucosa cells, hepatic cells, HeLa, MCF-7 or other cancer cells. In some embodiments, the cells reside in vitro (e.g., in culture) or in vivo. In some embodiments, when generated in culture, a cell-free conditioned medium (e.g., a mouse embryonic fibroblast-conditioned or MEF-conditioned medium) is used. For example, in some embodiments of the methods for reprogramming a human or mammalian cell that exhibits a first differentiated state or phenotype to a second differentiated state or phenotype by repeatedly or continuously introducing ssRNA or mRNA encoding one or more reprogramming factors, the cells for said reprogramming are incubated on feeder cells during and/or after said introducing; in other embodiments, the cells are incubated in a MEF-conditioned medium (e.g., prepared as described by Xu et al., 2001) in the absence of feeder cells during and/or after said introducing, rather than plating them on a feeder layer. In some embodiments, this method is faster and more efficient than other methods for reprogramming than published protocols comprising transfecting cells with DNA plasmids or lentiviral vectors encoding the same or similar reprogramming factors in non-MEF-conditioned medium (e.g., Aoi et al. 2008). In some other embodiments, the Stemgent PLURITON™ mRNA reprogramming medium is used to culture the somatic cells that are transfected with the purified RNA composition comprising ssRNA molecules that encode one or more iPS cell induction factors until dedifferentiated or iPS cells are induced, after which the dedifferentiated or iPS cells or iPSC colonies are cultured in another medium, such as NUTRISTEM™ medium. In some other embodiments (e.g., as described in EXAMPLE 11), another medium (e.g., the Feeder-free Reprogramming Medium developed by the present inventors for reprogramming human fibroblasts to iPSCs) is used for reprogramming and, in some other embodiments (e.g., as described in EXAMPLE 11), another medium is used for maintenance of the iPSCs or iPSC colonies generated from the reprogramming (e.g., in order to avoid redifferentiation of the dedifferentiated or iPS cells or colonies into somatic cells. As demonstrated below, such a Feeder-free Reprogramming Medium provided enhanced and feeder-free generation of dedifferentiated or iPS cells and colonies from human somatic cells (e.g., fibroblast cells). The invention is not limited, however, to the culturing conditions used. Any culturing condition or medium now known or later identified as useful for the methods of the invention (e.g., to generate dedifferentiated cells or iPS cells from somatic cells and maintain said cells) is contemplated for use with the invention. For example, although not preferred, in some embodiments of the method, a feeder cell layer is used instead of conditioned medium for culturing the cells that are treated using the method.

In some embodiments of these methods, the step of introducing mRNA comprises delivering the mRNA into the cell (e.g., a human or other animal somatic cell) with a transfection reagent (e.g., TRANSIT™ mRNA transfection reagent, MirusBio, Madison, WI). However, the invention is not limited by the nature of the transfection method utilized. Indeed, any transfection process known, or identified in the future that is able to deliver mRNA molecules into cells in vitro or in vivo, is contemplated, including methods that deliver the mRNA into cells in culture or in a life-supporting medium, whether said cells comprise isolated cells or cells comprising a eukaryotic tissue or organ, or methods that deliver the mRNA in vivo into cells in an organism, such as a human, animal, plant or fungus. In some embodiments, the transfection reagent comprises a lipid (e.g., liposomes, micelles, etc.). In some embodiments, the transfection reagent comprises a nanoparticle or nanotube. In some embodiments, the transfection reagent comprises a cationic compound (e.g., polyethylene imine or PEI). In some embodiments, the transfection method uses an electric current to deliver the mRNA into the cell (e.g., by electroporation).

The data presented herein shows that, with respect to the mRNA introduced into the cell, certain amounts of the mRNAs used in the EXAMPLES described herein resulted in higher efficiency and more rapid induction of pluripotent stem cells from the particular somatic cells used than other amounts of mRNA. However, the methods of the present invention are not limited to the use of a specific amount of mRNA to introduce into the cell. For example, in some embodiments, a total of three doses, with each dose comprising 18 micrograms of each of six different mRNAs, each encoding a different human reprogramming factor, was used to introduce the mRNA into approximately $3 \times 10^5$ human fibroblast cells in a 10-cm plate (e.g., delivered using a lipid-containing transfection reagent), although in other embodiments, higher or lower amounts of the mRNAs were used to introduce into the cells.

The invention is not limited to a particular chemical form of the mRNA used so long as the particular form of mRNA functions for its intended application, although certain forms of mRNA may produce more efficient results, which are preferred embodiments herein. In some preferred embodiments, the mRNA is polyadenylated. For example, in some preferred embodiments, the mRNA comprises a poly-A tail (e.g., a poly-A tail having 50-200 nucleotides, e.g., preferably 100-200, 150-200 nucleotides, or greater than 150 nucleotides), although in some embodiments, a longer or a shorter poly-A tail is used. In some embodiments, the mRNA used in the methods is capped. To maximize efficiency of expression and to minimize the innate immune response in the cells, it is preferred that the majority, and more preferably, all or substantially all of mRNA molecules contain a cap. Thus, in some preferred embodiments, the mRNA molecules used in the methods are synthesized in vitro by incubating uncapped primary RNA in the presence of with a capping enzyme system, which can result in approximately 100% of the RNA molecules being capped. In preferred embodiments, greater than 90%, greater than 95%, or greater than 98% of mRNA molecules are capped. In even more preferred embodiments, greater than 99%, greater than 99.5%, or greater than 99.9% of the population of mRNA molecules are capped. In preferred embodiments, the mRNA molecules used in the methods of the present invention have a cap with a cap1 structure, wherein the penultimate nucleotide with respect to the cap nucleotide has a methyl group on the 2'-position of the ribose. For example, in some embodiments, mRNA that has cap1 structure is synthesized by incubating in vitro-transcribed RNA with SCRIPTCAP™ capping enzyme and the SCRIPTCAP™ 2'-O-methyl-transferase enzymes (CELLSCRIPT, INC., Madison, WI) or the equivalent capping enzyme components in the T7 mSCRIPT™ standard mRNA production system, as described in the product literature provided with those products (CELLSCRIPT, INC., Madison, WI). In some embodiments, the mRNA used in the methods of the present invention has a modified cap nucleotide. For example, in some embodiments, mRNA comprising a modified cap nucleotide is synthesized as described in U.S. patent application Ser. No. 11/787,352 (Publication No. 20070281336). Thus, in some preferred embodiments, the primary RNA used in the capping enzyme reaction is synthesized by in vitro transcription (IVT) of a DNA molecule that encodes the RNA to be synthesized. The DNA that encodes the RNA to be synthesized is joined to an RNA polymerase promoter, to which, an RNA polymerase binds and initiates transcription therefrom. The IVT can be performed using any RNA polymerase so long as synthesis of the template that encodes the RNA is specifically and sufficiently initiated from a respective cognate RNA polymerase promoter. In some preferred embodiments, the RNA polymerase is selected from among T7 RNA polymerase, SP6 RNA polymerase and T3 RNA polymerase.

Thus, mRNA that has a cap1 structure, prepared by post-transcriptional capping of in vitro-transcribed RNA is preferred for the methods comprising introducing purified mRNA comprising or consisting of at least one modified ribonucleoside, which mRNA encodes at least one reprogramming factor, into a cell that exhibits a first differentiated state or phenotype to generate a reprogrammed cell that exhibits a second differentiated state or phenotype. However, in some other embodiments, capped RNA is synthesized co-transcriptionally by using a dinucleotide cap analog in the IVT reaction (e.g., using an AMPLICAP™ T7 Kit or a MESSAGEMAX™ T7 ARCA-CAPPED MESSAGE Transcription Kit; CELLSCRIPT, INC., Madison, WI, USA). If capping is performed co-transcriptionally, preferably the dinucleotide cap analog is an anti-reverse cap analog (ARCA). However, use of a separate IVT reaction, followed by capping with a capping enzyme system, which results in approximately 100% of the RNA being capped, is preferred over co-transcriptional capping, which typically results in only about 80% of the RNA being capped. Thus, in some preferred embodiments, a high percentage of the mRNA molecules used in a method of the present invention are capped (e.g., greater than 80%, greater than 90%, greater than 95%, greater than 98%, greater than 99%, greater than 99.5%, or greater than 99.9% of the population of mRNA molecules are capped). In some preferred embodiments, the mRNA used in the methods of the present invention has a cap with a cap1 structure, meaning that the penultimate nucleotide with respect to the cap nucleotide has a methyl group on the 2'-position of the ribose. Capped RNA synthesized co-transcriptionally by using a dinucleotide cap analog in the IVT reaction can be converted to mRNA that has a cap1 structure by incubating said capped RNA with an RNA 2'-O-methyltransferase enzyme (e.g., SCRIPTCAP™ 2'-O-methyl-transferase enzyme, CELLSCRIPT, INC.) according to information and protocols provided in the product literature.

The present researchers previously found that cap1 mRNA is often expressed into protein at higher levels than the corresponding cap0 mRNA when introduced into living cells in culture. Therefore, the use of mRNA that has a cap1 structure is preferred for all of the methods herein. However, although mRNA that has a cap1 structure is preferred, in some embodiments, mRNA used in the methods has a cap with a cap0 structure, meaning that the penultimate nucleotide with respect to the cap nucleotide does not have a methyl group on the 2'-position of the ribose. With some but not all transcripts, transfection of eukaryotic cells with mRNA having a cap with a cap1 structure results in a higher level or longer duration of protein expression in the transfected cells compared to transfection of the same cells with the same mRNA but with a cap having a cap0 structure. In some embodiments, the mRNA used in the methods of the present invention has a modified cap nucleotide.

In some experiments performed prior to the experiments presented in the EXAMPLES herein, the present Applicants found that, when 1079 or IMR90 human fibroblast cells were transfected with OCT4 mRNA that contained either uridine or pseudouridine in place of uridine, the pseudouridine-containing mRNA was expressed at a higher level or for a longer duration than the mRNA that contained uridine. Therefore, in some preferred embodiments, one or more or all of the uridines contained in the mRNA(s) used in the methods of the present invention is/are replaced by pseudouridine (e.g., by substituting pseudouridine-5'-triphosphate in the IVT reaction to synthesize the RNA in place of uridine-5'-triphosphate). However, in some embodiments, the mRNA used in the methods of the invention contains uridine and does not contain pseudouridine. In addition, in order to accomplish specific goals, a nucleic acid base, sugar moiety, or internucleoside linkage in one or more of the nucleotides of the ssRNA or mRNA that is introduced into a eukaryotic cell in the methods of the invention may comprise a modified nucleic acid base, sugar moiety, or internucleoside linkage.

The invention is also not limited with respect to the source of the in vitro-synthesized ssRNA or mRNA that is delivered into the eukaryotic cell in the methods of the invention. In some embodiments, such as those described in the EXAMPLES, the ssRNA or mRNA is synthesized in vitro by transcription of a DNA template comprising a gene cloned in a linearized plasmid vector or a PCR or RT-PCR amplification product, capping using a capping enzyme system, and polyadenylation using a poly-A polymerase. In some other embodiments, the ssRNA or mRNA that is delivered into the eukaryotic cell is derived from a cell or a biological sample. For example, in some embodiments, the mRNA derived from a cell or biological sample is obtained by amplifying the mRNA from the cell or biological sample using an RNA amplification reaction. In some preferred embodiments, the mRNA derived from the cell or biological sample is amplified to generate sense RNA according to the methods described in U.S. Pat. No. 8,039,214, which is incorporated herein by reference.

With respect to the methods comprising introducing mRNA encoding one or more iPSC cell induction factors in order to generate a dedifferentiated cell (e.g., an iPS cell), the invention is not limited by the nature of the iPS cell induction factors used. Any mRNA encoding one or more protein induction factors now known, or later discovered, that find use in dedifferentiation, are contemplated for use in the present invention. In some embodiments, one or more mRNAs encoding for KLF4, LIN28, wild-type c-MYC, mutant c-MYC(T58A) (Wang X et al., 2011; Wasylishen A R, et al. 2011), L-MYC, NANOG, OCT4, or SOX2 are employed. OCT-3/4 proteins and certain protein members of the SOX gene family (SOX1, SOX2, SOX3, and SOX15) have been identified as transcriptional regulators involved in the induction process. Additional genes encode certain protein members the KLF family (KLF1, KLF2, KLF4, and KLF5), the MYC family (c-MYC(WT), c-MYC(T58A), L-MYC, and N-MYC), NANOG, and LIN28, which have been identified to increase the induction efficiency. One or more these factors may be used in certain embodiments.

While the compositions and methods of the invention may be used to generated iPS cells, the invention is not limited to the generation of such cells. For example, in some embodiments, mRNA encoding one or more reprogramming factors is introduced into a cell in order to generate a cell with a changed state of differentiation compared to the cell into which the mRNA was introduced. For example, in some embodiments, mRNA encoding one or more iPS cell induction factors is used to generate a dedifferentiated cell that is not an iPS cell. Such cells find use in research, drug screening, and other applications.

In some embodiments, the present invention further provides methods employing the dedifferentiated cells generated by the above methods. For example, such cells find use in research, drug screening, and therapeutic applications in humans or other animals. For example, in some embodiments, the cells generated find use in the identification and characterization of iPS cell induction factors as well as other factors associated with differentiation or dedifferentiation. In some embodiments, the generated dedifferentiated cells are transplanted into an organism or into a tissue residing in vitro or in vivo. In some embodiments, an organism, tissue, or culture system housing the generated cells is exposed to a test compound and the effect of the test compound on the cells or on the organism, tissue, or culture system is observed or measured.

In some other embodiments, a dedifferentiated cell generated using the above methods (e.g., an iPS cell) is further treated to generate a differentiated cell that has the same state of differentiation or cell type compared to the somatic cell from which the dedifferentiated cell was generated. In some other embodiments, the dedifferentiated cell generated using the above methods (e.g., an iPS cell) is further treated to generate a differentiated cell that has a different state of differentiation or cell type compared to the somatic cell from which the dedifferentiated cell was generated. In some embodiments, the differentiated cell is generated from the generated dedifferentiated cell (e.g., the generated iPS cell) by introducing mRNA encoding one or more reprogramming factors into the generated iPS cell and maintaining the cell into which the mRNA is introduced under conditions wherein the cell is viable and is differentiated into a cell that has a changed state of differentiation or cell type compared to the generated dedifferentiated cell (e.g., the generated iPS cell) into which the mRNA encoding the one or more reprogramming factors is introduced. In some of these embodiments, the generated differentiated cell that has the changed state of differentiation is used for research, drug screening, or therapeutic applications (e.g., in humans or other animals). For example, the generated differentiated cells find use in the identification and characterization of reprogramming factors associated with differentiation. In some embodiments, the generated differentiated cells are transplanted into an organism or into a tissue residing in vitro or in vivo. In some embodiments, an organism, tissue, or culture system housing the generated differentiated cells is exposed to a test compound and the effect of the test compound on the cells or on the organism, tissue, or culture system is observed or measured.

In some preferred embodiments of the method comprising introducing mRNA encoding one or more iPSC induction factors into a somatic cell and maintaining the cell under conditions wherein the cell is viable and the mRNA that is introduced into the cell is expressed in sufficient amount and for sufficient time to generate a dedifferentiated cell (e.g., wherein the dedifferentiated cell is an induced pluripotent stem cell), the sufficient time to generate a dedifferentiated cell is less than one week. However, in some embodiments of the method, the sufficient time to generate a dedifferentiated cell (e.g., an iPS cell) is at least eight days. In some embodiments of the method, the sufficient time to generate a dedifferentiated cell (e.g., an iPS cell) is greater than eight days (e.g., 9 days, 10 days, 11 days, 12 days, 13 days, 14 days, 15 days, 16 days, 17 days, 18 days, or more). Among other factors the particular iPS cell induction factors used and their doses and relative doses, as well as the feeder cells (if used), media and other growth conditions affect the amount of time that is sufficient time to generate a dedifferentiated cell (e.g., an iPS cell). For example, the present applicants found that under the same culture conditions, the use of ssRNA molecules encoding L-MYC required a longer time (e.g., at least about 17 days) to generate iPS cells than when ssRNA molecules encoding c-MYC were used (e.g., in one experiment, requiring only about 10-12 days to generate iPS cells). In some preferred embodiments of this method, the reprogramming efficiency for generating dedifferentiated cells is greater than or equal to 50 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 100 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 150 dedifferentiated cells (e.g., iPSCs) per 3×10$^5$ input cells into which the mRNA is introduced. In some preferred embodiments of this method, the reprogramming efficiency for generating dedifferentiated cells is greater than or equal to 200 dedifferentiated cells (e.g., iPSCs) per 3×10$^5$ input cells into which the mRNA is introduced. In some preferred embodiments of this method, the reprogramming efficiency for generating dedifferentiated cells is greater than or equal to 300 dedifferentiated cells (e.g., iPSCs) per 3×10$^5$ input cells into which the mRNA is introduced. In some preferred embodiments of this method, the reprogramming efficiency for generating dedifferentiated cells is greater than or equal to 400 dedifferentiated cells (e.g., iPSCs) per 3×10$^5$ input cells into which the mRNA is introduced. In some preferred embodiments of this method, the reprogramming efficiency for generating dedifferentiated cells is greater than or equal to 500 dedifferentiated cells (e.g., iPSCs) per 3×10$^5$ input cells into which the mRNA is introduced. In some preferred embodiments of this method, the reprogramming efficiency for generating dedifferentiated cells is greater than or equal to 600 dedifferentiated cells per 3×10$^5$ input cells (e.g., iPSCs) into which the mRNA is introduced. In some preferred embodiments of this method, the reprogramming efficiency for generating dedifferentiated cells is greater than or equal to 700 dedifferentiated cells (e.g., iPSCs) per 3×10$^5$ input cells into which the mRNA is introduced. In some preferred embodiments of this method, the reprogramming efficiency for generating dedifferentiated cells is greater than or equal to 800 dedifferentiated cells (e.g., iPSCs) per 3×10$^5$ input cells into which the mRNA is introduced. In some preferred embodiments of this method, the reprogramming efficiency for generating dedifferentiated cells is greater than or equal to 900 dedifferentiated cells (e.g., iPSCs) per 3×10$^5$ input cells into which the mRNA is introduced. In some preferred embodiments of this method, the reprogramming efficiency for generating dedifferentiated cells is greater than or equal to 1000 dedifferentiated cells (e.g., iPSCs) per 3×10$^5$ input cells into which the mRNA is introduced. Thus, in some preferred embodiments, this method was greater than 2-fold more efficient than the published protocol comprising delivery of reprogramming factors with a viral vector (e.g., a lentivirus vector). In some preferred embodiments, this method was greater than 5-fold more efficient than the published protocol comprising delivery of reprogramming factors with a viral vector (e.g., a lentivirus vector). In some preferred embodiments, this method was greater than 10-fold more efficient than the published protocol comprising delivery of reprogramming factors with a viral vector (e.g., a lentivirus vector). In some preferred embodiments, this method was greater than 20-fold more efficient than the published protocol comprising delivery of reprogramming factors with a viral vector (e.g., a lentivirus vector). In some preferred embodiments, this method was greater than 25-fold more efficient than the published protocol comprising delivery of reprogramming factors with a viral vector (e.g., a lentivirus vector). In some preferred embodiments, this method was greater than 30-fold more efficient than the published protocol comprising delivery of reprogramming factors with a viral vector (e.g., a lentivirus vector). In some preferred embodiments, this method was greater than 35-fold more efficient than the published protocol comprising delivery of reprogramming factors with a viral vector (e.g., a lentivirus vector). In some preferred embodiments, this method was greater than 40-fold more efficient than the published protocol comprising delivery of reprogramming factors with a viral vector (e.g., a lentivirus vector).

The present invention further provides compositions (systems, kits, reaction mixtures, cells, mRNA) used or useful in the methods and/or generated by the methods described herein. For example, in some embodiments, the present invention provides an mRNA encoding an iPS cell induction factor, the mRNA having pseudouridine in place of uridine.

The present invention further provides compositions comprising a transfection reagent and an mRNA encoding an iPS cell induction factor (e.g., a mixture of transfection reagent and mRNA).

In some embodiments, the compositions comprise mRNA encoding a plurality (e.g., 2 or more, 3 or more, 4 or more, 5 or more, or 6) of iPS cell induction factors, including, but not limited to, KLF4, LIN28, c-MYC, NANOG, OCT4, and SOX2.

The compositions may further comprise any other reagent or component sufficient, necessary, or useful for practicing any of the methods described herein. Such reagents or components include, but are not limited to, transfection reagents, culture medium (e.g., MEF-condition medium), cells (e.g., somatic cells, iPS cells), containers, boxes, buffers, inhibitors (e.g., RNase inhibitors), labels (e.g., fluorescent, luminescent, radioactive, etc.), positive and/or negative control molecules, reagents for generating capped mRNA, dry ice or other refrigerants, instructions for use, cell culture equipment, detection/analysis equipment, and the like.

In certain embodiments, the ssRNAs or mRNAs comprising a composition, kit or method of the invention are purified or treated to generate purified or treated RNA compositions or ssRNA or mRNA preparations that have most of the contaminating RNA molecules removed (e.g., molecules that cause an immunogenic response in the cells). In certain embodiments, the ssRNA or mRNA used in the purified or treated RNA composition or preparation is purified to remove the contaminants, including the RNA contaminants (e.g., dsRNA contaminants) so that it is substantially, practically free, extremely free or absolutely free of said contaminants. The present invention is not limited with respect to the purification or treatment methods used to purify the ssRNA or mRNA for methods herein that use a purified or treated RNA composition (e.g., comprising a ssRNA or mRNA) to induce a biological or biochemical effect (e.g, for reprogramming a human or mammalian cell from a first differentiated state or phenotype to a second differentiated state or phenotype), and the invention includes use of any method that is known in the art or developed in the future in order to purify the ssRNA or mRNA and remove contaminants, including RNA contaminants, that interfere with the intended use of the ssRNA or mRNA. For example, in preferred embodiments, the purification of the ssRNA or mRNA removes contaminants that are toxic to the cells (e.g., by inducing an innate immune response in the cells, or, in the case of RNA contaminants comprising dsRNA, by inducing RNA interference (RNAi), e.g., via siRNA or long RNAi molecules) and contaminants that directly or indirectly decrease translation of the mRNA in the cells). In some embodiments, the ssRNA or mRNA is purified by HPLC using a method described herein, including in the EXAMPLES. In certain embodiments, the ssRNA or mRNA is purified using on a polymeric resin substrate comprising a C18 derivatized styrene-divinylbenzene copolymer and a triethylamine acetate (TEAA) ion pairing agent is used in the column buffer along with the use of an acetonitrile gradient to elute the ssRNA or mRNA and separate it from the RNA contaminants in a size-dependent manner; in some embodiments, the ssRNA or mRNA purification is performed using HPLC, but in some other embodiments a gravity flow column is used for the purification. In some embodiments, the ssRNA or mRNA is purified using a method described in the book entitled "*RNA Purification and Analysis*" by Douglas T. Gjerde, Lee Hoang, and David Hornby, published by Wiley-VCH, 2009, herein incorporated by reference. In some embodiments, the ssRNA or mRNA purification is carried out in a non-denaturing mode (e.g., at a temperature less than about 50 degrees C., e.g., at ambient temperature). In some embodiments, the ssRNA or mRNA purification is carried out in a partially denaturing mode (e.g., at a temperature less than about 50 degrees C. and 72 degrees C.). In some embodiments, the ssRNA or mRNA purification is carried out in a denaturing mode (e.g., at a temperature greater than about 72 degrees C.). Of course, those with knowledge in the art will know that the denaturing temperature depends on the melting temperature (Tm) of the ssRNA or mRNA that is being purified as well as on the melting temperatures of RNA, DNA, or RNA/DNA hybrids which contaminate the ssRNA or mRNA. In some other embodiments, the ssRNA or mRNA is purified as described by Mellits K H et al., 1990). After observing that incubation of in vitro-transcribed RNA (IVT-RNA) with RNase III using conditions as described by Robertson et al. (Robertson, H D et al., 1968) antagonized activation of DAI in a cell-free in vitro translation system, these authors used a three step purification to remove the contaminants which may be used in embodiments of the present invention. Step 1 was 8% polyacrylamide gel electrophoresis in 7 M urea (denaturing conditions). The major RNA band was excised from the gel slice and subjected to 8% polyacrylamide gel electrophoresis under nondenaturing condition (no urea) and the major band recovered from the gel slice. Further purification was done on a cellulose CF-11 column using an ethanol-salt buffer mobile phase which separates double stranded RNA from single stranded RNA (Franklin R M. 1966. *Proc. Natl. Acad. Sci. USA* 55: 1504-1511; Barber R. 1966. *Biochem. Biophys. Acta* 114:422; and Zelcer A et al. 1982. *J. Gen. Virol.* 59: 139-148, all of which are herein incorporated by reference) and the final purification step was cellulose chromatography. A similar 3-step IVT-RNA purification method comprising denaturing gel electrophoresis, non-denaturing gel electrophoresis and CF-11 chromatography was used by Pe'ery and Mathews (Pe'ery T and Mathews M B. 1997). These authors said that RNase III might be an optional pretreatment or in place of the nondenaturing gel, provided that the RNA was not sensitive to the enzyme, which they observed cut some ssRNAs. In some other embodiments, the ssRNA or mRNA is purified using an hydroxylapatite (HAP) column under either non-denaturing conditions or at higher temperatures (e.g., as described by Pays E. 1977. *Biochem. J.* 165: 237-245; Lewandowski L J et al. 1971. *J. Virol.* 8: 809-812; Clawson G A and Smuckler E A. 1982. *Cancer Research* 42: 3228-3231; and/or Andrews-Pfannkoch C et al. 2010. *Applied and Environmental Microbiology* 76: 5039-5045, all of which are herein incorporated by reference). In some other embodiments, the ssRNA or mRNA is purified by weak anion exchange liquid chromatography under non-denaturing conditions (e.g., as described by Easton L E et al. 2010. *RNA* 16: 647-653 to clean up in vitro transcription reactions, herein incorporated by reference). In some embodiments, the ssRNA or mRNA is purified using one or more of any of the methods described herein or any other method known in the art or developed in the future. In still another embodiment, the ssRNA or mRNA used in the compositions, kits or methods of the present invention is purified using a process which comprises treating the ssRNA or mRNA with an enzyme that specifically acts (e.g., digests) one or more contaminant RNA or contaminant nucleic acids (e.g., including DNA), but which does not act on (e.g., does not digest) the desired ssRNA or mRNA. For example, in some embodiments, the ssRNA or mRNA used in the compositions and methods of the present invention is purified using a process which comprises treating the mRNA with a ribonuclease III (RNase III) enzyme (e.g., *E. coli* RNase III) and the ssRNA or mRNA is then purified away from the RNase III digestion products. A ribonuclease III (RNase III) enzyme herein means an enzyme that digests dsRNA greater than about twelve basepairs to short dsRNA fragments. In some embodiments, the ssRNA or mRNA used in the compositions, kits or methods of the present invention is purified using a process which comprises treating the ssRNA or mRNA with one or more other enzymes that specifically digest one or more contaminant RNAs or contaminant nucleic acids (e.g., including DNA).

In some embodiments, the results described herein demonstrate a method of the present invention for reprogramming a cell that exhibits a first state of differentiation or phenotype to a cell that exhibits a second state of differentiation or phenotype(e.g., reprogramming a mouse mesenchymal stem cell to a myoblast cell; e.g., reprogramming a human fibroblast cell to a neuron cell; ore.g., reprogramming a somatic cell; e.g., a fibroblast, keratinacyte or blood cell to a dedifferentiated or iPS cell), comprising: repeatedly (e.g., on or during each of 2, 3, 4, 5, 6, 7, 8, 9, 10, 11, 12, 13, 14, 15, 16, 17 18 or >18 days) or continuously introducing into a cell that exhibits a first state of differentiation or phenotype an mRNA reprogramming mix comprising pseudouridine-modified (GAΨC) mRNA encoding one or more protein reprogramming factors (e.g., one or more transcription factors), wherein the GAΨC mRNA: (i) exhibits a cap on its 5' terminus and a polyA tail on its 3' terminus; (ii) is purified (e.g., by HPLC or gravity-flow or low-pressure chromatography or electrophoresis) or treated with a dsRNA-specific endoribonuclease (e.g., RNase III) under conditions wherein: e.g., for mRNA encoding MYOD protein, less than 1% of the total RNA comprising said mRNA reprogramming mix used for said introducing comprises dsRNA; e.g., for mRNA encoding protein reprogramming factors for inducing neuron cells or iPS cells, less than 0.01% of the total RNA comprising said mRNA reprogramming mix used for said introducing comprises dsRNA; and maintaining the cell under conditions to generate a reprogrammed cell that exhibits a second state of differentiation or phenotype. In some preferred embodiments, the cap exhibits a cap1 structure, wherein the 5' penultimate nucleotide comprises a 2'-O-methyl group.

In certain other embodiments, these results demonstrate a method of the present invention for reprogramming a cell that exhibits a first state of differentiation (e.g., a somatic cell; e.g., a fibroblast, keratinacyte, a blood cell) or phenotype to a cell that exhibits a second state of differentiation (e.g., a dedifferentiated or iPS cell), comprising: repeatedly (e.g., on or during each of 2, 3, 4, 5, 6, 7, 8, 9, 10, 11, 12, 13, 14, 15, 16, 17 18, 19, 20, or >20 days) or continuously introducing into the cell that exhibits a first state of or phenotype an mRNA reprogramming mix comprising unmodified GAUC mRNA encoding one or more protein reprogramming factors (e.g., one or more transcription factors), wherein the unmodified GAUC mRNA: (i) exhibits a cap on its 5' terminus and a polyA tail on its 3' terminus; (ii) is purified (e.g., by HPLC or gravity-flow or low-pressure chromatograph or electrophoresis) or treated with a dsRNA-specific endoribonuclease (e.g., RNase III) under conditions wherein (e.g., for mRNA encoding MYOD protein, less than 0.1% of the total RNA comprising said mRNA reprogramming mix used for said introducing comprises dsRNA; e.g., for mRNA encoding protein reprogramming factors for inducing iPS cells, less than 0.004% of the total RNA comprising said mRNA reprogramming mix used for said introducing comprises dsRNA); And culturing the cell under conditions to generate a reprogrammed cell that exhibits a second state of differentiation or phenotype. In some preferred embodiments, the cap exhibits a cap1 structure, wherein the 5' penultimate nucleotide comprises a 2'-O-methyl group. In some preferred embodiments of the method for reprogramming a cell that exhibits a first differentiated state or phenotype to a cell that exhibits a second differentiated state or phenotype, the cell that exhibits a first differentiated state or phenotype is a somatic cell (e.g., a human fibroblast or keratinocyte cell), the mRNA reprogramming mix used for said introducing (e.g., transfection) into the cell that exhibits the first state of differentiation comprises either pseudouridine-modified GAΨC mRNAs, pseudouridine- and 5-methylcytidine-modified GAΨm$^5$C mRNAs, or unmodified GAUC mRNAs that exhibit a cap1 structure, in each case with polyA-tails with at least 50 A nucleosides (e.g., about 150 A nucleosides); wherein said mRNA reprogramming mix encodes a mix selected from among: $K_{(1-3)}MO_3S$; $K_{(1-3)}MO_3SL$; and $K_{(1-3)}MO_3SLN$; wherein M=c-MYC(T58A) or c-MYC; and wherein said the mRNAs in said mRNA reprogramming mix are RNase III-treated and are absolutely free of dsRNA; and the cell that exhibits a second differentiated state or phenotype is an or iPS cell.

EXAMPLES

The present invention will now be illustrated by the following examples, which are not to be considered limiting in any way.

General Materials and Methods, Particularly Those Pertaining to Development of the RNase III Treatment Method The following description illustrates examples of the materials and methods generally used herein. Whenever possible, applicants have tried to point out when other materials or methods, or deviations from or modifications of the general materials and methods were used in particular EXAMPLES or experiments described below. However, those with knowledge, after reading the descriptions below, will understand how modify the specific embodiments described without deviating from the scope of the present invention.

Production of an RNA Substrate Comprising Both dsRNA and ssRNA Portions for Use in Simultaneously Assaying RNase III Activities on Both dsRNA and ssRNA A T7 and T3 RNA polymerase promoter-containing plasmid DNA construct was used for generation of an RNA substrate comprising a dsRNA central portion with a 5'-terminal ssRNA portion on one strand and a 3'-terminal ssRNA portion on the other strand for use in assaying RNase III activities on both dsRNA and ssRNA simultaneously. A 1671-basepair insert, as shown in FIG. 1, was cut from the plasmid backbone with ClaI and then single-stranded RNA (ssRNA) was generated by in vitro transcription of each DNA strand (FIG. 1) in two separate reactions using either a T7-Scribe™ Standard RNA IVT Kit (CELLSCRIPT, INC., Madison, WI, USA) or an AmpliScribe™ T3 High Yield transcription Kit (epicentre, Madison, WI), respectively. Following DNase I treatment to remove the DNA template, the ssRNA transcripts were precipitated with one volume of 5 M ammonium acetate and were resuspended in 10 mM Tris-HCl (pH 7.5) with 1 mM EDTA. The two strands of ssRNA were annealed by incubating equivalent amounts of the T7- and T3-transcribed ssRNAs at 94° C. for 2 minutes, 72° C. for 10 minutes and then slowly cooling to room temperature. The resulting annealed RNA was 1671 bases in length with a 255-base single-stranded region on one end and a 136-base single-stranded region on the other end.

Production of a Control ssRNA

A T7 RNA polymerase promoter-containing plasmid construct with a 955 base insert was linearized with EcoRI. The T7-Scribe™ Standard RNA IVT Kit was used to transcribe RNA from the template. DNase I treatment and ammonium acetate precipitation were performed as described above and the ssRNA transcript was resuspended in water.

Simultaneous Assay of RNase III Activity on dsRNA and ssRNA Substrates Under Different Reaction Conditions One microgram of the RNA substrate comprising both dsRNA and ssRNA portions, (referred to herein as either the "RNA substrate" or the "dsRNA substrate") was adjusted to a final concentration of 20 ng/microliter, and treated with 20 nM RNase III using the incubated MINiMMUNE™ dsRNA removal kit (CELLSCRIPT, INC., Madison, WI, USA) at 37° C. for 10 minutes in a 50-microliter reaction mixture that varied in composition. In one embodiment, the reaction mixture contained final concentrations of 33 mM Tris-acetate (pH 8) as a buffer, 200 mM potassium acetate as a monovalent salt, and between 1 mM to 10 mM magnesium acetate as the divalent magnesium cation source. Reactions also contained 0.8 units per microliter SCRIPTGUARD™ RNase inhibitor (CELLSCRIPT, INC., Madison, WI, USA). The reactions were stopped by the addition of EDTA to the same final concentration as the concentration of divalent magnesium cations used in the assay (e.g., 1 mM to 10 mM final).

Digestion of the RNA substrate was analyzed by denaturing gel electrophoresis. Briefly, 10-microliter samples of each 50-microliter RNase III reaction was analyzed by denaturing gel electrophoresis on a 1% agarose, 1 M urea gel in 1× TBE buffer. Samples were denatured for 2 minutes at 94° C. in formamide-containing loading buffer and run next to RNA Millennium™ markers (Ambion/Life Technologies). Gels were stained with SYBR® Gold nucleic acid gel stain (Invitrogen/Life Technologies).

Dot Blot Assays for Assay or Quantification of dsRNA Using dsRNA-Specific Antibodies Appropriate dilutions of RNA samples (5 microliters/sample) for the intended assay purpose were applied to Nytran SPC positively charged nylon membranes (Thermo Scientific, Waltham, MA). The RNA was allowed to dry on the nylon membrane for 30 minutes at room temperature. The membranes were then blocked in blocking buffer (25 mM Tris pH 7.5, 150 mM NaCl, 0.05% Tween 20, 5% W/V dry milk) at room temperature for 1 hour on a rotating platform. The primary antibodies (J2 or K1 antibodies, English & Scientific Consulting, Szirák, Hungary) were then added at 1 microgram/ml in blocking buffer at room temperature for 1 hour on a rotating platform. The membranes were then washed 6 times for 5 minutes with 20 mls of wash buffer (25 mM Tris-HCl, pH 7.5, 150 mM NaCl, 0.05% Tween 20). Membranes were then incubated at room temperature for 1 hour on a rotating platform in blocking buffer to which a 1:1000 dilution of the secondary antibody (Anti-mouse IgG HRP, Cell Signaling Technologies, Danvers, MA) was added. The membranes were again washed 6 times for 5 minutes with 20 mls of wash buffer (25 mM Tris pH 7.5, 150 mM NaCl, 0.05% Tween 20). Then, equal volumes of SUPERSIGNAL WEST PICO™ Chemiluminescent Substrates (Thermo Scientific, Waltham, MA) were added and the color was allowed to develop for 5 minutes on a rotating platform. The dots were imaged by exposing the film in the dark room and then developing the film in Kodak Developer (Sigma, St. Louis, MO) for 1 minute and Kodak Fixer (Sigma, St. Louis, MO) for 1 minute.

General Materials and Methods, Particularly Those Pertaining to Reprogramming of Cells Exhibiting a First Differentiated State or Phenotype to a Second Differentiated State or Phenotype (e.g., Reprogramming of Human Somatic Cells to iPS Cells)

Methods for Using Feeder Cells and Plating BJ Fibroblasts for Reprogramming to iPSCs with mRNAs Encoding iPSC Reprogramming Factors Nuff cells (Human Foreskin Fibroblast P9 irradiated (donor 11) (GlobalStem, Rockville, MD) were plated at a density of $5 \times 10^5$ cells/well in a gelatin-coated 6-well dish. The Nuffs were grown overnight at 37° C., 5% $CO_2$ in Nuff culture medium (DMEM Invitrogen cat #11965-118, 10% Hyclone FBS Fisher cat #SH30070.03HI, GLUTAMAX™ Invitrogen cat #35050-061, Pen/Strep Invitrogen cat #15140-122). BJ Fibroblasts (ATCC) were plated at $1 \times 10^4$ cells per well on Nuffs cells which had been plated the previous day. The cells were then incubated in BJ Fibroblast medium (Advanced MEM, 10% Hyclone FBS Fisher cat #SH30070.03HI, GLUTAMAX Invitrogen cat #35050-061, Pen/Strep Invitrogen cat #15140-122) overnight at 37° C., 5% $CO_2$.

TransIT™ mRNA Transfection Protocol

BJ fibroblast medium was removed from BJ fibroblasts plated on Nuff feeder cells and replaced by PLURITON™ mRNA reprogramming medium (Stemgent, Cambridge, MA)(base medium with supplement and penicillin/streptomycin) (2 mls) with or without 4 microliters of B18R recombinant protein (EBiosciences, San Diego, CA) to a final concentration of 200 ng/ml. The media were changed immediately before each transfection with Mirus mRNA Transfection Reagent (Mirus Bio, Madison, WI). To transfect the BJ fibroblasts, 0.6 to 1.4 micrograms of the 3:1:1:1:1 mRNA mix comprising OCT4, SOX2, KLF4, LIN28 and either c-MYC(T58A) or cMYC was added to 120 microliters of OptiMEM medium and then TransIT™ Boost (2 microliters per microgram of mRNA) and TransIT™ mRNA transfection reagent (microliters per microgram of mRNA) (Mirus Bio) were mixed with the mRNA. The mRNA-TransIT mix was incubated for 2 minutes and then added to each well of BJ fibroblasts on Nuff feeders in PLURITON medium. The following day, the PLURITON media were changed before transfecting the same dose of mRNA using TransIT Boost and TransIT mRNA transfection reagent. Nuff-conditioned PLURITON medium was replaced by PLURITON medium on the sixth day of transfections. Unless otherwise indicated, a total of 18 transfections were performed for each reprogramming experiment.

Embryoid Body Spontaneous Differentiation Protocol

Some iPS colonies that were picked and passaged multiple times (at least 5 times) were processed for embryoid body spontaneous differentiation as previously described (Huangfu et al., 2008). Briefly, the iPS colonies were dissociated with Collagenase IV and incubated for 8 days in low-binding 6-well dishes in iPSC medium (DMEM/F12 medium supplemented with 20% KNOCKOUT™ serum replacer, 0.1 mM L-glutamine, non-essential amino acids, and penicillin/streptomycin (all from Invitrogen). One half of the medium was changed every day during the 8 day period. After eight days in suspension culture, the embryoid bodies were transferred to gelatin-coated 6-well dishes in the same medium (DMEM/F12 medium supplemented with 20% KNOCKOUT™ serum replacer, 0.1 mM L-glutamine, non-essential amino acids, and penicillin/streptomycin) and incubated for an additional 8 days. The cultures were washed in PBS and then fixed in 4% paraformaldehyde in PBS for 30 minutes are room temperature. The cells were then stained using antibodies that recognize Desmin (Thermo Scientific, Fremont, CA), α-Smooth muscle actin (SMA) (Sigma, St. Louis MO), Alpha fetoprotein (AFP) (Sigma, St. Louis MO), SOX17 (R&D Systems, Minneapolis, MN), and Class III beta-tubulin (Covance, Emeryville, CA). These primary antibodies were recognized with the secondary antibody anti-mouse 555 fluorescent antibody (Cell Signaling Technologies, Danvers, MA). Images were taken on a TS100 epifluorescent Nikon Microscope.

Alkaline Phosphatase Staining as an iPS Cell Marker

Cells are washed once in 1×PBS, followed by fixing in 4% paraformaldehyde in PBS for 5 minutes. The cell were then washed two times in PBS followed by two washes in TBST (25 mM Tris, pH 7.5, 150 mM NaCl, 0.5% TWEEN™ 20). The cells were then washed in AP Buffer (0.1 M Tris, pH 9.5, 0.1 M NaCl, 5 mM $MgCl_2$). Then 132 microliters of 50 mg/ml nitroblue tetrazolium (NBT) in 70% dimethylformamide (DMF) and 64 microliters of 50 mg/ml bromochloro-indolyl phosphate (BCIP) in 100% dimethylformamide (DMF) were added to each 20 mls of AP buffer, which was then added to the cells for 5-10 minutes until stain developed. Once the purple color developed, the cells were washed at least three times with TBST, and optionally two times with 1×PBS, and stained colonies were counted, or stored in PBS for imaging and colony counting.

Live Cell Immunostaining of iPSC Colonies with Tra-1-60

TRA-1-60 is considered to be one relatively stringent marker of fully reprogrammed iPS cells (Chan et al. 2009). The Tra-1-60 live cell imaging was done with the StainAlive Dylight™ 488 Mouse anti-Human Tra-1-60 antibody (Stemgent) according to the manufacturer's specifications. Briefly, a sterile, TRA-1-60 antibody (StainAlive™ DyLight™ 488 anti-human TRA-1-60 antibody; Stemgent) was diluted 1:100 in reprogramming medium. On day 18 of the reprogramming protocol, the medium was removed and the cells were incubated in TRA-1-60-containing media for 30 minutes at 37° C. with 5% $CO_2$. The cells were then washed twice with medium to remove the unbound antibody and the cells were maintained in fresh reprogramming medium during immunofluorescent imaging. This antibody allows live cell staining, instead of fixing the cells and sacrificing them for the imaging.

Methods for Fixed Cell Immunostaining of iPSCs iPSC colonies were washed twice in 1× phosphate-buffered solution (PBS) and fixed in 4% paraformaldehyde in PBS at room temperature for half an hour. After 3 washes in 1×PBS, cells were washed 3 times in wash buffer, (PBS with 0.1% Triton-X100), and blocked for one hour at room temperature in blocking solution, 0.1% triton-X100, 1% BSA, 2% FBS in PBS. Primary antibodies were diluted 1:500 in blocking solution and applied to cells overnight at 4° C. Cells were washed 6 times in wash buffer. Secondary antibodies were diluted 1:1,000 in blocking buffer, were applied for 2 hours at room temperature in the dark. After 6 washes with wash buffer, cells were washed twice in 1×PBS before imaging. Primary antibodies used were:
OCT4 Rabbit Antibody (Santa Cruz Biotechnology); TRA-1-60 Mouse Antibody (Cell Signaling Technology); LIN28 Mouse Antibody (Cell Signaling Technology); NANOG Rabbit Antibody (Cell Signaling Technology); SSEA4 Mouse Antibody (Cell Signaling Technology); TRA-1-81 Mouse Antibody (Cell Signaling Technology); and DNMT 3B Rabbit Antibody (Cell Signaling Technology). Secondary antibodies used were: Alexa Fluor® 488 Anti-Rabbit (Molecular Probes, Life Technologies) and Alexa Fluor® 555 Anti-Mouse (Molecular Probes, Life Technologies).

Construction of DNA Templates for In Vitro Transcription of ssRNAs or mRNAs Encoding iPSC Reprogramming Factors (e.g., iPSC Reprogramming or Induction Factors)

Open reading frames (ORFs) of human most human genes (e.g., KLF4, LIN28, NANOG, OCT4. SOX2) were PCR-amplified from cDNA clones (e.g., Open Biosystems, Huntsville, AL), or, in some cases, the ORF of certain genes were obtained by RT-PCR from cell total RNA (e.g., c-MYC ORF was obtained by RT-PCR from HeLa cell total RNA), cloned into a pUC-based plasmid vector downstream of a T7 RNA polymerase promoter (Mackie 1988, Studier and Moffatt 1986), and sequenced to confirm the accuracy of the cloned ORF. In some preferred embodiments, the above ORFs were ligated into EcoRV (for c-MYC) or EcoRV/SpeI (for KLF4, LIN28, NANOG, OCT4, and SOX2) sites between the 5' and 3' Xenopus laevis beta-globin untranslated regions described (Krieg and Melton 1984).

In some specific embodiments, the pUC19-based vector was modified by inserting a T7 promoter followed by the 5' UTR of Xenopus laevis β-globin, a multiple cloning site consisting of restriction sites BglII, EcoRV and SpeI for insertion of a gene of interest, and finally the 3' UTR of Xenopus laevis β-globin. Plasmids were linearized with SalI prior to in vitro transcription; for example the T7 RNA polymerase promoter (underlined/bold), 5' and 3' Xenopus laevis beta-globin UTRs (underlined/italics), and the SalI restriction site (GTCGAC/underlined) are depicted in SEQ ID NO. 1. The pUC19-based DNA plasmids comprising SEQ ID NO. 1 with DNA inserts encoding an iPSC induction factor [e.g., OCT4 (SEQ ID NO. 2), SOX2 (SEQ ID NO. 3), KLF4 (SEQ ID NO. 4), LIN28 (SEQ ID NO. 5), NANOG (SEQ ID NO. 6) and MYC; e.g., either cMYC wild-type long (SEQ ID NO. 7), cMYC(T58A) short (SEQ ID NO. 8), cMYC wild-type short (SEQ ID NO. 9), or L-MYC (SEQ ID NO. 10) mRNA] were each linearized by overnight incubation with SalI, and then purified by phenol/chloroform or phenol/chloroform/isoamyl alcohol extraction. The linear DNA was precipitated with sodium acetate/ethanol precipitation followed by a 70% ethanol wash. Linear DNA was reconstituted in water and run on an agarose gel to check that the plasmid was fully linearized. The SalI-treated plasmid DNAs were reconstituted in water and run on an agarose gel to check that all of each plasmid was linearized for use in in vitro transcription. Then the linearized plasmid was used as a template for in vitro transcription as described herein.

In Vitro Synthesis of mRNAs Encoding iPSC Induction Factors for Reprogramming

The T7 mSCRIPT™ mRNA production system (CELLSCRIPT, INC, Madison, WI, USA) was used to produce unmodified mRNA with a 5' Cap1 structure and a 3' poly(A) tail (e.g., with approximately 150 A residues). The T7 mSCRIPT™ mRNA production system was also used to produce pseudouridine- and or 5-methylcytidine-modified mRNA with a 5' cap 1 structure and a 3' poly(A) tail (e.g., with approximately 150 A residues), except that pseudouridine-5'-triphosphate (TRILINK, San Diego, CA or CELLSCRIPT, INC.) or 5-methylcytidine-5'-triphosphate (TRILINK, San Diego, CA) was used in place of uridine-5'-triphosphate or cytidine-5'-triphosphate, respectively, in the in vitro transcription reactions. For example, the linearized templates were used for in vitro transcription as described in the literature provided with the T7 mSCRIPT™ standard mRNA production system (CELLSCRIPT, INC., Madison, WI, USA), as follows: 1 microgram of linear DNA template was used in 1× reactions along with 2 microliters of 10× T7-SCRIBE™ transcription buffer, 1.8 microliters of 100 mM ATP, 1.8 microliters of 100 mM CTP or $m^5CTP$ (Trilink Biotechnologies, San Diego, CA), 1.8 microliters of 100 mM GTP, 1.8 microliters of 100 mM UTP or 4P (CELLSCRIPT), 2 microliters of 100 mM DTT, 0.5 microliter SCRIPTGUARD™ RNase inhibitor, and 2 microliters T7-SCRIBE™ enzyme solution.

Following in vitro transcription (IVT), the DNA templates were digested with DNase I and then in vitro-transcribed mRNAs were cleaned up by phenol-chloroform extraction and ammonium acetate precipitation as described in the RNA Quick Cleanup Method section. Briefly, the in vitro transcription reactions were incubated at 37° C. for 1 hour followed by adding 1 microliter of RNase-free DNase I and incubating for 15 additional minutes at 37° C. The RNA is precipitated by adding an equal volume of 5M ammonium acetate followed by incubation on ice for 10 minutes. Then the RNA is pelleted by spinning at 13,000 rpms for 10 minutes. The pellet is washed with 70% ethanol and resuspended in water.

The in vitro-transcribed mRNAs were then treated with RNase III as described in the RNase III treatment method section, after which the mRNAs were again cleaned up as described in the RNA Quick Cleanup Method section.

Each of the mRNAs was then capped to cap1 mRNA (or in other embodiments, to cap0 mRNA) using the SCRIPT-CAP™ capping enzyme and the SCRIPTCAP™ 2'-O- methyl-transferase enzymes (or for cap0 mRNA, only the SCRIPTCAP™ capping enzyme) as described in the T7 mSCRIPT™ standard mRNA production system: Briefly, 60 micrograms of in vitro-transcribed RNA was added to 10 microliters of SCRIPTCAP™ capping buffer, 5 microliters of 20 mM GTP, 2.5 microliters of S-adenosyl-methionine (SAM), 2.5 microliters of SCRIPTGUARD™ RNase Inhibitor, 4 microliters of SCRIPTCAP™ 2'-O-Methyltransferase, 4 microliters of SCRIPTCAP™ capping enzyme, and water to 100 microliters. All capping reactions were incubated at 37° C. for 1 hour followed by going directly into the poly(A) tailing reaction.

Synthesis of Poly (A) Tailed mRNA was performed using the T7 m SCRIPT™ RNA production system (CELLSCRIPT, Inc.) as follows: 12 microliters of 10× A-Plus Tailing Buffer, 6 microliters of 20 mM ATP, 5 microliters of A-PLUS™ poly(A) polymerase, and 0.5 microliter of SCRIPTGUARD™ RNase inhibitor were added to the 100 microliters of 5'-capped in vitro-transcribed RNA and incubated at 37° C. for 30 minutes (to generate a poly(A) tail of approximately 150 bases) or for 1 hour (to generate a poly(A) tail of >200 bases. Capped and polyadenylated mRNAs were cleaned up as described in the RNA Quick Cleanup Method section or as otherwise described in the T7 mSCRIPT™ standard mRNA production system. Thus, reactions were terminated by two phenol/chloroform/isoamyl extractions followed by precipitation with an equal volume of 5M ammonium acetate. The mRNA/5M ammonium acetate mixes were spun at 13,000 rpm for 10 minutes, washed in 70% ethanol and resuspended in sterile water.

In some experiments, the in vitro-transcribed mRNAs encoding iPSC reprogramming factors were evaluated for expression following transfection of human cells. For example, in some experiments, in vitro-transcribed cap1, poly(A)-tailed (with ~150 A nucleotides) mRNAs made with pseudouridine-5'-triphosphate substituting for uridine-5'-triphosphate (Kariko et al., 2008) and encoding KLF4, LIN28, c-MYC, NANOG, OCT4 or SOX2 each resulted in expression and proper subcellular localization of each respective protein product in newborn fetal foreskin 1079 human fibroblasts. For example, in some experiments, 1079 fibroblasts were transfected with up to 4 micrograms of one of these mRNAs per well of a 6-well dish and then analyzed by immunofluorescence analysis 24 hours post-transfection. Briefly, the 1079 cells were washed with PBS and fixed in 4% paraformaldehyde in PBS for 30 minutes at room temperature, then washed 3 times for 5 minutes each wash with PBS followed by three washes in PBS+0.1% Triton X-100, blocked in blocking buffer (PBS+0.1% Triton, 2% FBS, and 1% BSA) for 1 hour at room temperature, and then incubated for 2 hours at room temperature with the primary antibody (e.g., mouse anti-human OCT4 Cat #sc-5279, Santa Cruz Biotechnology, Santa Cruz, CA; rabbit anti-human NANOG Cat #3580; rabbit anti-human KLF4 Cat #4038; mouse anti-human LIN28 Cat #5930; rabbit anti-human c-MYC Cat #5605; or rabbit anti-human SOX2 Cat #3579; all from Cell Signaling Technology, Beverly, MA) at a 1:500 dilution in blocking buffer. After washing 5 times in PBS+0.1% Triton X-100, the cells were incubated for 2 hours with anti-rabbit ALEXA Fluor 488 antibody (Cat #4412, Cell Signaling Technology), anti-mouse FITC secondary (Cat #F5262, Sigma), or an anti-mouse Alexa Fluor 555 (Cat #4409, Cell Signaling Technology) at 1:1000 dilutions in blocking buffer. Images were taken on a Nikon TS100F inverted microscope (Nikon, Tokyo, Japan) with a 2-megapixel monochrome digital camera (Nikon) using NIS-elements software (Nikon). Endogenous KLF4, LIN28, NANOG, OCT4 and SOX2 protein levels were undetectable by immunofluorescence in untransfected 1079 cells, although, in some cases, endogenous levels of c-MYC were relatively high in untransfected 1079 cells. Transfections with mRNAs encoding the transcription factors, KLF4, c-MYC, NANOG, OCT4, and SOX2 all resulted in primarily nuclear localization of each protein 24 hours after mRNA transfections, whereas the cytoplasmic mRNA binding protein, LIN28, was localized to the cytoplasm.

Example of Use of the In Vitro-Transcribed Capped and Poly(A)-Tailed mRNAs Encoding iPSC Reprogramming Factors for Reprogramming Human or Mouse Somatic Cells to iPS Cells Unless otherwise indicated for a particular experiment, the mRNA reprogramming factors used in methods for induction of iPSCs were diluted to 100 ng/ml and a mix was made containing the factors in a 3:1:1:1:1 molar ratio of OCT4/SOX2/KLF4/LIN28/MYC (e.g. cMYC, cMYC (T58A) or L-MYC), and aliquoted into aliquots containing about 1 to 1.4 micrograms of total RNA. For example, in one embodiment comprising use of 1.1 micrograms total per day per well of mRNA for reprogramming, was prepared in a 3:1:1:1:1 molar ratio of OCT4, SOX2, KLF4, LIN28 and c-MYC or c-MYC(T58A) by mixing the following volumes of a 100 ng/ml solution of each mRNA reprogramming factor: OCT4, 385.1 microliters; SOX2, 119.2 microliters; KLF4, 155.9 microliters; LIN28, 82.5 microliters; c-MYC or c-MYC(T58A), 147.7 microliters; plus 109.6 microliters of water, making a total volume of 1 ml. [Alternatively, in some embodiments, a portion of the water was replaced by an aqueous solution of mRNA encoding enhanced green fluorescent protein (EGFP) at 100 ng/ml as a transfection marker.]

RNA Quick Cleanup Method

The protocol below provides quick RNA cleanup method for removal of enzymes, nucleotides, small oligonucleotides, and other in vitro transcription (IVT) or RNase III treatment reaction components from RNA. It is not intended as a method for extensive purification of ssRNA or mRNA. This cleanup method comprises phenol-chloroform extraction followed by ammonium acetate precipitation to removes protein and selectively precipitate RNA, leaving residual undigested DNA and unincorporated nucleoside-5'-triphosphates in the supernatant. Without limiting the method with respect to specific RNA quantities purified or specific volumes of reagents, which can be scaled or adjusted, one embodiment of the method used with respect to the present invention is presented below.

1. Adjust a 20-microliter IVT reaction volume to 200 microliters total using RNase-Free Water (add 179 microliters to the reaction).
2. Add one volume (200 microliters) of TE-saturated phenol/chloroform. Vortex for 10 seconds.
3. Spin in a microcentrifuge at >10,000×g for 5 minutes to separate the phases.
4. Remove the aqueous (upper) phase with a pipette and transfer to a clean tube.
5. Add one volume (200 microliters) of 5 M ammonium acetate, mix well then incubate for 15 minutes on ice.
6. Pellet the RNA by centrifugation at >10,000×g for 15 minutes at 4 degrees C.
7. Remove the supernatant with a pipette and gently rinse the pellet with 70% ethanol.

8. Remove the 70% ethanol with a pipette without disturbing the RNA pellet.
9. Allow the pellet to dry, then resuspend in 50-75 microliters of RNase-free water and quantify the RNA by spectrophotometry or fluorimetry.

Example of an RNase III Treatment Method of the Present Invention

One hundred micrograms of in vitro-transcribed ssRNA, capped and/or polyadenylated ssRNA, or mRNA, which has preferably been cleaned up using the RNA Quick Cleanup Method described herein, is incubated in a 200-microliter reaction mixture containing 33 mM Tris-acetate (pH 8) as a buffer, 200 mM potassium acetate as a monovalent salt, and between about 1 mM and 4 mM (more preferably, about 2-3 mM, and most preferably 2 mM) magnesium acetate as the magnesium salt, and 20 nM RNAse III (CELLSCRIPT, INC., Madison, WI 53713) for 30 minutes at 37° C. Unless otherwise stated the ssRNAs were treated with RNase III using the RNase III treatment described herein with 1 or 2 mM magnesium acetate and 150 mM potassium acetate. However, in some experiments described herein, up to about 10 mM magnesium acetate was used for the RNase III treatment in order to evaluate the effect of different divalent magnesium cation concentrations on the activity of RNase III for dsRNA removal. (In some embodiments, the RNAse III treatment reactions also contain an RNase inhibitor (e.g., 0.8 units/microliter SCRIPTGUARD™ RNase inhibitor; CELLSCRIPT, INC.). The RNase III treatment reactions are stopped by the addition of EDTA to a concentration sufficient to complex the magnesium cations (e.g., 1 mM EDTA final if 1 mM magnesium acetate is used). In preferred embodiments, the ssRNA or mRNA is further cleaned up using the RNA Quick Cleanup method, which comprises extraction using TE-saturated phenol/chloroform, precipitation with 1 volume of 5 M ammonium acetate, and washing of the RNA pellet with 70% ethanol (as described herein for the RNA Quick Cleanup Method). In some embodiments, the RNase III-treated ssRNA or mRNA is then resuspended in water.

Example 1: Magnesium Cation Concentration During RNase III Treatment has Important Effects on ssRNA Integrity and the Completeness of RNase III Digestion of dsRNA One microgram of dsRNA was treated with 20 nanomolar RNase III in reaction buffers containing from 0 to 10 mM magnesium acetate in the buffer. The ideal treatment conditions would digest the 1671-nucleotide long dsRNA region of the transcript and leave two single-stranded RNA fragments of 255 and 136 nucleotides in length intact (FIG. 1).

Figure 2:
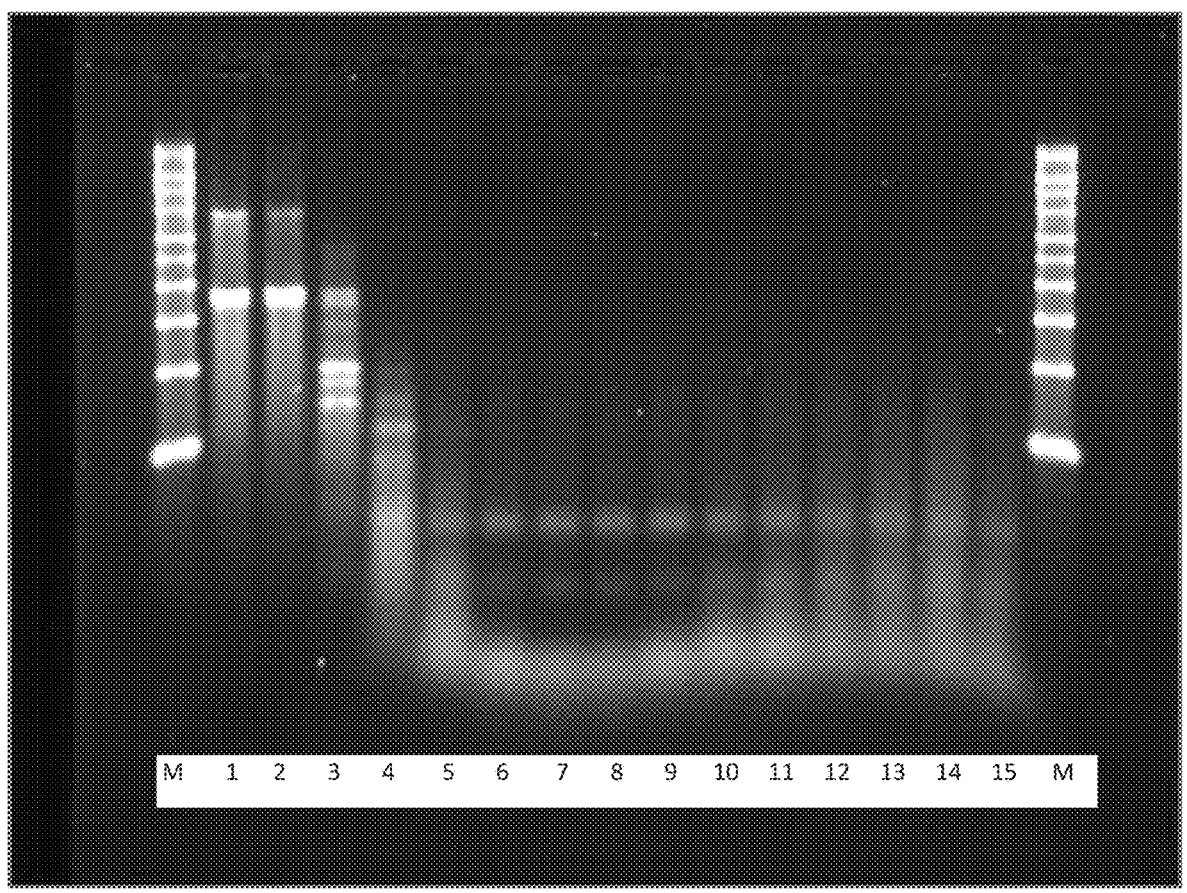
FIG. 2 shows that the ability of RNase III to digest dsRNA while maintaining the integrity of ssRNA varies based on the concentration of divalent magnesium cations in the reaction. The electrophoresis gel depicts digestion of one microgram of the RNA substrate shown in FIG. 1 by RNase III at a concentration of 20 nM in a reaction mixture containing 33 mM Tris-acetate, pH8, 200 mM potassium acetate and different concentrations of magnesium acetate ($Mg(OAc)_2$). Lane M) RNA millennium markers (0.5 kb, 1.0, 1.5, 2.0, 2.5, 3, 4, 5, 6, 9 kb); Lane 1): No RNase III control with the intact RNA substrate; Lanes 2)-15): RNase III+$Mg(OAc)_2$ at: 2) 0 mM; 3) 0.1 mM; 4) 0.25 mM; 5) 0.5 mM; 6) 1 mM; 7) 2 mM; 8) 3 mM; 9) 4 mM; 10) 5 mM; 11) 6 mM; 12) 7 mM; 13) 8 mM; 14) 9 mM; and 15) 10 mM.

As shown in FIG. 2, the dsRNA band was digested by the RNase III. Most importantly, the ssRNA bands were of the correct size and intact, based on minimal smearing below the bands, at magnesium acetate concentrations between about 1 and 4 mM. The fact that the amount of smearing below the ssRNA bands steadily increased, beginning at about 5 mM and steadily becoming worse as magnesium acetate concentrations increased to 10 mM, indicated that an optimal concentration of magnesium acetate for RNase III digestion was in the range of about 1 mM to about 4 mM, and more preferably about 1 mM to 3 mM. This was a big surprise, because those who had worked in the art on RNase III, at least as far as we are aware, had not taught that the concentration of magnesium acetate was important for the RNase III reaction, having stated that it could be used at broad range of concentrations up to 100 mM. Therefore, our observation that there was significant and increasing smearing of the ssRNA bands, particularly at magnesium acetate concentrations of 5 mM and above was surprising and unexpected. This result showed for the first time that a much lower divalent magnesium cation concentration than previously stated was needed in order to maintain the integrity of the ssRNA, and that the 10 mM concentration which had been used in the art was too high and led to significant degradation of ssRNA. Still further, as shown elsewhere herein, the digestion of dsRNA was incomplete when the RNase III treatment was performed using the 10 mM magnesium cation concentration, which was very surprising because this level of magnesium cations for RNase III digestion has been taught in the art for about 35 years without question or change.

Still further, as shown in EXAMPLE 9, the biological effectiveness of single-stranded modified mRNAs (e.g., pseudouridine-modified mRNAs) for expression of encoded proteins comprising iPSC reprogramming factors was greater if the modified mRNAs encoding the iPSC reprogramming factors were treated with the RNase III treatment using 2 mM $Mg^{2+}$ rather than 10 mM $Mg^{2+}$. Even more surprising, the effectiveness of RNase III-treated unmodified (GAUC) ssRNAs or mRNAs encoding iPS cell induction factors that were treated with the RNase III using 2 mM $Mg^{2+}$ rather than 10 mM $Mg^{2+}$ were very different—with no iPS cells being induced using 10 mM $Mg^{2+}$, but many iPS cells being induced by the mRNAs that were treated with RNase III using 2 mM $Mg^{2+}$ (e.g., EXAMPLE 10).

Example 2: The Effects of Divalent Magnesium Cation Concentration on the Completeness of RNase III Digestion of dsRNA is Detectable Using dsRNA-Specific Monoclonal Antibody J2

Different known amounts of a dsRNA substrate were digested with using the RNase III treatment in the presence of different concentrations of divalent magnesium cations and then the amounts of detectable dsRNA remaining were analyzed by dot blot assays using the dsRNA-specific monoclonal Antibody J2.

As was previously reported (Leonard et al., 2008), dsRNA stretches of 40-bps or more are needed to dimerize TLR3s to elicit an innate immune response. Antibody J2 can recognize dsRNA of 40-bps or more. Accordingly, the J2 monoclonal antibody was chosen because it can recognize only biologically relevant sizes of dsRNA that will induce interferon production through activation of TLR3.

Figure 3:
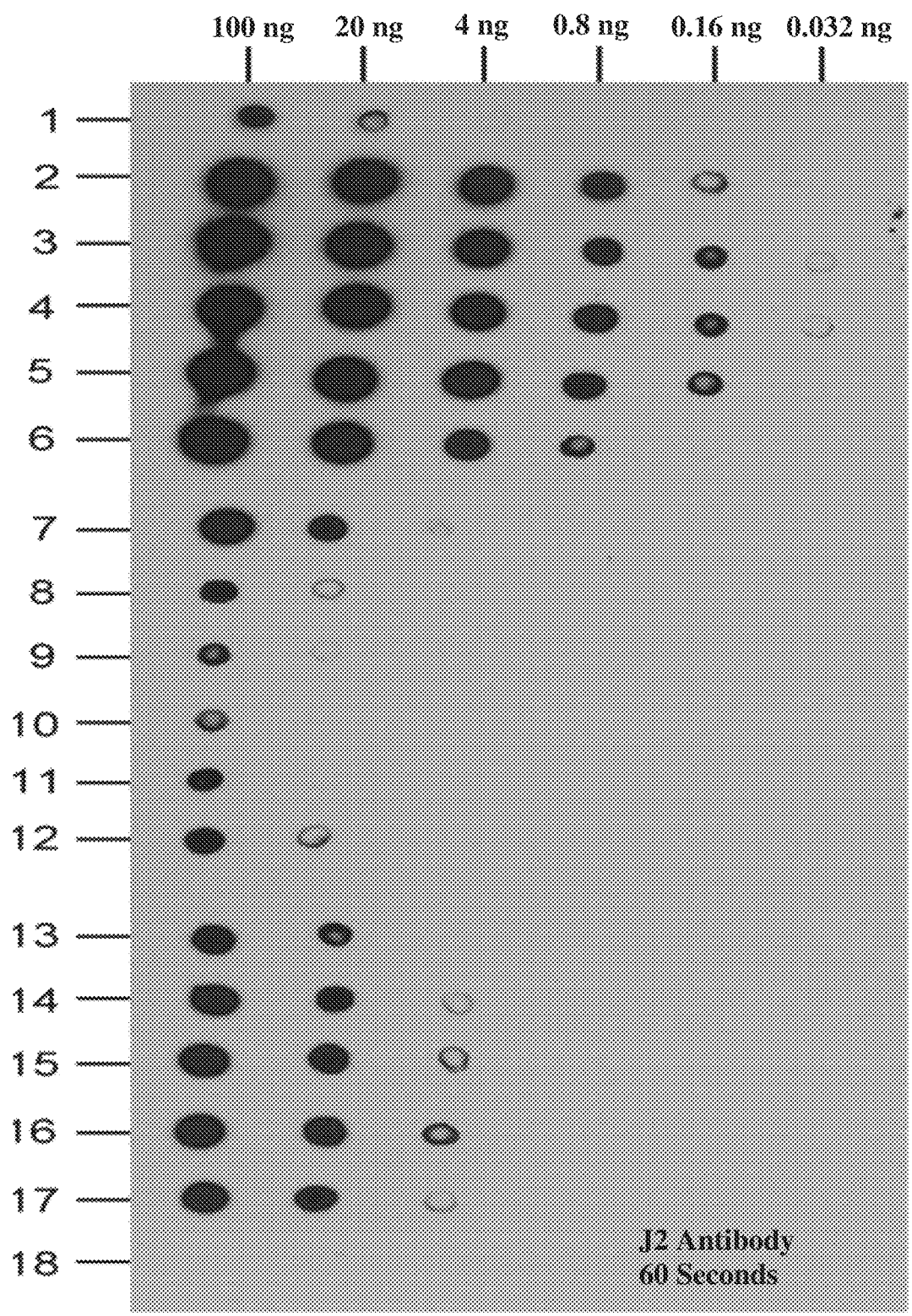
FIG. 3 shows that digestion of different starting amounts of Luc2 dsRNA by RNase III, as detected on dot blots using the dsRNA-specific monoclonal Antibody J2, varies with the [$Mg^{2+}$] used for RNase III treatment. Row: 1) Poly I:C; 2) LIN28 dsRNA; 3) Luc2 dsRNA minus RNase III plus 1.0 mM $Mg(OAc)_2$; Rows 4)-17) depict Luc2 dsRNA plus RNase III plus $Mg(OAc)_2$ at: 4) 0 mM; 5) 0.1 mM; 6) 0.25 mM; 7) 0.5 mM; 8) 1 mM; 9) 2 mM; 10) 3 mM; 11) 4 mM; 12) 5 mM; 13) 6 mM; 14) 7 mM; 15) 8 mM; 16) 9 mM; 17) 10 mM; Row: 18) cMYC mRNA plus RNase III plus 1 mM $Mg(OAc)_2$.

The dot blot assay results, as depicted in FIG. 3, show that the digestion of dsRNA contaminants by RNase III varied with the concentration of divalent magnesium cations present in the reaction. In this case, most of the dsRNA contaminant was digested at a final concentration of magnesium acetate less than about 5 mM, and digestion appeared to be complete between about 2 mM and about 4 mM of divalent magnesium cations.

Example 3: Effect of $Mg^e$ Cation Concentration on Completeness of dsRNA Digestion by RNase III Compositions as Detected Using dsRNA-Specific Monoclonal Antibody K1

Samples containing different known amounts of dsRNA were treated with RNase III in the presence of varying amounts of divalent magnesium cations and then analyzed by dot blot assay for the amount of dsRNA remaining using the monoclonal antibody K1 after RNase III treatment.

As discussed in EXAMPLE 2, dsRNA stretches of 40 bps or more are needed to dimerize TLR3s to elicit an innate immune response. Similar to the J2 monoclonal antibody, monoclonal antibody can recognize dsRNA of 40-bp or more. Accordingly, this antibody was chosen because it can recognize only biologically relevant dsRNA pieces that will induce interferon production through activation of TLR3.

Figure 4:
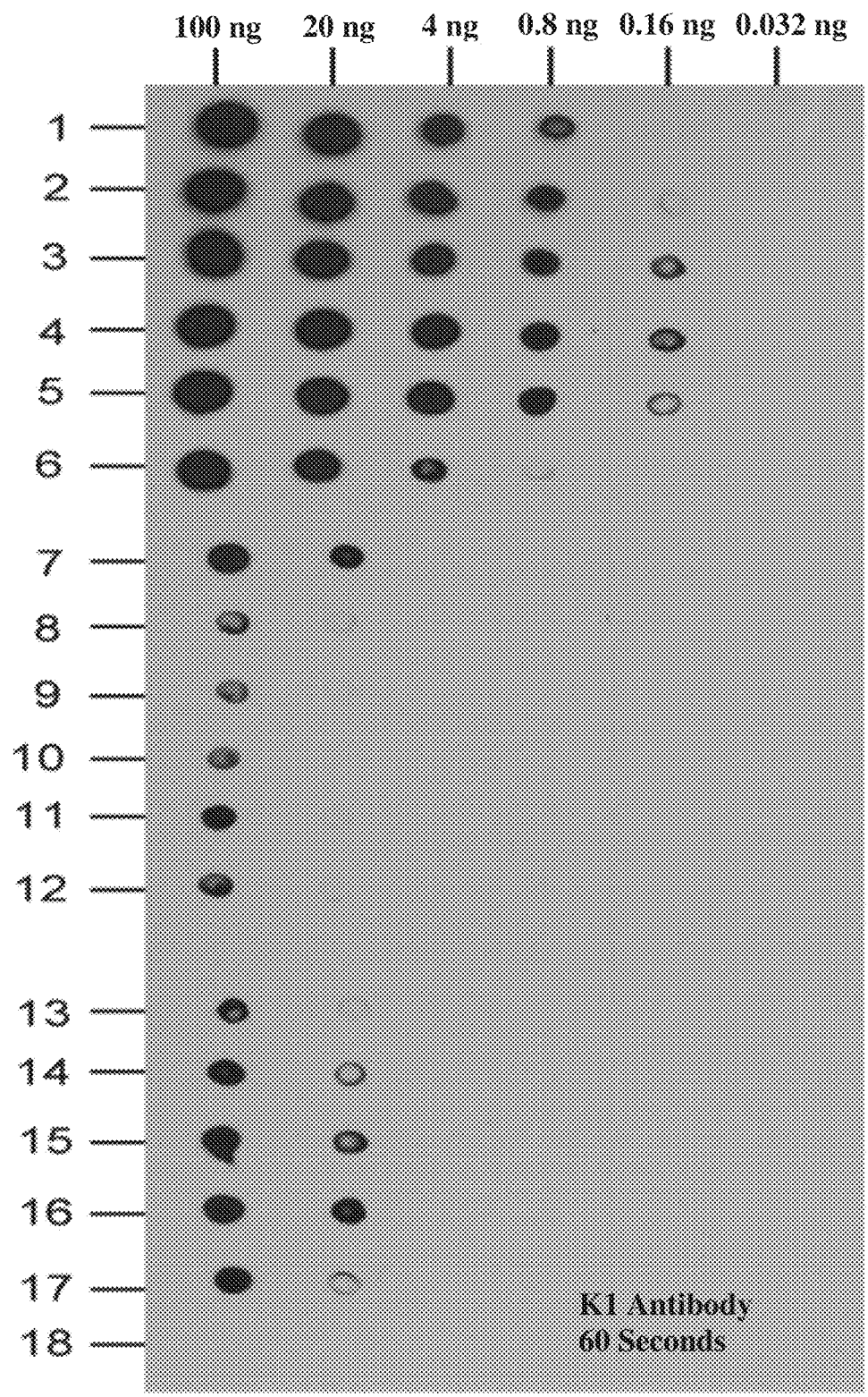
FIG. 4 shows that digestion of different starting amounts of Luc2 dsRNA by RNase III, as detected on dot blots using the dsRNA-specific monoclonal Antibody K1, also varies with the [$Mg^{2+}$] used for RNase III treatment. Row: 1) Poly I:C; 2) LIN28 dsRNA; 3) Luc2 dsRNA minus RNase III plus 1.0 mM $Mg(OAc)_2$; Rows 4)-17) depict Luc2 dsRNA plus RNase III plus $Mg(OAc)_2$ at: 4) 0 mM; 5) 0.1 mM; 6) 0.25 mM; 7) 0.5 mM; 8) 1 mM; 9) 2 mM; 10) 3 mM; 11) 4 mM; 12) 5 mM; 13) 6 mM; 14) 7 mM; 15) 8 mM; 16) 9 mM; 17) 10 mM; and Row: 18) cMYC mRNA plus RNase III plus 1 mM $Mg(OAc)_2$.

The results, as depicted in FIG. 4, shows that the ability to digest dsRNA contaminants varied based upon the concentration of divalent magnesium cations used for the RNase III treatment. Using the K1 antibody, digestion of the dsRNA contaminant appeared to be almost complete at a final concentration of magnesium acetate between about 1 mM and 5 mM magnesium acetate, and digestion of the dsRNA appeared to be complete at between about 2 mM and 4 mM magnesium acetate.

Example 4: Effects of RNase III Treatment on Small (255-Nucleotide or 156-Nucleotide) and Large (955-Nucleotide) ssRNA Transcript Integrity and Degree of dsRNA Digestion with Different Concentrations of $Mg^{+2}$ One microgram of the RNA substrate comprising both 1671-basepair dsRNA and 255- and 136-nucleotide ssRNA portions, and a 955-nucleotide ssRNA control transcript were mixed and treated with 20 nanomolar RNase III in reaction buffers containing from 0 to 10 mM magnesium acetate. Ideally, the reaction would digest the 1671-basepair dsRNA portion of the RNA substrate and leave the 255-nucleotide and 136-nucleotide single-stranded RNA termini of this RNA substrate and the 955-nucleotide ssRNA control transcript undigested and intact.

Figure 5:
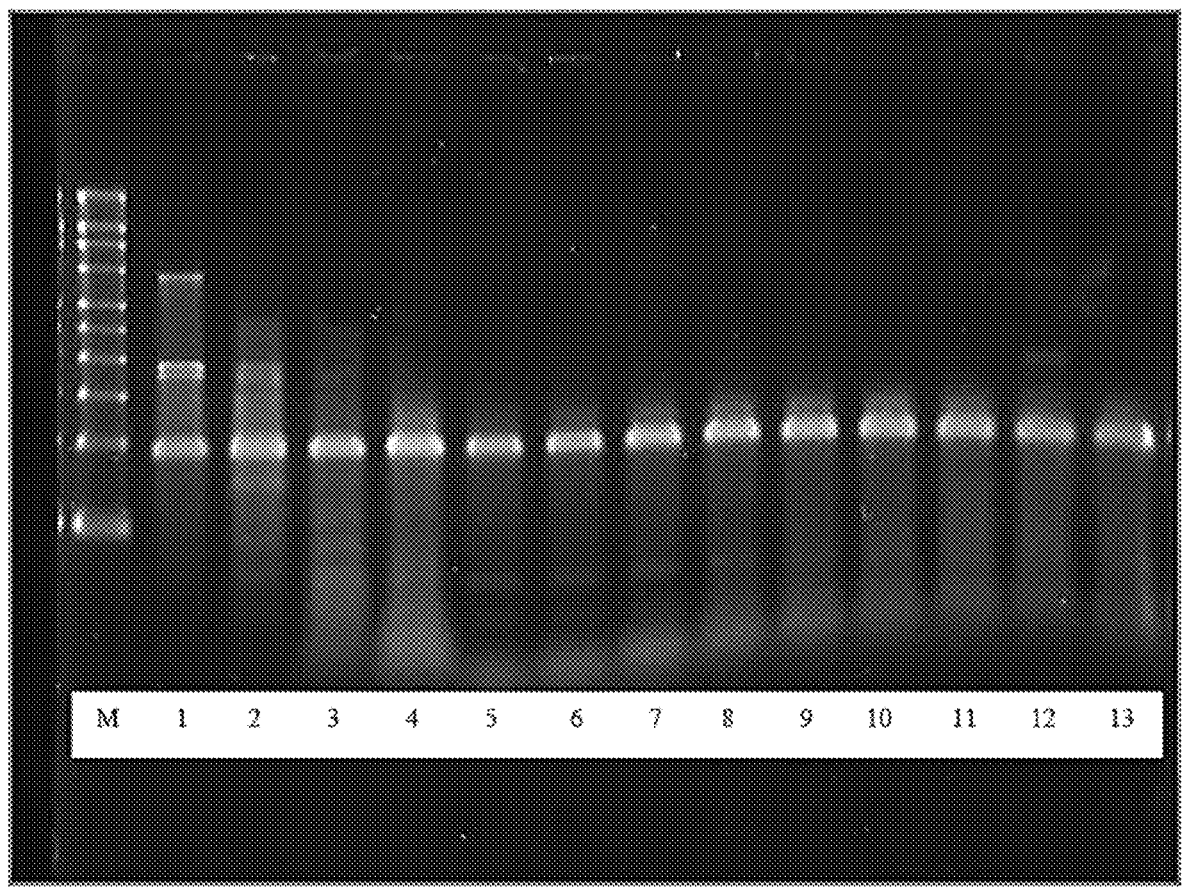
FIG. 5 shows that RNase III treatment can effectively digest dsRNA without affecting the integrity of either small (255-nt and 156-nt) or large (955-nt) ssRNA present in the same composition. The electrophoresis gel shows RNase III digestion of a mixture of the RNA substrate comprising a 1671-bp dsRNA region and 255-base and 136-base ssRNA tails and a 955-nucleotide ssRNA substrate in the presence of different concentrations of $Mg(OAc)_2$. Lanes M) RNA millennium markers (0.5, 1.0, 1.5, 2.0, 2.5, 3, 4, 5, 6, 9 Kb); Lanes 1)-13) RNase III in the presence of $Mg(OAc)_2$ at: 1) 0 mM; 2) 0.1 mM; 3) 0.25 mM; 4) 1 mM; 5) 2 mM; 6) 3 mM; 7) 4 mM; 8) 5 mM; 9) 6 mM; 10) 7 mM; 11) 8 mM; 12) 9 mM; and 13) 10 mM.

As can be seen from the results in FIG. 5, the ability to digest dsRNA contaminants while maintaining the integrity of both small and large ssRNA varied based upon the concentration of the divalent magnesium cation present in the reaction. In this case, an optimal dsRNA contaminant digestion occurred when the final concentration of magnesium acetate was between about 1 and 4 mM divalent magnesium, and preferably, between about 2 mM and about 3 mM divalent magnesium. At these concentrations of divalent magnesium cation, the dsRNA portion of the RNA substrate was approximately completely digested and minimal smearing of the ssRNA bands was observed on the gel, evidence that both ssRNA transcripts remained preserved and intact.

Example 5: Example of Analyses Performed to Evaluate the Effects of [Mg+2] in the Presence of Different Monovalent Salts, in this Case 200 mM Potassium Glutamate, on RNase III Activity on dsRNA and ssRNA, Including Effects on Completeness of dsRNA Digestion and Integrity of ssRNA One microgram of both dsRNA and ssRNA transcripts was treated with 20 nanomolar RNase III in reaction mixture containing 33 mM Tris-acetate, pH 8, 200 mM potassium glutamate (in place of potassium acetate) and varying concentrations of divalent cation ranging from 0 to 10 mM magnesium acetate.

Figure 6:
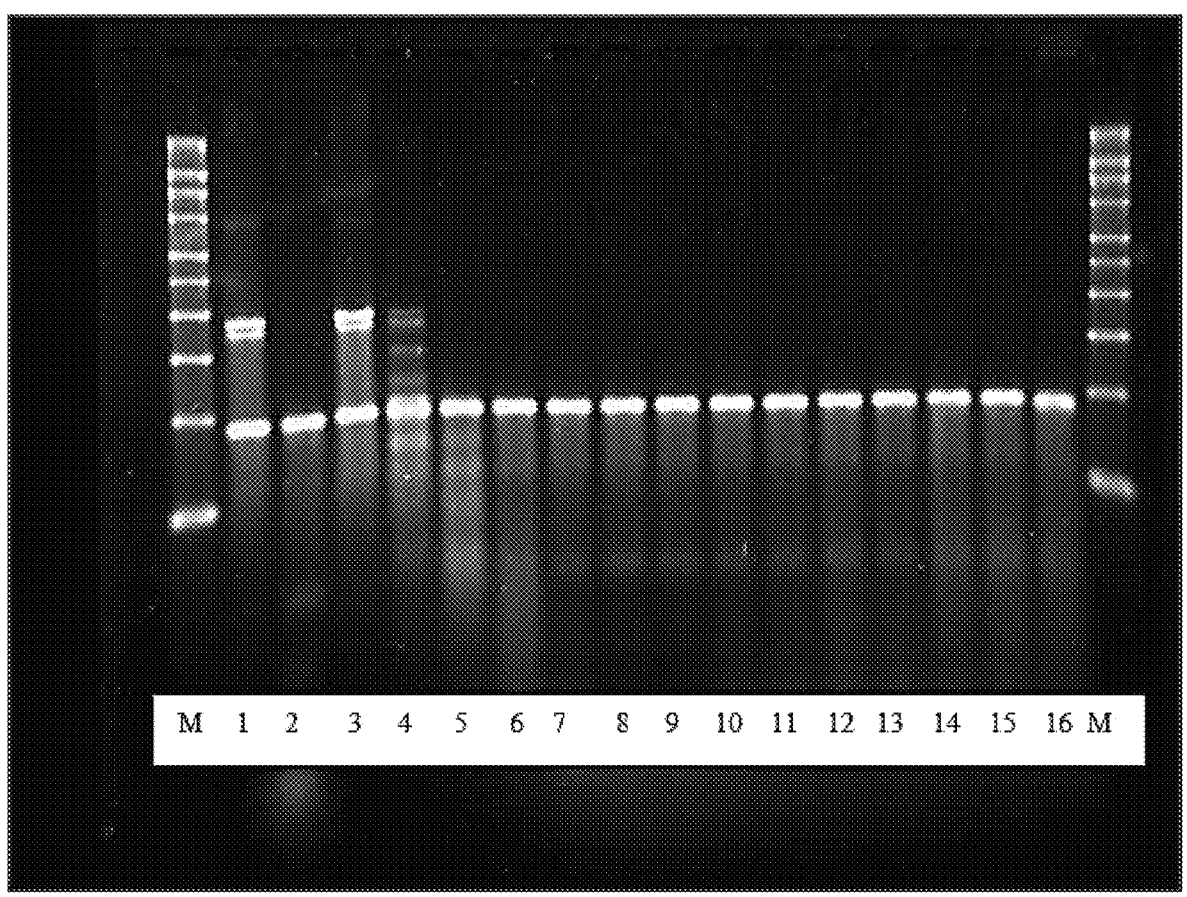
FIG. 6 shows an analyses performed on the effects of different concentrations of $Mg(OAc)_2$ on completeness of dsRNA digestion and integrity of ssRNA when the RNase III treatment was performed using 200 mM potassium glutamate as a monovalent salt. This is an example of one type of analysis which was also performed with other monovalent salts The electrophoresis gel shows RNase III digestion of a mixture of the RNA substrate comprising a 1671-bp dsRNA region and 255-base and 136-base ssRNA tails and a 955-nucleotide ssRNA substrate in the presence of different concentrations of $Mg(OAc)_2$. Lane M) RNA millennium markers (0.5, 1.0, 1.5, 2.0, 2.5, 3, 4, 5, 6, 9 Kb); Lane 1) No-RNase III control with standard pH 8 Tris-OAc buffer+KOAc salt; Lane 2) RNase III in standard pH 8 Tris-OAc buffer+1 mM $Mg(OAc)_2$+KOAc salt; Lanes 3)-16) RNase III in standard pH 8 Tris-OAc buffer+200 mM Kglutamate salt in the presence of $Mg(OAc)_2$ at: 3) 0 mM; 4) 0.1 mM; 5) 0.25 mM; 6) 0.5 mM; 7) 1 mM; 8) 2 mM; 9) 3 mM; 10) 4 mM; 11) 5 mM; 12) 6 mM; 13) 7 mM; 14) 8 mM; 15) 9 mM; and 16) 10 mM.

As can be seen from the results in FIG. 6, RNase III treatment is capable of effectively digesting dsRNA contaminants while maintaining the integrity of the ssRNA using different monovalent salts, in this case, potassium glutamate in place of potassium acetate. In the present EXAMPLE 5, optimal reactions included between about 1 and about 5 mM final concentration of magnesium acetate, and more preferably between about 2 and about 4 mM final concentration of magnesium acetate.

Figure 7:
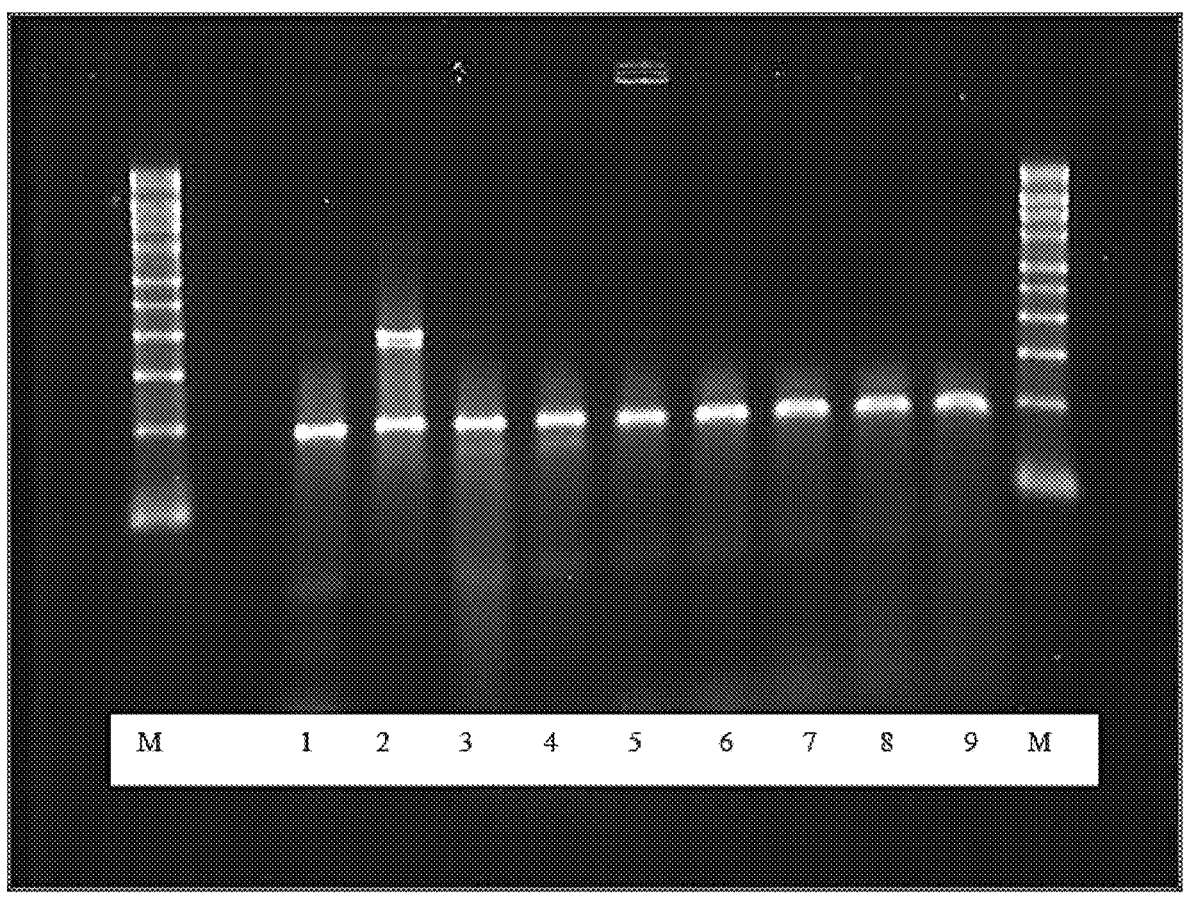
FIG. 7 shows the activity of RNase III on a mixture of both dsRNA and ssRNA substrates in the presence of 1 mM $Mg(OAc)_2$ and different concentrations of potassium glutamate as the monovalent salt. Lane M) RNA millennium markers (0.5, 1.0, 1.5, 2.0, 2.5, 3, 4, 5, 6, 9 Kb); Lane 1) 20 nM RNase III in standard pH 8 Tris-OAc buffer+1 mM $Mg(OAc)_2$+200 mM KOAc salt; Lane 2) No-RNase III control with standard pH 8 Tris-OAc buffer+1 mM Mg(OAc)$_2$+200 mM KOAc salt; Lanes 3)-9) RNase III in standard pH 8 Tris-OAc buffer+1 mM Mg(OAc)$_2$+Kglutamate salt at: 3) 0 mM; 4) 50 mM; 5) 100 mM; 6) 150 mM; 7) 200 mM; 8) 250 mM; and 9) 300 mM.

Example 6: Effect of RNase III on ssRNA Integrity and Degree of dsRNA Digestion Using 1 mM $Mg^{+2}$ and Different Concentrations of Potassium Glutamate In reactions containing both dsRNA and ssRNA transcripts, the concentration of potassium glutamate in the reaction was increased from 0 to 300 mM final concentration. Each reaction contained 20 nM RNase III, 33 mM Tris-acetate, 1 mM magnesium acetate and varying amounts of potassium glutamate. As can be seen in FIG. 7, RNase III exhibits superior binding patterns and contaminant digestion at specific concentrations of potassium glutamate salt. At this concentration of magnesium acetate, the dsRNA appeared to be approximately completely digested and the ssRNA was not significantly digested at all concentrations of potassium glutamate concentrations tested.

Example 7: Effect of the RNase III Treatments of dsRNA or ssRNA Substrates in Separate Reactions Comprising 1 mM Final Concentration of $Mg^{+2}$ and Varying Concentrations of Potassium Acetate as the Monovalent Salt Either dsRNA substrates or a ssRNA substrate were treated in separate reactions with RNase III in reaction mixtures containing 20 nM RNase III, 33 mM Tris-acetate, 1 mM magnesium acetate and varying final concentrations of potassium acetate between 0 and 300 mM.

Figure 8:
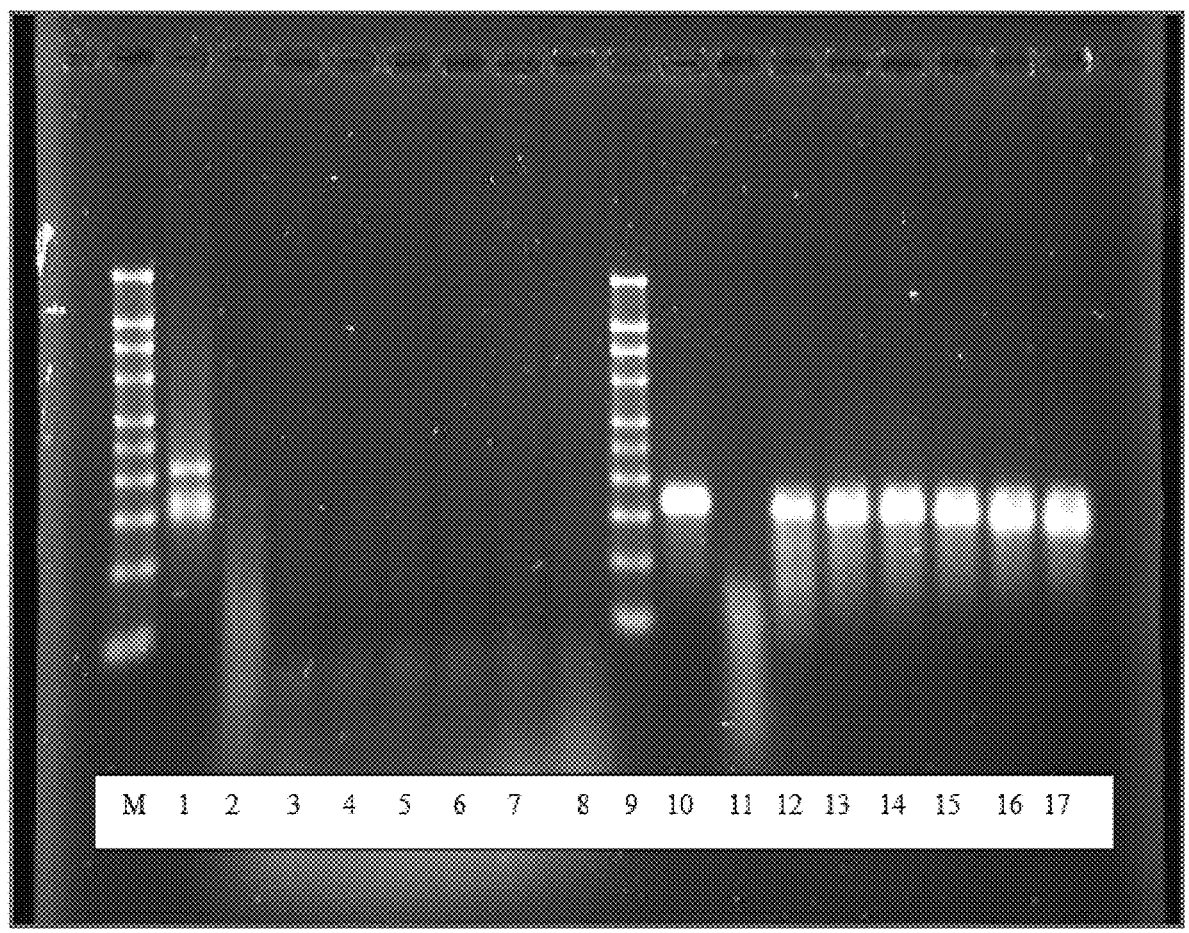
FIG. 8 shows the activity of RNase III in separate reactions containing either a dsRNA substrate (lanes 1-8) or a ssRNA substrate (lanes 10-17) in the presence of 1 mM Mg(OAc)$_2$ and different concentrations of potassium acetate (KOAc) salt. Lanes M) and 9) RNA millennium markers (0.5, 1.0, 1.5, 2.0, 2.5, 3, 4, 5, 6, 9 Kb); Lane 1) dsRNA substrate in no-RNase III control in standard pH 8 Tris-OAc buffer+1 mM Mg(OAc)$_2$+200 mM KOAc salt; Lanes 2)-8) dsRNA substrate+RNase III in standard pH 8 Tris-OAc buffer+1 mM Mg(OAc)$_2$+KOAc salt at: 2) 0 mM; 3) 50 mM; 4) 100 mM; 5) 150 mM; 6) 200 mM; 7) 250 mM; and 8) 300 mM; Lane 10) ssRNA substrate in no-RNase III control in standard pH 8 Tris-OAc buffer+1 mM Mg(OAc)$_2$+200 mM KOAc salt; Lanes 11)-17) ssRNA substrate+RNase III in standard pH 8 Tris-OAc buffer+1 mM Mg(OAc)$_2$+KOAc salt at: 11) 0 mM; 12) 50 mM; 13) 100 mM; 14) 150 mM; 15) 200 mM; 16) 250 mM; and 17) 300 mM.

As can be seen in FIG. 8, at a final concentration of 1 mM $Mg^{2+}$ cations, RNase III effectively digested the dsRNA substrate, but did not digest the ssRNA, at all concentration of potassium acetate between 50 and 300 mM final concentration. By comparing results such as those shown in this FIG. 8 and previous FIG. 7, the applicants concluded that a compound such as a monovalent salt is generally needed to maintain ionic strength, but, provided the final concentration is sufficient (e.g., at least about 50 mM final concentration), neither the identity nor the concentration of monovalent salt significantly affects the activity of RNase III on dsRNA or its specificity for dsRNA. This was surprising and unexpected in view of previous publications in the art which had advised that the concentration of monovalent salt was an important variable to optimize in order to affect the activity and specificity of RNase III for dsRNA. Without being bound by theory, the present applicants believe that the function of the monovalent salt with respect to the RNase III digestion is to maintain sufficient ionic strength to stabilize basepairing of dsRNA regions in the RNA, so that those dsRNA are not denatured during the RNase III treatment. As discussed elsewhere herein, contrary to what has previously been taught in the art, the applicants discovered that the final concentration of divalent magnesium cations is very important for the optimal activity and specificity of RNase III for dsRNA and that the final concentration of magnesium cations for optimal activity and specificity of RNase III for dsRNA is preferably about 1-4 mM, most preferably about 2-3 mM, which is much lower than previously taught in the art.

Figure 9:
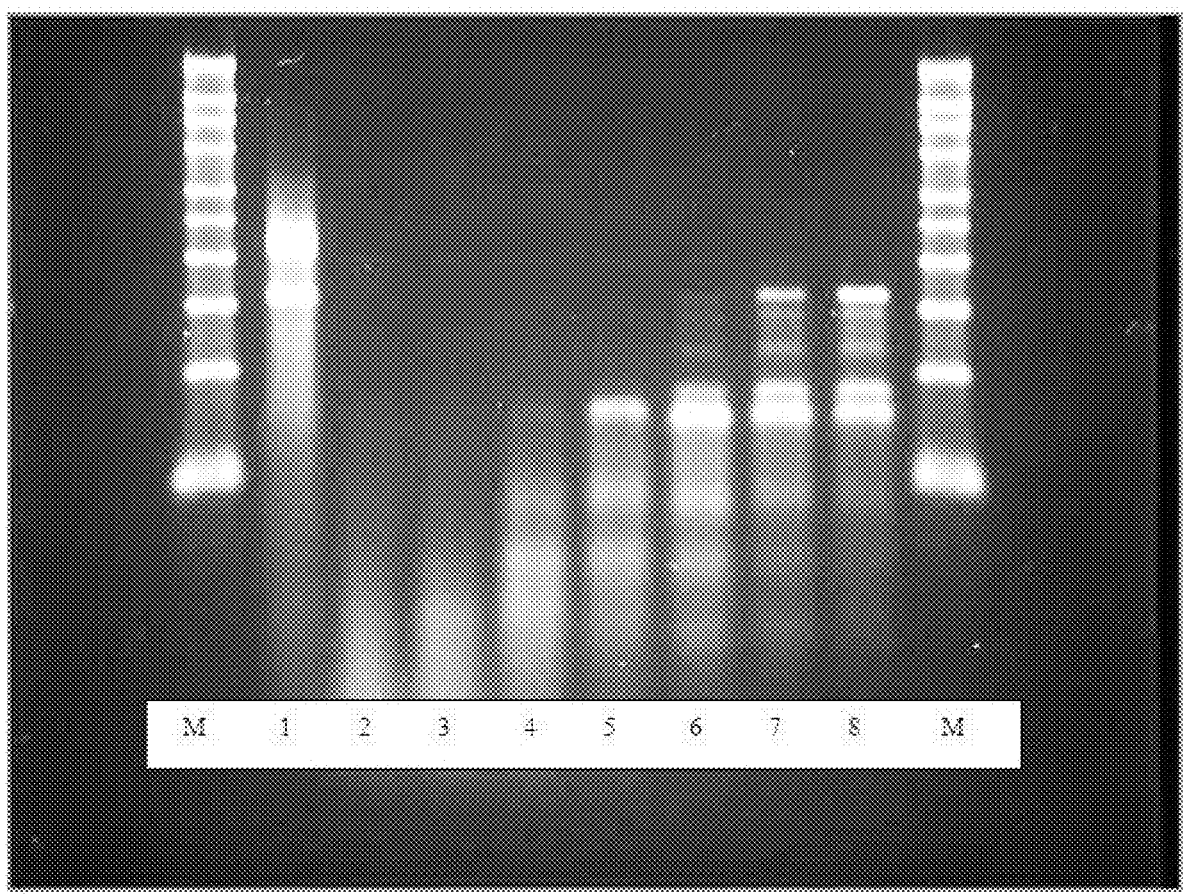
FIG. 9 shows the completeness of digestion of a dsRNA substrate by RNase III treatment in a reaction mixture consisting of 20 nM RNase III in 33 mM Tris-OAc buffer, pH 8, with 200 mM KOAc as the monovalent salt and 1 mM Mg(OAc)$_2$ for 10 minutes at 37° C., when the amount of dsRNA was varied from 1 microgram up to 20 micrograms. Lane M) RNA millennium markers (0.5, 1.0, 1.5, 2.0, 2.5, 3, 4, 5, 6, 9 Kb); Lane 1) 1 microgram dsRNA substrate in no-RNase III control in standard Tris-OAc buffer, pH 8+1 mM Mg(OAc)$_2$+200 mM KOAc salt; Lanes 2)-8)+RNase III and dsRNA at: 2) 1 microgram; 3) 2 micrograms; 4) 4 micrograms; 5) 8 micrograms; 6) 12 micrograms; 7) 16 micrograms; and 8) 20 micrograms.

Example 8: Effect of RNase III Treatment on ssRNA Integrity and Degree of dsRNA Digestion with Increasing Amounts of dsRNA Added to the Reaction Mixture The amount of dsRNA that can be digested in a 10 minute, 37° C. incubation with 20 nM RNase III was sequentially increased from one microgram (at a concentration of 20 ng/microliter final) to 20 micrograms (400 ng/microliter final). The reaction mixture contained 33 mM Tris-acetate, pH 8, 200 mM KOAc and 1 mM magnesium acetate. From the results in FIG. 9, only 1 microgram to 2 micrograms of dsRNA could be digested under these reaction conditions. One microgram of ssRNA is used in the RNase III treatment method described herein in order to assure complete digestion of dsRNA avoid any potential for insufficient RNase III due to a particular sample containing higher levels of dsRNA. However, those with knowledge will understand that less RNase III can be used and will understand that one could do a similar titration to that described here in order to determine the amount of RNase III needed for particular types of samples.

Example 9: Effect of RNase III Treatments in the Presence of Different Levels of Divalent Magnesium Cations on Levels of In Vivo Translation of Luciferase-Encoding mRNA Transfected into BJ Fibroblasts Firefly luciferase mRNA was treated for 20 minutes with RNase III in a reaction mixture containing 33 mM Tris-acetate, pH 8, 200 mM KOAc and either 2 mM or 10 mM magnesium acetate-based buffer. The RNase III-treated mRNA was cleaned up by phenol-chloroform extraction, precipitation using ammonium acetate, and washing with 70% ethanol (as in the RNA Quick Cleanup method described herein) and transfected into human BJ fibroblast cells in triplicate wells. Eighteen hours post-transfection, the cells were lysed and assayed for the amount of luciferase activity produced. The amount of luciferase activity (measured in relative light units, RLU) was averaged for duplicate assays of the triplicate samples (n=6) and was normalized by the amount of protein in the cell lysate.

Figure 10:
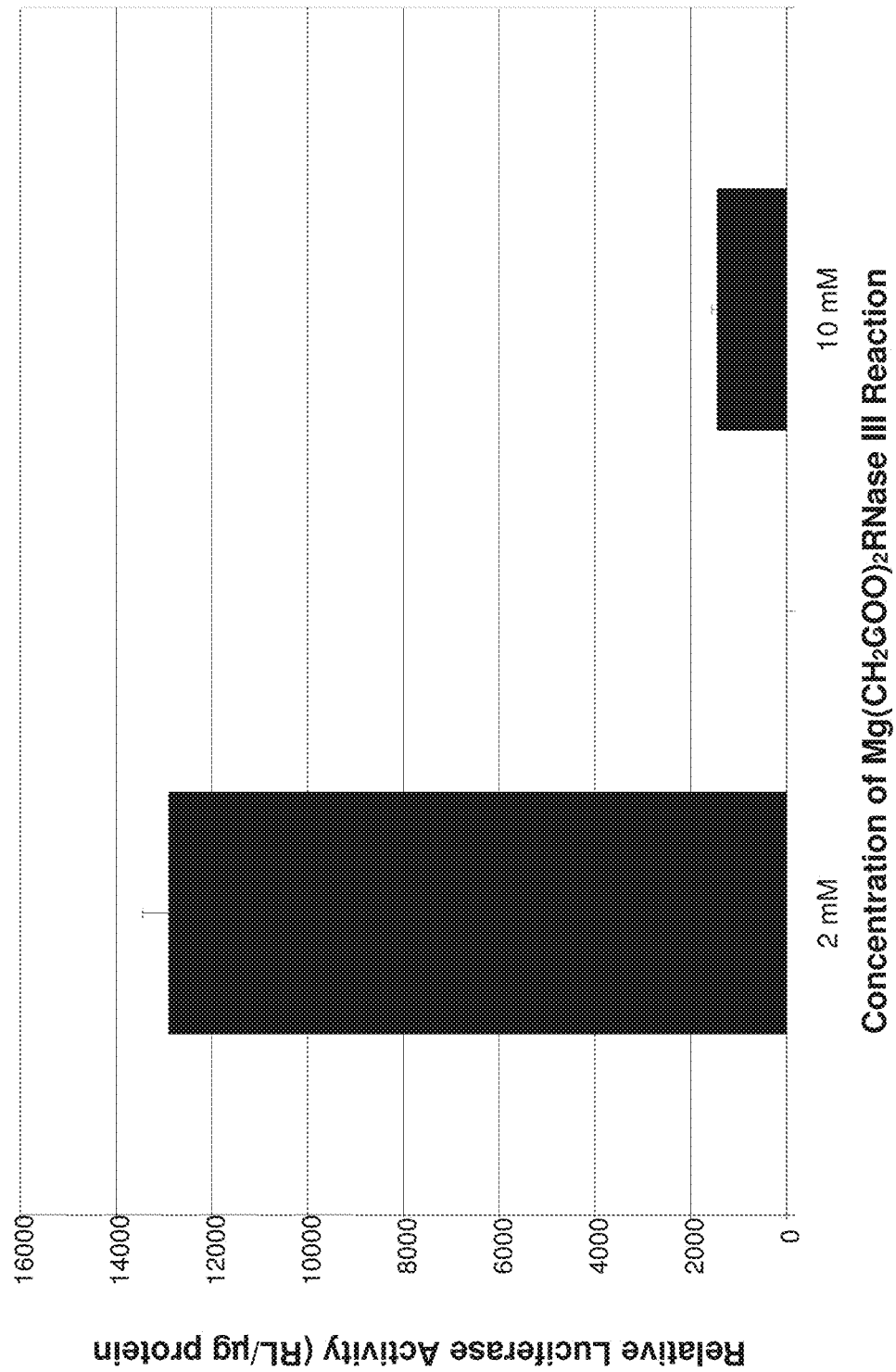
FIG. 10 shows that firefly luciferase mRNA subjected to the RNase III treatment in the presence of 2 mM Mg(OAc)$_2$ for 30 minutes exhibited several-fold higher levels of in vivo translation when transfected into BJ fibroblasts compared to the same mRNA subjected to the RNase III treatment in the presence of 10 mM Mg(OAc)$_2$ for 30 minutes. Following RNase III treatment, the firefly luciferase mRNA was cleaned up using the RNA Quick Cleanup method as described herein and transfected into BJ fibroblast cells in triplicate wells. 18 hours post-transfection, the cells were lysed and assayed for the amount of luciferase activity produced. The amount of luciferase activity (measured in relative light units, RLU) was averaged for duplicate assays of the triplicate samples (n=6) and was normalized by the amount of protein in the cell lysate.

As shown in FIG. 10, luciferase mRNA that was treated with RNase III using 2 mM divalent magnesium cations exhibited much higher (~9 fold) measured luciferase activity compared to luciferase mRNA treated with RNase III using 10 mM divalent magnesium cations. This further shows that the magnesium concentration used in the art for about 35 years does not result in optimal biological activity of RNase III-treated mRNA. Though surprising and unexpected, this result is consistent with our other findings that use of RNase III to treat ssRNA or mRNA did not digest dsRNA contaminants as effectively using 10 mM magnesium cations, as taught in the art, as using 1-4 mM magnesium cations. Still further, we found that 1-3 mM, and preferably about 2 mM magnesium cations, is most effective in digesting dsRNA contaminants, while not significantly digesting ssRNA. In EXAMPLE 10, we show the critical importance of using the discovered low concentrations of magnesium cations for RNase III treatments of ssRNA or mRNA that is repeatedly or continuously introduced in human or animal cells in order to induce a biological or biochemical effect. In EXAMPLE 10, the biological effect is reprogramming of human somatic cells to induced pluripotent stem cells.

Example 10: Effects of RNase III Treatments Using Different Levels of Mg2+ on the Ability of Unmodified Cap1, Poly(A)-Tailed (~150 Adenosines) mRNAs Encoding iPSC Reprogramming Factors to Reprogram Somatic Cells to Induced Pluripotent Stem Cells ("iPSCs") in the Absence of an Inhibitor of Innate Immune Response Pathways In this EXAMPLE 10, we show that mRNAs encoding iPSC reprogramming factors, wherein said mRNAs contain only unmodified (GAUC) nucleotides and do not contain a modified nucleotide that reduces an innate immune response (with the exception of the 5' terminal cap nucleotide comprising 7-methylguanine and the 2'-O-methylated 5' penultimate nucleotide to which the cap nucleotide is joined, both of which together comprise the cap1 cap structure) can be used to reprogram mammalian somatic cells to iPSCs without use of an innate immune response inhibitor such as B18R protein provided that the mRNAs are treated using the RNase III treatment methods described herein. Thus, in this experiment, we used an mRNA reprogramming factor mix comprising unmodified mRNAs encoding OCT4, SOX2, KLF4, LIN28, NANOG and cMYC(T58A) in a 3:1:1:1:1:1 molar ratio, wherein the mRNAs were treated with RNase III in the presence of 200 mM potassium acetate as a monovalent salt, and either 1, 2, 3, 4, 5 or 10 mM magnesium acetate in order to evaluate the importance of the divalent magnesium cation concentration in the RNase III treatment step for induction of iPSCs. In another aspect of this experiment, the mRNAs were treated with RNase III in the presence of 200 mM potassium glutamate to evaluate the effects of this monovalent salt in place of potassium acetate, and either 2 or 10 mM magnesium acetate in order to evaluate the importance of the divalent magnesium cation concentration in the RNase III treatment step for induction of iPSCs.

Methods for using feeder cells and plating BJ fibroblasts for reprogramming and for using TransIT™ (Mirus Bio) transfection reagent for reprogramming were as described above. Briefly, 1.25×10$^5$ BJ fibroblast cells were plated on 5×10$^5$ NuFF feeder cells. The cells were transfected daily for 13 days with 1.2 micrograms of a 100 ng per microliter mRNA reprogramming mix comprising a 3:1:1:1:1:1 molar ratio containing OCT4, SOX2, KLF4, LIN28, NANOG and cMYC(T58A). The transfection was performed with 2.4 microliters of each Mirus Bio TransIT™ Boost and TransIT™ Transfection Reagent as previously described. The PLURITON™ medium, with 1× penicillin/streptomycin, 1× PLURITON™ supplement and 0.5 U/ml SCRIPT-GUARD™ RNase Inhibitor was changed daily before the cells were transfected. On day 13, the cells were fixed, immunostained for the alkaline phosphatase iPSC marker, and the number of alkaline phosphatase-stained iPSC colonies were counted for each treatment.

As shown in the Table 1 below, the numbers of alkaline phosphatase-positive iPS cells induced in the cells transfected once daily with mRNAs that were treated with RNase III in the presence of 1 or 2 mM magnesium acetate were much higher than in cells transfected once daily with mRNAs treated with higher concentrations of magnesium acetate. In particular, no alkaline phosphatase-positive cells were induced in BJ fibroblast cells that were transfected once daily with the mRNA reprogramming mix comprising mRNAs that were treated with RNase III in the presence of 10 mM magnesium acetate in the presence of either potassium acetate or potassium glutamate as the monovalent salt.

TABLE 1

Ability of mRNAs treated with RNase III in the presence of different $Mg^{2+}$ concentrations to generate alkaline phosphatase-positive iPSCs following repeated transfections of BJ fibroblasts.

| Monovalent Potassium Salt Used for RNase III Treatment | Mg(OAc)$_2$ Concentraton Used for RNase III Treatment | Number of Alkaline Phosphatase-positive iPSC Colonies on Day 13 |
|---|---|---|
| Acetate | 1 mM | 110 |
| Acetate | 2 mM | 70 |
| Acetate | 3 mM | 3 |
| Acetate | 4 mM | 3 |
| Acetate | 5 mM | 2 |
| Acetate | 10 mM | 0 |
| Glutamate | 2 mM | 27 |
| Glutamate | 10 mM | 0 |

These results demonstrate that the RNase III treatment methods described herein, comprising treating in vitro-transcribed RNA with RNase III in the presence of about 1-4 mM $Mg^{2+}$, removed dsRNA to a sufficient extent to enable reprogramming of fibroblasts to iPSCs following repeated transfections of human BJ fibroblast somatic cells with this mRNA reprogramming mix comprising 6 different mRNAs encoding different protein reprogramming factors. In the presence of 1 or 2 mM $Mg^{2+}$, the RNase III treatment very effectively removed dsRNA from an mRNA reprogramming mix so that reprogramming of the BJ fibroblast somatic cells were efficiently reprogrammed to alkaline phosphatase-positive dedifferentiated cells or induced pluripotent stem cells. In contrast, an mRNA reprogramming mix comprising the same mRNAs treated using 10 mM $Mg^{2+}$, the concentration first recommended by Robertson et al. (Robertson H D et al., 1968) and believed to be subsequently used as the standard conditions by other researchers since that time, did not result in reprogramming of the BJ fibroblast somatic cells to alkaline phosphatase-positive dedifferentiated cells or induced pluripotent stem cells under otherwise the same conditions. The immunostaining differences were also supported by morphological differences observed between the cells treated with 1-2 mM compared to 10 mM $Mg^{2+}$. For example BJ fibroblasts transfected daily with mRNAs treated with RNase III in 2 mM $Mg^{2+}$ exhibited iPSC colonies, whereas BJ fibroblasts transfected daily with mRNAs treated with RNase III in 10 mM $Mg^{2+}$ did not exhibit a new morphology.

The present researchers believe successful reprogramming of human or animal somatic cells to iPSC cells using only unmodified ssRNA has not previously been reported or demonstrated. Without being bound by theory, we believe that others have not been successful in reprogramming human or animal cells with unmodified ssRNAs because they have not recognized the importance of purifying or treating in vitro-synthesized ssRNA in order to make ssRNAs that are at least practically free of dsRNA, and, even if they had recognized the importance and benefits of making ssRNAs that are at least practically free of dsRNA, they have not understood or developed a method for sufficiently purifying or treating said ssRNAs in order to make them at least practically free of dsRNA, and more preferably, extremely free or even absolutely free of dsRNA. For example, the present researchers have discovered simple, rapid and efficient methods for treating ssRNAs with a double-strand-specific RNase that results in ssRNAs that are at least practically free of dsRNA. One example of such a double-strand-specific RNase that can be used for this purpose is the endoribonuclease, RNase III. The present researchers also discovered, surprisingly and unexpectedly, that a method for using RNase III that was reported in the literature to remove dsRNA from ssRNA to remove the inhibitory activity of dsRNA on in vitro translation did not sufficiently remove dsRNA from ssRNAs so that the ssRNAs treated using that method could be used for translation in living cells or for reprogramming living human or animal cells from one state of differentiation to another state of differentiation (e.g., for reprogramming human or animal somatic cells to iPS cells). In fact, attempts by the present researchers to use ssRNAs that had been treated with RNase using the method in the literature for repeated transfections to generate iPSCs ultimately resulted in the death of those cells. Still further, not only did the method for using RNase III to remove dsRNA for in vitro applications not work for in vivo applications (and resulted in apoptosis of the cells transfected with ssRNAs so treated), but the method also degraded the ssRNAs that the present researchers desired to be translated in the living cells. In other words, not only did the RNase III method in the literature fail to sufficiently remove the undesired dsRNA, it also destroyed a portion of the desired ssRNAs that encode the proteins of interest. Next, the present researchers tried to modify all of the conditions that the authors of the RNase III method for making ssRNA for in vitro applications, unfortunately to no avail. Thus, although the authors of the existing method suggested that increasing the concentration of the monovalent salt in the RNase III reaction to a concentration that was higher or lower than what they suggested might be beneficial, the present inventors tried this without success. They also tried multiple different monovalent salts and varied their concentrations, but this also did not result in sufficient removal of the dsRNA for the ssRNAs to be used for reprogramming living cells, did not sufficiently reduce the toxicity of the ssRNAs, and still damaged or destroyed at least a portion of the desired ssRNAs. The change of other variables suggested by the authors of the published method also did not accomplish the intended goal. Without being bound by theory, the present researchers believe that the difficulty was due to the extremely low levels of dsRNA that can be detected by the innate immune response and other RNA sensors that are present in human and animal cells to protect those cells from infection by dsRNA viruses and other pathogens. Thus, due to the extreme sensitivity of human or animal cells to dsRNA that is introduced into those cells, a method that is suitable for reducing dsRNA from ssRNAs for use of the ssRNA for in vitro applications is not sufficient for making ssRNAs for introducing into living human or animal cells. Still further, those innate immune response and other RNA sensors (e.g., toll like receptors, e.g., TLR3, interferons, and other such sensors) are induced to higher levels if dsRNAs are introduced into said cells. In other words, if ssRNAs that are introduced into living human or animal cells contain even a minute quantity of contaminating dsRNA, that dsRNA induces innate immune response and other RNA sensors to respond, which can cause toxicity and inhibition of protein synthesis in said cells. The initial response may sensitize the cells to be even more responsive to subsequent repeated introductions of the ssRNAs into the cells, causing further toxicity and inhibition of protein synthesis (e.g., Kalal M et al. 2002; Stewart II, W E et al. 1972). If prolonged, these effects lead to increasing toxicity, and cell death. Thus, with respect to certain prior art methods for reprogramming human somatic cells to iPS cells, the innate immune response and other RNA sensor responses are induced each time the ssRNAs encoding reprogramming factors are introduced into the cells. For example, some of the molecules that are induced and activated by dsRNA are interferons, which can inhibit protein synthesis, induce cytotoxicity, and if prolonged, result in cell death.

Example 11. Feeder-Free Reprogramming of Human Somatic Cells to iPS Cells on MATRIGEL™ GFR Matrix Using Single-Stranded Pseudouridine-Containing mRNAs Encoding iPSC Induction Factors in the Absence of an Inhibitor or Agent that Reduces the Expression of an Innate Immune Response Pathway Materials and Methods for Example 11

In EXAMPLE 11 embodiments, each in vitro-synthesized pseudouridine-containing ssRNA (i.e., synthesized using ψTP in place of UTP in the IVT reaction) that encoded an iPSC induction factor [e.g., OCT4, SOX2, KLF4, LIN28, and either cMYC or cMYC(T58A)] or other pseudo-uridine-containing ssRNAs transfected together with the iPSC induction factors was treated with RNase III with 1 mM $Mg(OAc)_2$ prior to capping and tailing of the ssRNA. In this EXAMPLE 11, the RNAse III treatment reactions also contained 0.8 U/microliter SCRIPTGUARD™ RNase inhibitor (CELLSCRIPT, INC.).

Feeder-Free Reprogramming of Human Fibroblast Cells to iPSC Cells Using Single-Stranded mRNA iPSC Induction Factors Prior to use for reprogramming, BJ fibroblasts (ATCC) were plated $5 \times 10^4$ cells per well on 6-well tissue culture plates coated with 83 ng per well of MATRIGEL™ GFR matrix (BD Biosciences, San Jose, CA) in Advanced MEM (Invitrogen, Carlsbad, CA) supplemented with 10% FBS (Fisher) and 2 mM GLUTAMAX™-I (Invitrogen, Carlsbad, CA), a minimum essential medium (MEM) useful for growth of fibroblast cells.

On the following day, the medium was changed to a "Feeder-free Reprogramming Medium" developed by the present applicants. This Feeder-free Reprogramming Medium was composed of Dulbecco's modified Eagle medium with nutrient mixture F-12 (DMEM/F12; (DMEM/F12; Invitrogen, Carlsbad, CA) supplemented with 20% KNOCKOUT™ serum replacement (Invitrogen), 2 mM GLUTAMAX™-I (Invitrogen), 0.1 mM non-essential amino acids solution (Invitrogen), 2 micromolar of the transforming growth factor β (TGFβ) inhibitor STEMOLECULE™ SB431542 (Stemgent®, Cambridge, MA, USA), 0.5 micromolar of the MEK signaling pathway inhibitor STEMOLECULE™ PD0325901 (Stemgent), and/or 10 ng/ml the recombinant mouse cytokine, leukemia inhibitory factor (LIF or mLIF; Invitrogen, Carlsbad, CA), and 100 ng/ml basic human recombinant fibroblast growth factor (FGF; Invitrogen) with penicillin-streptomycin antibiotics. In some experiments, a lower or higher concentration of one or more of these inhibitors is used (e.g., 1-20 micromolar of the TGFβ inhibitor, 0.5-10 micromolar of the MEK signaling inhibitor, and/or 5-50 ng/ml the recombinant mouse cytokine, leukemia inhibitory factor). Since some of the molecules being inhibited may be introduced by the reagents or media used (e.g., TGFβ in the MATRIGEL™ or other extracellular matrix, the concentrations of the inhibitors used may vary based on the reagents and media used. In some experiments, the TGFβ inhibitor, MEK signaling inhibitor, and/or LIF was omitted from the feeder-free reprogramming medium. The Feeder-free Reprogramming Medium was changed daily one hour prior to each transfection with mRNA reprogramming factors. Cells were transfected daily for 18 consecutive days using the TRANSIT™ mRNA transfection kit (Mirus Bio LLC, Madison, WI, USA) as described in the product literature: Briefly, a solution comprising a mixture of all of the mRNA reprogramming factors was diluted with 250 microliters of OPTI-MEM® I reduced serum medium (Invitrogen, Carlsbad, CA), and then 2.4 microliters of TRANSIT™ BOOST was added and mixed, followed by 2.4 microliters of the TRANSIT™ transfection reagent. In some embodiments, no inhibitor of expression of an innate immune response pathway was used. In some other embodiments, 132 ng of pseudouridine-containing mRNA encoding the B18R protein was added to the reprogramming factors comprising mRNA encoding OCT4, SOX2, KLF4, LIN28, and cMYC for reprogramming BJ fibroblasts. This transfection mix was applied dropwise to cells. Cells were then incubated at 37° C. in 5% $CO_2$ until the next day's transfection. After 18 transfections, the medium was changed to a different "iPSC Maintenance Medium" that that was composed of DMEM/F12 supplemented with 20% KNOCKOUT™ serum replacement, 1 mM L-glutamine, 0.1 mM non-essential amino acids solution, and 100 ng/ml basic human recombinant fibroblast growth factor (FGF) (all from Invitrogen, Carlsbad, CA) with penicillin-streptomycin antibiotics for a few more days until iPSC colonies were big enough to pick manually.

In another experiment to evaluate the effect of using different concentrations of the TGFβ inhibitor, STEMOLECULE™ SB431542, reprogramming of BJ fibroblasts was performed as described above except that the concentration of the TGFβ inhibitor STEMOLECULE™ SB431542 was used in the reprogramming medium at a concentration of either 0, 1, 2, or 4 micromolar, and, in this experiment, the BJ fibroblast cells were transfected for only 17 consecutive days rather than for 18 days.

In another experiment to evaluate the effect of using different concentrations of the MEK inhibitor STEMOLECULE™ PD0325901, reprogramming of BJ fibroblasts was performed as described above with a 2 micromolar concentration of the TGFβ inhibitor, and the MEK inhibitor STEMOLECULE™ PD0325901 was used in the reprogramming medium at a concentration of 0, 0.5, 1, 2, 10, or 15 micromolar, and, in this experiment, the BJ fibroblast cells were transfected for only 17 consecutive days rather than for 18 days.

Maintenance of iPSC Colonies Generated from Feeder-Free Reprogramming of Human Somatic Cells Using Single-Stranded mRNA iPSC Induction Factors The iPSC colonies resulting from feeder-free reprogramming were manually picked and transferred into 12-well plates coated with 42 ng per well of MATRIGEL™ GFR matrix (BD Biosciences) containing a medium composed of one-half mTESR®-1 medium (StemCell Technologies, Vancouver, BC, Canada) and one-half of the above-described iPSC Maintenance Medium with 10 micromolar Y27632 STEMOLECULE™ ROCK inhibitor (Stemgent), a cell-permeable small molecule inhibitor of Rho-associated kinases. Plates were incubated at 37° C. in 5% $CO_2$ overnight, after which iPSC colonies were again manually picked and maintained in mTESR medium (StemCell Technologies). In order to expand the cultures, the iPSC colonies were passaged in dispase solution (1 mg/ml) in DMEM/F12 medium (StemCell Technologies, Vancouver, BC, Canada) in 6-well MATRIGEL™ GFR matrix-coated plates (BD Biosciences); the iPSCs were incubated in the dispase solution for 7 minutes at 37° C. and 5% $CO_2$, washed three times with 3 mls of DMEM/F12 medium, removed in mTESR®-1 medium (StemCell Technologies), and plated into wells of a fresh MATRIGEL™ GFR matrix-coated plate (BD Biosciences) at appropriate split ratios.

Immunocytochemistry of iPSC Colonies

Cells were washed twice in 1× phosphate-buffered solution (PBS) and fixed in 4% paraformaldehyde in PBS at room temperature for half an hour. After 3 washes in 1×PBS, cells were washed 3 times in wash buffer (0.1% Triton-X100 in PBS), and blocked for one hour at room temperature in blocking solution (0.1% Triton-X100, 1% BSA, 2% FBS in PBS). Primary antibodies were diluted 1 to 1,000 in blocking solution and applied to cells overnight at 4° C. Cells were washed 6 times in wash buffer and secondary antibodies, diluted 1 to 1,000 in blocking buffer, were applied for 2 hours at room temperature in the dark. After 6 washes with wash buffer, cells were washed twice in 1×PBS before imaging.

Protocol for Differentiation of Feeder-Free Reprogrammed iPSCs to Cardiomyocytes Induced pluripotent stem cell colonies were dissociated with TrypLE Select (Invitrogen, Carlsbad, CA) for 5 minutes at 37° C. in 5% $CO_2$. TrypLE was neutralized in 1:1 ratio with mTESR supplemented with 10 micromolar Y27632 ROCK inhibitor (Stemgent) and 25 micrograms/ml gentamicin (Invitrogen, Carlsbad, CA), spun down, and resuspended in the same medium. Dissociated iPSCs were seeded $5\times10^6$ cells in ultra low attachment T25 flasks (Corning Life Sciences, Lowell, MA) and incubated overnight at 37° C. in 5% $CO_2$. The next day, media was exchanged to 50% mTESR and 50% aggregate transition medium, DMEM GLUTAMAX™ (Invitrogen, Carlsbad, CA), 10% FBS (Fisher), 50 ng/ml FGFb (Invitrogen, Carlsbad, CA), and 25 micrograms/ml gentamicin (Invitrogen, Carlsbad, CA), and the aggregates were split into 2 ultra low attachment T25 flasks. For the following 12 days aggregates were fed cardiac induction medium, DMEM GLUTAMAX™ (Invitrogen, Carlsbad, CA), 10% FBS (Fisher), 50 ng/ml FGFb (Invitrogen, Carlsbad, CA). After aggregates began to beat, media was changed to cardiac maintenance media, DMEM low glucose (Invitrogen, Carlsbad, CA), 10% FBS, 25 micrograms/ml gentamicin.

Results for Example 11

Figure 11:
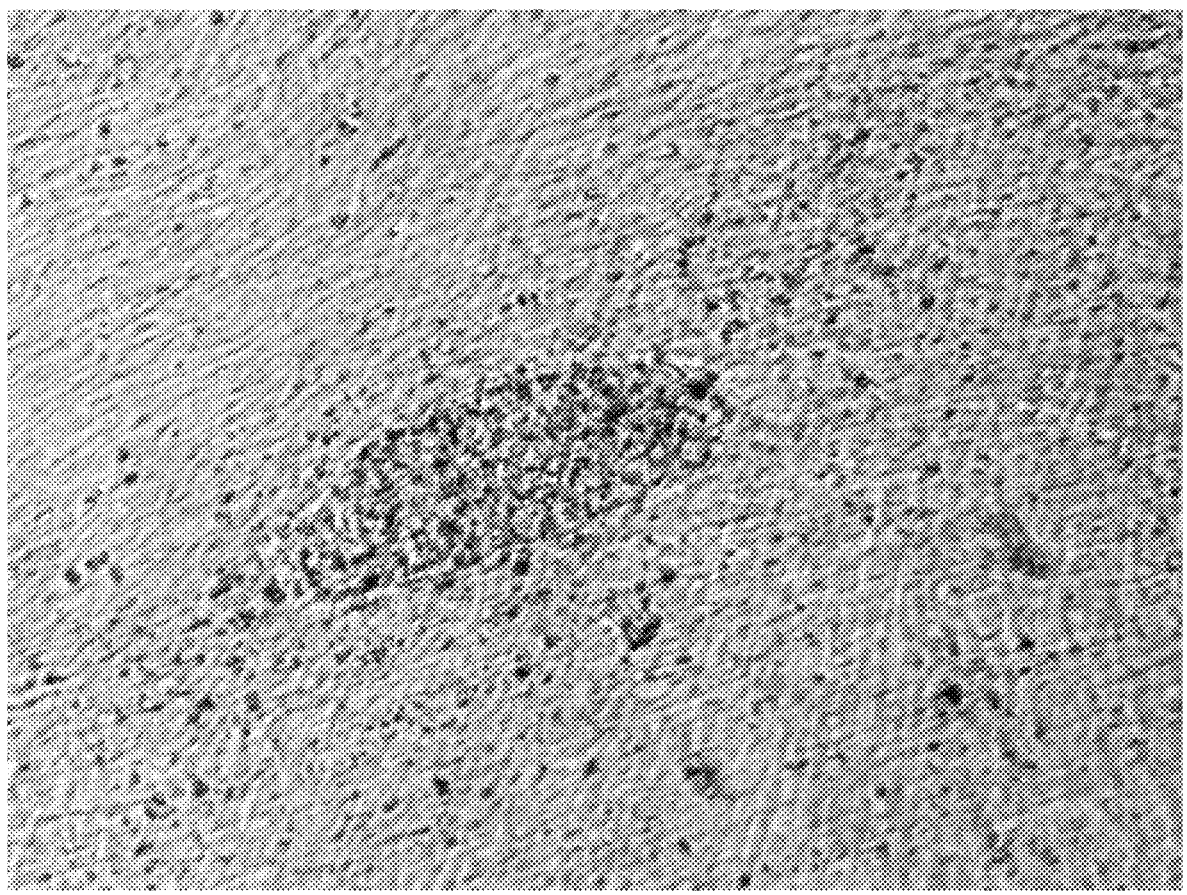
FIG. 11 shows a phase contrast image of an iPSC colony reprogrammed in EXAMPLE 11 from a human BJ fibroblast without use of a feeder layer and without using B18R protein or any other inhibitor or agent that reduces the expression of an innate immune response pathway. The iPSC colony within a confluent layer of BJ fibroblast cells is shown after 18 days of transfection with mRNA iPSC induction factors encoding: OCT4, SOX2, KLF4, LIN28, and cMYC(T58A) proteins.

BJ fibroblasts plated on MATRIGEL™ GFR matrix were transfected daily for 18 consecutive days with pseudouridine-containing mRNA reprogramming factors encoding OCT4, SOX2, KLF4, LIN28, and cMYC or cMYC(T58A) in Feeder-free Reprogramming Medium. The ssRNA reprogramming factors was composed of pseudouridine-containing mRNAs prepared as described above and in the literature provided with the T7 mSCRIPT™ standard mRNA production system (CELLSCRIPT, INC., Madison, WI, USA), except that pseudouridine 5' triphosphate (ΨTP) was substituted for uridine 5' triphosphate (UTP), and, prior to capping or polyadenylation, the in vitro-transcribed RNAs were treated using the RNase III treatment as described herein with a concentration of 1 mM Mg acetate. No feeder cells were used. Unless otherwise specifically stated, no B18R protein or other inhibitor or agent that reduces the expression of an innate immune response pathway was used. The cells survived and grew to confluence, and by the end of the transfection regimen, were actually over confluent. In experiments using pseudouridine-containing mRNA that encoded the cMYC(T58A) mutant of the cMYC protein, iPSC colonies began to appear around day 14, after 15 transfections (FIG. 11), based on the first day of transfection being counted as day 0. In experiments, using mRNA that encoded the wild-type long version of the cMYC protein, iPSC colonies began to appear around day 16. In this experiment, iPSC colonies were obtained only when LIF protein or a TGFβ or MEK small molecule inhibitor (e.g., SB431542 TGFβ inhibitor or PD0325901 MEK inhibitor) was present in the medium (FIG. 12). No iPSC colonies formed in the absence of these inhibitors.

Figure 13:
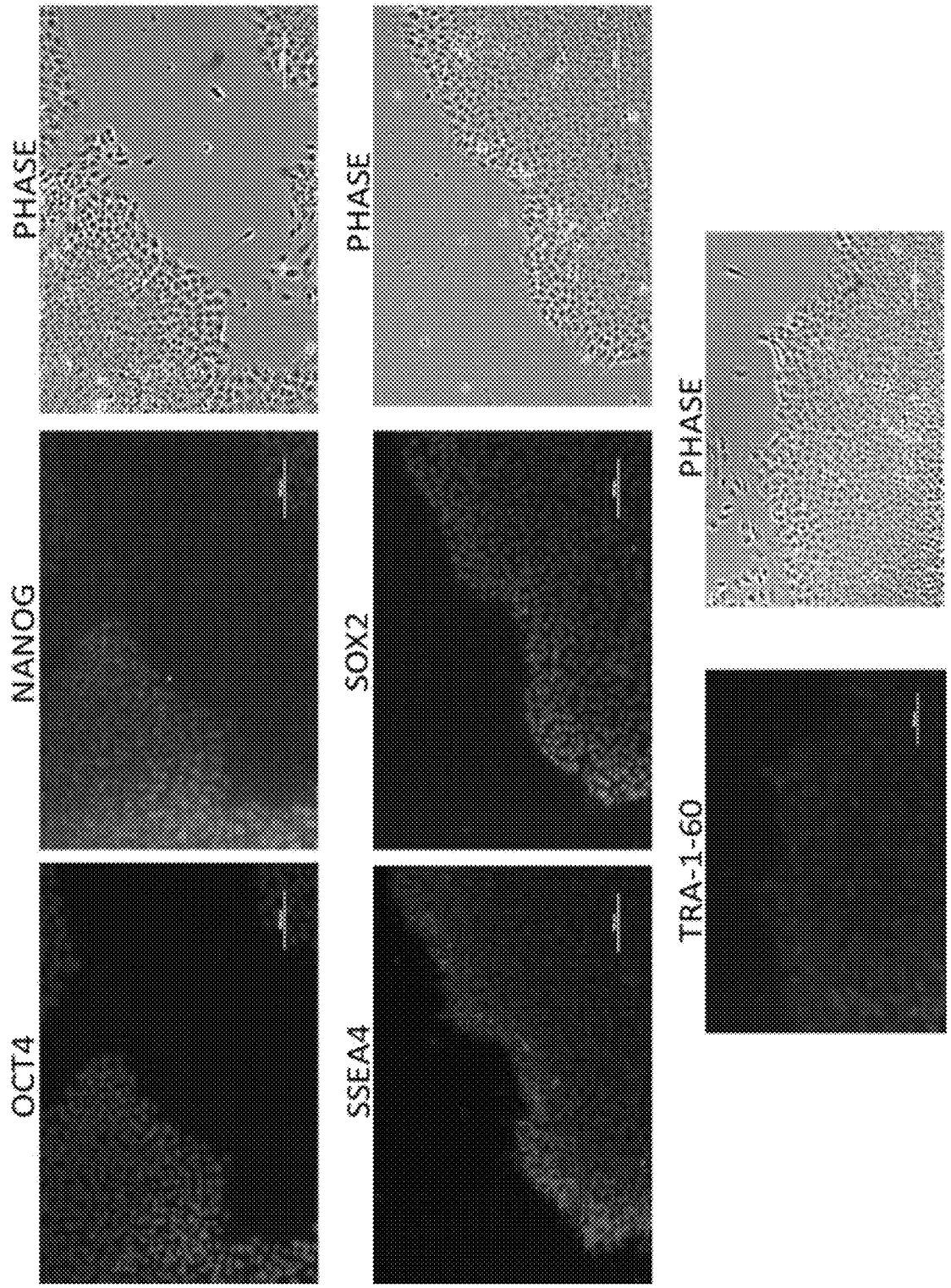
FIG. 13 shows that cells originating from an iPSC colony that were reprogrammed in EXAMPLE 11 from human BJ fibroblasts in the absence of feeder cells stain positive for the pluripotency markers OCT4, NANOG, SSEA4, SOX2, and TRA-1-60. In this embodiment, iPSCs were induced in the absence of feeder cells, but mRNA encoding B18R protein was also transfected into the BJ fibroblasts at the same time as the iPSC reprogramming factor mRNAs.

In other mRNA reprogramming experiments using PLURITON™ mRNA reprogramming medium (Stemgent) on MATRIGEL™ GFR matrix without feeder cells, massive cell death was observed in the first week of transfections with the same pseudouridine-containing mRNA reprogramming factors encoding OCT4, SOX2, KLF4, LIN28, and the wild-type long version of cMYC; all of the BJ fibroblast cells died in PLURITON™ medium and no iPSC colonies were observed. Using the pseudouridine-containing mRNA encoding OCT4, SOX2, KLF4, LIN28, and the cMYC (T58A) mutant in the absence of the small molecules, SB431542 (TGFβ inhibitor), PD0325901 (MEK Inhibitor), and LIF (leukemia inhibitor factor), a majority of the cells died in PLURITON™ medium, but a small number of surviving cells were able to form iPSC colonies after 18 transfections. However, many fewer iPSC colonies were generated from feeder-free BJ fibroblasts in PLURITON™ medium than were generated in feeder-free BJ fibroblasts transfected with the same pseudouridine-containing mRNA reprogramming factors encoding OCT4, SOX2, KLF4, LIN28, and the cMYC(T58A) in the Feeder-free Reprogramming Medium supplemented with SB431542 TGFβ inhibitor, PD0325901 MEK inhibitor, and LIF, as described in the present Example (e.g., see FIG. 12).

iPSC colonies that formed on MATRIGEL™ GFR matrix in the Feeder-free Reprogramming Medium and developed as described in the present Example stained positive for an alkaline phosphatase, characteristic of iPSC colonies (FIG. 12). After a couple of days in iPSC maintenance medium, iPSC colonies were manually picked, plated into fresh MATRIGEL™ GFR matrix-coated plates, and expanded. Cultures of each colony grew and could be expanded as expected for iPSCs, needing to be passaged every 3 to 4 days via splitting in dispase solution, and having been kept in culture for at least 10 passages to date. Cells from the colonies also stained positive for iPSC pluripotency markers: NANOG, TRA-1-60, SSEA4, OCT4, and SOX2 (e.g., FIG. 13). The immunostaining results shown in FIG. 13 are from an iPSC cell line established from an iPSC colony picked from a reprogramming experiment for reprogramming BJ fibroblasts to iPS cells, wherein 132 ng of pseudouridine-containing mRNA encoding the B18R protein was added to the reprogramming factors comprising pseudouridine-containing mRNAs encoding OCT4, SOX2, KLF4, LIN28, and cMYC. Other iPSC cell lines induced in the absence of mRNA encoding B18R protein or using other conditions described in this Example also stain positively for iPSC pluripotency markers.

It was previously determined that 1×10⁴ human BJ fibroblast cells was an optimal cell density per well in a 6-well dish for successful iPSC induction on feeder cells. Initial reprogramming experiments indicated that a cell density of 1×10⁴ BJ fibroblast cells per well was not sufficient for generating as many iPSC colonies from feeder cell-free reprogramming of the BJ fibroblasts on MATRIGEL™ GFR matrix as were generated from reprogramming using feeder cells. However, feeder cell-free reprogramming of higher numbers of BJ fibroblasts to iPSC colonies was achieved when the cell density per well of the BJ fibroblasts was increased to 5×10⁴ cells per well on MATRIGEL™ GFR matrix.

Table 2 below shows the number of iPSC colonies counted on Day 18 when BJ fibroblasts were transfected daily for 18 days with the mixture of pseudouridine-containing mRNAs encoding the five iPSC induction factors: OCT4, SOX2, KLF4, LIN28, and cMYC(T58A), as described above, and, additionally, with or without pseudouridine-containing mRNA encoding B18R protein, and plated at a cell density of 5×10⁴ cells per well on MATRIGEL™ GFR matrix in the iPSC Feeder-free Reprogramming Medium that we developed as described above, or at a cell density of 1×10⁴ cells on human neonatal fibroblast feeder cells in the Feeder-free Reprogramming Medium. The new iPS Feeder-free Reprogramming Medium used for reprogramming of the feeder-free cells on the MATRIGEL™ GFR matrix also contained the TGFβ inhibitor STEMOLECULE™ SB431542, the MEK inhibitor STEMOLECULE™ PD0325901, and the LIF protein as described above.

TABLE 2

Feeder-free Reprogramming of BJ Fibroblasts to iPSCs..

| Substrate | Pseudouridine-containing mRNA Encoding B18R Protein Used | Number of iPSC Colonies Observed |
|---|---|---|
| Feeder-free MATRIGEL matrix | YES | 72 |
| Feeder-free MATRIGEL matrix | NO | 102 |
| Human neonatal fibroblast feeders | YES | 81 |
| Human neonatal fibroblast feeders | NO | 76 |

Table 3 below shows the number of iPSC colonies counted on Day 17 when BJ fibroblasts were transfected daily for 17 days with the mixture of pseudouridine-containing mRNAs encoding the five iPSC induction factors: OCT4, SOX2, KLF4, LIN28, and cMYC(T58A) in the presence of the indicated concentrations of the TGFβ inhibitor STEMOLECULE™ SB431542 (Stemgent).

TABLE 3

Feeder-free Reprogramming of BJ Fibroblasts in the Presence of Different Concentrations of the TGFβ inhibitor STEMOLECULE ™ SB431542 (Stemgent).

| TGFβ inhibitor SB431542 Concentration (µM) | iPSC Colonies Observed |
|---|---|
| 0 | 0 |
| 1 | 9 |
| 2 | 71 |
| 4 | 160 |

Table 4 below shows the number of iPSC colonies counted on Day 17 when BJ fibroblasts were transfected daily for 17 days with the mixture of pseudouridine-containing mRNAs encoding the five iPSC induction factors: OCT4, SOX2, KLF4, LIN28, and cMYC(T58A) in the presence of 2 micromolar of the TGFβ inhibitor STEMOLECULE™ SB431542 (Stemgent) and the indicated concentrations of the MEK inhibitor STEMOLECULE™ PD0325901 (Stemgent).

TABLE 4

Feeder-free Reprogramming of BJ Fibroblasts in the Presence of Different Concentrations of the MEK inhibitor STEMOLECULE ™ PD0325901 (Stemgent).

| PD0325901 Concentration (µM) | iPSC Colonies Observed |
|---|---|
| 0 | 1 |
| 0.5 | 77 |
| 1 | 27 |
| 2 | 94 |
| 10 | 11 |
| 15 | 0 |

Differentiation of Feeder-Free Reprogrammed iPSCs to Cardiomyocytes

Induced pluripotent stem cells that were generated from feeder-free reprogramming of BJ fibroblasts using OCT4, SOX2, KLF4, LIN28, and cMYC pseudouridine-containing mRNA reprogramming factors and pseudouridine-containing mRNA encoding B18R differentiated into beating aggregates of cardiomyocyte cells using the protocol for cardiomyocyte differentiation as described in the Materials and Methods for EXAMPLE 11. Beating cardiomyocyte aggregates were first observed after 13 days. Videos of the beating cardiomyocyte aggregates were recorded.

Example 12. Studies on Variables Affecting Efficiency of mRNAs Encoding iPSC Induction Factors to Reprogram Human BJ Fibroblasts to iPS Cells Using Feeder Layers Materials and Methods for EXAMPLE 12

Methods for Using Feeder Cells and Plating BJ Fibroblasts for Reprogramming to iPSCs with mRNA iPSC Induction Factor Nuffs feeder cells and plating of BJ fibroblasts were done as described in the General Materials and Methods section. The mRNA reprogramming factors encoding OCT4, SOX2, KLF4, LIN28 and MYC (e.g., either c-MYC, c-MYC (T58A), or L-MYC) were prepared in a 3:1:1:1:1 molar ratio as described previously. Unless otherwise stated the ssRNAs were treated with RNase III using RNase III treatment as described herein with 1 mM or 2 mM magnesium acetate described herein.

RNAiMAX™ mRNA Transfection Protocol

BJ fibroblast media from BJ fibroblasts plated on Nuff feeder cells was removed and added to PLURITON™ mRNA reprogramming media (Stemgent, Cambridge, MA) (base media with supplement and penicillin/streptomycin) (2 mls) and 4 microliters of B18R recombinant protein (EBiosciences, San Diego, CA) was added to a final concentration of 200 ng/ml. The cells were incubated at 37° C. under 5% $CO_2$ for 4 hours before transfecting the mRNA. To transfect the BJ fibroblasts with 3:1:1:1:1 mRNA mix (OCT4, SOX2, KLF4, LIN28) and c-MYC(T58A) or cMYC, 12 microliters of the 100 ng/µl RNA mixture (1.2 micrograms total) was added to 48 microliters of OptiMEM™ medium (Invitrogen, Carlsbad, CA) in tube A. In some experiments, mRNA encoding EGFP protein was also added to make a 3:1:1:1:1:1 mRNA mix of OCT4, SOX2, KLF4, LIN28, c-MYC(T58A) and EGFP, and in some experiments, the total microgram amount of the mRNA mixture used for transfection was varied, as indicated for that experiment. In tube B, 54 microliters of OptiMEM medium was mixed with 6 microliters of RNAiMAX™ (Invitrogen, Carlsbad, CA). Five microliters of RNAiMAX™ was used for each 1 microgram of total RNA used for a transfection. Tube A was mixed with tube B for 15 minutes at room temperature and then the mix was added to the 2 mls of PLURITON medium already on the BJ fibroblasts plated on Nuffs. Unless otherwise indicated, the medium was changed 4 hours after each RNAiMAX™ transfection with new PLURITON medium with or without B18R protein at 200 ng/ml and incubated overnight at 37° C. in 5% $CO_2$. On the following day, the transfection mix was made in the same way as described above and the mRNA/RNAiMAX™ complexes were added to the medium already in each well without changing the medium prior to adding the mRNA/RNAiMAX™ complexes. The media were again changed 4 hours after the transfections and B18R protein was added at 200 ng/ml and the cells were incubated overnight at 37° C. in 5% $CO_2$. Nuff-conditioned PLURITON medium was used to replace PLURITON media on the sixth day of transfections. These transfections were repeated every day at the same time for 16 additional mRNA transfections for a total of 18 mRNA transfections.

However, in other experiments, as indicated in the RESULTS section, the medium was changed before every transfection with the mRNA mixtures encoding the iPSC induction factors and, in some cases, with or without additional mRNAs encoding other proteins, or, in some experiments, the medium was not changed 4 hours after the RNAiMAX™ transfections.

TransIT™ mRNA Transfection Protocol

BJ fibroblast media from BJ fibroblasts plated on Nuff feeder cells was removed and added to PLURITON™ mRNA reprogramming media (Stemgent, Cambridge, MA) (base media with supplement and penicillin/streptomycin) (2 mls) and 4 microliters of B18R recombinant protein (EBiosciences, San Diego, CA) was added to a final concentration of 200 ng/ml. The media can be changed immediately before each transfection with Mirus mRNA Transfection Reagent (Mirus Bio, Madison, WI). To transfect the BJ fibroblasts with 3:1:1:1:1 mRNA mix (OCT4, SOX2, KLF4, LIN28) and c-MYC(T58A) or cMYC, the mRNA mix (0.6 to 1.4 micrograms of total mRNA) was added to 120 microliters of OptiMEM [without TransIT Boost™ (Mirus Bio), TransIT and the mRNA mix volume] and then TransIT Boost (2 microliters per microgram of mRNA) and TransIT mRNA transfection reagent (2 microliters per microgram of mRNA) were mixed with the mRNA. The mRNA-TransIT mix was incubated for 2 minutes and then added to each well of BJ fibroblasts on Nuff feeders in PLURITON medium. The following day, the PLURITON media were changed before transfecting the same dose of mRNA using TransIT Boost and TransIT mRNA transfection reagent. Nuff-conditioned PLURITON medium was replaced by PLURITON medium on the sixth day of transfections. A total of 18 transfections were performed.

Embryoid Body Spontaneous Differentiation Protocol

The embryoid body spontaneous differentiation protocol was performed as previously described (Huangfu et al., 2008), and as summarized in the General Materials and Methods.

Live Cell Staining of iPSC Colonies with Tra-1-60

TRA-1-60 is considered to be one relatively stringent marker of fully reprogrammed iPS cells (Chan et al. 2009). The Tra-1-60 live cell imaging was done with the StainAlive Dylight 488 Mouse anti-Human Tra-1-60 antibody (Stemgent) according to the manufacturer's specifications.

Results for Example 12

RNase III Treatment Reduced the Level of dsRNA

Figure 14:
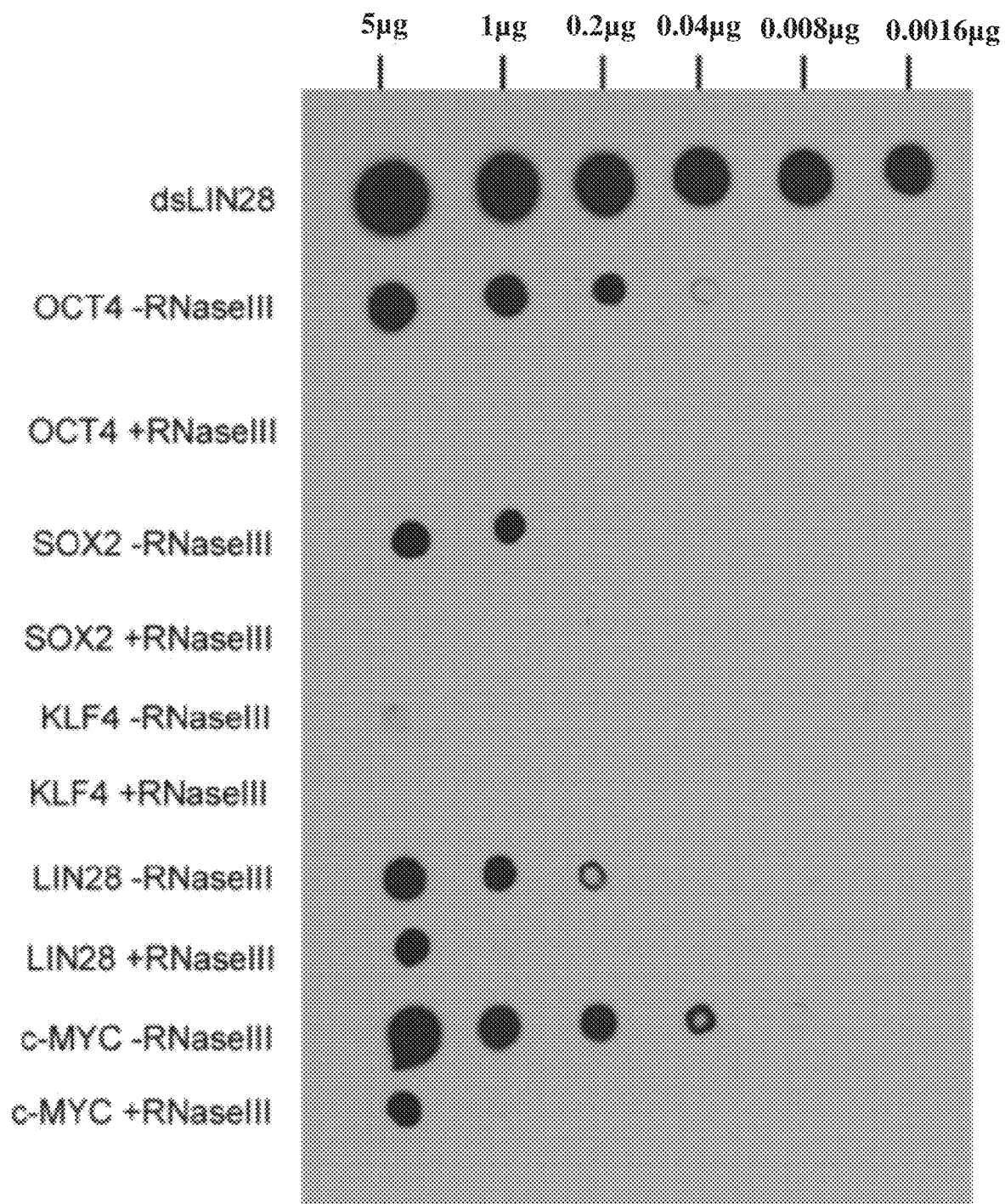
FIG. 14 shows that RNase III treatment of RNA greatly reduces the levels of dsRNA detectable by the JS antibody. All the RNAs shown were maude using ψTP in place of UTP.

The in vitro-transcribed RNAs used in these experiments were all treated with RNase III to remove dsRNA prior to capping and tailing reactions (FIG. 14). RNase III treating of the Ψ-mRNAs (or Ψ- and m5C-mRNAs, data not shown) resulted in undetectable levels of dsRNA that was recognized by the monoclonal dsRNA antibody J2 in dsRNA dot blot experiments when less than or equal to 1 microgram of RNA was spotted on the membrane (e.g., FIG. 14). We believed that removing dsRNA contaminants from our mRNAs would greatly reduce overall toxicity and therefore enhance cellular reprogramming when mRNAs were transfected for up to 18 straight days. To further reduce any potential innate immune reactivity to our mRNAs, we also incorporated pseudouridine (Ψ) in place of conventional uridine (and in some of our mRNAs, also 5-methylcytidine ($m^5C$) in place of cytidine); Drs. Kariko and Weissman and their co-workers (Kariko et al., 2005; Kariko et al., 2008; Kariko and Weissman, 2007) have shown that mRNAs containing these non-canonical nucleosides exhibit significantly reduced cellular immune responses.

iPSC Induction from BJ Fibroblasts Using RNAiMAX™ Protocols

When a 3:1:1:1:1 molar ratio of RNase III-treated Ψ- and m5C-mRNAs encoding OCT4, SOX2, KLF4, LIN28 and c-MYC or c-MYC(T58A) were introduced into BJ fibroblasts (grown on irradiated human Nuff feeder cells) using the RNAiMAX™ transfection reagent each day for 18 days, mesenchymal-to-epithelial transformation became obvious by day 12 of transfections, and tightly packed epithelial colonies with high nuclear-to-cytoplasmic ratios were generated by day 16 of transfections. BJ fibroblasts transfected with total daily doses of 1.2 micrograms mRNA showed Tra-1-60 positive colonies on day 18, both for the cells transfected with mRNA encoding c-MYC and for the cells transfected with mRNA encoding the c-MYC(T58A) mutant protein (FIG. 15).

Table 5 shows the relative numbers of iPSC colonies observed that were Tra-1-60-positive on day 18 of transfection when BJ fibroblasts were transfected using RNAiMAX™ with different doses of the RNase III-treated mRNAs encoding OCT4, SOX2, KLF4, LIN28 and c-MYC or c-MYC(T58A) that contained both Ψ and m⁵C modified nucleosides.

TABLE 5 iPSC induction from BJ fibroblasts using RNase III-treated Ψ- and m⁵C-modified mRNAs encoding OCT4, SOX2, KLF4, LIN28 and c-MYC or c-MYC(T58A) complexed with RNAiMax ™.

| Treatment | No. of iPSC Colonies On Reprogramming Day 18 (Tra-1-60 positive) |
|---|---|
| Untreated | 0 |
| Mock Transfected | 0 |
| 1.2 μg 5 Factors (cMYC) | 6 |
| 1.2 μg 5 Factors (cMYC) (+B18R 200 ng/ml) | 3 |
| 0.6 μg 5 Factors (cMYC) | 0 |
| 0.3 μg 5 Factors (cMYC) | 0 |
| 1.2 μg 5 Factors (cMYC T58A) | 38 |
| 1.2 μg 5 Factors (cMYC T58A) (+B18R 200 ng/ml) | 20 |
| 0.6 μg 5 Factors (cMYC T58A) | 3 |
| 0.3 μg 5 Factors (cMYC T58A) | 0 | mRNA mixes with c-MYC (T58A) in place of wild type c-MYC showed ~6 fold more colonies at the 1.2 micrograms mRNA dose and even resulted in Tra-1-60-positive colonies at the 0.6-microgram dose. Transfection mixes containing wild-type c-MYC did not result in any WPS colonies at the 0.6-microgram dose (Table 5). Addition of the B18R recombinant protein did not aid in reprogramming efficiency in this experiment and it even appeared to be detrimental, since it resulted in about half the Tra-1-60-positive iPSC colonies compared to wells without B18R protein (Table 5).

When the RNAiMAX™ transfection protocol was repeated with only the 3:1:1:1:1 molar ratio of RNase III-treated Ψ- and m⁵C-modified mRNAs encoding OCT4, SOX2, KLF4, LIN28 and c-MYC, we again saw a reduction in the number of colonies morphologically resembling iPS colonies when B18R protein was used (Table 6). Without being bound by theory, it is possible that B18R was not beneficial in this experiment because the RNase III-treated Ψ- and m⁵C-modified mRNAs did not elicit a substantial innate immune response.

TABLE 6 iPSC induction from BJ fibroblasts ± B18R Protein using RNase III-treated Ψ- and m⁵C-modified mRNAs encoding OCT4, SOX2, KLF4, LIN28 and c-MYC complexed with RNAiMax ™.

Figure 16:
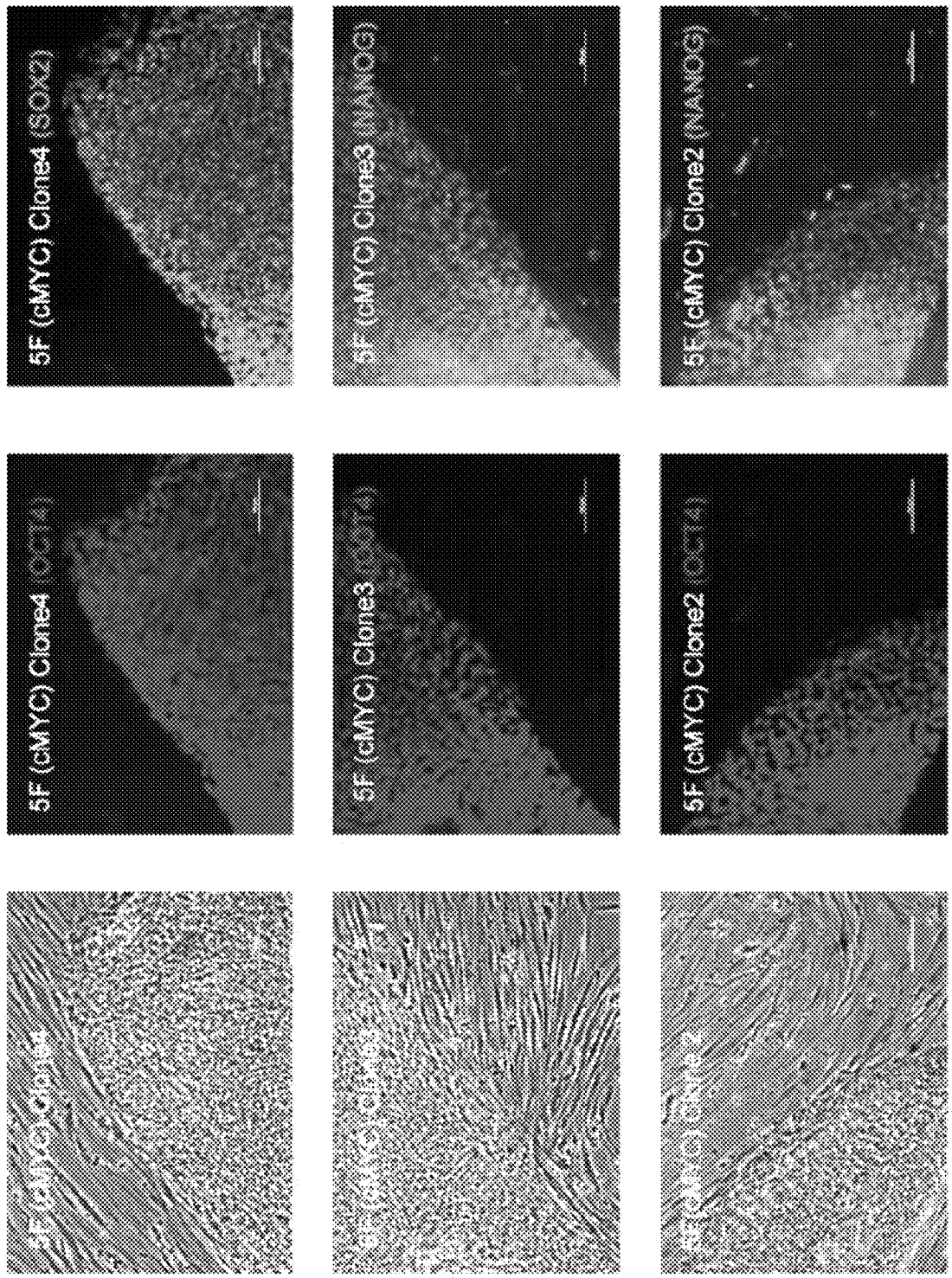
FIG. 16 shows that iPSC colonies reprogrammed from human BJ fibroblasts using mRNA reprogramming factors show stable expression of stem cell markers. iPSC colonies were manually picked and passaged five times on Nuff feeder layers in iPSC media containing 100 ng/nl of hFGF2. The iPSC colonies were fixed and processed for immunoflourescence with antibodies that recognize stem cell markers OCT4, SOX2 and NANOG.
Figure 17A:
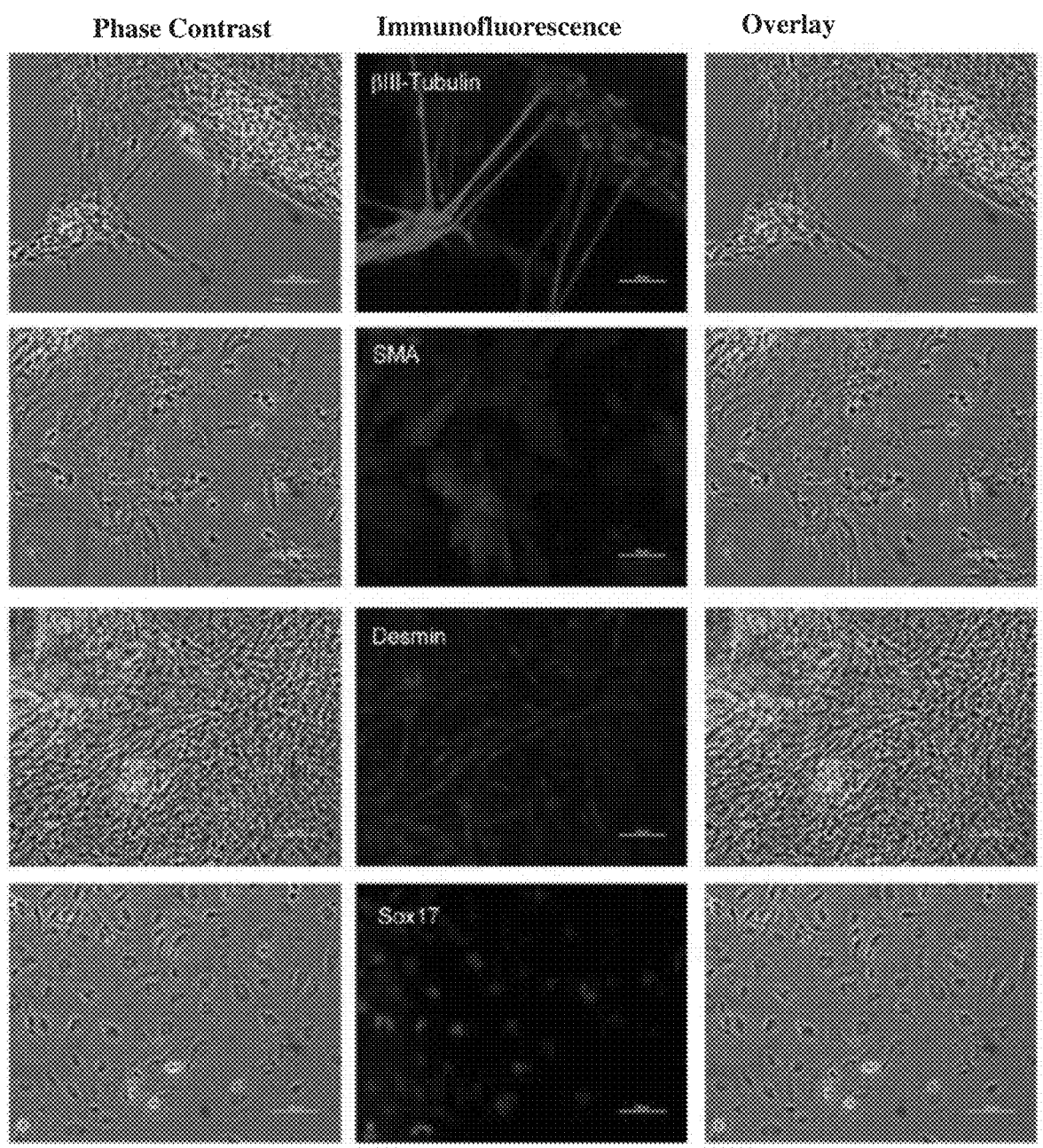
FIG. 17A-C shows that iPSC clonal colonies generated by reprogramming of human BJ fibroblasts to iPS cells using mRNA reprogramming factors encoding the iPSC induction factors that were picked and cloned differentiated into all three germ layers. The iPSC colonies were passaged 7 times and allowed to differentiate in an embryoid body spontaneous differentiation protocol. The differentiated cells expressed markers of endoderm (AFP and SOX17), mesoderm (SMA and Desmin), and ectoderm (class III beta-tubulin, also known as βIII-tubulin) after they were fixed and processed for immunofluorescence with antibodies that recognized those markers.
Figure 17B:
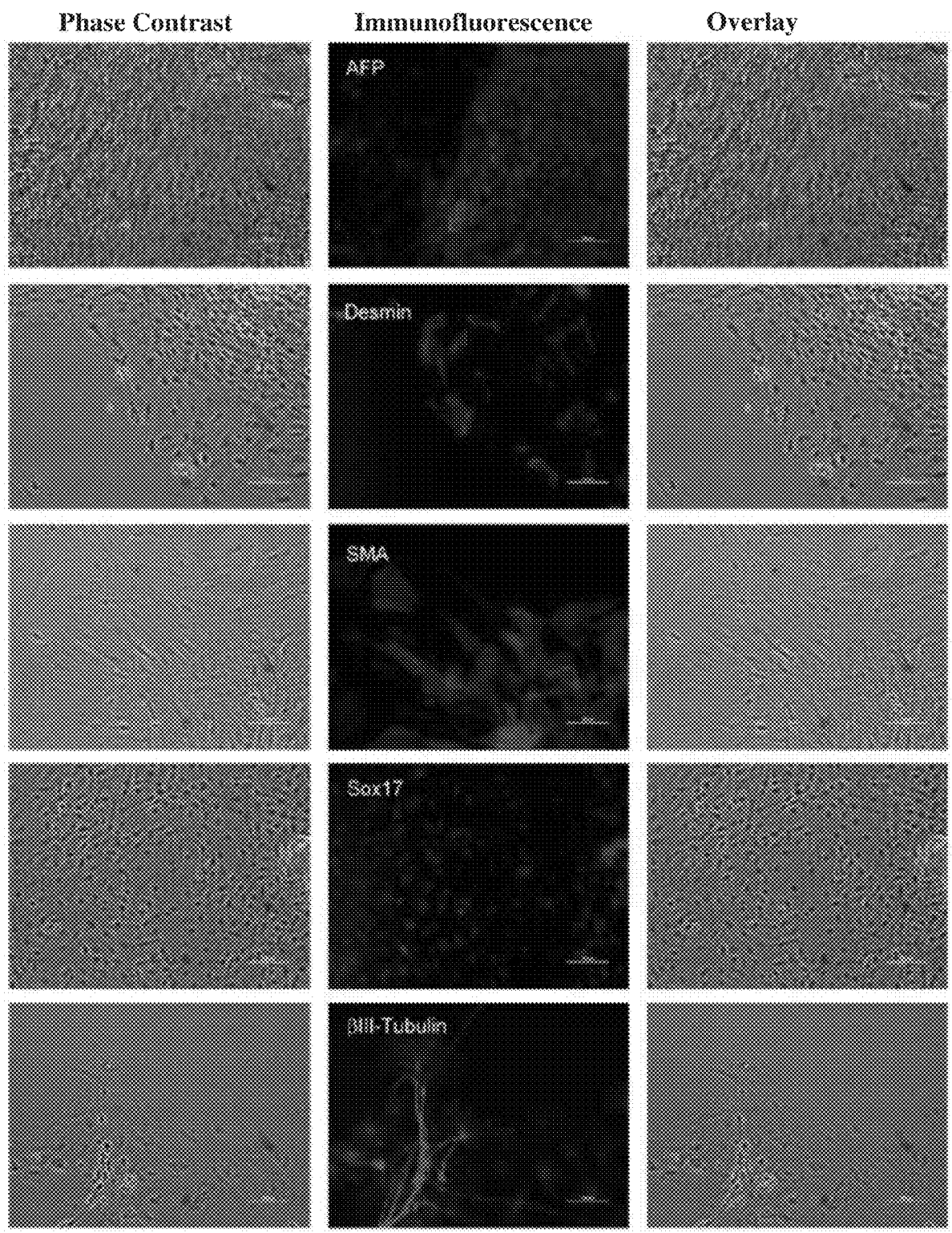
Figure 17C:
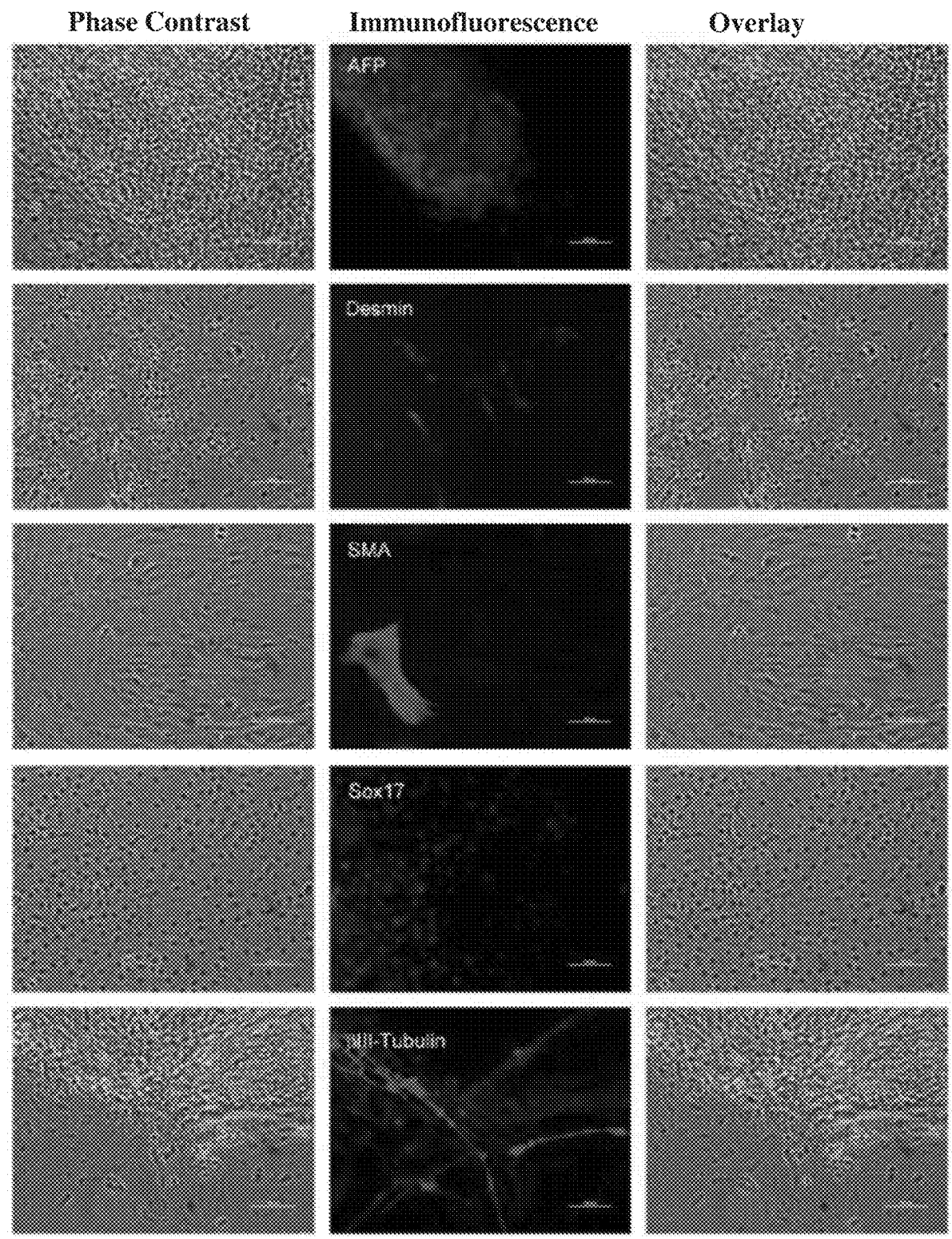

| Amount of mRNA Mix Used for Transfection Using RNAiMAX ™ | Additional Treatment | No. of iPSC Colonies (based on cell morphology) |
|---|---|---|
| None - Mock Transfection | None | 0 |
| 1.2 μg mRNA mix | None | 20 |
| 1.2 μg mRNA mix | +B18R Protein | 8 |
| 0.8 μg mRNA mix | None | 5 |
| 0.8 μg mRNA mix | +B18R Protein | 3 |
| 0.6 μg mRNA mix | None | 0 | iPSC Colonies from BJ Fibroblasts Redifferentiated into all Three Germ Layers Multiple colonies were manually picked from the first RNAiMAX™ transfection experiment (Table 5) and plated onto new Nuff feeder layers in iPSC media with 100 ng/ml hFGF2. These colonies were passaged between 5 and 10 times before some were frozen while other were tested for expression of stem cells markers like OCT4, NANOG, SOX2 (FIG. 16). Other iPSC clones were tested for their ability to differentiate into the three germ layers as would be expected if these iPSC colonies are truly pluripotent. Three different iPSC clones made from BJ fibroblasts transfected using RNAiMAX™ with the 3:1:1:1:1 molar ratio of RNase III-treated Ψ- and m⁵C-modified miRNAs encoding OCT4, SOX2, KLF4, LIN28 and c-MYC at a dose of 1.2 micrograms/ml per day for 18 days were passaged 7 times and tested in embryoid body spontaneous differentiation assays (Huangfu et al., 2008). After 8 days in suspension culture followed by 8 more days of attachment to gelatin coated plates, all 3 clones differentiated into all three germ layers marked by endoderm markers (AFP and SOX17), mesoderm markers (SMA and Desmin) and the ectoderm neuronal marker class III beta-tubulin) (FIGS. 17A, B and C). With iPSC Clone 2, beating cardiac myocytes were generated in one of the wells.

iPSC Induction from BJ Fibroblasts Using TransIT™ Protocols

Figure 18:
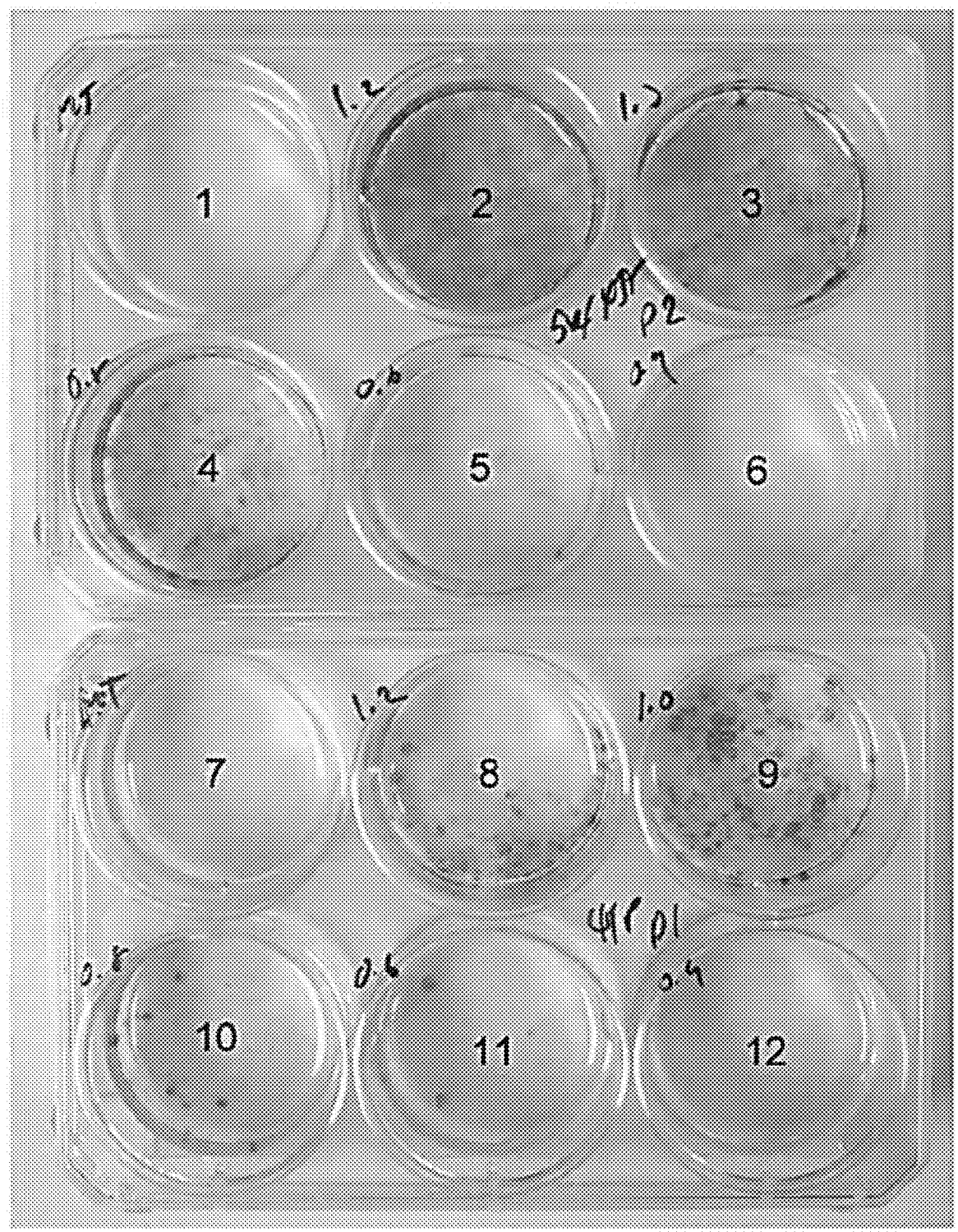
FIG. 18 shows that iPSC colonies that were obtained by reprogramming of human BJ fibroblasts to iPS cells using mRNA reprogramming factors encoding the iPSC induction factors were stained by alkaline phosphatase, a commonly used embryonic stem cell marker (Takahashi and Yamanaka, 2006).

Similar iPSC reprogramming experiments performed using the TransIT™ mRNA transfection reagent (Mirus Bio, Madison, WI, USA) resulted in many more iPSC colonies and the iPSC colonies appeared earlier than were obtained using RNAiMAX™ transfection reagent (FIG. 18). For example, we were able to see iPSC colonies forming in the wells transfected daily with the 1.2-micrograms dose of the 3:1:1:1:1 molar ratio of RNase III-treated Ψ- and m⁵C-mRNAs encoding OCT4, SOX2, KLF4, LIN28 and c-MYC wells as early as transfection day 10.

TABLE 7 iPSC induction from BJ fibroblasts transfected with RNase III-treated Ψ-modified or Ψ- and m⁵C-modified mRNAs using TransIT ™.

| Number on Plate | Treatment | Number of Alkaline Phosphatase-Positive iPSC Colonies on Day 15 |
|---|---|---|
| 1 | Mock Transfected | 0 |
| 2 | 1.2 μg of Ψ- and m⁵C-mRNA | 321 |
| 3 | 1.0 μg of Ψ- and m⁵C-mRNA | 125 |
| 4 | 0.8 μg of Ψ- and m⁵C-mRNA | 13 |
| 5 | 0.6 μg of Ψ- and m⁵C-mRNA | 0 |
| 6 | 0.4 μg of Ψ- and m⁵C-mRNA | 0 |
| 7 | Mock Transfected | 0 |
| 8 | 1.2 μg of Ψ-mRNA | 49 |
| 9 | 1.0 μg of Ψ-mRNA | 168 |
| 10 | 0.8 μg of Ψ-mRNA | 8 |
| 11 | 0.6 μg of Ψ-mRNA | 4 |
| 12 | 0.4 μg of Ψ-mRNA | 0 |

Table 7 shows the number of iPSC colonies generated from human BJ fibroblasts transfected daily with amounts of the 3:1:1:1:1 molar ratio of RNase III-treated Ψ- or Ψ- and m⁵C-modified mRNAs encoding iPSC induction factors (OCT4, SOX2, KLF4, LIN28, cMYC), as indicated. After 15 days, the cells were fixed and stained for alkaline phosphatase, a stem cell marker.

Evaluation of iPSC Induction Using mRNAs Encoding Different Combinations of Reprogramming Factors Based on the finding that the TransIT™ reagent resulted in an impressive increase in the number iPSC colonies generated from BJ fibroblasts compared to using the RNAiMAX™ reagent, the TransIT™ reagent was then used to evaluate different combinations of reprogramming factors.

Figure 19:
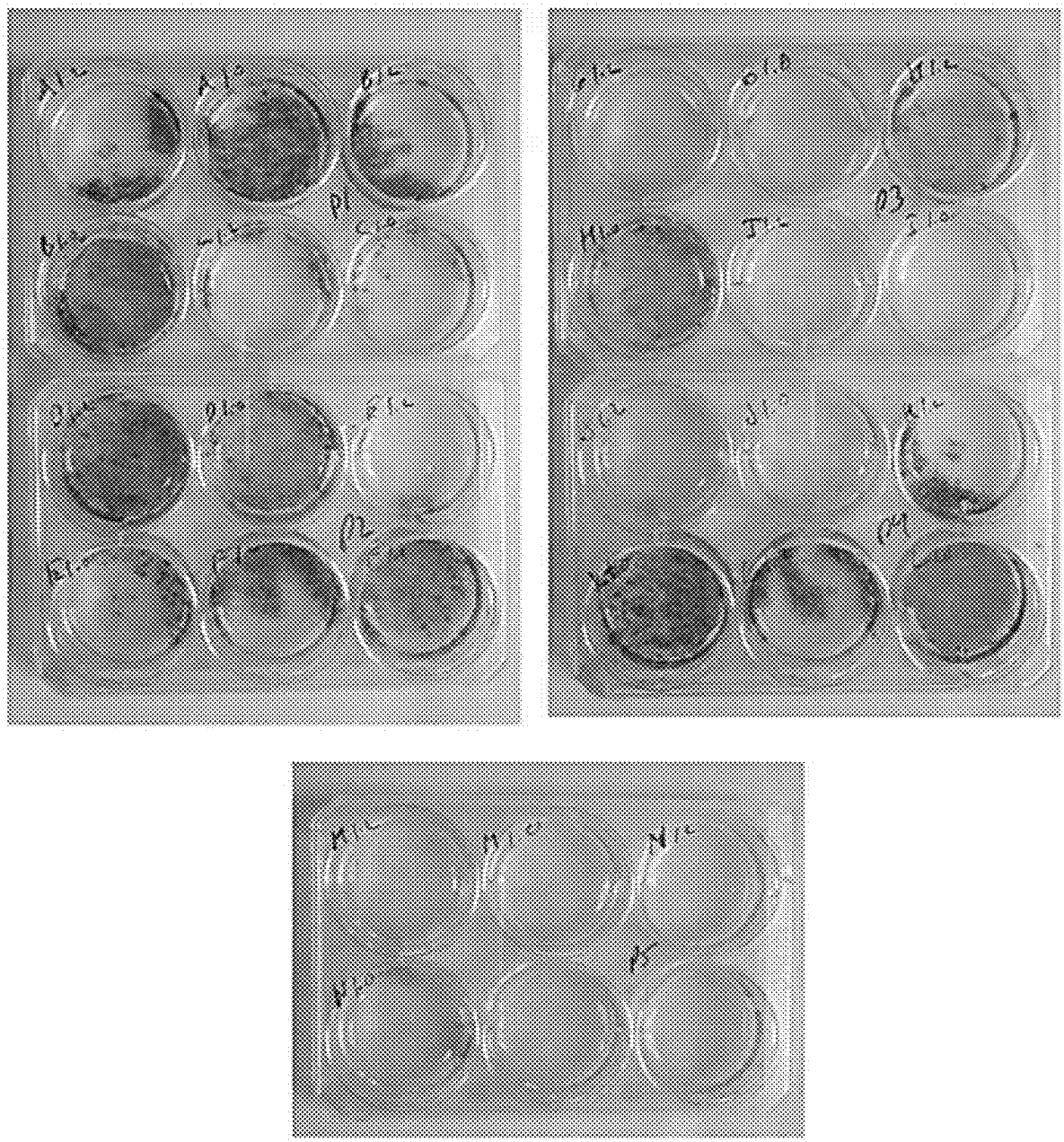
FIG. 19 shows that mRNA encoding L-MYC can substitute for c-MYC for reprogramming human BJ fibroblasts to iPSC cells. The BJ fibroblasts were transfected with RNase III-treated Ψ-mRNA or Ψ- and m5C-mRNA encoding OCT4, SOX2, KLF4, LIN28 and L-MYC for 17 days.

We found that use of mRNAs encoding the four iPSC induction factors (OCT4, SOX2, KLF4, c-MYC) shown to generate iPSCs by Takahashi and Yamanaka (2006) were sufficient to reprogram BJ fibroblasts to alkaline phosphatase-positive iPSC colonies by reprogramming day 18. In these experiments, induction of iPSC colonies using Ψ- and m⁵C-modified mRNA induction factors encoding OCT4, SOX2, KLF4, c-MYC did not appear to be more efficient than using only Ψ-modified mRNAs that encoded those proteins (FIG. 19).

Yu et al. (2007) showed that human somatic cells could be reprogrammed by overexpressing OCT4, SOX2, LIN28 and NANOG as reprogramming factors using lentiviral systems. Possibly higher amounts of the mRNAs or more treatments with mRNAs encoding these factors could be successful. However, we did not observe any alkaline phosphatase-positive iPSC colonies by reprogramming day 18 using the amounts of RNase III-treated mRNA induction factors encoding only OCT4, SOX2, LIN28 and NANOG evaluated, whether those mRNAs were only Ψ-modified or both Ψ- and m⁵C-modified.

Figure 20:
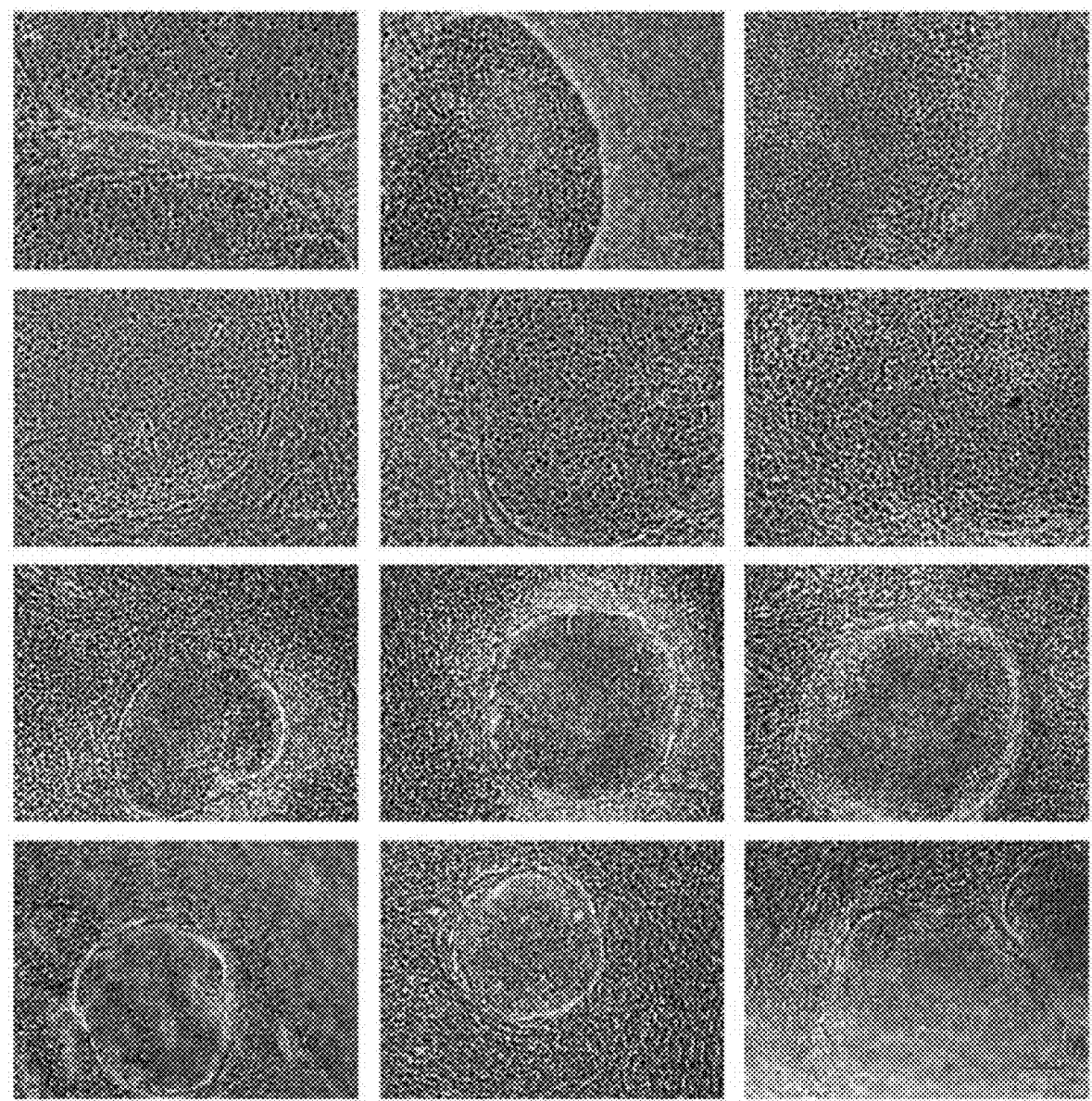
FIG. 20 shows examples of iPSC colonies generated from BJ fibroblasts after 17 daily transfections with RNase III-treated Ψ-mRNA or Ψ- and $m^5C$-mRNA encoding OCT4, SOX2, KLF4, LIN28 and L-MYC for 17 days. Examples of iPSC colonies observed on day 17 are shown at 10× (top 6 images with scale bars) and 4× (bottom 6 images with scale bars) magnification.

Nakagawa M et al. (2010) showed that L-MYC, a member of the MYC oncogene family with less oncogenic activity than c-MYC, could be used in place of c-MYC for iPSC induction. We found that RNase III-treated Ψ-modified or Ψ- and m⁵C-modified mRNA encoding L-MYC was also able to be used in place of c-MYC for iPSC reprogramming of BJ fibroblasts in various combinations of mRNA iPSC induction factors. However, efficiency of iPSC colony generation using mRNAs encoding L-MYC was generally lower than when using mRNAs encoding c-MYC (Table 8 and FIG. 19 and FIG. 20).

Nakagawa M et al. (2010) showed that human cells can be reprogrammed to a pluripotent state by using lentiviral systems to overexpress only three factors (OCT4, SOX2 and KLF4). We did not observe generation of alkaline phosphatase-positive iPSC colonies by reprogramming day 18 using the amounts of RNase III-treated mRNA induction factors encoding only OCT4, SOX2 and KLF4 without c-MYC or L-MYC, whether those mRNAs were only Ψ-modified or both Ψ- and m⁵C-modified (Table 8 and FIG. 19). Possibly higher amounts of the mRNAs or more treatments with mRNAs encoding these factors could be successful.

When reprogramming factors were expressed in somatic cells using episomal vectors, others have found that introduction of expression of 6 factors (OCT4, SOX2, KLF4, LIN28, c-MYC and NANOG) resulted in the highest level of iPSC induction.

We found that RNase III-treated Ψ-modified or Ψ- and m⁵C-modified mRNA encoding all six factors, including NANOG, generally resulted in a slight increase in the number of alkaline phosphatase- (ALKP-) positive colonies compared to OCT4, SOX2, KLF4, LIN28 and c-MYC without NANOG (Table 8 and FIG. 19). In this particular experiment, we also observed formation of iPSC colonies on day 10 when mRNA encoding NANOG was included, compared to day 11 or day 12 when mRNA encoding NANOG was not included with the OCT4, SOX2, KLF4, LIN28 and c-MYC mRNAs.

TABLE 8 iPSC Induction of BJ Fibroblasts by different kinds and amounts of reprogramming mRNAs.

| Plate Numbering | Total Amount, Identity and Modification of RNase III-treated mRNAs Used for Transfection | No. of Alkaline Phosphatase-Positive Colonies On Day 17 |
|---|---|---|
| Plate 5 (last 2 wells) | Untreated BJ Fibroblasts | 0 |
| Plate1 (A1.2) | 1.2 µg Total Ψ-mRNA Encoding OCT, SOX2, KLf4, LIN28, cMYC | 108 |
| Plate1 (A1.0) | 1.0 µg Total Ψ-mRNA Encoding OCT, SOX2, KLf4, LIN28, cMYC | 278 |
| Plate1 (B1.2) | 1.2 µg Total Ψ- & m⁵C-mRNA Encoding OCT, SOX2, KLf4, LIN28, cMYC | 85 |
| Plate1 (B1.0) | 1.0 µg Total Ψ- & m⁵C-mRNA Encoding OCT, SOX2, KLf4, LIN28, cMYC | 268 |
| Plate1 (C1.2) | 1.2 µg Total Ψ-mRNA Encoding OCT, SOX2, KLf4, LIN28, L-MYC | 36 |
| Plate1 (C1.0) | 1.0 µg Total Ψ-mRNA Encoding OCT, SOX2, KLf4, LIN28, L-MYC | 34 |
| Plate2 (D1.2) | 1.2 µg Total Ψ- & m⁵C-mRNA Encoding OCT, SOX2, KLf4, LIN28, L-MYC | 171 |
| Plate2 (D1.0) | 1.0 µg Total Ψ- & m⁵C-mRNA Encoding OCT, SOX2, KLf4, LIN28, L-MYC | 107 |
| Plate2 (E1.2) | 1.2 µg Total Ψ-mRNA Encoding OCT, SOX2, KLf4, cMYC | 28 |
| Plate2 (E1.0) | 1.0 µg Total Ψ-mRNA Encoding OCT, SOX2, KLf4, cMYC | 87 |
| Plate2 (F1.2) | 1.2 µg Total Ψ- & m⁵C-mRNA Encoding OCT, SOX2, KLf4, cMYC | 207 |
| Plate2 (F1.0) | 1.0 µg Total Ψ- & m⁵C-mRNA Encoding OCT, SOX2, KLf4, cMYC | 255 |
| Plate3 (G1.2) | 1.2 µg Total Ψ-mRNA Encoding OCT, SOX2, KLf4, L-MYC | 0 |
| Plate3 (G1.0) | 1.0 µg Total Ψ-mRNA Encoding OCT, SOX2, KLf4, L-MYC | 3 |
| Plate3 (H1.2) | 1.2 µg Total Ψ- & m⁵C-mRNA Encoding OCT, SOX2, KLf4, L-MYC | 44 |
| Plate3 (H1.0) | 1.0 µg Total Ψ- & m⁵C-mRNA Encoding OCT, SOX2, KLf4, L-MYC | 17 |
| Plate3 (I1.2) | 1.2 µg Total Ψ-mRNA Encoding OCT, SOX2, KLf4 | 0 |
| Plate3 (I1.0) | 1.0 µg Total Ψ-mRNA Encoding OCT, SOX2, KLf4 | 0 |
| Plate4 (J1.2) | 1.2 µg Total Ψ- & m⁵C-mRNA Encoding OCT, SOX2, KLf4 | 0 |
| Plate4 (J1.0) | 1.0 µg Total Ψ- & m⁵C-mRNA Encoding OCT, SOX2, KLf4 | 0 |
| Plate4 (K1.2) | 1.2 µg Total Ψ-mRNA Encoding OCT, SOX2, KLf4, LIN28, cMYC, NANOG | 97 |
| Plate4 (K1.0) | 1.0 µg Total Ψ-mRNA Encoding OCT, SOX2, KLf4, LIN28, cMYC, NANOG | 364 |
| Plate4 (L1.2) | 1.2 µg Total Ψ- & m⁵C-mRNA Encoding OCT, SOX2, KLf4, LIN28, cMYC, NANOG | 150 |
| Plate4 (L1.0) | 1.0 µg Total Ψ- & m⁵C-mRNA Encoding OCT, SOX2, KLf4, LIN28, cMYC, NANOG | 303 |
| Plate5 (M1.2) | 1.2 µg Total Ψ-mRNA Encoding OCT, SOX2, LIN28, NANOG | 0 |
| Plate5 (M1.0) | 1.0 µg Total Ψ-mRNA Encoding OCT, SOX2, LIN28, NANOG | 0 |
| Plate5 (N1.2) | 1.2 µg Total Ψ- & m⁵C-mRNA Encoding OCT, SOX2, LIN28, NANOG | 0 |
| Plate5 (N1.0) | 1.0 µg Total Ψ- & m⁵C-mRNA Encoding OCT, SOX2, LIN28, NANOG | 0 |

Example 13. Reprogramming BJ Fibroblasts to iPS Cells Using RNase III-Treated Cap1 Poly-A-Tailed ψ-Modified mRNAs Encoding OCT4, SOX2, KLF4, LIN28, NANOG and cMYC Reprogramming Factors Materials and Methods for Example 13 mRNA Reprogramming Factors

Cap1 5'-capped ψ-modified mRNAs encoding OCT4, SOX2, KLF4, LIN28, NANOG and cMYC with an approximately 150-base poly(A) tail (with tail length verified by denaturing agarose gel electrophoresis) were prepared and then mixed in a 3:1:1:1:1:1 molar as described above. The RNase III treatment to remove dsRNA was performed using the in vitro-transcribed RNA prior to capping and tailing in the presence of 1 mM magnesium acetate.

Brief Description of the Reprogramming Method

BJ fibroblasts cells (ATCC) were plated onto irradiated feeder cells-human NuFF cells (newborn foreskin fibroblasts; Globalstem) in PLURITON™ medium plus supplement (Stemgent) with penicillin/streptomycin (pen/strep) antibiotics, and transfected daily for 18 days with 800 ng of the 3:1:1:1:1:1 mRNA mix TransIT™ mRNA transfection reagent (2 microliters per microgram of RNA; Mirus Bio). The cell media was changed daily, 1 hour prior to transfection, with SCRIPTGUARD™ RNase inhibitor (0.4 U/ml; CELLSCRIPT) added to the media prior to transfection. The cells in each culture well were split 1-to-3 and transferred into 3 replicate wells on Day 8 after the 9th transfection.

Detailed Description of the Reprogramming Method $2.5 \times 10^5$ passage 9, mitotically-inactivated NuFF cells (GlobalStem) were plated on gelatin-coated, 6-well plates in NuFF media (DMEM [Life Technologies], 10% fetal bovine serum (FBS, Thermo Fisher), 1× GLUTAMAX (Life Technologies) and 1× penicillin/streptomycin (Life Technologies). Twenty-four hours later, the media was removed and $10^4$ BJ fibroblasts (ATCC) were plated per well on the NuFF feeder cells in fibroblast medium, (EMEM [ATCC] supplemented with 10% FBS and 1× pen/strep).

PLURITON™ reprogramming medium (Stemgent), with freshly added 1× PLURITON™ supplement and 1× pen/strep, was changed daily one hour prior to mRNA transfections. SCRIPTGUARD™ RNase inhibitor was added to the PLURITON™ reprogramming media (and to the NuFF-conditioned PLURITON™ reprogramming media described below) to a final concentration of 0.4 U/ml. The medium was then added to cells daily, 1 hour or less before the transfections.

Cells were transfected on 18 consecutive days using the TransIT®-mRNA transfection kit (Mirus Bio). 800 ng reprogramming mRNA mix was diluted in 250 microliters Opti-MEM I (Life Technologies) and 1.6 microliters of TransIT BOOST™ was added, reaction components were mixed, then 1.6 microliters of the TransIT transfection reagent was added and the reaction components were mixed. After 2-5 minutes incubation at room temperature, the transfection mix was applied drop-wise to cells. Cells were then incubated at 37° C. in 5% $CO_2$ overnight. After 6 daily transfections in PLURITON™ medium, the medium was changed to NuFF-Conditioned PLURITON™ reprogramming media. This PLURITON™-based medium was previously incubated on NuFF feeder cells for 24 hours, was collected and stored frozen until used. When needed, the conditioned medium was thawed, filtered and PLURITON™ supplement and antibiotics were added fresh, daily. After the last of the 18 daily transfections, the cells were live stained with an antibody to TRA-1-60, to confirm iPSC colony production.

In Vivo Immunostaining Methods

A sterile, TRA-1-60 antibody (StainAlive™ DyLight™ 488 anti-human TRA-1-60 antibody; Stemgent) was diluted 1:100 in PLURITON™ medium. On day 18 of the reprogramming protocol, the medium was removed and the cells were incubated in TRA-1-60-containing media for 30 minutes at 37° C. with 5% $CO_2$. The cells were then washed twice with PLURITON™ medium to remove the unbound antibody and the cells were maintained in fresh reprogramming medium during immunofluorescent imaging. This antibody allows live cell staining, instead of fixing the cells and sacrificing them for the imaging. Based on morphology and TRA-1-60 antibody staining, hundreds of iPSC colonies were generated per well of BJ fibroblast cells transfected with pseudouridine-modified mRNA that had been treated with RNase III, but only 2 iPSC colonies were seen with the dual-modified pseudouridine- and 5-methylcytidine-containing mRNA that had been treated with RNase III. After iPSC cell colonies were confirmed by morphology and TRA-1-60 staining, on day 19 they were picked and plated on fresh NuFF feeder cells in NuFF-conditioned medium.

Picking of Reprogrammed iPSC Colonies

Colonies of iPSCs were manually picked from reprogramming plates and expanded for further characterization. In manual picking, colonies were dissected with a pipette, physically removed from the reprogramming plate, and the pieces were re-seeded onto fresh NuFF feeder cell plates with 10 uM Y27632 ROCK inhibitor (Stemgent) in the NuFF-conditioned medium. The cells were expanded and split when 60-70% confluent with collagenase IV as described below.

Maintaining iPSCs

Induced pluripotent stem cell cultures were expanded and maintained either on feeder-dependent or feeder-free, MATRIGEL® 6-well plates. In feeder-dependent culturing of iPSCs, the cells were maintained on either irradiated human neonatal fibroblasts (GlobalStem) or irradiated embryonic mouse fibroblasts (R&D Systems) seeded at $2.5 \times 10^5$ cells per well. iPSC colonies on feeder plates were kept in iPSC maintenance medium, DMEM/F12 supplemented with 20% Knockout Serum Replacement, 1 mM L-Glutamine, 0.1 mM non-essential amino acids solution, 10 ng/ml basic human recombinant FGF (all from Invitrogen) with penicillin-streptomycin antibiotics. The medium was changed daily. Cultures were split when the cell population grew to about 60% to 70% confluency using collagenase IV as described below.

In feeder-free culturing of iPSCs, colonies were maintained on 6-well tissue culture plates coated with 83 ng per well of MATRIGEL™ (BD Biosciences). Colonies on MATRIGEL™ plates were kept in mTESR (STEMCELL Technologies) media that was changed daily. Cultures were split when the cell population grew to about 60% to 70% confluency using dispase as described below.

Splitting iPSCs

For cultures maintained on feeders, the day before splitting, 0.1% gelatin coated plates were seeded with feeder cells, either irradiated human neonatal fibroblasts (GlobalStem) or irradiated embryonic mouse fibroblasts (R&D Systems) at $2.5 \times 10^5$ cells per well. Cells were washed once with 1× phosphate-buffered saline solution (PBS), and 1 ml of 1 mg/ml collagenase type IV solution in DMEM/F12 (Invitrogen) was applied. iPSC colonies were incubated in collagenase IV at 37° C. and 5% $CO_2$ for 8 to 10 minutes until the edges of the colonies began to lift up. Colonies were gently washed 3 times with 2 to 3 mls of DMEM/F12, and removed and broken up in iPSC maintenance medium, DMEM/F12 supplemented with 20% Knockout Serum Replacement, 1 mM L-Glutamine, 0.1 mM non-essential amino acids solution, 10 ng/ml basic human recombinant FGF (all from Invitrogen) with penicillin-streptomycin antibiotics, in volumes to reach the appropriate split ratios. Split cultures were plated on fresh plates pre-seeded with feeders in iPSC maintenance medium.

For feeder-free maintenance of iPSC cultures, 6 well tissue culture plates were coated with 83 ng per well of MATRIGEL (BD Biosciences) at room temperature at least one hour prior to use. In passaging iPSC cultures, medium was removed and replaced with 1 ml of a 1 mg/ml dispase solution in DMEM/F12 (STEMCELL Technologies). Cultures were incubated at 37° C. and 5% $CO_2$ for 8 to 10 minutes until the edges of the colonies began to lift up. iPSC colonies were gently washed 3 times with 2 to 3 mls of DMEM/F12, and removed and broken up in fresh media, mTESR™ (STEMCELL Technologies) before plating on a new MATRIGEL plate.

On day 28, after 10 days of culture, after picking colonies on day 19 and one subsequent collagenase passaging of the cells, some of the cells were fixed and immunostained.

Methods for Immunostaining of iPSCs iPSC colonies were washed twice in 1× phosphate-buffered solution (PBS) and fixed in 4% paraformaldehyde in PBS at room temperature for half an hour. After 3 washes in 1×PBS, cells were washed 3 times in wash buffer, (PBS with 0.1% Triton-X100), and blocked for one hour at room temperature in blocking solution, 0.1% triton-X100, 1% BSA, 2% FBS in PBS. Primary antibodies were diluted 1:500 in blocking solution and applied to cells overnight at 4° C. Cells were washed 6 times in wash buffer. Secondary antibodies were diluted 1:1,000 in blocking buffer, were applied for 2 hours at room temperature in the dark. After 6 washes with wash buffer, cells were washed twice in 1×PBS before imaging. Images are shown in FIG. 13. FIG. 15, FIG. 16, FIG. 17, FIG. 22, FIG. 31 and FIG. 26.

Primary Antibodies Used:
  Oct4 Rabbit Antibody (Santa Cruz Biotechnology)
  Tra-1-60 Mouse Antibody (Cell Signaling Technology)
  Lin28 Mouse Antibody (Cell Signaling Technology)
  NANOG Rabbit Antibody (Cell Signaling Technology)
  SSEA4 Mouse Antibody (Cell Signaling Technology)

Secondary Antibodies Used:
  Alexa Fluor® 488 Anti-Rabbit (Molecular Probes, Life Technologies)
  Alexa Fluor® 555 Anti-Mouse (Molecular Probes, Life Technologies)

Differentiation into Cardiomyocytes
  Some iPSC colonies were differentiated into cardiomyocytes as described in EXAMPLE 11.

Results for Example 13

By day 18, >>100 colonies of iPSC colonies were present in each of 3 replicate wells of BJ fibroblasts that had been transfected with 18 daily doses of 800 ng of the 3:1:1:1:1 molar mix of RNase III-treated, pseudouridine-modified mRNA encoding OCT4, SOX2, KLF4, LIN28, NANOG and cMYC. iPSC colonies were too numerous to count and some iPSC colonies were already beginning to differentiate into other cell types by day 18. (100 iPSC colonies would represent an efficiency of ~1% iPSC induction).

Figure 21B:
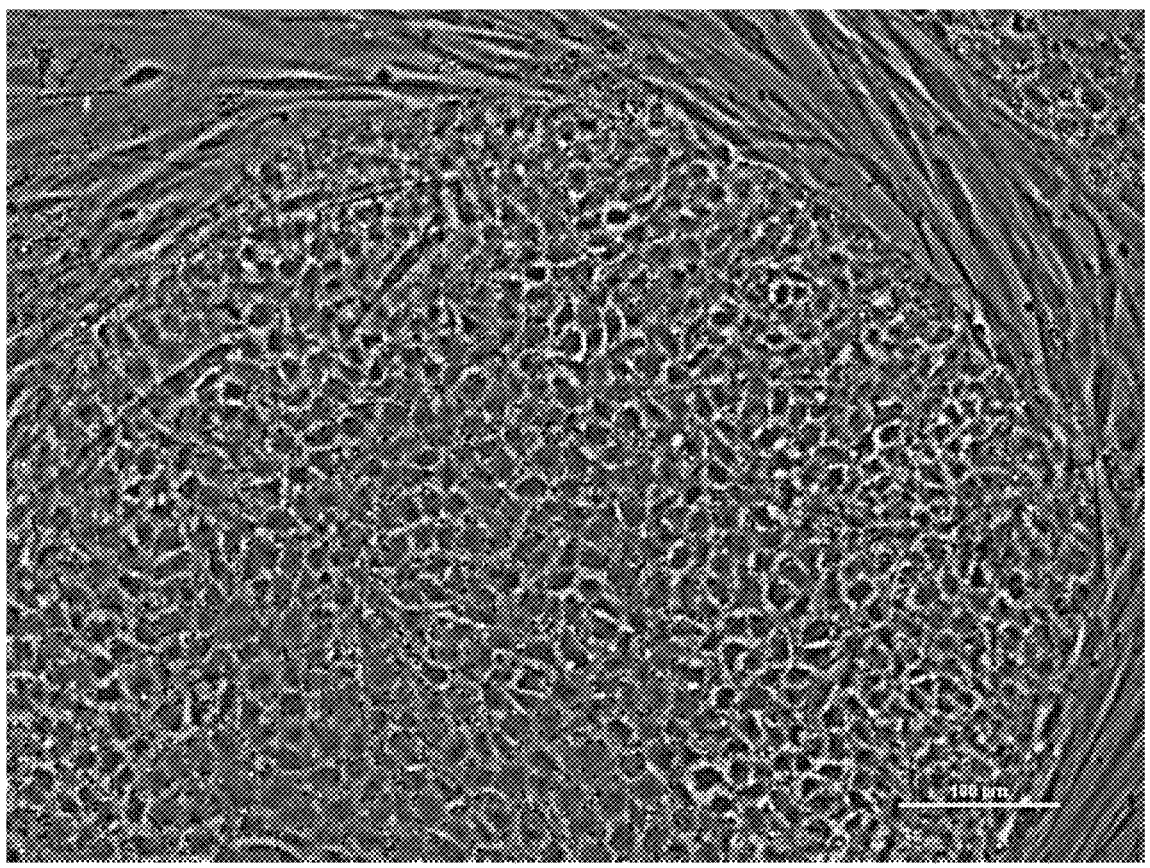
FIG. 21B shows is a larger amplification of a smaller iPSC colony and most of its border. The iPSC colony stains positively for both TRA-1-60 (tumor-related antigen 1-60) and OCT4. Many of the surrounding cells are also OCT4 positive. The images were taken 10 days after the last transfection of mRNA reprogramming factors and show 10× magnification.

The iPSC colonies exhibited iPSC colony morphology (FIG. 21).

Figure 22A:
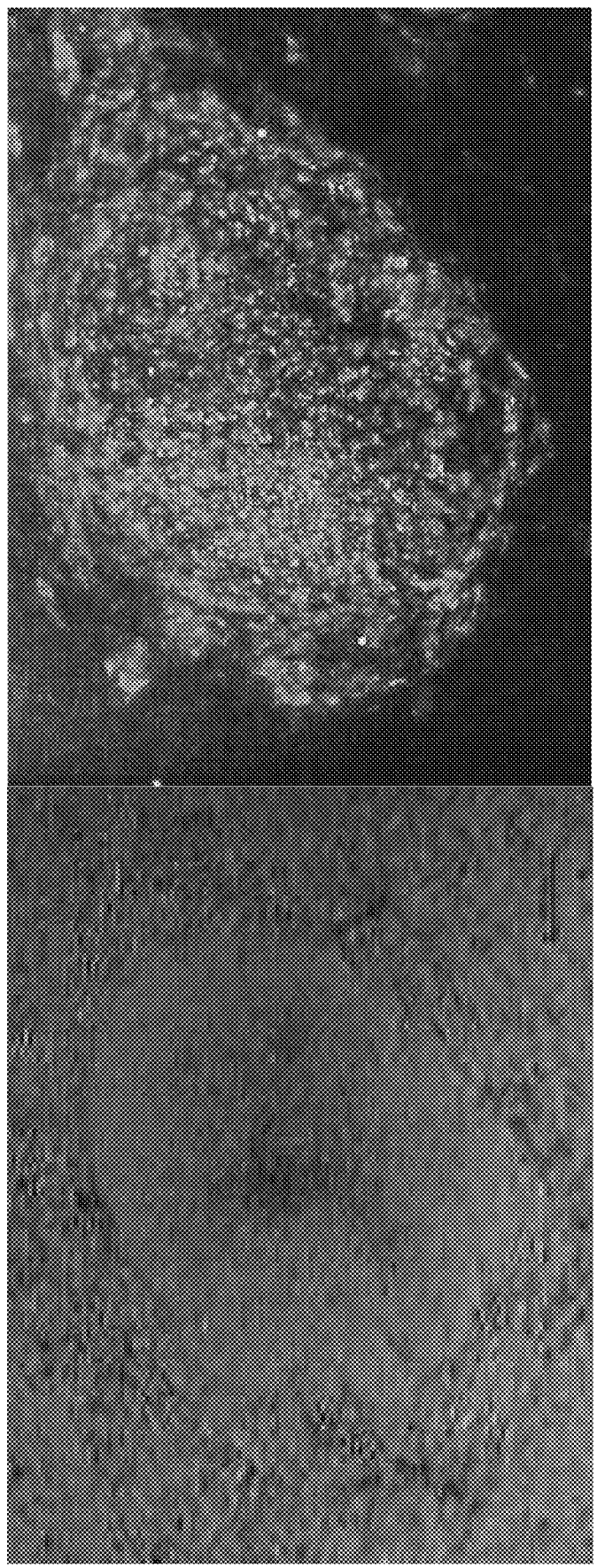
FIG. 22A-FIG. 22B shows an iPSC colony surrounded by fibroblasts that expresses Tra-1-60.
Figure 22B:
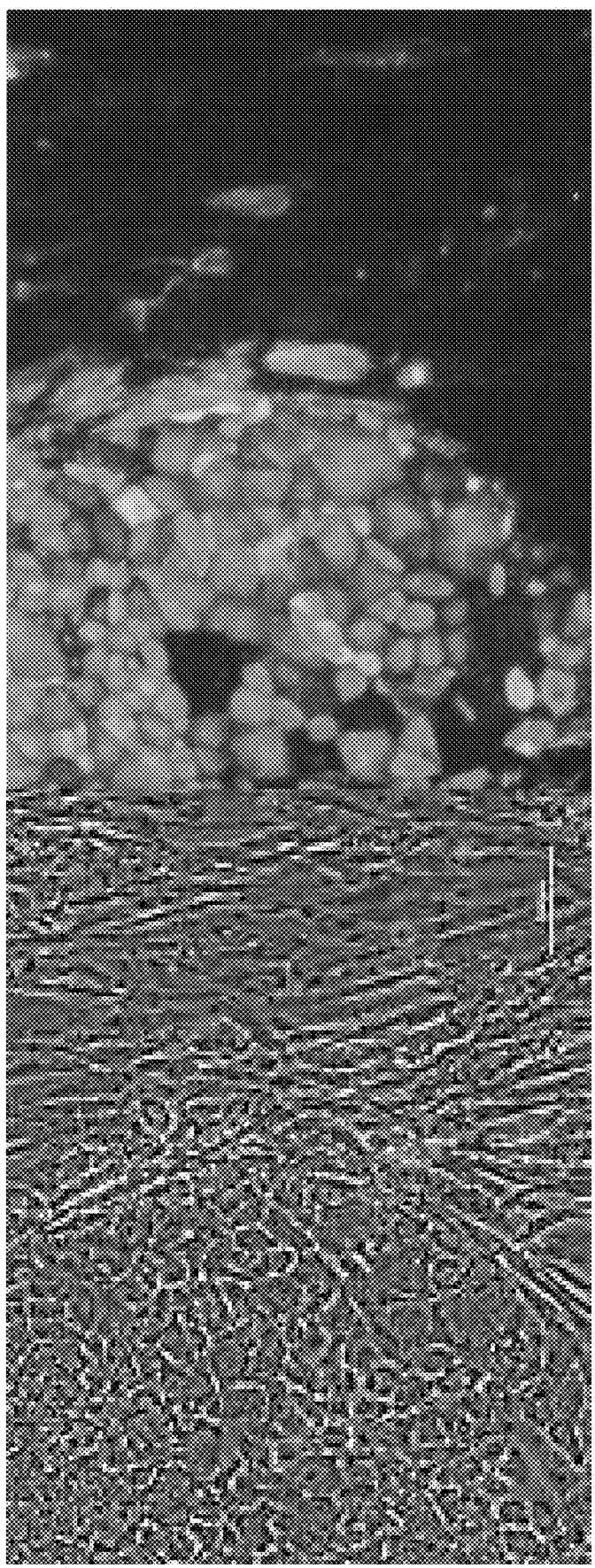
Figure 22C:
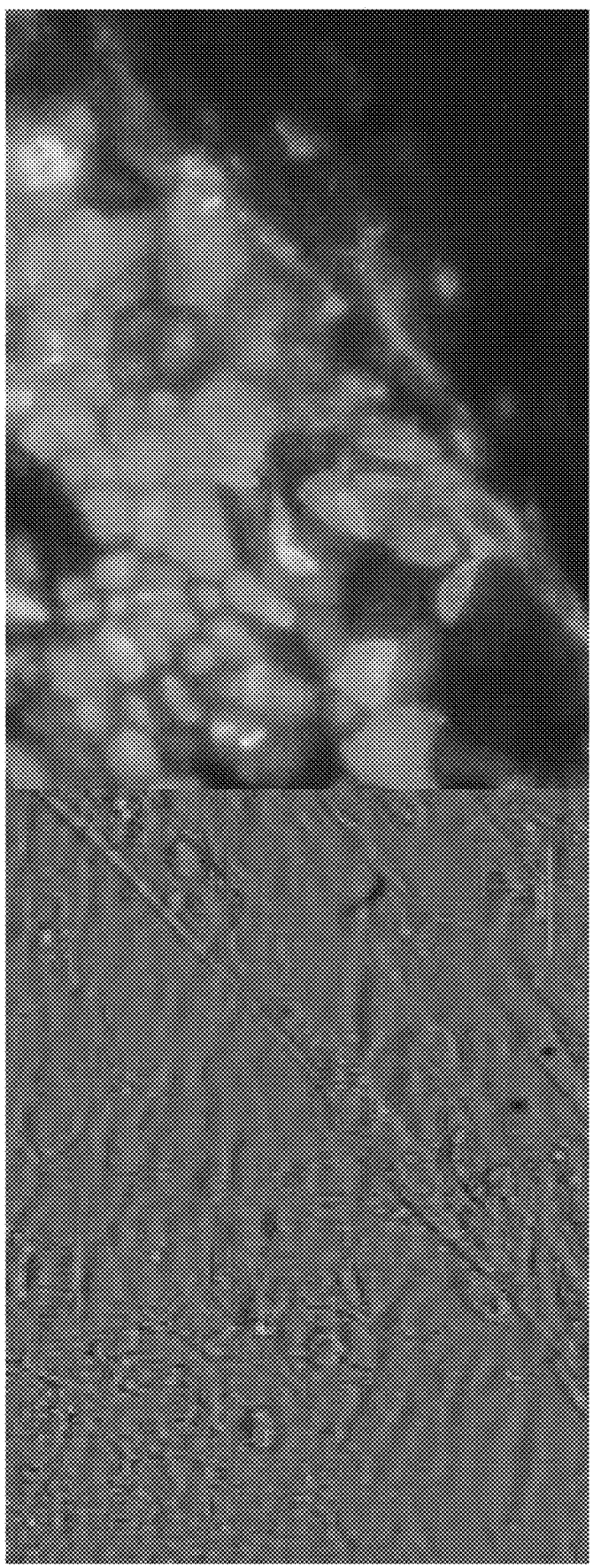
FIG. 22C shows 20× magnification.

Live iPSC colonies stained positively for the stem cell marker Tra-1-60 (FIG. 22).

One of the 3 wells was also treated with B18R protein from Transfection #10 to #18, but no benefit was seen in that this well had a similar number of iPSC colonies as the well that did not receive B18R protein.

Greater than 50 iPSC colonies were picked on Day 19. Some iPSC colonies were collagenase-treated and transferred; the remaining colonies were transferred to new feeder cells on day 21.

Of iPSC colonies that were cultured >90% survived and were cultured for greater than 10 passages.

Figure 23:
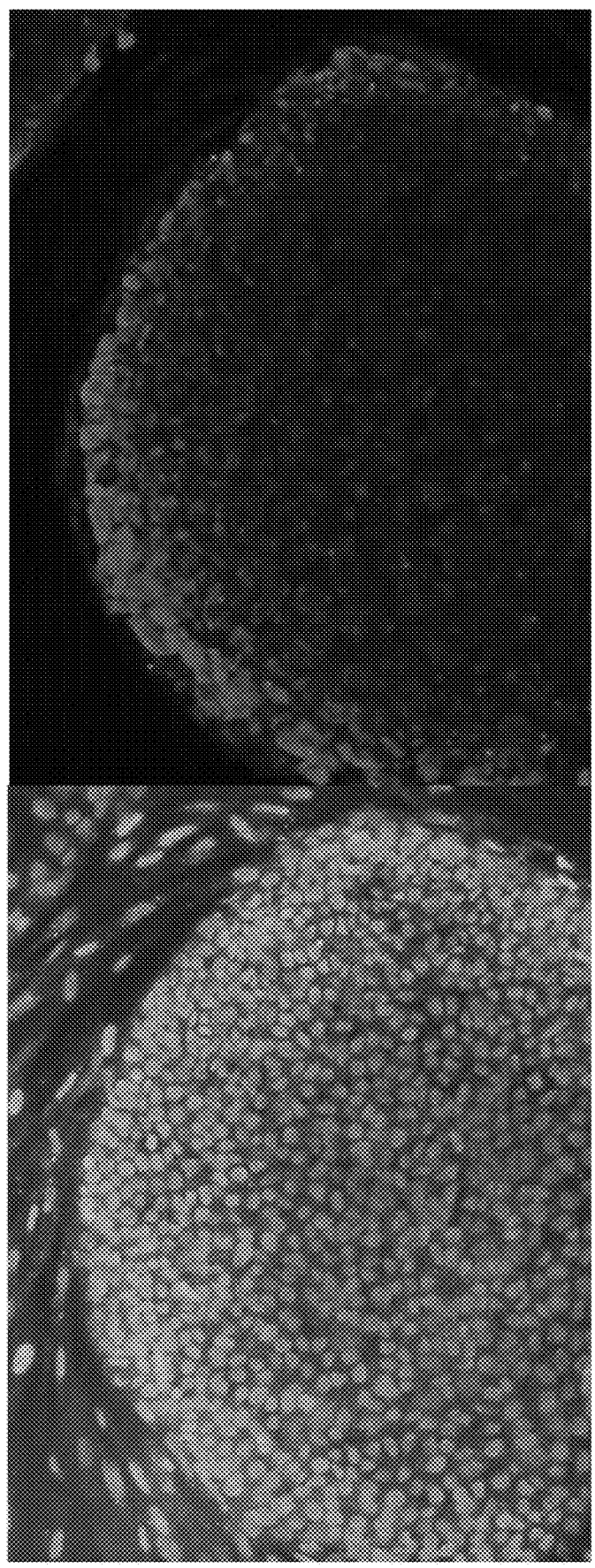
FIG. 23A-FIG. 23J shows images of immunostained iPSCs generated from BJ fibroblasts.
Figure 23:
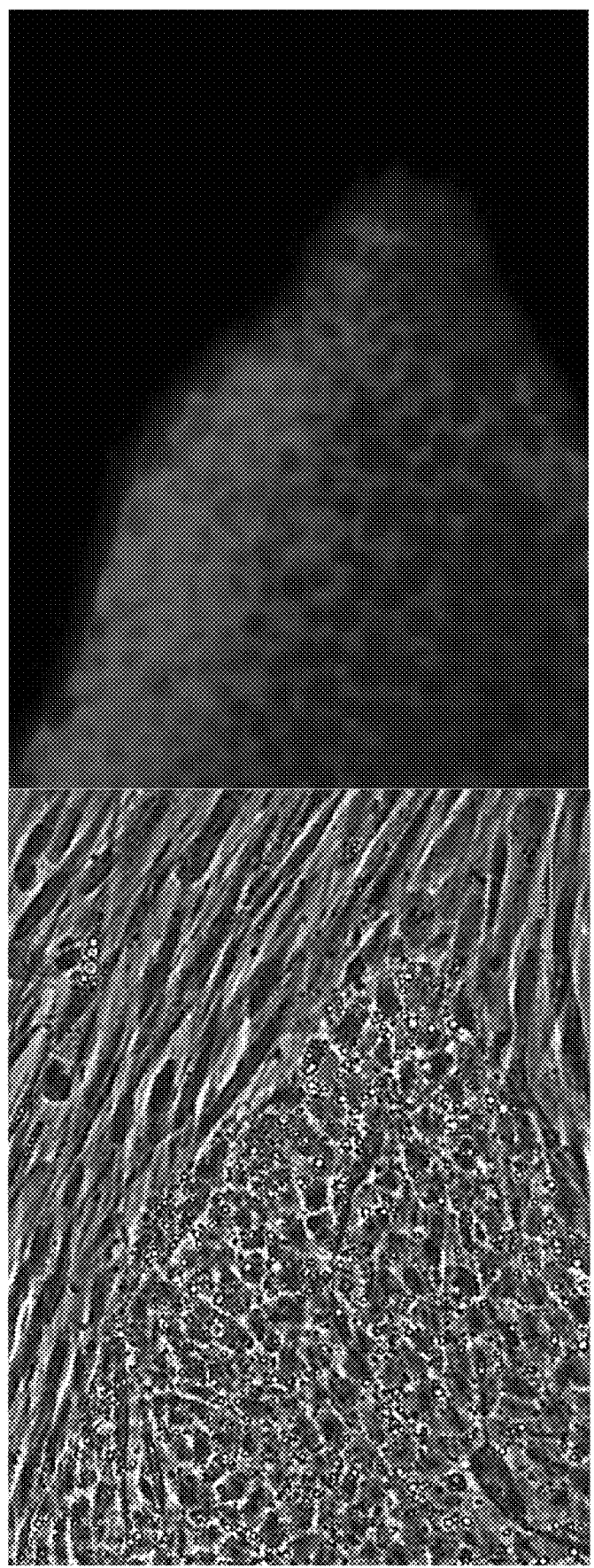
Figure 23E:
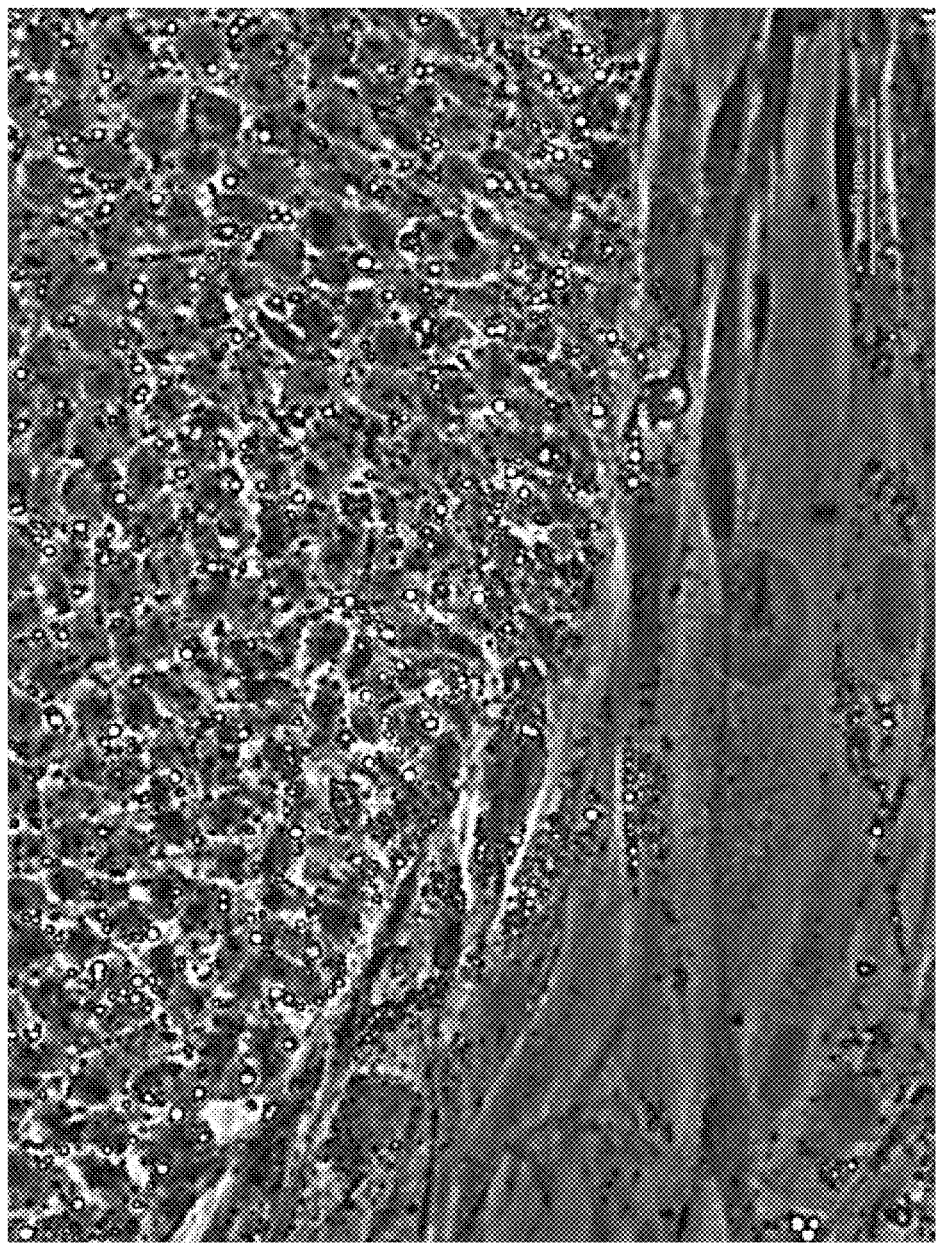
Figure 23:
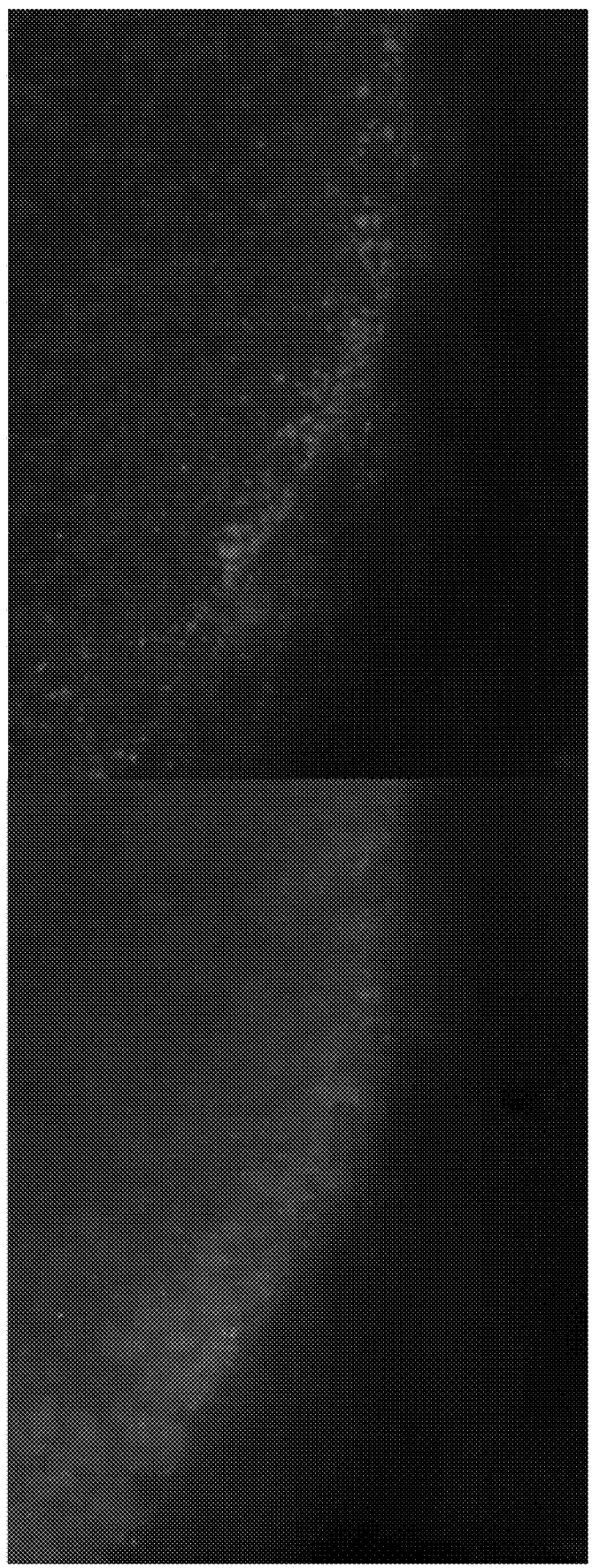
Figure 23H:
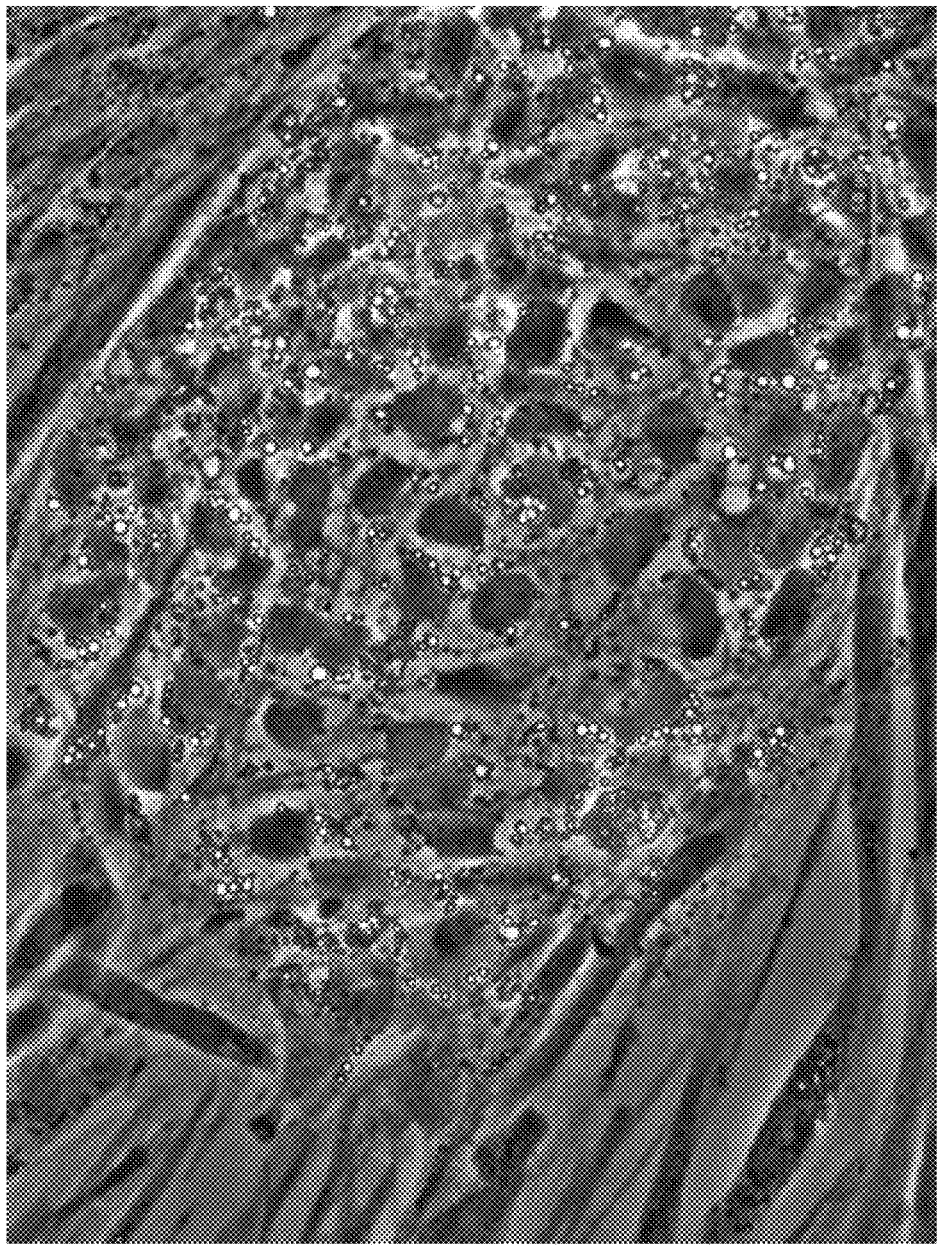
Figure 23:
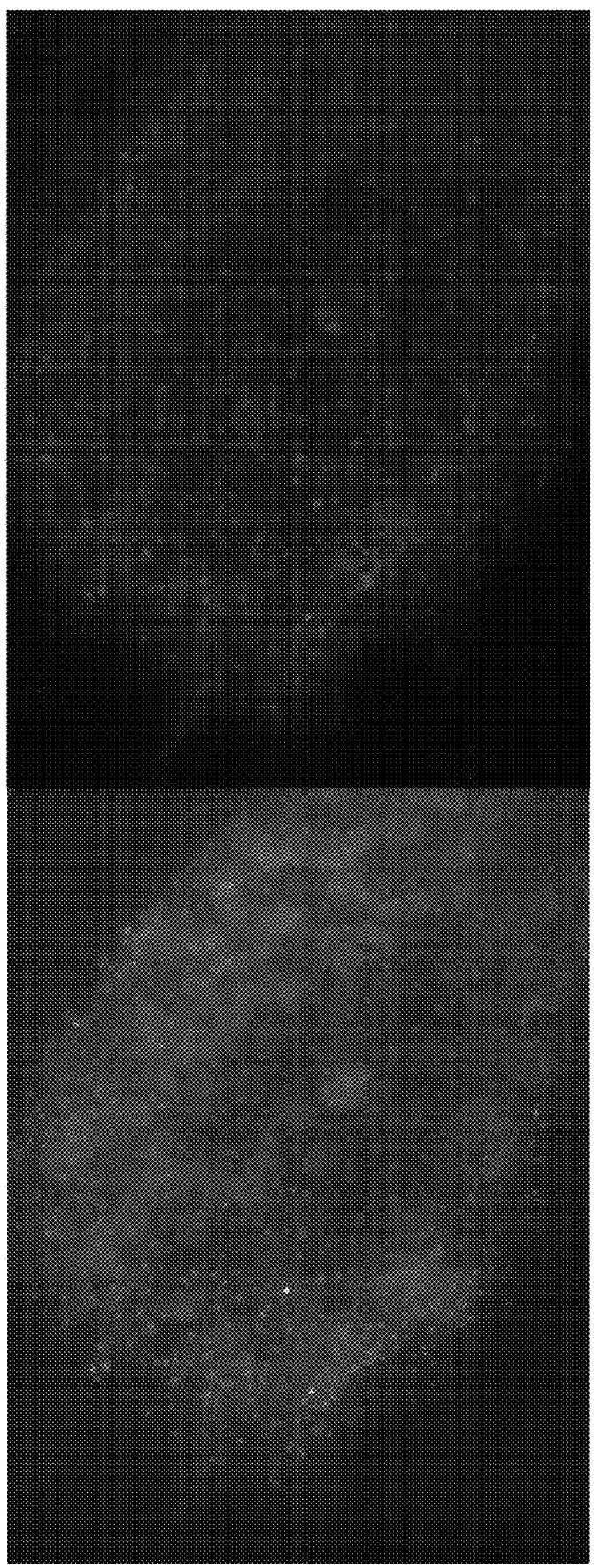
Figure 27A:
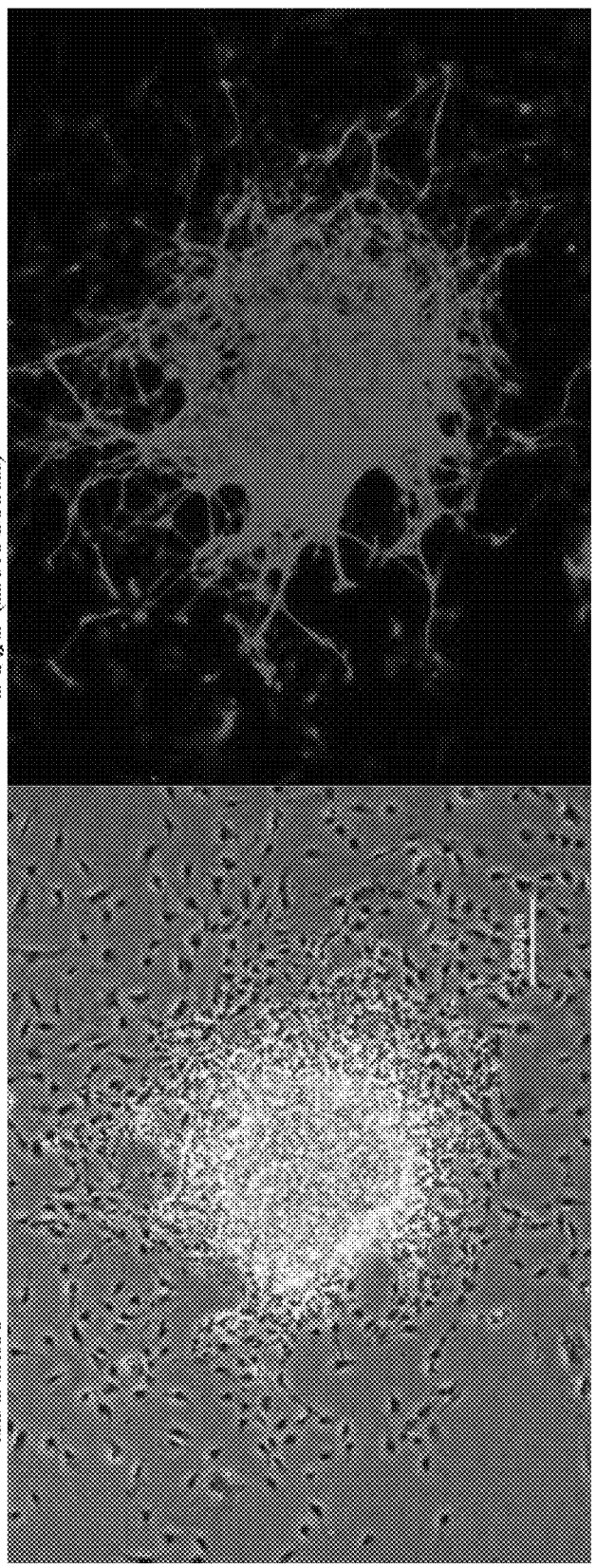
FIG. 27A-FIG. 27J shows that iPSCs induced by RNase III-treated, cap1 5'-capped, 150-base poly(A)-tailed, ψ-modified mRNAs encoding a 3:1:1:1:1:1 mixture of OCT4, SOX2, KLF4, LIN28, NANOG and cMYC are pluripotent based on ability to differentiate into cells of all 3 germ layers.
Figure 27B:
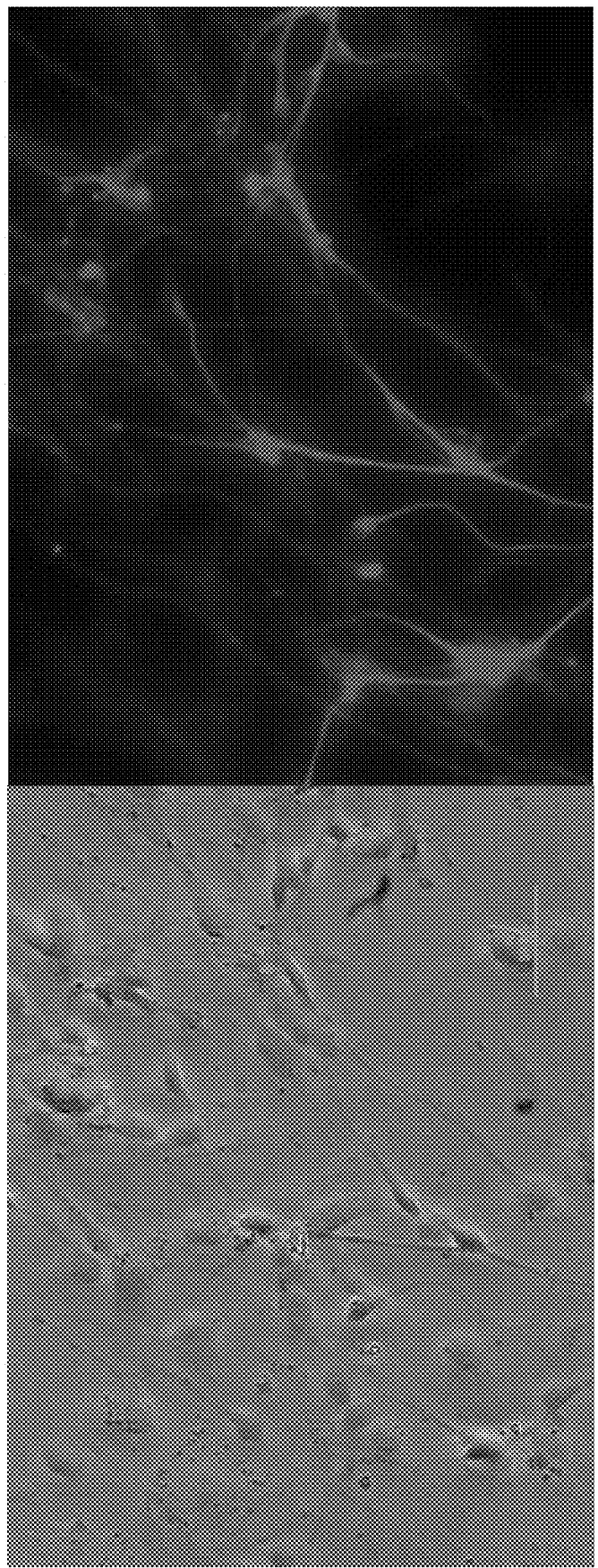
Figure 27C:
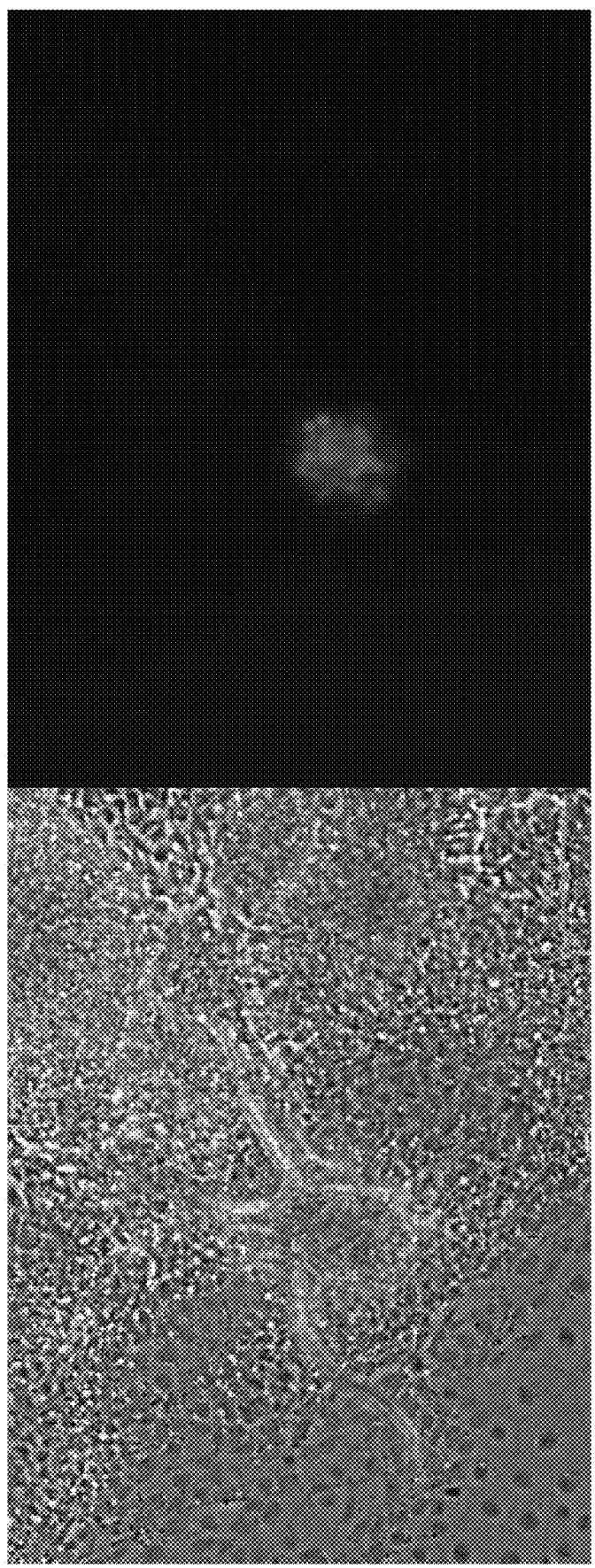
Figure 27D:
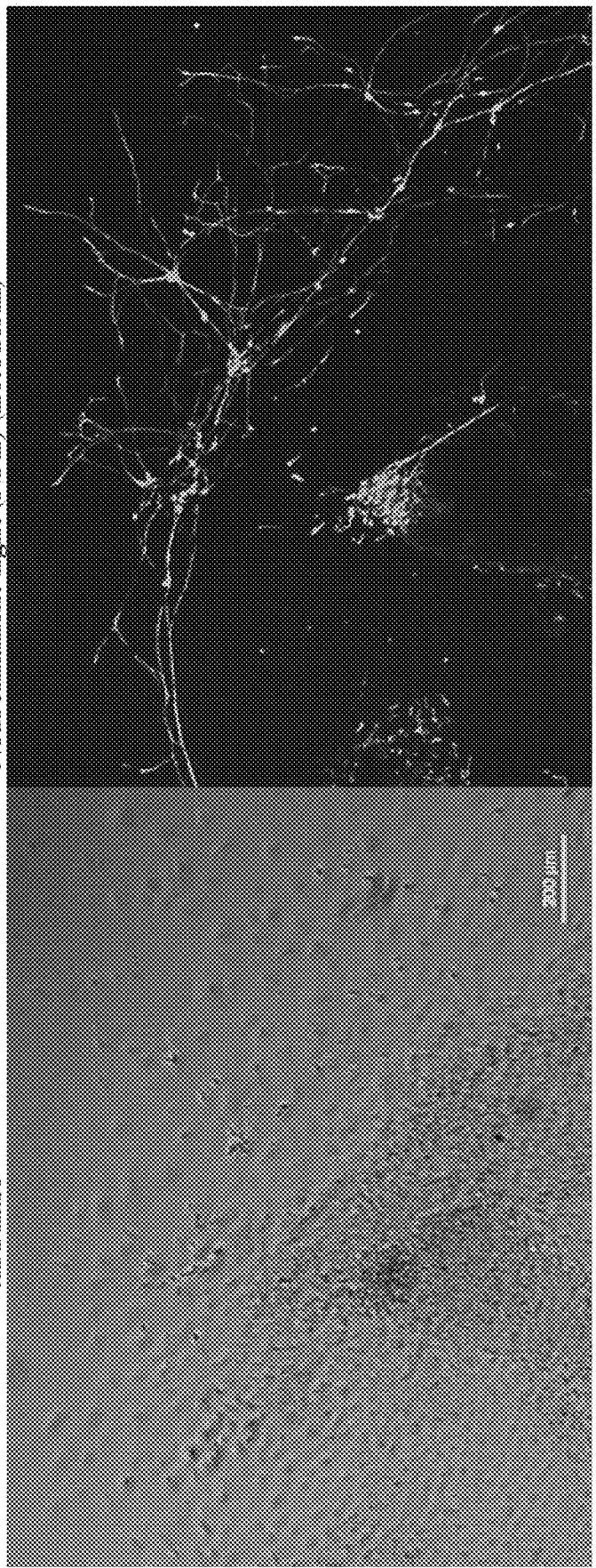
Figure 27E:
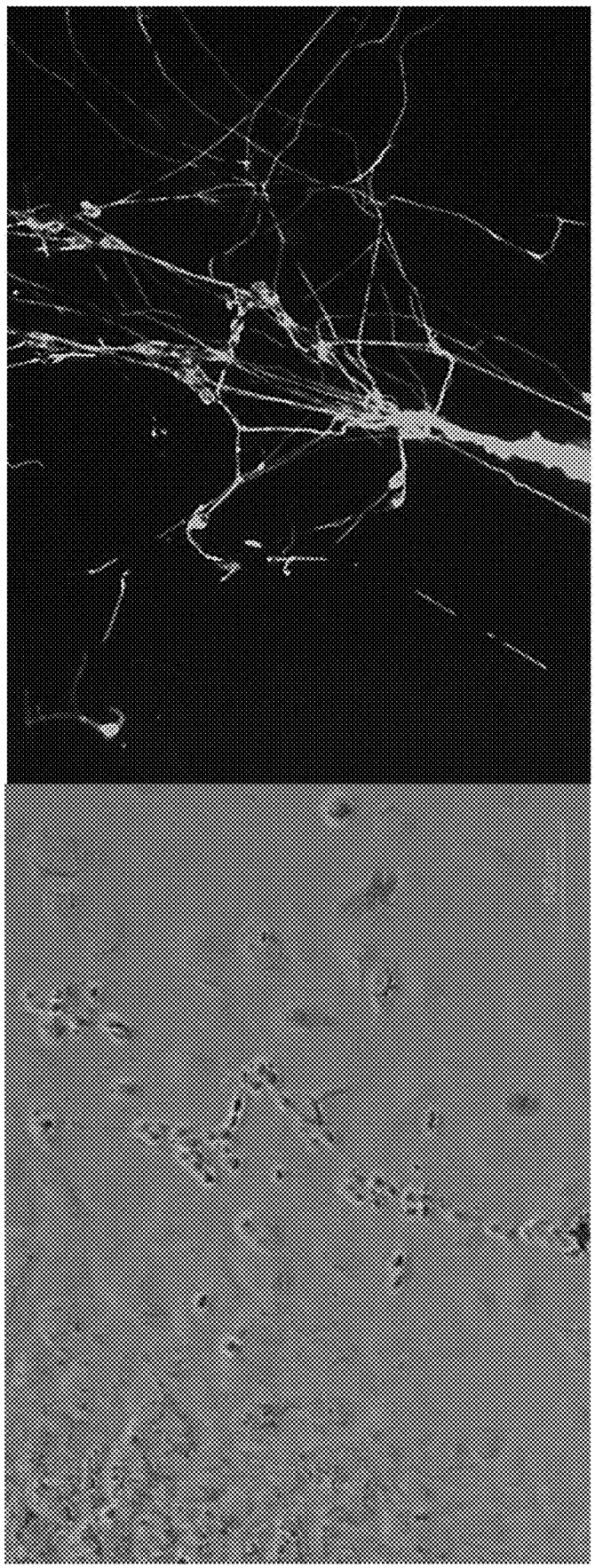
Figure 27F:
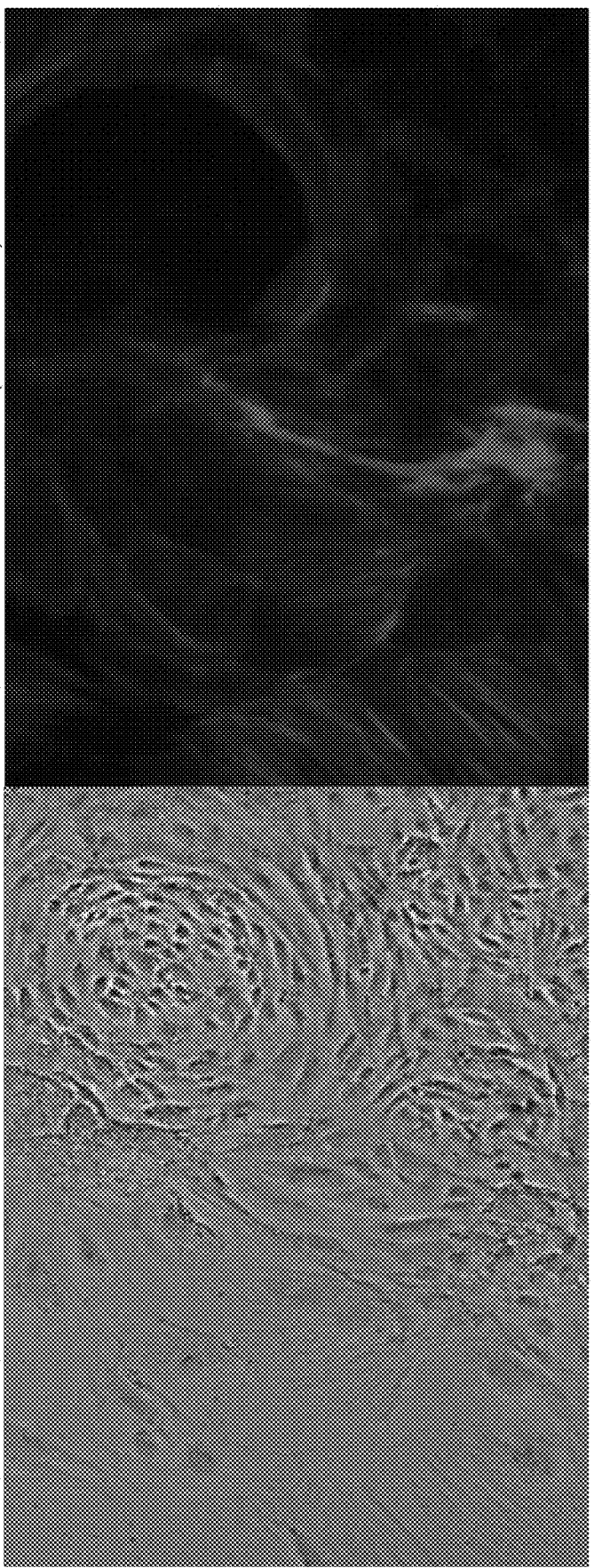
Figure 27G:
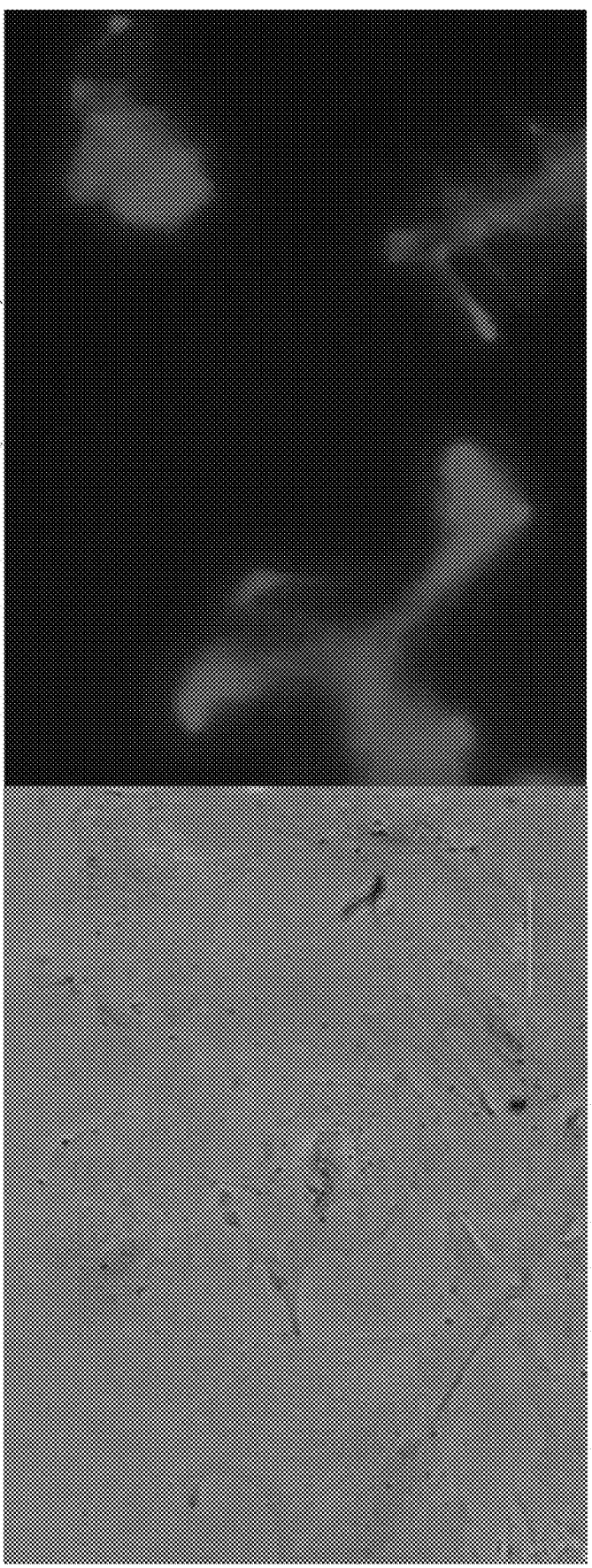
Figure 27H:
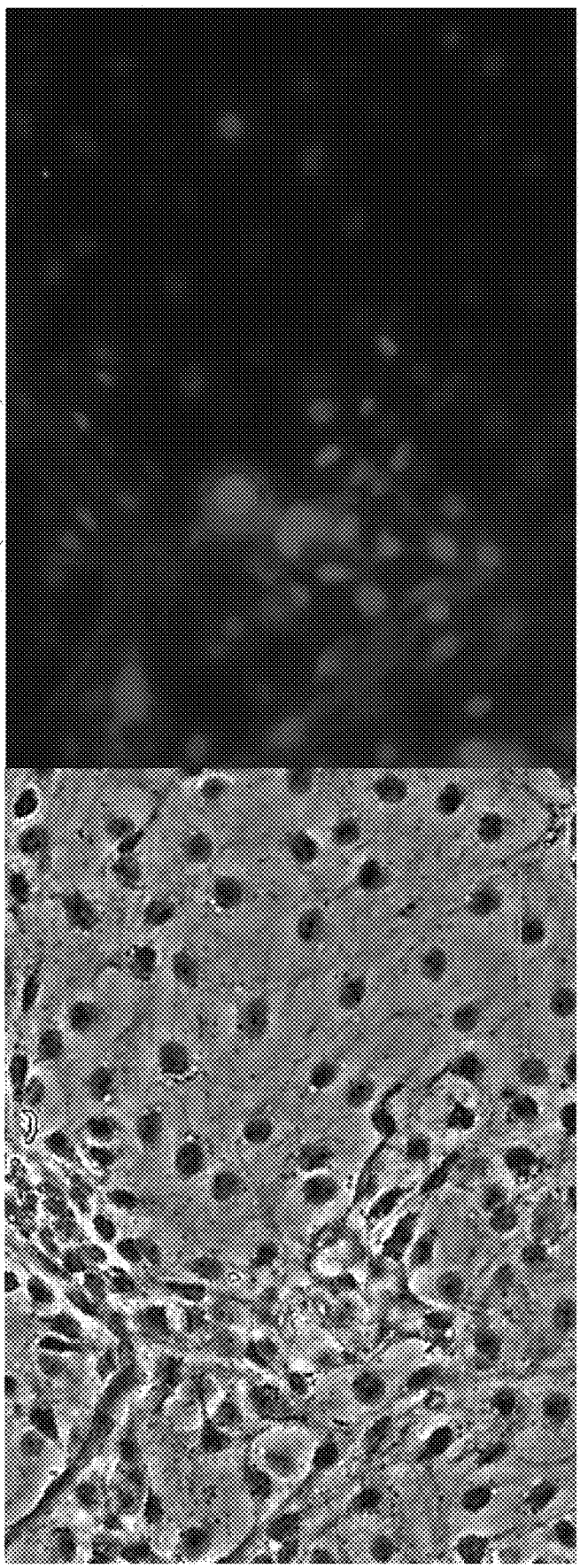
Figure 27I:
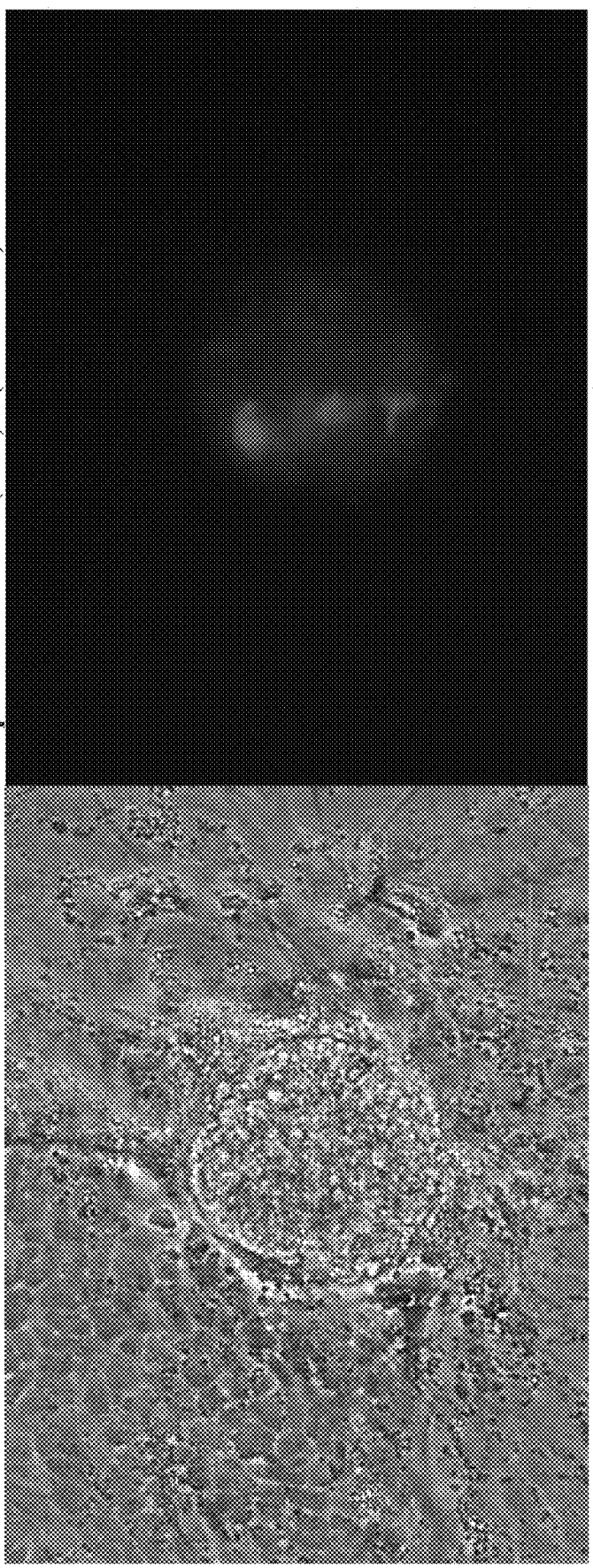
Figure 27J:
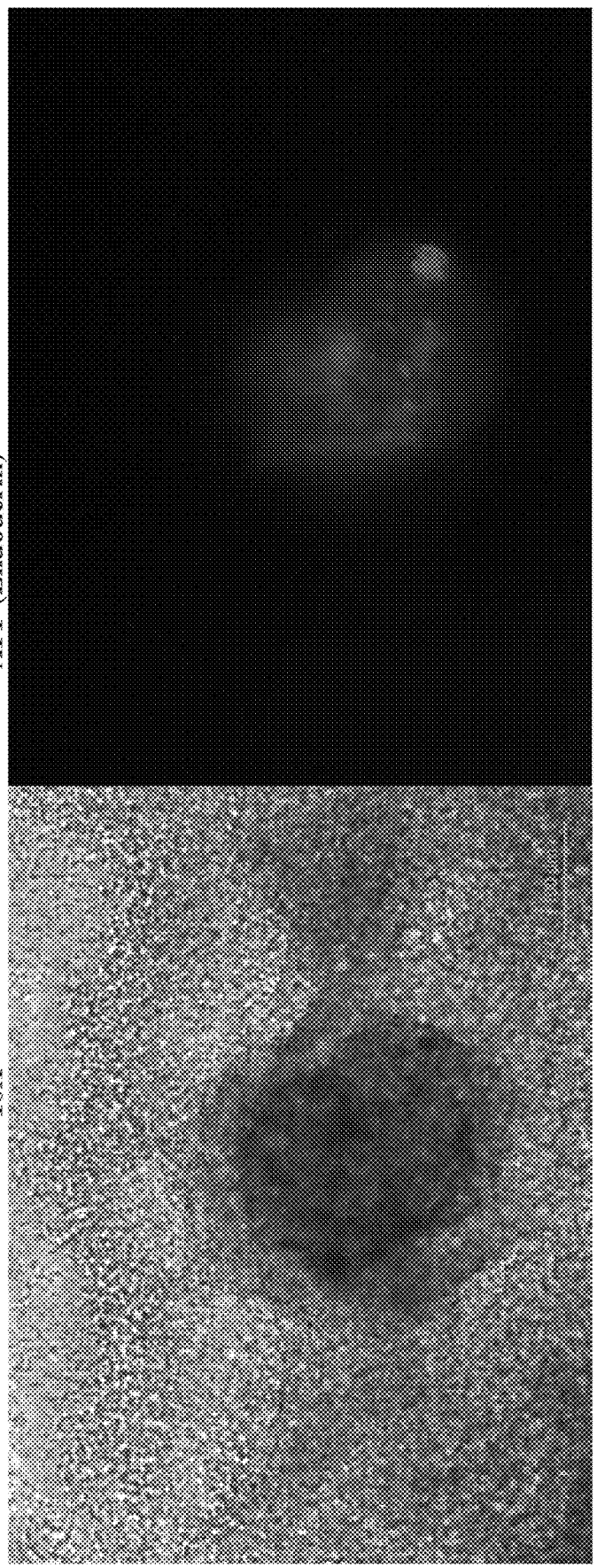

Some of the iPSC colonies were fixed and immunostained positively for stem cell markers on day 28, 10 days of iPSC culture after the last transfection (FIG. 23).

Some of the iPSC colonies were propagated and differentiated into beating cardiomyocytes.

Example 14. Additional Experiments on Reprogramming of BJ Fibroblasts to iPSCs and Further Characterization of iPSC Colonies Materials and Methods for Example 14

Brief Description of the Reprogramming Method

The iPSC reprogramming factors were composed of cap1 5'-capped ψ-modified mRNAs encoding OCT4, SOX2, KLF4, LIN28, NANOG and cMYC with an approximately 150-base poly(A) tail (with tail length verified by denaturing agarose gel electrophoresis) were prepared and then mixed in a 3:1:1:1:1:1 molar as described above. The RNase III treatment to remove dsRNA was performed using the in vitro-transcribed RNA prior to capping and tailing in the presence of 1 mM magnesium acetate. BJ fibroblasts cells (ATCC) were reprogrammed using the iPSC reprogramming factors in a similar reprogramming method to that described in EXAMPLE 13, except that the BJ fibroblasts were transfected daily for 18 days with one microgram (instead of 800 ng) of the 3:1:1:1:1 mRNA mix TransIT™ mRNA transfection reagent (2 microliters per microgram of RNA; Mirus Bio). Some BJ fibroblast cells in this EXAMPLE 14 were pretreated with B18R recombinant protein (eBioscience) prior to being treated with the mRNA reprogramming factors, in which cases, the B18R protein solution was added to the reprogramming medium several hours before adding the mRNA reprogramming factors. Some of the iPSC colonies were also transferred to an artificial extracellular (MATRIGEL™) matrix for propagation in order to propagate the iPSCs in the absence of feeder cells. The iPSCs propagated on MATRIGEL matrix were used for isolation and purification of mRNA from the iPSCs for gene expression analysis by qRT-PCR without also isolating contaminating feeder cell mRNA. For feeder-free culturing, iPSC colonies were maintained on 6-well plates coated with hES-qualified MATRIGEL™ matrix (BD Biosciences). The MATRIGEL matrix was thawed on ice, diluted in DMEM/F12 media and plates were coated for one hour at room temperature prior to use. iPSC colonies on MATRIGEL-coated plates were kept in mTESR medium (STEMCELL Technologies) that was changed daily. Cultures were split when the cell population grew to about 60% to 70% confluency as described below. In passaging iPSC cultures, medium was removed and replaced with 1 ml of a 1 mg/ml dispase solution in DMEM/F12 medium (STEMCELL Technologies). Cultures were incubated at 37° C. and 5% $CO_2$ for 8 to 10 minutes until the edges of the colonies began to lift up. Colonies were gently washed 3 times with 2 to 3 mls of DMEM/F12, and removed and broken up in fresh mTESR medium (STEMCELL Technologies) before plating on a new MATRIGEL-coated plate. mTeSR was supplemented with 10 uM Y27632 ROCK inhibitor (Stemgent). Plates were incubated at 37° C. in 5% $CO_2$ overnight. Cultures were maintained in mTESR for expansion and RNA purification for qRT-PCR experiments as described below.

Detailed Description of the Reprogramming Method for Example 14

The BJ fibroblast cells were reprogrammed to iPSCs using the materials, methods and protocols presented below.

Materials—for Reprogramming of Human Fibroblasts to iPSCs

PLURITON™ Reprogramming Media (Stemgent, Cat #00-0070)
DMEM, High glucose (GIBCO, Cat #11965-092, Life Technologies)
EMEM (ATCC, Cat #302003)
Defined fetal bovine serum (Hyclone Cat #SH30070.03, Thermo)
GLUTAMAX™-1 (GIBCO, Cat #35050-061, Life Technologies)
Penicillin 10000 IU/Streptomycin 10000 micrograms (200×) (MP Biomedicals, Cat #1670249, Thermo)
OPTI-MEM® I Reduced Serum Medium 1× (Invitrogen, Cat #11058-021)
Neonatal Human Foreskin Fibroblasts (NuFF), P9, IRR (GlobalStem Cat #GSC-3001G)—passage 9, irradiated
BJ Human Newborn Fibroblasts (ATCC, Cat #CRL-2522)
B18R Recombinant Protein Carrier-Free (eBioscience Cat #34-8185-85)
Recombinant Human Fibroblast Growth Factor-basic (FGFb) (AA 10-155) (GIBCO, Cat #PHG0023, Life Technologies)
TransIT®-mRNA Transfection Kit (Mirus Bio, Cat #2256)
UltraPure water with 0.1% Gelatin (Millipore, Cat #ES-006-B)
0.025% Trypsin, 0.02% EDTA for Primary Cells (GIBCO, Cat #R-001-100, Life Technologies)
Trypsin Neutralizer Solution (GIBCO, Cat #R-002-100, Life Technologies)

Media Composition

NuFF Culture Medium—DMEM high glucose, 10% defined FBS, 1× GlutaMAX-1, 1× Pen/Strep
BJ Fibroblast Medium—EMEM, 10% defined FBS, 1× Pen/Strep
PLURITON™ Reprogramming Medium—Pluriton Medium, 1× Pluriton Supplement, 1× Pen/Strep
NuFF Conditioned, PLURITON™ Reprogramming Medium—25 ml Pluriton Reprogramming Medium (above) collected after 24 hours on 4×10⁶ NuFFs cells, collected daily, pooled, filter sterilized, and stored in frozen aliquots.

Solution Composition

FGFb—dilute to 4 micrograms/ml and 50 micrograms/ml working stocks in PBS with 0.1% BSA
Collagenase—make up 1 mg/ml in DMEM/F12 media

Preparation

Thaw Pluriton Supplement at 4° C. and aliquot and freeze at −70° C.
Thaw Pluriton Media at 4° C. for 2 days
Thaw at 4C and aliquot B18R protein, store at −70° C.
Coat flasks with gelatin 4+ hours before needed for NuFF cells
Plate 4×10⁶ NuFFs per T75 flask in 25 ml media—for conditioned media (takes 7 days)
Coat 6-well plates with gelatin for 4+ hours before needed for NuFF cells
Plate NuFFs in 6 well dishes for reprogramming (day −2)
Plate BJ fibroblasts 10' cells per well of 6-well dish
Transcribe, cap, tail and quantify mRNA
Mix KLMOS mRNA to 1:1:1:3:1 molar ratio in sterile water
Make Pluriton media fresh daily by adding supplement and Pen/Strep to 1×

Generation of NuFF-Conditioned Pluriton Medium (Start on Day −2)

1. Add 8 ml 0.1% gelatin solution to a T75 tissue culture flask.
2. Incubate the flask at least 4 hours at 37° C. and 5% $CO_2$.
3. Plate inactivated Newborn Human Foreskin Fibroblasts (NuFFs) at a density of 4×10⁶ cells in 25 ml of NuFF Culture Medium in a T75 flask.
4. Incubate the NuFF cells overnight at 37° C. and 5% $CO_2$.
5. The following day, aspirate the NuFF Culture Medium from the flask and discard.
6. Add 10 ml of PBS to wash. Aspirate the PBS and discard.
7. Add 25 ml of Pluriton Medium supplemented with 25 microliters of 4 micrograms/ml FGF-basic Solution and 125 microliters of 200× Penicillin/Streptomycin to the NuFFs in the T75 flask.
8. Incubate the cells and medium overnight at 37° C. and 5% $CO_2$.

9. After 24 hours, collect the NuFF-Conditioned Medium and store at −20° C.
10. Add 25 ml of fresh Pluriton Medium supplemented with 25 microliters of FGFb Solution and 125 microliters of Penicillin/Streptomycin to the NuFFs in the T75 flask.
11. Incubate overnight at 37° C. and 5% $CO_2$.
12. Repeat steps 7 through 9 daily for five additional days. Pool in orange capped sterile bottle and keep at −20C until final collection. Note: Six days of medium collection will yield a total of ~150 ml of NuFF-Conditioned Pluriton Medium.
13. Thaw all frozen aliquots of NuFF-Conditioned Pluriton Medium at 4° C.
14. Pool aliquots and filter-sterilize using a 0.22 µm pore size, low protein-binding filter.
15. Aliquot 20-40 ml of the filtered NuFF-Conditioned Pluriton Medium into 50 ml conical tubes.
16. Store aliquots at −20° C. until needed on Days 6 to 20 of reprogramming.

Prior to Use of NuFF-Conditioned Pluriton Medium:
1. Thaw one aliquot of NuFF-Conditioned Pluriton Medium and one aliquot of Pluriton Supplement 2500× at 4° C.
2. Just prior to use, add 4 microliters of the Pluriton Supplement 2500× to 10 ml of equilibrated NuFF-Conditioned Pluriton Medium.

Reprogramming Timeline
Day minus 2 Gelatin Coat plates—incubate 4 hours at 37° C.
Plate NuFF cells.
(Also plate NuFF cells to make conditioned medium.)
Day minus 1 Plate BJ cells on NuFF cells.
(Change medium on NuFF flasks for conditioned medium.)
Day 0-5 Change medium to fresh Pluriton Reprogramming Medium.
Transfect Cells and Collect conditioned medium from flasks to use from Day 6-17.)
Day 6-17 Change media to fresh NuFF conditioned Pluriton
Reprogramming Medium.
Transfect Cells.
Day 18 Examine Cells and identify colonies.
Gelatin coat fresh plates and plate NuFF feeder cells.
Day 19+ Pick colonies and transfer onto fresh NuFF feeder cells.
Change media to iPSC media.
~Day 18-22 Cells can be fixed, stained, collagenased to new plates or MEF or NuFF feeder cells, plated on MATRIGEL™ and the media can be changed to a number of ES or iPS cell media.

Step-by-Step Protocol Used for Reprogramming of Human Fibroblasts to iPSCs:
Plate Human NuFF Feeder Cells (Day −2)
1. Add 1 ml of 0.1% gelatin in 6 wells of a 6-well tissue culture plate.
2. Incubate the plate at least 4 hours at 37° C. and 5% CO2.
3. Thaw one vial (4-5×10⁶ cells) of mitotically inactivated human newborn foreskin fibroblasts (NuFFs) and plate at a density of 2.5 to 5×10⁵ cells per well in NuFF Culture Medium in the 6 wells of the 6-well plate coated with gelatin.
4. Incubate the cells overnight at 37° C. and 5% CO2.
Plate the BJ Fibroblasts on the Feeder Layer (Day −1)
1. Aspirate the NuFF culture medium from the cells and discard.
2. Plate BJ fibroblasts at 1×10¹ cells per well in BJ media on top of the NuFF cells.
3. Incubate cells overnight at 37° C. and 5% CO2.
Reprogram Cells (Day 0)
Add B18R protein to the wells of cells to be pre-treated with this protein inhibitor.
1. Aspirate the BJ medium from the target cells and add 2 ml per well of Pluriton Complete with or without B18R protein to a final concentration of 200 ng/ml.
2. Incubate the plate for a minimum of 4 hours at 37° C. and 5% $CO_2$ if using B18R protein. NOTE: If not using B18R protein, incubate the plate at 37° C. and 5% $CO_2$ for 1 hour before the first transfection.
Prepare mRNA Transfection Complex Comprising the mRNA Reprogramming Mix
1. Thaw mRNA reprogramming mix on ice.
2. Add 250 microliters of OPTI-MEM to a sterile 1.5-ml microcentrifuge tube.
3. Add 8-12 microliters of 100 ng/microliter mRNA reprogramming Premix to the OPTI-MEM and pipet to mix.
4. Add 2 microliters of TransIT Boost Reagent per 1 microgram of mRNA used. Pipet up and down to mix.
5. Add 2 microliters of TransIT mRNA Transfection Reagent per 1 microgram of mRNA used. Pipet to mix.
6. Incubate at RT 2-5 minutes and add drop wise to cells.
7. Gently rock the 6-well plate from side-to-side and front-to-back to distribute the mRNA Transfection Complex across the well.
8. Incubate the plate for ~23 hours at 37° C. and 5% CO2.
Notes: The transfection complex comprising the mRNA reprogramming mix must be mixed well after each addition to cells to ensure the best transfection efficiency. Only a few reactions should be prepared at a time, so that the mRNA transfection reagent can be added quickly after the TransIT® Boost reagent.
Reprogram Cells (for Day 1 Through Day 5)
1. Equilibrate Pluriton medium and make Complete with P/S and Supplement (and B18R protein when included in treatment).
2. Aspirate the culture medium and discard.
3. Add 2 ml of Pluriton mRNA Reprogramming Medium to each well (including with B18R protein when used in the treatment).
4. Incubate at 37° C. and 5% CO2 for 1 hour.
5. Prepare mRNA Transfection Complex as described for day 0.
6. Transfect cells as described for day 0.
7. Incubate the plate O/N at 37° C. and 5% $CO_2$.
8. Repeat steps 1 through 8 four additional times (day 2 through day 5).
Reprogram Cells on Each of Days 6 Through 17, Each Time Changing the Medium to NuFF Conditioned Medium and Continuing Transfections.)
1. Thaw NuFF Conditioned Pluriton media and supplement and B18R protein
2. Equilibrate NuFF Pluriton Media and make Complete with P/S and Supplement (and B18R protein when used)
3. Aspirate the culture medium containing the mRNA Transfection Complex.
4. Add 2 ml of conditioned mRNA Reprogramming Medium (with or without B18R protein) to each well.
5. Incubate at 37° C. and 5% CO2 for 1 hour.

6. Prepare mRNA Transfection Complex as described for day 0.
7. Transfect cells as described for day 0.
8. Incubate the plate O/N at 37° C. and 5% CO2.
9. Repeat steps 1 through 8 twelve additional times (day 6 through day 17).

Identification of Primary iPS Cell Colonies (Day 18 Through Day 20)
1. After transfections are completed, incubate for 1 to 3 days to allow colonies to expand.
2. Replace medium daily with 2 ml per well of NuFF-Conditioned Pluriton Medium with Pluriton Supplement 2500× but without B18R protein.
3. Prior to manual isolation, primary iPS cell colonies can be identified using sterile, live-staining antibodies, such as StainAlive™ DyLight™ 488 Mouse anti-Human without harm to the cells.
4. Cells can be next be fixed and stained for alkaline phosphatase activity, fixed and stained with antibodies or kept alive and picked or collagenase transferred to fresh fibroblast feeder layer-coated plates.

APPENDIX B

Passaging Cells in mRNA Reprogramming Medium

Note: Cells in the most confluent wells may be passaged on approximately day 6 or day 7 to allow for further proliferation and colony formation.

Cells should be passaged after a 4 hour transfection, thereby replacing the daily medium change. Passaging, if needed, should take place after day 6 or day 7. A new plate containing NuFF feeder cells at $2.5 \times 10^5$ cells per well should be plated the day prior to passaging, as done on Day Minus 2.
1. Warm Trypsin/EDTA and Trypsin Neutralizer in a 37° C. waterbath.
2. Add 1 ml of PBS per well of cells to be passaged. Aspirate the PBS wash.
3. Add 0.5 ml of Trypsin/EDTA to the well. Gently rock the plate to evenly distribute the enzyme across the well.
4. Incubate the cells for 5 minutes at 37° C. and 5% $CO_2$.
5. Remove plate from the incubator and gently tap the side of the well to assist the dissociation and release the cells from the culture surface.
6. Add 0.5 ml of Trypsin Neutralizer to the well.
7. Gently pipet the cells in the well three times with a 1 ml pipet tip.
8. Collect the cells and transfer to a 15 ml conical tube.
9. Add 1 ml of Pluriton Medium to the well to collect any remaining cells.
10. Transfer the additional 1 ml of cells to the cell suspension in the 15 ml conical tube.
11. Centrifuge for 5 minutes at 200× g.
12. Aspirate the supernatant and resuspend the pellet in 1 ml of warm Pluriton Medium.
13. Aspirate the NuFF Culture Medium from the wells of a prepared NuFF feeder plate.
14. Add 1 ml of PBS per well to rinse. Aspirate the PBS.
15. Add 2 ml of Pluriton mRNA Reprogramming Medium with B18R protein and Y27632 to each well.
Note: B18R protein should be added to a final concentration of 200 ng/ml and Y27632 ROCK inhibitor) should be added to a final concentration of 10 µM.
16. Dispense the resuspended cells to the prepared wells of the NuFF feeder plate.

Note: A 1:6 split ratio is recommended, but can be varied depending on the confluency of the well and the proliferation rate of the cells. One to 6 wells of cells can be replated, however it is important to choose a number of wells plated to continue reprogramming comparable with the amount of mRNA available for the remainder of the reprogramming experiment.
17. Incubate the cells overnight at 37° C. and 5% $CO_2$.

Materials for iPS Cell Growth, Isolation, Maintenance or Confirmation

StainAlive DyLight 488 Mouse anti-Human Tra-1-60 Antibody (Stemgent, Cat #09-0068)
Y27632 Rock I Inhibitor (Stemgent, Cat #04-0012)
10× PBS without calcium or magnesium(Lonza Biowhittaker, Cat #17-517Q, Thermo)
Collagenase Type IV, 250 U/mg (GIBCO, Cat #17104-019)
iMEF—irradiated mouse embryonic fibroblasts (R&D Systems Cat #PSC001)
BD MATRIGEL™ hESC-qualified Matrix (BD Cat #354277, Thermo)
mTeSR® 1 Medium Kit—Basal Medium plus 5× Supplement (STEMCELL Technologies, Cat #05850)
Dispase 5 mg/ml (STEMCELL Technologies, Cat #07913)
Synth-a-Freeze, cell freezing media, (GIBCO, Cat #A12542-01, Life Technologies)
DMEM/F12 (1:1) Media (GIBCO, Cat #11330, Life Technologies)
KNOCKOUT™ SR Serum Replacement for ES cells (GIBCO, Cat #10828, Life Technologies)
MEM Non-Essential Amino Acids Solution NEAA (100×) (GIBCO, Cat #11140, Life Technologies)
Beta-mercaptoethanol (Sigma, Cat #63689)
Alkaline Phosphatase Staining Kit II (Stemgent, Cat #00-0055)
Bovine Serum Albumin (for FGFb)
Paraformaldehyde 95% (Sigma, Cat #158127)
Antibodies, wash buffers, etc
iPS Cell Medium—DMEM/F12, 20% Knockout SR, 10 ng/ml FGFb, 1× non-essential amino acids, 1× Pen/Strep, 0.1 mM beta-Mercaptoethanol (bME), 1× GLUTAMAX™
mTeSR 1 Medium—mTeSR 1 plus 1× Supplement Materials and Methods for Characterizing iPSC Colonies Generated Using the Methods Immunostaining materials and methods were identical to those used in EXAMPLE 13, except that two additional antibodies—the TRA-1-81 Mouse Antibody (Cell Signaling Technology) and DNMT 3B Rabbit Antibody (Cell Signaling Technology)—were also used.

Q-PCR Assays of Gene Expression Levels in iPSCs Generated Using the Methods Compared to Expression Levels in BJ Fibroblast Somatic Cells from which the iPSCs were Generated In order to determine if genes that are known to be up-regulated in embryonic stem cells or iPS cells generated using other methods were also up-regulated in the iPSCs generated using mRNA iPSC reprogramming factors according to the methods described herein, qRT-PCR was performed on total cellular RNA isolated from generated iPSC colonies and from BJ fibroblasts.

Thus, total cellular RNA was isolated from BJ fibroblasts and from iPS cell colonies grown on an artificial extracellular matrix (MATRIGEL™ matrix by BD Bioscience) to minimize fibroblast contamination. The iPSCs used were obtained iPSC "clonal" colonies that had been picked and passaged 5 times during a period of one month after the last day of transfection with the mRNA reprogramming factors. An entire well of these "clonal" colonies was lysed and pooled for the RNA preparation. cDNA was synthesized by reverse transcription of 1 microgram of the total cellular RNA from BJ fibroblasts and from the clonal colonies of iPSCs, respectively, using oligo $d(T)_{20}VN$ primers. Then, real-time PCR (qPCR) was performed on the cDNAs using the SsoFAST™ EvaGreen PCR Supermix (BioRad) and PCR primers (designed based on information in Assen, 2008) to analyze the relative mRNA expression levels encoding the following proteins:

GAPDH—a housekeeping gene, comparable in expression in both cell types.

NANOG—Nanog homeobox—involved in cell differentiation, proliferation, embryo development, somatic stem-cell maintenance and more.

OCT4—(POU5F1) POU class 5 homeobox 1—plays a role in embryonic development especially during early embryogenesis and it is necessary for ES cell pluripotency.

CRIPTO—(TDGF1) Teratocarcinoma-derived growth factor 1—an extra-cellular, membrane-bound signaling protein that plays an essential role in embryonic development and tumor growth.

GBX2—Gastrulation brain homeobox 2—a DNA binding transcription factor involved in a series of developmental processes.

GDF3—Growth Differentiation Factor 3—a member of the bone morphogenetic protein (BMP) family and the TGF-beta superfamily. The members regulate cell growth and differentiation in both embryonic and adult tissues.

REX1—(REXO1) RNA exonuclease 1 homolog—involved in proliferation and differentiation cMYC—a multifunctional, nuclear phosphoprotein acting as a transcription factor that plays a role in cell cycle progression, apoptosis, and cellular transformation.

The cDNA samples were PCR-amplified in triplicate and the qPCR results obtained using the values were averaged and the data were expressed as cycle threshold or CT values. The CT value is the PCR cycle number at which the reporter fluorescence is greater than the threshold and produces the first clearly detectable increase in fluorescence over background or baseline variability. This is the most accurate method of comparing expression levels by PCR before there is a plateau in product formation.

Embryoid Body Spontaneous Differentiation of iPSCs

The same iPSC colony line that was analyzed by qPCR was used in the embryoid body spontaneous differentiation protocol as described in EXAMPLE 12 in order to analyze the ability of the cells to differentiate into cells representing all three germ layers. Briefly, a colony was picked and expanded for 17 passages, then frozen down for a week, then brought up and passaged 4 more times. Large colonies were allowed to form, were detached from the MATRIGEL™ matrix surface with dispase, and were kept in suspension culture for 8 days in iPS media with no FGFb to allow embryoid body formation. As described previously, the embryoid bodies were then plated on gelatin coated plates and allowed to attach and spontaneously differentiate in iPS media without FGFb for an additional 7 days. The cells were then fixed and incubated with antibodies for various markers as previously described. Immunofluorescence was performed and the cells were imaged.

Results for Example 14

By Day 10, there was a dramatic morphology change in the wells from long thin fibroblast morphology to smaller, rounder epithelial cell morphology (FIG. 24). Based on the final results of this and other reprogramming experiments with the mRNA reprogramming factors used, this morphology change appears to be a reproducible sign that reprogramming of the BJ fibroblasts to iPSC colonies will be successful.

iPSC colonies were first detected on Day 16 based on visual inspection (e.g., FIG. 25).

The iPSC colony counts in the wells on Day 18 were less impressive than in EXAMPLE 13. Without being bound by theory, we believe that we damaged the cells when we attempted splitting iPSC colonies using trypsin on Day 10.

In this experiment, the presence of B18R protein, there were about 10 times more iPSC colonies generated on Day 18 from the RNase III-treated mRNA reprogramming factors that contained only pseudouridine than were generated by the same mRNA reprogramming factors that contained both pseudouridine and 5-methylcytidine modifications.

iPSC colonies were picked from a well containing cells that were reprogrammed in the absence of B18R protein using 18 daily doses of 800 ng of RNase III-treated mRNA reprogramming factors that contained only pseudouridine modification, and were passaged and maintained in long-term culture.

iPSC colonies were also picked from the well generated by the same treatment regime but with B18R protein. These iPS cells were maintained in culture for 2 months. No differences in morphology or propagation characteristics were observed between the iPSCs generated with or without B18R protein.

Some iPSC colonies were collagenase split and transferred to feeder cells on Day 21.

Some iPSC colonies were fixed and immunostained on Day 46 (after approximately one month of iPSC culture after the last transfection (FIG. 26).

Some iPSC colonies were passaged on MATRIGEL matrix in the absence of feeder cells; after five passages and about one month in culture, RNA was isolated from some of these iPSC colonies and for gene expression analysis by qPCR, as described. Examples of qPCR results are provided in FIG. 34 through FIG. 37.

Results of Gene Expression of iPSC Colonies Versus BJ Fibroblasts by qPCR

Figure 34:
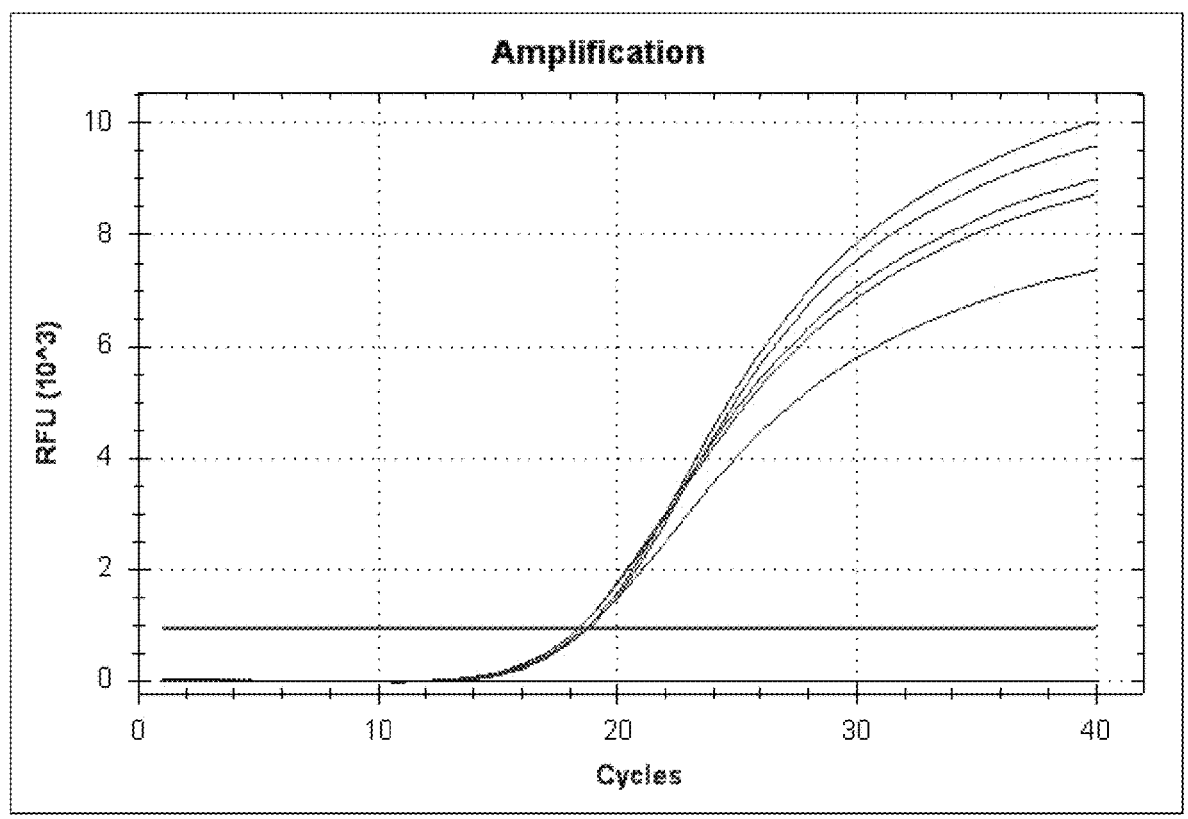
FIG. 34 shows a qPCR gene expression assay comparison of GAPDH levels obtained from the total cellular RNA isolated from generated iPSC colonies with total cellular RNA isolated from BJ fibroblasts. GAPDH is a housekeeping gene, comparable in expression in both iPSC and BJ fibroblast cell types. GAPDH gene expression levels were measured by their cycle threshold (CT) values, the PCR cycle number at which the reporter fluorescence is greater than the threshold and produces the first clearly detectable increase in fluorescence over background or baseline variability. All of the traces cross the threshold (base line) at the same CT value.
Figure 35:
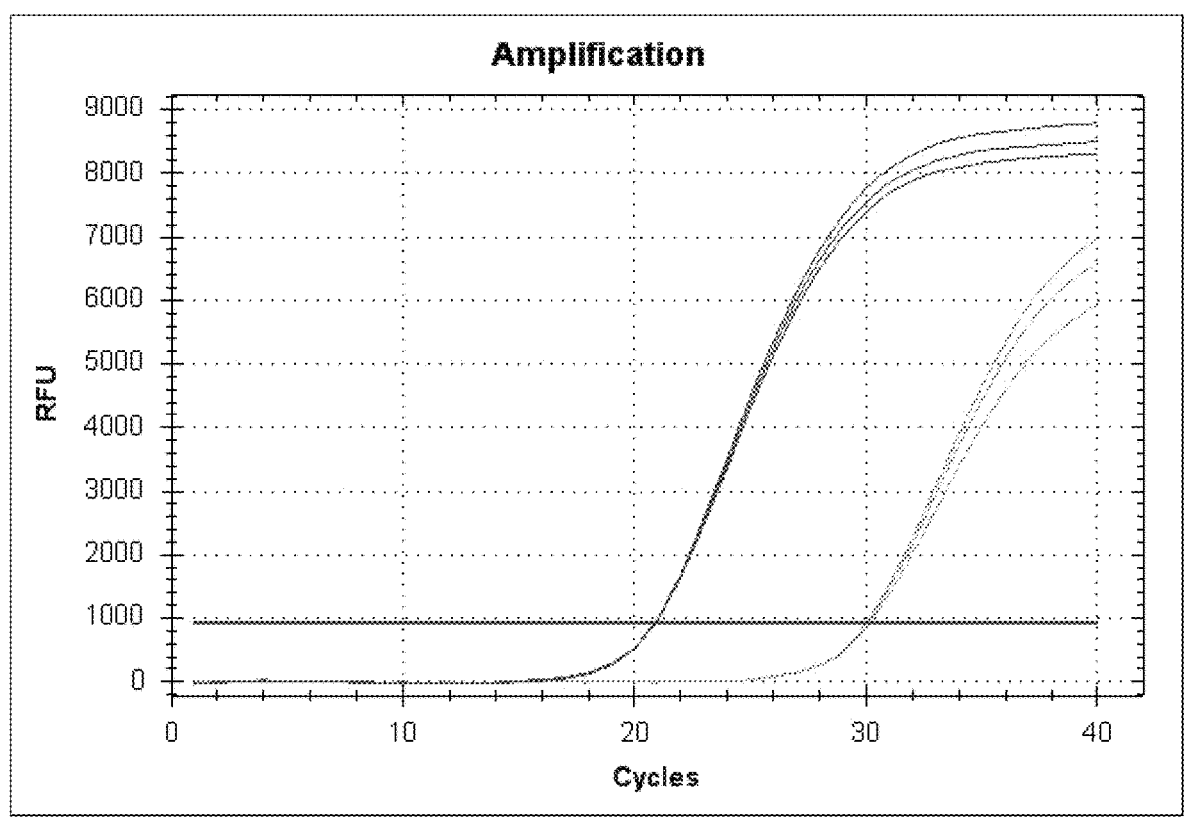
FIG. 35 shows a qPCR gene expression assay comparison of CRIPTO (TDGF1), a Teratocarcinoma-derived growth factor and known pluripotency factor, obtained from cellular RNA isolated from generated iPSC colonies and cellular RNA isolated from BJ fibroblasts. CRIPTO gene expression levels were determined by their respective CT values. The delta CT or change in expression is 9.2 cycles, which is a 588-fold increase in expression in the reprogramming iPSC colonies over that of the BJ fibroblasts.
Figure 36:
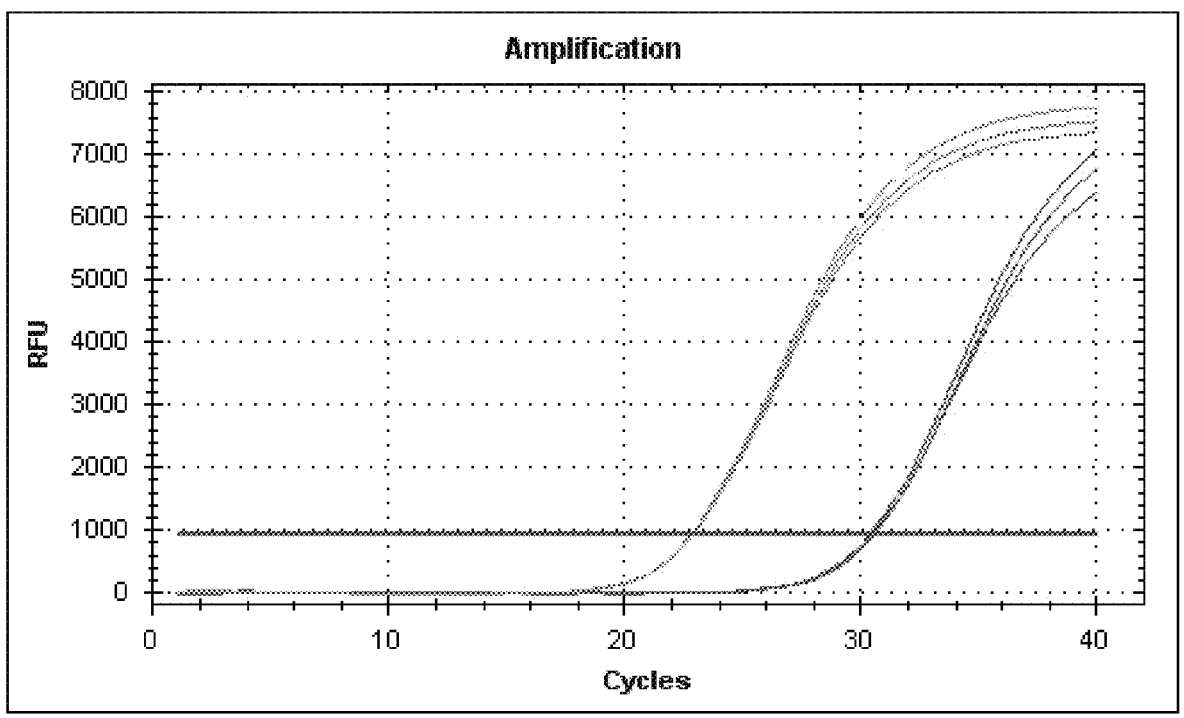
FIG. 36 shows a qPCR gene expression assay comparison of NANOG, a pluripotency factor involved in cell differentiation, proliferation, embryo development, somatic stem-cell maintenance, obtained from cellular RNA isolated from generated iPSC colonies and cellular RNA isolated from BJ fibroblasts. NANOG gene expression levels were determined by their respective CT values. The delta CT of 7.5 cycles represents a 181-fold increase in expression in the reprogrammed iPSC colonies over that of the BJ fibroblasts.
Figure 37:
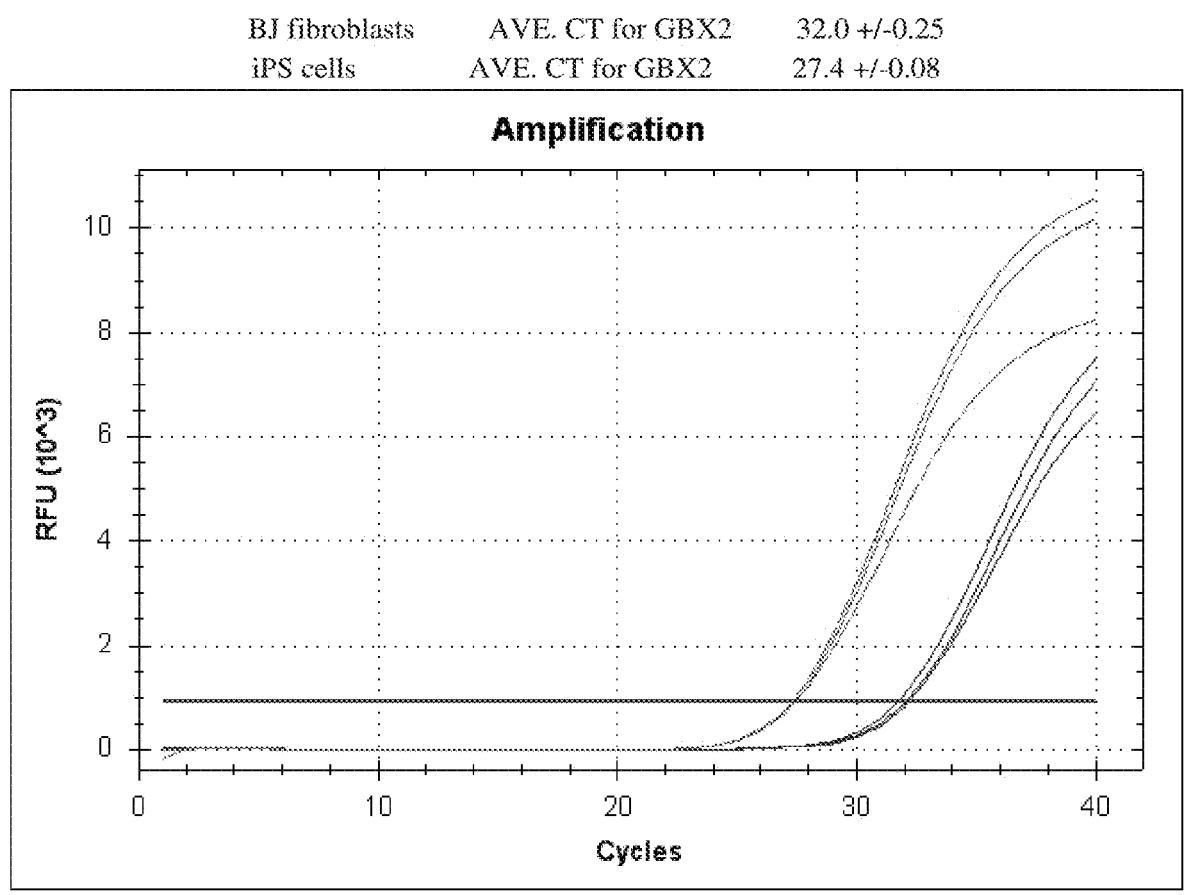
FIG. 37 shows a qPCR gene expression assay comparison of GBX2, a DNA binding transcription factor involved in a series of developmental processes and known pluripotency factor, obtained from cellular RNA isolated from generated iPSC colonies and cellular RNA isolated from BJ fibroblasts. GBX2 gene expression levels were determined by their respective CT values. The delta CT of 4.6 cycles represents a 24-fold increase in expression in the reprogrammed iPSC colonies over that of the BJ fibroblasts.

GAPDH primers were used to show that the amount of input cDNA and therefore the input starting RNA amounts were equivalent. As shown in FIG. 34, both BJ fibroblasts and iPSC colonies expressed a large, almost equivilant amount of GAPDH, so CTs shown in FIG. 34 were not normalized.

Unlike the similar levels of GAPDH, the expression of every pluripotency factor (FIG. 35 to FIG. 37) was higher in the iPS cells than in the BJ fibroblasts.

CRIPTO is a dramatic example of the change in expression levels. The average cycle threshold for RNA encoding CRIPTO in BJ fibroblasts was approximately 30 cycles, whereas the average CT value for RNA encoding CRIPTO in iPSC colonies derived from the BJ fibroblasts was approximately 21 (FIG. 35); this 9-cycle difference represents a 588-fold increase in CRIPTO expression. A CT of 20 cycles also indicates the large abundance of this message in the iPS cell RNA.

Summary of Expression Differences for all qRT-PCR Primer Pairs Tested

| | Protein encoded by RNA | | | | | | | |
|---|---|---|---|---|---|---|---|---|
| | GAPDH CT | NANOG CT | OCT4 CT | CRIPTO CT | GBX2 CT | GDF3 CT | REX1 CT | cMyc CT |
| BJ Cells | 18.5 | 30.4 | 29.6 | 30.1 | 32 | ND | ND | 26.2 |
| iPS Cells | 18.7 | 22.9 | 20.7 | 20.9 | 27.4 | 25.8 | 23.1 | 25.5 |
| Delta CT | 0.2 | 7.5 | 8.9 | 9.2 | 4.6 | ND | ND | 0.7 |
| Fold Difference | 1.15 | 181 | 478 | 588 | 24.25 | ND | ND | 1.62 |

As would be expected for true iPSCs, all of the above markers except for the housekeeping gene GAPDH were expressed at much higher levels in iPSC colonies than in BJ fibroblasts. The similar CT values for GAPDH in both types of cells, shows that equal amounts of RNA were compared. The fold difference was too great to be determined for BJ fibroblast genes with nondetectable (ND) levels of expression.

Pluripotency Demonstrated by Ability of iPSCs to Spontaneously Differentiate into Embryoid Bodies Containing Cells of all Three Germ Layers As shown in FIG. 27, the iPSCs induced by RNase III-treated [with 1 mM Mg(OAc)$_2$], cap1 5'-capped, 150-base poly(A)-tailed, ψ-modified mRNAs encoding a 3:1:1:1:1:1 mixture of OCT4, SOX2, KLF4, LIN28, NANOG and cMYC and subjected to the embryoid body spontaneous differentiation protocol stained positively for markers representing all 3 germ layers of cells, demonstrating the pluripotency of the cells. Thus, cells were found that expressed the ectoderm markers, neuronal class III class III beta-tubulin (TUJ1), Glial Fibrillary Acidic Protein (GFAP) and neurofilament-light (NF-L), the mesoderm markers, alpha-smooth muscle actin (SMA) and desmin, and the endoderm markers, transcription factor SOX17 and alpha-fetoprotein (AFP).

Example 15. Evaluations of HPLC Versus the RNase III Treatment Method for Preparing Reprogramming Factors Comprising Pseudouridine-Modified ssRNA Encoding iPS Cell Induction Factors for Reprogramming BJ Fibroblasts to iPS Cells Materials and Methods for Example 15

In one experiment, iPSC reprogramming factors composed of cap1 5'-capped ψ-modified mRNAs encoding OCT4, SOX2, KLF4, LIN28 and cMYC(T58), each with an approximately 150-base poly(A) tail (with tail length verified by denaturing agarose gel electrophoresis) were prepared as previously described, but without doing the RNase III treatment. The cap1, poly(A)-tailed mRNAs were each then split into 3 portions. One-third of each mRNA was purified by RNARx LLC (Wayne, PA) using HPLC as described (Karikó et al., 2011). One third of each mRNA was left unpurified and one third of each mRNA was treated with RNAse III using an RNase III treatment method with 1 mM Mg(OAc)$_2$ and cleaned up using the RNA Quick Cleanup method described herein; (note, this time, the RNase III treatment was performed after capping and tailing had been done rather than after the in vitro transcriptions). Then, all 5 of the mRNA reprogramming factors from each portion (i.e., either all that had been HPLC-purified, all that were unpurified, or all that were RNase III-treated) were mixed to a 3:1:1:1:1 molar ratio of ψ-modified mRNAs encoding, respectively, OCT4, SOX2, KLF4, LIN28 and cMYC(T58) to make an HPLC-purified mRNA reprogramming mix, and untreated mRNA reprogramming mix, and an RNase III-treated reprogramming mix. Then, 1.2 micrograms of each mRNA reprogramming mix was used for reprogramming ten thousand cells per well of BJ fibroblasts (plated on NuFFs) to iPSCs, essentially as described in EXAMPLE 14, with additional experimental variables shown in the table of iPSC reprogramming results.

Spontaneous Differentiation of iPSCs into 3 Germ Layers

Selected iPSC colonies were picked and used in the embryoid body spontaneous differentiation protocol as describe in EXAMPLE 14 in order to evaluate their pluripotency.

Results for Example 15 iPSC colonies were detected by day 13 in wells of BJ fibroblasts transfected with the RNase III-treated mRNA reprogramming mix or with the HPLC-purified mRNA reprogramming mix. All of the cells in the wells transfected with the unpurified mRNA reprogramming mix died during the reprogramming process, even with the addition of B18R protein. The addition of B18R protein did improve the efficiency of reprogramming BJ fibroblasts to iPSCs in wells treated with either the RNase III-treated mRNA reprogramming mix or in wells treated with the HPLC-purified mRNA reprogramming mix.

iPSC Colony Propagation iPSC colonies from replicate wells reprogrammed with the HPLC-purified mRNA reprogramming mix and the RNase III-treated mRNA reprogramming mix were picked and enzymatically passaged with collagenase onto irradiated mouse embryonic fibroblast feeder cells in iPS cell maintenance medium containing 10 ng/ml of FGFb. The iPSC colonies were propagated and maintained a morphology and growth rate as expected for iPSCs for more than 9 passages in culture, after which they were frozen and stored in a freezer.

Alkaline Phosphatase Staining of iPSC Colonies

Figure 28:
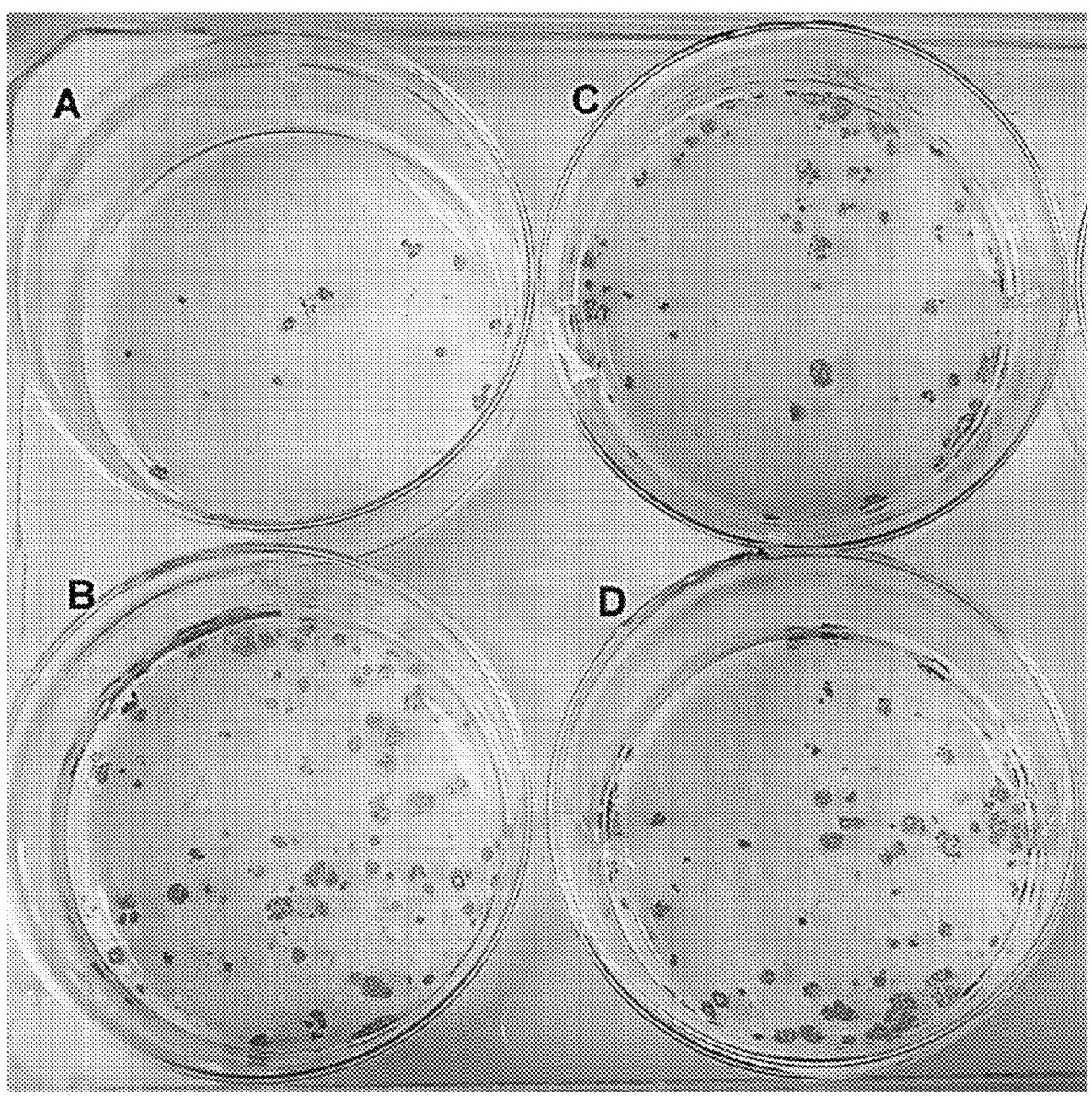
FIG. 28 shows alkaline phosphatase-positive colonies generated from BJ fibroblasts transfected daily for 18 days with 1.2 micrograms of a 3:1:1:1:1 molar ratio of HPLC-purified or RNase III-treated pseudouridine-modified mRNAs encoding OCT4, SOX2, KLF4, LIN28 and cMYC (T58A) using the TRANSIT™ mRNA transfection reagent, with or without prior treatment with B18R protein. BJ fibroblasts on feeder cells were transfected daily for 18 days, either in the presence or in the absence of B18R protein, with 1.2 micrograms/well/day of a 3:1:1:1:1 molar ratio of ψ-modified single-stranded mRNAs encoding, respectively, OCT4, SOX2, KLF4, LIN28 and cMYC(T58) using the TransIT™ mRNA transfection reagent (Mirus Bio). In order to make the ψ-modified mRNAs substantially free of dsRNA, the ψ-modified mRNAs were either HPLC purified or RNase III treated prior to being used for reprogramming. On Day 20, plates containing iPSC colonies were fixed with 4% paraformaldehyde and stained to detect alkaline phosphatase-positive colonies, which is indicative of iPSC colonies. Plate A: HPLC-purified, no B18R protein; Plate B: HPLC-purified, +B18R protein; Plate C: RNase III-treated, no B18R protein; Plate D: RNase III-treated, +B18R protein. No alkaline phosphatase-positive colonies were present on plates of cells that were transfected with the ψ-modified mRNAs that were not HPLC purified or RNase III treated.

On day 20, plates containing iPSC colonies were fixed with 4% paraformaldehyde and stained to detect alkaline phosphatase-positive colonies, as previously described. Images of plates of the BJ fibroblasts with colonies of cells that stain positively for alkaline phosphatase, a marker for iPSC colonies, are shown in FIG. 28. The numbers of alkaline phosphatase-stained iPSC colonies obtained using ψ-modified single-stranded mRNA reprogramming factors from which dsRNA was removed by either HPLC purification or using the RNase III treatment described herein so that said mRNA reprogramming factors were practically free, extremely free or absolutely free of dsRNA, compared to using unpurified ψ-modified single-stranded mRNA reprogramming factors, are summarized in the Table below.

Immunostaining

Figure 33A:
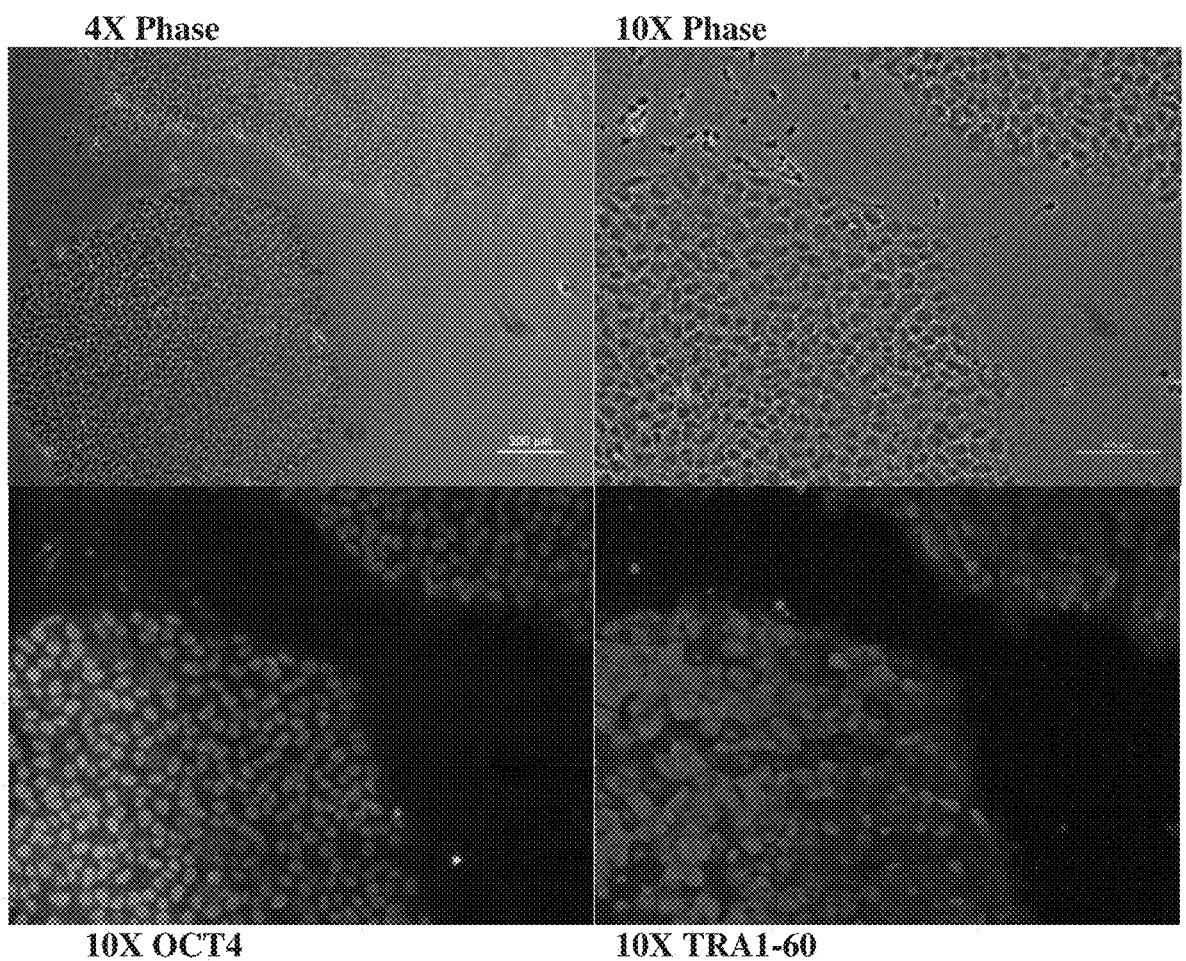
FIG. 33A-FIG. 33B shows images of phase contrast and fixed immunostained iPSCs generated from BJ fibroblasts using HPLC-purified, ψ-modified mRNAs encoding OCT4, SOX2, KLF4, LIN28 and cMYC(T58A) iPSC induction factors.
Figure 33B:
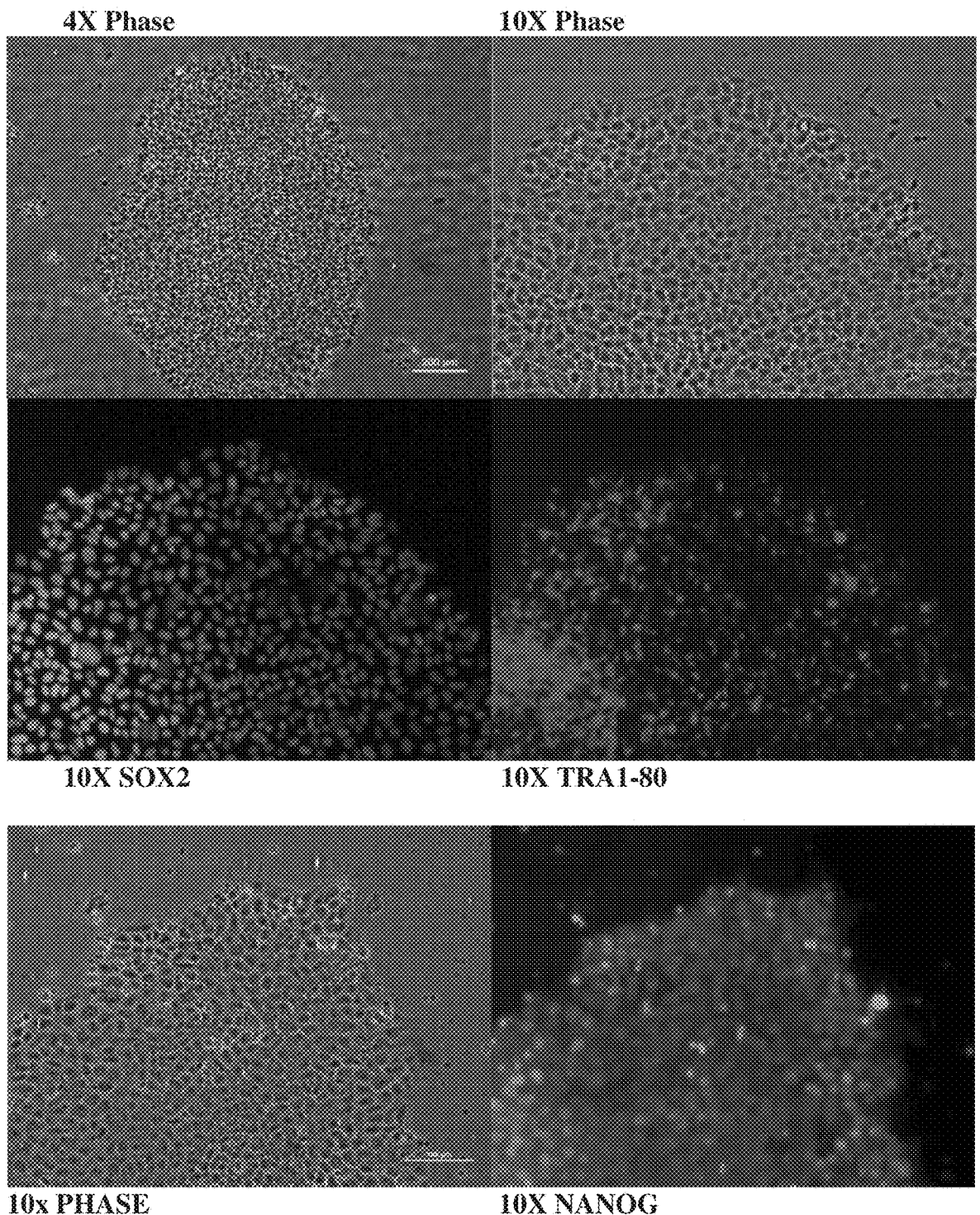

After 1 week of storage in the freezer, frozen HPLC-purified pseudouridine-modified mRNA-derived iPSCs were thawed, transferred to plates coated with MATRIGEL™ artificial matrix, and propagated in mTeSR™ medium. The iPSC colonies were passaged an additional 4 times before a plate was fixed and the cells were immunostained with antibodies to OCT4, TRA1-60, SOX2, TRA1-80 and NANOG pluripotency markers characteristic of iPS cells using immunostaining methods as described previously. As shown in FIG. 33, the iPSCs induced from BJ fibroblasts using HPLC-purified pseudouridine-modified mRNA reprogramming factors were immunostained positively for these pluripotency markers.

Summary of iPSC Reprogramming with
ψ-Modified mRNA Reprogramming Factors

| Treatment Type | B18R Protein Used | Degree of Toxicity Observed | Number of Alkaline Phosphatase-Positive iPSC Colonies | Plate Label in Image Below |
|---|---|---|---|---|
| HPLC-purified | NO | Feeder cells dead, but iPSC colonies present | 15 | A |
| HPLC-purified | YES | Feeder cells OK and iPSC colonies present | ~100 | B |
| RNase III-Treated | NO | | ~50 | C |
| RNase III-Treated | YES | | ~100 | D |
| Unpurified | NO | Cells dead | 0 | — |
| Unpurified | YES | Cells dead | 0 | — |

Pluripotency of iPSCs

Embryoid bodies spontaneously differentiated from picked iPSC colonies that had been induced from BJ fibroblasts by HPLC-purified, ΨI-modified miRNAs encoding the indicated reprogramming factors and then grown for 4 to 11 passages in medium in wells coated with MATRIGEL™ matrix as described in EXAMPLE 14. Differentiated cells that stained positively for markers representing all 3 germ layers were observed. For example, cells were observed that expressed the ectoderm marker, neuronal class III beta-tubulin (TUJ1), the mesoderm markers, alpha-smooth muscle actin (SMA) and desmin, and the endoderm markers, transcription factor SOX17 and alpha fetoprotein (AFP).

Example 16. Evaluation of Additional Variables Related to Use of RNase III-Treated Modified mRNA Reprogramming Factors Encoding iPS Cell Induction Factors for Reprogramming BJ Fibroblasts to iPS Cells Materials and Methods for Example 16

The goals of the experiments described in EXAMPLE 16 were to determine (1) whether RNase III-treated mRNA could produce a significant number of colonies without the use of an inhibitor of expression of an innate immune response pathway, such as B18R protein (2) which mRNA encoding a cMYC protein—mRNA encoding the wild-type cMYC or mRNA encoding the cMYC(T58A) mutant protein—is more efficient for reprogramming BJ fibroblasts into iPSC colonies and (3) whether 10,000 BJ fibrobroblast cells per well is the optimal number of cells for efficient reprogramming to iPSC colonies.

The materials and methods used were similar to those described for EXAMPLES 4-8 above. The mRNA reprogramming factor mix was composed of ψ-modified mRNAs (GAψC) encoding the 3:1:1:1:1 molar mix of OCT4, SOX2, KLF4, LIN28, and cMYC or cMYC(T58A) that were treated with RNase III in a reaction mix containing 1 mM magnesium acetate in order to make the mRNA reprogramming factor mix have a low enough level of dsRNA so as to not interfere with transfection and cell survival. This RNase III-treated mRNA reprogramming factor mix was then transfected every day for 18 days at a dose of 1.2 micrograms per well per day (unless a different mRNA dose is otherwise stated in the respective results table) using the TransIT™ mRNA transfection reagent (Mirus Bio) into $10^4$ (unless a different number of cells is stated in the respective results table) BJ fibroblasts/well for 8 days in a row in 6-well plates containing on top of NuFF feeder cells. The experimental variables are listed in the results tables for each experiment. iPSC colony counts were made by immunostaining live cells with StainAlive™ DyLight™ 488 anti-human TRA-1-60 antibody (Stemgent), as described herein, and manually counting stained iPSC colonies in each visual field using a grid. There was variation in colony size and staining intensity, and sometimes there were "too many colonies to count" (e.g., see FIG. 28), making it challenging or impossible to properly count them. For example, there were more than 300 colonies in each well designated as "too many colonies to count" or "TMTC". Therefore, the iPSC colony counts are approximate.

Results for Example 16

Figure 30:
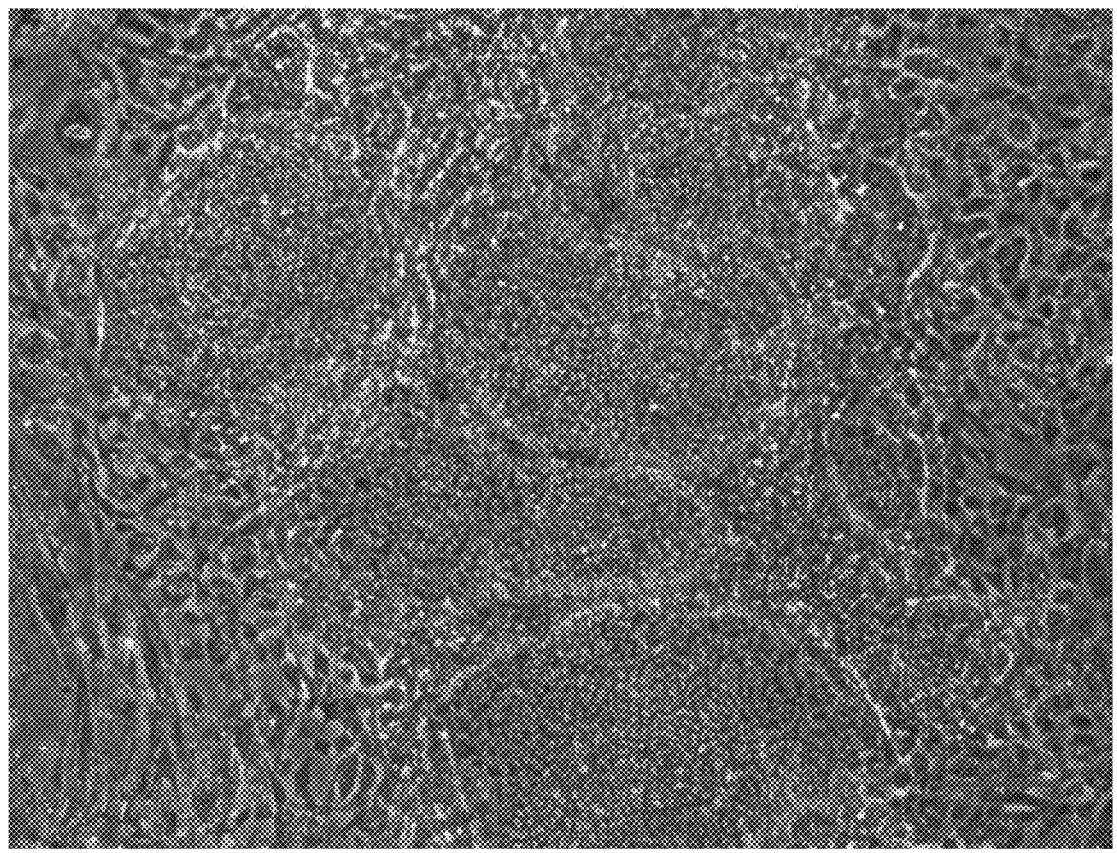
FIG. 30 shows an example of a well with efficient induction of iPSC colonies from BJ fibroblasts transfected with pseudouridine-modified mRNAs encoding OCT4, SOX2, KLF4, LIN28 and cMYC(T58A), wherein the cells were pre-treated with B18R protein prior to the transfections.

Efficient Reprogramming of BJ Fibroblasts to iPSC Colonies by RNase II-Treated Pseudouridine-Modified mRNA Reprogramming Factors in the Presence or Absence of B18R Protein iPSC colonies were first detected on Day 13 in two different wells of BJ fibroblasts that were transfected with RNAse III-treated (1 mM MgOAc)₂ pseudouridine-modified mRNA reprogramming factors in the absence of B18 protein in the medium. However, iPSC colonies were also induced beginning a day or two later in wells of BJ fibroblasts that were transfected with RNAse III-treated pseudouridine-modified mRNA reprogramming factors in the presence of 200 ng/ml of B18R recombinant human protein in the medium. iPSC colonies induced in the presence of B18R protein are shown in the image in FIG. 30. In fact, in this experiment, it was impossible to determine an effect of B18R protein because the entire well was full of colonies—with hundreds of colonies per well of a 6-well plate—in both cases and the number of colonies were too many to count (TMTC). (If only 100 iPSC colonies had been present per well, the iPSC induction efficiency would have been 1%)

| mRNA Type Used | Type of MYC protein encoded by mRNA in the mRNA reprogramming mix | B18R Protein Used | iPSC Colony Count on Day 18 |
| --- | --- | --- | --- |
| GAψC | cMYC(T58A) | NO | TMTC |
| GAψC | cMYC(T58A) | YES | TMTC |

Similar experiments in which ω-modified mRNA encoding reprogramming factors was used for transfection ±B18R protein in the medium and wherein iPSC colonies generated could be counted are shown below. E.g., in one experiment evaluating use of mRNA encoding cMYC wild-type protein versus mRNA encoding cMYC(T58A) mutant protein for reprogramming, more iPSC colonies were observed on Day 18 when B18R protein was added to the medium one hour prior to every transfection, as shown above. This experiment also indicated that mRNA encoding cMYC(T58A) increased the iPSC colony induction compared to using mRNA encoding wild-type cMYC.

| mRNA Type Used | Type of MYC protein encoded by mRNA in the mRNA reprogramming mix | B18R Protein Used | iPSC Colony Count on Day 18 |
| --- | --- | --- | --- |
| GAψC | cMYC wild-type | NO | 105 |
| GAψC | cMYC wild-type | YES | 157 |
| GAψC | cMYC(T58A) | NO | 182 |
| GAψC | cMYC(T58A) | YES | TMTC |

Another experiment was done to determine whether the number of BJ fibroblast cells that were transfected with the RNase III-treated pseudouridine-modified mRNA reprogramming factors was optimal for reprogramming using either mRNA encoding cMYC wild-type protein or mRNA encoding cMYC(T58A) mutant protein in the mRNA reprogramming mix. If too few BJ fibroblast cells were being plated, there would be fewer iPSC colonies induced, whereas if too many BJ fibroblast cells were being plated (and the cells weren't split mid-reprogramming), the iPSC colonies would become confluent and couldn't easily be picked, which would result in fewer usable iPSC colonies. Based on the result of this experiment, plating 5000 to 10,000 passage-number-4 BJ fibroblast cells per well was ideal, as shown in the results table below. However, in subsequent experiments, we found that later-passage-number BJ fibroblast cells grew more slowly, so it appeared to be better to use more cells with later-passage BJ fibroblast cells. Thus, the ideal number of cells will vary by the growth rate of the BJ fibroblasts, with younger cells usually growing more rapidly and older cells growing more slowly. Based on the results of this experiment, mRNA encoding the cMYC (T58A) gave twice as many iPSC colonies under otherwise similar conditions compared to mRNA encoding the wild-type cMYC protein. Thus, mRNA encoding the cMYC (T58A) mutant protein appeared to be beneficial for iPSC induction efficiency, as shown in the results table below.

Transfection of too many BJ fibroblasts per well results in fewer iPSC colonies and mRNA encoding cMYC(T58A) results in more iPSC colonies than mRNA encoding wild-type cMYC

| mRNA Type Used | Type of MYC protein encoded by mRNA in the mRNA reprogramming mix | Number of BJ Fibroblast Cells Plated Per Well | Alk Phos-Positive iPSC Colony Count on Day 18 |
| --- | --- | --- | --- |
| GAψC | cMYC wild-type | $5 \times 10^3$ | 80 |
| GAψC | cMYC wild-type | $10^4$ | 105 |
| GAψC | cMYC wild-type | $2.5 \times 10^4$ | 14 |
| GAψC | cMYC(T58A) | $5 \times 10^3$ | 203 |
| GAψC | cMYC(T58A) | $10^4$ | 182 |
| GAψC | cMYC(T58A) | $2.5 \times 10^4$ | 41 |

Example 17. Reprogramming BJ Fibroblasts to WPS Cells Using RNase III-Treated Cap1 Poly-A-Tailed Unmodified (GAUC) mRNAs Encoding OCT4, SOX2, KLF4, LIN28, NANOG and cMYC Reprogramming Factors Materials and Methods for Example 17

As demonstrated in the above Examples, we have been able to repeatably and efficiently reprogram BJ fibroblast cells to iPSC colonies using a ssRNA reprogramming factor mix comprising a 3:1:1:1:1 molar ratio of pseudouridine-modified and/or 5-methylcytidine-modified mRNAs encoding OCT4, SOX2, KLF4, LIN28, and cMYC, cMYC(T58A) or L-MYC, wherein the modified mRNAs were either HPLC purified or were RNase III treated in a reaction mixture containing low levels of divalent magnesium cations prior to their use in reprogramming. In view of the surprisingly and unexpectedly successful results in reprogramming human or animal somatic cells to iPSC colonies using modified mRNA reprogramming factors that were treated with RNase III in the presence of low levels of divalent magnesium, we decided to evaluate whether it might be possible to reprogram such somatic cells to iPSC colonies using ssRNA reprogramming factors comprising unmodified mRNAs encoding OCT4, SOX2, KLF4, LIN28, and cMYC(T58A). The present researchers believe that successful reprogramming of human or animal somatic cells to iPSC colonies that could be propagated in culture for long periods, sufficient to form iPSC colony lines, using only unmodified ssRNA has not previously been reported or demonstrated. Thus, in view of the success of the present researchers in developing a method for treating in vitro-synthesized modified ssRNA with a dsRNA-specific RNase (e.g., RNase III) in order to generate ssRNAs encoding reprogramming factors with reduced dsRNA, wherein said ssRNAs were intact and functional in reprogramming human or animal somatic cells to iPSCs, as reported herein, we decided to evaluate whether the same RNase III treatment method described herein could be used to make unmodified ssRNAs encoding the same reprogramming factors that had very low levels of dsRNA, and if so, whether such treated ssRNAs could be used to reprogram human or animal somatic cells to iPS cells. Surprisingly and unexpectedly, this experiment was successful, as reported below.

Thus, a ssRNA reprogramming factor mix comprising a 3:1:1:1:1 molar ratio of unmodified cap1 5'capped and poly(A)-tailed (to ~150-base poly-A tail length) mRNAs encoding OCT4, SOX2, KLF4, LIN28, and cMYC(T58A) were synthesized by in vitro transcription as described herein above, except that the RNA was synthesized using only GTP, ATP, CTP, and UTP without use of pseudouridine-5'-triphosphate, 5-methylcytidine-5'-triphosphate or another modified nucleoside-5'-triphosphate and treated with RNase III in a reaction comprising 1 mM of magnesium acetate, also as described herein above. Dot blot assays with the J2 dsRNA-specific antibody were performed to verify digestion of the dsRNA in the RNase III-treated ssRNAs. Then, 10,000 cells per well of BJ fibroblasts on NuFF feeder cells in wells of a 6-well plate were transfected daily with a dose of either 1.0, 1.2, or 1.4 micrograms of the ssRNA reprogramming mix every day for at least 18 days using the TransIT™ mRNA transfection reagent (Mirus Bio), all as described in the General Materials and Methods. The experimental variables are listed in the results table below for each experiment. On Day 18 of the reprogramming protocol, the iPSC colony counts were made by immunostaining live cells with StainAlive™ DyLight™ 488 anti-human TRA-1-60 antibody (Stemgent), as described in EXAMPLE 16 and elsewhere herein, and manually counting stained iPSC colonies in each visual field using a grid. The results are presented in the table below.

Results for Example 17

Hundreds of iPSC colonies were generated from unmodified mRNA that was treated with RNase III using methods as described herein.

| mRNA Type Used | Type of MYC Protein Encoded by mRNA in the mRNA Reprogramming Mix | B18R Protein Used | Total Micrograms of mRNAs in Reprogramming Mix Per Transfection | Alk Phos-Positive iPSC Colony Count on Day 18 |
|---|---|---|---|---|
| GAUC | cMYC(T58A) | NO | 1.0 micrograms per well | 262 |
| GAUC | cMYC(T58A) | NO | 1.2 micrograms per well | 244 |
| GAUC | cMYC(T58A) | NO | 1.4 micrograms per well | 88 |
| GAUC | cMYC(T58A) | YES | 1.2 micrograms per well | TMTC |

As shown in the table above, all three different daily doses of a ssRNA reprogramming mix comprising unmodified mRNAs encoding OCT4, SOX2, KLF4, LIN28, and cMYC (T58A) that were used to transfect BJ fibroblasts for 18 days resulted in generation of iPSC colonies. However, this ssRNA reprogramming mix comprising unmodified mRNAs was clearly more toxic to the cells than the ssRNA reprogramming mix comprising pseudouridine-modified mRNAs. Thus, one microgram of the reprogramming mix per well, rather than 1.2 micrograms per well, resulted in less early toxicity and, therefore, more cells that survived to the epithelial transition and formed iPSC colonies. When 1.4 micrograms of reprogramming mix was used daily, most of the feeder cells died, resulting in colonies attached to very few cells as seen in the images in FIG. 31.

Colonies induced using RNase III-treated unmodified mRNAs encoding OCT4, SOX2, KLF4, LIN28, and cMYC (T58A) iPSC induction factors were confirmed to be iPSC colonies based on morphology, ability to be propagated for greater than 16 passages in culture, positive in vivo immunostaining for the TRA-1-60 using a TRA-1-60 anti-human antibody and StainAlive™ DyLight™ 488 (Stemgent), and positive immunofluorescent staining of paraformaldehyde-fixed cells using antibodies for the iPSC markers OCT4, TRA1-60, NANOG, TRA 1-81 and SSEA4, performed as described in EXAMPLE 13 (FIG. 32).

The present researchers believe successful reprogramming of human or animal somatic cells to iPSC cells using only unmodified ssRNA has not previously been reported or demonstrated. Without being bound by theory, we believe that others have not been successful in reprogramming human or animal cells with unmodified ssRNAs because they have not recognized the significance of the low levels of dsRNA contaminants generated during in vitro-transcription of ssRNA. Therefore, they did not recognize the importance of purifying or treating such in vitro-synthesized ssRNA in order to remove all or almost all of the dsRNA contaminants. Still further, they have not understood or developed a method for sufficiently purifying or treating said ssRNAs in order to effectively remove all or almost all of dsRNA contaminants. The present researchers have discovered simple, rapid and efficient methods for treating ssRNAs with a double-strand-specific RNase that results in ssRNAs that are free or almost free of dsRNA contaminants. One example of such a double-strand-specific RNase that can be used for this purpose is the endoribonuclease, RNase III. However, the present researchers also discovered, surprisingly and unexpectedly, that treating ssRNA with RNase III using the optimal conditions known in the art since 1968 (Robertson, H D et al. 1968) did not sufficiently remove dsRNA so that the treated ssRNAs could be used for translation in living cells or for reprogramming living human or animal cells from one state of differentiation to another state of differentiation (e.g., for reprogramming human or animal somatic cells to iPS cells). In fact, when the present researchers treated ssRNAs encoding iPSC reprogramming factors with RNase III using the method in the literature, all of the cells that were repeatedly transfected with the treated ssRNAs in order to try to generate iPSCs ultimately died. Detailed analysis of the RNase III activity and specificity under different conditions, as described in EXAMPLES 1-9, revealed that the reaction conditions in the literature did not sufficiently remove small amounts of dsRNA contaminants from in vitro-transcribed ssRNA for use in introducing into living cells and that those conditions also resulted in significant degradation of the treated ssRNAs that the present researchers desired to be translated in the living cells. In other words, not only did the RNase III method in the literature fail to sufficiently remove the undesired dsRNA, it also destroyed a portion of the desired ssRNAs that encoded the proteins of interest. Next, the present researchers tried to modify the conditions that were suggested by various authors who had developed or used the RNase III method in the literature, including for example, changing the type or concentration of monovalent salt, the pH, and the amount of enzyme used, but to no avail. Thus, although the literature pertaining to RNase III suggested that changing the concentration of the monovalent salt in the RNase III reaction might be beneficial, the present inventors tried ranges of concentrations of different monovalent salts without success. Changes of variables suggested in the literature did not result in sufficient removal of the dsRNA for the ssRNAs to be used for reprogramming living cells, did not sufficiently reduce the toxicity of the ssRNAs, and still result in damage or destruction of at least a portion of the desired ssRNAs.

Without being bound by theory, the present researchers believe that the high cellular toxicity is due to the extremely low levels of dsRNA that are detected by the innate immune response and other RNA sensors that are present in human and animal cells to protect those cells from infection by dsRNA viruses and other pathogens. Thus, due to the extreme sensitivity of human or animal cells to dsRNA that is introduced into those cells, a method that is suitable for reducing dsRNA from ssRNAs for in vitro applications is not necessarily sufficient for making ssRNAs for introducing into living human or animal cells. The innate immune response and other RNA sensors (e.g., toll like receptors, e.g., TLR3, interferons, and other such sensors) are induced to higher levels if even a certain small quantity of dsRNA is introduced into said cells. Still further, inductions of certain RNA sensors may sensitize the cells to future introductions of the same ssRNA. In addition, the toxic effects of the innate immune response may be cumulative. For example, repeated introductions of dsRNA induces interferons, which results in phosphorylation of PKR, which results in inhibition of protein synthesis in the cells, which, in turn, can lead to prolonged toxicity to the cells and, ultimately, programmed cell death (apoptosis). Thus, with respect to the methods for reprogramming human somatic cells to iPS cells, wherein one introduces ssRNAs encoding reprogramming factors every day for 18 or more days in order to generate the iPS cells, the innate immune response and other RNA sensor responses are induced each time the ssRNAs encoding reprogramming factors are introduced into the cells.

Example 18. Feeder-Free Reprogramming of 1079 Fibroblast Cells to iPS Cells Using Single-Stranded mRNA Encoding iPSC Induction Factors Materials and Methods for Example 18

In this EXAMPLE 18, 1079 fibroblast cells (ATCC, Manassas, VA) were plated at cell densities of $1\times10^4$, $2\times10^4$, $3\times10^4$, $4\times10^4$, or $5\times10^4$ cells per well in 6-well tissue culture plates coated with 83 ng-per-well of MATRIGEL™ GFR matrix (BD Biosciences, San Jose, CA) in fibroblast medium composed of Advanced MEM (Invitrogen, Carlsbad, CA) supplemented with 10% FBS (Fisher) and 2 mM GLUTAMAX-I (Invitrogen Carlsbad, CA) prior to their use for reprogramming.

On the following day, the medium was changed to reprogramming medium, composed of DMEM/F12 (Invitrogen Carlsbad, CA) supplemented with 20% KNOCKOUT™ Serum Replacement (Invitrogen Carlsbad, CA), 2 mM GLUTAMAX-I (Invitrogen), 0.1 mM non-essential amino acids solution (Invitrogen Carlsbad, CA), 100 ng/ml basic human recombinant FGF (Invitrogen Carlsbad, CA), 2 micromolar TGFβ inhibitor STEMOLECULE SB431542 (Stemgent, Cambridge, MA), 0.5 micromolar MEK inhibitor STEMOLECULE PD0325901 (Stemgent Cambridge, MA), and 10 ng/ml recombinant mouse LIF (Invitrogen Carlsbad, CA) with penicillin-streptomycin antibiotics. Reprogramming was performed with pseudouridine-containing, RNase III-treated mRNAs encoding OCT4, SOX2, KLF4, LIN28, and cMYC(T58A) iPSC induction factors in the feeder-free reprogramming medium as previously described for BJ fibroblasts in EXAMPLE 11.

Results for Example 18

As previously found using BJ fibroblasts in EXAMPLE 11, 1079 fibroblast cells were also successfully reprogrammed into iPS cells using a 3:1:1:1:1 mixture of pseudouridine-containing, RNase III-treated mRNAs encoding the reprogramming factors, OCT4, SOX2, KLF4, LIN28, and cMYC(T58A) in the feeder-free reprogramming medium as described above.

Reprogramming of the 1079 fibroblast cells was observed in wells plated with $1\times10^4$ and $2\times10^4$ cells per well. More iPSC colonies were induced at the lowest cell density tested ($1\times10^4$ cells per well), with 24 iPSC colonies observed, versus only 8 iPSC colonies in the well plated with $2\times10^4$ cells. At higher cell densities, no reprogramming was observed with the rapidly-growing 1079 fibroblast cells due to the cells overgrowing the wells before reprogramming occurred.

Example 19. Variation of Stoichiometry of mRNAs Encoding iPSC Reprogramming Factors In this experiment, we compared reprogramming of human fibroblasts to iPSCs using an mRNA mix encoding KLF4, LIN28, cMYC(T58A), OCT4 and SOX2 in in a molar ratio of 3:1:1:3:1 with the previously describe mRNA mix having a molar ratio of 1:1:1:3:1.

Materials and Methods for Example 19

$10^4$ BJ fibroblasts (passage 6) were plated on $4\times10^5$ NuFF feeder cells in Pluriton reprogramming media as previously described. The media containing RNase Inhibitor was changed prior to daily transfections. mRNA mixes comprising RNase III-treated (in 2 mM $Mg^{2+}$) cap1, poly(A)-tailed (~150 As), pseudouridine-modified mRNA encoding KLF4, LIN28, cMYC(T58A), OCT4 and SOX2 were synthesized as previously described. In Experiment 19-1, the mRNA mixes were diluted in 60 microliters of Stemfect Buffer, combined with the Stemfect Transfection Reagent diluted in 60 microliters of Stemfect Buffer, and the mix was incubated at room temperature for 15 minutes and added dropwise to the cells during each of eighteen daily transfections. In Experiment 19-2, either 1.0 microgram, 1.2 microgram or 1.4 microgram of each mRNA mix was transfected with 4, 4.8 or 5.6 microliters of Stemfect Transfection Reagent, respectively, and only 15 transfections were performed. The mRNA reprogramming mixes were produced with mRNA encoding KLF4 at 1×, 2× and 3× molar ratios compared to the LIN28, cMYC(T58A), and SOX2 mRNAs (i.e., with 1:1:1:3:1; 2:1:1:3:1; and 3:1:1:3:1 stoichiometries).

After completion of all transfections, wells with iPSC colonies were fixed and stained with alkaline phosphatase after representative colonies were picked for expansion. Alkaline phosphatase-positive colony counts obtained and imaged.

Experiment 19-1: No. Of Alkaline Phosphatase-Positive Colonies Obtained

| mRNA Reprogramming Mix | mRNA Type | AMT of RNA (μg) | Transfn Reagent and vol (μl) | Alk Phos-Positive Colony Count | Well No. |
|---|---|---|---|---|---|
| 4F KMO₃S | Ψ RIII Cap 1 | 1.0 | SF 4 | 3 | 1 |
| 4F KMO₃S | Ψ RIII Cap 1 | 1.2 | SF 4.8 | 29 | 2 |
| 4F KMO₃S | Ψ RIII Cap 1 | 1.4 | SF 5.6 | 44 | 3 |
| 5F KLMO₃S | Ψ RIII Cap 1 | 1.0 | SF 4 | 13 | 7 |
| 5F KLMO₃S | Ψ RIII Cap 1 | 1.2 | SF 4.8 | 57 | 8 |
| 6F KLMNO₃S | Ψ RIII Cap 1 | 1.0 | SF 4 | 39 | 9 |

| mRNA Reprogramming Mix | mRNA Type | AMT of RNA (μg) | Transfn Reagent and vol (μl) | Alk Phos-Positive Colony Count | Well No. |
|---|---|---|---|---|---|
| (+Nanog) 6F KLMNO₃S | Ψ RIII Cap 1 | 1.2 | SF 4.8 | 109 | 10 |
| (+Nanog) 5F K₃LMO₃S | Ψ RIII Cap 1 | 1.0 | SF 4 | 40 | 11 |
| 5F K₃LMO₃S | Ψ RIII Cap 1 | 1.2 | SF 4.8 | 148 | 12 |
| Transfection Optim. | | | Stemfect | | |
| 5F KLMO₃S | Ψ RIII Cap 1 | 1.0 | SF 3 | 6 | 13 |
| 5F KLMO₃S | Ψ RIII Cap 1 | 1.0 | SF 4 | 16 | 14 |
| 5F KLMO₃S | Ψ RIII Cap 1 | 1.0 | SF 5 | 31 | 15 |
| 5F KLMO₃S | Ψ RIII Cap 1 | 1.0 | SF 6 | 7 | 16 |

Summary of Results for Example 19 Experiment 19-1

As seen previously, including miRNA encoding NANOG in the mRNA mix resulted in more iPSC colonies than the 5 factor mix that did not include NANOG. The 6 factor mix (KLMNO₃S) produced the most colonies and the earliest colonies.

An interesting result from this experiment was the effect of increasing the amount of miRNA encoding KLF4 in the reprogramming mRNA mix. The 5 factor mix using a 3:1:1:311 ratio of KLMO and S resulted in the first colonies, the largest colonies, and the most colonies. The 6 factor mix was the best.

The most beneficial effect of using more mRNA encoding KLF4 was the uniform morphology of the iPSC colonies generated. With other mRNA mixes with KLF4 mRNA representing a 1-fold molar ratio, we have observed iPSC colonies of varying size and cell stage; the first iPSC colonies have often begun to differentiate before the last transfection was performed. Some of the iPSC colonies also have exhibited what the present researchers believe to be incompletely reprogrammed cells surrounding them. Some representative images of typical iPSC colonies obtained are shown in FIG. 38 and FIG. 39.

Figure 38:
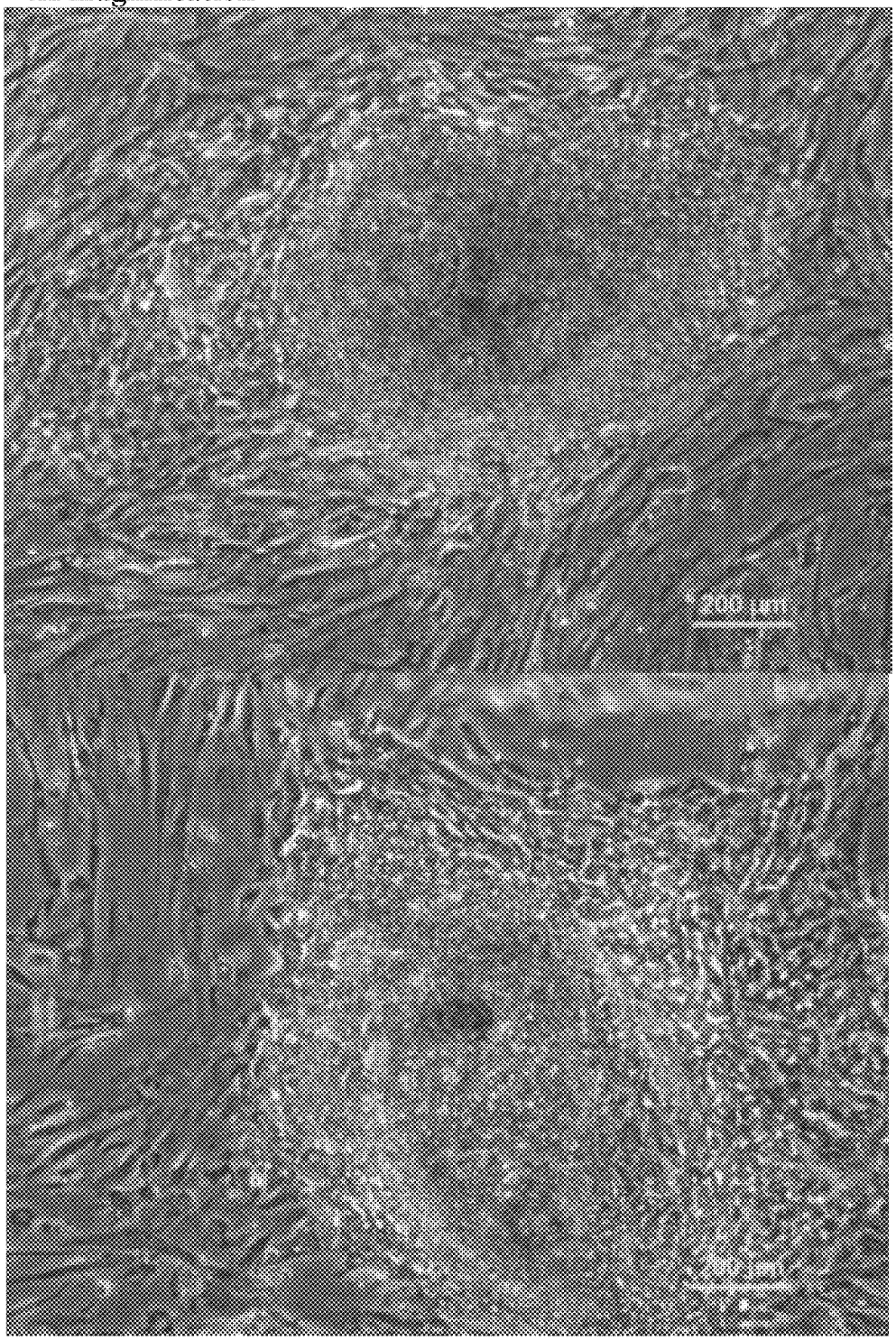
FIG. 38 shows images of 5-factor pseudouridine-modified RNase III-treated KLMO3S (1:1:1:3:1) iPSCs.
Figure 39:
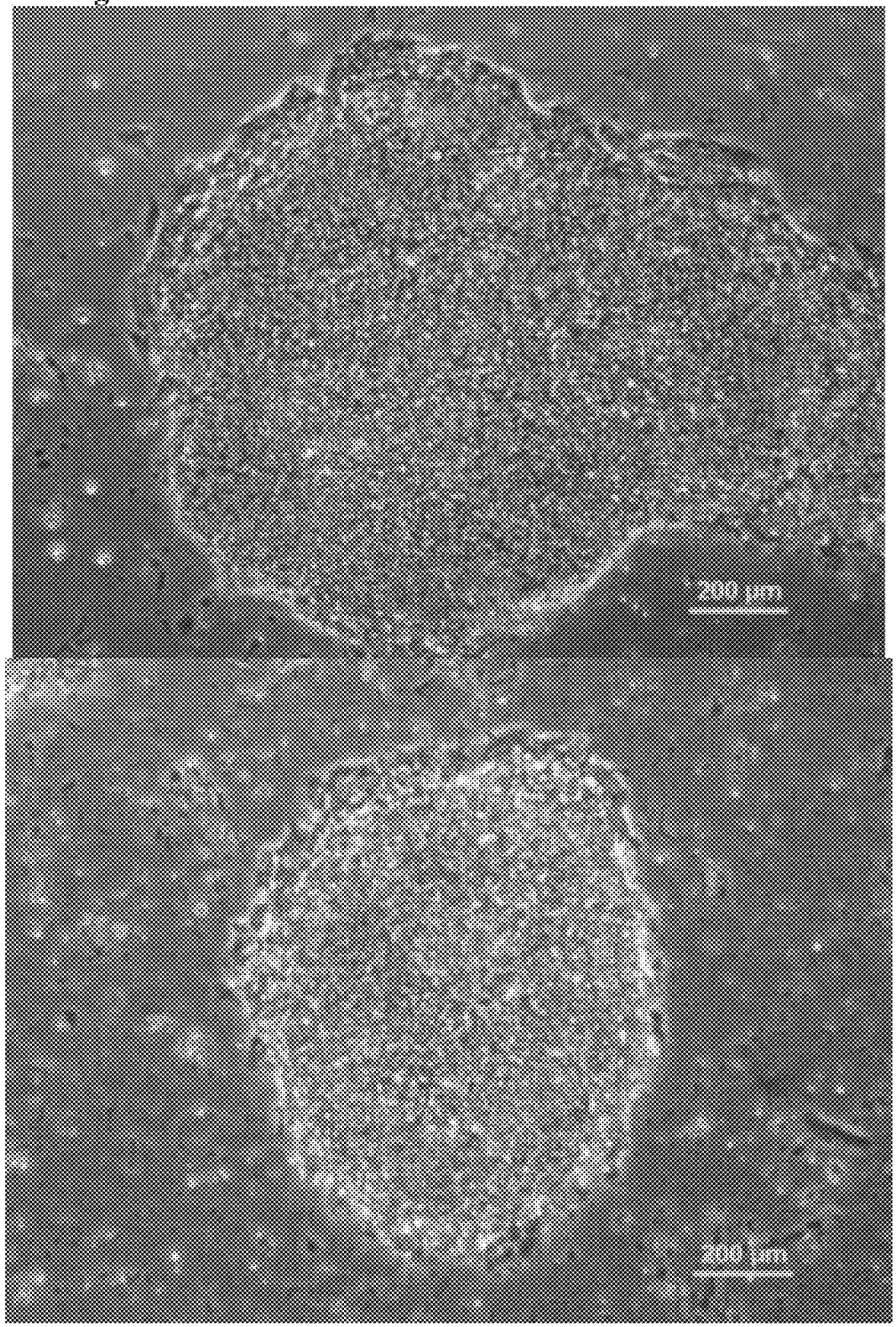
FIG. 39 shows images of 5 factor pseudouridine-modified, RNase III-treated $K_3LMO_3S$ (3:1:1:3:1) iPSCs.
Figure 41:
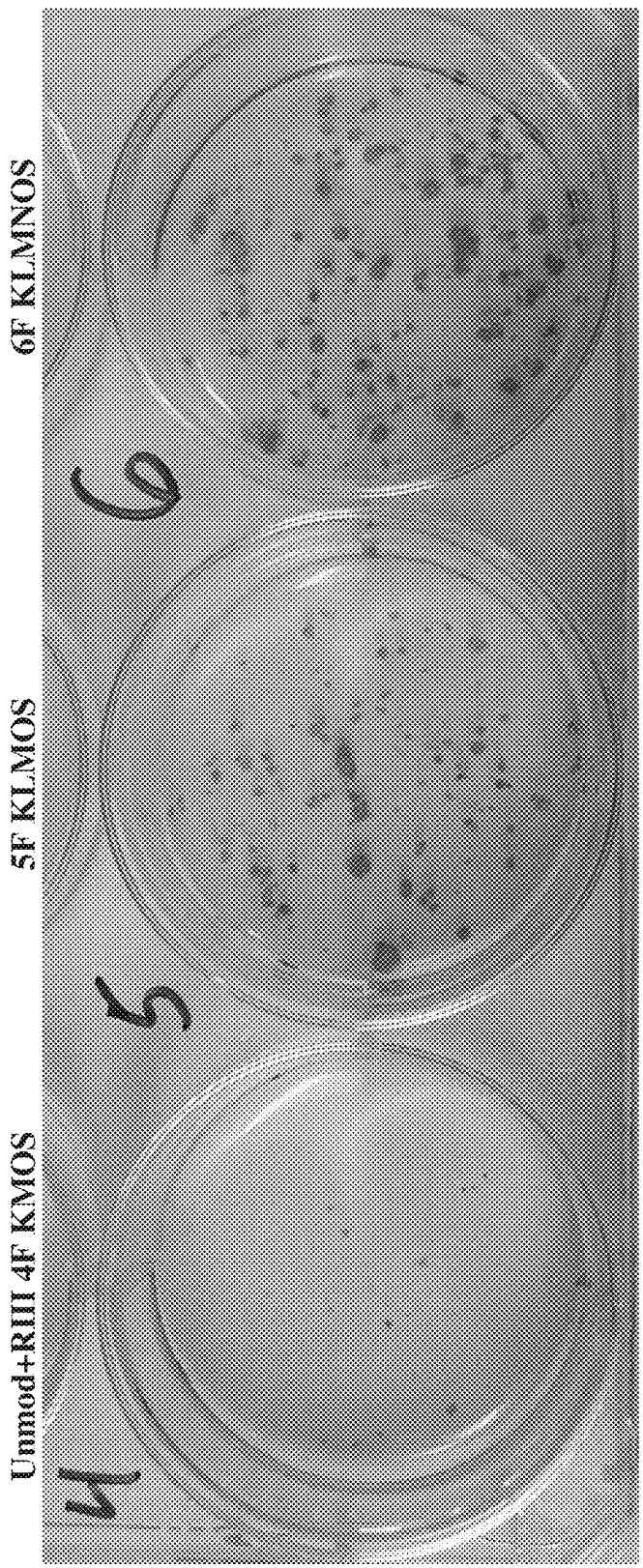
FIG. 41 shows alkaline phosphatase-positive colonies generated from BJ fibroblasts transfected with RNase III-treated unmodified mRNAs encoding KMOS, KLMOS, and KLMNOS.

As can be seen in FIG. 38, some of the 5-factor pseudouridine-modified, RNase III-treated KLMO3S (1:1:1:3:1) iPSCs are regular in shape, but many of the cells are not. There are larger epithelial cells around these two colonies. The scattered cells around the periphery are the feeder cells. As can be seen in FIG. 39, all of the 5 factor pseudouridine-modified, RNase III-treated K₃LMO₃S (3:1:1:3:1) iPSCs had more regular borders. These cells also tended to kill off the feeder cells surrounding the iPSC colonies. These colonies were larger and easier to pick for propagation because they were more uniform.

Having control over the factor stoichiometry is one of the benefits of using mRNA for reprogramming, such as to find the ideal ratios of mRNAs encoding different reprogramming factors to achieve a particular effect.

Currently the only drawback to elevating the KLF4 level is the feeder cell layer death, but because the colonies thrived and were easy to work with, this may actually be a benefit. As is shown in FIG. 40, when alkaline phosphatase stained, the benefits to the colonies resulting from the elevated KLF4 mRNA in the mRNA mix can clearly be seen (see FIG. 40B).

Experiment 19-2: Effect of Amount of mRNA Encoding KLF4 in 5-Factor mRNA Mixes Comprising RNase III-Treated CAP1 GAψC-mRNAs on Induction of iPSCs from BJ Fibroblasts

| Total Amount of mRNA | mRNA Mix | Amount of Klf4 mRNA in Mix | Epith Cells Noted | Observations | No. of Alk. Phos.-Positive Colonies | Well # |
|---|---|---|---|---|---|---|
| 1.0 μg | KLMO₃S | 1X | | | 149 | 28 |
| 1.0 μg | K₂LMO₃S | 2X | Very Early | | 181 | 19 |
| 1.0 μg | K₃LMO₃S | 3X | Very Early | | 73 | 22 |
| 1.2 μg | KLMO₃S | 1X | | TMTCA | 400+ | 29 |
| 1.2 μg | K₂LMO₃S | 2X | Earliest | TMTCA | 400+ | 20 |
| 1.2 μg | K₃LMO₃S | 3X | Earliest | | 194 | 23 |
| 1.4 μg | KLMO₃S | 1X | | TMTCA | 400+ | 30 |
| 1.4 μg | K₂LMO₃S | 2X | Earliest | TMTCA | 400+ | 21 |
| 1.4 μg | K₃LMO₃S | 3X | Earliest | | ~300 | 24 |

*TMTCA = Too many Alk Phos-Positive colonies to count accurately; N/A = Not Applicable.

Summary of Results for Example 19 Experiment 19-2

There was definitely a reproducible benefit to increasing the amount of mRNA encoding KLF4 in the mRNA reprogramming mixes. The K₃LMO₃S mRNA mix caused feeder cell death as seen in the previous experiments. However, the K₂LMO₃S and K₃LMO₃S mixes resulted in earlier epithelial cell formation and iPSC colonies that were reproducibly larger and easier to pick. In this experiment, the K₂LMO₃S mRNA mix resulted early induction of iPSC colonies with less cell death (including feeder cell death) and higher numbers of iPSC colonies than the K₃LMO₃S mRNA mix, so that fewer transfections could be performed to obtain good numbers of iPSC colonies efficiently.

Example 20. Effect of Different Caps and Other Variations on iPSC Reprogramming

Materials and Methods for Example 20

Sets of different reprogramming mRNAs were synthesized that varied by cap, nucleotide composition and RNAse III (RIII) treatment. APEX™ phosphatase (Epicentre, Madison, WI, USA) was used to treat some co-transcriptionally ARCA-capped mRNAs (see table below). Reprogramming mRNAs encoding KLF4 (K), LIN28 (L), cMYC(T58A)

(M), OCT4 (O) and SOX2 (S) were mixed to maintain a 3-fold molar excess of OCT4 over the other factors, regardless of the number of factors encoded in the mRNA mixes.

$10^4$ BJ fibroblasts (passage 6) were plated on $4\times10^5$ NuFF feeder cells in Pluriton reprogramming media as previously described. When B18R protein was used, the medium was changed four hours prior to the first transfection and B18R protein (200 ng/ml media) was added to the well. For subsequent transfections, the B18R protein and RNase Inhibitor (0.5U/ml medium) was added to cells in fresh medium, which was changed prior to daily transfections. Eighteen transfections were performed using 1.2 micrograms of mRNA diluted in 60 microliters of Stemfect Buffer combined with 4.8 microliters of the Stemfect transfection reagent diluted in 60 microliters of Stemfect buffer. Each mRNA mix was incubated at room temperature for 15 minutes and added dropwise to the cells.

The colonies were fixed and stained with alkaline phosphatase after representative colonies were picked for expansion. Colony counts were performed on fixed, alkaline phosphatase-positive cells, as presented in the table below.

Results for Example 20

No. Of Alkaline Phosphatase-Positive Colonies Obtained:

| mRNA mix | Cap Type | AMT of RNA (μg) | B18R Protein Used | Alk Phos-Positive iPSC Colony Count | Well No. |
|---|---|---|---|---|---|
| mRNA Reprogramming Mix | | | | | |
| unmod. RIII 4F KMOS | Cap 1 | 1.2 | NO | 18 | 4 |
| unmod. RIII 5F KLMOS | Cap 1 | 1.2 | NO | 111 | 5 |
| unmod. RIII 6F KLMNOS | Cap 1 | 1.2 | NO | 140 | 6 |
| ψ-modified mRNA Reprogramming Mix | | | | | |
| ψ RIII 5F KLMOS | Cap 0 | 1.2 | NO | 223 | 9 |
| ψ RIII 5F KLMOS | Cap 0 | 1.2 | YES | 162 | 10 |
| ψ RIII 5F KLMOS | Cap 1 | 1.2 | NO | 214 | 13 |
| ψ RIII 5F KLMOS | Cap 1 | 1.2 | YES | 115 | 14 |
| ψ RIII 5F KLMOS | ARCA | 1.2 | NO | 317 | 17 |
| ψ RIII 5F KLMOS | ARCA | 1.2 | YES | 292 | 18 |
| ψ & $m^5C$ 5F KLMOS (no RIII) | ARCA + Phos | 1.2 | NO | 5 | 21 |
| ψ & $m^5C$ 5F KLMOS (no RIII) | ARCA + Phos | 1.2 | YES | 102 | 22 |

(RIII = RNase III-treated. O is in 3-fold molar excess over other reprogramming mRNAs.)

No. of Alkaline Phosphatase-Positive Colonies Obtained: iPSC Colony Counts for Each Well are Given Below:

| mRNA mix | Cap Type | AMT of RNA (μg) | B18R Protein Used | No. of Alk Phos-Positive Colonies | Well No. |
|---|---|---|---|---|---|
| unmod. RIII 4F KMOS | Cap 1 | 1.0 | NO | 3 | 1 |
| unmod. RIII 5F KLMOS | Cap 1 | 1.0 | NO | 18 | 2 |
| unmod. RIII 6F KLMNOS | Cap 1 | 1.0 | NO | 34 | 3 |
| unmod. RIII 4F KMOS | Cap 1 | 1.2 | NO | 18 | 4 |
| unmod. RIII 5F KLMOS | Cap 1 | 1.2 | NO | 111 | 5 |
| unmod. RIII 6F KLMNOS | Cap 1 | 1.2 | NO | 140 | 6 |
| ψ RIII 5F KLMOS | Cap 0 | 1.0 | NO | 66 | 7 |
| ψ RIII 5F KLMOS | Cap 0 | 1.0 | YES | 38 | 8 |
| ψ RIII 5F KLMOS | Cap 0 | 1.2 | NO | 223 | 9 |
| ψ RIII 5F KLMOS | Cap 0 | 1.2 | YES | 162 | 10 |
| ψ RIII 5F KLMOS | Cap 1 | 1.0 | NO | 73 | 11 |
| ψ RIII 5F KLMOS | Cap 1 | 1.0 | YES | 70 | 12 |
| ψ RIII 5F KLMOS | Cap 1 | 1.2 | NO | 214 | 13 |
| ψ RIII 5F KLMOS | Cap 1 | 1.2 | YES NO | 115 | 14 |
| ψ RIII 5F KLMOS | ARCA | 1..0 | NO | 120 | 15 |
| ψ RIII 5F KLMOS | ARCA | 1.0 | YES | 45 | 16 |
| ψ RIII 5F KLMOS | ARCA | 1.2 | NO | 317 | 17 |
| ψ RIII 5F KLMOS | ARCA | 1.2 | YES | 292 | 18 |
| ψ $m^5C$ 5F KLMOS (no RIII) | ARCA + Phos | 1.0 | NO | 0 | 19 |
| ψ $m^5C$ 5F KLMOS (no RIII) | ARCA + Phos | 1.0 | YES | 34 | 20 |
| ψ $m^5C$ 5F KLMOS (no RIII) | ARCA + Phos | 1.2 | NO | 5 | 21 |
| ψ $m^5C$ 5F KLMOS (no RIII) | ARCA + Phos | 1.2 | YES | 102 | 22 |

(RIII = RNase III-treated. O is always in 3-fold molar excess over other reprogramming mRNAs.)

Summary of Selected Results for Example 20

Induced pluripotent stem cell colonies were generated using unmodified mRNAs encoding only 4 factors (KMOS). Some colonies were picked to expand and maintain. The cells tolerated the Stemfect RNA Transfection reagent with unmodified mRNA without a media change post-transfection. B18R protein consistently decreased the colony counts from RNase III-treated-, ψ-modified mRNA mixes. The only benefit for use of B18R protein was with dual (ψ- and m5C-) modified mRNA that wasn't treated with RNAse III. As can be seen in FIG. 43C, fewer colonies were obtained with the dual modified (ψ- and m5C-) ARCA-co-transcriptionally-capped mRNA mix, even though it was phosphatased and B18R protein was added to the medium.

Figure 42:
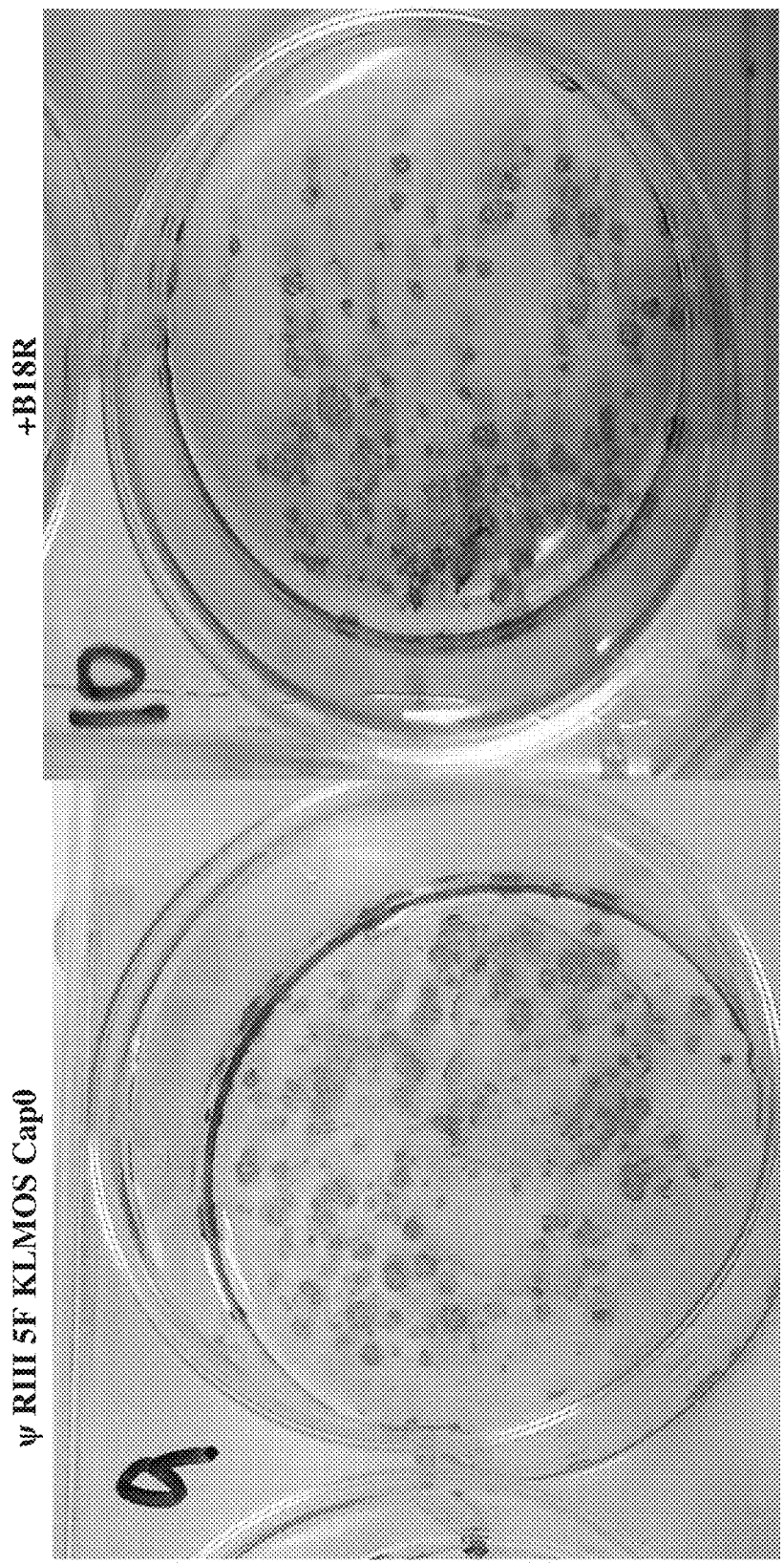
FIG. 42 shows alkaline phosphatase-positive colonies generated from BJ fibroblasts transfected with RNase III-treated pseudouridine-modified, Cap0 mRNAs encoding KLMOS and KLMOS+B18R.

The number of colonies from Cap0 and Cap1 RIII-treated, ψ-modified mRNA mixes were very similar (see FIG. 42 and FIG. 43A).

As is shown in FIG. 43B. the ARCA-capped, ψ-modified RIII-treated mRNA mix produced iPSC colonies from post-transcriptionally-capped mRNA mixes in this experiment. The tail lengths of these mRNA were slightly shorter than the Cap0 and Cap1 mRNA tails. Denaturing gel tail length comparisons aren't as accurate on pseudoU-modified mRNA, but the tails appeared to be ~120 bases on the Cap0 and Cap1 mRNAs and at least 100 bases on the ARCA-capped mRNAs. Some colonies were picked and removed for propagation before staining.

Example 21. Additional Studies on Effect of Different Caps and Other Variations on iPSC Reprogramming Materials and Methods for Example 21 mRNAs encoding 5 reprogramming factors ($KLM_{T584}OS$) were synthesized using standard unmodified GAUC NTPs. The RNAs were either synthesized co-transcriptionally capped with the ARCA cap analog, or post-transcriptionally capped to either have a Cap0 or Cap1. All of the mRNAs were poly(A) tailed using poly(A) polymerase to a length of ~150 As. Some of the ARCA-capped mRNAs were also treated with Apex phosphatase.

5-Factor reprogramming mixes were made (KLM$_{T58A}$OS with standard 1:1:1:3:1 stoichiometry) and 1.2 micrograms of each mRNA mix was transfected with 4.8 microliters Stemgent's STEMFECT™ Transfection Reagent daily into $10^4$ BJ fibroblasts passage 5 plated on $4 \times 10^5$ NuFF cells. Some wells had 200 ng or 400 ng B18R protein added per ml of medium. After 18 transfections, the cells were grown for 2 more days, a few iPSC colonies were picked and the rest were stained for alkaline phosphatase activity to count iPSC colonies.

Experiment 1: No. of Alkaline Phosphatase-Positive Colonies from Each Type of mRNA Mix.

to 15). 2× B18R did not seem to increase the number of iPSC colonies, but the results were mixed. In one case, 1 mM Mg(OAc)$_2$ was better than 2 mM in the RNase III buffer; in one case it was not (wells 12 to 15).

Cap1 Results

Use of Cap1 unmodified mRNAs that were treated with RNase III was sufficient to produce iPSC colonies, whereas RNase III-treated Cap0- or ARCA-capped unmodified mRNAs did not induce iPSC colonies. B18R protein did seem to increase the number of iPSC colonies from RNase III-treated, Cap1 unmodified mRNAs. No difference could be determined when 1 or 2 mM Mg2+ was used in the RNase III buffer; the iPSC colony counts were either similar or there were too many colonies to count.

| Cap Type | RNase III | RIII Buffer Mg Concn | Treated with APEX ™ Phosphatase | B18R Protein Used | Observations | No. of Alk Phos-Positive Colonies | Well No. |
|---|---|---|---|---|---|---|---|
| ARCA (co-trans) | NO | N/A | NO | NO | Cells died | 0 | 1 |
| ARCA | NO | N/A | YES | NO | Cells died | 0 | 2 |
| ARCA | NO | N/A | YES | YES 200 ng | | 106 | 3 |
| ARCA | YES | 2 mM | NO | NO | | 0 | 4 |
| ARCA | YES | 2 mM | YES | NO | | 0 | 5 |
| ARCA | YES | 2 mM | YES | YES 200 ng | | 278 | 6 |
| ARCA | YES | 2 mM | NO | YES 200 ng | | 90 | 7 |
| ARCA | YES | 2 mM | NO | YES 400 ng | | 93 | 8 |
| Cap0 | NO | N/A | N/A | NO | Cells died | 0 | 9 |
| Cap0 | YES | 1 mM | N/A | NO | | 0 | 10 |
| Cap0 | YES | 2 mM | N/A | NO | | 0 | 11 |
| Cap0 | YES | 1 mM | N/A | YES 200 ng | | 400+ | 12 |
| Cap0 | YES | 2 mM | N/A | YES 200 ng | | 283 | 13 |
| Cap0 | YES | 1 mM | N/A | YES 400 ng | | 252 | 14 |
| Cap0 | YES | 2 mM | N/A | YES 400 ng | | 344 | 15 |
| Cap1 | NO | N/A | N/A | NO | Cells died | 0 | 16 |
| Cap1 | YES | 1 mM | N/A | NO | | 394 | 17 |
| Cap1 | YES | 2 mM | N/A | NO | | 386 | 18 |
| Cap1 | YES | 1 mM | N/A | YES 200 ng | | 400+ | 19 |
| Cap1 | YES | 2 mM | N/A | YES 200 ng | | 400+ | 20 |
| Cap1 | YES | 1 mM | N/A | YES 400 ng | | 400+ | 21 |
| Cap1 | YES | 2 mM | N/A | YES 400 ng | | 400+ | 22 |

Results for Example 21

ARCA Results

Unmodified, ARCA co-transcriptionally capped mRNA produced iPSC colonies if the mRNA was treated with phosphatase and the cells are treated with B18R (well #3). The Stemfect Transfection Reagent's low toxicity may also play a role in making this possible. RNase III-treatment of the ARCA mRNA was not enough to produce colonies (wells #4 & 5) unless the cells were also treated with B18R (wells 6, 7 & 8). RNase III-treatment significantly increased the number of iPSC colonies obtained with ARCA+phosphatase treatment+B18R in the medium (well #6 versus 3). The APex Phosphatase treatment seemed to significantly improve the iPSC colony count (well 6, versus Wells 7 & 8). Increasing the B18R concentration from 200 ng/ml of media to 400 ng/ml of media did not increase the iPSC colony count (well 8 versus well 7).

Cap0 Results

In this experiment, RNase III-treatment of the Cap0 mRNA was not enough to produce iPSC colonies (wells #10 & 11) unless the cells were also treated with B18R (wells 12

Comparisons

Cap0 and Cap1 unmodified mRNA mixes produced more iPSC colonies than the ARCA-capped mRNA mRNA mixes. Cap1, RNAse III-treated unmodified mRNA reprogramming mixes induced iPSC colonies without B18R protein, but Cap0 and ARCA mRNA mixes did not. If RNAse III treatment and B18R protein were used together with Cap0 or Cap1 unmodified mRNAs, numerous iPSC colonies were induced. Picked and propagated alkaline phosphatase-positive iPSC colonies from six different wells (well numbers 3, 6, 13, 17, 18, and 20) all stained positive for immunofluorescent TRA1-60, SOX2, OCT4, SSEA4, and NANOG pluripotency markers.

Followup Experiment

The same RNase III-treated (with 1 or 2 mM Mg2+) unmodified mRNA reprogramming mixes containing mRNAs encoding 5 reprogramming factors (KLM$_{T58A}$OS) (wherein the mRNAs were either co-transcriptionally capped with the ARCA cap analog, or enzymatically capped post-transcriptionally to generate either Cap0 or Cap1 mRNA, and enzymatically poly-A tailed (~150 A nucleotides) using poly(A) polymerase) were used for reprogramming of BJ fibroblasts as described above in this EXAMPLE 21, except that 0.5 micrograms of each mRNA mix, complexed with 2.5 microliters of Invitrogen's RNAiMAX™ transfection reagent instead of Stemgent's STEMFECT reagent, was transfected daily for 18 days into $5 \times 10^3$ BJ fibroblasts (passage 5) plated on $2.5 \times 10^5$ NuFF cells in 12-well plates (rather than 6-well plates). Some wells also had 200 or 400 ngs of B18R protein added per ml of medium. As a positive control for reprogramming, an RNase III (with 2 mM Mg2+)-treated pseudouridine-modified mRNA mix encoding the 5 $KLM_{T58A}OS$ reprogramming factors was also similarly transfected into BJ fibroblast cells in one well. The cells died in all but two of the wells by the end of the transfections, apparently because the RNAiMAX transfection reagent was too toxic for the cells under the conditions used. Only a few alkaline phosphatase-positive colonies were generated using the RNase III-treated pseudouridine-modified mRNA positive control mix. No other conclusions could be made from this experiment.

Example 22. Reprograming of Human Neonatal Keratinocytes (HEKn) to iPSCs Using RNAse III-Treated, Cap1, Poly(A)-Tailed mRNAs Encoding Protein Reprogramming Factors is Reproducible and Very Efficient Materials and Methods for Example 22

Keratinocyte Reprogramming Protocol

In general, many steps of the Keratinocyte Reprogramming Protocol developed and used herein are similar to the steps in the protocol for reprogramming fibroblasts to iPSCs in the section entitled "Detailed Description of the Reprogramming Method for EXAMPLE 14," with some additional steps as described herein below.

Primary neonatal keratinocytes are propagated in a serum-free, low calcium medium that promotes a highly proliferative and undifferentiated state. In the presence of physiological levels of calcium, the cells terminally differentiate into fully stratified epidermis. In order to reprogram these cells most efficiently, the first 3 transfections are performed with the cells growing in low calcium keratinocyte medium (EpiLife Medium with Human Keratinocyte Growth Supplement from Life Technologies) without feeder cells. $2 \times 10^5$ HEKn cells are plated and transfected daily 3 times. Four hours after the third transfection, the cells are treated with 0.025% trypsin/EDTA solution and are transferred to NuFF cell feeder layers in Pluriton reprogramming medium as described previously for fibroblast reprogramming. From this point on the cells are transfected in PLURITON™ Reprogramming Medium and Conditioned Medium as described previously.

More specifically, $2 \times 10^5$ HEKn cells (passage 4) were plated (on plastic) per well of a 6-well dish. The cells were maintained in EpiLife medium with 60 micromolar calcium and supplemented with Human Keratinocyte Growth Supplement (HKGS) both from Cascade Biologics (sold through Life Technologies). The cells were transfected daily with 4 microliters of Stemfect RNA Transfection Reagent per microgram of mRNA mix. The Stemfect reagent is diluted in 60 microliters of its own buffer. The 1.2 micrograms of mRNA is also diluted in 60 microliters of Stemfect Buffer. The mixes were combined, incubated at room temperature for 15 minutes and added drop-wise to the cells. The medium was changed daily before the transfection and 0.5 units of SCRIPTGUARD™ RNase inhibitor (CELLSCRIPT, INC., Madison, WI, USA) were added per ml of medium. Thus, in some embodiments, an RNase inhibitor (e.g., SCRIPTGUARD™ RNase inhibitor is added with the RNA comprising ssRNA or mRNA encoding one or more proteins for inducing a biological or biochemical effect (e.g., for reprogramming a somatic cell, e.g., a keratinocyte, to an iPSC).

The first 3 transfections were performed with the cells maintained in EpiLife low calcium medium. Four hours after the third transfection the cells were trypsinized with 0.025% trypsin/EDTA solution and the cells from each well were plated onto NuFF feeder cells in Pluriton reprogramming medium with standard levels of supplement and penicillin-streptomycin as previously described. The next 6 transfections were performed in Pluriton Reprogramming medium and the final 9 transfections were performed with cells maintained in NuFF conditioned Pluriton medium.

mRNAs were synthesized either using standard unmodified ATP, CTP, GTP and UTP or using ATP, CTP, GTP and ψTP. All were capped to make a Cap1 structure and tailed using poly(A) polymerase as previously described. In one experiment, HEKn human neonatal keratinocytes were reprogrammed using the reprogramming method of the present invention by transfecting $2 \times 10^5$ HEKn cells with 1-1.5 micrograms of a pseudoU-modified, RNase III-treated, mRNA mix of $KLM_{T58A}OS$ (1:1:1:3:1) daily for 14 days. Alkaline phosphatase-positive colonies indicative of iPSCs were obtained and, following picking and passaging, tested colonies were also positive for the immunofluorescent pluripotency markers TRA1-60, SOX2, OCT4, SSEA4, and NANOG. Further, when some of these iPSC colonies were allowed to differentiate in the embryoid body spontaneous differentiation protocol, selected differentiated cells expressed markers of all three germ layers, including endoderm (AFP and SOX17), mesoderm (SMA and Desmin), and ectoderm (class III beta-tubulin) when cells were fixed and processed for immunofluorescence with antibodies that recognized those markers. This led us to perform additional experiments on reprogramming of HEKn cells using different mRNA reprogramming mixes.

A 6-factor mRNA reprogramming mix ($KLM_{T58A}NOS$) was made with RNase III-treated unmodified mRNAs for reprogramming. Reprogramming with mRNA encoding NANOG in the mRNA mix consistently yields more and earlier iPSC colonies than 5-factor mixes. A second 6-factor mRNA reprogramming mix encoding the same factors was made with RNase III-treated, ψ-modified mRNAs. These mRNA mixes were compared in reprogramming to a 5-factor mRNA reprogramming mix made with a 3 times higher molar ratio of KLF4 mRNA (3:1:1:3:1), which had resulted in more iPSC colonies, more uniform colonies and earlier colonies than a 1:1:1:3:1 mRNA mix.

1.2 micrograms or 1.5 micrograms of each mRNA mix was transfected with 4.8 microliters or 6 microliters of Stemgent's Stemfect Transfection Reagent daily into $2 \times 10^5$ HEKn cells (passage 5) plated on plastic for the first 2, 3 or 4 days and then trypsinized and plated on $4 \times 10^5$ NuFF cells 4 hours post-transfection. By day 4, the HEKn cells that were still growing on plastic were already confluent. This makes them terminally differentiate, so the day 4 transfer wells were dropped from the experiment.

After only 14 daily transfections, many iPSC colonies were apparent so no more transfections were performed and the cells were grown for 2 more days, colonies were picked, fixed, stained for alkaline phosphatase and counted.

The Table Below is a Summary of the Colony Counts Resulting from Each Type of mRNA Mix.

| Substitutions | RNase III Treated | Type of mix | Amount of RNA Transfected Daily (µg) | Number of Days before plated on NuFFs | Number of Alk Phos-positive iPSC Colonies after 14 Transfections | Well No. |
|---|---|---|---|---|---|---|
| Unmodified | Yes | 6F KLMNO3S | 1.2 | 2 | 1 | 1 |
| Unmodified | Yes | 6F KLMNO3S | 1.5 | 2 | 1 | 2 |
| PseudoU (Ψ) | Yes | 6F KLMNO3S | 1.2 | 2 | 1 | 3 |
| PseudoU (Ψ) | Yes | 6F KLMNO3S | 1.5 | 2 | 5 | 4 |
| PseudoU (Ψ) | Yes | 5F K3LMO3S | 1.2 | 2 | 12 | 5 |
| PseudoU (Ψ) | Yes | 5F K3LMO3S | 1.5 | 2 | 106 | 6 |
| Unmodified | Yes | 6F KLMNO3S | 1.2 | 3 | 4 | 7 |
| Unmodified | Yes | 6F KLMNO3S | 1.5 | 3 | 5 | 8 |
| PseudoU (Ψ) | Yes | 6F KLMNO3S | 1.2 | 3 | 26 | 9 |
| PseudoU (Ψ) | Yes | 6F KLMNO3S | 1.5 | 3 | 111 | 10 |
| PseudoU (Ψ) | Yes | 5F K3LMO3S | 1.2 | 3 | 195 | 11 |
| PseudoU (Ψ) | Yes | 5F K3LMO3S | 1.5 | 3 | 400+ | 12 |

Results for Example 22

Representative alkaline phosphatase-positive colonies, which were observed in all of the wells, were picked and propagated for further IPSC characterization. Reprogramming of primary human neonatal keratinocytes was reproducible and efficient. In this Example, three was the best number of transfections to perform before the cells were plated on feeder cells (for this number of starting keratinocyte cells). We observed that fewer than 105 HEKn cells should be plated per 6 well to avoid overgrowth and terminal differentiation of the target cells. If too many cells were plated, the cells wouldn't replate well on feeder cells. More RNA and Stemfect reagent needed to be used for high efficiency reprogramming. A total of 1.5 micrograms comprising all of the mRNAs per well was more efficient than 1.2 micrograms per well. Using more mRNA encoding KLF4 in the mix produced more iPSC colonies in fewer days. Induction of iPSC colonies with RNAse III-treated unmodified mRNAs were observed, but reprogramming was inefficient. Picked and propagated alkaline phosphatase-positive colonies from well numbers 2, 9 and 11 all stained positive for immunofluorescent TRA1-60, SOX2, OCT4, SSEA4, and NANOG pluripotency markers.

Example 23. Feeder-Free Reprogramming Using Unmodified or Pseudouridine-Modified mRNAs Encoding Reprogramming Factors Materials and Methods for Example 23

Feeder-free reprogramming was performed as previously described using BJ fibroblasts at passage 4, except 16 consecutive transfections were done rather than 18 transfections. Cells were transfected with cap1 mRNA encoding the 5 reprogramming factors, OCT4, SOX2, KLF4, LIN28 and cMYC (T58A). The mRNA used contained one of the following: unmodified NTPs with RNase III treatment after IVT, unmodified NTPs without RNase III treatment after IVT, or a pseudouridine only substitution with RNAse III treatment after IVT. RNase III treatment of the mRNAs was performed as previously described. Colony counts were done on day 18 based on morphology.

Results for Example 23

No iPSC colonies were observed when unmodified mRNAs were used for reprogramming without RNAse III treatment of the mRNAs after IVT. Induced pluripotent stem cell colonies were observed in wells treated with unmodified mRNAs that were RNase III-treated after IVT. However, more colonies were seen if pseudouridine was substituted for uridine in the mRNAs.

| Treatment | Number of iPSC Colonies Observed by Morphology |
|---|---|
| Unmodified + RNase III | 27 |
| Unmodified − RNase III | 0 |
| ΨTP modified + RNase III | 51 |

Example 24. Differentiation of Reprogrammed iPSC Colonies Induced from BJ Fibroblasts Using RNase III-Treated ψ-Modified mRNAs Encoding iPSC Induction Factors in Feeder-Free Medium Materials and Methods for Example 24

Feeder-free reprogrammed iPS cells using Ψ-substituted mRNA encoding the five reprogramming factors, OCT4, SOX2, KLF4, LIN28, and cMYC were put through the cardiomyocyte differentiation protocol as previously described. Movies of beating aggregates were recorded.

Aggregates, beating and non-beating, were dissociated using 10× trypsin (Invitrogen, Carlsbad, CA). Briefly, aggregates were resuspended in 10× trypsin, incubated at 37° C. for 5 minutes, and broken up using a pipet. The trypsin was neutralized with cardiomyocyte maintenance medium, and the cells were spun down at 1,200 rpms for 5 minutes. Cells were resuspended in cardiomyocyte maintenance medium and plated onto 6 well tissue culture plates pre-coated with 0.1% gelatin. Media was changed the following 2 days. Cells were then fixed and stained for class III beta-tubulin, cardiac troponinT, and sox17.

Results for Example 24

Figure 45C:
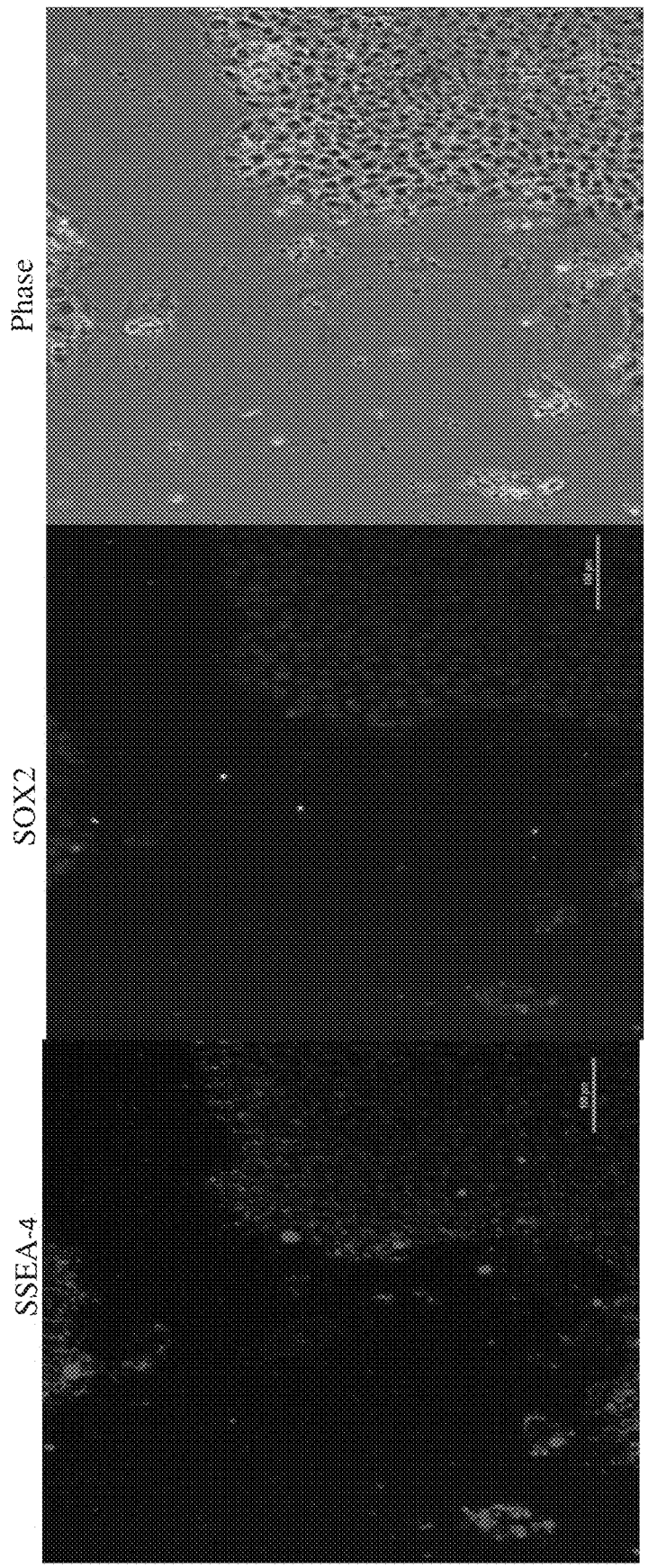
FIG. 45C shows cells stained for SSEA-4 and SOX2, and FIG. 45D. shows cells stained for TRA1-60.
Figure 45D:
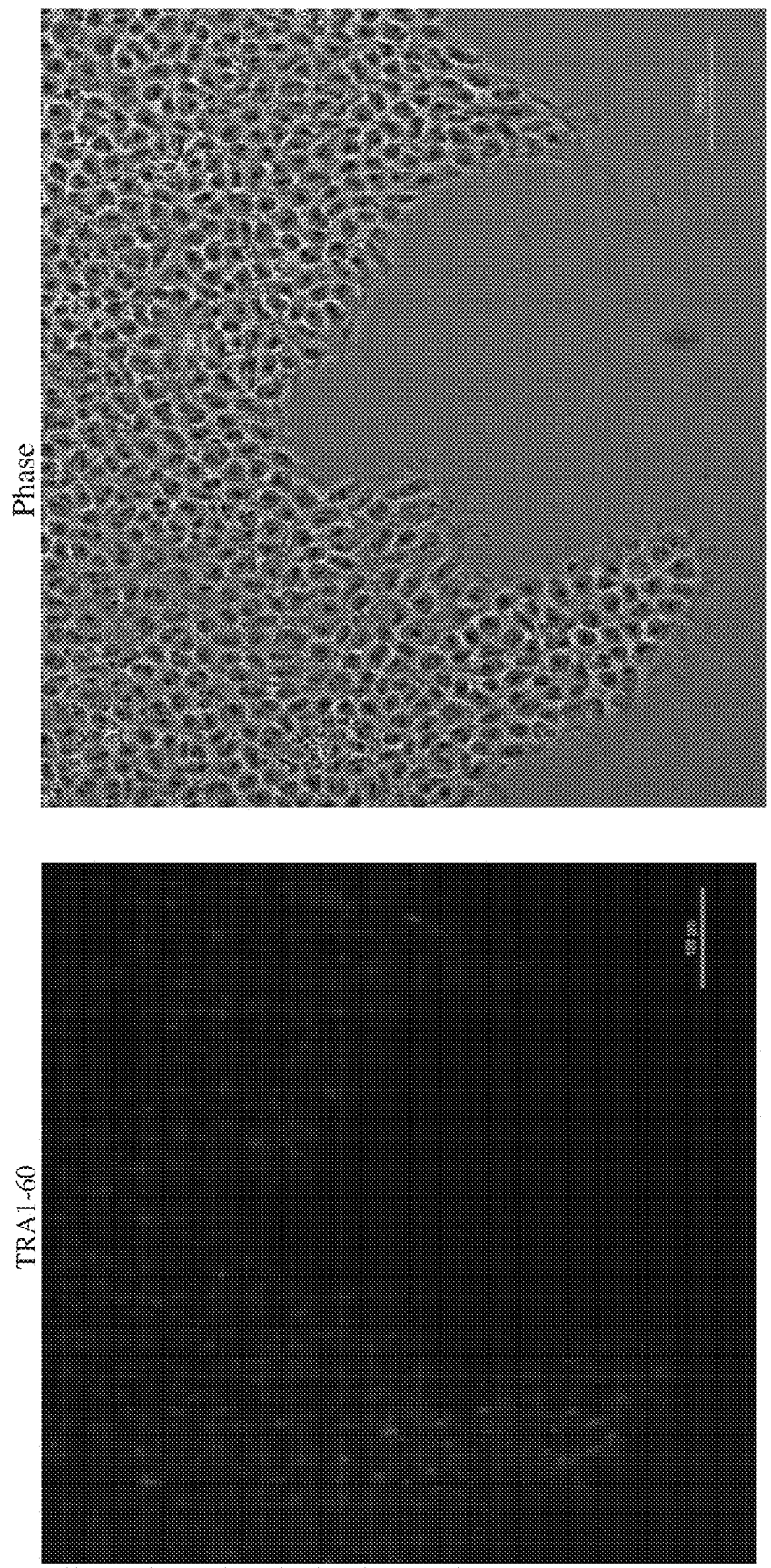
FIG. 45 shows images of immunostained feeder-free reprogrammed iPS cells generated from BJ fibroblasts using only Ψ-modified mRNA encoding the five reprogramming factors, OCT4, SOX2, KLF4, LIN28, and cMYC and then differentiated into cardiomyocytes.
FIG. 45A. shows differentiated cells stained for class III beta-tubulin, cardiac troponinT, and sox17.
FIG. 45B shows that the iPS cells stained for pluripotency markers prior to differentiation into cardiomyocytes.

Feeder-free reprogrammed iPSCs were put into cardiomyocyte differentiation. Beating aggregates were observed on day 12 of differentiation, and videos of the beating aggregates were recorded. After completion of the differentiation protocol, aggregates, both beating and non-beating, were dissociated and plated onto gelatin to see if cells originating from the other 2 germ layers also formed from these iPSCs. Cells staining positive for a neuronal makers, class III beta-tubulin, were observed indicating the potential of the iPSCs to differentiate into ectoderm originating cells. As is shown in FIG. 45, cells staining positive for SOX17, a transcription factor found in cells of the endoderm lineage, were also observed. Cells were also seen that stained positive for cardiac troponinT, which is a marker of cardiomyocytes, which have a mesoderm origin. Thus, the feeder-free reprogrammed iPSCs were able to differentiate into cells of all 3 germ layers.

Example 25. Forward Differentiation of iPSCs Induced from BJ Fibroblasts Using RNase III-Treated or HPLC-Purified Unmodified or ψ-Modified mRNAs Encoding iPSC Induction Factors Materials and Methods for Example 25 iPSCs derived from BJ fibroblasts were maintained in culture originally on NUFF feeder cells in iPS medium with 10 ng/ml FGFb, then on MATRIGEL artificial matrix in mTeSR media as previously described. Three different iPSC lines were differentiated, one from RNAse III-treated mRNA and two from HPLC-purified mRNA.

Pseudouridine-Modified, RNAse III-Treated mRNA

Line 1 (TN4w4) was derived from BJ cells reprogrammed with pseudoU-modified, RNase III-treated (with 1 mM MgOAc) mRNA of 1:1:1:3:1 molar stoichiometric mix of KLM(long)OS. The reprogramming involved 18 daily transfections of mRNA into BJ fibroblasts plated on NuFF cells in Pluriton media, as previously described. (Note this is the same iPSC line that was examined by qPCR to BJ fibroblasts to compare expression patterns.) A colony was picked and expanded for 17 passages, then frozen down for a week, then brought up and passaged 4 more times. Large colonies were allowed to form, were detached from the matrigel surface with dispase, and were kept in suspension culture for 8 days in iPS media with no FGFb to allow embryoid body formation. As described previously, the embryoid bodies were then plated on gelatin coated plates and allowed to attach and spontaneously differentiate in iPS media without FGFb for an additional 7 days. The cells were then fixed and incubated with antibodies for various markers as previously described. Immunofluorescence was performed and the cells were imaged.

Results for Example 25

The iPSCs stain positively for markers representing all 3 germ layers of cells. Cells were found that expressed the ectoderm markers, neuronal class III beta-tubulin (TUJ1), Glial Fibrillary Acidic Protein (GFAP) and neurofilament-light (NF-L), the mesoderm markers, alpha-smooth muscle actin (SMA) and desmin, and the endoderm markers, transcription factor SOX17 and alpha fetoprotein (AFP). Thus, pseudouridine-modified, RNAse III-treated cap1, poly(A)-tailed, mRNA mixes can be used to generate iPSCs that differentiated into cells of all 3 germ layers.

Line 2 iPSC Differentiation: Pseudouridine-Modified, HPLC-Purified mRNA

Line 2 (TN8w3) was derived as described above from pseudoU-modified, HPLC-purified, mRNA mixes that contained the shorter cMyc T58A mRNA. The line has been passaged 11 times before embryoid bodies were formed.

Figure 47B:
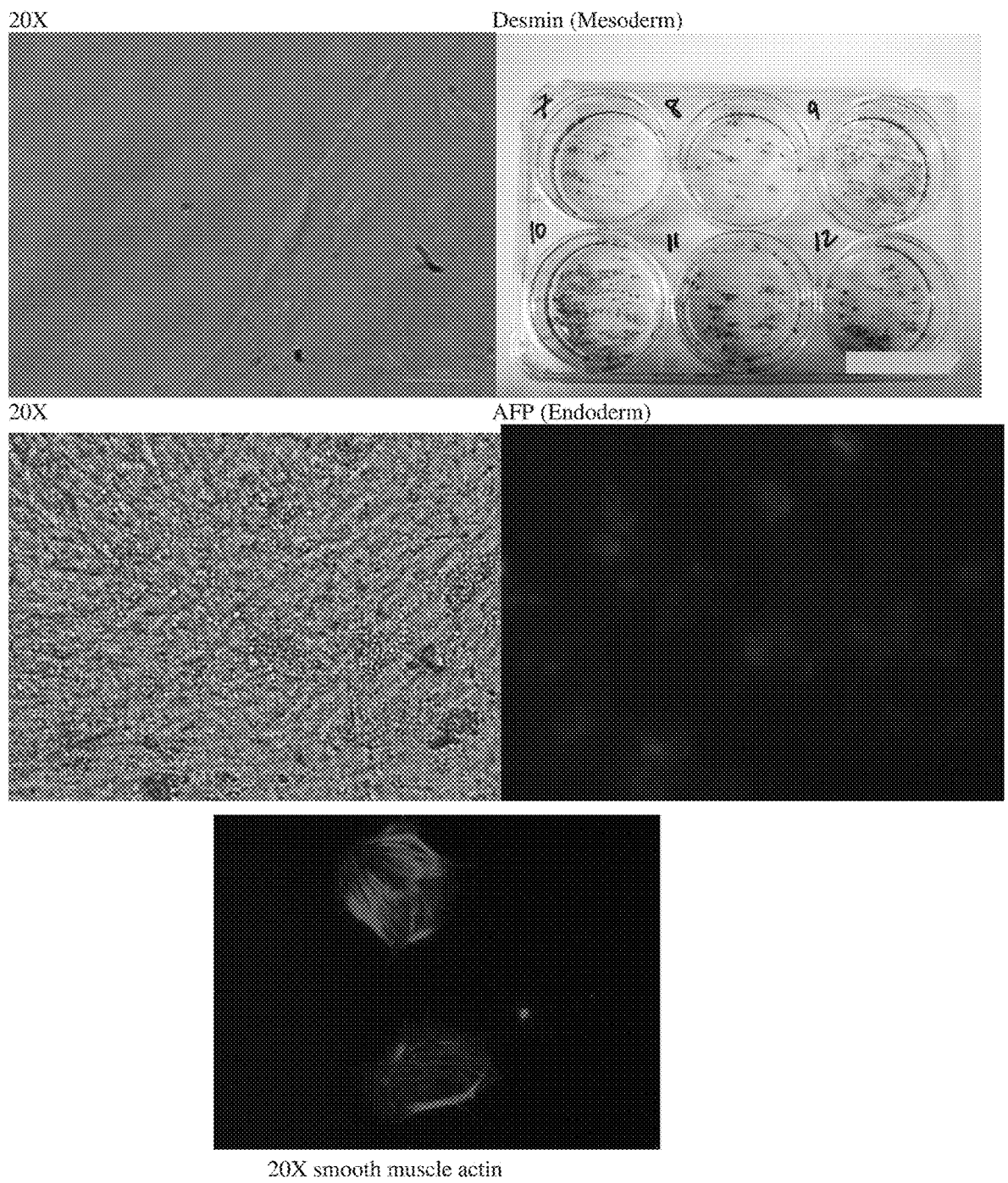
FIG. 47 shows images of immunostained feeder-free reprogrammed iPS cells (11 passages) generated from BJ fibroblasts that were HPLC-purified, mRNA III-treated mixtures that contained the shorter cMyc T58A mRNA. The iPSCs stain positively for markers representing all 3 germ layers of cells. Cells were found that expressed the ectoderm marker, neuronal class III beta-tubulin (TUJ1), the mesoderm markers, alpha-smooth muscle actin (SMA) (all shown in FIG. 47A) and desmin (FIG. 47B), and the endoderm markers, transcription factor SOX17 (FIG. 47A) and alpha fetoprotein (AFP) and smooth muscle actin (FIG. 47B).

As is shown in FIG. 47, the iPSCs stain positively for markers representing all 3 germ layers of cells. Cells were found that expressed the ectoderm marker, neuronal class III beta-tubulin (TUJ1), the mesoderm markers, alpha-smooth muscle actin (SMA) and desmin, and the endoderm markers, transcription factor SOX17 and alpha fetoprotein (AFP).

Line 3 iPSC Differentiation: Pseudouridine-Modified HPLC-Purified mRNA

Line 3 (TN18w35) was derived (as Line 2 was) from pseudoU-modified, HPLC-purified, mRNA mixes that contained the shorter cMyc T58A mRNA. The line has been passaged 4 times before embryoid bodies were formed. This is a newer line, but was confirmation of reprogramming with HPLC-purified mRNA.

Figure 48A:
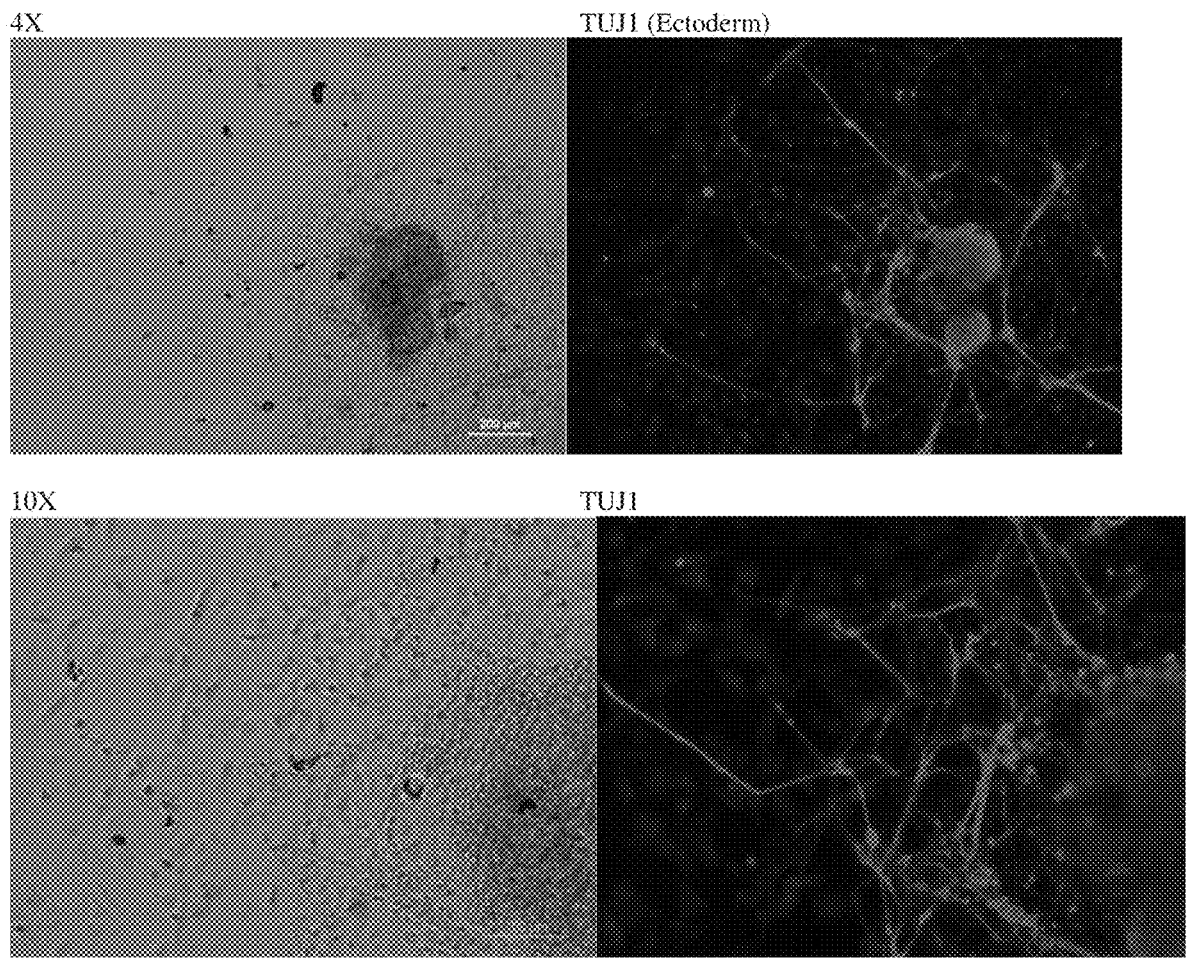
Figure 48B:
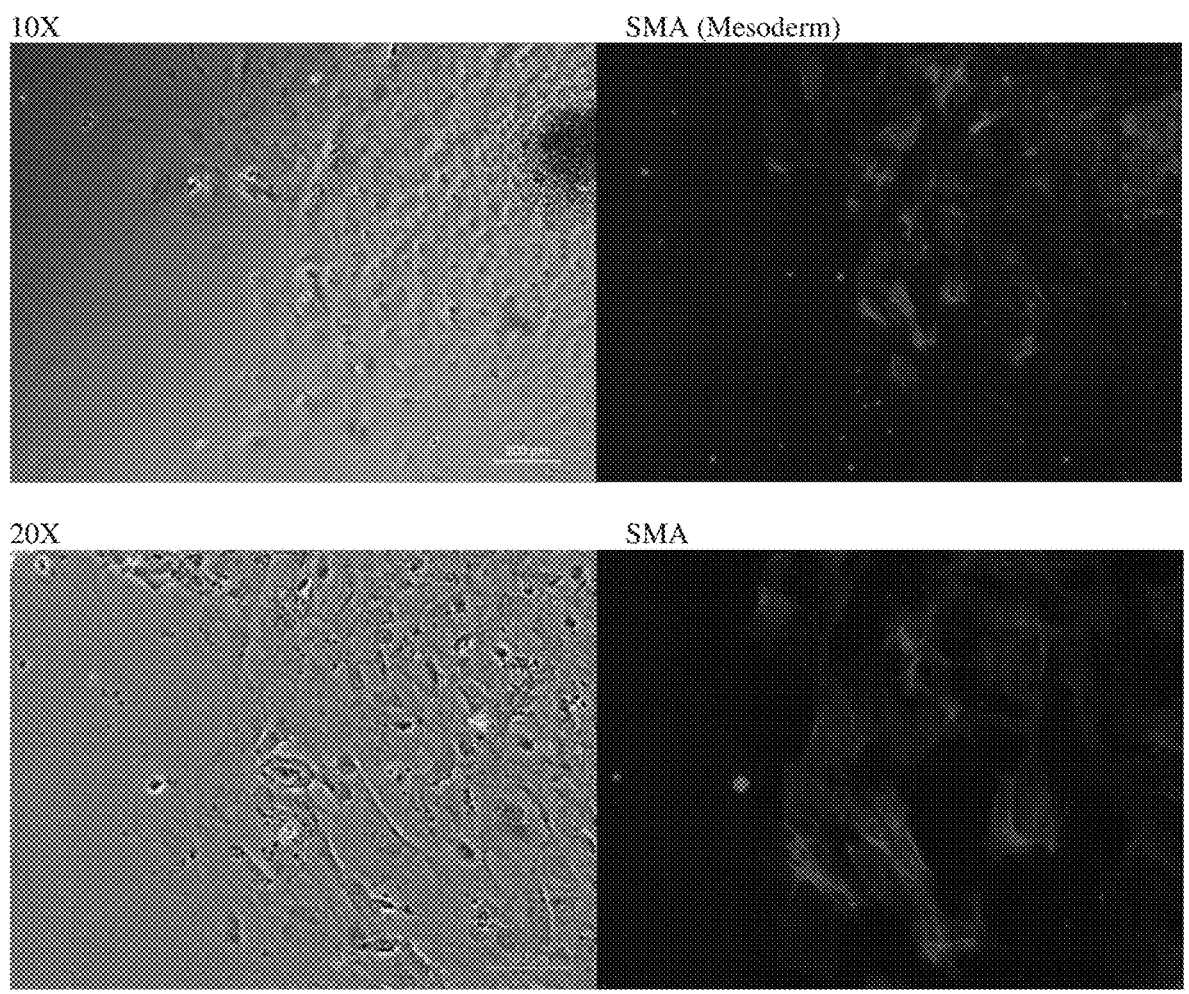

The iPSCs stain positively for markers representing all 3 germ layers of cells. Cells were found that expressed the ectoderm marker neuronal class III beta-tubulin (TUJ1), the mesoderm markers alpha-smooth muscle actin (SMA) and desmin, and the endoderm marker SOX17. Results are shown in FIG. 48.

Example 26. Use of Single-Stranded Pseudouridine-Containing mRNAs Encoding iPSC Induction Factors for Feeder-Free Reprogramming of Human Somatic Cells to iPS Cells on Tissue Culture Plates that were Pre-Coated with Vitronectin XF or that were without Coating with Vitronectin or any Other Extracellular Matrix or Biological Substrate Pseudouridine-modified RNA encoding SOX2, KLF4, LIN28, OCT4, and cMYC(T58A) reprogramming factors were in vitro-transcribed, treated with RNAse III with 2 mM magnesium acetate, and then enzymatically capped, and poly(A)-tailed, all as previously described.

For feeder-free reprogramming on Vitronectin XF-coated plates, Thermo Scientific Nunc Untreated Multidishes (Fisher Scientific, catalog no. 12-566-80; Thermo Scientific no. 150239), were coated with Vitronectin XF™ (Primorigen Biosciences, Inc. Madison, WI, USA) according to manufacturer's instructions and incubated at 37° C. at least 3 hours before plating cells.

For feeder-free reprogramming directly on plates without coating (e.g., without coating with vitronectin or any other extracellular matrix or biological substrate), Thermo Scientific Nunc Nunclon delta treated Multidishes (Fisher Scientific, catalog no. 14-832-11; Thermo Scientific no. 140675) were used; this product is listed as "Nunclon delta treated," which the supplier describes as "not coated with any chemical reagents," but "a surface modification which enhances cell attachment and growth for adherent cell lines."

BJ fibroblasts were plated onto either the Vitronectin XF-coated tissue culture plates or the tissue culture plates without vitronectin or any other coating at $1\times10^5$ or $5\times10^4$ cells per well in a minimum essential medium (MEM) useful for growth of fibroblast cells comprising: Advanced MEM (Invitrogen, Carlsbad, CA, USA) supplemented with 10% FBS (Fisher Scientific), 2 mM GLUTAMAX™-I (Invitrogen) and penicillin-streptomycin antibiotics, and incubated overnight at 37° C., 5% $CO_2$.

The following day, the medium was replaced with a Feeder-free Reprogramming Medium developed by the present Applicants consisting of Dulbecco's modified Eagle medium with nutrient mixture F-12 (DMEM/F12; (DMEM/F12; Invitrogen) supplemented with 20% KNOCKOUT™ serum replacement (Invitrogen), 2 mM GLUTAMAX™-I (Invitrogen), 0.1 mM non-essential amino acids solution (Invitrogen), 8 micromolar transforming growth factor β (TGFβ) inhibitor STEMOLECULE™ SB431542 (Stemgent®, Cambridge, MA, USA), 0.5 micromolar MEK signaling pathway inhibitor STEMOLECULE™ PD0325901 (Stemgent), and 100 ng/ml basic human recombinant fibroblast growth factor (FGFb; Invitrogen) with penicillin-streptomycin antibiotics. Medium was replaced daily prior to transfection of reprogramming mRNAs using RNAiMAX transfection reagent (Invitrogen). A mRNA/RNAiMAX complex in Opti-MEMI Reduced Serum Medium (Invitrogen) was prepared separately for each well containing cells to be reprogrammed: briefly, the mRNA reprogramming mix for one well of a plate was added to a first 60-microliter aliquot of Opti-MEMI Reduced Serum Medium; then this mRNA-containing first aliquot was combined with a second 60-microliter aliquot of Opti-MEMI Reduced Serum Medium containing 5 microliters of RNAiMAX transfection reagent per microgram of mRNA added; and finally, this mRNA/RNAiMAX complex in Opti-MEMI Reduced Serum Medium was incubated at room temperature for 15 minutes and then added dropwise to the cells in the well. Once the medium/mRNA/RNAiMAX mixture was added to all wells, the plates were incubated overnight at 37° C., 5% $CO_2$. For feeder-free reprogramming in Vitronectin XF-coated plates, cells were transfected in this way for 21 consecutive days. For feeder-free reprogramming of cells in plates that were not pre-coated with vitronectin or another extracellular matrix or biological substrate, cells were transfected in this way for 18 consecutive days. Following the last transfection, cells were maintained in iPSC Maintenance Medium until the colonies were large enough to pick.

Several days after the last transfection, the number of colonies that exhibited the morphology characteristic of iPS colonies were counted in wells of each type of plate using the above treatment protocols (i.e., in wells of the Vitronectin XF-coated plates and in wells of the plates which were not pre-coated with vitronectin or another extracellular matrix or biological substrate), and then representative iPSC colonies from each type of treatment and protocol were manually picked, and grown in half mTESR/half iPSC Maintenance Medium on plates coated with Vitronectin XF™ (Primorigen Biosciences, Inc.) to generate iPSC cell lines for further characterization. Putative iPS cell lines were then transitioned and maintained on Vitronectin XF in mTESR™ medium (Stem Cell Technologies, Vancouver, BC, Canada). Once expanded, these lines were then characterized by staining for pluripotency markers and by using them in the embryoid body spontaneous differentiation protocol, as previously described.

Results for Feeder-Free Reprogramming of BJ Fibroblasts to iPS Cells

Colonies characteristic of iPS cells were visually observed forming after 17 transfections, both on the plates coated with Vitronectin XF and on the plates which were not pre-coated with vitronectin or another extracellular matrix or other biological substrate.

The tables below show the number of iPSC colonies induced in wells for each type of plate and treatment protocol.

Number of iPSC Colonies Reprogrammed on Feeder-free Vitronectin XF-coated Plates

| Cell density Plated | mRNA Dose (μg/well/day) | No. of iPSC Colonies Observed |
| --- | --- | --- |
| $1 \times 10^5$ | Mock (No RNA) | 0 |
| $1 \times 10^5$ | 1.0 | 31 |
| $1 \times 10^5$ | 1.2 | 48 |
| $5 \times 10^4$ | Mock (No RNA) | 0 |
| $5 \times 10^4$ | 1.0 | 17 |
| $5 \times 10^4$ | 1.2 | 18 |

Number of iPSC Colonies Induced Directly on Nunc Cell Culture Treated Multidish Plates That Were Not Coated with an Extracellular Matrix or Other Biological Substrate.

| Cell Density Plated | mRNA Dose (μg/well/day) | No. of iPSC Colonies Observed |
| --- | --- | --- |
| $1 \times 10^5$ | Mock (No RNA) | 0 |
| $1 \times 10^5$ | 0.8 | 11 |
| $1 \times 10^5$ | 1.0 | 3 |
| $1 \times 10^5$ | 1.2 | 0 |
| $1 \times 10^5$ | 1.4 | 1 |
| $5 \times 10^4$ | Mock (No RNA) | 0 |
| $5 \times 10^4$ | 0.8 | 3 |
| $5 \times 10^4$ | 1.0 | 1 |
| $5 \times 10^4$ | 1.2 | 1 |
| $5 \times 10^4$ | 1.4 | 2 |

Representative cell lines from both Vitronectin XF-coated plates and from plates which were not pre-coated with vitronectin or another extracellular matrix or other biological substrate stained positively for the pluripotency markers OCT4, NANOG, TRA-1-60, SSEA4 and SOX2, and, when subjected to the embryoid body spontaneous differentiation protocol, cells of these cell lines spontaneously differentiated into cells of all 3 germ layers, as shown by positive immunofluorescent staining for markers specific for cells of each germ layer, including for SOX17 (endoderm), DESMIN (mesoderm), and BETA-III tubulin (ectoderm).

As described above, these exemplary experiments further demonstrated embodiments of the present invention, wherein said introducing of modified mRNA comprising pseudouridine-containing mRNA encoding iPSC induction factors induced reprogramming of mammalian cells that exhibited a first differentiated state or phenotype (in this case, somatic cells comprising human BJ fibroblasts) to cells that exhibited a second state of differentiation or phenotype (in this case, iPS cells). Still further into this particular embodiment, said reprogramming was in the absence of any inhibitor or agent that reduces expression or activity of an innate immune response pathway (e.g., B18R protein was not present prior to, during, or after said introducing of the pseudouridine-containing mRNA into said cells).

One other embodiment of the present invention is a Feeder-free Reprogramming Medium consisting of Dulbecco's modified Eagle medium with nutrient mixture F-12 (DMEM/F12; Invitrogen) supplemented with 20% KNOCKOUT™ serum replacement (Invitrogen), 2 mM GLUTAMAX™-I (Invitrogen), 0.1 mM non-essential amino acids solution (Invitrogen), and 0.5-15 micromolar MEK signaling pathway inhibitor STEMOLECULE™ PD0325901 (Stemgent). In some embodiments, the Feeder-free Reprogramming Medium further comprises transforming growth factor β (TGFβ) inhibitor STEMOLECULE™ SB431542 (Stemgent®, Cambridge, MA, USA). In some embodiments, the Feeder-free Reprogramming Medium further comprises 100 ng/ml basic human recombinant fibroblast growth factor (FGFb; Invitrogen). In some embodiments, the Feeder-free Reprogramming Medium further comprises penicillin and streptomycin antibiotics.

Example 27. Further Studies on the Abilities of Unmodified and Pseudouridine-Modified mRNAs Having Different Caps to Reprogram Somatic Cells to iPSCs with or without RNase III Treatment or HPLC Purification Materials and Methods for Example 27

Synthesis of mRNAs for Reprogramming

The mRNAs referred to only as "CAP0 OR CAP1" without additional designation of a dinucleotide cap analog were synthesized by in vitro transcription (IVT) of DNA templates encoding the 5 reprogramming factors (KLM$_{T58A}$OS) as described in the T7 mScript™ Standard mRNA Production System (CELLSCRIPT, INC., Madison, WI, USA) for unmodified (GAUC) mRNA. Pseudouridine-(ψ-) modified mRNA, was similarly synthesized by IVT, except with pseudouridine-5'-triphosphate (ψTP) in place of UTP. The IVT-mRNAs were then post-transcriptionally capped to CAP0 using SCRIPTCAP™ capping enzyme or to CAP1 using SCRIPTCAP™ capping enzyme and SCRIPTCAP™ RNA 2'-O-methyltransferase, as described in the T7 mScript™ Standard mRNA Production System, or as described for the separate SCRIPTCAP™ capping enzyme and/or SCRIPTCAP™ RNA 2'-O-methyltransferase products (CELLSCRIPT, INC.). For mRNAs capped with a β-S-ARCA D1 or β-S-ARCA D2 dinucleotide cap analogs, also herein referred to specifically as D1 or D2 thio-ARCAs, or generally as thio-ARCAs (Grudzien-Nogalska E et al. 2007; Kowalska, J et al., 2008), the mRNAs were made by co-transcriptional capping by including the respective dinucleotide cap analog in the IVT reaction at a molar ratio of 4-to-1 with GTP, at concentrations as described in a MessageMAX™ T 7 ARCA-Capped Message Transcription Kit (CELLSCRIPT, INC. Cat. No. C-MMA60710), except that the respective β-S-ARCA D1 or D2 dinucleotide cap was used in place of the ARCA provided in the kit. All of the mRNAs were enzymatically tailed using A-PLUS™ poly-A polymerase (CELLSCRIPT, INC., Catalog No. C-PAP5104H) to generate a poly-A tail of ~150 nt, as described by the manufacturer. The mRNAs that were treated using the RNase III treatment method disclosed herein in the presence of 2 mM magnesium acetate. Certain CAP1 pseudouridine-modified mRNAs were HPLC purified by Dr. Drew Weissman and Dr. Katalin Karikó of RNARx LLC (Wayne, PA) using HPLC as described (Karikó et al., 2011).

Reprogramming with GAUC Unmodified mRNA Mixes

Five-factor mRNA reprogramming mixes (KLM$_{T58A}$OS) encoding KLF4 (K), LIN28 (L), cMYC(T58A)(MT58A), OCT4 (O) and SOX2 (S) were made in a molar ratio of 1:1:1:3:1, and 1.2 micrograms of each mRNA mix was complexed with 4.8 microliters of STEMFECT™ transfection reagent (Stemgent) and transfected daily into 10$^1$ BJ fibroblasts (passage 5) plated on 4×10$^5$ NuFF cells. No inhibitor of innate immune response pathway (e.g., B18R protein) was used for reprogramming in the experiments reported here. In some cases, 2 mM valproic acid was added; however, these experiments will not be discussed further since all of the cells treated with valproic acid died. Cells were transfected with unmodified GAUC mRNA reprogramming mixes for 18 daily transfections, after which the cells were grown for 2 more days, a few colonies were picked for expansion and the rest were stained for alkaline phosphatase activity, which is indicative of iPSCs, and alkaline phosphatase-positive colonies were counted. Cells reprogrammed using pseudouridine-modified GAψC mRNA reprogramming mixes were transfected for only 15 daily transfections, and in some cases, 1.0, 1.2 or 1.4 micrograms of each pseudouridine-modified GAψC mRNA reprogramming mix was transfected with 4, 4.8 and 5.6 microliters of STEMFECT transfection reagent, respectively. The other steps of the reprogramming method using pseudouridine-modified GAψC mRNA reprogramming mixes were as described for the unmodified GAUC mRNA.

Results for Example 27

Comparison of iPSC Induction Using HPLC-Purified Versus RNase III-Treated Pseudouridine-Modified CAP1 KLMO$_3$S mRNA Reprogramming Mixes

| Purification or Treatment Method | Micrograms of mRNA Reprogramming Mix Transfected Per Day | Observations | No. of Alkaline Phosphatase-Positive Colonies |
|---|---|---|---|
| None | 1.2 | CELLS DEAD | 0 |
| HPLC | 1.0 | | 148 |
| HPLC | 1.2 | TMTCA | 400+ |
| HPLC | 1.4 | TMTCA | 400+ |
| RNase III | 1.0 | | 149 |
| RNase III | 1.2 | TMTCA | 400+ |
| RNase III | 1.4 | TMTCA | 400+ |

TMTCA = Too many colonies to count accurately.

The above results show that mRNA reprogramming mixes comprising pseudouridine-modified mRNAs were highly toxic to cells into which they were transfected daily for 15 days. However, when the same mRNA reprogramming mixes were purified by HPLC or were treated using the RNase III treatment methods described herein, the cells survived and iPSC cells were induced. The fact that the numbers of alkaline phosphatase-positive colonies, which is indicative of iPS cells, were nearly identical for the wells transfected with HPLC-purified and the RNase III-treated reprogramming mRNAs (e.g., 148 alkaline phosphatase-positive iPSC colonies induced using 1.0 micrograms per well of reprogramming mix made using HPLC-purified mRNAs versus 149 alkaline phosphatase-positive iPSC colonies induced using 1.0 micrograms per well of reprogramming mix made using the same lots of mRNAs that were treated using the RNase III treatment methods described herein) strongly indicates that dsRNA the primary RNA contaminant that results in cell death and the inability to reprogram somatic cells using mRNA reprogramming mixes comprising mRNAs which have not been HPLC-purified or RNase III-treated. In view of the equivalent effectiveness of the RNase III treatment methods described herein to HPLC purification in removing dsRNA contaminant molecules from mRNA, other important benefits of the present RNase III treatment method make it advantageous over HPLC purification.

Reprogramming of Somatic Cells to iPS Cells Using In Vitro-Synthesized Unmodified GAUC mRNAs Encoding KLMO$_3$S Reprogramming Factors and Comprising Co-Transcriptionally-Synthesized Thio Caps or Enzymatically Post-Transcriptionally Synthesized Cap0 or Cap1 Caps

| CAP Type | NTP mix | Subjected to the RNase III Treatment | Observations | No. of Alkaline Phosphatase-Positive Colonies |
|---|---|---|---|---|
| No RNA Control | None | NO | No significant toxicity | 0 |
| β-S-ARCA D1 | GAUC | NO | Cells died | 0 |
| β-S-ARCA D2 | GAUC | NO | Cells died | 0 |
| CAP0 | GAUC | YES | | 4 |
| CAP1 | GAUC | YES | | 289 |

The results above showed that mRNA reprogramming mixes comprising unmodified mRNAs were highly toxic to cells into which they were transfected daily for 18 days. However, when the same mRNA reprogramming mixes were treated using RNase III treatment with 2 mM Mg$^{2+}$, the cells survived and iPSC cells were induced. The results further showed that mRNA reprogramming mixes comprising unmodified GAUC mRNAs that exhibited a CAP1 structure were much more effective for reprogramming somatic cells to iPS cells than unmodified (GAUC) mRNAs that exhibited a CAP1 structure. Thus, in preferred embodiments of the reprogramming methods, compositions and kits of the invention comprising mRNA reprogramming mixes comprising unmodified mRNAs, the unmodified mRNAs exhibit a CAP1 structure.

Example 28. Effects of Pseudouridine-Modified (GAψC) or Unmodified (GAUC) dsRNA on Reprogramming of Human BJ Fibroblasts to iPS Cells Using RNase III-Treated Cap1 Poly(A)-Tailed GAψC of GAUC mRNAs Encoding KLMO$_3$S Reprogramming Factors Overview Previous results, including those discussed in EXAMPLE 27, showed the equivalence of the RNase III treatment methods (e.g., using about 2 mM Mg$^{2+}$) to HPLC for removing contaminant dsRNA from mRNA reprogramming mixes (e.g., 148 alkaline phosphatase-positive iPSC colonies were induced using 1.0 micrograms per well of reprogramming mix made using HPLC-purified pseudouridine-modified CAP1 KLM$_{(T58A)}$O$_3$S mRNAs versus 149 alkaline phosphatase-positive iPSC colonies induced using 1.0 micrograms per well of a reprogramming mix made using the same lots of mRNAs that were treated using the RNase III treatment methods described herein). Since approximately all of the dsRNA contaminants are removed using these methods, the present researchers saw this as an opportunity to analyze the levels of dsRNA contaminant that would result in toxicity and that would reduce or inhibit reprogramming, such as reprogramming of human or mammalian somatic cells to iPS cells, by adding back different known amounts of dsRNA to the mRNA reprogramming mixes. In order to avoid a biological effect (e.g., a biological effect due to RNA interference), the dsRNA chosen to add to the mRNA reprogramming mixes was a dsRNA made using a DNA template that was not present in the cells into which the mRNA reprogramming mixes were introduced; a 1.67-Kb firefly luciferase gene (luc2), which did not appear to be present in human cells, was chosen as the template for making dsRNA for this purpose. After making luc2 dsRNA by IVT, various amounts of the 1.6-Kb luc2 dsRNA were added to mRNA reprogramming mixes comprising mRNAs that were treated using the RNase III treatment method with 2 mM Mg2+ before the transfection reagent was added; in separate wells of 6-well plates, pseudouridine-modified (GAψC) or unmodified (GAUC) luc2 dsRNA was added to a reprogramming mix comprising either RNase III-treated pseudouridine-modified (GAψC) CAP1 KLM$_{(T58A)}$O$_3$S mRNAs or RNase III-treated unmodified (GAUC) CAP1 KLM$_{(T58A)}$O$_3$S mRNAs in order to try to tease out any differences between the cells' reaction to dsRNA and the cells' reaction to pseudouridine-modified versus unmodified mRNA.

Summary of the Protocol

Except for controls, all mRNAs in mRNA reprogramming mixes were treated using the RNAse III treatment method with 2 mM Mg2+.

All mRNAs were post-transcriptionally capped using SCRIPTCAP™ capping enzyme system and SCRIPT-CAP™ RNA 2'-O-methyltransferase to CAP1.

All mRNAs were poly-A tailed to ~150 As using A-PLUS™ poly-A polymerase.

Two different mRNA reprogramming mixes: one comprising unmodified (GAUC) mRNAs and one comprising pseudouridine-modified (GAψC) mRNAs.

5-Factor mRNA reprogramming mixes encoding KLM$_{(T58A)}$OS in a molar ratio of 1:1:1:3:1 were used; K=KLF4; L=LIN28; M$_{(T58A)}$=cMYC(T58A); O=OCT4; S=SOX2.

Cells were transfected with mRNA reprogramming mixes were transfected daily with a total of 1.2 micrograms of mRNA encoding all 5 protein factors (KLM$_{(T58A)}$OS) per well for 14 days for GAψC mRNAs or for 18 days for GAUC mRNAs. The indicated amounts of luc2 dsRNA was combined with the mRNA reprogramming mix prior to complexing with the STEMFECT™ transfection reagent, and then added the mRNA/dsRNA/transfection reagent complex was added to the medium as described.

Materials and Methods for Example 28

Synthesis of Luc2 dsRNA

Both pseudouridine-modified GAψC dsRNA and unmodified GAUC dsRNAs comprising sense and antisense ssRNA for a genetically engineered form of the firefly (*Photinus pyralis*) luciferase gene designated "luc2" (~1.67 Kbp) were produced as follows: Two linear DNA templates for separate in vitro transcription of sense and antisense ssRNAs were generated by restriction endonuclease linearization of a pGL4.19 [luc2-Neo] plasmid (Promega, Madison, WI, USA) that was modified by PCR to insert T7 and T3 RNA polymerase promoters, respectively. Each sense or antisense ssRNA strand was synthesized separately by in vitro transcription of a linear luc2 DNA template using either 17 RNA polymerase or T3 RNA polymerase, such as with a commercially available INCOGNITO™ T7 Ψ-RNA transcription kit (CELLSCRIPT, INC., Madison, WI, USA) for making GAψC RNA, or a T7-FLASHSCRIBE™ transcription kit or a T7-SCRIBE™ standard RNA IVT kit for making GAUC RNA (CELLSCRIPT), or similar homebrew kits containing T3 RNA polymerase. The firefly luc2 dsRNA was not capped or tailed. Each sense or antisense ssRNA was then separately resuspended in $T_{10}E1$, combined in equal amounts, annealed at 94° C. for 2 minutes, 70° C. for 10 minutes, and then slow-cooled to room temperature in a beaker of water. Fresh dsRNA dilutions were made daily in water because of the extremely low amounts of luc2 dsRNA added to the mRNA reprogramming mixes. The amount of luc2 dsRNA added for each daily treatment and the dsRNA added as a percentage of the total amount of RNA transfected per day are listed in the table below.

The Reprogramming Protocol

As in previous experiments, $10^4$ BJ fibroblasts (passage 6) were plated on NUFFs and the medium was changed to Stemgent's PLURITON medium (with supplement and pen/strep) with RNase Inhibitor added to 0.5U/ml of medium. The STEMFECT transfection reagent was used as previously described. Briefly, 1.2 micrograms of the appropriate mRNA reprogramming mix was added to STEMFECT buffer with varied amounts of either pseudouridine-modified or unmodified dsRNA. The STEMFECT transfection reagent was separately diluted in STEMFECT transfection buffer the two mixes were combined and incubated at RT for 15 minutes. The mixture was then added drop-wise to the cells which were in 2 mls of PLURITON reprogramming medium/well. The medium was changed daily prior to transfection. The cells transfected with pseudouridine-modified mRNA reprogramming mixes were transfected daily for a total of 14 times. The cells transfected with unmodified GAUC mRNA reprogramming mixes were transfected 18 times. Observations on cell health and morphology were made for the duration of the 20-day experiment. The cells were allowed to form iPSC colonies for 1-2 days after the transfections before the cells were scored for proper colony morphology and stained for enumeration of alkaline phosphatase-positive iPSC colonies.

Overview of Experiment and Final Alkaline Phosphatase-Positive iPSC Colony Count

| Well No. | dsRNA as % of total RNA transfected (%) | FF Luc2 dsRNA Type/ Reprogramming mRNA Type* | Amount of Reprogramming mRNA per well (micrograms) | Amount of dsRNA per well (nanograms) | Final No. of Alkaline Phosphatase-positive Colonies[+] |
|---|---|---|---|---|---|
| 1 | 0 | None/None | 0 | 0 | 0 |
| 6 | 0 | None/U | 1.2 | 0 | 234 |
| 7/8 | 2.5 | U/U | 1.2 | 31 | 0 |
| 9/10 | 0.5 | U/U | 1.2 | 6 | 0 |
| 11/12 | 0.1 | U/U | 1.2 | 1.2 | 0 |
| 13/14 | 0.05 | U/U | 1.2 | 0.6 | 0 |
| 15/16 | 0.02 | U/U | 1.2 | 0.24 | 0 |
| 17/18 | 0.01 | U/U | 1.2 | 0.12 | 0 |
| 19/20 | 0.008 | U/U | 1.2 | 0.096 | 0 |
| 21/22 | 0.004 | U/U | 1.2 | 0.048 | 0 |
| 23/24 | 0.0008 | U/U | 1.2 | .0096 | 1/0 |
| 25/26 | 0.00016 | U/U | 1.2 | .00192 | 50/38 |
| 27 | 0 | None/Ψ | 1.2 | 0 | 400+ |
| 28 | 2.5 | Ψ/Ψ | 1.2 | 30 | 0 |
| 29 | 0.5 | Ψ/Ψ | 1.2 | 6 | 0 |
| 30 | 0.1 | Ψ/Ψ | 1.2 | 1.2 | 0 |
| 31 | 0.05 | Ψ/Ψ | 1.2 | 0.6 | 0 |
| 32 | 0.02 | Ψ/Ψ | 1.2 | 0.24 | 0 |
| 33 | 0.01 | Ψ/Ψ | 1.2 | 0.12 | 0 |
| 34 | 0.008 | Ψ/Ψ | 1.2 | 0.096 | 2 |
| 35 | 0.004 | Ψ/Ψ | 1.2 | 0.048 | 5 |
| 36 | 0.0008 | Ψ/Ψ | 1.2 | .0096 | 400+ |
| 37 | 0.00016 | Ψ/Ψ | 1.2 | .00192 | 400+ |
| 38 | 0 | None/Ψ | 1.2 | 0 | 400+ |
| 39 | 2.5 | U/Ψ | 1.2 | 30 | 0 |
| 40 | 0.5 | U/Ψ | 1.2 | 6 | 0 |
| 41 | 0.1 | U/Ψ | 1.2 | 1.2 | 0 |

-continued

| Well No. | dsRNA as % of total RNA transfected (%) | FF Luc2 dsRNA Type/ Reprogramming mRNA Type* | Amount of Reprogramming mRNA per well (micrograms) | Amount of dsRNA per well (nanograms) | Final No. of Alkaline Phosphatase-positive Colonies+ |
|---|---|---|---|---|---|
| 42 | 0.05 | U/Ψ | 1.2 | 0.6 | 0 |
| 43 | 0.02 | U/Ψ | 1.2 | 0.24 | 0 |
| 44 | 0.01 | U/Ψ | 1.2 | 0.12 | 0 |
| 45 | 0.008 | U/Ψ | 1.2 | 0.096 | 0 |
| 46 | 0.004 | U/Ψ | 1.2 | 0.048 | 0 |
| 47 | 0.0008 | U/Ψ | 1.2 | .0096 | 15 |
| 48 | 0.00016 | U/Ψ | 1.2 | .00192 | 400+ |
| 2/3 | 0.1 | U/None | 0 | 1.2 | 0 |
| 4/5 | 0.004 | Ψ/None | 0 | 0.048 | 0 |

*U = unmodified GAUC RNA,
Ψ = pseudouridine-modified GAΨC RNA;
+400+ = there are more than 400 colonies, too many to count accurately Results and Observations for Example 28

Background and Introduction

We determined in previous experiments (e.g., as in other above Examples) that no alkaline phosphatase-positive iPSC colonies were induced when by BJ fibroblasts or keratinocytes were repeatedly transfected with mRNA reprogramming mixes comprising CAP1 pseudouridine-modified GAΨC mRNAs or GAUC miRNAs encoding KLM$_{(T58A)}$O$_3$S unless the dsRNA contaminants arising during in vitro transcription were removed using a method such as HPLC or the RNase III treatment method as described herein.

Still further, we demonstrated in EXAMPLE 27 that mRNA reprogramming mixes comprising pseudouridine-modified CAP1 mRNAs that were treated with the RNase III treatment method with 2 mM Mg$^{2+}$, as described herein, resulted in reprogramming of almost the same number of BJ fibroblasts to alkaline phosphatase-positive iPSC colonies as did the same quantity of the same mRNA reprogramming mix comprising the same mRNAs except that they were purified using HPLC. This showed that dsRNA was the main contaminant that inhibited reprogramming and that the RNase III treatment methods described herein were as effective as HPLC in removing the dsRNA contaminant molecules. Therefore, all mRNA reprogramming mixes encoding KLM$_{(T58A)}$O$_3$S used in this EXAMPLE 28, including both those comprising CAP1 pseudouridine-modified GAΨC mRNAs and those comprising CAP1 unmodified GAUC mRNAs, were treated using RNase III treatment in the presence of 2 mM of Mg$^{2+}$ as described herein.

In the Absence of Added dsRNA, RNase III-Treated GAΨC or GAUC Reprogramming mRNA Mixes Efficiently Reprogrammed BJ Fibroblasts to iPS Cells As shown in the above table, all of the mRNA reprogramming mixes comprising mRNAs that were treated with the RNase III induced large numbers of alkaline phosphatase-positive iPSC colonies when no dsRNA was added to the mRNA reprogramming mixes. Thus, GAΨC reprogramming mRNAs induced >400 iPSC colonies per well (wells 27 & 38), which was "too numerous to count accurately," and the GAUC reprogramming mRNAs induced 234 iPSC colonies (well 6). As found in previous experiments, the number of iPSC colonies induced by unmodified GAUC reprogramming mRNAs was only about half of the numbers and took longer to form colonies compared to those induced by the modified GAΨC reprogramming mRNAs. No colonies were induced in control wells that lacked any reprogramming mRNAs (wells 1-5).

Addition of dsRNA to RNase III-Treated GAΨC or GAUC Reprogramming mRNA Mixes Increased Cell Toxicity and Decreased iPSC Reprogramming Efficiency The Applicants were surprised by the unexpectedly low levels of dsRNA that were toxic for the BJ fibroblasts and feeder cells and by the even lower levels of dsRNA that were required in order to successfully reprogram the BJ fibroblasts to iPS cells.

For example, with respect to toxicity, we found that addition of dsRNA to the mRNA reprogramming mixes to a level of 0.01% or more of the total mass of RNA added was toxic to the cells, whether the dsRNA or the mRNA reprogramming mixes, or both, comprised modified GAΨC RNA or unmodified GAUC RNA. Thus, all of the cells were dead by day 6 of the treatments if more than 1 ng of dsRNA was added with the 1.2-micrograms-per-well per day of mRNA reprogramming mix (i.e., wherein the dsRNA was 0.1% or more of the total RNA added). All of the cells were dead by the day 10 if more than 240 pg of dsRNA was added with the 1.2-micrograms-per-well per day of mRNA reprogramming mix (i.e., wherein the dsRNA was 0.02% or more of the total mass of RNA added per well). Still further, the cells were dead by the 13$^{th}$ transfection if more than 120 pg of dsRNA was added with the 1.2-micrograms-per-well per day of mRNA reprogramming mix (wherein the dsRNA was 0.01% or more of the total mass of RNA added per well).

Surprisingly and unexpectedly, it was necessary to reduce the level of dsRNA added to the mRNA reprogramming mix much more still in order to successfully reprogram the BJ fibroblasts to iPS cells during the 14-to-18-day iPSC reprogramming protocol.

For example in some embodiments of the method for reprogramming of the present invention wherein an mRNA reprogramming mix comprising RNase III-treated pseudouridine-modified GAΨC mRNAs encoding one or more reprogramming factors are repeatedly or continuously introduced (e.g., transfected) into a cell that exhibits a first state of differentiation (e.g., a somatic cell; e.g., a fibroblast or keratinocyte) under conditions wherein the cell exhibits a second state of differentiation (e.g., a dedifferentiated state, a transdifferentiated state, or a differentiated state; e.g., an iPSC state of differentiation), the amount of dsRNA contaminant molecules in the mRNA reprogramming mix used for said introducing into the cell that exhibits the first state of differentiation is less than about 0.01% (and preferably less than about 0.001%) of the total RNA used for said introducing. For example, when the BJ fibroblast cells were transfected with pseudouridine-modified GAΨC dsRNA added to an mRNA reprogramming mix comprising RNase III-treated pseudouridine-modified GAΨC mRNAs, iPSCs were not induced until the amount of dsRNA was 0.008% or less of the total mass of RNA per well. Even at that level of dsRNA, only 2 iPSC colonies were induced (well 34) in the presence of 96 pg of dsRNA added with the 1.2-micrograms-per-well per day of mRNA reprogramming mix (i.e., wherein the dsRNA was 0.008% of the total mass of RNA added per well). Still further, only 5 iPSC colonies were induced (well 35) in the presence of 48 pg of dsRNA added with the 1.2-micrograms-per-well per day of mRNA reprogramming mix (i.e., wherein the dsRNA was 0.004% of the total mass of RNA added per well). When 1.92 pg of GAΨC dsRNA was added with the 1.2-micrograms-per-well per day of mRNA reprogramming mix (wherein the dsRNA was 0.0008% of the total mass of RNA added per well), no inhibition of iPSC induction was observed for the mRNA reprogramming mix comprising modified GAΨC mRNAs (well 36).

Only 1 iPSC colony was induced in one of two replicate wells (wells 23 and 24) transfected with 9.6 pg of dsRNA added with the 1.2-micrograms-per-well per day of mRNA reprogramming mix (i.e., wherein the dsRNA was 0.0008% of the total mass of RNA added per well). More iPSC colonies were induced (50 & 38 colonies in replicate wells 25 and 26) with only 1.92 pg of dsRNA added with the 1.2-micrograms-per-well per day of mRNA reprogramming mix (i.e., wherein the dsRNA was only 0.00016% of the total mass of RNA added per well), but even this small amount of the ~1.67 Kbp dsRNA decreased the number of viable reprogrammed iPSC colonies by about 80% compared to the number of iPSC colonies induced when no dsRNA was added to the mRNA reprogramming mix (234 colonies).

In one additional set of experiments, BJ fibroblast cells were transfected with unmodified GAUC dsRNA and an mRNA reprogramming mix comprising RNase III-treated pseudouridine-modified GAΨC mRNAs; it will be recognized that this is an artificial situation that is unlikely to occur, since dsRNA contaminant molecules are generated during in vitro transcription reactions and will comprise modified or unmodified RNA based on whatever NTPs are used in the IVT reaction. Therefore, the dsRNA will not comprise unmodified RNA and the mRNA made by IVT modified RNA. Nevertheless, in this set of experiments BJ fibroblast cells were transfected with unmodified GAUC dsRNA and an mRNA reprogramming mix comprising RNase III-treated pseudouridine-modified GAΨC mRNAs in order to determine if dsRNA comprising GAΨC RNA had a different effect on cell toxicity and reprogramming of somatic cells to iPS cells than dsRNA comprising GAUC RNA. Thus, the highest dose of dsRNA at which iPSC colonies were induced was at 9.6 pg of dsRNA added with the 1.2-micrograms-per-well per day of mRNA reprogramming mix (wherein the dsRNA was 0.0008% of the total mass of RNA added per well); at this dose, 15 iPSC colonies were induced (well 47). The cells tolerate this reprogramming mix better though. The cells were healthier and more colonies were obtained at the lowest dose of dsRNA. This amount of unmodified GAUC dsRNA was similar to the highest dose of unmodified GAUC dsRNA at which iPSC colonies were induced when an mRNA reprogramming mix comprising unmodified GAUC mRNAs was used (wells 23 and 24). However, in the presence of unmodified GAUC dsRNA, the use of an mRNA reprogramming mix comprising GAΨC mRNAs did seem to reduce cell toxicity and increase reprogramming efficiency compared to the use of an mRNA reprogramming mix comprising GAUC mRNAs (e.g., compare well 47 with wells 23 and 24, and well 48 with wells 25 and 26). The results with GAΨC dsRNA with an mRNA reprogramming mix comprising GAΨC mRNA (e.g., wells 35, 36 and 37) further demonstrates the benefits of reduced toxicity and increased reprogramming efficiency by using pseudouridine-modified mRNAs in the mRNA reprogramming mixes.

Example 29. Effects of Adding Unmodified (GAUC), Pseudouridine-Modified (GAψC), or Pseudouridine- and 5-Methylcytidine-Modified (GAψm⁵C) Luc2 dsRNA on Reprogramming of Mouse C3H/10T1/2 Cells to Myoblast Cells Using a Reprogramming Mix Comprising RNase III-Treated Cap1, Poly(A)-Tailed GAUC, GAψC OR GAψm⁵C mRNA Encoding MYOD Protein Synthesis of Double-Stranded Luciferase2 RNA (Luc2 dsRNA)

Linear DNA templates encoding a genetically engineered form of the firefly (*Photinus pyralis*) luciferase gene, designated "luc2," were used to generate sense and antisense ssRNAs as described in EXAMPLE 28, except that either GAUC or GAψC or GAψm⁵C NTP mixes were used for in vitro transcription of both the sense and antisense ssRNAs. The sense and antisense ssRNAs were then separately resuspended in water, combined in equal amounts, and annealed to generate luc2 dsRNAs comprising GAUC or GAψC or GAψm⁵C nucleotides using the following protocol: 250 microliters each of sense and antisense luc2 ssRNAs (each at 1 microgram/ml) comprising the same nucleotide composition were added together and heated at 95°C for 2 minutes, followed by 70° C. (5 minutes), 60° C. (10 minutes), 50° C. (10 minutes), 40° C. (10 minutes), 30° C. (10 minutes) and then allowed to cool to room temperature for 30 minutes. The GAUC, GAψC and GAψm⁵C dsRNA products were all confirmed to be double-stranded.

Synthesis of mRNA Encoding MYOD

A mouse MYOD DNA template for preparing mouse mRNA comprising or consisting of unmodified mouse MYOD mRNA (GAUC) for use in reprogramming mouse mesenchymal stem cells to myoblast cells was prepared as follows: DNA encoding MYOD mRNA, which mRNA exhibited the coding sequence or cds given as SEQ ID NO: 16, was cloned into pUC19-based plasmid DNA that contained a cassette exhibiting SEQ ID NO: 1, comprising a T7 RNA polymerase promoter followed by 5' Xenopus Beta Globin (UTR), a cloning site (into which the MYOD cds was inserted directly downstream of a Kozak translational initiation site GCCACC), and a 3' Xenopus Beta Globin 3' UTR. The DNA plasmid was linearized with Sal I and purified as previously described for other DNA plasmids as described herein, and then used as a DNA template for in vitro transcription of mRNA encoding MYOD (or MYOD mRNA).

Synthesis of MYOD mRNAs for Reprogramming

CAP1, poly(A)-tailed (~150 nts) unmodified (GAUC) mRNA encoding the MYOD protein, as encoded by the above-described MYOD DNA template, was synthesized by in vitro transcription (IVT) of said DNA template as using the T7 mScript™ Standard mRNA Production System (CELLSCRIPT, INC., Madison, WI, USA) as described by the manufacturer. CAP1, poly(A)-tailed (~150 nts) pseudouridine-modified (GAψC) mRNA and pseudouridine- and 5-methylcytidine-modified (GAψm$^5$C) mRNAs were each similarly synthesized by IVT using a T7 mScript™ Standard mRNA Production System, except that NTP mixes comprising GAψC NTPs or GAψm$^5$C NTPs, respectively, were used in place of UTP or CTP. Portions of each of these unmodified (GAUC) and modified (GAψC and GAψm$^5$C) mRNAs were treated using RNase III treatment in the presence of 2 mM magnesium acetate as disclosed herein.

Reprogramming of Mouse C3H10T1/2 Mesenchymal Stem Cells to Myoblast Cells Using CAP1 Unmodified MYOD mRNA and Effect of Luc2 dsRNA Mouse C3H10T1/2 cells were plated at 2×10$^5$ cells per well of a gelatin-coated 6-well dish and grown overnight in DMEM, 10% FBS, GLUTAMAX, and pen/strep. The next day, the cells were switched to differentiation medium comprising DMEM+2% horse serum, GLUTAMAX, and pen/strep. Cells were transfected using RNAiMAX transfection reagent (Invitrogen, Inc.) with 1.0 micrograms/ml of the above-described unmodified (GAUC) mRNA or GAψC modified mRNA or GAψm$^5$C modified mRNA encoding MYOD protein, either alone with no luc2 dsRNA, or together with luc2 dsRNA comprising the same type of nucleotides (GAUC, GAψC or GAψm$^5$C) as the mRNA encoding MYOD protein, with each respective luc2 dsRNA in varying concentrations between 0.000001 and 0.1 micrograms/ml. Briefly, each GAUC, GAψC or GAψm$^5$C MYOD mRNA and the corresponding luc2 dsRNA were added to a first tube containing a total volume of 60 microliters and an amount of RNAiMAX transfection solution equal to 5 microliters per microgram of RNA in the first tube was added to a second tube and the final volume was adjusted to 60 microliters. The first and second tubes were mixed, incubated at room temperature for 15 minutes, and the mRNA/RNAiMAX mix was added to 2 mls of differentiation medium already on the cells. The medium was changed with new differentiation medium 4 hours post transfection. Twenty-four hours after the first transfection, another transfection with the same treatment was administered. The medium was again changed 4 hours post transfection. Forty-eight hours after the first transfection, the cells were fixed and immunofluorescence was performed to detect Myosin Heavy Chain (MHC) expression. a marker of myoblast or muscle differentiation.

Results of Example 29

The percentage of contaminant dsRNA must be less than about 0.1% (and preferably less than about 0.01%) of the total amount of RNA to reprogram mesenchymal stem cells to myoblast cells using unmodified MYOD mRNA or GAψC-modified MYOD mRNA.

| Amount of RNase III-Treated GAUC or GAψC MYOD mRNA (μg/ml) | Amount of Respective GAUC or GAψC* Luc2 dsRNA Transfected (μg/ml) | dsRNA as % of Total RNA Transfected | Presence of Myosin Heavy Chain Immunofluorescent Staining |
| --- | --- | --- | --- |
| 1.0 | 0 | 0 | YES |
| 1.0 | 0.1 | 10% | No |
| 1.0 | 0.01 | 1% | No |
| 1.0 | 0.001 | 0.1% | No |
| 1.0 | 0.0001 | 0.01% | YES |
| 1.0 | 0.00001 | 0.001% | YES |
| 1.0 | 0.000001 | 0.0001% | YES |
| Untreated Mock Transfected | Untreated Mock Transfected | N/A | No |
|  |  | N/A | No |

*GAUC luc2 dsRNA is used with GAUC MYOD mRNA and GAψC luc2 dsRNA is used with GAψC MYOD mRNA.
N/A = Not Applicable.

The percentage of contaminant dsRNA must be less than 1% (and preferably 0.1% or less) of the total amount of RNA to reprogram mesenchymal stem cells to myoblast cells using GAψm$^5$C-modified MYOD mRNA.

| Amount of RNase III-Treated GAψm$^5$C MYOD mRNA (μg/ml) | Amount of GAψm$^5$C Luc2 dsRNA Transfected (μg/ml) | dsRNA as % of Total RNA Transfected | Presence of Myosin Heavy Chain Immunofluorescent Staining |
| --- | --- | --- | --- |
| 1.0 | 0 | 0 | YES |
| 1.0 | 0.1 | 10% | No |
| 1.0 | 0.01 | 1% | No |
| 1.0 | 0.001 | 0.1% | YES |
| 1.0 | 0.0001 | 0.01% | YES |
| 1.0 | 0.00001 | 0.001% | YES |
| 1.0 | 0.000001 | 0.0001% | YES |
| Untreated Mock Transfected | Untreated Mock Transfected | N/A | No |
|  |  | N/A | No |

Example 30. Direct Reprogramming of Human Fibroblasts to Neurons by Repeated Introduction of Pseudouridine-Modified (GAΨC) mRNAs Encoding ASCL1, MYT1L, NEUROD1 and POU3F2 Protein Transcription Factors

Introduction

Recently, Pang et al. and others (Pang, Z P et al., 2011; Ladewig J, et al. 2012) described the conversion of human fibroblasts to neurons by the introduction of doxycycline-inducible lentiviral vectors encoding four transcription factors (ASCL1, MYT1L, NEUROD1 and POU3F2), building on work of other researchers (e.g., Vierbuchen T, et al. 2010; Yang N, et al. 2011). In this Example, we show highly efficient direct reprogramming (e.g., transdifferentiation) of human fibroblasts to neurons by repeatedly introducing into the fibroblast cells a reprogramming mix comprising pseudouridine-modified mRNAs encoding protein transcription factors (e.g., ASCL1, MYT1L, NEUROD1 and POU3F2), wherein the mRNAs were treated using the RNase III treatment method with 2 mM Mg$^{2+}$, thereby reprogramming the fibroblasts to neural cells.

Materials and Methods for Reprogramming Fibroblasts to Neurons

Example 30 Details

IMR90 fetal human lung fibroblasts (passage P15) were seeded on gelatin-coated plates at 1.5×10$^5$ cells per well of a 6-well plate in EMEM (ATCC Cat. No. 30-2003) medium supplemented with 10% fetal bovine serum and 1× penicillin-streptomycin. The cells in each well were transfected daily (e.g., in this example, for 6 days) with a reprogramming mix comprising a total of 0.6 microgram of RNase III-treated (with 2 mM $Mg^{2+}$), pseudouridine-modified (GAΨC) recombinant mRNAs (encoding each of ASCL1 (A), MYT1L (M), NEUROD1 (N) and POU3F2 (P) protein transcription factors in a 1:1:1:1 molar ratio of AMNP) complexed with the STEMFECT™ transfection reagent (4 microliters per microgram mRNA). The recombinant mRNAs were made by in vitro transcription of linearized pUC19-derived DNA templates that contained a cassette (SEQ ID No: 1) comprising: a T7 promoter, a 5' UTR of Xenopus laevis β-globin, and a 3' UTR of Xenopus laevis β-globin; into which a DNA sequence encoding mRNA, which mRNA exhibits a coding sequence as given in the following SEQ ID No: ASCL1 (SEQ ID No: 11), MYT1L (SEQ ID No: 12), NEUROD1 (SEQ ID No: 13), or POU3F2 (SEQ ID No: 14 or SEQ ID No: 15) protein was inserted. Recombinant CAP1 mRNAs (with an ~150 nt polyA tail) encoding ASCL1, NEUROD1 and POU3F2 were prepared as described in the literature provided with the T7 mSCRIPT™ standard mRNA production system (CELLSCRIPT, INC., Madison, WI, USA), except that pseudouridine 5' triphosphate (ΨTP) was substituted for uridine 5' triphosphate (UTP) for IVT, and, prior to capping or polyadenylation, the in vitro-transcribed RNAs were treated using RNase III treatment as described herein with a concentration of 2 mM magnesium acetate. Recombinant MYT1L mRNA encoding MYT1L (with an ~150 nt polyA tail) was prepared as described in the literature provided with the MessageMAX™ T 7 ARCA-Capped Message Transcription Kit (CELLSCRIPT), except with ΨTP in place of UTP during IVT and, prior to polyadenylation with A-PLUS™ polyA polymerase (CELLSCRIPT), the in vitro-transcribed RNA was treated using RNase III treatment, as described herein, with 2 mM magnesium acetate; this mRNA it was not phosphatase-treated. The cells were kept in EMEM medium for the first 2 days of transfections then changed to N3 medium for the remainder of the experiment. N3 medium (Wernig M, et al. 2002) is DMEM/F12 medium (Life Technologies) supplemented with 25 micrograms per milliliter insulin, 50 micrograms per milliliter transferrin, 30 nanomolar sodium selenite, 20 nanomolar progesterone, 100 nanomolar putrescine (all from SIGMA) and supplemented with fresh FGFb daily to 10 nanograms per milliliter (R&D Systems) and 1× penicillin-streptomycin. The medium was changed daily before transfection and was supplemented with 0.5 U/ml of SCRIPTGUARD™ RNase inhibitor (CELLSCRIPT). The AMNP mRNA mix: STEMFECT™ transfection reagent complex were made as per manufacturer's protocol (STEMGENT, Cambridge, MA, USA), incubated 15 minutes at room temperature, and added to the cells. Phase contrast images of the cells were taken on day 6 and the cells were fixed on day 7 and immunofluorescently stained for the presence of the neuronal marker microtubule-associated protein-2 (MAP2). This is a microtubule assembly protein that is thought to play an essential role in neurogenesis.

Results for Reprogramming Fibroblasts to Neurons

By the $6^{th}$ transfection the morphology of most of the cells in the AMNP (ASCL1, MYT1L, NEUROD1, and POU3F2)-transfected wells had dramatically changed to a morphology (FIG. 50 and FIG. 51) and immunofluorescent staining of the cells was positive for MAP2, which showed that the fibroblasts had been reprogrammed (transdifferentiated directly to neurons. This reprogramming process was rapid and highly efficient.

Studies on the Effects of Adding Luc2 dsRNA on Reprogramming of Fibroblasts to Neurons Materials and Methods In another experiment, various amounts of either unmodified GAUC luc2 dsRNA or modified GAψC luc2 dsRNA were added to reprogramming mixes comprising RNase III-treated GAψC-mRNAs encoding ASCL1, MYT1L, NEUROD1, and POU3F2 (AMNP) to determine and quantify the effects of unmodified and ψ-modified dsRNA on reprogramming (transdifferentiation) of fibroblasts to neurons. As in similar experiments in all previous EXAMPLES, luc2 dsRNA was used because, since it is not naturally present in human cells, it was believed that it would not cause a biological or biochemical effect (e.g., due to RNA interference) as might occur if a dsRNA was used which exhibited a sequence encoded by a gene that was present in the cells.

As described above for EXAMPLE 30 Details, IMR90 fetal lung fibroblasts (P16) were seeded on gelatin-coated plates at $1.5 \times 10^5$ cells per well of a 6-well plate in EMEM media. Cells in each well were transfected daily with an mRNA reprogramming mix comprising a total of 600 nanograms of RNase III-treated pseudouridine-modified mRNAs encoding ASCL1, MYT1L, NEUROD1, and POU3F2 plus or minus various amounts of either unmodified GAUC or pseudouridine-modified (GAψC-) luc2 dsRNA, all complexed with the STEMFECT transfection reagent (4 microliter/microgram mRNA), for 4 days. The luc2 dsRNAs were added to mRNA reprogramming mixes as in previous experiments to determine and quantify the effects of dsRNA on reprogramming fibroblasts to iPSCs (e.g., see EXAMPLE 28). All of the mRNAs were pseudouridine-modified and RNAse III-treated. All had CAP1-caps added enzymatically except for MYT1L, which was co-transcriptionally capped with ARCA, and all were enzymatically polyadenylated to generate a poly(A) tail with ~150 A residues. The cells were kept in EMEM medium for the first transfection, then changed to N3 medium for the remainder of the experiment. The medium was changed daily before transfection and was supplemented with 0.5 U/ml of SCRIPTGUARD RNase Inhibitor.

Results of Studies on the Effects of Adding Luc2 dsRNA on Reprogramming of Fibroblasts to Neurons After the $4^{th}$ transfection, some cells in wells transfected with mRNAs encoding AMNP had changed morphology. Images were taken of the cells on day 5. Transfections were stopped and the cells were cultured for an additional 5 days to allow the neurons to mature. Then, the cells were immunostained to detect expression of neuronal markers, including MAP2 and NeuN, and the numbers of neurons in each well based on morphology and immunostaining were counted. Neurons were induced in the absence of added Luc2 dsRNA and in the presence of certain levels of added Luc2 dsRNA. When unmodified GAUC Luc2 dsRNA was added daily with the GAψC-mRNAs encoding ASCL1, MYT1L, NEUROD1, and POU3F2 (AMNP) reprogramming factors, neurons were induced only if the amount of added unmodified GAψC Luc2 dsRNA was less than about 0.01% of the total mass of RNA used for reprogramming, and significant numbers of neurons were generated only if the amount of added unmodified GAUC Luc2 dsRNA was less than about 0.001% of the total mass of RNA used for reprogramming. When modified GAψC Luc2 dsRNA was added daily with the GAψC-mRNAs encoding AMNP reprogramming factors, neurons were induced only if pseudouridine-modified GAψC Luc2 dsRNA was less than about 0.02% of the total mass of RNA used for reprogramming, and significant numbers of neurons were generated only if the amount of added unmodified GAUC Luc2 dsRNA was less than about 0.004% of the total mass of RNA used for reprogramming.

REFERENCES

Each and all of the following are incorporated herein by reference.

Angel M and Yanik M F. 2010. Innate immune suppression enables frequent transfection with RNA encoding reprogramming proteins. PloS ONE 5(7): el 1756.

Aoi T et al. 2008. Generation of pluripotent stem cells from adult mouse liver and stomach cells. Science 321: 699-702.

Aasen T et al. 2008. Efficient and rapid generation of induced pluripotent stem cells from human keratinocytes. Nature Biotechnology 26: 1276-1284.

Banerjee A K. 1980. 5'-terminal cap structure in eucaryotic messenger ribonucleic acids. Microbiol Rev 44: 175-205.

Cazenave, C., and Uhlenbeck, O. C. 1994. RNA template-directed RNA synthesis by T7 RNA polymerase. Proc Natl Acad Sci USA 91: 6972-6976.

Chan E M, et al. 2009. Live cell imaging distinguishes bona fide human iPS cells from partially reprogrammed cells. Nat Biotechnol 27: 1033-1037.

Dahl G and Sooknanan R. 2011. Synthesis of tagged nucleic acids. U.S. Pat. No. 8,039,214.

Dahl G and Sooknanan R. 2012. Synthesis of tagged nucleic acids. U.S. Pat. No. 8,329,887.

Dunn, J J. 1976. RNase III cleavage of single-stranded RNA. J Biol Chem 25: 3807-3814.

Dunn, J J. 1982. Ribonuclease III. In 'The Enzymes' vol 15 (P Boyer, ed.) Academic Press, NY. 485-499.

Drews K et al. 2012. The cytotoxic and immunological hurdles associated with non-viral mRNA-mediated reprogramming of human fibroblasts. Biomaterials 33: 4059-4068.

Ebert A D et al. 2009. Induced pluripotent stem cells from a spinal muscular atrophy patient. Nature 457: 277-280.

Edmonds M. 1990. Polyadenylate polymerases. Methods Enzymol 181: 161-170.

Filippov V et al. 2000. A novel type of RNase III family proteins in eukaryotes. Gene. 245: 213-221.

Gantier M P and Williams B R G. 2007. The response of mammalian cells to double-stranded RNA. Cytokine Growth Factor Rev 18: 363-371.

Gershon P D. 2000. Poly(A)-tail of two polymerase structures. Nat Struct Biol 7: 819-821.

Gonzalez F, et al. 2009. Generation of mouse-induced pluripotent stem cells by transient expression of a single nonviral polycistronic vector. Proc Natl Acad Sci USA 106: 8918-8922.

Graf T and Enver T. 2009. Forcing cells to change lineages. Nature 462: 587-594.

Grudzien E et al. 2004. Novel cap analogs for in vitro synthesis of mRNAs with high translational efficiency. RNA 10: 1479-1487.

Grudzien-Nogalska E et al. 2007. Phosphorothioate cap analogs stabilize mRNA and increase translational efficiency in mammalian cells. RNA 13: 1745-1755.

Guillerez, J et al. U.S. Pat. No. 7,335,471 and U.S. Patent Application No. 20040091854.

Hagen F S and Young E T. 1978. Effect of RNase III on efficiency of translation of bacteriophage T7 lysozyme mRNA. J Virol 26: 793-804.

Higman M A et al. 1992. The vaccinia virus mRNA (guanine-N7-)-methyltransferase requires both subunits of the mRNA capping enzyme for activity. J Biol Chem 267: 16430-16437.

Higman M A et al. 1994. The mRNA (guanine-7-)methyltransferase domain of the vaccinia virus mRNA capping enzyme. Expression in *Escherichia coli* and structural and kinetic comparison to the intact capping enzyme. J Biol Chem 269: 14974-14981.

Hornung V et al. 2006. 5'-Triphosphate RNA is the ligand for RIG-I. Science 314: 994-997.

Huangfu D et al. 2008. Induction of pluripotent stem cells from primary human fibroblasts with only Oct4 and Sox2. Nat Biotechnol 26: 1269-1275.

Jemiely J et al. 2003. Novel "anti-reverse" cap analogs with superior translational properties. RNA 9: 1108-1122.

Jendrisak J et al. Kits and methods for generating 5' capped RNA. U.S. patent application Ser. No. 11/787,352; Publication No. 20070281336.

Jiang F et al. 2011. Structural basis of RNA recognition and activation by innate immune receptor RIG-I. Nature 479: 423-427.

Kalal M et al. 2002. Tipping the balance between necrosis and apoptosis in human and murine cells treated with interferon and dsRNA. Cell Death and Differentiation 9: 981-994.

Kariko K et al. 2004. mRNA is an endogenous ligand for toll-like receptor 3. J Biol Chem 279: 12542-12550.

Kariko et al. 2005. Suppression of RNA recognition by Toll-like receptors: the impact of nucleoside modification and the evolutionary origin of RNA. Immunity 23: 165-175.

Kariko K et al. 2008. Incorporation of pseudouridine into mRNA yields superior nonimmunogenic vector with increased translational capacity and biological stability. Mol Ther 16: 1833-1840.

Kariko K et al. 2011(A). RNA preparations comprising purified modified RNA for reprogramming cells. U.S. Patent Application Publication No. 20110143397.

Kariko K et al. 2011(B). Generating the optimal mRNA for therapy: HPLC purification eliminates immune activation and improves translation of nucleoside-modified, protein-encoding mRNA. Nucleic Acids Res. 39: e142.

Kariko K and Weissman D. 2012. RNA containing modified nucleosides and methods of use thereof. U.S. Pat. No. 8,278,036.

Kato H et al. 2008. Length-dependent recognition of double-stranded ribonucleic acids by retinoic acid-inducible gene-I and melanoma differentiation-associated gene 5. J Exp. Med. 205: 1601-1610.

Kiyota E et al. 2011. An *Arabidopsis* RNase III-like protein, AtRTL2, cleaves double-stranded RNA in vitro. J Plant Res. 124: 405-414.

Kowalska J et al. 2008. Synthesis and characterization of mRNA cap analogs containing phosphorothioate substitutions that bind tightly to eIF4E and are resistant to the decapping pyrophosphatase DcpS. *RNA* 14: 1119-1131.

Kozak M. 1987. An analysis of 5'-noncoding sequences from 699 vertebrate messenger RNAs. *Nucleic Acids Res.* 15: 8125-8148.

Ladewig J, et al. 2012. Small molecules enable highly efficient neuronal conversion of human fibroblasts. *Nat Methods* 9:575-578.

Lee Y et al. 2003. The nuclear RNase III Drosha initiates microRNA processing. *Nature* 425: 415-419.

Lee G, et al. 2009. Modelling pathogenesis and treatment of familial dysautonomia using patient-specific iPSCs. *Nature* 461: 402-406.

Leonard J et al. 2008. The TLR3 signaling complex forms by cooperative receptor dimerization. *Proc Natl Acad Sci USA* 105: 258-263.

Li H-L et al. 1993. Ribonuclease III cleavage of bacteriophage T7 processing signal. Divalent cation specificity, and specific anion effects. *Nucleic Acids Res* 21: 1919-1925.

Lukacs N. 1994. Detection of virus infection in plants and differentiation between coexisting viruses by monoclonal antibodies to double-stranded RNA. *J. Virol.* Methods 47: 255-272.

Lukacs N. 1997. Detection of sense: antisense duplexes by structure-specific anti-RNA antibodies. In: Antisense Technology. A Practical Approach, C. Lichtenstein and W. Nellen (eds), pp. 281-295. IRL Press, Oxford.

Mackie G A. 1988. Vectors for the synthesis of specific RNAs in vitro. *Biotechnology* 10: 253-267.

Maehr R et al. 2009. Generation of pluripotent stem cells from patients with type 1 diabetes. *Proc Natl Acad Sci USA* 106: 15768-15773.

Martin S A et al. 1975. Purification of mRNA guanylyltransferase and mRNA (guanine-7-) methyltransferase from vaccinia virions. *J Biol Chem* 250: 9322-9329.

Matsuda, S et al. 2000. Molecular cloning and characterization of a novel human gene HERNA which encodes a putative RNA-helicase. *Biochim. Biophys. Acta.* 1490: 163-169.

McAllister W T and Raskin C A. 1993. The phage RNA polymerases are related to DNA polymerases and reverse transcriptases. *Molecular Microbiology* 10: 1-6.

Mellits K H et al. 1990. Removal of double-stranded contaminants from RNA transcripts: synthesis of adenovirus VA RNAi from a T7 vector. *Nucleic Acids Res* 18: 5401-5406.

Minskaia E et al. 2006. Discovery of an RNA virus 3'->5' exoribonuclease that is critically involved in coronavirus RNA synthesis. *Proc Natl Acad Sci USA*. 103: 5108-5113.

Myette J R and Niles E G. 1996. Domain structure of the vaccinia virus mRNA capping enzyme. Expression in *Escherichia coli* of a subdomain possessing the RNA 5'-triphosphatase and guanylyltransferase activities and a kinetic comparison to the full-size enzyme. *J Biol Chem* 271: 11936-11944.

Nakagawa M et al. 2008. Generation of induced pluripotent stem cells without Myc from mouse and human fibroblasts. *Nat Biotechnol* 26: 101-106.

Nicholson, A. W. 1996. Structure, reactivity, and biology of double-stranded RNA. *Progr Nucleic Acid Res Mol Biol* 52: 1-65.

Okita K et al. 2008. Generation of mouse induced pluripotent stem cells without viral vectors. *Science* 322: 949-953.

Ozawa T et al. 2006. Amplification and analysis of cDNA generated from a single cell by 5'-RACE: application to isolation of antibody heavy and light chain variable gene sequences from single B cells. *Biotechniques* 40: 469-470, 472, 474 passim.

Pang Z P et al. 2011. Induction of human neuronal cells by defined transcription factors. *Nature* 476: 220-223.

Peng Z H et al. 2002. Synthesis and application of a chain-terminating dinucleotide mRNA cap analog. *Org Lett* 4: 161-164.

Pe'ery T and Mathews M B. 1997. Synthesis and purification of single-stranded RNA for use in experiments with PKR and in cell-free translation systems. *METHODS: A Companion to Methods in Enzymology* 11: 371-381.

Pichlmair A et al. 2006. RIG-I-mediated antiviral responses to single-stranded RNA bearing 5'-triphosphates. *Science* 314: 997-1001.

Plews J R et al. 2010. Activation of pluripotency genes in human fibroblast cells by a novel mRNA based approach. *PLoS ONE* 5: e14397.

Probst J et al. 2006. Characterization of the ribonuclease activity on the skin surface. *Genet Vaccines Ther.* 4: 4 doi:10.1186/1479-0556-4-4.

Qi, X et al. 2010. Cap binding and immune evasion revealed by Lassa nucleoprotein structure. *Nature* 468: 779-783.

Robertson, H D et al. 1968. Purification of Ribonuclease III from *Escherichia coli*. *J Biol Chem* 243: 82-91.

Robertson HD and Hunter T. 1975. Sensitive methods for detection and characterization of double helical ribonucleic acid. *J Biol Chem* 250: 418-425.

Robertson HD. 1982. *Escherichia coli* ribonuclease III cleavage sites. Cell 30: 669-672.

Robertson H D et al. 1996. Paradoxical interactions between human delta hepatitis agent RNA and cellular protein kinase PKR. *J Virology* 70: 5611-5617.

Sahin U et al. 2011. Use of RNA for reprogramming somatic cells. U.S. Patent Application No. 20110065103.

Saito T et al. 2008. Innate immunity induced by composition-dependent RIG-I recognition of hepatitis C virus RNA. *Nature* 454: 523-527.

Schlee M et al. 2009. Approaching the RNA ligand for RIG-I. *Immunol Rev* 227: 66-74.

Schönborn J et al. 1991. Monoclonal antibodies to double-stranded RNA as probes of RNA structure in crude nucleic acid extracts. *Nucleic Acids Res.* 19: 2993-3000.

Shuman S. 1995. Capping enzyme in eukaryotic mRNA synthesis. *Prog Nucleic Acid Res Mol Biol* 50: 101-129.

Shuman. 2001. Structure, mechanism, and evolution of the mRNA capping apparatus. *Prog Nucleic Acid Res Mol Biol* 66: 1-40.

Shuman S et al. 1980. Purification and characterization of a GTP-pyrophosphate exchange activity from vaccinia virions. Association of the GTP-pyrophosphate exchange activity with vaccinia mRNA guanylyltransferase. RNA (guanine-7-) methyltransferase complex (capping enzyme). *J Biol Chem* 255: 11588-11598.

Stadtfeld M et al. 2008. Induced pluripotent stem cells generated without viral integration. *Science* 322: 945-949.

Stepinski J et al. 2001. Synthesis and properties of mRNAs containing the novel "anti-reverse" cap analogs 7-methyl (3'-O-methyl) GpppG and 7-methyl (3'-deoxy)GpppG. *RNA* 7: 1486-1495.

Stewart II, W E et al. 1972. Increased susceptibility of cells treated with interferon to the toxicity of polyriboinosinic: polyribocytidylic acid. *Proc Nat Acad Sci USA* 69: 1851-1854.

Studier F W and Moffatt B A. 1986. Use of bacteriophage T7 RNA polymerase to direct selective high-level expression of cloned genes. *J Mol Biol* 189: 113-130.

Sul, J-Y et al. 2012. Perspectives on cell reprogramming with RNA. *Cell* 30: 243-249. Takahashi K and Yamanaka S. 2006. Induction of pluripotent stem cells from mouse embryonic and adult fibroblast cultures by defined factors. *Cell* 126: 663-676.

Takahashi K and Yamanaka S. 2006. Induction of pluripotent stem cells from mouse embryonic and adult fibroblast cultures by defined factors. *Cell* 126: 663-676.

Takahashi K et al. 2007. Induction of pluripotent stem cells from adult human fibroblasts by defined factors. *Cell* 131: 861-872.

Triana-Alonso F J et al. 1995. Self-coded 3'-extension of run-off transcripts produces aberrant products during in vitro transcription with T7 RNA polymerase. *J Biol Chem* 270: 6298-6307.

Wan Y and Chang H Y. 2010. HOTAIR: Flight of noncoding RNA in genome regulation: Prospects and mechanisms. *Cell Cycle* 9: 3391-3392.

Uzri D and Gehrke L. 2009. Nucleotide sequences and modifications that determine RIG-I/RNA binding and signaling activities. *J. Virol.* 83: 4174-4184.

Vierbuchen T, et al. 2010. Direct conversion of fibroblasts to functional neurons by defined factors. *Nature* 463: 1035-1041.

Wang S P et al. 1997. Phylogeny of mRNA capping enzymes. *Proc Natl Acad Sci USA* 94: 9573-9578.

Wang X et al. 2011. Phosphorylation regulates c-Myc's oncogenic activity in the mammary gland. *Cancer Res.* 71: 925-936.

Warren, L et al. 2010. Highly efficient programming to pluripotency and directed differentiation of human cells with synthetic modified mRNA. *Cell Stem Cell* 7: 1-13.

Wasylishen A R et al. 2011. New model systems provide insights into Myc-induced transformation. *Oncogene.* 30: 3727-3734.

Wernig M, et al. 2002. Tau EGFP embryonic stem cells: an efficient tool for neuronal lineage selection and transplantation. *J. Neurosci. Res.* 69: 918-924.

Wianny F and Zernicka-Goetz M. 2000. Specific interference with gene function by double-stranded RNA in early mouse development. *Nat. Cell Biol.* 2: 70-75.

Wilusz J and Shenk T. 1988. A 64 kd nuclear protein binds to RNA segments that include the AAUAAA polyadenylation motif. *Cell* 52: 221-228.

Woltjen K et al. 2009. piggyBac transposition reprograms fibroblasts to induced pluripotent stem cells. *Nature* 458: 766-770.

Woo C J and Kingston R E, 2007). "HOTAIR lifts noncoding RNAs to new levels". Cell 129: 1257-1259.

Wu, H., Xu, H., Miraglia, L. J., and Crooke, S. T. 2000. Human RNase III is a 160-kDa protein involved in preribosomal RNA processing [In Process Citation]. *J. Biol. Chem.* 275: 36957-65.

Xu C et al. 2001. Feeder-free growth of undifferentiated human embryonic stem cells. *Nat Biotechnol* 19: 971-974.

Yakubov E et al. 2010. Reprogramming of human fibroblasts to pluripotent stem cells using mRNA of four transcription factors. *Biochim Biophys Res Comm* 394: 189-193.

Yang S et al. 2001. Specific double-stranded RNA interference in undifferentiated mouse embryonic stem cells. *Mol Cell Biol* 21: 7807-7816.

Yang N, et al. 2011. Induced neuronal cells: how to make and define a neuron. *Cell Stem Cell* 9: 517-525.

Yanik M F and Angel M. 2010. U.S. patent application Ser. No. 12/428,378, Published as US 2010/0273220.

Yu J et al. 2007. Induced pluripotent stem cell lines derived from human somatic cells. *Science.* 318: 1917-1920.

Yu J et al. 2009. Human induced pluripotent stem cells free of vector and transgene sequences. *Science* 324: 797-801.

Yu J et al. 2007. Induced pluripotent stem cell lines derived from human somatic cells. *Science* 318: 1917-1920.

Zhou H et al. 2009. Generation of induced pluripotent stem cells using recombinant proteins. *Cell Stem Cell* 4: 381-384.

Zust, R et al. 2011. Ribose 2'-O-methylation provides a molecular signature for the distinction of self and non-self mRNA dependent on the RNA sensor Mda5. *Nature Immunol.* 12: 137-143.

Product literature, including all descriptions and protocols therein, for the A-PLUS™ poly(A) polymerase tailing kit, the AMPLICAP-MAX™ T7 high yield message maker kit, the AMPLICAP™ SP6 high yield message maker kit, Anti-reverse cap analog (ARCA), the INCOGNITO™ SP6 Ψ-RNA transcription kit, INCOGNITO™ T7 ARCA 5mC- & Ψ-RNA transcription kit, the INCOGNITO™ T7 5mC- and Ψ-RNA transcription kit, the INCOGNITO™ T7 Ψ-RNA transcription kit, the MESSAGEMAX™ T7 ARCA-capped message transcription kit, the SCRIPT-CAP™ m$^7$G capping system, the SCRIPTCAP™ 2'-O-methyltransferase kit, SCRIPTGUARD™ RNase inhibitor, the SP6-SCRIBE™ standard RNA IVT kit, the 17 mSCRIPT™ standard mRNA production system, and the T7-SCRIBE™ Standard RNA IVT Kit (all available on the web at www.cellscript.com or from CELLSCRIPT, Inc., Madison, WI, USA) and Monoclonal J2 Antibody and Monoclonal Antibody K1 (available from English Scientific & Consulting, Szirák, Hungary) are incorporated herein by reference.

We claim:

1. A method of generating a purified RNA preparation comprising:
   a) performing in vitro transcription (IVT) such that an IVT RNA composition is generated that comprises single-strand RNA (ssRNA) and double-stranded RNA (dsRNA) contaminants, wherein said ssRNA encodes a protein;
   b) contacting said IVT RNA composition with a prokaryotic endoRNase III to generate a reaction mixture, wherein magnesium cations are present in said reaction mixture at a concentration of about 1-4 mM, and wherein said prokaryotic endoRNase III digests all, or practically all, of said dsRNA contaminants to generate dsRNA digestion products; and
   c) purifying said ssRNA to generate a purified composition comprising said ssRNA, and wherein 0.05% 0.01% or less of the mass of RNA in said purified composition is dsRNA of 30 basepairs or longer.

2. The method of claim 1, wherein said magnesium cations are present in said reaction mixture at a concentration of about 1-2 mM.

3. The method of claim 1, wherein said ssRNA comprises mRNA.

4. The method of claim 3, wherein said mRNA encodes a human cell reprogramming factor protein or a human therapeutic protein.

5. The method of claim 1, wherein said ssRNA comprises one or more modified nucleosides.

6. The method of claim 5, wherein said one or more modified nucleosides are selected from the group consisting of: pseudouridine (ψ), 1-methyl-pseudouridine (m$^1$Ψ), 5-methylcytidine (m$^5$C), 5-methyluridine (m$^5$U), 2'-O-methyluridine (Um or m$^{2'-O}$U), 2-thiouridine (s$^2$U), and N6-methyladenosine.

7. The method of claim 1, further comprising: d) repeatedly transfecting isolated human or animal cells with said purified composition, without inducing significant cytotoxicity or cell death in said cells.

8. The method of claim 7, wherein said ssRNA comprises mRNA encoding reprogramming factors.

9. The method of claim 7, wherein said ssRNA comprises mRNA that encodes at least one protein selected from the group consisting of: OCT4, SOX2; KLF4; LIN28; NANOG; MYC; c-MYC; c-MYC(T58A); and L-MYC.

10. The method of claim 1, wherein 0.001% or less of the mass of RNA in said purified composition is dsRNA of 30 basepairs or longer.

11. The method of claim 1, wherein 0.0002% or less of the mass of RNA in said purified composition is dsRNA of 30 basepairs or longer.

12. The method of claim 1, wherein said ssRNA comprises a cap structure.

13. The method of claim 1, wherein said ssRNA comprises a Cap I structure where the 5' penultimate nucleoside comprises a 2'-O-methyl-ribosyl group.

14. The method of claim 1, wherein said ssRNA comprises a poly A tail.

15. The method of claim 1, wherein said prokaryotic endoRNase III is from *E. coli*.

16. The method of claim 1, wherein all, or practically all, of said dsRNA contaminants are digested by said prokaryotic endoRNase III to a size of about 12 to 15 bp in length.

* * * * *